United States Patent
Brown et al.

(10) Patent No.: US 8,669,249 B2
(45) Date of Patent: Mar. 11, 2014

(54) POLY (ADP-RIBOSE) POLYMERASE (PARP) INHIBITORS

(75) Inventors: Jason W. Brown, San Diego, CA (US); Anthony R. Gangloff, San Diego, CA (US); Andrew John Jennings, San Diego, CA (US); Phong H. Vu, San Diego, CA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 173 days.

(21) Appl. No.: 13/260,680

(22) PCT Filed: Mar. 26, 2010

(86) PCT No.: PCT/US2010/028878
§ 371 (c)(1),
(2), (4) Date: Nov. 8, 2011

(87) PCT Pub. No.: WO2010/111626
PCT Pub. Date: Sep. 30, 2010

(65) Prior Publication Data
US 2012/0094992 A1    Apr. 19, 2012

Related U.S. Application Data

(60) Provisional application No. 61/164,132, filed on Mar. 27, 2009.

(51) Int. Cl.
*C07D 265/36* (2006.01)
*C07D 413/06* (2006.01)
*A61K 31/538* (2006.01)

(52) U.S. Cl.
USPC ........................ 514/230.5; 544/105

(58) Field of Classification Search
USPC ........................ 544/105; 514/230.5
See application file for complete search history.

(56) References Cited

U.S. PATENT DOCUMENTS

| | | | |
|---|---|---|---|
| 4,929,269 | A | 5/1990 | Watson et al. |
| 6,191,127 | B1 | 2/2001 | Holscher et al. |
| 2004/0029734 | A1 | 2/2004 | Tsukamoto et al. |
| 2005/0075347 | A1 | 4/2005 | Albrecht et al. |
| 2007/0179165 | A1 | 8/2007 | Gyorkos et al. |
| 2012/0022056 | A1* | 1/2012 | Bentley et al. ........... 514/230.2 |

FOREIGN PATENT DOCUMENTS

WO    2006/024517    3/2006
WO    WO 2006024517 A1 *    3/2006

OTHER PUBLICATIONS

Smid, Pieter et al. "Synthesis, structure-activity relationships, and biological properties of 1-heteroaryl-4[w-(1H-indol-3-yl)alkyl]piperazines, novel potential antipsychotics combining potent dopamine d2 receptor antagonism with potent serotonin reuptake inhibition" Journal of Medicinal Chemistry, 2005, vol. 48, pp. 6855-6869. XP002458793.
Dai, Wei-Min et al. "Microwave-assisted on-pot regioselective synthesis of 2-alkyl-3,4-dihydro-3-oxo-2h-1,4-benzoxazines" Tetrahedron, vol. 61, 2005, p. 6879-6885.
Shaaban, Mohamed R. et al. "Highly regioselective anodic monofluorination of 2H-1,4-benzoxazin-3(4H)-one derivatives1" Synlett, 2001, No. 10, p. 1644-1646. XP002591505.
Database CA [Online] Chemical Abstract Services, 1963, Bassignana, P. et al. "Infrared spectra of some compounds with thiazole and oxazole rings. The C:N bond", Database accession No. 1963:472873, XP002591503.
Database CA [Online] Chemical Abstract Sercies, 1938, Coles, Harold W. et al. "Preparation of 2-methyl-8-carboxy-3-keto-3,4-dihydro-1,4-benzoxazine" Journal of American Chemical Society, vol. 60, p. 1627-1628. STN, Database Accession No. 1938:44905 XP002591504.

* cited by examiner

*Primary Examiner* — Kahsay Habte
(74) *Attorney, Agent, or Firm* — Matthew J. Russo; Mitchell R. Brustein

(57) ABSTRACT

Compounds of the following formula are provided for use in inhibiting Poly (ADP-ribose) Polymerase (PARP):

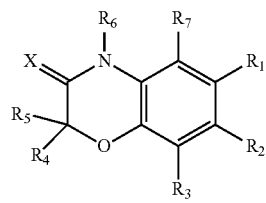

wherein the variables are defined herein. Also provided are pharmaceutical compositions, kits and articles of manufacture comprising such compounds, methods and intermediates useful for making the compounds, and methods of using the compounds.

12 Claims, No Drawings

POLY (ADP-RIBOSE) POLYMERASE (PARP) INHIBITORS

CROSS-REFERENCE TO RELATED APPLICATION

This application claims the benefit of U.S. Provisional Application No. 61/164,132, filed Mar. 27, 2009, which is incorporated herein by reference.

FIELD OF THE INVENTION

The present invention relates to compounds that may be used to inhibit Poly (ADP-ribose) Polymerase (PARP), as well as compositions of matter, kits and articles of manufacture comprising these compounds. The invention also relates to methods for inhibiting PARP and treatment methods using compounds according to the present invention. In addition, the invention relates to methods of making the compounds of the present invention, as well as intermediates useful in such methods.

BACKGROUND OF THE INVENTION

The present invention relates to inhibitors of the enzyme poly(ADP-ribose)polymerase (PARP), previously known as poly(ADP-ribose)synthase and poly(ADP-ribosyl)transferase. PARP constitutes a super family of proteins containing PARP catalytic domains. These proteins include PARP-1, PARP-2, PARP-3, vaultPARP and TiPARP. PARP-I consists of an amino (N)-terminal DNA-binding domain (DBD) containing two zinc fingers; an automodification domain; and a carboxy (C)-terminal catalytic domain.

PARP is a nuclear and cytoplasmic enzyme that cleaves NAD+ to nicotinamide and ADP-ribose to form long and branched ADP-ribose polymers on target proteins, including topoisomerases, histones and PARP itself PARP has been implicated in several biological processes, including DNA repair, gene transcription, cell cycle progression (including proliferation and differentiation), cell death, chromatin functions, genomic (e.g., chromosomal) stability and telomere length.

Activation of PARP and the resultant formation of poly (ADP-ribose) can be induced by DNA strand breaks after exposure to chemotherapy, ionizing radiation, oxygen free radicals, or nitric oxide (NO). Because this cellular ADP-ribose transfer process is associated with the repair of DNA strand breakage in response to DNA damage caused by radiotherapy or chemotherapy, it can contribute to the resistance that often develops to various types of cancer therapies. Consequently, inhibition of PARP is expected to retard intracellular DNA repair and enhance the antitumor effects of cancer therapies.

In addition, tankyrases (e.g., tankyrase-1 and tankyrase-2) which bind to the telomeric protein TRF-1, a negative regulator of telomere length maintenance, have a catalytic domain that is homologous to PARP. It has been proposed that telomere function in human cells is regulated by poly(ADP-ribosyl)ation. As a consequence of regulation of telomerase activity by tankyrase, PARP inhibitors are expected to have utility as agents for use in cancer therapy (e.g., to shorten the lifespan of immortal tumor cells) or as anti-aging therapeutics, since telomere length is believed to be associated with cell senescence.

In addition, PARP modulation has been implicated in vascular and cardiovascular diseases, metabolic diseases, inflammatory diseases, reperfusion injuries, ischemic conditions, neurodegenerative diseases and more.

There is a continued need to find new therapeutic agents to treat human diseases. PARP is an especially attractive target for the discovery of new therapeutics due to its important role in cancers, vascular and cardiovascular diseases, metabolic diseases, inflammatory diseases, reperfusion injuries, ischemic conditions, neurodegenerative diseases and other diseases.

SUMMARY OF THE INVENTION

The present invention relates to compounds that have activity for inhibiting PARP. The present invention also provides compositions, articles of manufacture and kits comprising these compounds. In addition, the invention relates to methods of making the compounds of the present invention, as well as intermediates useful in such methods.

In one embodiment, a pharmaceutical composition is provided that comprises a PARP inhibitor according to the present invention as an active ingredient. Pharmaceutical compositions according to the invention may optionally comprise 0.001%-100% of one or more inhibitors of this invention. These pharmaceutical compositions may be administered or co-administered by a wide variety of routes, including for example, orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compositions may also be administered or co-administered in slow release dosage forms.

The invention is also directed to kits and other articles of manufacture for treating disease states associated with PARP.

In one embodiment, a kit is provided that comprises a composition comprising at least one PARP inhibitor of the present invention in combination with instructions. The instructions may indicate the disease state for which the composition is to be administered, storage information, dosing information and/or instructions regarding how to administer the composition. The kit may also comprise packaging materials. The packaging material may comprise a container for housing the composition. The kit may also optionally comprise additional components, such as syringes for administration of the composition. The kit may comprise the composition in single or multiple dose forms.

In another embodiment, an article of manufacture is provided that comprises a composition comprising at least one PARP inhibitor of the present invention in combination with packaging materials. The packaging material may comprise a container for housing the composition. The container may optionally comprise a label indicating the disease state for which the composition is to be administered, storage information, dosing information and/or instructions regarding how to administer the composition. The kit may also optionally comprise additional components, such as syringes for administration of the composition. The kit may comprise the composition in single or multiple dose forms.

Also provided are methods for preparing compounds, compositions and kits according to the present invention. For example, several synthetic schemes are provided herein for synthesizing compounds according to the present invention.

Also provided are methods for using compounds, compositions, kits and articles of manufacture according to the present invention.

In one embodiment, the compounds, compositions, kits and articles of manufacture are used to inhibit PARP.

In another embodiment, the compounds, compositions, kits and articles of manufacture are used to treat a disease state for which PARP possess activity that contributes to the pathology and/or symptomology of the disease state.

In another embodiment, a compound according to the present invention is administered to a subject wherein PARP activity within the subject is altered, preferably reduced.

In another embodiment, a prodrug of a compound according to the present invention is administered to a subject that is converted to the compound in vivo where it inhibits PARP.

In another embodiment, a method of inhibiting PARP is provided that comprises contacting a PARP with a compound according to the present invention.

In another embodiment, a method of inhibiting PARP is provided that comprises causing a compound according to the present invention to be present in a subject in order to inhibit PARP in vivo.

In another embodiment, a method of inhibiting a PARP is provided that comprises administering a first compound to a subject that is converted in vivo to a second compound wherein the second compound inhibits PARP in vivo. It is noted that the compounds of the present invention may be the first or second compounds.

In another embodiment, a therapeutic method is provided that comprises administering a compound according to the present invention.

In another embodiment, a method is provided for treating a condition in a patient that is known to be mediated by PARP, or which is known to be treated by PARP inhibitors, the method comprising administering to the patient a therapeutically effective amount of a compound according to the present invention.

In another embodiment, a method is provided for treating a disease state for which PARP possess activity that contributes to the pathology and/or symptomology of the disease state, the method comprising: causing a compound according to the present invention to be present in a subject in a therapeutically effective amount for the disease state.

In another embodiment, a method is provided for treating a disease state for which PARP possess activity that contributes to the pathology and/or symptomology of the disease state, the method comprising: administering a first compound to a subject that is converted in vivo to a second compound such that the second compound is present in the subject in a therapeutically effective amount for the disease state. It is noted that the compounds of the present invention may be the first or second compounds.

In another embodiment, a method is provided for treating a disease state for which PARP possess activity that contributes to the pathology and/or symptomology of the disease state, the method comprising: administering a compound according to the present invention to a subject such that the compound is present in the subject in a therapeutically effective amount for the disease state.

In another embodiment, a method is provided for using a compound according to the present invention in order to manufacture a medicament for use in the treatment of a disease state that is known to be mediated by PARP, or that is known to be treated by PARP inhibitors.

It is noted in regard to all of the above embodiments that the present invention is intended to encompass all pharmaceutically acceptable ionized forms (e.g., salts) and solvates (e.g., hydrates) of the compounds, regardless of whether such ionized forms and solvates are specified since it is well known in the art to administer pharmaceutical agents in an ionized or solvated form. It is also noted that unless a particular stereochemistry is specified, recitation of a compound is intended to encompass all possible stereoisomers (e.g., enantiomers or diastereomers depending on the number of chiral centers), independent of whether the compound is present as an individual isomer or a mixture of isomers. Further, unless otherwise specified, recitation of a compound is intended to encompass all possible resonance forms and tautomers. With regard to the claims, the language "compound comprising the formula," "compound having the formula" and "compound of the formula" is intended to encompass the compound and all pharmaceutically acceptable ionized forms and solvates, all possible stereoisomers, and all possible resonance forms and tautomers unless otherwise specifically specified in the particular claim.

It is further noted that prodrugs may also be administered which are altered in vivo and become a compound according to the present invention. The various methods of using the compounds of the present invention are intended, regardless of whether prodrug delivery is specified, to encompass the administration of a prodrug that is converted in vivo to a compound according to the present invention. It is also noted that certain compounds of the present invention may be altered in vivo prior to inhibiting PARP and thus may themselves be prodrugs for another compound. Such prodrugs of another compound may or may not themselves independently have PARP inhibitory activity.

DEFINITIONS

Unless otherwise stated, the following terms used in the specification and claims shall have the following meanings for the purposes of this Application.

It is noted that, as used in the specification and the appended claims, the singular forms "a," "an" and "the" include plural referents unless the context clearly dictates otherwise. Further, definitions of standard chemistry terms may be found in reference works, including Carey and Sundberg "ADVANCED ORGANIC CHEMISTRY $4^{TH}$ ED." Vols. A (2000) and B (2001), Plenum Press, New York. Also, unless otherwise indicated, conventional methods of mass spectroscopy, NMR, HPLC, protein chemistry, biochemistry, recombinant DNA techniques and pharmacology, within the skill of the art are employed.

"Alicyclic" means a moiety comprising a non-aromatic ring structure. Alicyclic moieties may be saturated or partially unsaturated with one, two or more double or triple bonds. Alicyclic moieties may also optionally comprise heteroatoms such as nitrogen, oxygen and sulfur. The nitrogen atoms can be optionally quaternerized or oxidized and the sulfur atoms can be optionally oxidized. Examples of alicyclic moieties include, but are not limited to moieties with ($C_{3-8}$) rings such as cyclopropyl, cyclohexane, cyclopentane, cyclopentene, cyclopentadiene, cyclohexane, cyclohexene, cyclohexadiene, cycloheptane, cycloheptene, cycloheptadiene, cyclooctane, cyclooctene, and cyclooctadiene.

"Aliphatic" means a moiety characterized by a straight or branched chain arrangement of constituent carbon atoms and may be saturated or partially unsaturated with one, two or more double or triple bonds.

"Alkenyl" means a straight or branched, carbon chain that contains at least one carbon-carbon double bond (—CR=CR'— or —CR=CR'R", wherein R, R' and R" are each independently hydrogen or further substituents). Examples of alkenyl include vinyl, allyl, isopropenyl, pentenyl, hexenyl, heptenyl, 1-propenyl, 2-butenyl, 2-methyl-2-butenyl, and the like. In particular embodiments, "alkenyl,"

either alone or represented along with another radical, can be a $(C_{2-20})$alkenyl, a $(C_{2-15})$alkenyl, a $(C_{2-10})$alkenyl, a $(C_{2-5})$alkenyl or a $(C_{2-3})$alkenyl. Alternatively, "alkenyl," either alone or represented along with another radical, can be a $(C_2)$alkenyl, a $(C_3)$alkenyl or a $(C_4)$alkenyl.

"Alkenylene" means a straight or branched, divalent carbon chain having one or more carbon-carbon double bonds (—CR═CR'—, wherein R and R' are each independently hydrogen or further substituents). Examples of alkenylene include ethene-1,2-diyl, propene-1,3-diyl, methylene-1,1-diyl, and the like. In particular embodiments, "alkenylene," either alone or represented along with another radical, can be a $(C_{2-20})$ alkenylene, a $(C_{2-15})$ alkenylene, a $(C_{2-10})$ alkenylene, a $(C_{2-5})$ alkenylene or a $(C_{2-3})$ alkenylene. Alternatively, "alkenylene," either alone or represented along with another radical, can be a $(C_2)$ alkenylene, a $(C_3)$ alkenylene or a $(C_4)$ alkenylene.

"Alkoxy" means an oxygen moiety having a further alkyl substituent. The alkoxy groups of the present invention can be optionally substituted.

"Alkyl" represented by itself means a straight or branched, saturated or unsaturated, aliphatic radical having a chain of carbon atoms, optionally with one or more of the carbon atoms being replaced with oxygen (See "oxaalkyl"), a carbonyl group (See "oxoalkyl"), sulfur (See "thioalkyl"), and/or nitrogen (See "azaalkyl"). $(C_X)$alkyl and $(C_{X-Y})$alkyl are typically used where X and Y indicate the number of carbon atoms in the chain. For example, $(C_{1-6})$alkyl includes alkyls that have a chain of between 1 and 6 carbons (e.g., methyl, ethyl, propyl, isopropyl, butyl, sec-butyl, isobutyl, tert-butyl, vinyl, allyl, 1-propenyl, isopropenyl, 1-butenyl, 2-butenyl, 3-butenyl, 2-methylallyl, ethynyl, 1-propynyl, 2-propynyl, and the like). Alkyl represented along with another radical (e.g., as in arylalkyl, heteroarylalkyl and the like) means a straight or branched, saturated or unsaturated aliphatic divalent radical having the number of atoms indicated or when no atoms are indicated means a bond (e.g., $(C_{6-10})$aryl$(C_{1-3})$alkyl includes, benzyl, phenethyl, 1-phenylethyl, 3-phenylpropyl, 2-thienylmethyl, 2-pyridinylmethyl and the like). In particular embodiments, "alkyl," either alone or represented along with another radical, can be a $(C_{1-20})$alkyl, a $(C_{1-15})$alkyl, a $(C_{1-10})$alkyl, a $(C_{1-5})$alkyl or a $(C_{1-3})$alkyl. Alternatively, "alkyl," either alone or represented along with another radical, can be a $(C_1)$alkyl, a $(C_2)$alkyl or a $(C_3)$alkyl.

"Alkylene", unless indicated otherwise, means a straight or branched, saturated or unsaturated, aliphatic, divalent radical. $(C_X)$alkylene and $(C_{X-Y})$alkylene are typically used where X and Y indicate the number of carbon atoms in the chain. For example, $(C_{1-6})$alkylene includes methylene (—CH$_2$—), ethylene (—CH$_2$CH$_2$—), trimethylene (—CH$_2$CH$_2$CH$_2$—), tetramethylene (—CH$_2$CH$_2$CH$_2$CH$_2$—) 2-butenylene (—CH$_2$CH═CHCH$_2$—), 2-methyltetramethylene (—CH$_2$CH(CH$_3$)CH$_2$CH$_2$—), pentamethylene (—CH$_2$CH$_2$CH$_2$CH$_2$CH$_2$—) and the like. In particular embodiments, "alkylene," either alone or represented along with another radical, can be a $(C_{1-20})$alkylene, a $(C_{1-15})$alkylene, a $(C_{1-10})$alkylene, a $(C_{1-5})$alkylene or a $(C_{1-3})$alkylene. Alternatively, "alkylene," either alone or represented along with another radical, can be a $(C_1)$alkylene, a $(C_2)$alkylene or a $(C_3)$alkylene.

"Alkylidene" means a straight or branched, saturated or unsaturated, aliphatic radical connected to the parent molecule by a double bond. $(C_X)$alkylidene and $(C_{X-Y})$alkylidene are typically used where X and Y indicate the number of carbon atoms in the chain. For example, $(C_{1-6})$alkylidene includes methylene (═CH$_2$), ethylidene (═CHCH$_3$), isopropylidene (═C(CH$_3$)$_2$), propylidene (═CHCH$_2$CH$_3$), allylidene (═CH—CH═CH$_2$), and the like. In particular embodiments, "alkylidene," either alone or represented along with another radical, can be a $(C_{1-20})$alkylidene, a $(C_{1-15})$alkylidene, a $(C_{1-10})$alkylidene, a $(C_{1-5})$alkylidene or a $(C_{1-3})$alkylidene. Alternatively, "alkylidene," either alone or represented along with another radical, can be a $(C_1)$alkylidene, a $(C_2)$alkylidene or a $(C_3)$alkylidene.

"Alkynyl" means a straight or branched, carbon chain that contains at least one carbon-carbon triple bond (—C≡C— or —C≡CR, wherein R is hydrogen or a further substituent). Examples of alkynyl include ethynyl, propargyl, 3-methyl-1-pentynyl, 2-heptynyl and the like. In particular embodiments, "alkynyl," either alone or represented along with another radical, can be a $(C_{2-20})$alkynyl, a $(C_{2-15})$alkynyl, a $(C_{2-10})$alkynyl, a $(C_{2-5})$alkynyl or a $(C_{2-3})$alkynyl. Alternatively, "alkynyl," either alone or represented along with another radical, can be a $(C_2)$alkynyl, a $(C_3)$alkynyl or a $(C_4)$alkynyl.

"Alkynylene" means a straight or branched, divalent carbon chain having one or more carbon-carbon triple bonds (—CR═CR'—, wherein R and R' are each independently hydrogen or further substituents). Examples of alkynylene include ethyne-1,2-diyl, propyne-1,3-diyl, and the like. In particular embodiments, "alkynylene," either alone or represented along with another radical, can be a $(C_{2-20})$ alkynylene, a $(C_{2-15})$ alkynylene, a $(C_{2-10})$ alkynylene, a $(C_{2-5})$ alkynylene or a $(C_{2-3})$ alkynylene. Alternatively, "alkynylene," either alone or represented along with another radical, can be a $(C_2)$ alkynylene, a $(C_3)$ alkynylene or a $(C_4)$ alkynylene.

"Amido" means the radical —C(═O)—NR—, —C(═O)—NRR', —NR—C(═O)— and/or —NR—C(═O)R', wherein each R and R' are independently hydrogen or a further substituent.

"Amino" means a nitrogen moiety having two further substituents where, for example, a hydrogen or carbon atom is attached to the nitrogen. For example, representative amino groups include —NH$_2$, —NHCH$_3$, —N(CH$_3$)$_2$, —NH((C$_{1-10}$)alkyl), —N((C$_{1-10}$)alkyl)$_2$, —NH(aryl), —NH(heteroaryl), —N(aryl)$_2$, —N(heteroaryl)$_2$, and the like. Optionally, the two substituents together with the nitrogen may also form a ring. Unless indicated otherwise, the compounds of the invention containing amino moieties may include protected derivatives thereof. Suitable protecting groups for amino moieties include acetyl, tert-butoxycarbonyl, benzyloxycarbonyl, and the like.

"Animal" includes humans, non-human mammals (e.g., dogs, cats, rabbits, cattle, horses, sheep, goats, swine, deer, and the like) and non-mammals (e.g., birds, and the like).

"Aromatic" means a moiety wherein the constituent atoms make up an unsaturated ring system, all atoms in the ring system are sp$^2$ hybridized and the total number of pi electrons is equal to 4n+2. An aromatic ring may be such that the ring atoms are only carbon atoms or may include carbon and non-carbon atoms (See "heteroaryl").

"Aryl" means a monocyclic or polycyclic ring assembly wherein each ring is aromatic or when fused with one or more rings forms an aromatic ring assembly. If one or more ring atoms is not carbon (e.g., N, S), the aryl is a heteroaryl. $(C_X)$aryl and $(C_{X-Y})$aryl are typically used where X and Y indicate the number of carbon atoms in the ring. In particular embodiments, "aryl," either alone or represented along with another radical, can be a $(C_{3-14})$aryl, a $(C_{3-10})$aryl, a $(C_{3-7})$aryl, a $(C_{8-10})$aryl or a $(C_{5-7})$aryl. Alternatively, "aryl," either alone or represented along with another radical, can be a $(C_5)$aryl, a $(C_6)$aryl, a $(C_7)$aryl, a $(C_8)$aryl, a $(C_9)$aryl or a $(C_{10})$aryl.

"Aryloxy" means an oxygen moiety having a further aryl substituent. The aryloxy groups of the present invention can be optionally substituted.

"Azaalkyl" means an alkyl, as defined above, except where one or more of the carbon atoms forming the alkyl chain are replaced with substituted or unsubstituted nitrogen atoms (—NR— or —NRR', wherein R and R' are each independently hydrogen or further substituents). For example, a $(C_{1-10})$azaalkyl refers to a chain comprising between 1 and 10 carbons and one or more nitrogen atoms.

"Bicycloalkyl" means a saturated or partially unsaturated fused, spiro or bridged bicyclic ring assembly. In particular embodiments, "bicycloalkyl," either alone or represented along with another radical, can be a $(C_{4-15})$bicycloalkyl, a $(C_{4-10})$bicycloalkyl, a $(C_{6-10})$bicycloalkyl or a $(C_{8-10})$bicycloalkyl. Alternatively, "bicycloalkyl," either alone or represented along with another radical, can be a $(C_8)$bicycloalkyl, a $(C_9)$bicycloalkyl or a $(C_{10})$bicycloalkyl.

"Bicycloaryl" means a fused, spiro or bridged bicyclic ring assembly wherein at least one of the rings comprising the assembly is aromatic. $(C_X)$bicycloaryl and $(C_{X-Y})$bicycloaryl are typically used where X and Y indicate the number of carbon atoms in the bicyclic ring assembly and directly attached to the ring. In particular embodiments, "bicycloaryl," either alone or represented along with another radical, can be a (a $(C_{4-15})$bicycloaryl, a $(C_{4-10})$bicycloaryl, a $(C_{6-10})$bicycloaryl or a $(C_{8-10})$bicycloaryl. Alternatively, "bicycloalkyl," either alone or represented along with another radical, can be a $(C_8)$bicycloaryl, a $(C_9)$bicycloaryl or a $(C_{10})$bicycloaryl.

"Bridging ring" and "bridged ring" as used herein refer to a ring that is bonded to another ring to form a compound having a bicyclic or polycyclic structure where two ring atoms that are common to both rings are not directly bound to each other. Non-exclusive examples of common compounds having a bridging ring include borneol, norbornane, 7-oxabicyclo[2.2.1]heptane, and the like. One or both rings of the bicyclic system may also comprise heteroatoms.

"Carbamoyl" means the radical —OC(O)NRR', wherein R and R' are each independently hydrogen or further substituents.

"Carbocycle" means a ring consisting of carbon atoms.

"Carbonyl" means the radical —C(=O)— and/or —C(=O)R, wherein R is hydrogen or a further substituent. It is noted that the carbonyl radical may be further substituted with a variety of substituents to form different carbonyl groups including acids, acid halides, aldehydes, amides, esters, and ketones.

"Carboxy" means the radical —C(=O)—O— and/or —C(=O)—OR, wherein R is hydrogen or a further substituent. It is noted that compounds of the invention containing carboxy moieties may include protected derivatives thereof, i.e., where the oxygen is substituted with a protecting group. Suitable protecting groups for carboxy moieties include benzyl, tert-butyl, and the like.

"Cyano" means the radical —CN.

"Cycloalkyl" means a non-aromatic, saturated or partially unsaturated, monocyclic, bicyclic or polycyclic ring assembly. $(C_X)$cycloalkyl and $(C_{X-Y})$cycloalkyl are typically used where X and Y indicate the number of carbon atoms in the ring assembly. For example, $(C_{3-10})$cycloalkyl includes cyclopropyl, cyclobutyl, cyclopentyl, cyclohexyl, cyclohexenyl, 2,5-cyclohexadienyl, bicyclo[2.2.2]octyl, adamantan-1-yl, decahydronaphthyl, oxocyclohexyl, dioxocyclohexyl, thiocyclohexyl, 2-oxobicyclo[2.2.1]hept-1-yl, and the like. In particular embodiments, "cycloalkyl," either alone or represented along with another radical, can be a $(C_{3-14})$cycloalkyl, a $(C_{3-10})$cycloalkyl, a $(C_{3-7})$cycloalkyl, a $(C_{8-10})$cycloalkyl or a $(C_{5-7})$cycloalkyl. Alternatively, "cycloalkyl," either alone or represented along with another radical, can be a $(C_5)$cycloalkyl, a $(C_6)$cycloalkyl, a $(C_7)$cycloalkyl, a $(C_8)$cycloalkyl., a $(C_9)$cycloalkyl or a $(C_{10})$cycloalkyl.

"Cycloalkylene" means a divalent, saturated or partially unsaturated, monocyclic, bicyclic or polycyclic ring assembly. $(C_X)$cycloalkylene and $(C_{X-Y})$cycloalkylene are typically used where X and Y indicate the number of carbon atoms in the ring assembly. In particular embodiments, "cycloalkylene," either alone or represented along with another radical, can be a $(C_{3-14})$cycloalkylene, a $(C_{3-10})$cycloalkylene, a $(C_{3-7})$cycloalkylene, a $(C_{8-10})$cycloalkylene or a $(C_{5-7})$cycloalkylene. Alternatively, "cycloalkylene," either alone or represented along with another radical, can be a $(C_5)$cycloalkylene, a $(C_6)$cycloalkylene, a $(C_7)$cycloalkylene, a $(C_8)$cycloalkylene., a $(C_9)$cycloalkylene or a $(C_{10})$cycloalkylene.

"Disease" specifically includes any unhealthy condition of an animal or part thereof and includes an unhealthy condition that may be caused by, or incident to, medical or veterinary therapy applied to that animal, i.e., the "side effects" of such therapy.

"Fused ring" as used herein refers to a ring that is bonded to another ring to form a compound having a bicyclic structure where the ring atoms that are common to both rings are directly bound to each other. Non-exclusive examples of common fused rings include decalin, naphthalene, anthracene, phenanthrene, indole, furan, benzofuran, quinoline, and the like. Compounds having fused ring systems may be saturated, partially saturated, carbocyclics, heterocyclics, aromatics, heteroaromatics, and the like.

"Halo" means fluoro, chloro, bromo or iodo.

"Heteroalkyl" means alkyl, as defined in this Application, provided that one or more of the atoms within the alkyl chain is a heteroatom. In particular embodiments, "heteroalkyl," either alone or represented along with another radical, can be a hetero$(C_{1-20})$alkyl, a hetero$(C_{1-15})$alkyl, a hetero$(C_{1-10})$alkyl, a hetero$(C_{1-5})$alkyl, a hetero$(C_{1-3})$alkyl or a hetero$(C_{1-2})$alkyl. Alternatively, "heteroalkyl," either alone or represented along with another radical, can be a hetero$(C_1)$alkyl, a hetero$(C_2)$alkyl or a hetero$(C_3)$alkyl.

"Heteroaryl" means a monocyclic, bicyclic or polycyclic aromatic group wherein at least one ring atom is a heteroatom and the remaining ring atoms are carbon. Monocyclic heteroaryl groups include, but are not limited to, cyclic aromatic groups having five or six ring atoms, wherein at least one ring atom is a heteroatom and the remaining ring atoms are carbon. The nitrogen atoms can be optionally quaternerized and the sulfur atoms can be optionally oxidized. Heteroaryl groups of this invention include, but are not limited to, those derived from furan, imidazole, isothiazole, isoxazole, oxadiazole, oxazole, 1,2,3-oxadiazole, pyrazine, pyrazole, pyridazine, pyridine, pyrimidine, pyrroline, thiazole, 1,3,4-thiadiazole, triazole and tetrazole. "Heteroaryl" also includes, but is not limited to, bicyclic or tricyclic rings, wherein the heteroaryl ring is fused to one or two rings independently selected from the group consisting of an aryl ring, a cycloalkyl ring, a cycloalkenyl ring, and another monocyclic heteroaryl or heterocycloalkyl ring. These bicyclic or tricyclic heteroaryls include, but are not limited to, those derived from benzo[b]furan, benzo[b]thiophene, benzimidazole, imidazo[4,5-c]pyridine, quinazoline, thieno[2,3-c]pyridine, thieno[3,2-b]pyridine, thieno[2,3-b]pyridine, indolizine, imidazo[1,2a]pyridine, quinoline, isoquinoline, phthalazine, quinoxaline, naphthyridine, quinolizine, indole, isoindole, indazole, indoline, benzoxazole, benzopyrazole, benzothiazole, imidazo[1,5-a]pyridine, pyrazolo[1,5-a]pyridine, imidazo[1,2-a]pyrimidine, imidazo[1,2-c]pyrimidine, imidazo[1,5-a]pyrimidine, imidazo[1,5-c]pyrimidine, pyrrolo[2,3-b]pyridine, pyrrolo[2,3-c]pyridine, pyrrolo[3,2-c]pyridine, pyrrolo[3,2-b]pyridine, pyrrolo[2,3-d]pyrimidine, pyrrolo[3,2-d]pyrimidine, pyrrolo[2,3-b]pyrazine, pyrazolo[1,5-a]pyridine, pyrrolo[1,2-b]pyridazine, pyrrolo[1,2-c]pyrimidine, pyrrolo[1,2-a]pyrimidine, pyrrolo[1,2-a]pyrazine, triazo[1,5-a]pyridine, pteridine, purine, carbazole, acridine, phenazine, phenothiazene, phenoxazine, 1,2-dihydropyrrolo[3,2,1-hi]indole, indolizine, pyrido[1,2-a]indole and 2(1H)-pyridinone. The bicyclic or tricyclic heteroaryl rings can be attached to the parent molecule through either the heteroaryl group itself or the aryl, cycloalkyl, cycloalkenyl or heterocycloalkyl group to which it is fused. The heteroaryl groups of this invention can be substituted or unsubstituted. In particular embodiments, "heteroaryl," either alone or represented along with another radical, can be a hetero($C_{1-13}$)aryl, a hetero($C_{2-13}$)aryl, a hetero($C_{2-6}$)aryl, a hetero($C_{3-9}$)aryl or a hetero($C_{5-9}$)aryl. Alternatively, "heteroaryl," either alone or represented along with another radical, can be a hetero($C_3$)aryl, a hetero($C_4$)aryl, a hetero($C_5$)aryl, a hetero($C_6$)aryl, a hetero($C_7$)aryl, a hetero($C_8$)aryl or a hetero($C_9$)aryl.

"Heteroatom" refers to an atom that is not a carbon atom. Particular examples of heteroatoms include, but are not limited to, nitrogen, oxygen, and sulfur.

"Heteroatom moiety" includes a moiety where the atom by which the moiety is attached is not a carbon. Examples of heteroatom moieties include —NR—, —N'(O$^-$)═, —O—, —S— or —S(O)$_2$—, wherein R is hydrogen or a further substituent.

"Heterobicycloalkyl" means bicycloalkyl, as defined in this Application, provided that one or more of the atoms within the ring is a heteroatom. For example hetero($C_{9-12}$)bicycloalkyl as used in this application includes, but is not limited to, 3-aza-bicyclo[4.1.0]hept-3-yl, 2-aza-bicyclo[3.1.0]hex-2-yl, 3-aza-bicyclo[3.1.0]hex-3-yl, and the like. In particular embodiments, "heterobicycloalkyl," either alone or represented along with another radical, can be a hetero($C_{1-14}$)bicycloalkyl, a hetero($C_{4-14}$)bicycloalkyl, a hetero($C_{4-9}$)bicycloalkyl or a hetero($C_{5-9}$)bicycloalkyl. Alternatively, "heterobicycloalkyl," either alone or represented along with another radical, can be a hetero($C_5$)bicycloalkyl, hetero($C_6$)bicycloalkyl, hetero($C_7$)bicycloalkyl, hetero($C_8$)bicycloalkyl or a hetero($C_9$)bicycloalkyl.

"Heterobicycloaryl" means bicycloaryl, as defined in this Application, provided that one or more of the atoms within the ring is a heteroatom. For example, hetero($C_{4-12}$)bicycloaryl as used in this Application includes, but is not limited to, 2-amino-4-oxo-3,4-dihydropteridin-6-yl, tetrahydroisoquinolinyl, and the like. In particular embodiments, "heterobicycloaryl," either alone or represented along with another radical, can be a hetero($C_{1-14}$)bicycloaryl, a hetero($C_{4-14}$)bicycloaryl, a hetero($C_{4-9}$)bicycloaryl or a hetero($C_{5-9}$)bicycloaryl. Alternatively, "heterobicycloaryl," either alone or represented along with another radical, can be a hetero($C_5$)bicycloaryl, hetero($C_6$)bicycloaryl, hetero($C_7$)bicycloaryl, hetero($C_8$)bicycloaryl or a hetero($C_9$)bicycloaryl.

"Heterocycloalkyl" means cycloalkyl, as defined in this Application, provided that one or more of the atoms forming the ring is a heteroatom selected, independently from N, O, or S. Non-exclusive examples of heterocycloalkyl include piperidyl, 4-morpholyl, 4-piperazinyl, pyrrolidinyl, perhydropyrrolizinyl, 1,4-diazaperhydroepinyl, 1,3-dioxanyl, 1,4-dioxanyl and the like. In particular embodiments, "heterocycloalkyl," either alone or represented along with another radical, can be a hetero($C_{1-13}$)cycloalkyl, a hetero($C_{1-9}$)cycloalkyl, a hetero($C_{1-6}$)cycloalkyl, a hetero($C_{5-9}$)cycloalkyl or a hetero($C_{2-6}$)cycloalkyl. Alternatively, "heterocycloalkyl," either alone or represented along with another radical, can be a hetero($C_2$)cycloalkyl, a hetero($C_3$)cycloalkyl, a hetero($C_4$)cycloalkyl, a hetero($C_5$)cycloalkyl, a hetero($C_6$)cycloalkyl, hetero($C_7$)cycloalkyl, hetero($C_8$)cycloalkyl or a hetero($C_9$)cycloalkyl.

"Heterocycloalkylene" means cycloalkylene, as defined in this Application, provided that one or more of the ring member carbon atoms is replaced by a heteroatom. In particular embodiments, "heterocycloalkylene," either alone or represented along with another radical, can be a hetero($C_{1-13}$)cycloalkylene, a hetero($C_{1-9}$)cycloalkylene, a hetero($C_{1-6}$)cycloalkylene, a hetero($C_{5-9}$)cycloalkylene or a hetero($C_{2-6}$)cycloalkylene. Alternatively, "heterocycloalkylene," either alone or represented along with another radical, can be a hetero($C_2$)cycloalkylene, a hetero($C_3$)cycloalkylene, a hetero($C_4$)cycloalkylene, a hetero($C_5$)cycloalkylene, a hetero($C_6$)cycloalkylene, hetero($C_7$)cycloalkylene, hetero($C_8$)cycloalkylene or a hetero($C_9$)cycloalkylene.

"Hydroxy" means the radical —OH.

"IC$_{50}$" means the molar concentration of an inhibitor that produces 50% inhibition of the target enzyme.

"Imino" means the radical —CR(═NR') and/or —C(═NR')—, wherein R and R' are each independently hydrogen or a further substituent.

"Isomers" means compounds having identical molecular formulae but differing in the nature or sequence of bonding of their atoms or in the arrangement of their atoms in space. Isomers that differ in the arrangement of their atoms in space are termed "stereoisomers." Stereoisomers that are not mirror images of one another are termed "diastereomers" and stereoisomers that are nonsuperimposable mirror images are termed "enantiomers" or sometimes "optical isomers." A carbon atom bonded to four nonidentical substituents is termed a "chiral center." A compound with one chiral center has two enantiomeric forms of opposite chirality. A mixture of the two enantiomeric forms is termed a "racemic mixture." A compound that has more than one chiral center has $2^{n-1}$ enantiomeric pairs, where n is the number of chiral centers. Compounds with more than one chiral center may exist as ether an individual diastereomer or as a mixture of diastereomers, termed a "diastereomeric mixture." When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well known in the art (e.g., see "Advanced Organic Chemistry", 4th edition, March, Jerry, John Wiley & Sons, New York, 1992).

"Leaving group" means the group with the meaning conventionally associated with it in synthetic organic chemistry, i.e., an atom or group displaceable under reaction (e.g., alkylating) conditions. Examples of leaving groups include, but are not limited to, halo (e.g., F, Cl, Br and I), alkyl (e.g., methyl and ethyl) and sulfonyloxy (e.g., mesyloxy, ethanesulfonyloxy, benzenesulfonyloxy and tosyloxy), thiomethyl, thienyloxy, dihalophosphinoyloxy, tetrahalophosphoxy, benzyloxy, isopropyloxy, acyloxy, and the like.

"Moiety providing X atom separation" and "linker providing X atom separation" between two other moieties mean that the chain of atoms directly linking the two other moieties is X atoms in length. When X is given as a range (e.g., $X_1$-$X_2$), then the chain of atoms is at least $X_1$ and not more than $X_2$ atoms in length. It is understood that the chain of atoms can be formed from a combination of atoms including, for example, carbon, nitrogen, sulfur and oxygen atoms. Further, each atom can optionally be bound to one or more substituents, as valencies allow. In addition, the chain of atoms can form part of a ring. Accordingly, in one embodiment, a moiety providing X atom separation between two other moieties (R and R') can be represented by R-(L)$_x$-R' where each L is independently selected from the group consisting of CR"R'", NR"", O, S, CO, CS, C=NR"", SO, SO$_2$, and the like, where any two or more of R", R'", R"" and R"" can be taken together to form a substituted or unsubstituted ring.

"Nitro" means the radical —NO$_2$.

"Oxaalkyl" means an alkyl, as defined above, except where one or more of the carbon atoms forming the alkyl chain are replaced with oxygen atoms (—O— or —OR, wherein R is hydrogen or a further substituent). For example, an oxa (C$_{1-10}$)alkyl refers to a chain comprising between 1 and 10 carbons and one or more oxygen atoms.

"Oxoalkyl" means an alkyl, as defined above, except where one or more of the carbon atoms forming the alkyl chain are replaced with carbonyl groups (—C(=O)— or —C(=O)—R, wherein R is hydrogen or a further substituent). The carbonyl group may be an aldehyde, ketone, ester, amide, and acid or acid halide. For example, an oxo(C$_{1-10}$)alkyl refers to a chain comprising between 1 and 10 carbon atoms and one or more carbonyl groups.

"Oxy" means the radical —O— or —OR, wherein R is hydrogen or a further substituent. Accordingly, it is noted that the oxy radical may be further substituted with a variety of substituents to form different oxy groups including hydroxy, alkoxy, aryloxy, heteroaryloxy or carbonyloxy.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo [2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like.

Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

"Polycyclic ring" includes bicyclic and multi-cyclic rings. The individual rings comprising the polycyclic ring can be fused, spiro or bridging rings.

"Prodrug" means a compound that is convertible in vivo metabolically into an inhibitor according to the present invention. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-b-hydroxynaphthoates, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, a compound comprising an amine group may be administered as an amide that is converted by hydrolysis in vivo to the amine compound.

"Protected derivatives" means derivatives of inhibitors in which a reactive site or sites are blocked with protecting groups. Protected derivatives are useful in the preparation of inhibitors or in themselves may be active as inhibitors. A comprehensive list of suitable protecting groups can be found in T. W. Greene, *Protecting Groups in Organic Synthesis,* 3rd edition, John Wiley & Sons, Inc. 1999.

"Ring" and "ring assembly" means a carbocyclic or a heterocyclic system and includes aromatic and non-aromatic systems. The system can be monocyclic, bicyclic or polycyclic. In addition, for bicyclic and polycyclic systems, the individual rings comprising the polycyclic ring can be fused, spiro or bridging rings.

"Subject" and "patient" include humans, non-human mammals (e.g., dogs, cats, rabbits, cattle, horses, sheep, goats, swine, deer, and the like) and non-mammals (e.g., birds, and the like).

"Substituent convertible to hydrogen in vivo" means any group that is convertible to a hydrogen atom by enzymological or chemical means including, but not limited to, hydrolysis and hydrogenolysis. Examples include hydrolyzable groups, such as acyl groups, groups having an oxycarbonyl group, amino acid residues, peptide residues, o-nitrophenylsulfenyl, trimethylsilyl, tetrahydropyranyl, diphenylphosphinyl, and the like. Examples of acyl groups include formyl, acetyl, trifluoroacetyl, and the like. Examples of groups having an oxycarbonyl group include ethoxycarbonyl, t-butoxycarbonyl [(CH$_3$)$_3$C—OCO—], benzyloxycarbonyl, p-methoxybenzyloxycarbonyl, vinyloxycarbonyl, β-(p-toluenesulfonyl)ethoxycarbonyl, and the like. Examples of suitable amino acid residues include amino acid residues per se and amino acid residues that are protected with a protecting group. Suitable amino acid residues include, but are not limited to, residues of Gly (glycine), Ala (alanine; CH$_3$CH(NH$_2$) CO—), Arg (arginine), Asn (asparagine), Asp (aspartic acid), Cys (cysteine), Glu (glutamic acid), His (histidine), Ile (isoleucine), Leu (leucine; (CH$_3$)$_2$CHCH$_2$CH(NH$_2$)CO—), Lys (lysine), Met (methionine), Phe (phenylalanine), Pro (proline), Ser (serine), Thr (threonine), Trp (tryptophan), Tyr (tyrosine), Val (valine), Nva (norvaline), Hse (homoserine), 4-Hyp (4-hydroxyproline), 5-Hyl (5-hydroxylysine), Orn (ornithine) and β-Ala. Examples of suitable protecting groups include those typically employed in peptide synthesis, including acyl groups (such as formyl and acetyl), arylmethyloxycarbonyl groups (such as benzyloxycarbonyl and p-nitrobenzyloxycarbonyl), t-butoxycarbonyl groups [(CH$_3$)$_3$ C—OCO—], and the like. Suitable peptide residues include peptide residues comprising two to five, and optionally two to three, of the aforesaid amino acid residues. Examples of such peptide residues include, but are not limited to, residues of such peptides as Ala-Ala [CH$_3$CH(NH$_2$)CO—NHCH(CH$_3$)CO—], Gly-Phe, Nva-Nva, Ala-Phe, Gly-Gly, Gly-Gly-Gly, Ala-Met, Met-Met, Leu-Met and Ala-Leu. The residues of these amino acids or peptides can be present in stereochemical configurations of the D-form, the L-form or mixtures thereof. In addition, the amino acid or peptide residue may have an asymmetric carbon atom. Examples of suitable amino acid residues having an asymmetric carbon atom include residues of Ala, Leu, Phe, Trp, Nva, Val, Met, Ser, Lys, Thr and Tyr. Peptide residues having an asymmetric carbon atom include peptide residues having one or more constituent amino acid residues having an asymmetric carbon atom. Examples of suitable amino acid protecting groups include those typically employed in peptide synthesis, including acyl groups (such as formyl and acetyl), arylmethyloxycarbonyl groups (such as benzyloxycarbonyl and p-nitrobenzyloxycarbonyl), t-butoxycarbonyl groups [(CH$_3$)$_3$C—OCO—], and the like. Other examples of substituents "convertible to hydrogen in vivo" include reductively eliminable hydrogenolyzable groups. Examples of suitable reductively eliminable hydrogenolyzable groups include, but are not limited to, arylsulfonyl groups (such as o-toluenesulfonyl); methyl groups substituted with phenyl or benzyloxy (such as benzyl, trityl and benzyloxymethyl); arylmethoxycarbonyl groups (such as benzyloxycarbonyl and o-methoxybenzyloxycarbonyl); and halogenoethoxycarbonyl groups (such as β,β,β-trichloroethoxycarbonyl and β-iodoethoxycarbonyl).

"Substituted or unsubstituted" means that a given moiety may consist of only hydrogen substituents through available valencies (unsubstituted) or may further comprise one or more non-hydrogen substituents through available valencies (substituted) that are not otherwise specified by the name of the given moiety. For example, isopropyl is an example of an ethylene moiety that is substituted by —CH$_3$. In general, a non-hydrogen substituent may be any substituent that may be bound to an atom of the given moiety that is specified to be substituted. Examples of substituents include, but are not limited to, aldehyde, alicyclic, aliphatic, (C$_{1-10}$)alkyl, alkylene, alkylidene, amide, amino, aminoalkyl, aromatic, aryl, bicycloalkyl, bicycloaryl, carbamoyl, carbocyclyl, carboxyl, carbonyl group, cycloalkyl, cycloalkylene, ester, halo, heterobicycloalkyl, heterocycloalkylene, heteroaryl, heterobicycloaryl, heterocycloalkyl, oxo, hydroxy, iminoketone, ketone, nitro, oxaalkyl, and oxoalkyl moieties, each of which may optionally also be substituted or unsubstituted. In one particular embodiment, examples of substituents include, but are not limited to, hydrogen, halo, nitro, cyano, thio, oxy, hydroxy, carbonyloxy, (C$_{1-10}$)alkoxy, (C$_{6-12}$)aryloxy, hetero(C$_{1-10}$)aryloxy, carbonyl, oxycarbonyl, amido, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl(C$_{1-10}$)alkyl, (C$_{1-10}$)azaalkyl, imino(C$_{1-10}$)alkyl, (C$_{3-12}$)cyclo alkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{4-12}$)bicycloaryl(C$_{1-5}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{6-12}$)aryl, hetero(C$_{1-10}$)aryl, (C$_{9-12}$)bicycloaryl and hetero(C$_{4-12}$)bicycloaryl. In addition, the substituent is itself optionally substituted by a further substituent. In one particular embodiment, examples of the further substituent include, but are not limited to, hydrogen, halo, nitro, cyano, thio, oxy, hydroxy, carbonyloxy, (C$_{1-10}$)alkoxy, (C$_{6-12}$)aryloxy, hetero(C$_{1-10}$)aryloxy, carbonyl, oxycarbonyl, amido, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl(C$_{1-10}$)alkyl, (C$_{1-10}$)azaalkyl, imino(C$_{1-10}$)alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{4-12}$)bicycloaryl(C$_{1-5}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{6-12}$)aryl, hetero(C$_{1-10}$)aryl, (C$_{9-12}$)bicycloaryl and hetero(C$_{4-12}$)bicycloaryl.

"Sulfinyl" means the radical —SO— and/or —SO—R, wherein R is hydrogen or a further substituent. It is noted that the sulfinyl radical may be further substituted with a variety of substituents to form different sulfinyl groups including sulfinic acids, sulfinamides, sulfinyl esters, and sulfoxides.

"Sulfonyl" means the radical —SO$_2$— and/or —SO$_2$—R, wherein R is hydrogen or a further substituent. It is noted that the sulfonyl radical may be further substituted with a variety of substituents to form different sulfonyl groups including sulfonic acids, sulfonamides, sulfonate esters, and sulfones.

"Therapeutically effective amount" means that amount which, when administered to an animal for treating a disease, is sufficient to effect such treatment for the disease.

"Thio" denotes replacement of an oxygen by a sulfur and includes, but is not limited to, —SR, —S— and =S containing groups.

"Thioalkyl" means an alkyl, as defined above, except where one or more of the carbon atoms forming the alkyl chain are replaced with sulfur atoms (—S— or —S—R, wherein R is hydrogen or a further substituent). For example, a thio(C$_{1-10}$)alkyl refers to a chain comprising between 1 and 10 carbons and one or more sulfur atoms.

"Thiocarbonyl" means the radical —CS)— and/or —C(=S)—R, wherein R is hydrogen or a further substituent. It is noted that the thiocarbonyl radical may be further substituted with a variety of substituents to form different thiocarbonyl groups including thioacids, thioamides, thioesters, and thioketones.

"Treatment" or "treating" means any administration of a compound of the present invention and includes:

(1) preventing the disease from occurring in an animal which may be predisposed to the disease but does not yet experience or display the pathology or symptomatology of the disease, (2) inhibiting the disease in an animal that is experiencing or displaying the pathology or symptomatology of the diseased (i.e., arresting further development of the pathology and/or symptomatology), or (3) ameliorating the disease in an animal that is experiencing or displaying the pathology or symptomatology of the diseased (i.e., reversing the pathology and/or symptomatology).

It is noted in regard to all of the definitions provided herein that the definitions should be interpreted as being open ended in the sense that further substituents beyond those specified may be included. Hence, a C$_1$ alkyl indicates that there is one carbon atom but does not indicate what the substituents on the carbon atom are. Hence, a (C$_1$)alkyl comprises methyl (i.e., —CH$_3$) as well as —CRR'R" where R, R', and R" may each independently be hydrogen or a further substituent where the atom attached to the carbon is a heteroatom or cyano. Hence, CF$_3$, CH$_2$OH and CH$_2$CN, for example, are all (C$_1$)alkyls. Similarly, terms such as alkylamino and the like comprise dialkylamino and the like.

A compound having a formula that is represented with a dashed bond is intended to include the formulae optionally having zero, one or more double bonds, as exemplified and shown below:

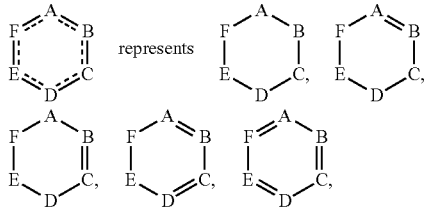

etc.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

DETAILED DESCRIPTION OF THE INVENTION

The present invention relates to compounds that may be used to inhibit PARP. The present invention also relates to pharmaceutical compositions, kits and articles of manufacture comprising such compounds. In addition, the present invention relates to methods and intermediates useful for making the compounds. Further, the present invention relates to methods of using said compounds. It is noted that the compounds of the present invention may also possess activity for other members of the same protein family and thus may be used to address disease states associated with these other family members.

PARP Inhibitors

In one of its aspects, the present invention relates to compounds that are useful as PARP inhibitors. In one embodiment, PARP inhibitors of the present invention comprise:

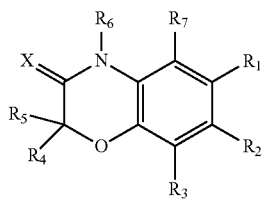

or a polymorph, solvate, ester, tautomer, enantiomer, pharmaceutically acceptable salt or prodrug thereof, wherein X is selected from the group consisting of O, S and $NR_8$;

$R_1$ is selected from the group consisting of hydrogen, halo, cyano, thio, oxy, hydroxy, carbonyloxy, $(C_{1-10})$alkoxy, $(C_{6-12})$aryloxy, hetero$(C_{1-10})$aryloxy, carbonyl, thiocarbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, amino$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{4-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{6-12})$aryl, hetero$(C_{1-10})$aryl, $(C_{9-12})$bicycloaryl and hetero$(C_{4-12})$bicycloaryl, each substituted or unsubstituted;

$R_2$ is selected from the group consisting of hydrogen, halo, nitro, cyano, thio, oxy, hydroxy, carbonyloxy, $(C_{1-10})$alkoxy, $(C_{6-12})$aryloxy, hetero$(C_{1-10})$aryloxy, carbonyl, thiocarbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, amino$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{4-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{6-12})$aryl, hetero$(C_{1-10})$aryl, $(C_{9-12})$bicycloaryl and hetero$(C_{4-12})$bicycloaryl, each substituted or unsubstituted;

$R_3$ is selected from the group consisting of hydrogen, halo, nitro, cyano, thio, oxy, hydroxy, carbonyloxy, $(C_{1-10})$alkoxy, $(C_{6-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, amino$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{4-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{6-12})$aryl, hetero$(C_{1-10})$aryl, $(C_{9-12})$bicycloaryl and hetero$(C_{4-12})$bicycloaryl, each substituted or unsubstituted;

$R_4$ and $R_5$ are each independently selected from the group consisting of hydrogen, halo, nitro, cyano, thio, oxy, hydroxy, carbonyloxy, $(C_{1-10})$alkoxy, $(C_{6-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, amino$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{4-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{6-12})$aryl, hetero$(C_{1-10})$aryl, $(C_{9-12})$bicycloaryl and hetero$(C_{4-12})$bicycloaryl, each substituted or unsubstituted;

$R_6$ is selected from the group consisting of hydrogen, carbonyloxy, carbonyl, oxycarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{4-12})$bicycloaryl$(C_{1-5})$alkyl, hetero$(C_{1-10})$alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{6-12}$)aryl, hetero($C_{1-10}$)aryl, ($C_{9-12}$)bicycloaryl and hetero($C_{4-12}$)bicycloaryl, each substituted or unsubstituted;

$R_7$ is selected from the group consisting of hydrogen, halo, nitro, cyano, thio, oxy, hydroxy, carbonyloxy, ($C_{1-10}$)alkoxy, ($C_{6-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, amino($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{4-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{6-12}$)aryl, hetero($C_{1-10}$)aryl, ($C_{9-12}$)bicycloaryl and hetero($C_{4-12}$)bicycloaryl, each substituted or unsubstituted; and $R_8$ is selected from the group consisting of hydrogen, hydroxy, carbonyloxy, ($C_{1-10}$)alkoxy, ($C_{6-12}$)aryloxy, hetero($C_{1-10}$)aryloxy, carbonyl, oxycarbonyl, amino, ($C_{1-10}$)alkylamino, sulfonamido, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{4-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{6-12}$)aryl, hetero($C_{1-10}$)aryl, ($C_{9-12}$)bicycloaryl and hetero($C_{4-12}$)bicycloaryl, each substituted or unsubstituted.

In one variation of the above embodiment, when $R_4$ and $R_5$ are each independently hydrogen, oxycarbonyl or ($C_{1-10}$) oxoalkyl, then $R_1$ or $R_2$ are selected from the group consisting of substituted amido, C($C_{1-10}$)alkylamino, carbonyloxy, carbonyl($C_{1-10}$)alkylamino, substituted sulfonamido and ($C_{2-10}$) alkyl.

In another variation of the above embodiment and variation, when $R_2$, $R_3$ and $R_7$ are each hydrogen or halo, $R_6$ is selected from the group consisting of hydrogen, ($C_{1-5}$)alkyl and aryl($C_{1-5}$)alkyl, and $R_1$ is selected from the group consisting of an optionally substituted hetero($C_{3-12}$)cycloalkyl, hetero($C_{3-12}$)cycloalkyl($C_{1-3}$)alkoxy, hetero($C_{3-12}$)cycloalkyl($C_{1-3}$)alkyl, ($C_{3-12}$)cycloalkylcarbonyl and hetero($C_{3-12}$)bicycloaryl, then at least one of $R_4$ and $R_5$ is methyl.

In another variation of the above embodiment and variations, $R_1$ is not

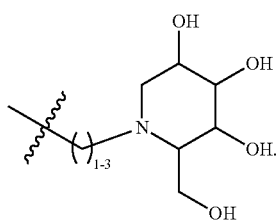

In another variation of the above embodiment and variations, $R_1$, $R_2$, $R_3$, $R_4$, $R_5$, $R_6$ and $R_7$ are not all hydrogen.

In another embodiment, PARP inhibitors of the present invention comprise:

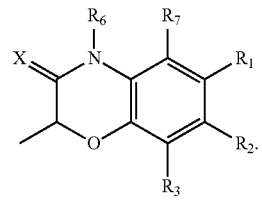

In still another embodiment, PARP inhibitors of the present invention comprise:

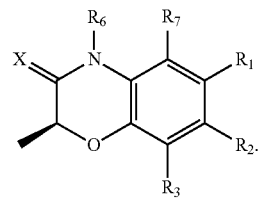

In yet another embodiment, PARP inhibitors of the present invention comprise:

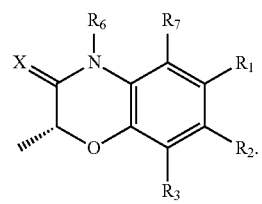

In a further embodiment, PARP inhibitors of the present invention comprise:

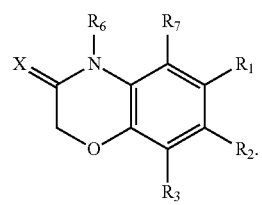

In another variation of each of the above embodiments and variations, X is O. In still another variation of each of the above embodiments and variations, X is S. In yet another variation of each of the above embodiments and variations, X is $NR_8$.

In another variation of each of the above embodiments and variations, $R_1$ is -$L_1$-$R_9$;

$L_1$ is absent or a linker providing 1, 2, 3, 4, 5 or 6 atom separation between $R_9$ and the ring to which $L_1$ is attached, wherein the atoms of the linker providing the separation are selected from the group consisting of carbon, oxygen, nitrogen, and sulfur; and $R_9$ is selected from the group consisting of hydrogen, halo, nitro, cyano, thio, oxy, hydroxy, carbonyloxy, ($C_{1-10}$)

alkoxy, $(C_{6-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cyclo alkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{4-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{6-12})$aryl, hetero$(C_{1-10})$aryl, $(C_{9-12})$bicycloaryl and hetero$(C_{4-12})$bicycloaryl, each substituted or unsubstituted.

In another variation of each of the above embodiments and variations, $R_2$ is $-L_{1'}-R_{9'}$;

$L_{1'}$ is absent or a linker providing 1, 2, 3, 4, 5 or 6 atom separation between $R_{9'}$ and the ring to which $L_{1'}$ is attached, wherein the atoms of the linker providing the separation are selected from the group consisting of carbon, oxygen, nitrogen, and sulfur; and $R_{9'}$ is selected from the group consisting of hydrogen, halo, nitro, cyano, thio, oxy, hydroxy, carbonyloxy, $(C_{1-10})$alkoxy, $(C_{6-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cyclo alkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{4-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{6-12})$aryl, hetero$(C_{1-10})$aryl, $(C_{9-12})$bicycloaryl and hetero$(C_{4-12})$bicycloaryl, each substituted or unsubstituted.

In still another variation of each of the above embodiments and variations, $L_1$ or $L_{1'}$ are each independently selected from the group consisting of —$(CR_{10}R_{11})_r$—, —CO—, —CS—, —C(=NR$_{12}$)—, $(C_{6-12})$arylene, —NR$_{13}$—, —O—, —S—, —SO$_2$— and combinations thereof;

r is 1, 2 or 3;

$R_{10}$ and $R_{11}$ are each independently selected from the group consisting of hydrogen, halo, nitro, cyano, thio, oxy, hydroxy, carbonyloxy, $(C_{1-10})$alkoxy, $(C_{6-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{4-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{6-12})$aryl, hetero$(C_{1-10})$aryl, $(C_{9-12})$bicycloaryl and hetero$(C_{4-12})$bicycloaryl, each substituted or unsubstituted, or alternatively one of $R_{10}$ or $R_{11}$ is absent from each of two neighboring —$(CR_{10}R_{11})$— groups so that a double bond joins the two —$(CR_{10}R_{11})$— groups together to form one of —$CR_{10}$=$CR_{10}$—, —$CR_{10}$=$CR_{11}$—, —$CR_{11}$=$CR_{10}$—, or —$CR_{11}$=$CR_{11}$—; and $R_{12}$ and $R_{13}$ are each independently selected from the group consisting of hydrogen, hydroxy, carbonyloxy, $(C_{1-10})$alkoxy, $(C_{6-12})$aryloxy, hetero$(C_{1-10})$aryloxy, carbonyl, oxycarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{4-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{6-12})$aryl, hetero$(C_{1-10})$aryl, $(C_{9-12})$bicycloaryl and hetero$(C_{4-12})$bicycloaryl, each substituted or unsubstituted.

In yet another variation of each of the above embodiments and variations, $L_1$ or $L_{1'}$ are each independently —$CR_{10}R_{11}$—;

$R_{10}$ and $R_{11}$ are each independently selected from the group consisting of hydrogen, halo, nitro, cyano, thio, oxy, hydroxy, carbonyloxy, $(C_{1-10})$alkoxy, $(C_{6-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{4-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{6-12})$aryl, hetero$(C_{1-10})$aryl, $(C_{9-12})$bicycloaryl and hetero$(C_{4-12})$bicycloaryl, each substituted or unsubstituted.

In yet another variation of each of the above embodiments and variations, $L_1$ or $L_{1'}$ are each independently —$CR_{10}R_{11}$—$CR_{10}R_{11}$—;

$R_{10}$ and $R_{11}$ are each independently selected from the group consisting of hydrogen, halo, nitro, cyano, thio, oxy, hydroxy, carbonyloxy, $(C_{1-10})$alkoxy, $(C_{6-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{4-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{6-12})$aryl, hetero$(C_{1-10})$aryl, $(C_{9-12})$bicycloaryl and hetero$(C_{4-12})$bicycloaryl, each substituted or unsubstituted, or alternatively one of $R_{10}$ or $R_{11}$ is absent from each of two neighboring —$(CR_{10}R_{11})$— groups so that a double bond joins the two —$(CR_{10}R_{11})$— groups together to form one of —$CR_{10}$=$CR_{10}$—, —$CR_{10}$=$CR_{11}$—, —$CR_{11}$=$CR_{10}$—, or —$CR_{11}$=$CR_{11}$—.

In another variation of each of the above embodiments and variations, $L_1$ or $L_{1'}$ are each independently absent. In yet another variation of each of the above embodiments and variations, $L_1$ or $L_{1'}$ are each independently —CH$_2$—. In a further variation of each of the above embodiments and variations, $L_1$ or $L_{1'}$ are each independently -CH$_2$CH$_2$—. In a further variation of each of the above embodiments and variations, $L_1$ or $L_{1'}$ are each independently —CO—. In a further variation of each of the above embodiments and variations, $L_1$ or $L_{1'}$ are each independently-$SO_2$—. In a further variation of each of the above embodiments and variations, $L_1$ or $L_{1'}$ are each independently —$COCR_{10}R_{11}$—. In a further variation of each of the above embodiments and variations, $L_1$ or $L_{1'}$ are each independently —$SO_2CR_{10}R_{11}$—. In a further variation of each of the above embodiments and variations, $L_1$ or $L_{1'}$ are each independently —$CR_{10}R_{11}$—CO—. In a further variation of each of the above embodiments and variations, $L_1$ or $L_{1'}$ are each independently —$CR_{10}R_{11}$—OCO—. In a further variation of each of the above embodiments and variations, $L_1$ or $L_{1'}$ are each independently —$CR_{10}R_{11}$—$NR_{13}CR_{10}R_{11}$—CO—.

In a further variation of each of the above embodiments and variations, $L_1$ or $L_{1'}$ are each independently:

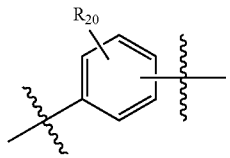

wherein $R_{20}$ is selected from the group consisting of hydrogen, halo, nitro, cyano, thio, oxy, hydroxy, carbonyloxy, $(C_{1-10})$alkoxy, $(C_{6-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{4-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{6-12})$aryl, hetero$(C_{1-10})$aryl, $(C_{9-12})$bicycloaryl and hetero$(C_{4-12})$bicycloaryl, each substituted or unsubstituted.

In a further variation of each of the above embodiments and variations, $L_1$ or $L_{1'}$ are each independently:

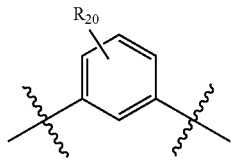

In a further variation of each of the above embodiments and variations, $L_1$ or $L_{1'}$ are each independently:

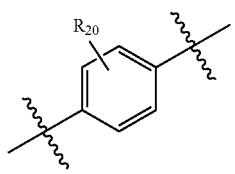

In a further variation of each of the above embodiments and variations, $L_1$ or $L_{1'}$ are each independently:

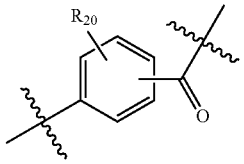

In a further variation of each of the above embodiments and variations, $L_1$ or $L_{1'}$ are each independently:

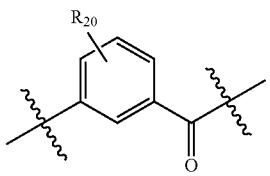

In a further variation of each of the above embodiments and variations, $L_1$ or $L_{1'}$ are each independently:

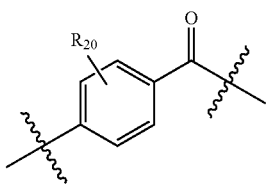

In another variation of the above embodiments, $R_2$ is a substituted or unsubstituted $(C_{1-3})$alkyl. In yet another variation of the above embodiments, $R_2$ is halo. In yet another variation of the above embodiments, $R_2$ is hydrogen.

In a further variation of each of the above embodiments and variations, $R_3$ is a substituted or unsubstituted $(C_{1-3})$alkyl. In still a further variation of each of the above embodiments and variations, $R_3$ is a substituted or unsubstituted $(C_{1-3})$alkoxy. In another variation of each of the above embodiments and variations, $R_3$ is halo. In yet another variation of the above embodiments, $R_3$ is hydrogen. In one variation of each of the above embodiments, $R_3$ is methyl. In another variation of each of the above embodiments, $R_3$ is methoxy. In a further variation of each of the above embodiments, $R_3$ is fluoro.

In a further variation of each of the above embodiments and variations, $R_4$ is hydrogen. In still a further variation of each of the above embodiments and variations, $R_4$ is a substituted or unsubstituted $(C_{1-3})$alkyl. In yet a further variation of each of the above embodiments and variations, $R_4$ is halo. In yet another variation of the above embodiments, $R_4$ is methyl. In yet another variation of the above embodiments, $R_4$ is fluoro.

In a further variation of each of the above embodiments and variations, $R_5$ is hydrogen. In still a further variation of each of the above embodiments and variations, $R_5$ is a substituted or unsubstituted $(C_{1-3})$alkyl. In yet a further variation of each of the above embodiments and variations, $R_5$ is halo. In yet another variation of the above embodiments, $R_5$ is methyl. In yet another variation of the above embodiments, $R_5$ is fluoro.

In yet another variation of the above embodiments, $R_4$ and $R_5$ are both hydrogen.

In a further variation of each of the above embodiments and variations, $R_6$ is a substituted or unsubstituted $(C_{1-3})$alkyl. In yet another variation of the above embodiments, $R_6$ is hydrogen.

In a further variation of each of the above embodiments and variations, $R_7$ is a substituted or unsubstituted $(C_{1-3})$alkyl. In a further variation of each of the above embodiments and variations, $R_7$ is halo. In yet another variation of the above embodiments, $R_7$ is hydrogen.

In a further variation of each of the above embodiments and variations, $R_8$ is hydrogen. In a further variation of each of the above embodiments and variations, $R_8$ is a substituted or unsubstituted $(C_{1-3})$alkyl.

In a further variation of each of the above embodiments and variations, each $R_9$ or $R_{9'}$ is independently selected from the group consisting of $(C_{3-12})$cycloalkyl, hetero$(C_{3-12})$cycloalkyl, $(C_{9-12})$bicycloalkyl, hetero$(C_{3-12})$bicycloalkyl, $(C_{6-12})$aryl, hetero$(C_{1-10})$aryl, $(C_{9-12})$bicycloaryl and hetero$(C_{4-12})$bicycloaryl, each substituted or unsubstituted. In a further variation of each of the above embodiments and variations, each $R_9$ or $R_{9'}$ is independently hydrogen.

In still a further variation of each of the above embodiments and variations, each $R_9$ or $R_{9'}$ is independently:

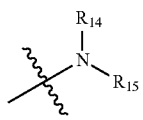

wherein:
$R_{14}$ and $R_{15}$ are each independently selected from the group consisting of hydrogen, carbonyl, oxycarbonyl, amino, $(C_{1-10})$alkylamino, sulfonamido, imino, sulfonyl, sulfinyl, $(C_{1-10})$alkyl, halo$(C_{1-10})$alkyl, hydroxy $(C_{1-10})$alkyl, carbonyl$(C_{1-10})$alkyl, hydroxycarbonyl $(C_{1-10})$alkyl, aminocarbonyl$(C_{1-10})$alkyl, thiocarbonyl $(C_{1-10})$alkyl, sulfonyl$(C_{1-10})$alkyl, sulfinyl$(C_{1-10})$alkyl, aza$(C_{1-10})$alkyl, imino$(C_{1-10})$alkyl, $(C_{3-12})$cycloalkyl $(C_{1-5})$alkyl, hetero$(C_{3-12})$cycloalkyl$(C_{1-10})$alkyl, aryl $(C_{1-10})$alkyl, hetero$(C_{1-10})$aryl$(C_{1-5})$alkyl, $(C_{9-12})$bicycloaryl$(C_{1-5})$alkyl, hetero$(C_{4-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{6-12})$aryl, hetero$(C_{1-10})$aryl, $(C_{9-12})$bicycloaryl and hetero$(C_{4-12})$bicycloaryl, each substituted or unsubstituted, or $R_{14}$ and $R_{15}$ are taken together to form a substituted or unsubstituted ring.

In yet a further variation of each of the above embodiments and variations, each $R_9$ or $R_{9'}$ is independently a substituted or unsubstituted piperazinyl.

In still a further variation of each of the above embodiments and variations, each $R_9$ or $R_{9'}$ is independently:

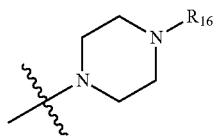

wherein:
$R_{16}$ is selected from the group consisting of hydrogen, hydroxy, carbonyloxy, $(C_{1-10})$alkoxy, $(C_{6-12})$aryloxy, hetero$(C_{1-10})$aryloxy, carbonyl, oxycarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{4-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{6-12})$aryl, carbonyl$(C_{6-12})$aryl, amino$(C_{6-12})$aryl, hetero$(C_{1-10})$aryl, $(C_{9-12})$bicycloaryl and hetero$(C_{4-12})$bicycloaryl, each substituted or unsubstituted.

In still another variation of each of the above embodiments and variations, each $R_9$ or $R_{9'}$ is independently a substituted or unsubstituted piperidinyl.

In yet another variation of each of the above embodiments and variations, each $R_9$ or $R_{9'}$ is independently:

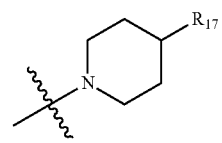

wherein:
$R_{17}$ is selected from the group consisting of hydrogen, halo, nitro, cyano, thio, oxy, hydroxy, carbonyloxy, $(C_{1-10})$alkoxy, $(C_{6-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl $(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cyclo alkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{4-12})$bicycloaryl $(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{6-12})$aryl, carbonyl$(C_{6-12})$aryl, amino $(C_{6-12})$aryl, hetero$(C_{1-10})$aryl, $(C_{9-12})$bicycloaryl and hetero$(C_{4-12})$bicycloaryl, each substituted or unsubstituted.

In a further variation of each of the above embodiments and variations, each $R_9$ or $R_{9'}$ is independently a substituted or unsubstituted 1,2,3,6-tetrahydropyridinyl.

In still a further variation of each of the above embodiments and variations, each $R_9$ or $R_{9'}$ is independently:

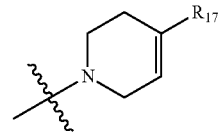

wherein:
$R_{17}$ is selected from the group consisting of hydrogen, halo, nitro, cyano, thio, oxy, hydroxy, carbonyloxy, $(C_{1-10})$alkoxy, $(C_{6-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl $(C_{1-10})$alkyl, thiocarbonyl$(C_{1-10})$alkyl, sulfonyl$(C_{1-10})$ alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cyclo alkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{4-12}$)bicycloaryl ($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{6-12}$)aryl, carbonyl($C_{6-12}$)aryl, amino($C_{6-12}$)aryl, hetero($C_{1-10}$)aryl, ($C_{9-12}$)bicycloaryl and hetero($C_{4-12}$)bicycloaryl, each substituted or unsubstituted.

In yet a further variation of each of the above embodiments and variations, each $R_9$ or $R_{9'}$ is independently a substituted or unsubstituted 3-oxo-piperazinyl.

In another variation of each of the above embodiments and variations, each $R_9$ or $R_{9'}$ is independently:

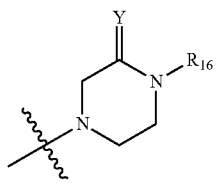

wherein:
Y is selected from the group consisting of O and S; and
$R_{16}$ is selected from the group consisting of hydrogen, hydroxy, carbonyloxy, ($C_{1-10}$)alkoxy, ($C_{6-12}$)aryloxy, hetero($C_{1-10}$)aryloxy, carbonyl, oxycarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{4-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{6-12}$)aryl, carbonyl($C_{6-12}$)aryl, amino($C_{6-12}$)aryl, hetero($C_{1-10}$)aryl, ($C_{9-12}$)bicycloaryl and hetero($C_{4-12}$)bicycloaryl, each substituted or unsubstituted.

In still another variation of each of the above embodiments and variations, Y is O.

In another variation of each of the above embodiments and variations, $R_{10}$ is hydrogen.

In another variation of each of the above embodiments and variations, $R_{10}$ is a substituted or unsubstituted ($C_{1-3}$)alkyl. In another variation of each of the above embodiments and variations, $R_{10}$ is halo.

In another variation of each of the above embodiments and variations, $R_{11}$ is hydrogen. In another variation of each of the above embodiments and variations, $R_{11}$ is a substituted or unsubstituted ($C_{1-3}$)alkyl. In another variation of each of the above embodiments and variations, $R_{11}$ is halo.

In yet another variation of each of the above embodiments and variations, one of $R_{10}$ and $R_{11}$ is hydrogen.

In still a further variation of each of the above embodiments and variations, $R_{12}$ is hydrogen. In still a further variation of each of the above embodiments and variations, $R_{12}$ is a substituted or unsubstituted ($C_{1-3}$)alkyl.

In yet a further variation of each of the above embodiments and variations, $R_{13}$ is hydrogen. In yet a further variation of each of the above embodiments and variations, $R_{13}$ is a substituted or unsubstituted ($C_{1-3}$)alkyl.

In yet a further variation of each of the above embodiments and variations, $R_{14}$ is selected from the group consisting of phenyl, biphenyl, cyclohexyl, benzyl, cyclohexylmethyl, phenethyl, $CH_2CO_2H$, or $CH_2C(=O)NR'R''$ wherein R' and R'' are each independently hydrogen, ($C_{1-10}$)alkyl, ($C_{6-12}$)aryl, or R' and R'' together form a hetero($C_{1-10}$)cycloalkyl; each substituted or unsubstituted.

In yet a further variation of each of the above embodiments and variations, $R_{15}$ is hydrogen. In yet a further variation of each of the above embodiments and variations, $R_{15}$ is a substituted or unsubstituted ($C_{1-3}$)alkyl.

In yet a further variation of each of the above embodiments and variations, $R_{14}$ and $R_{15}$ taken together form a substituent selected from the group consisting of piperidin-1-yl, piperazin-1-yl, 5,6-dihydropyridin-1(2H)-yl, 3-oxopiperazin-1-yl, 3,4-dihydroisoquinolin-2(1H)-yl, 3,4-dihydroquinolin-1(2H)-yl, pyrrolidin-1-yl, and 1H-imidazol-2-yl, each substituted or unsubstituted.

In still another variation of each of the above embodiments and variations, $R_{16}$ is selected from the group consisting of ($C_{3-12}$)cycloalkyl, hetero($C_{3-12}$)cycloalkyl, ($C_{9-12}$)bicycloalkyl, hetero($C_{3-12}$)bicycloalkyl, ($C_{6-12}$)aryl, hetero($C_{1-10}$)aryl, ($C_{9-12}$)bicycloaryl and hetero($C_{4-12}$)bicycloaryl, each substituted or unsubstituted. In yet another variation of each of the above embodiments and variations, $R_{16}$ is a substituted or unsubstituted phenyl. In a further variation of each of the above embodiments and variations, $R_{16}$ is a substituted or unsubstituted 4-chlorophenyl. In still a further variation of each of the above embodiments and variations, $R_{16}$ is a substituted or unsubstituted pyridinyl.

In yet a further variation of each of the above embodiments and variations, $R_{16}$ has the formula:

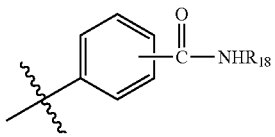

wherein:
$R_{18}$ is selected from the group consisting of hydrogen, hydroxy, carbonyloxy, ($C_{1-10}$)alkoxy, ($C_{6-12}$)aryloxy, hetero($C_{1-10}$)aryloxy, carbonyl, oxycarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{4-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{6-12}$)aryl, hetero($C_{1-10}$)aryl, ($C_{9-12}$)bicycloaryl and hetero($C_{4-12}$)bicycloaryl, each substituted or unsubstituted.

In another variation of each of the above embodiments and variations, $R_{16}$ has the formula:

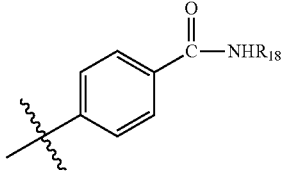

wherein:
$R_{18}$ is selected from the group consisting of hydrogen, hydroxy, carbonyloxy, ($C_{1-10}$)alkoxy, ($C_{6-12}$)aryloxy, hetero($C_{1-10}$)aryloxy, carbonyl, oxycarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{4-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{6-12}$)aryl, hetero($C_{1-10}$)aryl, ($C_{9-12}$)bicycloaryl and hetero($C_{4-12}$)bicycloaryl, each substituted or unsubstituted.

In still another variation of each of the above embodiments and variations, $R_{16}$ is further substituted with a substituent selected from the group consisting of halo, cyano and a substituted carbonyl. In yet another variation of each of the above embodiments and variations, $R_{16}$ is substituted with a substituent having the formula —C(=O)—$R_{19}$, wherein $R_{19}$ is selected from the group consisting of thio, oxy, hydroxy, carbonyloxy, ($C_{1-10}$)alkoxy, ($C_{6-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{4-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{6-12}$)aryl, hetero($C_{1-10}$)aryl, ($C_{9-12}$)bicycloaryl and hetero($C_{4-12}$)bicycloaryl, each substituted or unsubstituted.

In a further variation of each of the above embodiments and variations, $R_{17}$ is selected from the group consisting of ($C_{3-12}$)cycloalkyl, hetero($C_{3-12}$)cycloalkyl, ($C_{9-12}$)bicycloalkyl, hetero($C_{3-12}$)bicycloalkyl, ($C_{6-12}$)aryl, hetero($C_{1-10}$)aryl, ($C_{9-12}$)bicycloaryl and hetero($C_{4-12}$)bicycloaryl, each substituted or unsubstituted. In still a further variation of each of the above embodiments and variations, $R_{17}$ is a substituted or unsubstituted phenyl. In yet a further variation of each of the above embodiments and variations, $R_{17}$ is a substituted or unsubstituted 4-chlorophenyl. In another variation of each of the above embodiments and variations, $R_{17}$ is a substituted or unsubstituted pyridinyl.

In still another variation of each of the above embodiments and variations, $R_{17}$ has the formula:

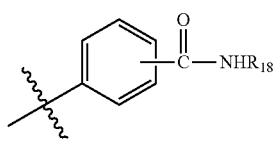

wherein:
$R_{18}$ is selected from the group consisting of hydrogen, hydroxy, carbonyloxy, ($C_{1-10}$)alkoxy, ($C_{6-12}$)aryloxy, hetero($C_{1-10}$)aryloxy, carbonyl, oxycarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{4-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{6-12}$)aryl, hetero($C_{1-10}$)aryl, ($C_{9-12}$)bicycloaryl and hetero($C_{4-12}$)bicycloaryl, each substituted or unsubstituted.

In yet another variation of each of the above embodiments and variations, $R_{17}$ has the formula:

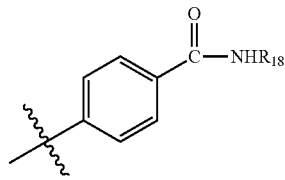

wherein:
$R_{18}$ is selected from the group consisting of hydrogen, hydroxy, carbonyloxy, ($C_{1-10}$)alkoxy, ($C_{6-12}$)aryloxy, hetero($C_{1-10}$)aryloxy, carbonyl, oxycarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{4-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{6-12}$)aryl, hetero($C_{1-10}$)aryl, ($C_{9-12}$)bicycloaryl and hetero($C_{4-12}$)bicycloaryl, each substituted or unsubstituted.

In a further variation of each of the above embodiments and variations, $R_{17}$ is substituted with a substituent selected from the group consisting of halo, cyano and a substituted carbonyl. In still a further variation of each of the above embodiments and variations, $R_{17}$ is substituted with a substituent having the formula —C(=O)—$R_{19}$, wherein $R_{19}$ is selected from the group consisting of hydrogen, halo, nitro, cyano, thio, oxy, hydroxy, carbonyloxy, ($C_{1-10}$)alkoxy, ($C_{6-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{4-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{6-12}$)aryl, hetero($C_{1-10}$)aryl, ($C_{9-12}$)bicycloaryl and hetero($C_{4-12}$)bicycloaryl, each substituted or unsubstituted.

In yet a further variation of each of the above embodiments and variations, $R_{18}$ is hydrogen. In yet a further variation of each of the above embodiments and variations, $R_{18}$ is a substituted or unsubstituted ($C_{1-3}$)alkyl.

In yet a further variation of each of the above embodiments and variations, $R_{19}$ is hydroxyl. In yet a further variation of each of the above embodiments and variations, $R_{19}$ is alkoxy. In yet a further variation of each of the above embodiments and variations, $R_{19}$ is alkylamino.

In yet a further variation of each of the above embodiments and variations, $R_{20}$ is hydrogen. In yet a further variation of each of the above embodiments and variations, $R_{20}$ is a substituted or unsubstituted $(C_{1-3})$alkyl. In yet a further variation of each of the above embodiments and variations, $R_{20}$ is halo.

In yet a further variation of each of the above embodiments and variations, r is 1. In yet a further variation of each of the above embodiments and variations, r is 2.

The present invention also relates to specific compounds described in the examples, below, including those for which PARP inhibition data is provided in Table 1, as well as tautomers and stereoisomers of the specific compounds, and the pharmaceutically acceptable salts of the specific compounds, tautomers, and stereoisomers.

In another of its aspects, the present invention relates to methods of making compounds that are useful as PARP inhibitors.

In still another of its aspects, the present invention relates to intermediates that are useful in making PARP inhibitors.

It is noted that the compounds of the present invention may be in the form of a pharmaceutically acceptable salt, biohydrolyzable ester, biohydrolyzable amide, biohydrolyzable carbamate, solvate, hydrate or prodrug thereof. For example, the compound optionally comprises a substituent that is convertible in vivo to a different substituent such as hydrogen.

It is further noted that the compound may be present as a mixture of stereoisomers, or the compound may be present as a single stereoisomer.

In another of its aspects, there is provided a pharmaceutical composition comprising as an active ingredient a compound according to any one of the above embodiments and variations. In one particular variation, the composition is a solid formulation adapted for oral administration. In another particular variation, the composition is a liquid formulation adapted for oral administration. In yet another particular variation, the composition is a tablet. In still another particular variation, the composition is a liquid formulation adapted for parenteral administration.

The present invention also provides a pharmaceutical composition comprising a compound according to any one of the above embodiments and variations, wherein the composition is adapted for administration by a route selected from the group consisting of orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, and intrathecally.

In yet another of its aspects, there is provided a kit comprising a compound of any one of the above embodiments and variations; and instructions which comprise one or more forms of information selected from the group consisting of indicating a disease state for which the composition is to be administered, storage information for the composition, dosing information and instructions regarding how to administer the composition. In one particular variation, the kit comprises the compound in a multiple dose form.

In still another of its aspects, there is provided an article of manufacture comprising a compound of any one of the above embodiments and variations; and packaging materials. In one variation, the packaging material comprises a container for housing the compound. In one particular variation, the container comprises a label indicating one or more members of the group consisting of a disease state for which the compound is to be administered, storage information, dosing information and/or instructions regarding how to administer the compound. In another variation, the article of manufacture comprises the compound in a multiple dose form.

In a further of its aspects, there is provided a therapeutic method comprising administering a compound of any one of the above embodiments and variations to a subject.

In another of its aspects, there is provided a method of inhibiting PARP comprising contacting PARP with a compound of any one of the above embodiments and variations.

In yet another of its aspects, there is provided a method of inhibiting PARP comprising causing a compound of any one of the above embodiments and variations to be present in a subject in order to inhibit PARP in vivo.

In a further of its aspects, there is provided a method of inhibiting PARP comprising administering a first compound to a subject that is converted in vivo to a second compound wherein the second compound inhibits PARP in vivo, the second compound being a compound according to any one of the above embodiments and variations.

In another of its aspects, there is provided a method of treating a disease state for which PARP possesses activity that contributes to the pathology and/or symptomology of the disease state, the method comprising causing a compound of any one of the above embodiments and variations to be present in a subject in a therapeutically effective amount for the disease state.

In yet another of its aspects, there is provided a method of treating a disease state for which PARP possesses activity that contributes to the pathology and/or symptomology of the disease state, the method comprising administering a compound of any one of the above embodiments and variations to a subject, wherein the compound is present in the subject in a therapeutically effective amount for the disease state.

In a further of its aspects, there is provided a method of treating a disease state for which PARP possesses activity that contributes to the pathology and/or symptomology of the disease state, the method comprising administering a first compound to a subject that is converted in vivo to a second compound wherein the second compound inhibits PARP in vivo, the second compound being a compound according to any one of the above embodiments and variations.

In one variation of each of the above methods the disease state is selected from the group consisting of cancers (including cancers where DNA damaging (e.g., alkylating) agents, cytotoxic drugs, radiation therapy and/or topoisomerase inhibitors are a standard of care (e.g., in combination with chemo- and/or radiosensitizers for cancer treatment); cancers which are deficient in Homologous Recombination (HR) dependent DNA DSB repair; BRCA-I and BRCA-2 deficient tumors; bladder cancer; blood-borne cancers (e.g., acute lymphoblastic leukemia("ALL"), acute lymphoblastic B-cell leukemia, acute lymphoblastic T-cell leukemia, acute myeloblasts leukemia ("AML"), acute promyelocytic leukemia ("APL"), acute monoblastic leukemia, acute erythroleukemic leukemia, acute megakaryoblastic leukemia, acute myelomonocytic leukemia, acute nonlymphocytic leukemia, acute undifferentiated leukemia, chronic myelocytic leukemia("CML"), chronic lymphocytic leukemia("CLL"), hairy cell leukemia and multiple myeloma); bone cancer; breast cancer; carcinomas (e.g., squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, bile duct carcinoma, choriocarcinoma, seminoma, embryonal carcinoma, small cell lung carcinoma, bladder carcinoma and epithelial carcinoma); CNS and brain cancers (e.g., glioma (e.g., pilocytic astrocytoma, astrocytoma, anaplastic astrocytoma, or glioblastoma multiforms), pilocytic astrocytoma, astrocytoma, anaplastic astrocytoma, glioblastoma multiforme, medulloblastoma, craniopharyngioma, ependymoma, pinealoma, hemangioblastoma, acoustic neuroma, oligodendroglioma, meningioma, vestibular schwannoma, adenoma, metastatic brain cancer, meningioma, spinal tumor and medulloblastoma); cervical cancer; colon cancer; colorectal cancer; esophageal cancer; hepatomas; head and neck cancer; kidney cancer; acute and chronic leukemias (e.g., lymphoblastic, myelogenous, lymphocytic and myelocytic leukemias); liver cancer; lung cancer; lymphomas (e.g., such as Hodgkin's disease, non-Hodgkin's Lymphoma, Multiple myeloma, Waldenstrom's macroglobulinemia, Heavy chain disease and Polycythemia vera); melanomas; nasal cancer; neuroblastomas; oral cancer; ovarian cancer; pancreatic cancer; prostate cancer; retinoblastomas; skin cancer; solid tumors (e.g., such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma and rhabdomyosarcoma); stomach cancer; testicular cancer; throat cancer; uterine cancer and Wilms' tumor); cardiovascular diseases (including chronic heart failure; atherosclerosis; congestive heart failure; circulatory shock; cardiomyopathy; cardiac transplant; myocardial infarction and cardiac arrhythmia (e.g., atrial fibrillation, supraventricular tachycardia, atrial flutter and paroxysmal atrial tachycardia)); vascular diseases other than cardiovascular diseases (including peripheral arterial occlusion; thromboangitis obliterans; Reynaud's disease and phenomenon; acrocyanosis; erythromelalgia; venous thrombosis; varicose veins; arteriovenous fistula; lymphedema and lipedema); metabolic diseases (including diabetes (e.g., diabetes mellitus (e.g., Type I diabetes (Insulin Dependent Diabetes Mellitus), Type II diabetes (Non-Insulin Dependent Diabetes Mellitus), gestational diabetes, autoimmune diabetes, insulinopathies, diabetes due to pancreatic disease, diabetes associated with other endocrine diseases (such as Cushing's Syndrome, acromegaly, pheochromocytoma, glucagonoma, primary aldosteronism or somatostatinoma), Type A insulin resistance syndrome, Type B insulin resistance syndrome, lipatrophic diabetes, and diabetes induced by β-cell toxins); and diabetic complications (e.g., diabetic cataract, glaucoma, retinopathy, nephropathy (e.g., microaluminuria and diabetic nephropathy), mononeuropathy, autonomic neuropathy, polyneuropathy, gangrene of the feet, atherosclerotic coronary arterial disease, peripheral arterial disease, non-ketotic hyperglycemic-hyperosmolar coma, mononeuropathies, autonomic neuropathy, foot ulcers, joint problems, skin or mucous membrane complications (e.g., infection, shin spot, candidal infection or necrobiosis lipoidica diabeticorumobesity), hyperlipidemia, hypertension, syndrome of insulin resistance, coronary artery disease, foot ulcers, joint problems, fungal infections, bacterial infections, cardiomyopathy, immune-complex vasculitis and systemic lupus erythematosus (SLE))); inflammatory diseases (including conditions resulting from organ transplant rejection; chronic inflammatory diseases of the joints (e.g., arthritis, rheumatoid arthritis, osteoarthritis and bone diseases associated with increased bone resorption); inflammatory bowel diseases (e.g., ileitis, ulcerative colitis, Barrett's syndrome and Crohn's disease); inflammatory lung diseases (e.g., asthma, adult respiratory distress syndrome and chronic obstructive airway disease); inflammatory diseases of the eye (e.g., corneal dystrophy, trachoma, onchocerciasis, uveitis, sympathetic ophthalmitis and endophthalmitis); chronic inflammatory diseases of the gum (e.g., gingivitis and periodontitis); tuberculosis; leprosy; inflammatory diseases of the kidney (e.g., uremic complications, glomerulonephritis and nephrosis); inflammatory diseases of the skin (e.g., sclerodermatitis, psoriasis and eczema); inflammatory diseases of the central nervous system (e.g., chronic demyelinating diseases of the nervous system, multiple sclerosis, AIDS-related neurodegeneration, Alzheimer's disease, infectious meningitis, encephalomyelitis, Parkinson's disease, Huntington's disease, amyotrophic lateral sclerosis and viral or autoimmune encephalitis); inflammatory diseases of the heart (e.g., cardiomyopathy, ischemic heart disease, hypercholesterolemia and atherosclerosis); diseases that can have significant inflammatory components (e.g., preeclampsia, chronic liver failure, brain and spinal cord trauma and multiple organ dysfunction syndrome (MODS) (multiple organ failure (MOF))); systemic inflammation of the body, exemplified by gram-positive or gram negative shock, hemorrhagic or anaphylactic shock, or shock induced by cancer chemotherapy in response to pro-inflammatory cytokines, (e.g., shock associated with pro-inflammatory cytokines; and shock induced, for example, by a chemotherapeutic agent that is administered as a treatment for cancer); reperfusion injuries, including those resulting from naturally occurring episodes and during a surgical procedure (e.g., intestinal reperfusion injury; myocardial reperfusion injury; reperfusion injury resulting from cardiopulmonary bypass surgery, aortic aneurysm repair surgery, carotid endarterectomy surgery, or hemorrhagic shock; and reoxygenation injury resulting from transplantation of organs such as heart, lung, liver, kidney, pancreas, intestine or cornea); ischemic conditions, including those resulting from organ transplantation (e.g., stable angina, unstable angina, myocardial ischemia, hepatic ischemia, mesenteric artery ischemia, intestinal ischemia, critical limb ischemia, chronic critical limb ischemia, cerebral ischemia, acute cardiac ischemia, ischemic kidney disease, ischemic liver disease, ischemic retinal disorder, septic shock; and an ischemic disease of the central nervous system (e.g., stroke or cerebral ischemia)); neurodegenerative diseases (e.g., polyglutamine-expansion-related neurodegeneration, Huntington's disease, Kennedy's disease, spinocerebellar ataxia, dentatorubral-pallidoluysian atrophy (DRPLA), protein-aggregation-related neurodegeneration, Machado-Joseph's disease, Alzheimer's disease, Parkinson's disease, amyotrophic lateral sclerosis, spongiform encephalopathy, a prion-related disease and multiple sclerosis (MS)); tissue injuries; CNS diseases; heart attack; hematolymphoid system disorders; endocrine and neuroendocrine system disorders; urinary tract disorders; respiratory system disorders; female reproductive system disorders; male reproductive system disorders; retroviral infections; retinal damage; skin senescence; UV-induced skin damage; chronic or acute renal disease or failure; age-related cellular dysfunction; and fatty acid synthesis related diseases (e.g., obesity, diabetes and cardiovascular disease).

In another variation of each of the above methods, the PARP is a PARP-1, PARP-2, PARP-3, vaultPARP or TiPARP. It is noted that the compounds of the present invention may also possess inhibitory activity for other PARP family members and thus may be used to address disease states associated with these other family members. Further, the compounds of the present invention may also possess inhibitory activity for tankyrases (e.g., tankyrase-1 and tankyrase-2) and thus may be used to address disease states associated with these target proteins.

Salts, Hydrates, and Prodrugs of PARP Inhibitors

It should be recognized that the compounds of the present invention may be present and optionally administered in the form of salts, hydrates and prodrugs that are converted in vivo into the compounds of the present invention. For example, it is within the scope of the present invention to convert the compounds of the present invention into and use them in the form of their pharmaceutically acceptable salts derived from various organic and inorganic acids and bases in accordance with procedures well known in the art.

When the compounds of the present invention possess a free base form, the compounds can be prepared as a pharmaceutically acceptable acid addition salt by reacting the free base form of the compound with a pharmaceutically acceptable inorganic or organic acid, e.g., hydrohalides such as hydrochloride, hydrobromide, hydroiodide; other mineral acids and their corresponding salts such as sulfate, nitrate, phosphate, etc.; and alkyl and monoarylsulfonates such as ethanesulfonate, toluenesulfonate and benzenesulfonate; and other organic acids and their corresponding salts such as acetate, tartrate, maleate, succinate, citrate, benzoate, salicylate and ascorbate. Further acid addition salts of the present invention include, but are not limited to: adipate, alginate, arginate, aspartate, bisulfate, bisulfite, bromide, butyrate, camphorate, camphorsulfonate, caprylate, chloride, chlorobenzoate, cyclopentanepropionate, digluconate, dihydrogenphosphate, dinitrobenzoate, dodecylsulfate, fumarate, galacterate (from mucic acid), galacturonate, glucoheptonate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, iso-butyrate, lactate, lactobionate, malate, malonate, mandelate, metaphosphate, methanesulfonate, methylbenzoate, monohydrogenphosphate, 2-naphthalenesulfonate, nicotinate, nitrate, oxalate, oleate, pamoate, pectinate, persulfate, phenylacetate, 3-phenylpropionate, phosphate, phosphonate and phthalate. It should be recognized that the free base forms will typically differ from their respective salt forms somewhat in physical properties such as solubility in polar solvents, but otherwise the salts are equivalent to their respective free base forms for the purposes of the present invention.

When the compounds of the present invention possess a free acid form, a pharmaceutically acceptable base addition salt can be prepared by reacting the free acid form of the compound with a pharmaceutically acceptable inorganic or organic base. Examples of such bases are alkali metal hydroxides including potassium, sodium and lithium hydroxides; alkaline earth metal hydroxides such as barium and calcium hydroxides; alkali metal alkoxides, e.g., potassium ethanolate and sodium propanolate; and various organic bases such as ammonium hydroxide, piperidine, diethanolamine and N-methylglutamine. Also included are the aluminum salts of the compounds of the present invention. Further base salts of the present invention include, but are not limited to: copper, ferric, ferrous, lithium, magnesium, manganic, manganous, potassium, sodium and zinc salts. Organic base salts include, but are not limited to, salts of primary, secondary and tertiary amines, substituted amines including naturally occurring substituted amines, cyclic amines and basic ion exchange resins, e.g., arginine, betaine, caffeine, chloroprocaine, choline, N,N'-dibenzylethylenediamine (benzathine), dicyclohexylamine, diethanolamine, 2-diethylaminoethanol, 2-dimethylaminoethanol, ethanolamine, ethylenediamine, N-ethylmorpholine, N-ethylpiperidine, glucamine, glucosamine, histidine, hydrabamine, iso-propylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris-(hydroxymethyl)-methylamine (tromethamine). It should be recognized that the free acid forms will typically differ from their respective salt forms somewhat in physical properties such as solubility in polar solvents, but otherwise the salts are equivalent to their respective free acid forms for the purposes of the present invention.

N-oxides of compounds according to the present invention can be prepared by methods known to those of ordinary skill in the art. For example, N-oxides can be prepared by treating an unoxidized form of the compound with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0° C. Alternatively, the N-oxides of the compounds can be prepared from the N-oxide of an appropriate starting material.

Prodrug derivatives of compounds according to the present invention can be prepared by modifying substituents of compounds of the present invention that are then converted in vivo to a different substituent. It is noted that in many instances, the prodrugs themselves also fall within the scope of the range of compounds according to the present invention. For example, prodrugs can be prepared by reacting a compound with a carbamylating agent (e.g., 1,1-acyloxyalkylcarbonochloridate, para-nitrophenyl carbonate, or the like) or an acylating agent. Further examples of methods of making prodrugs are described in Saulnier et al. (1994), Bioorganic and Medicinal Chemistry Letters, Vol. 4, p. 1985.

Protected derivatives of compounds of the present invention can also be made. Examples of techniques applicable to the creation of protecting groups and their removal can be found in T. W. Greene, Protecting Groups in Organic Synthesis, $3^{rd}$ edition, John Wiley & Sons, Inc. 1999.

Compounds of the present invention may also be conveniently prepared, or formed during the process of the invention, as solvates (e.g., hydrates). Hydrates of compounds of the present invention may be conveniently prepared by recrystallization from an aqueous/organic solvent mixture, using organic solvents such as dioxin, tetrahydrofuran or methanol.

A "pharmaceutically acceptable salt", as used herein, is intended to encompass any compound according to the present invention that is utilized in the form of a salt thereof, especially where the salt confers on the compound improved pharmacokinetic properties as compared to the free form of compound or a different salt form of the compound. The pharmaceutically acceptable salt form may also initially confer desirable pharmacokinetic properties on the compound that it did not previously possess, and may even positively affect the pharmacodynamics of the compound with respect to its therapeutic activity in the body. An example of a pharmacokinetic property that may be favorably affected is the manner in which the compound is transported across cell membranes, which in turn may directly and positively affect the absorption, distribution, biotransformation and excretion of the compound. While the route of administration of the pharmaceutical composition is important, and various anatomical, physiological and pathological factors can critically affect bioavailability, the solubility of the compound is usually dependent upon the character of the particular salt form thereof, which it utilized. One of skill in the art will appreciate that an aqueous solution of the compound will provide the most rapid absorption of the compound into the body of a subject being treated, while lipid solutions and suspensions, as well as solid dosage forms, will result in less rapid absorption of the compound.

Compositions Comprising PARP Inhibitors

A wide variety of compositions and administration methods may be used in conjunction with the compounds of the present invention. Such compositions may include, in addition to the compounds of the present invention, conventional pharmaceutical excipients, and other conventional, pharmaceutically inactive agents. Additionally, the compositions may include active agents in addition to the compounds of the present invention. These additional active agents may include additional compounds according to the invention, and/or one or more other pharmaceutically active agents.

The compositions may be in gaseous, liquid, semi-liquid or solid form, formulated in a manner suitable for the route of administration to be used. For oral administration, capsules and tablets are typically used. For parenteral administration, reconstitution of a lyophilized powder, prepared as described herein, is typically used.

Compositions comprising compounds of the present invention may be administered or co-administered orally, parenterally, intraperitoneally, intravenously, intraarterially, transdermally, sublingually, intramuscularly, rectally, trans-buccally, intranasally, liposomally, via inhalation, vaginally, intraoccularly, via local delivery (for example by catheter or stent), subcutaneously, intraadiposally, intraarticularly, or intrathecally. The compounds and/or compositions according to the invention may also be administered or co administered in slow release dosage forms.

The PARP inhibitors and compositions comprising them may be administered or co administered in any conventional dosage form. Co-administration in the context of this invention is intended to mean the administration of more than one therapeutic agent, one of which includes a PARP inhibitor, in the course of a coordinated treatment to achieve an improved clinical outcome. Such co-administration may also be coextensive, that is, occurring during overlapping periods of time.

Solutions or suspensions used for parenteral, intradermal, subcutaneous, or topical application may optionally include one or more of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; agents for the adjustment of tonicity such as sodium chloride or dextrose, and agents for adjusting the acidity or alkalinity of the composition, such as alkaline or acidifying agents or buffers like carbonates, bicarbonates, phosphates, hydrochloric acid, and organic acids like acetic and citric acid. Parenteral preparations may optionally be enclosed in ampules, disposable syringes or single or multiple dose vials made of glass, plastic or other suitable material.

When compounds according to the present invention exhibit insufficient solubility, methods for solubilizing the compounds may be used. Such methods are known to those of skill in this art, and include, but are not limited to, using co-solvents, such as dimethylsulfoxide (DMSO), using surfactants, such as TWEEN, or dissolution in aqueous sodium bicarbonate. Derivatives of the compounds, such as prodrugs of the compounds may also be used in formulating effective pharmaceutical compositions.

Upon mixing or adding compounds according to the present invention to a composition, a solution, suspension, emulsion or the like may be formed. The form of the resulting composition will depend upon a number of factors, including the intended mode of administration, and the solubility of the compound in the selected carrier or vehicle. The effective concentration needed to ameliorate the disease being treated may be empirically determined.

Compositions according to the present invention are optionally provided for administration to humans and animals in unit dosage forms, such as tablets, capsules, pills, powders, dry powders for inhalers, granules, sterile parenteral solutions or suspensions, and oral solutions or suspensions, and oil-water emulsions containing suitable quantities of the compounds, particularly the pharmaceutically acceptable salts, preferably the sodium salts, thereof. The pharmaceutically therapeutically active compounds and derivatives thereof are typically formulated and administered in unit-dosage forms or multiple-dosage forms. Unit-dose forms, as used herein, refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes individually packaged tablet or capsule. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pint or gallons. Hence, multiple dose form is a multiple of unit-doses that are not segregated in packaging.

In addition to one or more compounds according to the present invention, the composition may comprise: a diluent such as lactose, sucrose, dicalcium phosphate, or carboxymethylcellulose; a lubricant, such as magnesium stearate, calcium stearate and talc; and a binder such as starch, natural gums, such as gum acaciagelatin, glucose, molasses, polyvinylpyrrolidine, celluloses and derivatives thereof, povidone, crospovidones and other such binders known to those of skill in the art. Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to form a solution or suspension. If desired, the pharmaceutical composition to be administered may also contain minor amounts of auxiliary substances such as wetting agents, emulsifying agents, or solubilizing agents, pH buffering agents and the like, for example, acetate, sodium citrate, cyclodextrin derivatives, sorbitan monolaurate, triethanolamine sodium acetate, triethanolamine oleate, and other such agents. Actual methods of preparing such dosage forms are known in the art, or will be apparent, to those skilled in this art; for example, see Remington's Pharmaceutical Sciences, Mack Publishing Company, Easton, Pa., 15th Edition, 1975. The composition or formulation to be administered will, in any event, contain a sufficient quantity of an inhibitor of the present invention to reduce PARP activity in vivo, thereby treating the disease state of the subject.

Dosage forms or compositions may optionally comprise one or more compounds according to the present invention in the range of 0.005% to 100% (weight/weight) with the balance comprising additional substances such as those described herein. For oral administration, a pharmaceutically acceptable composition may optionally comprise any one or more commonly employed excipients, such as, for example pharmaceutical grades of mannitol, lactose, starch, magnesium stearate, talcum, cellulose derivatives, sodium crosscarmellose, glucose, sucrose, magnesium carbonate, sodium saccharin, talcum. Such compositions include solutions, suspensions, tablets, capsules, powders, dry powders for inhalers and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparing these formulations are known to those skilled in the art. The compositions may optionally contain 0.01%-100% (weight/weight) of one or more PARP inhibitors, optionally 0.1-95%, and optionally 1-95%.

Salts, preferably sodium salts, of the inhibitors may be prepared with carriers that protect the compound against rapid elimination from the body, such as time release formulations or coatings. The formulations may further include other active compounds to obtain desired combinations of properties.

Formulations for Oral Administration

Oral pharmaceutical dosage forms may be as a solid, gel or liquid. Examples of solid dosage forms include, but are not limited to tablets, capsules, granules, and bulk powders. More specific examples of oral tablets include compressed, chewable lozenges and tablets that may be enteric-coated, sugar-coated or film-coated. Examples of capsules include hard or soft gelatin capsules. Granules and powders may be provided in non-effervescent or effervescent forms. Each may be combined with other ingredients known to those skilled in the art.

In certain embodiments, compounds according to the present invention are provided as solid dosage forms, preferably capsules or tablets. The tablets, pills, capsules, troches and the like may optionally contain one or more of the following ingredients, or compounds of a similar nature: a binder; a diluent; a disintegrating agent; a lubricant; a glidant; a sweetening agent; and a flavoring agent.

Examples of binders that may be used include, but are not limited to, microcrystalline cellulose, gum tragacanth, glucose solution, acacia mucilage, gelatin solution, sucrose and starch paste.

Examples of lubricants that may be used include, but are not limited to, talc, starch, magnesium or calcium stearate, lycopodium and stearic acid.

Examples of diluents that may be used include, but are not limited to, lactose, sucrose, starch, kaolin, salt, mannitol, and dicalcium phosphate.

Examples of glidants that may be used include, but are not limited to, colloidal silicon dioxide.

Examples of disintegrating agents that may be used include, but are not limited to, crosscarmellose sodium, sodium starch glycolate, alginic acid, corn starch, potato starch, bentonite, methylcellulose, agar and carboxymethylcellulose.

Examples of coloring agents that may be used include, but are not limited to, any of the approved certified water-soluble FD and C dyes, mixtures thereof; and water insoluble FD and C dyes suspended on alumina hydrate.

Examples of sweetening agents that may be used include, but are not limited to, sucrose, lactose, mannitol and artificial sweetening agents such as sodium cyclamate and saccharin, and any number of spray-dried flavors.

Examples of flavoring agents that may be used include, but are not limited to, natural flavors extracted from plants such as fruits and synthetic blends of compounds that produce a pleasant sensation, such as, but not limited to peppermint and methyl salicylate.

Examples of wetting agents that may be used include, but are not limited to, propylene glycol monostearate, sorbitan monooleate, diethylene glycol monolaurate, and polyoxyethylene lauryl ether.

Examples of anti-emetic coatings that may be used include, but are not limited to, fatty acids, fats, waxes, shellac, ammoniated shellac and cellulose acetate phthalates.

Examples of film coatings that may be used include, but are not limited to, hydroxyethylcellulose, sodium carboxymethylcellulose, polyethylene glycol 4000 and cellulose acetate phthalate.

If oral administration is desired, the salt of the compound may optionally be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it may optionally additionally comprise a liquid carrier such as a fatty oil. In addition, dosage unit forms may optionally additionally comprise various other materials that modify the physical form of the dosage unit, for example, coatings of sugar and other enteric agents.

Compounds according to the present invention may also be administered as a component of an elixir, suspension, syrup, wafer, sprinkle, chewing gum or the like. A syrup may optionally comprise, in addition to the active compounds, sucrose as a sweetening agent and certain preservatives, dyes and colorings and flavors.

The compounds of the present invention may also be mixed with other active materials that do not impair the desired action, or with materials that supplement the desired action, such as antacids, H2 blockers, and diuretics. For example, if a compound is used for treating asthma or hypertension, it may be used with other bronchodilators and antihypertensive agents, respectively.

Examples of pharmaceutically acceptable carriers that may be included in tablets comprising compounds of the present invention include, but are not limited to binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets may be compressed tablets to which different layers of pharmaceutically acceptable substances are applied. Film-coated tablets may be compressed tablets that have been coated with polymers or other suitable coating. Multiple compressed tablets may be compressed tablets made by more than one compression cycle utilizing the pharmaceutically acceptable substances previously mentioned. Coloring agents may also be used in tablets. Flavoring and sweetening agents may be used in tablets, and are especially useful in the formation of chewable tablets and lozenges.

Examples of liquid oral dosage forms that may be used include, but are not limited to, aqueous solutions, emulsions, suspensions, solutions and/or suspensions reconstituted from non-effervescent granules and effervescent preparations reconstituted from effervescent granules.

Examples of aqueous solutions that may be used include, but are not limited to, elixirs and syrups. As used herein, elixirs refer to clear, sweetened, hydroalcoholic preparations. Examples of pharmaceutically acceptable carriers that may be used in elixirs include, but are not limited to solvents. Particular examples of solvents that may be used include glycerin, sorbitol, ethyl alcohol and syrup. As used herein, syrups refer to concentrated aqueous solutions of a sugar, for example, sucrose. Syrups may optionally further comprise a preservative.

Emulsions refer to two-phase systems in which one liquid is dispersed in the form of small globules throughout another liquid. Emulsions may optionally be oil-in-water or water-in-oil emulsions. Examples of pharmaceutically acceptable carriers that may be used in emulsions include, but are not limited to non-aqueous liquids, emulsifying agents and preservatives.

Examples of pharmaceutically acceptable substances that may be used in non-effervescent granules, to be reconstituted into a liquid oral dosage form, include diluents, sweeteners and wetting agents.

Examples of pharmaceutically acceptable substances that may be used in effervescent granules, to be reconstituted into a liquid oral dosage form, include organic acids and a source of carbon dioxide.

Coloring and flavoring agents may optionally be used in all of the above dosage forms.

Particular examples of preservatives that may be used include glycerin, methyl and propylparaben, benzoic acid, sodium benzoate and alcohol.

Particular examples of non-aqueous liquids that may be used in emulsions include mineral oil and cottonseed oil.

Particular examples of emulsifying agents that may be used include gelatin, acacia, tragacanth, bentonite, and surfactants such as polyoxyethylene sorbitan monooleate.

Particular examples of suspending agents that may be used include sodium carboxymethylcellulose, pectin, tragacanth, Veegum and acacia. Diluents include lactose and sucrose. Sweetening agents include sucrose, syrups, glycerin and artificial sweetening agents such as sodium cyclamate and saccharin.

Particular examples of wetting agents that may be used include propylene glycol monostearate, sorbitan monooleate, diethylene glycol monolaurate, and polyoxyethylene lauryl ether.

Particular examples of organic acids that may be used include citric and tartaric acid.

Sources of carbon dioxide that may be used in effervescent compositions include sodium bicarbonate and sodium carbonate. Coloring agents include any of the approved certified water soluble FD and C dyes, and mixtures thereof.

Particular examples of flavoring agents that may be used include natural flavors extracted from plants such fruits, and synthetic blends of compounds that produce a pleasant taste sensation.

For a solid dosage form, the solution or suspension, in for example propylene carbonate, vegetable oils or triglycerides, is preferably encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. Re 28,819 and 4,358,603.

Injectables, Solutions, and Emulsions

The present invention is also directed to compositions designed to administer the compounds of the present invention by parenteral administration, generally characterized by subcutaneous, intramuscular or intravenous injection. Injectables may be prepared in any conventional form, for example as liquid solutions or suspensions, solid forms suitable for solution or suspension in liquid prior to injection, or as emulsions.

Examples of excipients that may be used in conjunction with injectables according to the present invention include, but are not limited to water, saline, dextrose, glycerol or ethanol. The injectable compositions may also optionally comprise minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow-release or sustained-release system, such that a constant level of dosage is maintained (see, e.g., U.S. Pat. No. 3,710,795) is also contemplated herein. The percentage of active compound contained in such parenteral compositions is highly dependent on the specific nature thereof, as well as the activity of the compound and the needs of the subject.

Parenteral administration of the formulations includes intravenous, subcutaneous and intramuscular administrations. Preparations for parenteral administration include sterile solutions ready for injection, sterile dry soluble products, such as the lyophilized powders described herein, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

When administered intravenously, examples of suitable carriers include, but are not limited to physiological saline or phosphate buffered saline (PBS), and solutions containing thickening and solubilizing agents, such as glucose, polyethylene glycol, and polypropylene glycol and mixtures thereof.

Examples of pharmaceutically acceptable carriers that may optionally be used in parenteral preparations include, but are not limited to aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles that may optionally be used include Sodium Chloride Injection, Ringers Injection, Isotonic Dextrose Injection, Sterile Water Injection, Dextrose and Lactated Ringers Injection.

Examples of nonaqueous parenteral vehicles that may optionally be used include fixed oils of vegetable origin, cottonseed oil, corn oil, sesame oil and peanut oil.

Antimicrobial agents in bacteriostatic or fungistatic concentrations may be added to parenteral preparations, particularly when the preparations are packaged in multiple-dose containers and thus designed to be stored and multiple aliquots to be removed. Examples of antimicrobial agents that may be used include phenols or cresols, mercurials, benzyl alcohol, chlorobutanol, methyl and propyl p-hydroxybenzoic acid esters, thimerosal, benzalkonium chloride and benzethonium chloride.

Examples of isotonic agents that may be used include sodium chloride and dextrose. Examples of buffers that may be used include phosphate and citrate. Examples of antioxidants that may be used include sodium bisulfate. Examples of local anesthetics that may be used include procaine hydrochloride. Examples of suspending and dispersing agents that may be used include sodium carboxymethylcellulose, hydroxypropyl methylcellulose and polyvinylpyrrolidone. Examples of emulsifying agents that may be used include Polysorbate 80 (TWEEN 80). A sequestering or chelating agent of metal ions includes EDTA.

Pharmaceutical carriers may also optionally include ethyl alcohol, polyethylene glycol and propylene glycol for water miscible vehicles and sodium hydroxide, hydrochloric acid, citric acid or lactic acid for pH adjustment.

The concentration of an inhibitor in the parenteral formulation may be adjusted so that an injection administers a pharmaceutically effective amount sufficient to produce the desired pharmacological effect. The exact concentration of an inhibitor and/or dosage to be used will ultimately depend on the age, weight and condition of the patient or animal as is known in the art.

Unit-dose parenteral preparations may be packaged in an ampoule, a vial or a syringe with a needle. All preparations for parenteral administration should be sterile, as is known and practiced in the art.

Injectables may be designed for local and systemic administration. Typically a therapeutically effective dosage is formulated to contain a concentration of at least about 0.1% w/w up to about 90% w/w or more, preferably more than 1% w/w of the PARP inhibitor to the treated tissue(s). The inhibitor may be administered at once, or may be divided into a number of smaller doses to be administered at intervals of time. It is understood that the precise dosage and duration of treatment will be a function of the location of where the composition is parenterally administered, the carrier and other variables that may be determined empirically using known testing protocols or by extrapolation from in vivo or in vitro test data. It is to be noted that concentrations and dosage values may also vary with the age of the individual treated. It is to be further understood that for any particular subject, specific dosage regimens may need to be adjusted over time according to the individual need and the professional judgment of the person administering or supervising the administration of the formulations. Hence, the concentration ranges set forth herein are intended to be exemplary and are not intended to limit the scope or practice of the claimed formulations.

The PARP inhibitor may optionally be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the disease state and may be empirically determined.

Lyophilized Powders

The compounds of the present invention may also be prepared as lyophilized powders, which can be reconstituted for administration as solutions, emulsions and other mixtures. The lyophilized powders may also be formulated as solids or gels.

Sterile, lyophilized powder may be prepared by dissolving the compound in a sodium phosphate buffer solution containing dextrose or other suitable excipient. Subsequent sterile filtration of the solution followed by lyophilization under standard conditions known to those of skill in the art provides the desired formulation. Briefly, the lyophilized powder may optionally be prepared by dissolving dextrose, sorbitol, fructose, corn syrup, xylitol, glycerin, glucose, sucrose or other suitable agent, about 1-20%, preferably about 5 to 15%, in a suitable buffer, such as citrate, sodium or potassium phosphate or other such buffer known to those of skill in the art at, typically, about neutral pH. Then, a PARP inhibitor is added to the resulting mixture, preferably above room temperature, more preferably at about 30-35° C., and stirred until it dissolves. The resulting mixture is diluted by adding more buffer to a desired concentration. The resulting mixture is sterile filtered or treated to remove particulates and to insure sterility, and apportioned into vials for lyophilization. Each vial may contain a single dosage or multiple dosages of the inhibitor.

Topical Administration

The compounds of the present invention may also be administered as topical mixtures. Topical mixtures may be used for local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The PARP inhibitors may be formulated as aerosols for topical application, such as by inhalation (see, U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will typically have diameters of less than 50 microns, preferably less than 10 microns.

The inhibitors may also be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the PARP inhibitor alone or in combination with other pharmaceutically acceptable excipients can also be administered.

Formulations for Other Routes of Administration

Depending upon the disease state being treated, other routes of administration, such as topical application, transdermal patches, and rectal administration, may also be used. For example, pharmaceutical dosage forms for rectal administration are rectal suppositories, capsules and tablets for systemic effect. Rectal suppositories are used herein mean solid bodies for insertion into the rectum that melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax, (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The typical weight of a rectal suppository is about 2 to 3 gm. Tablets and capsules for rectal administration may be manufactured using the same pharmaceutically acceptable substance and by the same methods as for formulations for oral administration.

Examples of Formulations

The following are particular examples of oral, intravenous and tablet formulations that may optionally be used with compounds of the present invention. It is noted that these formulations may be varied depending on the particular compound being used and the indication for which the formulation is going to be used.

| ORAL FORMULATION | |
| --- | --- |
| Compound of the Present Invention | 10-100 mg |
| Citric Acid Monohydrate | 105 mg |
| Sodium Hydroxide | 18 mg |
| Flavoring | |
| Water | q.s. to 100 mL |

| INTRAVENOUS FORMULATION | |
| --- | --- |
| Compound of the Present Invention | $0_{.1-10}$ mg |
| Dextrose Monohydrate | q.s. to make isotonic |
| Citric Acid Monohydrate | 1.05 mg |
| Sodium Hydroxide | 0.18 mg |
| Water for Injection | q.s. to 1.0 mL |

| TABLET FORMULATION | |
| --- | --- |
| Compound of the Present Invention | 1% |
| Microcrystalline Cellulose | 73% |
| Stearic Acid | 25% |
| Colloidal Silica | 1%. |

Kits Comprising PARP Inhibitors

The invention is also directed to kits and other articles of manufacture for treating diseases associated with PARP. It is noted that diseases are intended to cover all conditions for which the PARP possess activity that contributes to the pathology and/or symptomology of the condition.

In one embodiment, a kit is provided that comprises a composition comprising at least one inhibitor of the present invention in combination with instructions. The instructions may indicate the disease state for which the composition is to be administered, storage information, dosing information and/or instructions regarding how to administer the composition. The kit may also comprise packaging materials. The packaging material may comprise a container for housing the composition. The kit may also optionally comprise additional components, such as syringes for administration of the composition. The kit may comprise the composition in single or multiple dose forms.

In another embodiment, an article of manufacture is provided that comprises a composition comprising at least one inhibitor of the present invention in combination with packaging materials. The packaging material may comprise a container for housing the composition. The container may optionally comprise a label indicating the disease state for which the composition is to be administered, storage information, dosing information and/or instructions regarding how to administer the composition. The kit may also optionally comprise additional components, such as syringes for administration of the composition. The kit may comprise the composition in single or multiple dose forms.

It is noted that the packaging material used in kits and articles of manufacture according to the present invention may form a plurality of divided containers such as a divided bottle or a divided foil packet. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container that is employed will depend on the exact dosage form involved, for example a conventional cardboard box would not generally be used to hold a liquid suspension. It is feasible that more than one container can be used together in a single package to market a single dosage form. For example, tablets may be contained in a bottle that is in turn contained within a box. Typically the kit includes directions for the administration of the separate components. The kit form is particularly advantageous when the separate components are preferably administered in different dosage forms (e.g., oral, topical, transdermal and parenteral), are administered at different dosage intervals, or when titration of the individual components of the combination is desired by the prescribing physician.

One particular example of a kit according to the present invention is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

Another specific embodiment of a kit is a dispenser designed to dispense the daily doses one at a time in the order of their intended use. Preferably, the dispenser is equipped with a memory-aid, so as to further facilitate compliance with the regimen. An example of such a memory-aid is a mechanical counter that indicates the number of daily doses that has been dispensed. Another example of such a memory-aid is a battery-powered micro-chip memory coupled with a liquid crystal readout, or audible reminder signal which, for example, reads out the date that the last daily dose has been taken and/or reminds one when the next dose is to be taken.

Dosage, Host and Safety

The compounds of the present invention are stable and can be used safely. In particular, the compounds of the present invention are useful as PARP inhibitors for a variety of subjects (e.g., humans, non-human mammals and non-mammals). The optimal dose may vary depending upon such conditions as, for example, the type of subject, the body weight of the subject, the route of administration, and specific properties of the particular compound being used. In general, the daily dose for oral administration to an adult (body weight of about 60 kg) is about 1 to 1000 mg, about 3 to 300 mg, or about 10 to 200 mg. It will be appreciated that the daily dose can be given in a single administration or in multiple (e.g., 2 or 3) portions a day.

Combination Therapies

A wide variety therapeutic agents may have a therapeutic additive or synergistic effect with PARP inhibitors according to the present invention. Combination therapies that comprise one or more compounds of the present invention with one or more other therapeutic agents can be used, for example, to: 1) enhance the therapeutic effect(s) of the one or more compounds of the present invention and/or the one or more other therapeutic agents; 2) reduce the side effects exhibited by the one or more compounds of the present invention and/or the one or more other therapeutic agents; and/or 3) reduce the effective dose of the one or more compounds of the present invention and/or the one or more other therapeutic agents.

In one embodiment, a method is provided for treating a cell proliferative disease state comprising treating cells with a compound according to the present invention in combination with an anti-proliferative agent, wherein the cells are treated with the compound according to the present invention before, at the same time, and/or after the cells are treated with the anti-proliferative agent, referred to herein as combination therapy. It is noted that treatment of one agent before another is referred to herein as sequential therapy, even if the agents are also administered together. It is noted that combination therapy is intended to cover when agents are administered before or after each other (sequential therapy) as well as when the agents are administered at the same time.

Examples of therapeutic agents that may be used in combination with PARP inhibitors include, but are not limited to, anticancer agents, alkylating agents, antibiotic agents, antimetabolic agents, hormonal agents, plant-derived agents, and biologic agents.

Alkylating agents are polyfunctional compounds that have the ability to substitute alkyl groups for hydrogen ions. Examples of alkylating agents include, but are not limited to, bischloroethylamines (nitrogen mustards, e.g. chlorambucil, cyclophosphamide, ifosfamide, mechlorethamine, melphalan, uracil mustard), aziridines (e.g. thiotepa), alkyl alkone sulfonates (e.g. busulfan), nitrosoureas (e.g. carmustine, lomustine, streptozocin), nonclassic alkylating agents (altretamine, dacarbazine, and procarbazine), platinum compounds (carboplastin and cisplatin). These compounds react with phosphate, amino, hydroxyl, sulfihydryl, carboxyl, and imidazole groups. Under physiological conditions, these drugs ionize and produce positively charged ion that attach to susceptible nucleic acids and proteins, leading to cell cycle arrest and/or cell death. Combination therapy including a PARP inhibitor and an alkylating agent may have therapeutic synergistic effects on cancer and reduce sides affects associated with these chemotherapeutic agents.

Antibiotic agents are a group of drugs that are produced in a manner similar to antibiotics as a modification of natural products. Examples of antibiotic agents include, but are not limited to, anthracyclines (e.g. doxorubicin, daunorubicin, epirubicin, idarubicin and anthracenedione), mitomycin C, bleomycin, dactinomycin, plicatomycin. These antibiotic agents interfere with cell growth by targeting different cellular components. For example, anthracyclines are generally believed to interfere with the action of DNA topoisomerase II in the regions of transcriptionally active DNA, which leads to DNA strand scissions. Bleomycin is generally believed to chelate iron and forms an activated complex, which then binds to bases of DNA, causing strand scissions and cell death. Combination therapy including a PARP inhibitor and an antibiotic agent may have therapeutic synergistic effects on cancer and reduce sides affects associated with these chemotherapeutic agents.

Antimetabolic agents are a group of drugs that interfere with metabolic processes vital to the physiology and proliferation of cancer cells. Actively proliferating cancer cells require continuous synthesis of large quantities of nucleic acids, proteins, lipids, and other vital cellular constituents. Many of the antimetabolites inhibit the synthesis of purine or pyrimidine nucleosides or inhibit the enzymes of DNA replication. Some antimetabolites also interfere with the synthesis of ribonucleosides and RNA and/or amino acid metabolism and protein synthesis as well. By interfering with the synthesis of vital cellular constituents, antimetabolites can delay or arrest the growth of cancer cells. Examples of antimetabolic agents include, but are not limited to, fluorouracil (5-FU), floxuridine (5-FUdR), methotrexate, leucovorin, hydroxyurea, thioguanine (6-TG), mercaptopurine (6-MP), cytarabine, pentostatin, fludarabine phosphate, cladribine (2-CDA), asparaginase, and gemcitabine. Combination therapy including a PARP inhibitor and a antimetabolic agent may have therapeutic synergistic effects on cancer and reduce sides affects associated with these chemotherapeutic agents.

Hormonal agents are a group of drug that regulate the growth and development of their target organs. Most of the hormonal agents are sex steroids and their derivatives and analogs thereof, such as estrogens, androgens, and progestins. These hormonal agents may serve as antagonists of receptors for the sex steroids to down regulate receptor expression and transcription of vital genes. Examples of such hormonal agents are synthetic estrogens (e.g. diethylstibestrol), antiestrogens (e.g. tamoxifen, toremifene, fluoxymesterol and raloxifene), antiandrogens (bicalutamide, nilutamide, flutamide), aromatase inhibitors (e.g., aminoglutethimide, anastrozole and tetrazole), ketoconazole, goserelin acetate, leuprolide, megestrol acetate, and mifepristone. Combination therapy including a PARP inhibitor and a hormonal agent may have therapeutic synergistic effects on cancer and reduce sides affects associated with these chemotherapeutic agents.

Plant-derived agents are a group of drugs that are derived from plants or modified based on the molecular structure of the agents. Examples of plant-derived agents include, but are not limited to, vinca alkaloids (e.g., vincristine, vinblastine, vindesine, vinzolidine, and vinorelbine), podophyllotoxins (e.g., etoposide (VP-16) and teniposide (VM-26)), taxanes (e.g., paclitaxel, and docetaxel). These plant-derived agents generally act as antimitotic agents that bind to tubulin and inhibit mitosis. Podophyllotoxins such as etoposide are believed to interfere with DNA synthesis by interacting with topoisomerase II, leading to DNA strand scission. Combination therapy including a PARP inhibitor and a plant-derived agent may have therapeutic synergistic effects on cancer and reduce sides affects associated with these chemotherapeutic agents.

Biologic agents are a group of biomolecules that elicit cancer/tumor regression when used alone or in combination with chemotherapy and/or radiotherapy. Examples of biologic agents include, but are not limited to, immuno-modulating proteins such as cytokines, monoclonal antibodies against tumor antigens, tumor suppressor genes, and cancer vaccines. Combination therapy including a PARP inhibitor and a biologic agent may have therapeutic synergistic effects on cancer, enhance the patient's immune responses to tumorigenic signals, and reduce potential sides affects associated with this chemotherapeutic agent.

Cytokines possess profound immunomodulatory activity. Some cytokines such as interleukin-2 (IL-2, aldesleukin) and interferon have demonstrated antitumor activity and have been approved for the treatment of patients with metastatic renal cell carcinoma and metastatic malignant melanoma. IL-2 is a T-cell growth factor that is central to T-cell-mediated immune responses. The selective antitumor effects of IL-2 on some patients are believed to be the result of a cell-mediated immune response that discriminate between self and nonself. Examples of interleukins that may be used in conjunction with PARP inhibitor include, but are not limited to, interleukin 2 (IL-2), and interleukin 4 (IL-4), interleukin 12 (IL-12).

Interferon include more than 23 related subtypes with overlapping activities, all of the IFN subtypes within the scope of the present invention. IFN has demonstrated activity against many solid and hematologic malignancies, the later appearing to be particularly sensitive.

Other cytokines that may be used in conjunction with a PARP inhibitor include those cytokines that exert profound effects on hematopoiesis and immune functions. Examples of such cytokines include, but are not limited to erythropoietin, granulocyte-CSF (filgrastin), and granulocyte, macrophage-CSF (sargramostim). These cytokines may be used in conjunction with a PARP inhibitor to reduce chemotherapy-induced myelopoietic toxicity.

Other immuno-modulating agents other than cytokines may also be used in conjunction with a PARP inhibitor to inhibit abnormal cell growth. Examples of such immuno-modulating agents include, but are not limited to bacillus Calmette-Guerin, levamisole, and octreotide, a long-acting octapeptide that mimics the effects of the naturally occurring hormone somatostatin.

Monoclonal antibodies against tumor antigens are antibodies elicited against antigens expressed by tumors, preferably tumor-specific antigens. For example, monoclonal antibody HERCEPTIN® (Trastruzumab) is raised against human epidermal growth factor receptor-2 (HER2) that is overexpressed in some breast tumors including metastatic breast cancer. Overexpression of HER2 protein is associated with more aggressive disease and poorer prognosis in the clinic. HERCEPTIN® is used as a single agent for the treatment of patients with metastatic breast cancer whose tumors over express the HER2 protein. Combination therapy including PARP inhibitor and HERCEPTIN® may have therapeutic synergistic effects on tumors, especially on metastatic cancers.

Another example of monoclonal antibodies against tumor antigens is RITUXAN® (Rituximab) that is raised against CD20 on lymphoma cells and selectively deplete normal and malignant CD20+ pre-B and mature B cells. RITUXAN® is used as single agent for the treatment of patients with relapsed or refractory low-grade or follicular, CD20+, B cell non-Hodgkin's lymphoma. Combination therapy including PARP inhibitor and RITUXAN® may have therapeutic synergistic effects not only on lymphoma, but also on other forms or types of malignant tumors.

Tumor suppressor genes are genes that function to inhibit the cell growth and division cycles, thus preventing the development of neoplasia. Mutations in tumor suppressor genes cause the cell to ignore one or more of the components of the network of inhibitory signals, overcoming the cell cycle check points and resulting in a higher rate of controlled cell growth—cancer. Examples of the tumor suppressor genes include, but are not limited to, DPC-4, NF-1, NF-2, RB, p53, WT1, BRCA1, and BRCA2.

DPC-4 is involved in pancreatic cancer and participates in a cytoplasmic pathway that inhibits cell division. NF-1 codes for a protein that inhibits Ras, a cytoplasmic inhibitory protein. NF-1 is involved in neurofibroma and pheochromocytomas of the nervous system and myeloid leukemia. NF-2 encodes a nuclear protein that is involved in meningioma, schwanoma, and ependymoma of the nervous system. RB codes for the pRB protein, a nuclear protein that is a major inhibitor of cell cycle. RB is involved in retinoblastoma as well as bone, bladder, small cell lung and breast cancer. P53 codes for p53 protein that regulates cell division and can induce apoptosis. Mutation and/or inaction of p53 are found in a wide ranges of cancers. WT1 is involved in Wilms tumor of the kidneys. BRCA1 is involved in breast and ovarian cancer, and BRCA2 is involved in breast cancer. The tumor suppressor gene can be transferred into the tumor cells where it exerts its tumor suppressing functions. Combination therapy including a PARP inhibitor and a tumor suppressor may have therapeutic synergistic effects on patients suffering from various forms of cancers.

Cancer vaccines are a group of agents that induce the body's specific immune response to tumors. Most of cancer vaccines under research and development and clinical trials are tumor-associated antigens (TAAs). TAAs are structures (i.e. proteins, enzymes or carbohydrates) which are present on tumor cells and relatively absent or diminished on normal cells. By virtue of being fairly unique to the tumor cell, TAAs provide targets for the immune system to recognize and cause their destruction. Example of TAAs include, but are not limited to gangliosides (GM2), prostate specific antigen (PSA), alpha-fetoprotein (AFP), carcinoembryonic antigen (CEA) (produced by colon cancers and other adenocarcinomas, e.g. breast, lung, gastric, and pancreas cancer s), melanoma associated antigens (MART-1, gp100, MAGE 1,3 tyrosinase), papillomavirus E6 and E7 fragments, whole cells or portions/lysates of antologous tumor cells and allogeneic tumor cells.

An adjuvant may be used to augment the immune response to TAAs. Examples of adjuvants include, but are not limited to, bacillus Calmette-Guerin (BCG), endotoxin lipopolysaccharides, keyhole limpet hemocyanin (GKLH), interleukin-2 (IL-2), granulocyte-macrophage colony-stimulating factor (GM-CSF) and cytoxan, a chemotherapeutic agent which is believe to reduce tumor-induced suppression when given in low doses.

Further examples of therapeutic agents that may be used in combination with PARP inhibitors include, but are not limited to, P13/Akt signaling inhibitors. Examples of P13/Akt inhibitors that may be used in combination with PARP inhibitors include, but are not limited to, human epidermal growth factor receptor (HER2) inhibitors. Examples of HER2 inhibitors include, but are not limited to, Herceptin® (Trastruzumab) and Tykerb® (Lapatinib). Tykerb®, a small molecule that can be administered orally, inhibits the tyrosine kinase components of ErbB1 and ErbB2 receptors. Stimulation of ErbB1 and ErbB2 is associated with cell proliferation and with multiple processes involved in tumor progression, invasion, and metastasis. Overexpression of these receptors has been reported in a variety of human tumors and is associated with poor prognosis and reduced overall survival.

Still further examples of therapeutic agents that may be used in combination with PARP inhibitors include, but are not limited to, histone deacetylase (HDAC) inhibitors. Examples of HDAC inhibitors that may be used in combination with PARP inhibitors include, but are not limited to, suberoylanilide hydroxamic acid (SAHA).

In addition, the PARP inhibitors of the present invention may be used in combination with aminoglyside antiobiotics, CHK inhibitors, cytotoxic drugs and/or topoisomerase inhibitors.

EXAMPLES

Preparation of PARP Inhibitors

Various methods may be developed for synthesizing compounds according to the present invention. Representative methods for synthesizing these compounds are provided in the Examples. It is noted, however, that the compounds of the present invention may also be synthesized by other synthetic routes that others may devise.

It will be readily recognized that certain compounds according to the present invention have atoms with linkages to other atoms that confer a particular stereochemistry to the compound (e.g., chiral centers). It is recognized that synthesis of compounds according to the present invention may result in the creation of mixtures of different stereoisomers (i.e., enantiomers and diastereomers). Unless a particular stereochemistry is specified, recitation of a compound is intended to encompass all of the different possible stereoisomers.

Various methods for separating mixtures of different stereoisomers are known in the art. For example, a racemic mixture of a compound may be reacted with an optically active resolving agent to form a pair of diastereomeric compounds. The diastereomers may then be separated in order to recover the optically pure enantiomers. Dissociable complexes may also be used to resolve enantiomers (e.g., crystalline diastereomeric salts). Diastereomers typically have sufficiently distinct physical properties (e.g., melting points, boiling points, solubilities, reactivity, etc.) and can be readily separated by taking advantage of these dissimilarities. For example, diastereomers can typically be separated by chromatography or by separation/resolution techniques based upon differences in solubility. A more detailed description of techniques that can be used to resolve stereoisomers of compounds from their racemic mixture can be found in Jean Jacques Andre Collet, Samuel H. Wilen, Enantiomers, Racemates and Resolutions, John Wiley & Sons, Inc. (1981).

Compounds according to the present invention can also be prepared as a pharmaceutically acceptable acid addition salt by reacting the free base form of the compound with a pharmaceutically acceptable inorganic or organic acid. Alternatively, a pharmaceutically acceptable base addition salt of a compound can be prepared by reacting the free acid form of the compound with a pharmaceutically acceptable inorganic or organic base. Inorganic and organic acids and bases suitable for the preparation of the pharmaceutically acceptable salts of compounds are set forth in the definitions section of this Application. Alternatively, the salt forms of the compounds can be prepared using salts of the starting materials or intermediates.

The free acid or free base forms of the compounds can be prepared from the corresponding base addition salt or acid addition salt form. For example, a compound in an acid addition salt form can be converted to the corresponding free base by treating with a suitable base (e.g., ammonium hydroxide solution, sodium hydroxide, and the like). A compound in a base addition salt form can be converted to the corresponding free acid by treating with a suitable acid (e.g., hydrochloric acid, etc).

The N-oxides of compounds according to the present invention can be prepared by methods known to those of ordinary skill in the art. For example, N-oxides can be prepared by treating an unoxidized form of the compound with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0° C. Alternatively, the N-oxides of the compounds can be prepared from the N-oxide of an appropriate starting material.

Compounds in an unoxidized form can be prepared from N-oxides of compounds by treating with a reducing agent (e.g., sulfur, sulfur dioxide, triphenyl phosphine, lithium borohydride, sodium borohydride, phosphorus trichloride, tribromide, or the like) in an suitable inert organic solvent (e.g., acetonitrile, ethanol, aqueous dioxane, or the like) at 0 to 80° C.

Prodrug derivatives of the compounds can be prepared by methods known to those of ordinary skill in the art (e.g., for further details see Saulnier et al. (1994), Bioorganic and Medicinal Chemistry Letters, Vol. 4, p. 1985). For example, appropriate prodrugs can be prepared by reacting a non-derivatized compound with a suitable carbamylating agent (e.g., 1,1-acyloxyalkylcarbonochloridate, para-nitrophenyl carbonate, or the like).

Protected derivatives of the compounds can be made by methods known to those of ordinary skill in the art. A detailed description of the techniques applicable to the creation of protecting groups and their removal can be found in T. W. Greene, Protecting Groups in Organic Synthesis, $3^{rd}$ edition, John Wiley & Sons, Inc. 1999.

Compounds according to the present invention may be conveniently prepared, or formed during the process of the invention, as solvates (e.g., hydrates). Hydrates of compounds of the present invention may be conveniently prepared by recrystallization from an aqueous/organic solvent mixture, using organic solvents such as dioxin, tetrahydrofuran or methanol.

Compounds according to the present invention can also be prepared as their individual stereoisomers by reacting a racemic mixture of the compound with an optically active resolving agent to form a pair of diastereomeric compounds, separating the diastereomers and recovering the optically pure enantiomer. While resolution of enantiomers can be carried out using covalent diastereomeric derivatives of compounds, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chromatography or, preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques Andre Collet, Samuel H. Wilen, Enantiomers, Racemates and Resolutions, John Wiley & Sons, Inc. (1981).

As used herein the symbols and conventions used in these processes, schemes and examples are consistent with those used in the contemporary scientific literature, for example, the Journal of the American Chemical Society or the Journal of Biological Chemistry. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

μL (microliters)
atm (atmosphere)
BOC (tert-butyloxycarbonyl)
BSA (Bovine Serum Albumin)
CDI (1,1-carbonyldiimidazole)
DCE (dichloroethane)
DMAP (4-dimethylaminopyridine)

Ac (acetyl)
ATP (Adenosine Triphophatase)
BOP (bis(2-oxo-3-oxazolidinyl)phosphinic chloride)
CBZ (benzyloxycarbonyl)
DCC (dicyclohexylcarbodiimide)
DCM (dichloromethane)
DME (1,2-dimethoxyethane)

| | |
|---|---|
| DMF (N,N-dimethylformamide) | DMPU (N,N'-dimethylpropyleneurea) |
| DMSO (dimethylsulfoxide) | EDCI (ethylcarbodiimide hydrochloride) |
| EDTA (Ethylenediaminetetraacetic acid) | Et (ethyl) |
| Et$_2$O (diethyl ether) | EtOAc (ethyl acetate) |
| FMOC (9-fluorenylmethoxycarbonyl) | g (grams) |
| h (hours) | HOAc or AcOH (acetic acid) |
| HOBT (1-hydroxybenzotriazole) | HOSu (N-hydroxysuccinimide) |
| HPLC (high pressure liquid chromatography) | Hz (Hertz) |
| i.v. (intravenous) | IBCF (isobutyl chloroformate) |
| i-PrOH (isopropanol) | L (liters) |
| M (molar) | mCPBA (meta-chloroperbenzoic acid) |
| Me (methyl) | MeOH (methanol) |
| mg (milligrams) | MHz (megahertz) |
| min (minutes) | mL (milliliters) |
| mM (millimolar) | mmol (millimoles) |
| mol (moles) | MOPS (Morpholinepropanesulfonic acid) |
| mp (melting point) | NaOAc (sodium acetate) |
| OMe (methoxy) | psi (pounds per square inch) |
| RP (reverse phase) | RT (ambient temperature) |
| SPA (Scintillation Proximity Assay) | TBAF (tetra-n-butylammonium fluoride) |
| TBS (t-butyldimethylsilyl) | tBu (tert-butyl) |
| TEA (triethylamine) | TFA (trifluoroacetic acid) |
| TFAA (trifluoroacetic anhydride) | THF (tetrahydrofuran) |
| TIPS (triisopropylsilyl) | TLC (thin layer chromatography) |
| TMS (trimethylsilyl) | TMSE (2-(trimethylsilyl)ethyl) |
| Tr (retention time) | |

All references to ether or Et$_2$O are to diethyl ether; and brine refers to a saturated aqueous solution of NaCl. Unless otherwise indicated, all temperatures are expressed in °C. (degrees Centigrade). All reactions are conducted under an inert atmosphere at RT unless otherwise noted.

$^1$H NMR spectra were recorded on a Bruker Avance 400. Chemical shifts are expressed in parts per million (ppm). Coupling constants are in units of Hertz (Hz). Splitting patterns describe apparent multiplicities and are designated as s (singlet), d (doublet), t (triplet), q (quartet), m (multiplet), br (broad).

Low-resolution mass spectra (MS) and compound purity data were acquired on a Waters ZQ LC/MS single quadrupole system equipped with electrospray ionization (ESI) source, UV detector (220 and 254 nm), and evaporative light scattering detector (ELSD). Thin-layer chromatography was performed on 0.25 mm E. Merck silica gel plates (60F-254), visualized with UV light, 5% ethanolic phosphomolybdic acid, Ninhydrin or p-anisaldehyde solution. Flash column chromatography was performed on silica gel (230-400 mesh, Merck).

The starting materials and reagents used in preparing these compounds are either available from commercial suppliers such as the Aldrich Chemical Company (Milwaukee, Wis.), Bachem (Torrance, Calif.), Sigma (St. Louis, Mo.), or may be prepared by methods well known to a person of ordinary skill in the art, following procedures described in such standard references as Fieser and Fieser's Reagents for Organic Synthesis, vols. 1-17, John Wiley and Sons, New York, N.Y., 1991; Rodd's Chemistry of Carbon Compounds, vols. 1-5 and supps., Elsevier Science Publishers, 1989; Organic Reactions, vols. 1-40, John Wiley and Sons, New York, N.Y., 1991; March J.: Advanced Organic Chemistry, 4th ed., John Wiley and Sons, New York, N.Y.; and Larock: Comprehensive Organic Transformations, VCH Publishers, New York, 1989.

The entire disclosures of all documents cited throughout this application are incorporated herein by reference.

Synthetic Schemes for Compounds of the Present Invention

Compounds according to the present invention may be synthesized according to the reaction schemes shown below. Other reaction schemes could be readily devised by those skilled in the art. It should also be appreciated that a variety of different solvents, temperatures and other reaction conditions can be varied to optimize the yields of the reactions.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in "Protective Groups in Organic Chemistry" John Wiley and Sons, 1991.

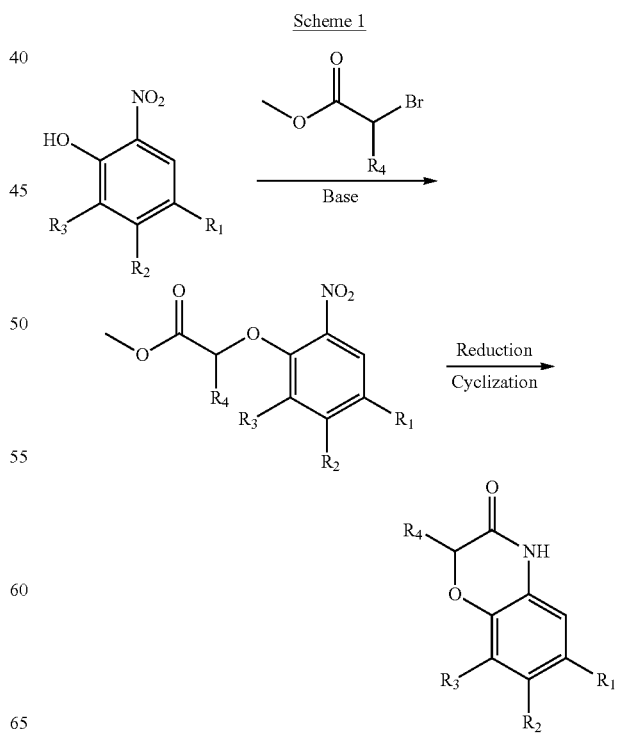

Scheme 1

A substituted phenol can be alkylated with various electrophiles such as α-bromoesters typically under basic conditions, in polar solvents such as DMF and at elevated temperatures. Reduction of the nitro group by, for example, heating with metals in acidic conditions such as iron dust in AcOH, results in cyclization of the intermediate amine to give the substituted benzoxazinone.

Scheme 2

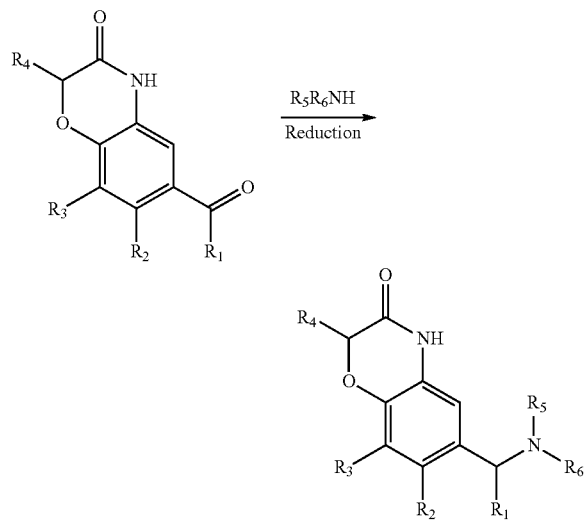

Treatment of the 6-carboxybenzoxazinone with an amine under reductive amination conditions, such as for example sodium triacetoxyborohydride in AcOH and dichloroethane solvent, yields the 6-aminomethyl derivative. Alternative borohydride reagents include for example NaCNBH$_3$.

Scheme 3

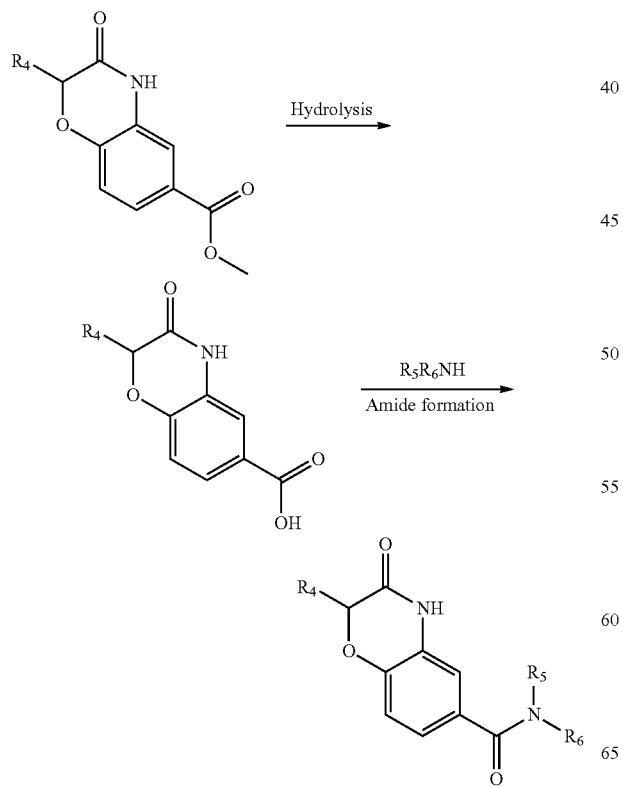

Hydrolysis of the 6-ester group can be accomplished with, for example, aqueous lithium hydroxide solution, followed by an acidic work-up to yield the carboxylic acid. Alternatively, other hydrolytic conditions can be utilized, both basic and acidic, including sodium hydroxide, potassium hydroxide, hydrochloric acid and others. Terminal carboxylic acids are converted to terminal carboxamides through activation of the acid with various coupling agents including HATU, followed by treatment with primary or secondary amines. Alternatively, other methods exist to convert carboxylic acids to carboxamides including conversion to an intermediate acid chloride or use of other activation reagents such as EDC, HOBt, EDAC, PyBOP, TATU and others.

Scheme 4

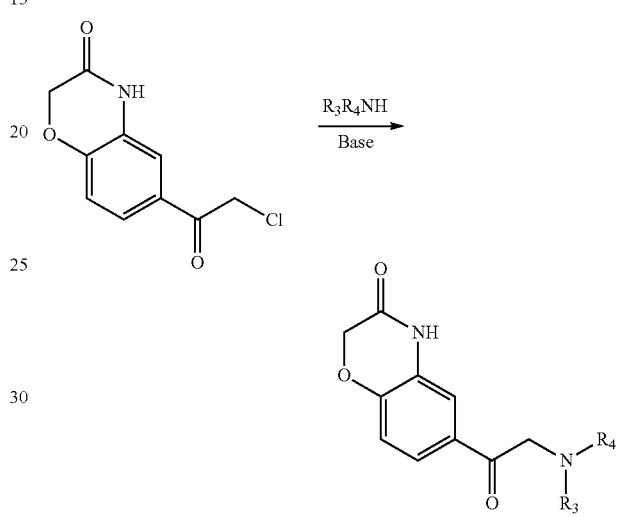

Amination of α-chloroketones under S$_N$2 displacement conditions can be performed by treatment with an amine, typically in the presence of a base such as triethylamine or by using an excess of the reactant amine, in a polar solvent such as EtOH, and often with heating.

Scheme 5

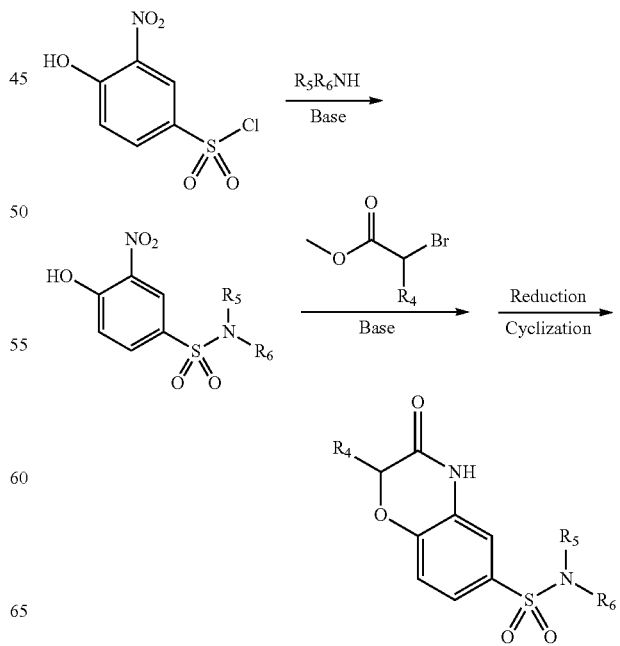

Treatment of a sulfonyl chloride with an amine, typically in the presence of a base yields the sulfonamide. The phenolic hydroxy group is then alkylated with an α-bromoester, typically in the presence of a base and polar solvent such as DMF and heating. Reduction and cyclization using conditions of Scheme 1 give the substituted benzoxazinone.

Scheme 6

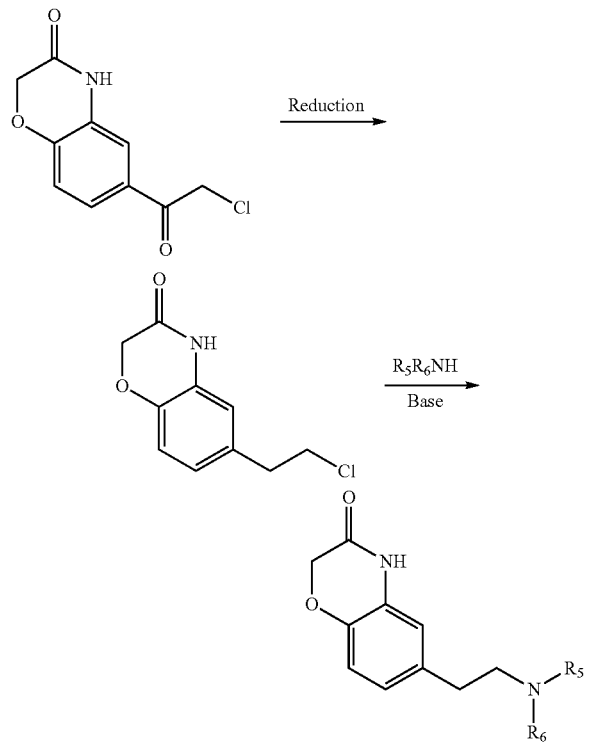

Scheme 7

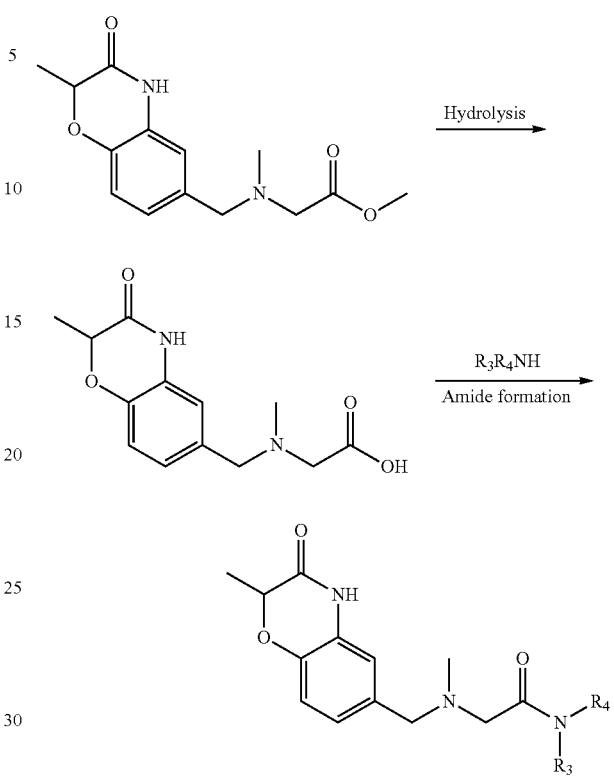

In similar fashion as for Scheme 3, hydrolysis of a terminal ester provides the terminal carboxylic acid. Likewise, treatment of the resultant acid with amine under coupling conditions yields the amide.

Scheme 8

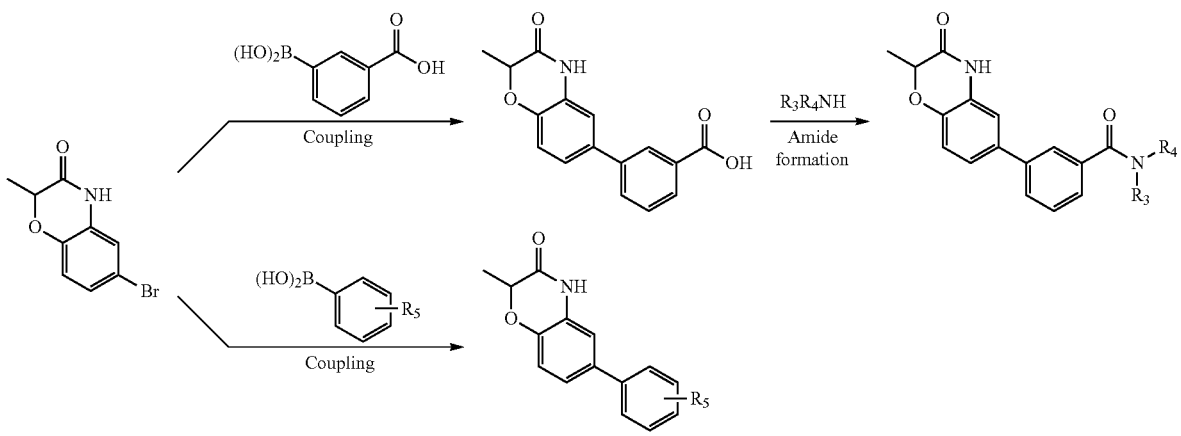

Reduction of the ketone group proceeds under conditions of, for example, triethylsilane with heating in TFA as solvent, affords the methylene product. Amination of the terminal chloro group, typically in the presence of a base such as $K_2CO_3$ and polar solvent such as DMF with heating, yields the desired terminal amine.

Treatment of 6-bromobenzoxazinones with phenyl boronic acids under "Suzuki" Pd-catalyzed coupling conditions, employing catalysts such as $Pd(PPh_3)_4$ and bases such as $Na_2CO_3$ with heating in polar solvents such as DMF, yield the phenyl-coupled product. A number of alternative Pd(0)

complexes known to those in the art can be utilized as catalysts. In similar fashion to Scheme 7, carboxylic acids can be converted to carboxamides.

Scheme 9

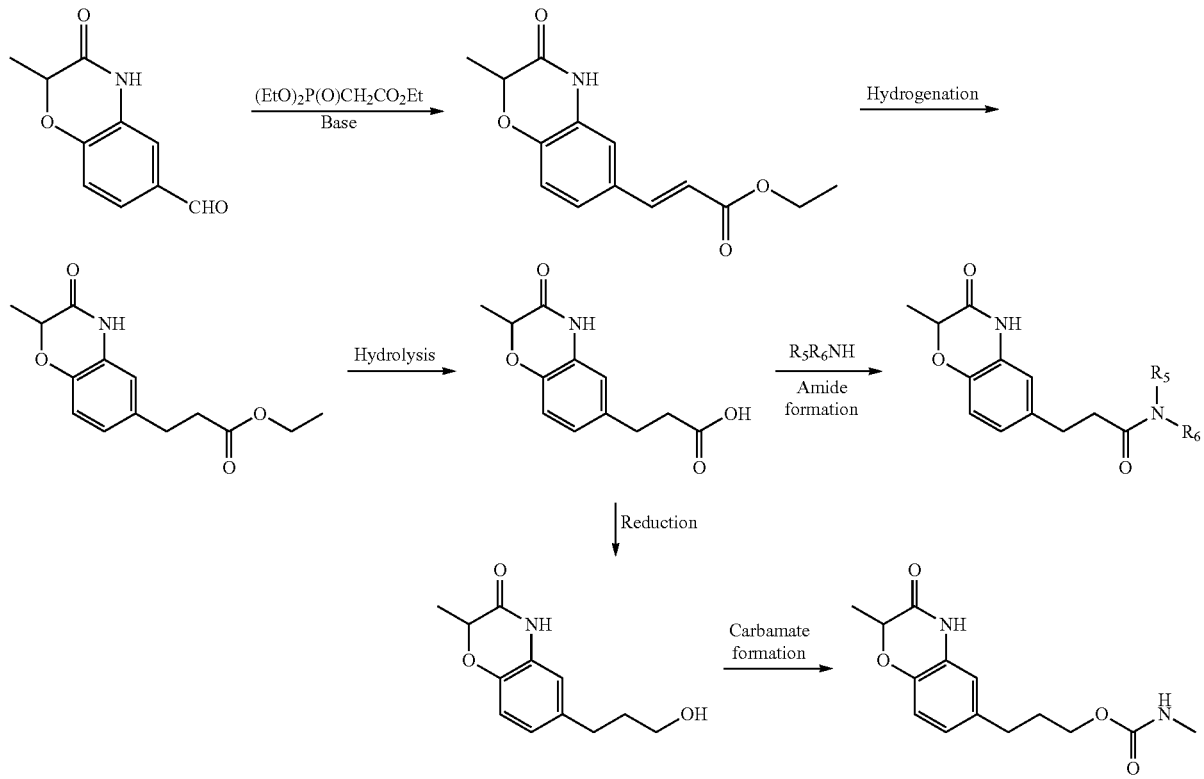

Subjecting 6-carboxybenzoxazinones to "Horner-Wadsworth-Emmons" reaction conditions, typically comprising a phosphonate ester, and a base such as tBuOK in THF with cooling, yields the desired styrene product. Hydrogenation of the styrene double-bond in the presence of hydrogen gas and catalysts such as palladium on carbon, typically in a solvent such as EtOH with optional heating, yields the reduced product. Hydrolysis of the ester under conditions typified in Scheme 7 affords the acid, and subsequent coupling with amines provides the amide. Alternatively, the acid can be reduced to the alcohol by treatment of the acid with reducing agents such as borane, typically in a solvent such as THF with cooling. Reaction of the alcohol with reagents including triphosgene followed by addition of an amine such as methylamine hydrochloride affords the methyl carbamate derivative.

Chiral components can be separated and purified using any of a variety of techniques known to those skilled in the art. For example, chiral components can be purified using supercritical fluid chromatography (SFC). In one particular variation, chiral analytical SFC/MS analyses are conducted using a Berger analytical SFC system (AutoChem, Newark, Del.) which consists of a Berger SFC dual pump fluid control module with a Berger FCM 1100/1200 supercritical fluid pump and FCM 1200 modifier fluid pump, a Berger TCM 2000 oven, and an Alcott 718 autosampler. The integrated system can be controlled by BI-SFC Chemstation software version 3.4. Detection can be accomplished with a Waters ZQ 2000 detector operated in positive mode with an ESI interface and a scan range from 200-800 Da with 0.5 second per scan. Chromatographic separations can be performed on a ChiralPak AD-H, ChiralPak AS-H, ChiralCel OD-H, or ChiralCel OJ-H column (5µ, 4.6×250 mm; Chiral Technologies, Inc. West Chester, Pa.) with 10 to 40% methanol as the modifier and with or without ammonium acetate (10 mM). Any of a variety of flow rates can be utilized including, for example, 1.5 or 3.5 mL/min with an inlet pressure set at 100 bar. Additionally, a variety of sample injection conditions can be used including, for example, sample injections of either 5 or 104 in methanol at 0.1 mg/mL in concentration.

In another variation, preparative chiral separations are performed using a Berger MultiGram II SFC purification system. For example, samples can be loaded onto a ChiralPak AD column (21×250 mm, 10µ). In particular variations, the flow rate for separation can be 70 mL/min, the injection volume up to 2 mL, and the inlet pressure set at 130 bar. Stacked injections can be applied to increase the efficiency.

In another variation, analytical and preparative HPLC separations were carried on a Waters purification system equipped with the following components: a Waters 2525 pump for single column analysis and purification and/or two Waters 2525 pumps with a column fluidic organizer (CFO) for two-column purifications (the early termination of run after peak collection utilized in case of two-pump and two-column applications); a Waters 515 pump as the make-up flow; a Waters 2767 automated sample manager with one analytical and one preparative injector to conduct sample injection as well as fraction collection; a Waters 2487 dual wavelength UV detector; a Waters 2420 ELSD detector; and a Waters ZQ 2000 Single Quadrupole Mass Spectrometer with an electrospray ion source. Mass spectrometric data were acquired in the full scan (200-800 amu) and positive ionization mode with dwell time of 1.0 s. The ion source parameters used were as following: sprayer voltage, 3.2 kV; cone voltage, 25 V; desolvation temperature, 350° C.; and source temperature, 150° C. The instrument resolution was 1000 (10% valley definition). MassLynx 4.1, AutoLynx, OpenLynx, and FractionLynx software programs were used for data acquisition, automation, and fraction collection control. The purification system allows for running either analytical or preparative separation based on user selected methods. The fraction collections were default by mass-trigger fractionation and UV or ELSD trigger as alternatives.

Acidic Mobile Phase

The analytical separations were carried on a Waters SunFire C18 50×4.6 mm I.D. 5 μm column at flow rate of 3.5 mL/min with gradient elution (a total of 3 or 5 minutes chromatographic time) and the preparative separations were achieved on a Waters SunFire C18 75×30 mm I.D. 5 μm OBD column with a Waters SunFire preparative 10×19 mm I.D. 5 μm guard column at flow rate 50 mL/min and gradient elution (a total of 8 minutes chromatographic time). Mobile phase A was 0.05% TFA in water and mobile phase B was 0.035% TFA in acetonitrile. For preparative chromatographic separation, a make-up flow (0.1% formic acid in 20/80, v/v, water/methanol) was used to assist the ionization of signals of mass spectrometer. In case of high throughput preparative purification with two-pump/two-column and early termination run after peak collection, the chromatographic time for each run was user-defined and usually between 4-5 minutes.

Basic Mobile Phase

The analytical separations were carried on a Gemini C18 50×4.6 mm I.D. 5 μm column (Phenomenex, Torrance, Calif.) at flow rate of 3.5 mL/min with gradient elution (a total of 3 or 5 minutes chromatographic time) and the preparative separations were achieved on a Phenomenex Gemini C18 75×30 mm I.D. 5 μm column with a Phenomenex Gemini preparative 10×19 mm I.D. 5 μm guard column at flow rate 50 mL/min with gradient elution (a total of 8 minutes chromatographic time). Mobile phase A was 10 mM NH$_4$HCO$_3$ in water at pH=9.5-10 and mobile phase B was 10 mM NH$_4$HCO$_3$ in 20/80 (v/v) water/acetonitrile at pH=9.5-10. In case of preparative chromatographic separation, a make-up flow (0.1% formic acid in 20/80, v/v, water/methanol) was used to assist the ionization of signals of mass spectrometer.

In each of the above reaction procedures or schemes, the various substituents may be selected from among the various substituents otherwise taught herein.

Descriptions of the syntheses of particular compounds according to the present invention based on the above reaction scheme are set forth herein.

Examples of PARP Inhibitors

The present invention is further exemplified, but not limited by, the following examples that describe the synthesis of particular compounds according to the invention.

General Procedure for Alkylation of Substituted-2-nitrophenols

Synthesis of methyl 2-(4-formyl-2-nitrophenoxy)acetate (1)

To a 200 mL round-bottomed flask was added 4-hydroxy-3-nitrobenzaldehyde (1.671 g, 10.0 mmol), methyl 2-bromoacetate (0.950 mL, 10.00 mmol), and K$_2$CO$_3$ (1.382 g, 10.00 mmol) in DMF (25 mL). The reaction was stirred at 80° C. for 2 hr. The reaction was poured over ice and the resulting solid was isolated by filtration, washed with water and dried in vacuo to give a light yellow solid (2.031 g, 85% yield). $^1$H NMR (400 MHz, DMSO-d$_6$) δ ppm 3.71 (s, 3H) 5.18 (s, 2H) 7.52 (d, J=8.84 Hz, 1 H) 8.14 (dd, J=8.84, 2.02 Hz, 1H) 8.44 (d, J=2.02 Hz, 1H) 9.95 (s, 1H). ESI-MS: m/z 240.1 (M+H)$^+$.

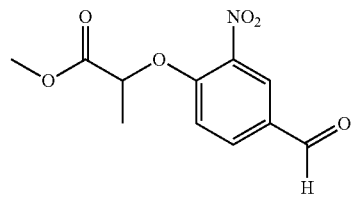 [SMILES: COC(=O)C(C)Oc1ccc(C=O)cc1[N+](=O)[O-]]

Methyl 2-(4-formyl-2-nitrophenoxy)propanoate (2)

Using 4-hydroxy-3-nitrobenzaldehyde as the phenol and methyl-2-bromopropanoate as the alkylating agent in the general procedure for alkylation of substituted-2-nitrophenols gives a light yellow solid (1.55 g, 61% yield): $^1$H NMR (400 MHz, DMSO-d$_6$) δ ppm 1.57 (d, J=6.82 Hz, 3H) 3.70 (s, 3H) 5.46 (q, J=6.65 Hz, 1H) 7.45 (d, J=8.84 Hz, 1H) 8.13 (d, J=8.84 Hz, 1H) 8.43 (s, 1H) 9.94 (s, 1 H). ESI-MS: m/z 254.1 (M+H)$^+$.

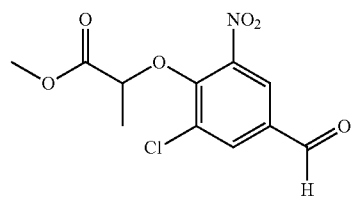 [SMILES: COC(=O)C(C)Oc1c(Cl)cc(C=O)cc1[N+](=O)[O-]]

Methyl 2-(2-chloro-4-formyl-6-nitrophenoxy)propanoate (3)

Using 3-chloro-4-hydroxy-5-nitrobenzaldehyde as the phenol and methyl-2-bromopropanoate as the alkylating agent in the general procedure for alkylation of substituted-2-nitrophenols gives a light yellow oil: $^1$H NMR (DMSO-d$_6$, 400 MHz): δ ppm 9.98 (s, 1H), 8.43 (d, J=1.8 Hz, 1H), 8.35 (d, J=2.0 Hz, 1H), 5.08-5.15 (m, 1H), 3.62 (s, 3H), 1.57 (d, J=6.8 Hz, 3H). ESI-MS: m/z 328.1 (M+H)$^+$.

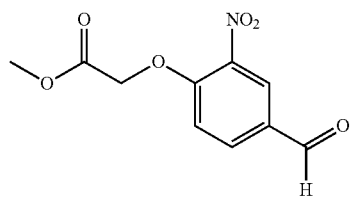

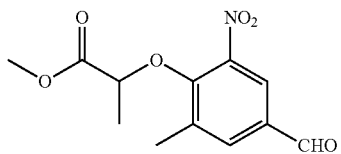 [SMILES: COC(=O)C(C)Oc1c(C)cc(C=O)cc1[N+](=O)[O-]]

Methyl 2-(4-formyl-2-methyl-6-nitrophenoxy)propanoate (4)

Using 4-hydroxy-3-methyl-5-nitrobenzaldehyde as the phenol and methyl-2-bromopropanoate as the alkylating agent in the general procedure for alkylation of substituted-2-nitrophenols gives a tan solid: $^1$H NMR (DMSO-$d_6$, 400 MHz): δ ppm 9.97 (s, 1H), 8.29 (d, J=1.5 Hz, 1H), 8.09 (d, J=1.5 Hz, 1 H), 4.82 (q, J=6.8 Hz, 1H), 3.62 (s, 3H), 2.42 (s, 3H), 1.52 (d, J=6.8 Hz, 3H). ESI-MS: m/z 268.1 (M+H)$^+$.

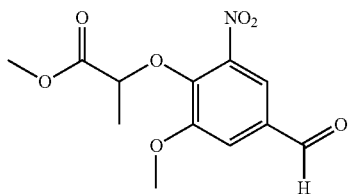 [SMILES: COC(=O)C(C)Oc1c(OC)cc(C=O)cc1[N+](=O)[O-]]

Methyl 2-(4-formyl-2-methoxy-6-nitrophenoxy)propanoate (5)

Using 4-hydroxy-3-methoxy-5-nitrobenzaldehyde as the phenol and methyl-2-bromopropanoate as the alkylating agent in the general procedure for alkylation of substituted-2-nitrophenols gives a dark oil: $^1$H NMR (DMSO-$d_6$, 400 MHz): δ ppm 9.95 (s, 1H), 8.03 (d, J=1.8 Hz, 1H), 7.80 (d, J=1.8 Hz, 1 H), 5.15 (q, J=6.8 Hz, 1H), 3.95 (s, 3H), 3.63 (s, 3H), 1.50 (d, J=6.8 Hz, 3H). ESI-MS: m/z 284.1 (M+H)$^+$.

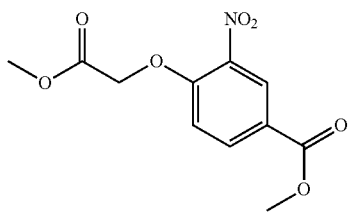 [SMILES: COC(=O)COc1ccc(C(=O)OC)cc1[N+](=O)[O-]]

Methyl 4-(2-methoxy-2-oxoethoxy)-3-nitrobenzoate (6)

Using methyl 4-hydroxy-3-nitrobenzoate as the phenol and methyl 2-bromoacetate as the alkylating agent in the general procedure for alkylation of substituted-2-nitrophenols gives a light yellow solid: $^1$H NMR (DMSO-$d_6$, 400 MHz): δ ppm 8.39 (d, J=2.0 Hz, 1H), 8.15 (dd, J=8.8, 2.3 Hz, 1H), 7.44 (d, J=8.8 Hz, 1H), 5.16 (s, 2H), 3.87 (s, 3H), 3.71 (s, 3H). ESI-MS: m/z 270.1 (M+H)$^+$.

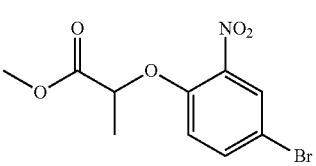 [SMILES: COC(=O)C(C)Oc1ccc(Br)cc1[N+](=O)[O-]]

Methyl 2-(4-bromo-2-nitrophenoxy)propanoate (7)

Using 4-bromo-2-nitrophenol as the phenol and methyl-2-bromopropanoate as the alkylating agent in the general procedure for alkylation of substituted-2-nitrophenols gives a dark red oil: $^1$H NMR (DMSO-$d_6$, 400 MHz): δ ppm 8.13 (d, J=2.5 Hz, 1H), 7.80 (dd, J=8.8, 2.5 Hz, 1H), 7.24 (d, J=9.1 Hz, 1H), 5.29 (q, J=6.8 Hz, 1H), 3.68 (s, 3H), 1.52 (d, J=6.6 Hz, 3H). ESI-MS: m/z 305.1 (M+H)$^+$.

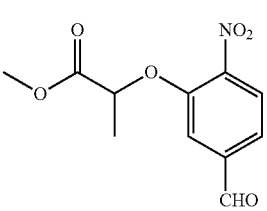 [SMILES: COC(=O)C(C)Oc1cc(C=O)ccc1[N+](=O)[O-]]

Methyl 2-(5-formyl-2-nitrophenoxy)propanoate (8)

Using 3-hydroxy-4-nitrobenzaldehyde as the phenol and methyl-2-bromopropanoate as the alkylating agent in the general procedure for alkylation of substituted-2-nitrophenols gives a tan solid: $^1$H NMR (DMSO-$d_6$, 400 MHz): δ ppm 10.03 (s, 1H), 8.08 (d, J=8.1 Hz, 1H), 7.62-7.79 (m, 2H), 5.43 (q, J=6.8 Hz, 1H), 3.69 (s, 3H), 1.55 (d, J=6.8 Hz, 3H). ESI-MS: m/z 254.1 (M+H)$^+$.

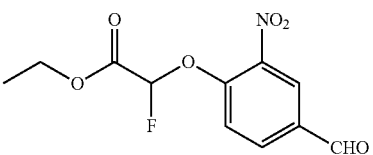 [SMILES: CCOC(=O)C(F)Oc1ccc(C=O)cc1[N+](=O)[O-]]

Ethyl 2-fluoro-2-(4-formyl-2-nitrophenoxy)acetate (9)

Using 3-hydroxy-4-nitrobenzaldehyde as the phenol and ethyl 2-bromo-2-fluoroacetate as the alkylating agent in the general procedure for alkylation of substituted-2-nitrophenols gives a yellow oil: $^1$H NMR (400 MHz, DMSO-$d_6$) δ ppm 1.26 (t, J=7.07 Hz, 3H), 4.26-4.38 (m, 2H), 6.83 (d, J=55.8 Hz, 1H), 7.76 (dd, J=8.84, 1.26 Hz, 1H), 8.28 (dd, J=8.59, 2.02 Hz, 1H) 8.54 (d, J=2.02 Hz, 1H), 10.02 (s, 1H). ESI-MS: m/z 272.1 (M+H)$^+$.

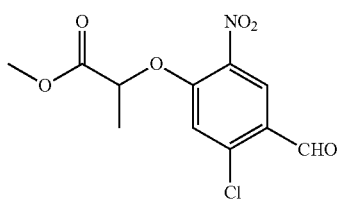 [SMILES: COC(=O)C(C)Oc1cc(Cl)c(C=O)cc1[N+](=O)[O-]]

Methyl 2-(5-chloro-4-formyl-2-nitrophenoxy)propanoate (10)

Using 2-chloro-3-hydroxy-4-nitrobenzaldehyde as the phenol and methyl-2-bromopropanoate as the alkylating agent in the general procedure for alkylation of substituted-2-nitrophenols gives an orange oil: $^1$H NMR (400 MHz, DMSO-d$_6$) δ ppm 1.57 (d, J=6.82 Hz, 3H), 3.71 (s, 3H), 5.57-5.62 (m, 1H), 7.67 (s, 1H), 8.35 (s, 1H), 10.17 (s, 1H). ESI-MS: m/z 288.1 (M+H)$^+$.

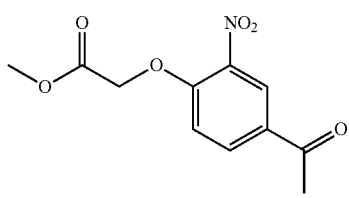 [SMILES: COC(=O)COc1ccc(C(C)=O)cc1[N+](=O)[O-]]

Methyl 2-(4-acetyl-2-nitrophenoxy)acetate (11)

Using 1-(4-hydroxy-3-nitrophenyl)ethanone as the phenol in the general procedure for alkylation of substituted-2-nitrophenols gives a yellow solid (2.235 g, 88% yield): $^1$H NMR (400 MHz, DMSO-d$_6$) δ ppm 2.59 (s, 3H) 3.71 (s, 3H) 5.16 (s, 2H) 7.43 (d, J=9.09 Hz, 1H) 8.17 (dd, J=8.84, 2.27 Hz, 1 H) 8.42 (d, J=2.02 Hz, 1H). ESI-MS: m/z 254.1 (M+H)$^+$.

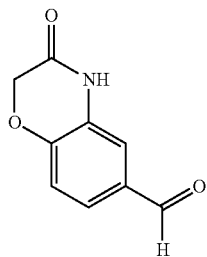 [SMILES: O=Cc1ccc2c(c1)NC(=O)CO2]

General Procedure for Reduction of Nitro Group and Subsequent Ring Closure

Synthesis of 3-oxo-3,4-dihydro-2H-benzo[b][1,4]oxazine-6-carbaldehyde (12)

To a 100 mL round-bottomed flask was added methyl 2-(4-formyl-2-nitrophenoxy)acetate (1) (1.381 g, 5.77 mmol) and iron (1.612 g, 28.9 mmol) in AcOH (23 mL). The reaction was stirred at 80° C. for 1 hr. The reaction was concentrated in vacuo and taken up in DCM/MeOH (1:1, 100 mL), filtered and the filtrate was concentrated in vacuo to give 4.3 g crude of a brown solid. The solid was taken up in water and filtered; the solid was washed with water and dried in vacuo to give a light brown solid (0.712 g, 70% yield). $^1$H NMR (400 MHz, DMSO-d$_6$) δ ppm 4.72 (s, 2 H) 7.14 (d, J=8.34 Hz, 1H) 7.38 (d, J=1.77 Hz, 1H) 7.54 (dd, J=8.21, 1.89 Hz, 1H) 9.84 (s, 1 H) 10.99 (s, 1H). ESI-MS: m/z 178.1 (M+H)$^+$.

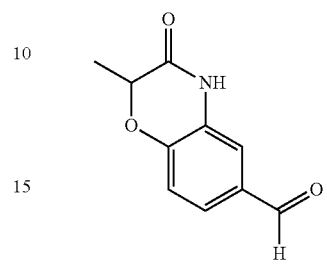

2-Methyl-3-oxo-3,4-dihydro-2H-benzo[b][1,4]oxazine-6-carbaldehyde (13)

Using 2-(4-formyl-2-nitrophenoxy)propanoate (2) (1.54 g, 6.08 mmol) in the general procedure for reduction of nitro group and subsequent ring closure gives a tan solid (1.049 g, 90% yield): $^1$H NMR (DMSO-d$_6$, 400 MHz): δ ppm 10.95 (s, 1H), 9.84 (s, 1H), 7.54 (dd, J=8.2, 1.9 Hz, 1H), 7.38 (d, J=1.8 Hz, 1H), 7.16 (d, J=8.3 Hz, 1H), 4.84 (q, J=6.8 Hz, 1H), 1.46 (d, J=6.8 Hz, 3 H). ESI-MS: m/z 192.0 (M+H)$^+$.

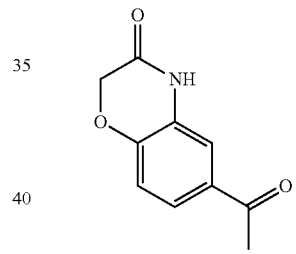

6-Acetyl-2H-benzo[b][1,4]oxazin-3(4H)-one (14)

Using methyl 2-(4-acetyl-2-nitrophenoxy)acetate (11) (2.235 g, 8.83 mmol) in the general procedure for reduction of nitro group and subsequent ring closure gives a tan solid (1.451 g, 86% yield): $^1$H NMR (400 MHz, DMSO-d$_6$) δ ppm 2.50 (s, 3H) 4.68 (s, 2H) 7.04 (d, J=8.34 Hz, 1H) 7.46 (d, J=1.77 Hz, 1H) 7.59 (dd, J=8.46, 1.89 Hz, 1H) 10.88 (s, 1H). ESI-MS: m/z 192.0 (M+H)$^+$.

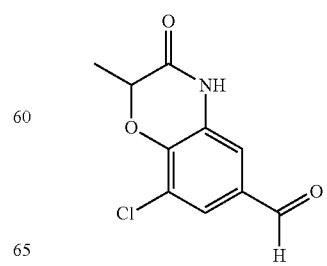

8-Chloro-2-methyl-3-oxo-3,4-dihydro-2H-benzo[b][1,4]oxazine-6-carbaldehyde (15)

Using 3 in the general procedure for reduction of nitro group and subsequent ring closure gives a tan solid: $^1$H NMR (DMSO-d$_6$, 400 MHz): δ ppm 11.14 (s, 1H), 9.83 (s, 1H), 7.69 (d, J=1.8 Hz, 1H), 7.34 (d, J=1.8 Hz, 1H), 4.99 (q, J=7.0 Hz, 1H), 1.49 (d, J=6.8 Hz, 3H). ESI-MS: m/z 226.1 (M+H)$^+$

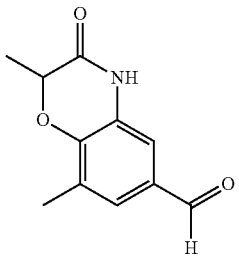

2,8-Dimethyl-3-oxo-3,4-dihydro-2H-benzo[b][1,4]oxazine-6-carbaldehyde (16)

Using 4 in the general procedure for reduction of nitro group and subsequent ring closure gives a tan solid: $^1$H NMR (DMSO-d$_6$, 400 MHz): δ ppm 10.89 (s, 1H), 9.81 (s, 1H), 7.44 (d, J=1.3 Hz, 1H), 7.24 (d, J=1.5 Hz, 1H), 4.78-4.87 (m, 1H), 2.24 (s, 3H), 1.45 (d, J=6.8 Hz, 3H). ESI-MS: m/z 206.1 (M+H)$^+$

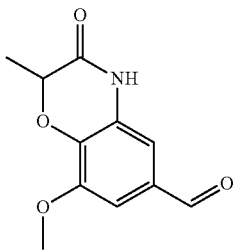 [SMILES: COc1cc(C=O)cc2c1OC(C)C(=O)N2]

8-Methoxy-2-methyl-3-oxo-3,4-dihydro-2H-benzo[b][1,4]oxazine-6-carbaldehyde (17)

Using 5 in the general procedure for reduction of nitro group and subsequent ring closure gives a tan solid: $^1$H NMR (DMSO-d$_6$, 400 MHz): δ ppm 10.92 (br. s., 1H), 9.82 (s, 1H), 7.25 (s, 1H), 7.08 (s, 1H), 4.79 (q, 1H), 3.86 (s, 3H), 1.45 (d, J=6.8 Hz, 3H). ESI-MS: m/z 222.1 (M+H)$^+$.

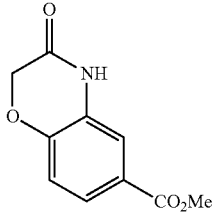 [SMILES: COC(=O)c1ccc2c(c1)NC(=O)CO2]

Methyl 3-oxo-3,4-dihydro-2H-benzo[b][1,4]oxazine-6-carboxylate (18)

Using 6 in the general procedure for reduction of nitro group and subsequent ring closure gives a white solid: $^1$H NMR (DMSO-d$_6$, 400 MHz): δ ppm 10.89 (s, 1H), 7.54 (dd, J=8.3, 2.0 Hz, 1H), 7.51 (d, J=1.8 Hz, 1H), 7.04 (d, J=8.1 Hz, 1H), 4.68 (s, 2H), 3.81 (s, 3H). ESI-MS: m/z 208.0 (M+H)$^+$.

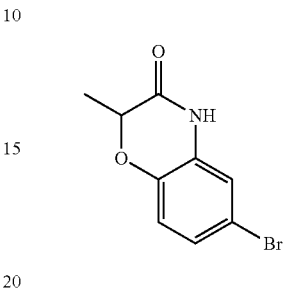

6-Bromo-2-methyl-2H-benzo[b][1,4]oxazin-3(4H)-one (19)

Using 7 in the general procedure for reduction of nitro group and subsequent ring closure gives a tan solid: $^1$H NMR (CHLOROFORM-d, 400 MHz): δ ppm 8.06 (br. s., 1H), 7.10 (dd, J=8.6, 1.8 Hz, 1H), 6.95 (d, J=2.0 Hz, 1H), 6.87 (d, J=8.6 Hz, 1H), 4.66 (q, J=6.8 Hz, 1H), 1.59 (d, J=6.8 Hz, 3H). ESI-MS: m/z 242.0 (M+H)$^+$.

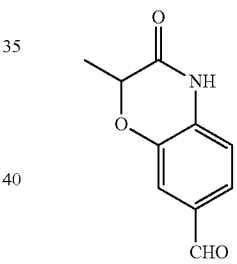

2-Methyl-3-oxo-3,4-dihydro-2H-benzo[b][1,4]oxazine-7-carbaldehyde (20)

Using 8 in the general procedure for reduction of nitro group and subsequent ring closure gives a off-white solid: $^1$H NMR (DMSO-d$_6$, 400 MHz): δ ppm 11.11 (s, 1H), 9.83 (s, 1H), 7.56 (dd, J=8.1, 1.8 Hz, 1H), 7.43 (d, J=1.8 Hz, 1H), 7.06 (d, J=7.8 Hz, 1H), 4.78 (q, J=6.8 Hz, 1H), 1.44 (d, J=6.8 Hz, 3H). ESI-MS: m/z 192.1 (M+H)$^+$.

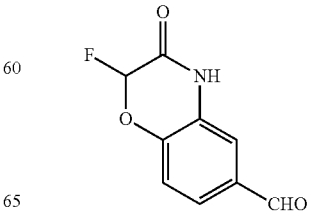

2-Fluoro-3-oxo-3,4-dihydro-2H-benzo[b][1,4]oxazine-6-carbaldehyde (21)

Using 9 in the general procedure for reduction of nitro group and subsequent ring closure gives a yellow solid. $^1$H NMR (400 MHz, DMSO-d$_6$) δ ppm 6.42 (d, J=51.5 Hz, 1H), 7.44 (d, J=8.1 Hz, 1H), 7.54 (d, J=1.5 Hz, 1H) 7.68 (dd, J=8.2, 1.9 Hz, 1H), 9.93 (s, 1H), 11.75 (s, 1H). ESI-MS: m/z 196.1 (M+H)$^+$.

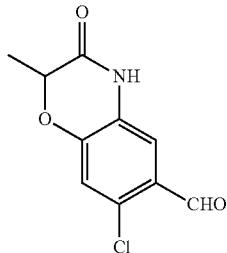

7-Chloro-2-methyl-3-oxo-3,4-dihydro-2H-benzo[b][1,4]oxazine-6-carbaldehyde (22)

Using 10 in the general procedure for reduction of nitro group and subsequent ring closure gives an off-white solid: ESI-MS: m/z 226.1 (M+H)$^+$.

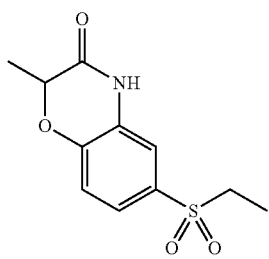 [SMILES: CCS(=O)(=O)c1ccc2c(c1)NC(=O)C(C)O2]

6-(Ethylsulfonyl)-2-methyl-2H-benzo[b][1,4]oxazin-3(4H)-one (23)

Using 4-(ethylsulfonyl)-2-nitrophenol and methyl 2-bromopropanoate in the general procedure for alkylation of substituted-2-nitrophenols followed by reaction of the product in the general procedure for reduction of nitro group and subsequent ring closure gives a white solid: $^1$H NMR (DMSO-d$_6$, 400 MHz): δ=10.96 (s, 1H), 7.43 (dd, J=8.3, 2.0 Hz, 1H), 7.37 (d, J=2.3 Hz, 1H), 7.19 (d, J=8.3 Hz, 1H), 4.85 (q, J=6.8 Hz, 1H), 3.23 (q, J=7.3 Hz, 2H), 1.46 (d, J=6.8 Hz, 3H), 1.10 ppm (t, J=7.5 Hz, 3H). ESI-MS: m/z 256.1 (M+H)$^+$.

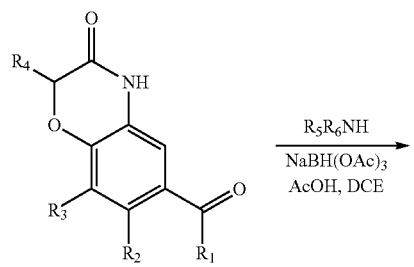

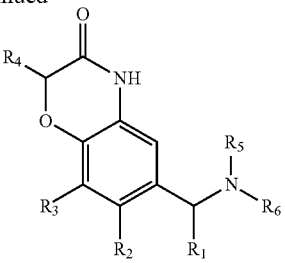

General Procedure for Reductive Aminations

To a 15 mL screw cap vial was added the carbonyl compound (0.564 mmol) and the amine (0.677 mmol) in 1,2-dichloroethane (4.0 mL) followed by AcOH (0.564 mmol) and sodium triacetoxyborohydride (144 mg, 0.677 mmol). The reaction was stirred at 23° C. for 18 hr. The reaction was diluted with water (5 mL) and the layers were separated. The aqueous layer was extracted with DCM and the combined organic layers were dried (MgSO$_4$) and concentrated in vacuo. The crude material was purified by prep HPLC-MS (5-95% MeCN in water) and the fractions were collected and concentrated in vacuo in yields ranging from 30-80%. Alternatively, the crude material was taken up in water (5 mL) and the resulting solid was isolated by filtration, washed with water and dried in vacuo to give the desired compound.

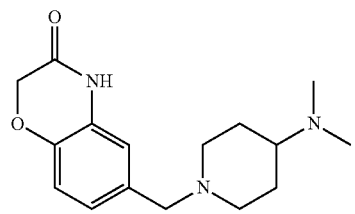 [SMILES: CN(C)C1CCN(Cc2ccc3c(c2)NC(=O)CO3)CC1]

6-((4-(Dimethylamino)piperidin-1-yl)methyl)-2H-benzo[b][1,4]oxazin-3(4H)-one (24)

Using 12 and N,N-dimethylpiperidin-4-amine in the general procedure for reductive aminations, the title compound was obtained as an off-white solid: $^1$H NMR (400 MHz, DMSO-d$_6$) δ ppm 1.72-1.86 (m, 2H) 2.18-2.28 (m, 2H) 2.75 (br. s., 6H) 2.95 (br. s., 2H) 3.32-3.55 (m, 3H) 4.23 (s, 2H) 4.61 (s, 2H) 6.98 (s, 1H) 7.00-7.08 (m, 2H) 10.13 (br. s., 1 H) 10.59 (br. s., 1H) 10.98 (s, 1H). ESI-MS: m/z 290.2 (M+H)$^+$.

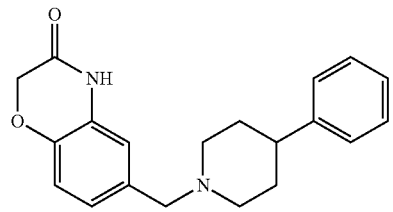 [SMILES: O=C1COc2ccc(CN3CCC(c4ccccc4)CC3)cc2N1]

6-((4-Phenylpiperidin-1-yl)methyl)-2H-benzo[b][1,4]oxazin-3(4H)-one (25)

Using 12 and 4-phenylpiperidine in the general procedure for reductive aminations, the title compound was obtained as a white solid: $^1$H NMR (400 MHz, DMSO-d$_6$) δ ppm 1.84 (br. s., 2 H) 1.98 (br. s., 2H) 2.79 (br. s., 1H) 3.05 (d, J=12.63 Hz, 2H) 3.43 (br. s., 2H) 4.26 (d, J=4.80 Hz, 2H) 4.63 (s, 2H) 7.01 (s, 1H) 7.07 (s, 2H) 7.20-7.26 (m, 3H) 7.33 (t, J=7.33 Hz, 2H) 10.99 (s, 1H). ESI-MS: m/z 323.2 (M+H)$^+$.

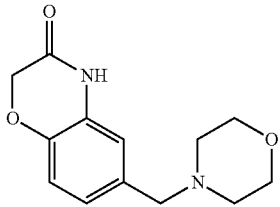 [SMILES: O=C1COc2ccc(CN3CCOCC3)cc2N1]

6-(Morpholinomethyl)-2H-benzo[b][1,4]oxazin-3(4H)-one (26)

Using 12 and morpholine in the general procedure for reductive aminations, the title compound was obtained as a white solid: $^1$H NMR (400 MHz, DMSO-d$_6$) δ ppm 2.92-3.16 (m, 2H) 3.16-3.37 (m, 2 H) 3.47-3.71 (m, 2H) 3.96 (d, J=12.13 Hz, 2H) 4.27 (s, 2H) 4.61 (s, 2H) 6.86-7.14 (m, 3 H) 10.07 (br. s., 1H) 10.99 (s, 1H). ESI-MS: m/z 249.1 (M+H)$^+$.

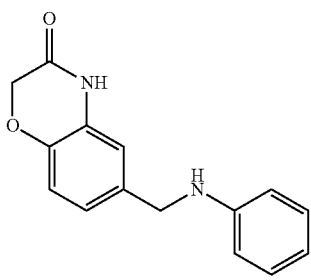 [SMILES: O=C1COc2ccc(CNc3ccccc3)cc2N1]

6-((Phenylamino)methyl)-2H-benzo[b][1,4]oxazin-3(4H)-one (27)

Using 12 and aniline in the general procedure for reductive aminations, the title compound was obtained as a white solid: $^1$H NMR (400 MHz, DMSO-d$_6$) δ ppm 4.18 (s, 2H) 4.53 (s, 2H) 6.52-6.70 (m, 3 H) 6.90 (s, 3H) 7.08 (t, J=7.58 Hz, 2H) 10.71 (s, 1H). ESI-MS: m/z 255.1 (M+H)$^+$.

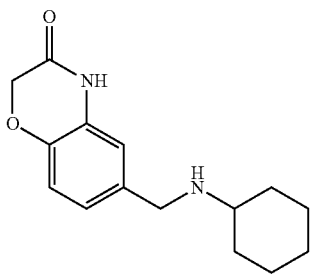 [SMILES: O=C1COc2ccc(CNC3CCCCC3)cc2N1]

6-((Cyclohexylamino)methyl)-2H-benzo[b][1,4]oxazin-3(4H)-one (28)

Using 12 and cyclohexylamine in the general procedure for reductive aminations, the title compound was obtained as a white solid: $^1$H NMR (400 MHz, DMSO-d$_6$) δ ppm 1.11 (br. s., 1H) 1.17-1.37 (m, 4H) 1.61 (d, J=12.88 Hz, 1H) 1.79 (br. s., 2H) 2.06 (br. s., 2H) 2.99 (br. s., 1H) 4.07 (d, J=5.56 Hz, 2H) 4.60 (s, 2H) 6.99 (s, 1H) 6.99-7.09 (m, 2H) 8.65 (br. s., 1H) 10.95 (s, 1H). ESI-MS: m/z 261.1 (M+H)$^+$.

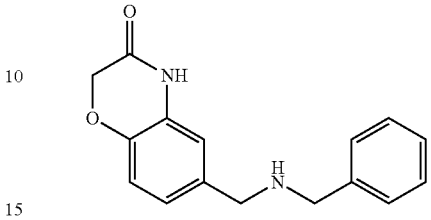

6-((Benzylamino)methyl)-2H-benzo[b][1,4]oxazin-3(4H)-one (29)

Using 12 and benzylamine in the general procedure for reductive aminations, the title compound was obtained as a white solid: $^1$H NMR (400 MHz, DMSO-d$_6$) δ ppm 4.08 (br. s., 2H) 4.16 (d, J=3.28 Hz, 2H) 4.60 (s, 2H) 6.92-7.09 (m, 3H) 7.35-7.53 (m, 5H) 10.95 (s, 1H). ESI-MS: m/z 269.1 (M+H)$^+$.

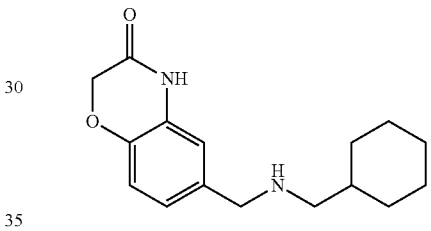

6-((Cyclohexylmethylamino)methyl)-2H-benzo[b][1,4]oxazin-3(4H)-one (30)

Using 12 and cyclohexylmethanamine in the general procedure for reductive aminations, the title compound was obtained as a white solid: $^1$H NMR (400 MHz, DMSO-d$_6$) δ ppm 0.92 (d, J=10.86 Hz, 2H) 1.16 (t, J=8.97 Hz, 3H) 1.57-1.76 (m, 6H) 2.74 (br. s., 2H) 4.04 (br. s., 2 H) 4.60 (s, 2H) 6.98 (s, 1H) 6.99-7.11 (m, 2H) 8.60 (br. s., 1H) 10.95 (s, 1H). ESI-MS: m/z 275.2 (M+H)$^+$.

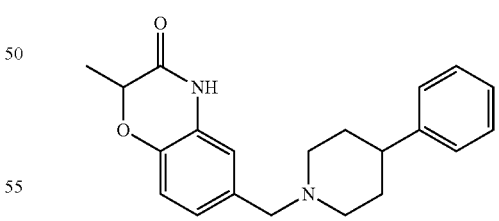

2-Methyl-6-((4-phenylpiperidin-1-yl)methyl)-2H-benzo[b][1,4]oxazin-3(4H)-one (31)

Using 13 and 4-phenylpiperidine in the general procedure for reductive aminations, the title compound was obtained as a grey solid: $^1$H NMR (400 MHz, DMSO-d$_6$) δ ppm 1.34-1.46 (m, 7H) 1.65-1.81 (m, 5H) 1.91 (s, 1H) 3.33-3.44 (m, 2H) 6.76-6.94 (m, 4H) 7.18-7.33 (m, 4H) 10.59 (br. s., 1H). ESI-MS: m/z 337.2 (M+H)$^+$.

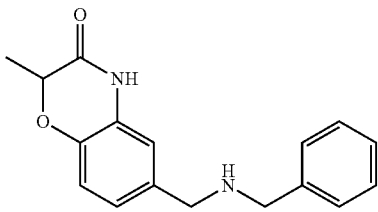

6-((Benzylamino)methyl)-2-methyl-2H-benzo[b][1,4]oxazin-3(4H)-one (32)

Using 13 and benzylamine in the general procedure for reductive aminations, the title compound was obtained as a tan solid: $^1$H NMR (400 MHz, DMSO-d$_6$) δ ppm $^1$H NMR (400 MHz, DMSO-d$_6$) δ ppm 1.39 (br. s., 3H) 1.57 (br. s., 1H) 3.50-3.61 (m, 2H) 3.65 (br. s., 2H) 4.59 (br. s., 1H) 6.74-6.99 (m, 3H) 7.13-7.38 (m, 5H) 10.66 (br. s., 1H). ESI-MS: m/z 283.1 (M+H)$^+$.

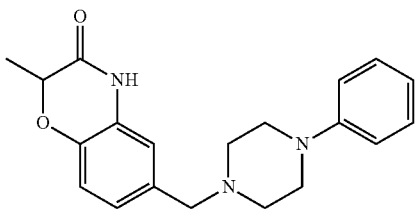

2-Methyl-6-((4-phenylpiperazin-1-yl)methyl)-2H-benzo[b][1,4]oxazin-3(4H)-one (33)

Using 13 and 1-phenylpiperazine in the general procedure for reductive aminations, the title compound was obtained as a white solid: $^1$H NMR (400 MHz, DMSO-d$_6$) δ ppm 1.44 (d, J=6.82 Hz, 3H) 2.89-2.99 (m, 2H) 3.10-3.22 (m, 2H) 3.36-3.45 (m, 2H) 3.83 (d, J=13.64 Hz, 2H) 4.33 (br. s., 2H) 4.72 (q, J=6.91 Hz, 1H) 6.86 (t, J=7.33 Hz, 1H) 6.97 (s, 1H) 7.01 (d, J=12.13 Hz, 2H) 7.07 (s, 2H) 7.26 (t, J=7.96 Hz, 2H) 9.80 (br. s., 1H) 10.95 (s, 1H). ESI-MS: m/z 338.2 (M+H)$^+$.

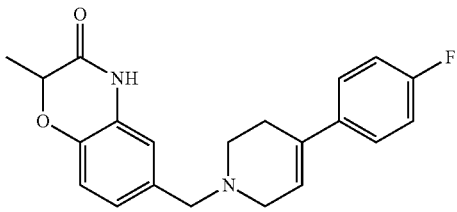 [SMILES: CC1Oc2ccc(CN3CC=C(c4ccc(F)cc4)CC3)cc2NC1=O]

6-((4-(4-Fluorophenyl)-5,6-dihydropyridin-1(2H)-yl)methyl)-2-methyl-2H-benzo[b][1,4]oxazin-3(4H)-one (34)

Using 13 and 4-(4-fluorophenyl)-1,2,3,6-tetrahydropyridine in the general procedure for reductive aminations, the title compound was obtained as a white solid: $^1$H NMR (400 MHz, DMSO-d$_6$) δ ppm 1.44 (d, J=6.82 Hz, 3H) 2.77 (br. s., 2H) 3.60 (br. s., 2H) 3.78 (br. s., 2H) 4.35 (t, J=5.43 Hz, 2H) 4.72 (q, J=6.99 Hz, 1 H) 6.15 (br. s., 1H) 7.04 (s, 1H) 7.05-7.13 (m, 2H) 7.23 (t, J=8.84 Hz, 2H) 7.46-7.58 (m, 2H) 9.85 (br. s., 1H) 10.94 (s, 1H). ESI-MS: m/z 352.0 (M+H)$^+$.

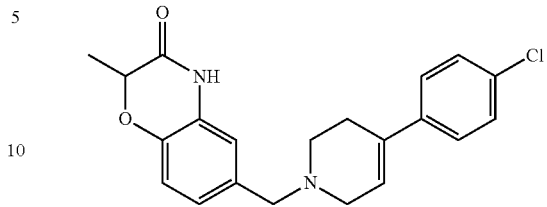

6-((4-(4-Chlorophenyl)-5,6-dihydropyridin-1(2H)-yl)methyl)-2-methyl-2H-benzo[b][1,4]oxazin-3(4H)-one (35)

Using 13 and 4-(4-chlorophenyl)-1,2,3,6-tetrahydropyridine in the general procedure for reductive aminations, the title compound was obtained as a white solid: $^1$H NMR (400 MHz, DMSO-d$_6$) δ ppm 1.44 (d, J=6.82 Hz, 3H) 2.76 (br. s., 2H) 3.23 (br. s., 1H) 3.60 (br. s., 1H) 3.79 (br. s., 2H) 4.35 (br. s., 2H) 4.72 (q, J=6.57 Hz, 1H) 6.22 (br. s., 1H) 6.96-7.14 (m, 3H) 7.48 (m, 4H) 9.94 (br. s., 1H) 10.94 (s, 1H). ESI-MS: m/z 369.2 (M+H)$^+$.

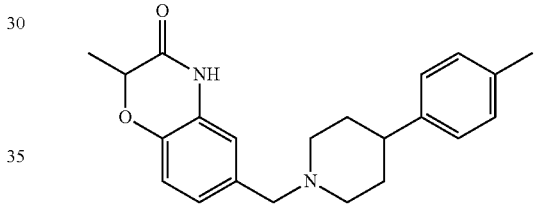

2-Methyl-6-((4-p-tolylpiperidin-1-yl)methyl)-2H-benzo[b][1,4]oxazin-3(4H)-one (36)

Using 13 and 4-(4-methylphenyl)piperazine in the general procedure for reductive aminations, the title compound was obtained as a white solid: $^1$H NMR (400 MHz, DMSO-d$_6$) δ ppm 1.44 (d, J=6.82 Hz, 3H) 1.81 (br. s., 2H) 1.95 (br. s., 2H) 2.26 (s, 3H) 2.66-2.83 (m, 1H) 3.05 (br. s., 2H) 3.43 (br. s., 2H) 4.26 (d, J=4.80 Hz, 2H) 4.72 (q, J=6.65 Hz, 1H) 7.01 (s, 1H) 7.04-7.19 (m, 6H) 9.43 (br. s., 1H) 10.94 (s, 1H). ESI-MS: m/z 351.3 (M+H)$^+$.

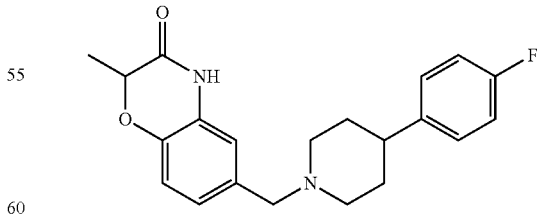

6-((4-(4-Fluorophenyl)piperidin-1-yl)methyl)-2-methyl-2H-benzo[b][1,4]oxazin-3(4H)-one (37)

Using 13 and 4-(4-fluorophenyl)piperidine in the general procedure for reductive aminations, the title compound was obtained as a white solid: ¹H NMR (400 MHz, DMSO-d₆) δ ppm 1.44 (d, J=6.82 Hz, 3H) 1.70-1.89 (m, 2H) 1.90-2.06 (m, 2H) 2.73-2.88 (m, 1H) 2.96-3.12 (m, 2H) 3.35-3.50 (m, 2H) 4.27 (br. s., 2H) 4.72 (d, J=6.82 Hz, 1 H) 7.01 (s, 1H) 7.07 (s, 2H) 7.16 (t, J=8.84 Hz, 2H) 7.26 (dd, J=8.84, 5.56 Hz, 2H) 10.94 (s, 1H). ESI-MS: m/z 354.2 (M+H)⁺.

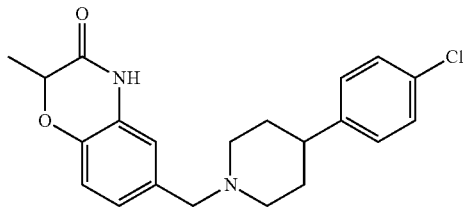 [SMILES: CC1Oc2ccc(CN3CCC(c4ccc(Cl)cc4)CC3)cc2NC1=O]

6-((4-(4-Chlorophenyl)piperidin-1-yl)methyl)-2-methyl-2H-benzo[b][1,4]oxazin-3(4H)-one (38)

Using 13 and 4-(4-chlorophenyl)piperidine in the general procedure for reductive aminations, the title compound was obtained as a white solid: ¹H NMR (400 MHz, DMSO-d₆) δ ppm 1.44 (d, J=6.82 Hz, 3H) 1.69-1.92 (m, 2H) 1.92-2.05 (m, 2H) 2.74-2.88 (m, 1H) 2.93-3.13 (m, 2H) 3.37-3.51 (m, 2H) 4.26 (d, J=5.05 Hz, 2H) 4.72 (q, J=6.91 Hz, 1H) 7.01 (s, 1H) 7.07 (s, 2H) 7.25 (d, J=8.59 Hz, 2H) 7.40 (d, J=8.59 Hz, 2H) 9.40 (br. s., 1H) 10.94 (s, 1H). ESI-MS: m/z 371.2 (M+H)⁺.

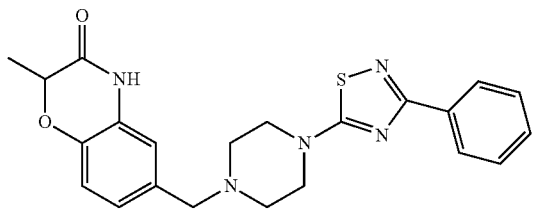 [SMILES: CC1Oc2ccc(CN3CCN(c4nc(-c5ccccc5)ns4)CC3)cc2NC1=O]

2-Methyl-6-((4-(3-phenyl-1,2,4-thiadiazol-5-yl)piperazin-1-yl)methyl)-2H-benzo[b][1,4]oxazin-3(4H)-one (39)

Using 13 and 3-phenyl-5-(piperazin-1-yl)-1,2,4-thiadiazole in the general procedure for reductive aminations, the title compound was obtained as a white solid, mp 192.5-221.2° C.: ¹H NMR (400 MHz, DMSO-d₆) δ ppm 1.44 (d, J=6.82 Hz, 3H) 3.25 (br. s., 2H) 3.37-3.71 (m, 4H) 4.12 (br. s., 2H) 4.33 (br. s., 2H) 4.72 (q, J=6.23 Hz, 1H) 6.89-7.17 (m, 3H) 7.40-7.59 (m, 3H) 7.97-8.24 (m, 2H) 10.95 (br. s., 1 H). ESI-MS: m/z 422.0 (M+H)⁺.

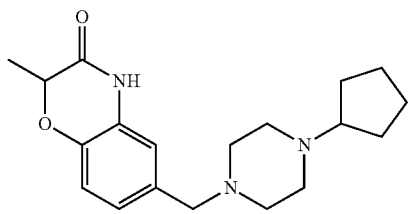 [SMILES: CC1Oc2ccc(CN3CCN(C4CCCC4)CC3)cc2NC1=O]

6-((4-Cyclopentylpiperazin-1-yl)methyl)-2-methyl-2H-benzo[b][1,4]oxazin-3(4H)-one (40)

Using 13 and 1-cyclopentylpiperazine in the general procedure for reductive aminations, the title compound was obtained as an off-white solid: ¹H NMR (400 MHz, DMSO-d₆) δ ppm 1.42 (d, J=6.57 Hz, 3H) 1.45-1.61 (m, 4H) 1.59-1.64 (m, 4H) 1.61-1.77 (m, 4H) 1.89-2.06 (m, 4H) 3.52 (br. s., 2H) 3.89 (br. s., 1H) 4.66 (q, J=6.65 Hz, 1H) 6.91 (s, 1H) 6.94-7.04 (m, 2H) 10.81 (br. s., 1H). ESI-MS: m/z 330.2 (M+H)⁺.

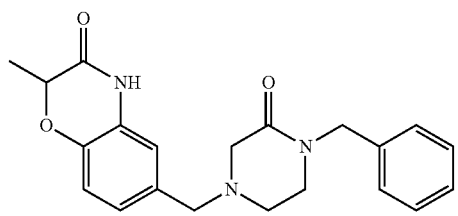 [SMILES: CC1Oc2ccc(CN3CCN(Cc4ccccc4)C(=O)C3)cc2NC1=O]

6-((4-Benzyl-3-oxopiperazin-1-yl)methyl)-2-methyl-2H-benzo[b][1,4]oxazin-3(4H)-one (41)

Using 13 and 1-benzylpiperazin-2-one in the general procedure for reductive aminations, the title compound was obtained as a white solid: ¹H NMR (400 MHz, DMSO-d₆) δ ppm 0.79-1.00 (m, 1H) 1.30-1.53 (m, 3H) 3.15-4.87 (m, 13H) 6.91-7.15 (m, 2H) 7.20-7.52 (m, 6H) 10.88 (br. s., 1H). ESI-MS: m/z 366.0 (M+H)⁺.

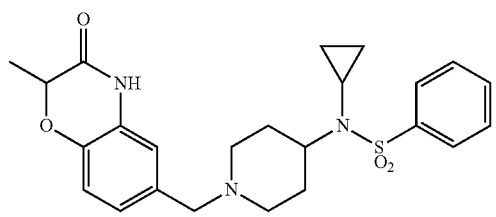 [SMILES: CC1Oc2ccc(CN3CCC(N(C4CC4)S(=O)(=O)c4ccccc4)CC3)cc2NC1=O]

N-Cyclopropyl-N-(1-((2-methyl-3-oxo-3,4-dihydro-2H-benzo[b][1,4]oxazin-6-yl)methyl)piperidin-4-yl)benzenesulfonamide (42)

Using 13 and N-cyclopropyl-N-(piperidin-4-yl)benzenesulfonamide in the general procedure for reductive aminations, the title compound was obtained as a white solid: ¹H NMR (400 MHz, DMSO-d₆) δ ppm 0.57-0.87 (m, 4H) 1.42 (d, J=6.57 Hz, 3H) 1.53-1.75 (m, 2H) 1.84-1.99 (m, 1H) 1.99-2.21 (m, 2 H) 3.04 (d, J=10.61 Hz, 2H) 3.33 (br. s., 2H) 3.83-4.11 (m, 1H) 4.11-4.23 (m, 3H) 4.30 (br. s., 1H) 4.70 (q, J=6.82 Hz, 2H) 6.95 (s, 1H) 6.97-7.16 (m, 2H) 7.54-7.79 (m, 3H) 7.81-7.96 (m, 2H) 9.57 (br. s., 1H) 10.91 (s, 1H). ESI-MS: m/z 456.0 (M+H)⁺.

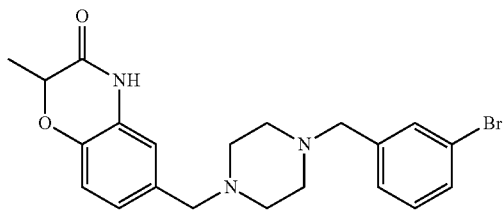 [SMILES: CC1Oc2ccc(CN3CCN(Cc4cccc(Br)c4)CC3)cc2NC1=O]

6-((4-(3-Bromobenzyl)piperazin-1-yl)methyl)-2-methyl-2H-benzo[b][1,4]oxazin-3(4H)-one (43)

Using 13 and 1-(3-bromobenzyl)piperazine in the general procedure for reductive aminations, the title compound was obtained as a white solid: $^1$H NMR (400 MHz, DMSO-$d_6$) δ ppm 1.42 (d, J=6.82 Hz, 3H) 2.95-3.24 (m, 6H) 3.85 (br. s., 2H) 4.10 (br. s., 2 H) 4.68 (q, J=6.82 Hz, 2H) 6.94 (s, 1H) 6.97-7.08 (m, 2H) 7.26-7.46 (m, 2H) 7.47-7.70 (m, 2H) 10.87 (br. s., 1H). ESI-MS: m/z 432.0 (M+H)$^+$.

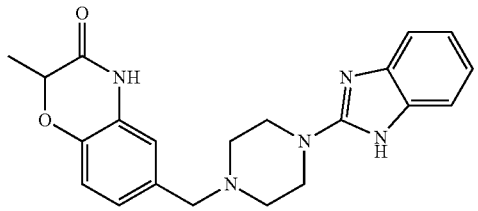 [SMILES: CC1Oc2ccc(CN3CCN(c4nc5ccccc5[nH]4)CC3)cc2NC1=O]

6-((4-(1H-Benzo[d]imidazol-2-yl)piperazin-1-yl)methyl)-2-methyl-2H-benzo[b][1,4]oxazin-3(4H)-one (44)

Using 13 and 2-(piperazin-1-yl)-1H-benzo[d]imidazole in the general procedure for reductive aminations, the title compound was obtained as a white solid: $^1$H NMR (400 MHz, DMSO-$d_6$) δ ppm 1.44 (d, J=6.82 Hz, 3H) 2.87-4.48 (m, 11H) 4.70 (q, J=6.57 Hz, 0H) 6.87-7.15 (m, 3H) 7.26 (d, 2H) 7.38-7.55 (m, 2H) 10.90 (br. s., 1 H). ESI-MS: m/z 378.0 (M+H)$^+$.

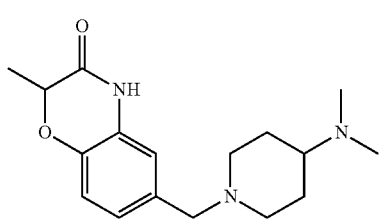

6-((4-(Dimethylamino)piperidin-1-yl)methyl)-2-methyl-2H-benzo[b][1,4]oxazin-3(4H)-one (45)

Using 13 and N,N-dimethylpiperidin-4-amine in the general procedure for reductive aminations, the title compound was obtained as a white solid: $^1$H NMR (400 MHz, DMSO-$d_6$) δ ppm $^1$H NMR (400 MHz, DMSO-$d_6$) δ ppm 1.43 (d, J=6.82 Hz, 3H) 1.82 (d, J=1.01 Hz, 2H) 2.13-2.28 (m, 2H) 2.76 (d, J=3.03 Hz, 6H) 2.86-3.02 (m, 2H) 3.35 (br. s., 1H) 3.42-3.56 (m, 2H) 4.23 (br. s., 2H) 4.71 (q, J=6.65 Hz, 1H) 6.97 (s, 1H) 7.05 (s, 2H) 10.10 (br. s., 1H) 10.94 (s, 1H). ESI-MS: m/z 303.2 (M+H)$^+$.

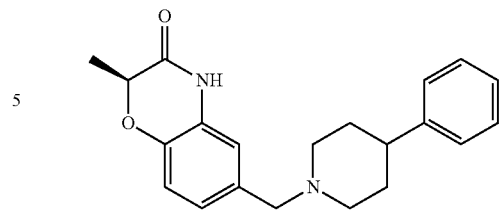

(S)-2-Methyl-6-((4-phenylpiperidin-1-yl)methyl)-2H-benzo[b][1,4]oxazin-3(4H)-one (46)

Chiral HPLC separation of Compound 31 provided the title compound as a white solid: $^1$H NMR (400 MHz, DMSO-$d_6$) δ ppm 1.41 (d, J=6.57 Hz, 3H) 1.71 (d, J=1.01 Hz, 2H) 1.78-1.91 (m, 4H) 1.94-2.08 (m, 2H) 2.82-2.95 (m, 2H) 3.38 (s, 2H) 4.63 (q, J=6.82 Hz, 1H) 6.78-6.93 (m, 3H) 7.17 (s, 1H) 7.20-7.33 (m, 4H). ESI-MS: m/z 337.2 (M+H)$^+$.

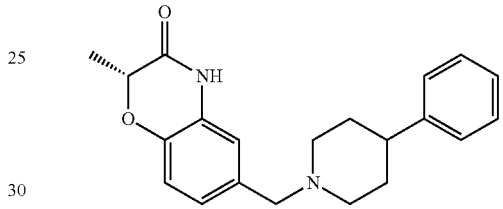

(R)-2-Methyl-6-((4-phenylpiperidin-1-yl)methyl)-2H-benzo[b][1,4]oxazin-3(4H)-one (47)

Chiral HPLC separation of Compound 31 provided the title compound as a white solid: $^1$H NMR (400 MHz, DMSO-$d_6$) δ ppm 1.41 (d, J=6.82 Hz, 3H) 1.54-1.67 (m, 2H) 1.69-1.80 (m, 2H) 2.01 (br. s., 2H) 2.89 (d, J=9.09 Hz, 2H) 3.38 (s, 2H) 4.63 (q, J=6.82 Hz, 1H) 6.76-6.93 (m, 3H) 7.13-7.20 (m, 1H) 7.20-7.34 (m, 5H). ESI-MS: m/z 337.2 (M+H)$^+$.

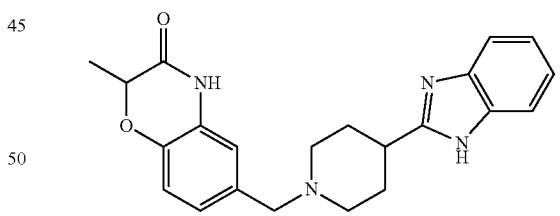

6-((4-(1H-Benzo[d]imidazol-2-yl)piperidin-1-yl)methyl)-2-methyl-2H-benzo[b][1,4]oxazin-3(4H)-one (48)

Using 13 and 2-(piperidin-4-yl)-1H-benzo[d]imidazole in the general procedure for reductive aminations, the title compound was obtained as an off-white solid: $^1$H NMR (400 MHz, DMSO-$d_6$) δ ppm 1.17 (t, J=7.33 Hz, 1H) 1.44 (d, J=6.82 Hz, 3H) 1.92-2.14 (m, 2H) 2.29-2.44 (m, 2H) 3.04-3.25 (m, 4H) 3.27-3.46 (m, 2H) 3.54 (br. s., 3H) 4.28 (s, 4H) 4.72 (q, J=6.65 Hz, 2H) 6.93-7.16 (m, 3H) 7.32-7.50 (m, 2 H) 7.59-7.82 (m, 2H) 9.74 (br. s., 1H) 10.85-11.02 (m, 1H). ESI-MS: m/z 377.3 (M+H)$^+$.

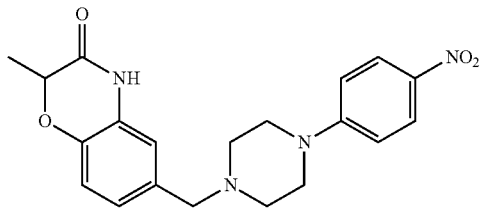 [SMILES: CC1Oc2ccc(CN3CCN(c4ccc([N+](=O)[O-])cc4)CC3)cc2NC1=O]

2-Methyl-6-((4-(4-nitrophenyl)piperazin-1-yl)methyl)-2H-benzo[b][1,4]oxazin-3(4H)-one (49)

Using 13 and 1-(4-nitrophenyl)piperazine in the general procedure for reductive aminations, the title compound was obtained as a yellow solid: $^1$H NMR (400 MHz, DMSO-$d_6$) δ ppm 1.41 (d, J=6.82 Hz, 3H) 2.39-2.48 (m, 4H) 3.38-3.51 (m, 6H) 4.64 (q, J=6.82 Hz, 1H) 6.80-6.94 (m, 3H) 7.02 (m, J=9.35 Hz, 2H) 8.05 (m, J=9.60 Hz, 2H) 10.63 (s, 1H). ESI-MS: m/z 383.2 (M+H)$^+$.

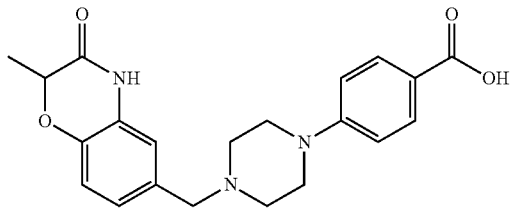

4-(4-((2-Methyl-3-oxo-3,4-dihydro-2H-benzo[b][1,4]oxazin-6-yl)methyl)piperazin-1-yl)benzoic acid (50)

Using 220 or 217 in the general procedure for hydrolysis of carboxylic esters, the title compound was obtained as a white solid: $^1$H NMR (400 MHz, DMSO-$d_6$) δ ppm 1.31-1.53 (m, 3H) 2.95-3.14 (m, 3H) 3.14-3.25 (m, 1H) 3.54 (br. s., 4H) 3.93-4.15 (m, 2H) 4.32 (br. s., 2H) 4.72 (q, J=6.74 Hz, 1H) 6.55 (br. s., 3H) 6.93-7.17 (m, 5H) 7.82 (d, J=8.84 Hz, 2H) 9.78 (br. s., 1H) 10.95 (s, 1H) 12.45 (br. s., 1H). ESI-MS: m/z 382.2 (M+H)$^+$.

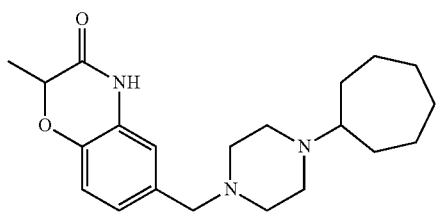 [SMILES: CC1Oc2ccc(CN3CCN(C4CCCCCC4)CC3)cc2NC1=O]

6-((4-Cycloheptylpiperazin-1-yl)methyl)-2-methyl-2H-benzo[b][1,4]oxazin-3(4H)-one (51)

Using 13 and 1-(4-cycloheptyl)piperazine in the general procedure for reductive aminations, the title compound was obtained as a white solid: $^1$H NMR (400 MHz, DMSO-$d_6$) δ ppm 1.36-1.55 (m, 8H) 1.56-1.72 (m, 4H) 1.85-2.05 (m, 2H) 2.92 (br. s., 2H) 3.07-3.28 (m, 2H) 3.28-3.58 (m, 5H) 4.04 (br. s., 2H) 4.67 (q, J=6.74 Hz, 1H) 6.95 (s, 1H) 7.00 (s, 2H) 10.84 (s, 1H). ESI-MS: m/z 358.3 (M+H)$^+$.

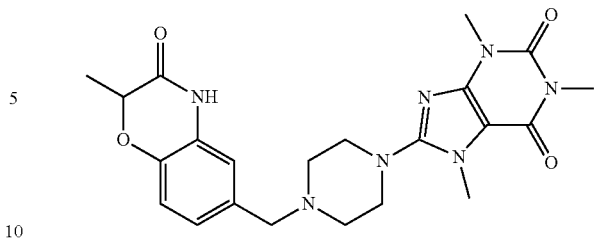

1,3,7-Trimethyl-8-(4-((2-methyl-3-oxo-3,4-dihydro-2H-benzo[b][1,4]oxazin-6-yl)methyl)piperazin-1-yl)-1H-purine-2,6(3H,7H)-dione (52)

Using 13 and 1,3,7-trimethyl-8-(piperazin-1-yl)-1H-purine-2,6(3H,7H)-dione in the general procedure for reductive aminations, the title compound was obtained as a white solid, mp 130.2-138.3° C.: $^1$H NMR (400 MHz, DMSO-$d_6$) δ ppm 1.43 (d, J=6.57 Hz, 3H) 3.13-3.33 (m, 3H) 3.33-3.49 (m, 3H) 3.65-3.77 (m, 10H) 4.34 (br. s., 2H) 4.72 (q, J=6.65 Hz, 1H) 7.01 (s, 1H) 7.07 (s, 2H) 9.94 (br. s., 1H) 10.95 (s, 1H). ESI-MS: m/z 454.2 (M+H)$^+$.

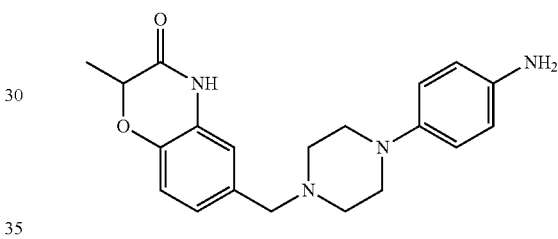

6-((4-(4-Aminophenyl)piperazin-1-yl)methyl)-2-methyl-2H-benzo[b][1,4]oxazin-3(4H)-one (53)

Using 13 and 4-(piperazin-1-yl)aniline in the general procedure for reductive aminations, the title compound was obtained as a tan solid: $^1$H NMR (400 MHz, DMSO-$d_6$) δ ppm 1.41 (d, J=6.82 Hz, 3H) 2.53-2.72 (m, 3H) 2.93 (br. s., 4H) 3.17 (d, J=5.05 Hz, 1H) 3.37-3.66 (m, 2H) 4.64 (q, J=6.74 Hz, 1H) 6.41-6.57 (m, 2H) 6.61-6.78 (m, 2H) 6.82-7.00 (m, 3H) 10.55-10.74 (m, 1H). ESI-MS: m/z 353.3 (M+H)$^+$.

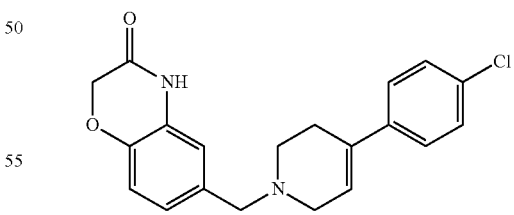

6-((4-(4-Chlorophenyl)-5,6-dihydropyridin-1(2H)-yl)methyl)-2H-benzo[b][1,4]oxazin-3(4H)-one (54)

Using 12 and 4-(4-chlorophenyl)-1,2,3,6-tetrahydropyridine in the general procedure for reductive aminations, the title compound was obtained as an off-white solid: $^1$H NMR (400 MHz, DMSO-$d_6$) δ ppm 2.68-2.83 (m, 2H) 3.13-3.30 (m, 1H) 3.52-3.68 (m, 1H) 3.71-3.85 (m, 2H) 4.34 (d, J=4.55

Hz, 2H) 4.63 (s, 2H) 6.21 (br. s., 1H) 6.98-7.13 (m, 3H) 7.48 (m, 4H) 9.88-10.08 (m, 1H) 10.99 (s, 1H). ESI-MS: m/z 355.2 (M+H)+.

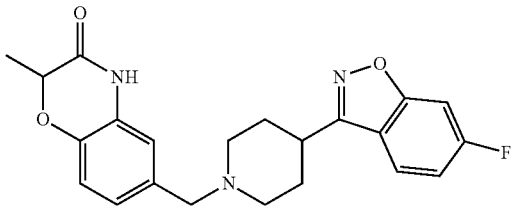 [SMILES: CC1Oc2ccc(CN3CCC(c4noc5cc(F)ccc45)CC3)cc2NC1=O]

6-((4-(6-Fluorobenzo[d] isoxazol-3-yl)piperidin-1-yl)methyl)-2-methyl-2H-benzo[b][1,4]oxazin-3(4H)-one (55)

Using 13 and 6-fluoro-3-(piperidin-4-yl)benzo[d]isoxazole in the general procedure for reductive aminations, the title compound was obtained as an off-white solid: $^1$H NMR (400 MHz, DMSO-d$_6$) δ ppm 1.37-1.49 (m, 3H) 1.94-2.13 (m, 2H) 2.29 (d, J=13.64 Hz, 2H) 3.03-3.22 (m, 2H) 3.29-3.59 (m, 2H) 4.25-4.39 (m, 2H) 4.72 (q, J=6.82 Hz, 1H) 6.98-7.17 (m, 3H) 7.35 (td, J=9.09, 2.02 Hz, 1H) 7.68-7.80 (m, 1H) 7.98-8.10 (m, 1H) 9.63 (br. s., 1H) 10.88-10.99 (m, 1H). ESI-MS: m/z 396.0 (M+H)+.

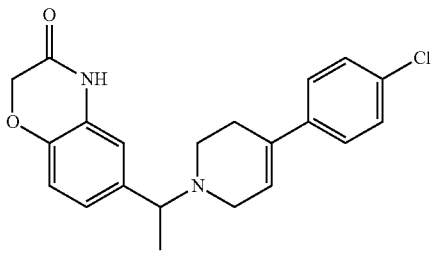 [SMILES: CC(c1ccc2c(c1)NC(=O)CO2)N1CC=C(c2ccc(Cl)cc2)CC1]

6-(1-(4-(4-Chlorophenyl)-5,6-dihydropyridin-1(2H)-yl)ethyl)-2H-benzo[b][1,4]oxazin-3(4H)-one (56)

Using 14 and 4-(4-chlorophenyl)-1,2,3,6-tetrahydropyridine in the general procedure for reductive aminations, the title compound was obtained as a white solid: $^1$H NMR (400 MHz, DMSO-d$_6$) δ ppm 1.65 (dd, J=10.86, 6.82 Hz, 3H) 2.67 (d, J=1.26 Hz, 1H) 2.83 (br. s., 1H) 3.50-3.65 (m, 1H) 3.77-3.98 (m, 1H) 4.03-4.17 (m, 1H) 4.43-4.58 (m, 1H) 4.63 (s, 2H) 6.12-6.30 (m, 1H) 6.95-7.18 (m, 3H) 7.35-7.57 (m, 4H) 9.85 (br. s., 1H) 10.95 (s, 1H). ESI-MS: m/z 368.1 (M+H)+.

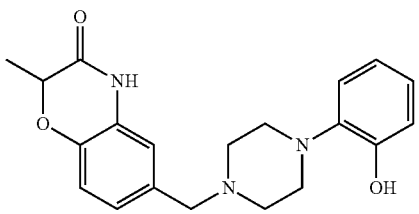

6-((4-(2-Hydroxyphenyl)piperazin-1-yl)methyl)-2-methyl-2H-benzo[b][1,4]oxazin-3(4H)-one (57)

Using 13 and 2-(piperazin-1-yl)phenol in the general procedure for reductive aminations, the title compound was obtained as a tan solid: $^1$H NMR (400 MHz, DMSO-d$_6$) δ ppm 1.41 (d, J=6.82 Hz, 3H) 2.92 (br. s., 4H) 3.36-3.55 (m, 2H) 4.63 (q, J=6.65 Hz, 1H) 6.62-7.02 (m, 7H) 8.91 (s, 1H) 10.61 (s, 1H). ESI-MS: m/z 354.2 (M+H)+.

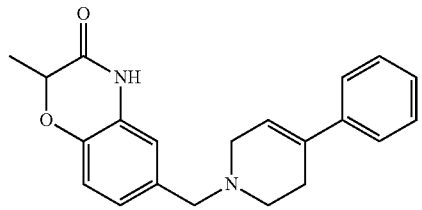 [SMILES: CC1Oc2ccc(CN3CC=C(c4ccccc4)CC3)cc2NC1=O]

2-Methyl-6-((4-phenyl-5,6-dihydropyridin-1(2H)-yl)methyl)-2H-benzo[b][1,4]oxazin-3(4H)-one (58)

Using 13 and 4-phenyl-1,2,3,6-tetrahydropyridine in the general procedure for reductive aminations, the title compound was obtained as a white solid, mp 247.9-255.3° C.: $^1$H NMR (400 MHz, DMSO-d$_6$) δ ppm 1.44 (d, J=6.57 Hz, 3H) 2.69-2.94 (m, 2H) 3.22 (br. s., 1H) 3.58 (br. s., 1H) 3.65-3.87 (m, 2H) 4.21-4.44 (m, 2H) 4.72 (q, J=6.82 Hz, 1H) 6.17 (br. s., 1H) 6.98-7.13 (m, 2H) 7.20 (d, J=8.34 Hz, 1H) 7.25-7.43 (m, 3H) 7.43-7.56 (m, 2H) 10.57 (br. s., 1H) 10.94 (s, 1H). ESI-MS: m/z 335.2 (M+H)+.

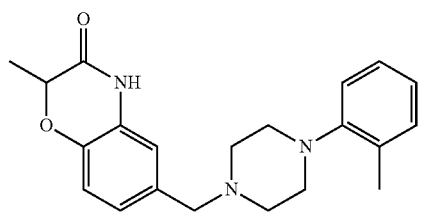

2-Methyl-6-((4-phenyl-5,6-dihydropyridin-1(2H)-yl)methyl)-2H-benzo[b][1,4]oxazin-3(4H)-one (59)

Using 13 and 1-o-tolylpiperazine in the general procedure for reductive aminations, the title compound was obtained as a white solid: $^1$H NMR (400 MHz, DMSO-d$_6$) δ ppm 1.43 (d, J=6.82 Hz, 3H) 2.25 (s, 3H) 2.95-3.11 (m, 2H) 3.11-3.26 (m, 4H) 3.26-3.39 (m, 4H) 4.32 (d, J=5.31 Hz, 2H) 4.71 (q, J=6.65 Hz, 1H) 6.94-7.12 (m, 4H) 7.12-7.28 (m, 3H) 10.55 (br. s., 1H) 10.94 (s, 1H). ESI-MS: m/z 352.2 (M+H)+.

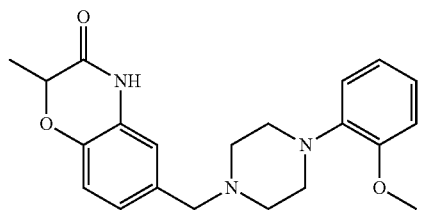

6-((4-(2-Methoxyphenyl)piperazin-1-yl)methyl)-2-methyl-2H-benzo[b][1,4]oxazin-3(4H)-one (60)

Using 13 and 1-(2-methoxyphenyl)piperazine in the general procedure for reductive aminations, the title compound was obtained as a white solid: $^1$H NMR (400 MHz, DMSO-$d_6$) δ ppm 1.34-1.49 (m, 3H) 2.86-3.07 (m, 2H) 3.09-3.27 (m, 2H) 3.35-3.41 (m, 2H) 3.42-3.56 (m, 2H) 3.78 (s, 3H) 4.30 (d, J=5.05 Hz, 2H) 4.71 (q, J=6.65 Hz, 1H) 6.83-7.12 (m, 6H) 7.18 (dd, J=8.21, 1.14 Hz, 1H) 10.44 (br. s., 1H) 10.93 (s, 1H). ESI-MS: m/z 368.2 (M+H)$^+$.

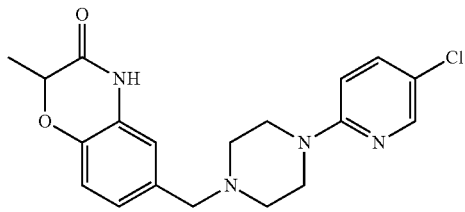 [SMILES: CC1Oc2ccc(CN3CCN(c4ccc(Cl)cn4)CC3)cc2NC1=O]

6-((4-(5-Chloropyridin-2-yl)piperazin-1-yl)methyl)-2-methyl-2H-benzo[b][1,4]oxazin-3(4H)-one (61)

Using 13 and 1-(5-chloropyridin-2-yl)piperazine in the general procedure for reductive aminations, the title compound was obtained as a white solid, mp 197.0-197.6° C.: $^1$H NMR (400 MHz, DMSO-$d_6$) δ ppm. 1.43 (d, J=6.82 Hz, 3H) 2.97-3.20 (m, 4H) 3.29-3.48 (m, 2H) 4.23-4.32 (m, 2H) 4.37 (d, J=11.62 Hz, 2H) 4.66-4.77 (m, 1H) 6.93-7.02 (m, 2H) 7.06 (s, 2H) 7.71 (dd, J=9.09, 2.53 Hz, 1H) 8.18 (d, J=2.53 Hz, 1H). ESI-MS: m/z 373.1 (M+H)$^+$.

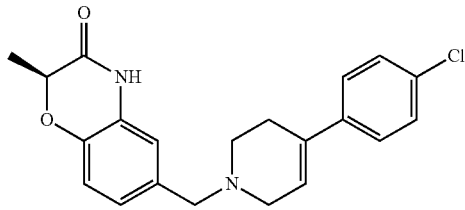 [SMILES: C[C@@H]1Oc2ccc(CN3CC=C(c4ccc(Cl)cc4)CC3)cc2NC1=O]

(S)-6-((4-(4-Chlorophenyl)-5,6-dihydropyridin-1(2H)-yl)methyl)-2-methyl-2H-benzo[b][1,4]oxazin-3(4H)-one (62)

Chiral HPLC separation of Compound 35 provided the title compound as a tan solid: $^1$H NMR (DMSO-$d_6$, 400 MHz): δ=7.41-7.49 (m, 2H), 7.31-7.41 (m, 2H), 6.79-6.93 (m, 3H), 6.19 (br. s., 1H), 4.63 (d, J=6.8 Hz, 1H), 3.48 (s, 2H), 2.57-2.68 (m, 2H), 2.45 (br. s., 2H), 1.84 (br. s., 2H), 1.41 ppm (d, J=6.6 Hz, 3H). ESI-MS: m/z 369.2 (M+H)$^+$.

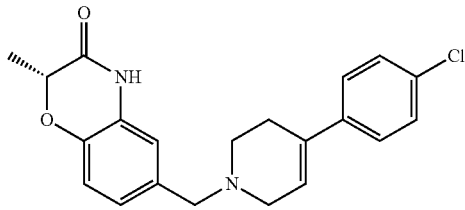 [SMILES: C[C@H]1Oc2ccc(CN3CC=C(c4ccc(Cl)cc4)CC3)cc2NC1=O]

(R)-6-((4-(4-Chlorophenyl)-5,6-dihydropyridin-1(2H)-yl)methyl)-2-methyl-2H-benzo[b][1,4]oxazin-3(4H)-one (63)

Chiral HPLC separation of Compound 35 provided the title compound as a tan solid: $^1$H NMR (DMSO-$d_6$, 400 MHz): δ=7.44 (br. s., 2H), 7.37 (br. s., 2H), 6.89 (br. s., 1H), 6.87 (d, J=6.3 Hz, 2H), 6.19 (br. s., 1H), 4.56-4.68 (m, 1H), 3.41-3.52 (m, 2H), 2.55-2.67 (m, 2H), 2.37-2.46 (m, 2H), 1.79-1.93 (m, 2H), 1.41 ppm (t, 3 H). ESI-MS: m/z 369.2 (M+H)$^+$.

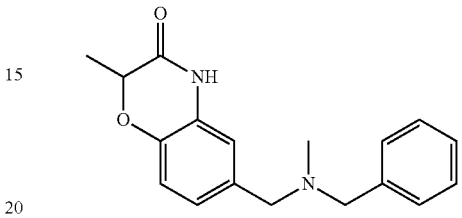

6-((Benzyl(methyl)amino)methyl)-2-methyl-2H-benzo[b][1,4]oxazin-3(4H)-one (64)

Using 13 and N-methyl-1-phenylmethanamine in the general procedure for reductive aminations, the title compound was obtained as an off-white solid: $^1$H NMR (DMSO-$d_6$, 400 MHz): δ=10.87 (s, 1H), 9.38 (br. s., 1H), 7.30-7.46 (m, 2H), 7.21-7.30 (m, 3H), 7.17 (d, J=1.8 Hz, 1H), 7.11 (dd, J=8.0, 1.9 Hz, 1H), 6.97 (d, J=8.1 Hz, 1H), 4.73 (d, J=6.8 Hz, 1 H), 4.26 (d, J=5.1 Hz, 2H), 3.46 (d, J=12.9 Hz, 2H), 2.98-3.10 (m, J=12.1 Hz, 2H), 2.76-2.85 (m, J=12.1, 12.1 Hz, 1H), 1.96-2.04 (m, 2H), 1.84 (q, J=11.8 Hz, 2H), 1.45 ppm (d, J=6.8 Hz, 3H). ESI-MS: m/z 297.3 (M+H)$^+$.

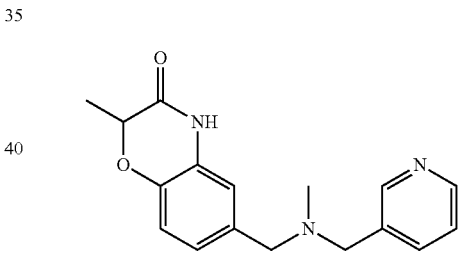

2-Methyl-6-((methyl(pyridin-3-ylmethyl)amino)methyl)-2H-benzo[b][1,4]oxazin-3(4H)-one (65)

Using 13 and N-methyl-1-(pyridin-3-yl)methanamine in the general procedure for reductive aminations, the title compound was obtained as a tan solid: $^1$H NMR (DMSO-$d_6$, 400 MHz): δ=10.64 (br. s., 1H), 8.52 (s, 1H), 8.40-8.49 (m, 1H), 7.73 (d, J=7.8 Hz, 1H), 7.36 (dd, J=7.6, 4.8 Hz, 1H), 6.93 (s, 1H), 6.79-6.91 (m, 2H), 4.62 (q, J=6.8 Hz, 1H), 3.49 (s, 2H), 3.41 (s, 2H), 2.06 (s, 3H), 1.40 ppm (d, J=6.8 Hz, 3H). ESI-MS: m/z 298.3 (M+H)$^+$.

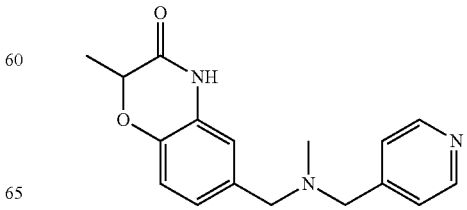

2-Methyl-6-((methyl(pyridin-4-ylmethyl)amino)methyl)-2H-benzo[b][1,4]oxazin-3(4H)-one (66)

Using 13 and N-methyl-1-(pyridin-4-yl)methanamine in the general procedure for reductive aminations, the title compound was obtained as an off-white solid: $^1$H NMR (DMSO-$d_6$, 400 MHz): δ=10.63 (s, 1H), 8.51 (d, J=6.1 Hz, 2H), 7.36 (d, J=5.8 Hz, 2H), 6.91-6.96 (m, 1H), 6.84-6.91 (m, 2H), 4.63 (q, J=6.8 Hz, 1H), 3.50 (s, 2H), 3.42 (s, 2H), 2.08 (s, 3H), 1.40 ppm (d, J=6.8 Hz, 3H). ESI-MS: m/z 296.2 (M+H)$^+$.

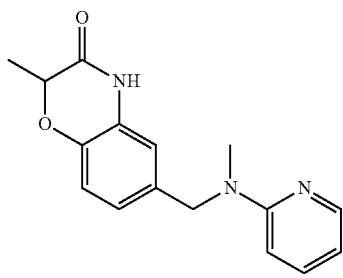 [SMILES: CC1Oc2ccc(CN(C)c3ccccn3)cc2NC1=O]

2-Methyl-6-((methyl(pyridin-2-yl)amino)methyl)-2H-benzo[b][1,4]oxazin-3(4H)-one (67)

Using 13 and N-methylpyridin-2-amine in the general procedure for reductive aminations, the title compound was obtained as a white solid: $^1$H NMR (DMSO-$d_6$, 400 MHz): δ=10.59 (s, 1H), 8.04 (dd, J=5.6, 1.3 Hz, 1H), 6.91 (d, J=8.1 Hz, 1H), 6.69-6.86 (m, 5H), 4.74 (s, 2H), 4.55-4.67 (m, 1H), 2.47 (s, 3H), 1.38 ppm (d, J=6.8 Hz, 3H). ESI-MS: m/z 284.2 (M+H)$^+$.

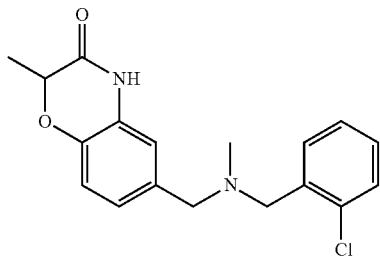 [SMILES: CC1Oc2ccc(CN(C)Cc3ccccc3Cl)cc2NC1=O]

6-(((2-Chlorobenzyl)(methyl)amino)methyl)-2-methyl-2H-benzo[b][1,4]oxazin-3(4H)-one (68)

Using 13 and 1-(2-chlorophenyl)-N-methylmethanamine in the general procedure for reductive aminations, the title compound was obtained as a brown solid: $^1$H NMR (DMSO-$d_6$, 400 MHz): δ=10.63 (br. s., 1H), 7.55 (br. s., 1H), 7.43 (br. s., 1H), 7.26-7.39 (m, 2H), 6.85-6.96 (m, 3H), 4.64 (br. s., 1H), 3.58 (s, 2H), 3.47 (s, 2H), 2.09 (s, 3H), 1.41 ppm (d, J=6.6 Hz, 3H). ESI-MS: m/z 331.2 (M+H)$^+$.

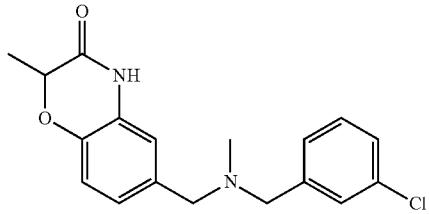 [SMILES: CC1Oc2ccc(CN(C)Cc3cccc(Cl)c3)cc2NC1=O]

6-(((3-Chlorobenzyl)(methyl)amino)methyl)-2-methyl-2H-benzo[b][1,4]oxazin-3(4H)-one (69)

Using 13 and 1-(3-chlorophenyl)-N-methylmethanamine in the general procedure for reductive aminations, the title compound was obtained as a brown solid: $^1$H NMR (DMSO-$d_6$, 400 MHz): δ=10.65 (br. s., 1H), 7.17-7.49 (m, 4H), 6.91 (d, J=14.9 Hz, 3 H), 4.62 (br. s., 1H), 3.47 (br. s., 2H), 3.41 (br. s., 2H), 2.05 (br. s., 3H), 1.40 ppm (d, J=6.3 Hz, 3H). ESI-MS: m/z 331.2 (M+H)$^+$.

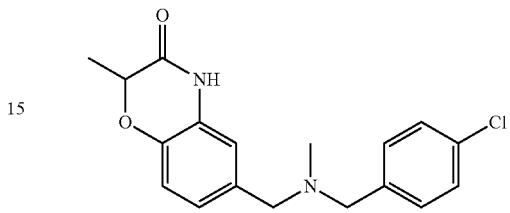

6-(((4-Chlorobenzyl)(methyl)amino)methyl)-2-methyl-2H-benzo[b][1,4]oxazin-3(4H)-one (70)

Using 13 and 1-(4-chlorophenyl)-N-methylmethanamine in the general procedure for reductive aminations, the title compound was obtained as a brown solid: $^1$H NMR (DMSO-$d_6$, 400 MHz): δ=10.62 (s, 1H), 7.22-7.49 (m, 4H), 6.76-6.99 (m, 3H), 4.63 (q, J=6.6 Hz, 1H), 3.45 (s, 2H), 3.39 (s, 2H), 2.05 (s, 3H), 1.40 ppm (d, J=6.6 Hz, 3H). ESI-MS: m/z 331.2 (M+H)$^+$.

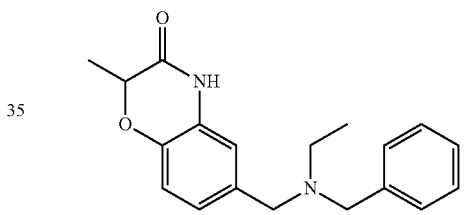

6-((Benzyl(ethyl)amino)methyl)-2-methyl-2H-benzo[b][1,4]oxazin-3(4H)-one (71)

Using 13 and N-benzylethanamine in the general procedure for reductive aminations, the title compound was obtained as a white solid: $^1$H NMR (DMSO-$d_6$, 400 MHz): δ=10.61 (s, 1H), 7.29-7.37 (m, 4H), 7.20-7.26 (m, 1H), 6.95 (d, J=1.0 Hz, 1H), 6.86-6.88 (m, 2H), 4.58-4.65 (m, 1H), 3.51 (s, 2H), 3.43 (s, 2H), 2.40 (q, J=7.1 Hz, 2H), 1.40 (d, J=6.8 Hz, 3H), 0.99 ppm (t, J=7.1 Hz, 3H). ESI-MS: m/z 311.3 (M+H)$^+$.

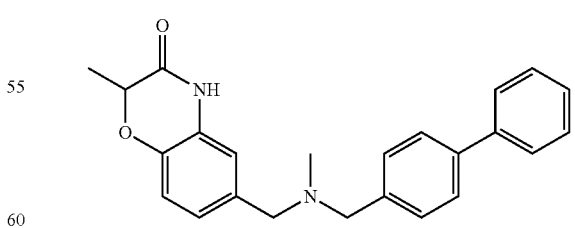

6-(((Biphenyl-4-ylmethyl)(methyl)amino)methyl)-2-methyl-2H-benzo[b][1,4]oxazin-3(4H)-one (72)

Using 13 and 1-(biphenyl-4-yl)-N-methylmethanamine in the general procedure for reductive aminations, the title compound was obtained as a white solid: $^1$H NMR (DMSO-d$_6$, 400 MHz): δ=10.64 (s, 1H), 7.60-7.70 (m, 4H), 7.40-7.49 (m, 4H), 7.32-7.38 (m, 1H), 6.86-6.98 (m, 3H), 4.59-4.67 (m, 1H), 3.51 (s, 2H), 3.43 (s, 2 H), 2.09 (s, 3H), 1.40 ppm (d, J=6.8 Hz, 3H). ESI-MS: m/z 373.4 (M+H)$^+$.

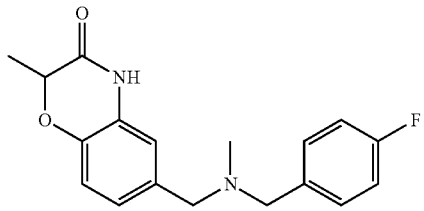 [SMILES: CC1Oc2ccc(CN(C)Cc3ccc(F)cc3)cc2NC1=O]

6-(((4-Fluorobenzyl)(methyl)amino)methyl)-2-methyl-2H-benzo[b][1,4]oxazin-3(4H)-one (73)

Using 13 and 1-(4-fluorophenyl)-N-methylmethanamine in the general procedure for reductive aminations, the title compound was obtained as a light brown solid: $^1$H NMR (DMSO-d$_6$, 400 MHz): δ=10.62 (s, 1H), 7.36 (dd, J=8.0, 5.9 Hz, 2H), 7.15 (t, J=8.8 Hz, 2H), 6.80-6.96 (m, 3H), 4.63 (q, J=6.8 Hz, 1H), 3.45 (s, 2H), 3.39 (s, 2H), 2.04 (s, 3 H), 1.40 ppm (d, J=6.6 Hz, 3H). ESI-MS: m/z 315.3 (M+H)$^+$.

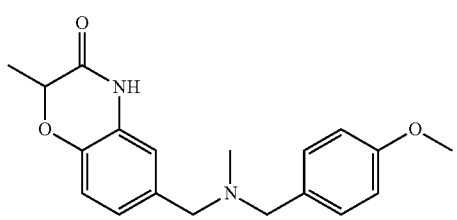

6-(((4-Methoxybenzyl)(methyl)amino)methyl)-2-methyl-2H-benzo[b][1,4]oxazin-3(4H)-one (74)

Using 13 and 1-(4-methoxyphenyl)-N-methylmethanamine in the general procedure for reductive aminations, the title compound was obtained as a white solid: $^1$H NMR (DMSO-d$_6$, 400 MHz): δ=10.62 (s, 1H), 7.24 (d, J=8.6 Hz, 2H), 6.82-6.93 (m, 5H), 4.58-4.66 (m, 1H), 3.73 (s, 3H), 3.39 (s, 2H), 3.36 (s, 2H), 2.03 (s, 3H), 1.40 ppm (d, J=6.8 Hz, 3 H). ESI-MS: m/z 327.3 (M+H)$^+$.

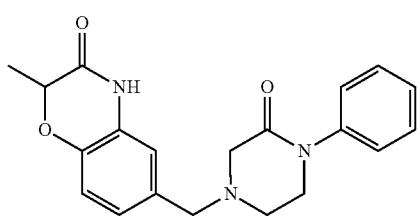 [SMILES: CC1Oc2ccc(CN3CCN(c4ccccc4)C(=O)C3)cc2NC1=O]

2-Methyl-6-((3-oxo-4-phenylpiperazin-1-yl)methyl)-2H-benzo[b][1,4]oxazin-3(4H)-one (75)

Using 13 and 1-phenylpiperazin-2-one in the general procedure for reductive aminations, the title compound was obtained as a white solid: $^1$H NMR (DMSO-d$_6$, 400 MHz):

δ=10.64 (br. s., 1H), 7.36-7.43 (m, 2H), 7.29-7.34 (m, 2H), 7.25 (tt, J=7.2, 1.3 Hz, 1H), 6.86-6.94 (m, 3H), 4.61-4.68 (m, 1H), 3.59-3.66 (m, 2H), 3.51 (s, 2H), 3.13 (s, 2H), 2.76 (t, J=5.3 Hz, 2H), 1.41 ppm (d, J=6.8 Hz, 3H). ESI-MS: m/z 352.3 (M+H)$^+$.

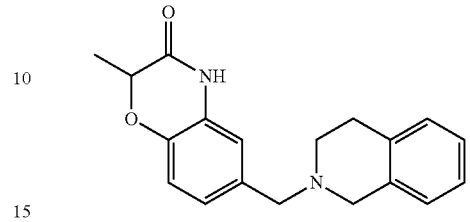

6-((3,4-Dihydroisoquinolin-2(1H)-yl)methyl)-2-methyl-2H-benzo[b][1,4]oxazin-3(4H)-one (76)

Using 13 and 1,2,3,4-tetrahydroisoquinoline in the general procedure for reductive aminations, the title compound was obtained as a brown solid: $^1$H NMR (DMSO-d$_6$, 400 MHz): δ=10.61 (s, 1H), 7.05-7.13 (m, 3H), 7.01 (d, J=6.6 Hz, 1H), 6.86-6.95 (m, 3 H), 4.65 (q, J=6.6 Hz, 1H), 3.55 (s, 2H), 3.51 (s, 2H), 2.78-2.85 (m, 2H), 2.67 (d, J=5.6 Hz, 2H), 1.42 ppm (d, J=6.6 Hz, 3H). ESI-MS: m/z 309.3 (M+H)$^+$.

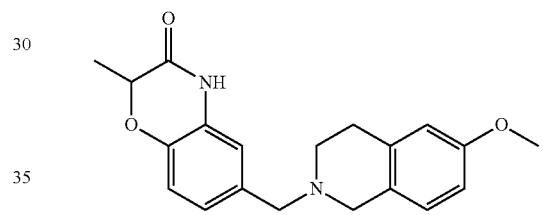

6-((6-Methoxy-3,4-dihydroisoquinolin-2(1H)-yl)methyl)-2-methyl-2H-benzo[b][1,4]oxazin-3(4H)-one (77)

Using 13 and 6-methoxy-1,2,3,4-tetrahydroisoquinoline in the general procedure for reductive aminations, the title compound was obtained as a white solid: $^1$H NMR (DMSO-d$_6$, 400 MHz): δ=10.60 (br. s., 1H), 6.92 (br. s., 3H), 6.66 (br. s., 3 H), 4.56-4.73 (m, 1H), 3.70 (br. s., 3H), 3.52 (br. s., 2H), 3.38-3.48 (m, 2H), 2.78 (br. s., 2 H), 2.62 (br. s., 2H), 1.31-1.52 ppm (m, 3H). ESI-MS: m/z 339.3 (M+H)$^+$.

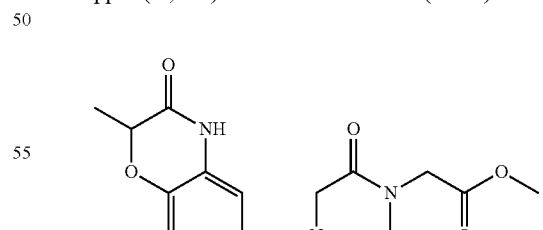

Methyl 2-(4-((2-methyl-3-oxo-3,4-dihydro-2H-benzo[b][1,4]oxazin-6-yl)methyl)-2-oxopiperazin-1-yl)acetate (78)

Using 13 and methyl 2-(2-oxopiperazin-1-yl)acetate in the general procedure for reductive aminations, the title compound was obtained as a white solid: $^1$H NMR (DMSO-d$_6$, 400 MHz): δ=10.88 (br. s., 1H), 7.03 (s, 2H), 6.98 (s, 1H), 4.70 (q, J=6.8 Hz, 1H), 4.18 (s, 2H), 3.70-3.75 (m, 2H), 3.67 (s, 3H), 3.55 (br. s., 2H), 3.34 (br. s., 4H), 1.43 ppm (d, J=6.8 Hz, 3H). ESI-MS: m/z 348.3 (M+H)$^+$.

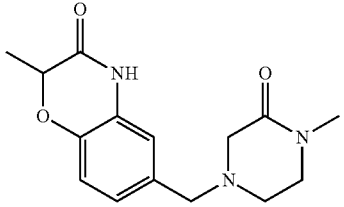

2-Methyl-6-((4-methyl-3-oxopiperazin-1-yl)methyl)-2H-benzo[b][1,4]oxazin-3(4H)-one (79)

Using 13 and methyl 1-methylpiperazin-2-one in the general procedure for reductive aminations, the title compound was obtained as a white solid: $^1$H NMR (DMSO-d$_6$, 400 MHz): δ=10.90 (br. s., 1H), 7.03 (d, J=18.9 Hz, 2H), 6.98 (s, 1H), 4.67-4.74 (m, 1H), 4.23 (br. s., 2H), 3.64 (br. s., 2H), 3.47 (br. s., 4H), 2.86 (s, 3H), 1.43 ppm (d, J=6.8 Hz, 3H). ESI-MS: m/z 290.2 (M+H)$^+$.

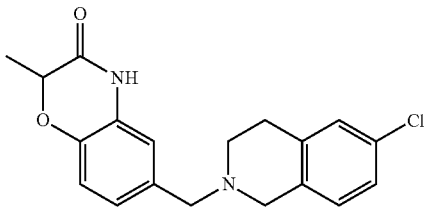 [SMILES: CC1Oc2ccc(CN3CCc4cc(Cl)ccc4C3)cc2NC1=O]

6-((6-Chloro-3,4-dihydroisoquinolin-2(1H)-yl)methyl)-2-methyl-2H-benzo[b][1,4]oxazin-3(4H)-one (80)

Using 13 and 6-chloro-1,2,3,4-tetrahydroisoquinoline in the general procedure for reductive aminations, the title compound was obtained as a light yellow solid: $^1$H NMR (DMSO-d$_6$, 400 MHz): δ=10.60 (s, 1H), 7.18 (d, J=2.0 Hz, 1H), 7.12-7.16 (m, 1H), 7.03-7.07 (m, 1H), 6.91 (d, J=1.8 Hz, 1H), 6.90 (s, 1H), 6.88 (d, J=1.8 Hz, 1H), 4.60-4.67 (m, 1H), 3.90 (s, 2H), 3.54 (s, 2H), 2.78-2.83 (m, 2H), 2.61-2.66 (m, 2 H), 1.41 ppm (d, J=6.6 Hz, 3H). ESI-MS: m/z 343.3 (M+H)$^+$.

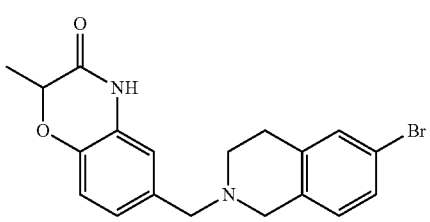 [SMILES: CC1Oc2ccc(CN3CCc4cc(Br)ccc4C3)cc2NC1=O]

6-((6-Bromo-3,4-dihydroisoquinolin-2(1H)-yl)methyl)-2-methyl-2H-benzo[b][1,4]oxazin-3(4H)-one (81)

Using 13 and 6-bromo-1,2,3,4-tetrahydroisoquinoline in the general procedure for reductive aminations, the title compound was obtained as a white solid: $^1$H NMR (DMSO-d$_6$, 400 MHz): δ=10.61 (br. s., 1H), 7.32 (d, J=1.8 Hz, 1H), 7.26 (dd, J=8.2, 2.1 Hz, 1H), 6.99 (d, J=8.1 Hz, 1H), 6.85-6.92 (m, 3H), 4.63 (d, J=6.8 Hz, 1H), 3.54 (s, 2H), 3.46 (s, 2H), 2.77-2.84 (m, 2H), 2.61-2.66 (m, 2H), 1.41 ppm (d, J=6.8 Hz, 3H). ESI-MS: m/z 387.2 (M+H)$^+$.

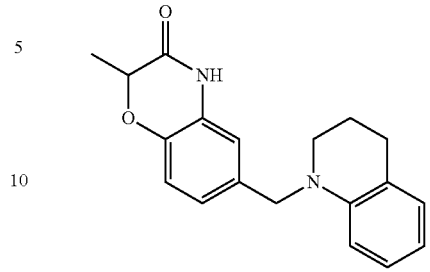

6-((3,4-Dihydroquinolin-1(2H)-yl)methyl)-2-methyl-2H-benzo[b][1,4]oxazin-3(4H)-one (82)

Using 13 and 1,2,3,4-tetrahydroquinoline in the general procedure for reductive aminations, the title compound was obtained as a tan solid: $^1$H NMR (DMSO-d$_6$, 400 MHz): δ=10.38 (s, 1H), 6.64-6.74 (m, 3H), 6.56-6.64 (m, 2H), 6.15-6.30 (m, 2H), 4.41 (q, J=6.8 Hz, 1H), 4.18 (s, 2H), 3.09-3.17 (m, 2H), 2.53 (t, J=6.3 Hz, 2H), 1.73 (dq, J=5.9, 5.8 Hz, 2H), 1.20 ppm (d, J=6.6 Hz, 3H). ESI-MS: m/z 309.3 (M+H)$^+$.

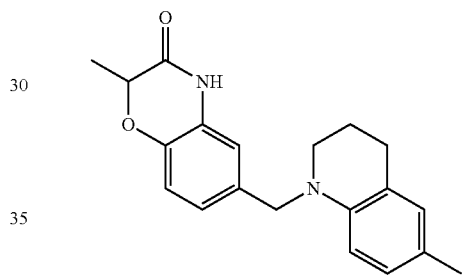

2-Methyl-6-((6-methyl-3,4-dihydroquinolin-1(2H)-yl)methyl)-2H-benzo[b][1,4]oxazin-3(4H)-one (83)

Using 13 and 6-methyl-1,2,3,4-tetrahydroquinoline in the general procedure for reductive aminations, the title compound was obtained as a tan solid: $^1$H NMR (DMSO-d$_6$, 400 MHz): δ=10.58 (s, 1H), 6.86-6.93 (m, 1H), 6.75-6.81 (m, 1H), 6.66-6.74 (m, 1H), 6.63 (s, 1H), 6.28-6.37 (m, 2H), 4.61 (q, J=6.8 Hz, 1H), 4.34 (s, 2H), 3.25-3.32 (m, 1H), 3.13 (td, J=5.4, 2.5 Hz, 1H), 2.69 (t, J=6.1 Hz, 1H), 2.61 (t, J=6.3 Hz, 1 H), 2.06-2.13 (m, 3H), 1.86-1.95 (m, 1H), 1.72-1.80 (m, 1H), 1.40 ppm (d, J=6.8 Hz, 3 H). ESI-MS: m/z 323.3 (M+H)$^+$.

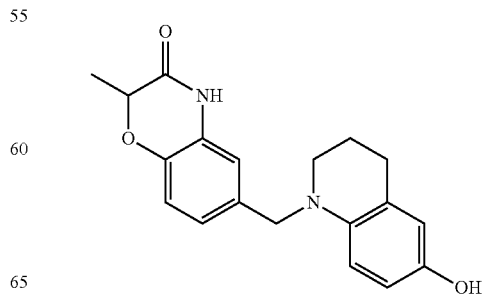

6-((6-Hydroxy-3,4-dihydroquinolin-1(2H)-yl)methyl)-2-methyl-2H-benzo[b][1,4]oxazin-3(4H)-one (84)

Using 13 and 6-hydroxy-1,2,3,4-tetrahydroquinoline in the general procedure for reductive aminations, the title compound was obtained as a pink solid: $^1$H NMR (DMSO-$d_6$, 400 MHz): δ=10.60 (s, 1H), 6.92 (d, J=8.8 Hz, 1H), 6.77-6.81 (m, 2H), 6.66 (d, J=8.1 Hz, 1H), 5.91 (dd, J=7.8, 2.3 Hz, 1H), 5.85 (d, J=2.3 Hz, 1H), 4.58-4.65 (m, 1H), 4.32 (s, 2H), 3.26-3.33 (m, 2H), 2.62 (t, J=6.3 Hz, 2H), 1.85-1.93 (m, 2H), 1.40 ppm (d, J=6.8 Hz, 3H). ESI-MS: m/z 325.3 (M+H)$^+$.

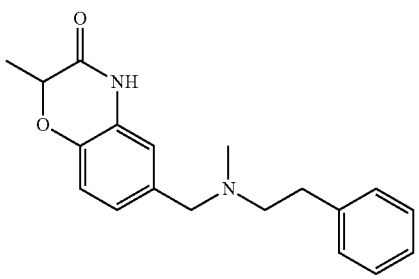 [SMILES: CC1Oc2ccc(CN(C)CCc3ccccc3)cc2NC1=O]

2-Methyl-6-((methyl(phenethyl)amino)methyl)-2H-benzo[b][1,4]oxazin-3(4H)-one (85)

Using 13 and N-methyl-2-phenylethanamine in the general procedure for reductive aminations, the title compound was obtained as an off-white solid: $^1$H NMR (400 MHz, DMSO-$d_6$) δ ppm 1.43 (d, J=6.82 Hz, 3H), 2.74 (s, 3H), 2.90-3.13 (m, 2H), 3.13-3.41 (m, 2H), 4.19-4.32 (m, 1H), 4.32-4.43 (m, 1H), 4.68-4.76 (m, 1H), 7.01-7.08 (m, 2H), 7.08-7.13 (m, 1H), 7.23-7.30 (m, 3H), 7.31-7.39 (m, 2H), 10.05 (br. s., 1H), 10.93 (s, 1H). ESI-MS: m/z 311.2 (M+H)$^+$.

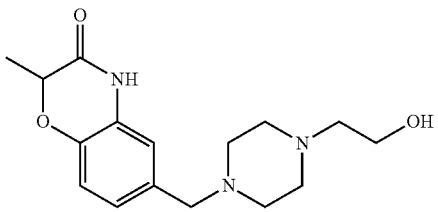 [SMILES: CC1Oc2ccc(CN3CCN(CCO)CC3)cc2NC1=O]

6-((4-(2-Hydroxyethyl)piperazin-1-yl)methyl)-2-methyl-2H-benzo[b][1,4]oxazin-3(4H)-one (86)

Using 13 and 2-(piperazin-1-yl)ethanol in the general procedure for reductive aminations, the title compound was obtained as a light yellow solid, mp 174.4-174.5° C.: $^1$H NMR (400 MHz, DMSO-$d_6$) δ ppm 10.86 (s, 1H), 6.97-7.04 (m, 2H), 6.91-6.97 (m, 1H), 4.68 (q, J=6.8 Hz, 1H), 3.92-4.17 (m, 2H), 3.68-3.75 (m, 2H), 3.12-3.41 (m, 7H), 1.43 (d, J=6.8 Hz, 3H). ESI-MS: m/z 306.3 (M+H)$^+$.

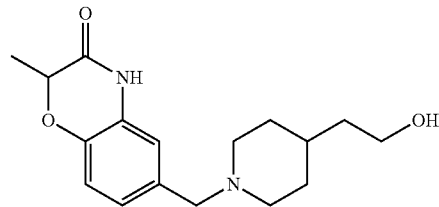 [SMILES: CC1Oc2ccc(CN3CCC(CCO)CC3)cc2NC1=O]

6-((4-(2-Hydroxyethyl)piperidin-1-yl)methyl)-2-methyl-2H-benzo[b][1,4]oxazin-3(4H)-one (87)

Using 13 and 2-(piperidin-4-yl)ethanol in the general procedure for reductive aminations, the title compound was obtained as a yellow oil: $^1$H NMR (400 MHz, DMSO-$d_6$) δ ppm 10.92 (br. s., 1H), 9.15-9.33 (m, 1H), 6.93-7.14 (m, 2H), 4.66-4.76 (m, 1H), 4.37-4.49 (m, 2H), 4.24-4.31 (m, 1H), 4.13-4.24 (m, 2H), 3.39-3.49 (m, 1H), 3.26-3.39 (m, 1H), 3.01-3.17 (m, 1H), 2.78-3.01 (m, 1H), 1.74-1.96 (m, 2H), 1.50-1.74 (m, 2H), 1.43 (d, J=6.8 Hz, 2H), 1.20-1.40 (m, 2H). ESI-MS: m/z 305.3 (M+H)$^+$.

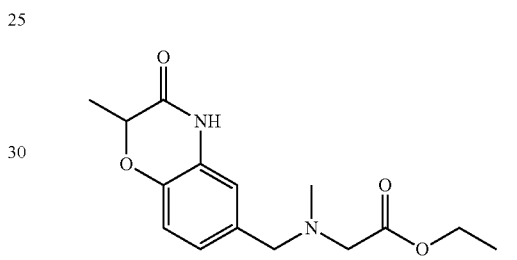

Ethyl 2-(methyl((2-methyl-3-oxo-3,4-dihydro-2H-benzo[b][1,4]oxazin-6-yl)methyl)amino)acetate (88)

Using 13 and ethyl 2-(methylamino)acetate in the general procedure for reductive aminations, the title compound was obtained as a tan solid: $^1$H NMR (DMSO-$d_6$, 400 MHz): δ=10.62 (s, 1H), 6.87-6.90 (m, 1H), 6.86 (d, J=1.8 Hz, 1H), 6.80-6.83 (m, 1H), 4.63 (d, J=6.8 Hz, 1H), 4.08 (d, J=7.1 Hz, 2H), 3.52 (s, 2H), 3.24 (s, 2H), 2.22 (s, 3H), 1.40 (d, J=6.8 Hz, 3H), 1.19 ppm (t, J=7.1 Hz, 3H). ESI-MS: m/z 293.2 (M+H)$^+$.

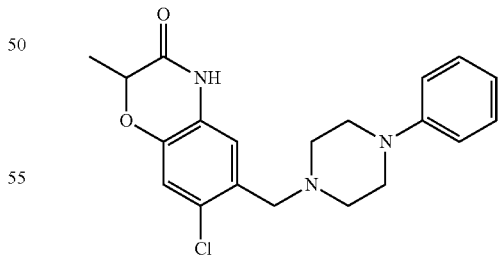

7-Chloro-2-methyl-6-((4-phenylpiperazin-1-yl)methyl)-2H-benzo[b][1,4]oxazin-3(4H)-one (89)

Using 22 and 1-phenylpiperazine in the general procedure for reductive aminations, the title compound was obtained as a tan solid: $^1$H NMR (400 MHz, DMSO-$d_6$) δ ppm 1.45 (d, J=6.82 Hz, 3H) 2.74-4.05 (m, 8H) 4.40-4.53 (m, 2H) 4.76-

4.83 (m, 1H) 6.84-6.90 (m, 1H) 6.96-7.02 (m, 2H) 7.18 (s, 1H) 7.23-7.31 (m, 3H) 9.92 (br. s., 1H) 11.11 (s, 1H). ESI-MS: m/z 372.3 (M+H)⁺.

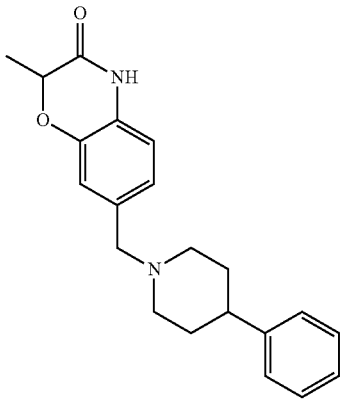 [SMILES: CC1Oc2cc(CN3CCC(c4ccccc4)CC3)ccc2NC1=O]

2-Methyl-7-((4-phenylpiperidin-1-yl)methyl)-2H-benzo[b][1,4]oxazin-3(4H)-one (90)

Using 20 and 4-phenylpiperidine in the general procedure for reductive aminations, the title compound was obtained as a white solid: ¹H NMR (DMSO-d₆, 400 MHz): δ=10.87 (s, 1 H), 9.38 (br. s., 1H), 7.30-7.46 (m, 2H), 7.21-7.30 (m, 3H), 7.17 (d, J=1.8 Hz, 1H), 7.11 (dd, J=8.0, 1.9 Hz, 1H), 6.97 (d, J=8.1 Hz, 1H), 4.73 (d, J=6.8 Hz, 1H), 4.26 (d, J=5.1 Hz, 2H), 3.46 (d, J=12.9 Hz, 2H), 2.98-3.10 (m, J=12.1 Hz, 2H), 2.76-2.85 (m, J=12.1, 12.1 Hz, 1H), 1.96-2.04 (m, 2H), 1.84 (q, J=11.8 Hz, 2H), 1.45 ppm (d, J=6.8 Hz, 3H). ESI-MS: m/z 337.3 (M+H)⁺.

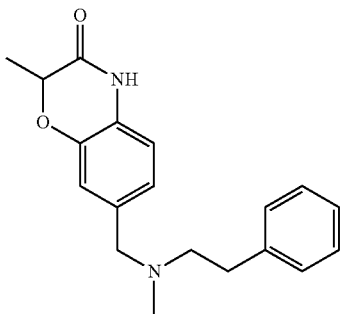 [SMILES: CC1Oc2cc(CN(C)CCc3ccccc3)ccc2NC1=O]

2-Methyl-7-((methyl(phenethyl)amino)methyl)-2H-benzo[b][1,4]oxazin-3(4H)-one (91)

Using 20 and N-methyl-2-phenylethanamine in the general procedure for reductive aminations, the title compound was obtained as a white solid: ¹H NMR (400 MHz, DMSO-d₆) δ ppm 1.43 (d, J=6.82 Hz, 3H), 2.74 (d, J=3.54 Hz, 3H), 2.93-3.12 (m, 2H), 3.13-3.38 (m, 2H), 4.18 (dd, J=12.88, 6.06 Hz, 1H), 4.38 (dd, J=12.76, 3.66 Hz, 1H), 4.72 (qd, J=6.78, 3.16 Hz, 1H), 6.95 (d, J=7.83 Hz, 1H), 7.11 (dd, J=8.08, 1.77 Hz, 1H), 7.17 (d, J=1.52 Hz, 1H), 7.24-7.30 (m, 3H), 7.32-7.38 (m, 2H), 9.81 (br. s., 1H), 10.86 (s, 1H). ESI-MS: m/z 311.3 (M+H)⁺.

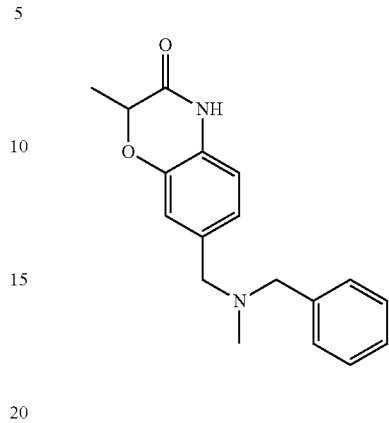

7-((Benzyl(methyl)amino)methyl)-2-methyl-2H-benzo[b][1,4]oxazin-3(4H)-one (92)

Using 20 and N-methyl-1-phenylmethanamine in the general procedure for reductive aminations, the title compound was obtained as a white solid: ¹H NMR (400 MHz, DMSO-d₆) δ ppm 1.43 (d, J=6.82 Hz, 3H), 2.52-2.54 (m, 2H), 4.09-4.23 (m, 2H), 4.30-4.49 (m, 2 H), 4.67-4.76 (m, 1H), 6.95 (d, J=7.83 Hz, 1H), 7.10 (dd, J=7.96, 1.89 Hz, 1H), 7.14-7.17 (m, 1H), 7.45-7.55 (m, 5H), 9.91 (br. s., 1H), 10.86 (s, 1H). ESI-MS: m/z 297.2 (M+H)⁺.

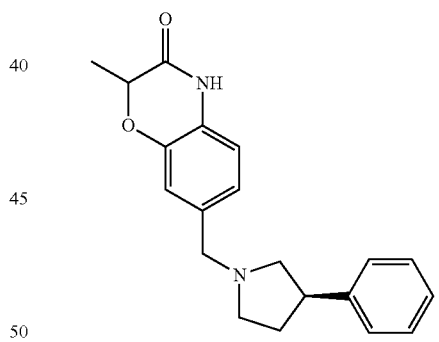

2-Methyl-7-(((R)-3-phenylpyrrolidin-1-yl)methyl)-2H-benzo[b][1,4]oxazin-3(4H)-one (93)

Using 20 and (R)-3-phenylpyrrolidine in the general procedure for reductive aminations, the title compound was obtained as a white solid: ¹H NMR (400 MHz, DMSO-d₆) δ ppm 1.43 (d, J=6.57 Hz, 3H), 2.05-2.26 (m, 1H), 2.26-2.48 (m, 1H), 3.11-3.36 (m, 2 H), 3.36-3.46 (m, 2H), 3.63-3.79 (m, 2H), 4.29-4.43 (m, 2H), 4.66-4.74 (m, 1H), 6.91-6.96 (m, 1H), 7.09-7.22 (m, 2H), 7.24-7.40 (m, 4H), 10.12-10.26 (m, 1H), 10.84 (s, 1H). ESI-MS: m/z 323.3 (M+H)⁺.

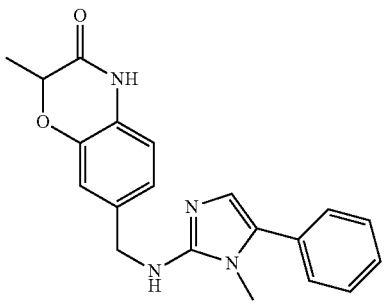 [SMILES: CC1Oc2cc(CNc3ncc(-c4ccccc4)n3C)ccc2NC1=O]

2-Methyl-7-((1-methyl-5-phenyl-1H-imidazol-2-ylamino)methyl)-2H-benzo[b][1,4]oxazin-3(4H)-one (94)

Using 20 and 1-methyl-5-phenyl-1H-imidazol-2-amine in the general procedure for reductive aminations, the title compound was obtained as a light yellow solid: ¹H NMR (400 MHz, DMSO-d₆) δ ppm 1.42 (d, J=6.82 Hz, 3H), 3.44 (s, 3H), 4.46 (d, J=5.81 Hz, 2H), 4.63-4.70 (m, 1H), 6.90 (d, J=8.08 Hz, 1H), 6.99-7.05 (m, 2 H), 7.28 (s, 1H), 7.46-7.55 (m, 4H), 8.60 (t, J=6.19 Hz, 1H), 10.70 (s, 1H), 12.65 (s, 1H). ESI-MS: m/z 349.3 (M+H)⁺.

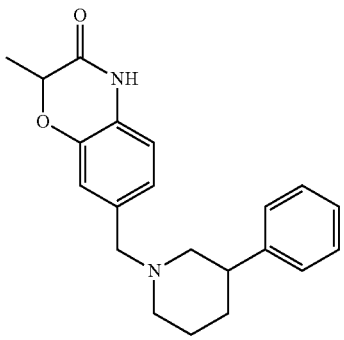 [SMILES: CC1Oc2cc(CN3CCCC(c4ccccc4)C3)ccc2NC1=O]

2-Methyl-7-((3-phenylpiperidin-1-yl)methyl)-2H-benzo[b][1,4]oxazin-3(4H)-one (95)

Using 20 and 3-phenylpiperidine in the general procedure for reductive aminations, the title compound was obtained as a white solid: ¹H NMR (400 MHz, DMSO-d₆) δ ppm 1.42 (d, J=6.57 Hz, 3H), 1.61-1.72 (m, 1H), 1.73-1.99 (m, 3H), 2.86-3.13 (m, 3H), 3.32-3.45 (m, 2H), 4.18-4.27 (m, 2H), 4.66-4.74 (m, 1H), 6.93 (dd, J=7.83, 0.76 Hz, 1H), 7.07 (dt, J=7.96, 1.96 Hz, 1H), 7.14 (s, 1H), 7.22-7.31 (m, 3H), 7.33-7.39 (m, 2H), 9.84 (br. s., 1 H), 10.84 (s, 1H). ESI-MS: m/z 337.3 (M+H)⁺.

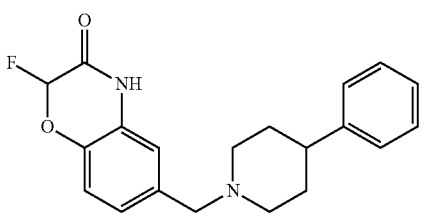 [SMILES: O=C1Nc2cc(CN3CCC(c4ccccc4)CC3)ccc2OC1F]

2-Fluoro-6-((4-phenylpiperidin-1-yl)methyl)-2H-benzo[b][1,4]oxazin-3(4H)-one (96)

Using 21 and 4-phenylpiperidine in the general procedure for reductive aminations, the title compound was obtained as a white solid, mp 217-221° C.: ¹H NMR (400 MHz, DMSO-d₆) δ ppm 11.38 (br. s., 1H), 7.26-7.33 (m, 2H), 7.21-7.26 (m, 2H), 7.12-7.21 (m, 2H), 7.05 (d, J=1.8 Hz, 1H), 7.00 (dd, J=8.2, 1.9 Hz, 1H), 3.44 (s, 2H), 2.85-2.95 (m, 2H), 2.43-2.49 (m, 1H), 1.97-2.10 (m, 2H), 1.57-1.78 (m, 4H). ESI-MS: m/z 341.3 (M+H)⁺.

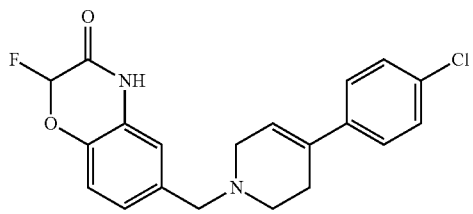 [SMILES: O=C1Nc2cc(CN3CC=C(c4ccc(Cl)cc4)CC3)ccc2OC1F]

6-((4-(4-Chlorophenyl)-5,6-dihydropyridin-1(2H)-yl)methyl)-2-fluoro-2H-benzo[b][1,4]oxazin-3(4H)-one (97)

Using 21 and 4-(4-chlorophenyl)-1,2,3,6-tetrahydropyridine in the general procedure for reductive aminations, the title compound was obtained as a white solid: ¹H NMR (400 MHz, DMSO-d₆) δ ppm 11.40 (br. s., 1H), 7.42-7.48 (m, J=8.6 Hz, 2H), 7.34-7.41 (m, J=8.8 Hz, 2H), 7.15 (d, J=8.1 Hz, 1H), 7.06 (d, J=1.5 Hz, 1H), 6.99-7.04 (m, 1H), 6.22-6.38 (m, 1H), 6.17-6.21 (m, 1H), 3.48-3.59 (m, 2H), 3.00-3.09 (m, 2H), 2.59-2.67 (m, 2H), 2.40-2.48 (m, 2H). ESI-MS: m/z 373.3 (M+H)⁺.

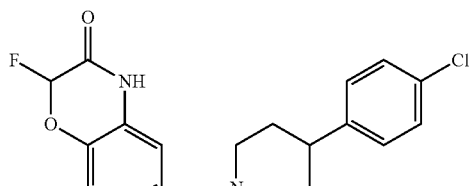

6-((4-(4-Chlorophenyl)piperidin-1-yl)methyl)-2-fluoro-2H-benzo[b][1,4]oxazin-3(4H)-one (98)

Using 21 and 4-(4-chlorophenyl)piperidine in the general procedure for reductive aminations, the title compound was obtained as a white solid: ¹H NMR (400 MHz, DMSO-d₆) δ ppm 11.36 (br. s., 1H), 7.31-7.37 (m, 2H), 7.24-7.29 (m, 2H), 7.14 (d, J=8.3 Hz, 1H), 7.03 (d, J=1.8 Hz, 1H), 6.97-7.02 (m, 1H), 6.21-6.37 (m, 1H), 3.44 (s, 2H), 2.89 (d, J=11.6 Hz, 2H), 1.97-2.08 (m, 2H), 1.68-1.77 (m, 2H), 1.53-1.68 (m, 2H). ESI-MS: m/z 375.3 (M+H)⁺.

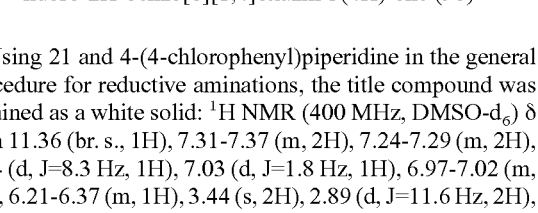

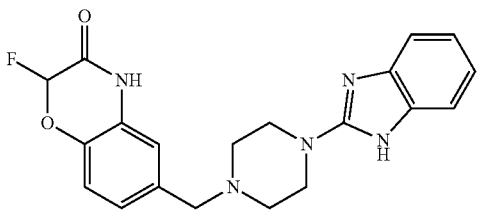 [SMILES: O=C1Nc2cc(CN3CCN(c4nc5ccccc5[nH]4)CC3)ccc2OC1F]

6-((4-(1H-Benzo[d]imidazol-2-yl)piperazin-1-yl)methyl)-2-fluoro-2H-benzo[b][1,4]oxazin-3(4H)-one (99)

Using 21 and 2-(4-(piperazin-1-yl)phenyl)-1H-benzo[d]imidazole in the general procedure for reductive aminations, the title compound was obtained as a white solid: $^1$H NMR (400 MHz, DMSO-d$_6$) δ ppm 11.73 (br. s., 1H), 7.43-7.49 (m, 2H), 7.26-7.34 (m, 3H), 7.12-7.22 (m, 2H), 6.38-6.44 (m, 1H), 6.30-6.38 (m, 1H), 4.15-4.30 (m, 2H), 3.71-3.99 (m, 3H), 3.17-3.46 (m, 4H). ESI-MS: m/z 382.3 (M+H)$^+$.

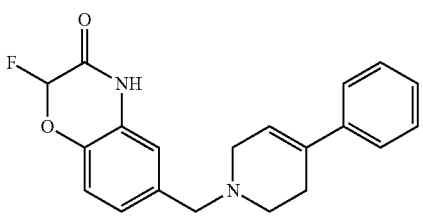 [SMILES: O=C1Nc2cc(CN3CC=C(c4ccccc4)CC3)ccc2OC1F]

2-Fluoro-6-((4-phenyl-5,6-dihydropyridin-1(2H)-yl)methyl)-2H-benzo[b][1,4]oxazin-3(4H)-one (100)

Using 21 and 4-phenyl-1,2,3,6-tetrahydropyridine in the general procedure for reductive aminations, the title compound was obtained as an off-white solid, mp 238.8-238.9° C.: $^1$H NMR (400 MHz, DMSO-d$_6$) δ ppm 11.37 (br. s., 1H), 7.42 (d, J=7.3 Hz, 2H), 7.33 (t, J=7.6 Hz, 2H), 7.21-7.27 (m, 1H), 7.15 (d, J=8.1 Hz, 1H), 7.06-7.10 (m, 1H), 7.02 (dd, J=8.3, 1.8 Hz, 1H), 6.11-6.18 (m, 1H), 3.49-3.59 (m, 2H), 3.00-3.10 (m, 2H), 2.59-2.70 (m, 2H), 2.42-2.49 (m, 2H). ESI-MS: m/z 339.3 (M+H)$^+$.

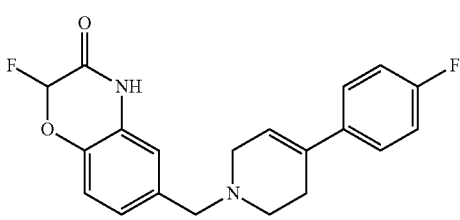 [SMILES: O=C1Nc2cc(CN3CC=C(c4ccc(F)cc4)CC3)ccc2OC1F]

2-Fluoro-6-((4-(4-fluorophenyl)-5,6-dihydropyridin-1(2H)-yl)methyl)-2H-benzo[b][1,4]oxazin-3(4H)-one (101)

Using 21 and 4-(4-fluorophenyl)-1,2,3,6-tetrahydropyridine in the general procedure for reductive aminations, the title compound was obtained as an off-white solid, mp 266.2-266.3° C.: $^1$H NMR (400 MHz, DMSO-d$_6$) δ ppm 11.21 (s, 1H), 7.39-7.50 (m, 2H), 7.10-7.19 (m, 3H), 7.07 (d, J=1.8 Hz, 1H), 7.02 (dd, J=8.3, 1.8 Hz, 1H), 6.29-6.38 (m, 1H), 6.08-6.14 (m, 1H), 3.48-3.59 (m, 2H), 2.99-3.08 (m, 2H), 2.59-2.68 (m, 2H), 2.39-2.49 (m, 2H). ESI-MS: m/z 357.3 (M+H)$^+$.

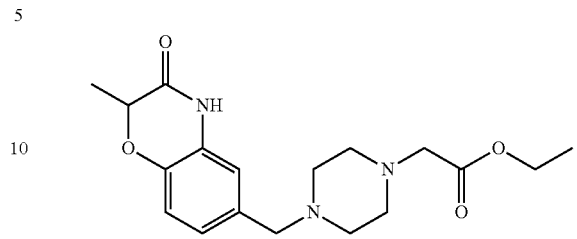

Ethyl 2-(4-((2-methyl-3-oxo-3,4-dihydro-2H-benzo[b][1,4]oxazin-6-yl)methyl)piperazin-1-yl)acetate (102)

Using 13 and ethyl 2-(piperazin-1-yl)acetate in the general procedure for reductive aminations, the title compound was obtained as a light yellow solid: $^1$H NMR (400 MHz, DMSO-d$_6$) δ ppm 10.59 (s, 1H), 6.85-6.90 (m, 1H), 6.84 (d, J=1.8 Hz, 1H), 6.78-6.83 (m, 1H), 4.62 (q, J=6.8 Hz, 1H), 4.07 (q, J=7.1 Hz, 2H), 3.34 (s, 2H), 3.18 (s, 2H), 2.42-2.50 (m, 4H), 2.34 (br. s., 4H), 1.40 (d, J=6.8 Hz, 3H), 1.18 (t, J=7.2 Hz, 3H). ESI-MS: m/z 348.3 (M+H)$^+$.

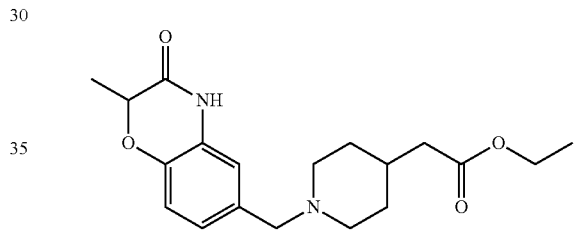

Ethyl 2-(1-((2-methyl-3-oxo-3,4-dihydro-2H-benzo[b][1,4]oxazin-6-yl)methyl)piperidin-4-yl)acetate (103)

Using 13 and ethyl 2-(piperidin-4-yl)acetate in the general procedure for reductive aminations, the title compound was obtained as a white solid: $^1$H NMR (400 MHz, DMSO-d$_6$) δ ppm 1.18 (t, J=7.07 Hz, 3H) 1.26-1.42 (m, 1H) 1.43 (d, J=6.82 Hz, 3H) 1.62-1.80 (m, 1H) 1.80-1.97 (m, 2H) 2.27 (d, J=6.82 Hz, 1H) 2.86-3.02 (m, 2H) 3.02-3.22 (m, 1H) 3.22-3.38 (m, 2H) 4.06 (q, J=7.07 Hz, 2H) 4.18 (d, J=5.31 Hz, 2H) 4.67-4.74 (m, 1H) 6.95-7.07 (m, 3H) 9.25-9.43 (m, 1H) 10.92 (s, 1H). ESI-MS: m/z 347.4 (M+H)$^+$.

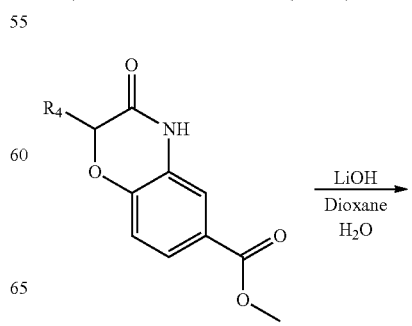

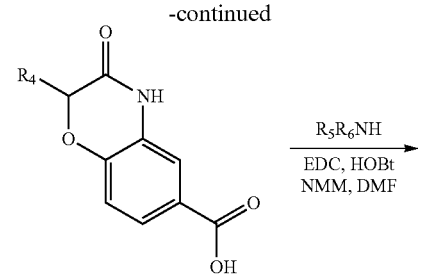

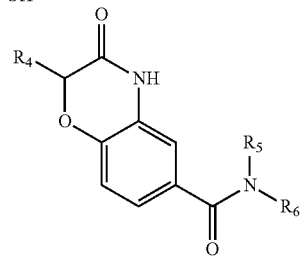

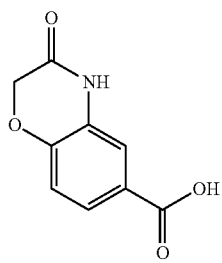

General Procedure for Hydrolysis of Carboxylic Esters

Synthesis of 3-Oxo-3,4-dihydro-2H-benzo[b][1,4]oxazine-6-carboxylic acid (104)

To a solution of 18 (1.0 mmol) in dioxane (4 mL) was added aqueous LiOH (1 M, 4 mL, 4.0 mmol). The solution was stirred at 23° C. for 1 h and then quenched with aqueous HCl (4 M, 2 mL, 8 mmol). The resulting solid was isolated by filtration, washed with water and dried in vacuo to give a white solid: $^1$H NMR (DMSO-$d_6$, 400 MHz): δ=12.81 (s, 1H), 10.88 (s, 1H), 7.48-7.54 (m, 2H), 7.01 (d, J=8.3 Hz, 1H), 4.67 ppm (s, 2H). ESI-MS: m/z 194.0 (M+H)$^+$.

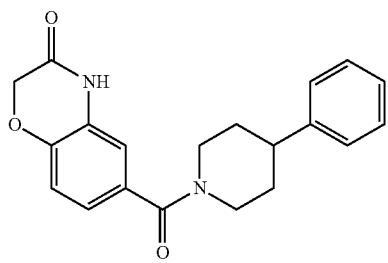 [SMILES: O=C1COc2ccc(C(=O)N3CCC(c4ccccc4)CC3)cc2N1]

General Procedure for Coupling an Amine to a Carboxylic Acid

Synthesis of 6-(4-phenylpiperidine-1-carbonyl)-2H-benzo[b][1,4]oxazin-3(4H)-one (105)

To a solution of 104 (0.5 mmol) in DMF (4 mL) was added 4-phenylpiperidine (0.75 mmol), EDC (0.6 mmol), and HOBt (0.6 mmol) followed by Hunig's base (1.5 mmol). The solu-tion was stirred at 23° C. for 4 h and then water (15 mL) was added. The resulting solid was isolated by filtration, washed with water and dried in vacuo to give a white solid: $^1$H NMR (DMSO-$d_6$, 400 MHz): δ=10.81 (s, 1H), 7.24-7.32 (m, 5H), 7.20 (t, J=6.9 Hz, 1H), 7.01 (d, J=1.5 Hz, 1H), 6.98 (d, J=10.9 Hz, 3H), 4.62 (s, 2H), 3.90 (s, 0H), 3.33 (s, 0H), 2.81 (t, J=12.0 Hz, 1H), 1.73-1.85 (m, 2 H), 1.59 ppm (dd, J=12.5, 3.7 Hz, 2H). ESI-MS: m/z 337.2 (M+H)$^+$.

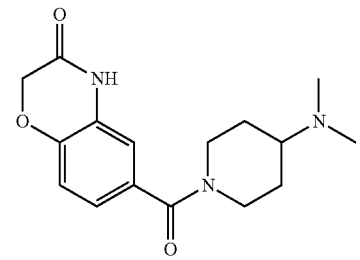 [SMILES: CN(C)C1CCN(C(=O)c2ccc3c(c2)NC(=O)CO3)CC1]

6-(4-(Dimethylamino)piperidine-1-carbonyl)-2H-benzo[b][1,4]oxazin-3(4H)-one (106)

Using 104 and N,N-dimethylpiperidin-4-amine in the general procedure for coupling an amine to a carboxylic acid, the title compound was obtained as a white solid: $^1$H NMR (DMSO-$d_6$, 400 MHz): δ=10.86 (s, 1H), 9.62 (br. s., 1H), 7.00 (s, 2H), 6.94 (d, J=1.0 Hz, 1 H), 4.63 (s, 2H), 3.44 (br. s., 1H), 2.76 (d, J=4.8 Hz, 6H), 1.98 (br. s., 2H), 1.56 ppm (br. s., 2H). ESI-MS: m/z 304.2 (M+H)$^+$.

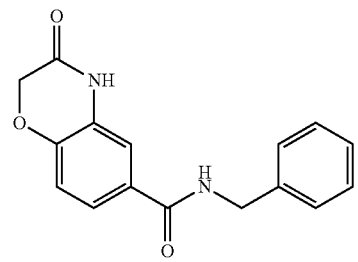 [SMILES: O=C1COc2ccc(C(=O)NCc3ccccc3)cc2N1]

N-Benzyl-3-oxo-3,4-dihydro-2H-benzo[b][1,4]oxazine-6-carboxamide (107)

Using 104 and benzylamine in the general procedure for coupling an amine to a carboxylic acid, the title compound was obtained as a white solid: $^1$H NMR (DMSO-$d_6$, 400 MHz): δ=10.85 (s, 1 H), 8.95 (t, J=5.9 Hz, 1H), 7.49 (dd, J=8.5, 1.9 Hz, 1H), 7.44 (d, J=1.8 Hz, 1H), 7.27-7.36 (m, 4H), 7.24 (d, J=6.8 Hz, 1H), 7.01 (d, J=8.3 Hz, 1H), 4.63 (s, 2H), 4.45 ppm (d, J=5.8 Hz, 2H). ESI-MS: m/z 283.1 (M+H)$^+$.

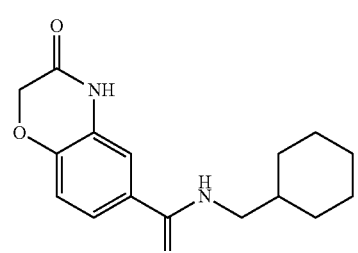

N-(Cyclohexylmethyl)-3-oxo-3,4-dihydro-2H-benzo[b][1,4]oxazine-6-carboxamide (108)

Using 104 and N-cyclohexylmethanamine in the general procedure for coupling an amine to a carboxylic acid, the title compound was obtained as a white solid: $^1$H NMR (DMSO-$d_6$, 400 MHz): δ=10.82 (s, 1H), 8.32 (t, J=5.8 Hz, 1H), 7.42 (dd, J=8.5, 2.1 Hz, 1 H), 7.39 (d, J=1.8 Hz, 1H), 6.98 (d, J=8.3 Hz, 1H), 4.62 (s, 2H), 3.06 (t, J=6.4 Hz, 2H), 1.67 (br. s., 4H), 1.59 (br. s., 1H), 1.51 (br. s., 1H), 1.08-1.24 (m, 3H), 0.91 ppm (br. s., 2H). ESI-MS: m/z 289.1 (M+H)$^+$.

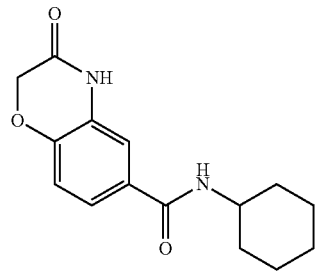

N-Cyclohexyl-3-oxo-3,4-dihydro-2H-benzo[b][1,4]oxazine-6-carboxamide (111)

Using 104 and N-cyclohexylamine in the general procedure for coupling an amine to a carboxylic acid, the title compound was obtained as a white solid: $^1$H NMR (DMSO-$d_6$, 400 MHz): δ=10.79 (s, 0H), 8.10 (d, J=7.8 Hz, 1H), 7.43 (dd, J=8.5, 1.9 Hz, 1H), 7.39 (s, 1 H), 6.97 (d, J=8.3 Hz, 1H), 4.62 (s, 2H), 3.64-3.79 (m, 1H), 1.65-1.85 (m, 4H), 1.53-1.65 (m, 1H), 1.19-1.34 ppm (m, 5H). ESI-MS: m/z 275.1 (M+H)$^+$.

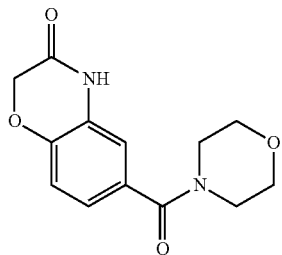 [SMILES: O=C1COc2ccc(C(=O)N3CCOCC3)cc2N1]

6-(Morpholine-4-carbonyl)-2H-benzo[b][1,4]oxazin-3(4H)-one (109)

Using 104 and morpholine in the general procedure for coupling an amine to a carboxylic acid, the title compound was obtained as a white solid: $^1$H NMR (DMSO-$d_6$, 400 MHz): δ=10.82 (s, 1H), 6.82-7.10 (m, 3H), 4.50-4.72 (m, 2H), 3.51-3.71 ppm (m, 8H). ESI-MS: m/z 263.1 (M+H)$^+$.

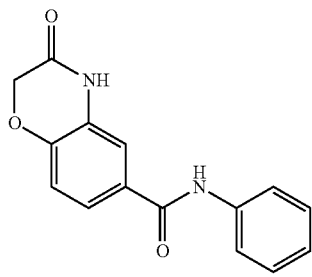 [SMILES: O=C1COc2ccc(C(=O)Nc3ccccc3)cc2N1]

3-Oxo-N-phenyl-3,4-dihydro-2H-benzo[b][1,4]oxazine-6-carboxamide (110)

Using 104 and aniline in the general procedure for coupling an amine to a carboxylic acid, the title compound was obtained as a white solid: $^1$H NMR (DMSO-$d_6$, 400 MHz): δ=10.90 (s, 1H), 10.16 (s, 1H), 7.75 (dt, J=8.6, 1.4 Hz, 2H), 7.59 (dd, J=8.5, 2.1 Hz, 1H), 7.48 (d, J=2.0 Hz, 1 H), 7.34 (t, J=8.0 Hz, 2H), 7.07 (d, J=8.6 Hz, 1H), 7.09 (dd, J=14.8, 1.1 Hz, 1H), 4.67 ppm (s, 2H). ESI-MS: m/z 269.1 (M+H)$^+$.

General Procedure for Alkylation of α-chloroketones

Synthesis of 6-(2-morpholinoacetyl)-2H-benzo[b][1,4]oxazin-3(4H)-one (112)

To a 20 mL scintillation vial with a magnetic stirrer was added commercially available 6-(2-chloroacetyl)-2H-benzo[b][1,4]oxazin-3(4H)-one (113 mg, 0.5 mmol) and EtOH (2.5 mL) followed by morpholine (96 mg, 1.1 mmol). The reaction was heated at 80° C. for 1 h then cooled to room temperature. The solution was diluted with Et$_2$O (10 mL) and the resulting solid was isolated by filtration, washed with Et$_2$O and dried in vacuo to give a white solid: $^1$H NMR (DMSO-d$_6$, 400 MHz): δ=10.91 (s, 1H), 9.31 (br. s., 1H), 7.65 (dd, J=8.3, 2.0 Hz, 1H), 7.55 (d, J=2.0 Hz, 1H), 7.03 (d, J=8.3 Hz, 1H), 4.68 (s, 2H), 3.67-3.87 (m, 6H), 3.58 (t, J=4.3 Hz, 2H), 3.07 ppm (d, J=5.1 Hz, 2H). ESI-MS: m/z 277.1 (M+H)$^+$.

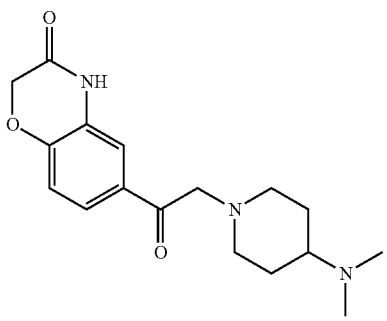 [SMILES: CN(C)C1CCN(CC(=O)c2ccc3c(c2)NC(=O)CO3)CC1]

6-(2-(4-(Dimethylamino)piperidin-1-yl)acetyl)-2H-benzo[b][1,4]oxazin-3(4H)-one (113)

Using N,N-dimethylpiperidin-4-amine in the general procedure for alkylation of α-chloroketones, the title compound was obtained as an orange solid: $^1$H NMR (DMSO-d$_6$, 400 MHz): δ=10.88 (br. s., 1H), 7.66 (dd, J=8.3, 2.0 Hz, 1H), 7.55 (d, J=2.0 Hz, 1H), 7.02 (d, J=8.6 Hz, 1H), 4.68 (s, 2H), 3.65 (s, 2H), 3.17 (d, J=4.3 Hz, 1H), 2.87 (d, J=11.1 Hz, 2 H), 2.14 (s, 6H), 2.05 (t, J=10.9 Hz, 2H), 1.67 (br. s., 2H), 1.36 ppm (dd, J=11.9, 3.0 Hz, 2 H). ESI-MS: m/z 318.2 (M+H)$^+$.

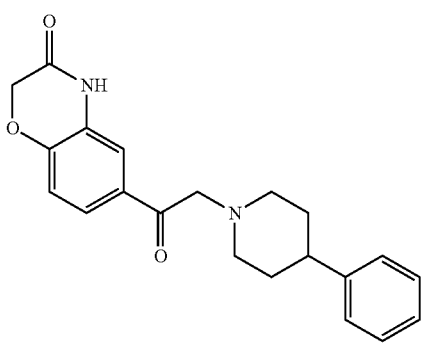 [SMILES: O=C1COc2ccc(C(=O)CN3CCC(c4ccccc4)CC3)cc2N1]

6-(2-(4-Phenylpiperidin-1-yl)acetyl)-2H-benzo[b][1,4]oxazin-3(4H)-one (114)

Using 4-phenylpiperidine in the general procedure for alkylation of α-chloroketones, the title compound was obtained as an orange solid: $^1$H NMR (DMSO-d$_6$, 400 MHz): δ=10.90 (br. s., 1 H), 7.69 (dd, J=8.3, 2.0 Hz, 1H), 7.59 (d, J=2.0 Hz, 1H), 7.26 (dq, J=14.3, 7.1 Hz, 4H), 7.11-7.35 (m, 1H), 7.04 (d, J=8.6 Hz, 1H), 4.69 (s, 2H), 3.73 (s, 2H), 3.17 (d, J=5.3 Hz, 1H), 2.97 (d, J=10.1 Hz, 2H), 2.21 (br. s., 2H), 1.61-1.81 ppm (m, 4H). ESI-MS: m/z 351.2 (M+H)$^+$.

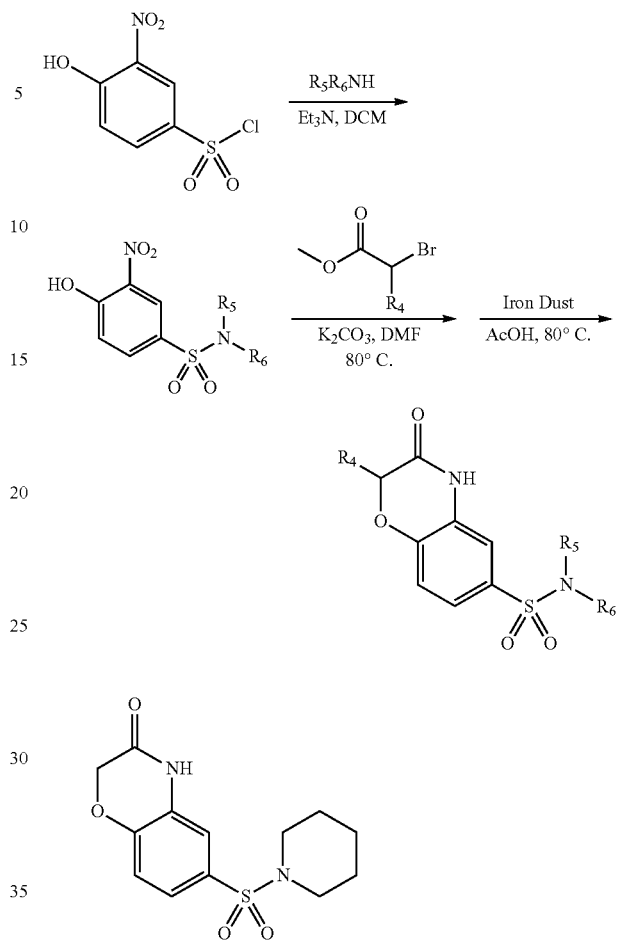

General Procedure for Alkylation of Sulfonyl Chlorides

Synthesis of 6-(piperidin-1-ylsulfonyl)-2H-benzo[b][1,4]oxazin-3(4H)-one (115)

To a 15 mL screw cap vial was added 4-hydroxy-3-nitrobenzene-1-sulfonyl chloride (238 mg, 1.0 mmol) and piperidine (102 mg, 1.2 mmol) in DCM (5.0 mL) followed by triethylamine (346 µL, 2.5 mmol). After stirring at 23° C. for 1 h, the reaction was concentrated in vacuo and the resulting residue was taken up in sat aqueous NaHCO$_3$. The resulting solid was isolated by filtration, washed with water and dried in vacuo to give a white solid. The material was subsequently alkylated using the general procedure for alkylation of substituted 2-nitrophenols using methyl bromoacetate as the alkylating agent followed by treatment in the general procedure for reduction of nitro group and subsequent ring closure to give the title compound as a white solid: $^1$H NMR (DMSO-d$_6$, 400 MHz): δ=10.91 (s, 1H), 7.21-7.32 (m, 2H), 7.15 (d, J=8.1 Hz, 1H), 4.71 (s, 2H), 2.85 (t, J=5.1 Hz, 4H), 1.46-1.62 (m, 4H), 1.37 ppm (d, J=5.1 Hz, 2H). ESI-MS: m/z 297.1 (M+H)$^+$.

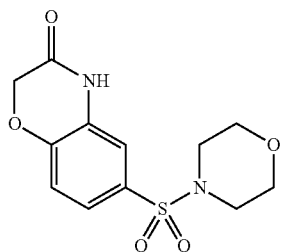 [SMILES: O=C1COc2ccc(S(=O)(=O)N3CCOCC3)cc2N1]

6-(Morpholinosulfonyl)-2H-benzo[b][1,4]oxazin-3(4H)-one (116)

Using morpholine in the general procedure for alkylation of sulfonyl chlorides, the title compound was obtained as a green solid: $^1$H NMR (DMSO-$d_6$, 400 MHz): δ=10.93 (s, 1H), 7.22-7.32 (m, 2H), 7.18 (d, J=8.3 Hz, 1H), 4.72 (s, 2H), 3.63 (d, J=3.8 Hz, 4H), 2.78-2.98 ppm (m, 4H). ESI-MS: m/z 299.1 (M+H)$^+$.

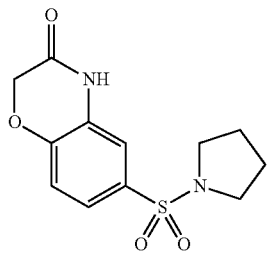 [SMILES: O=C1COc2ccc(S(=O)(=O)N3CCCC3)cc2N1]

6-(Pyrrolidin-1-ylsulfonyl)-2H-benzo[b][1,4]oxazin-3(4H)-one (117)

Using pyrrolidine in the general procedure for alkylation of sulfonyl chlorides, the title compound was obtained as a white solid: $^1$H NMR (DMSO-$d_6$, 400 MHz): δ=10.90 (s, 1H), 7.28-7.34 (m, 2H), 7.14 (d, J=8.3 Hz, 1H), 4.71 (s, 2H), 3.03-3.15 (m, 4H), 1.59-1.71 ppm (m, 4H). ESI-MS: m/z 283.1 (M+H)$^+$.

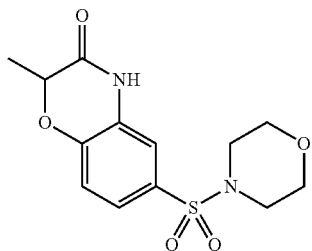 [SMILES: CC1Oc2ccc(S(=O)(=O)N3CCOCC3)cc2NC1=O]

2-Methyl-6-(morpholinosulfonyl)-2H-benzo[b][1,4]oxazin-3(4H)-one (118)

Using morpholine in the general procedure for alkylation of sulfonyl chlorides and methyl 2-bromopropanoate in the general procedure for alkylation of substituted 2-nitrophenols, the title compound was obtained as a white solid: $^1$H NMR (DMSO-$d_6$, 400 MHz): δ=10.90 (s, 1H), 7.22-7.35 (m, 2H), 7.13-7.22 (m, 1H), 4.86 (d, J=6.8 Hz, 1H), 3.54-3.69 (m, 4H), 2.75-2.93 (m, 4H), 1.46 ppm (d, J=6.8 Hz, 3H). ESI-MS: m/z 313.1 (M+H)$^+$.

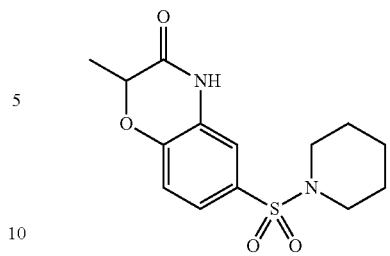

2-Methyl-6-(piperidin-1-ylsulfonyl)-2H-benzo[b][1,4]oxazin-3(4H)-one (119)

Using piperidine in the general procedure for alkylation of sulfonyl chlorides and methyl 2-bromopropanoate in the general procedure for alkylation of substituted 2-nitrophenols, the title compound was obtained as a tan solid: $^1$H NMR (DMSO-$d_6$, 400 MHz): δ=10.87 (s, 1H), 7.25 (t, J=2.8 Hz, 1H), 7.20-7.32 (m, 1H), 7.16 (d, J=8.3 Hz, 1H), 4.84 (q, J=6.8 Hz, 1H), 2.86 (t, J=5.3 Hz, 4H), 1.50-1.58 (m, 4H), 1.46 (d, J=6.8 Hz, 3H), 1.37 ppm (d, J=5.3 Hz, 2H). ESI-MS: m/z 311.1 (M+H)$^+$.

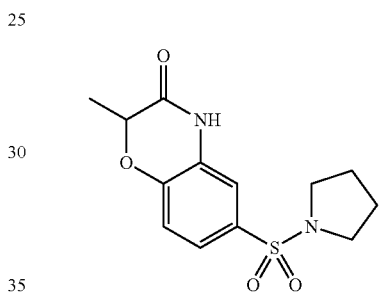

2-Methyl-6-(pyrrolidin-1-ylsulfonyl)-2H-benzo[b][1,4]oxazin-3(4H)-one (120)

Using pyrrolidine in the general procedure for alkylation of sulfonyl chlorides and methyl 2-bromopropanoate in the general procedure for alkylation of substituted 2-nitrophenols, the title compound was obtained as a white solid: $^1$H NMR (DMSO-$d_6$, 400 MHz): δ=10.90 (br. s., 1 H), 7.35 (d, J=6.1 Hz, 1H), 7.32 (t, J=2.8 Hz, 1H), 7.15 (d, J=8.1 Hz, 1H), 4.83 (q, J=6.8 Hz, 1H), 3.02-3.17 (m, 4H), 1.67 (ddd, J=6.5, 3.5, 3.3 Hz, 4H), 1.45 ppm (d, J=6.8 Hz, 3H). ESI-MS: m/z 297.1 (M+H)$^+$.

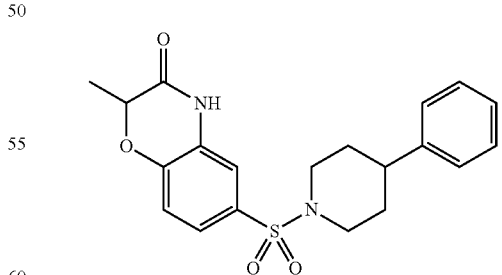

2-Methyl-6-(4-phenylpiperidin-1-ylsulfonyl)-2H-benzo[b][1,4]oxazin-3(4H)-one (121)

Using 4-phenylpiperidine in the general procedure for alkylation of sulfonyl chlorides and methyl 2-bromopropanoate in the general procedure for alkylation of substituted 2-nitrophenols, the title compound was obtained as an orange solid: $^1$H NMR (DMSO-$d_6$, 400 MHz): δ=10.90 (s, 1H), 7.23-7.37 (m, 5H), 7.19 (d, J=8.1 Hz, 3H), 4.85 (q, J=7.0 Hz, 1H), 3.71 (d, J=10.9 Hz, 1H), 2.50-2.56 (m, 2H), 2.34 (d, J=2.0 Hz, 2H), 1.77-1.88 (m, 2 H), 1.66 (d, J=12.9 Hz, 2H), 1.47 ppm (d, J=6.8 Hz, 3H). ESI-MS: m/z 387.1 (M+H)$^+$.

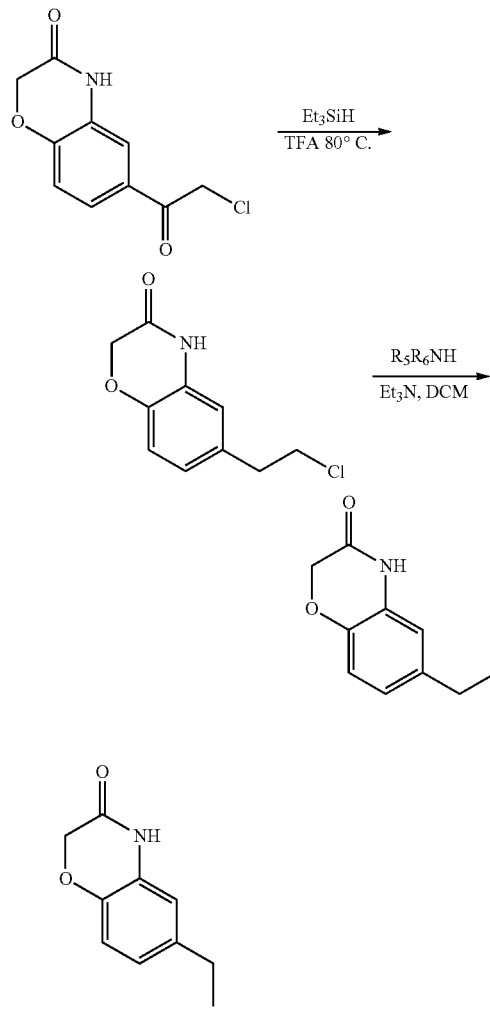

General Procedure for Reduction of Ketones

Synthesis of 6-Ethyl-2H-benzo[b][1,4]oxazin-3(4H)-one (122)

To a solution of 6-Acetyl-2H-benzo[b][1,4]oxazin-3(4H)-one (14) (0.5 mmol) in TFA (4 mL) was added Et$_3$SiH (1.0 mmol). The reaction was heated at 80° C. for 2 h and then concentrated in vacuo. The residue was treated with sat aqueous NaHCO$_3$ and the resulting solid was isolated by filtration, washed with water and dried in vacuo to give a white solid: $^1$H NMR (DMSO-$d_6$, 400 MHz): δ=10.63 (s, 1H), 6.81-6.87 (m, 1H), 6.71 (s, 1H), 6.74 (d, J=8.1 Hz, 1H), 4.51 (s, 2H), 2.46-2.54 (m, 2H), 1.12 ppm (t, J=7.6 Hz, 3H). ESI-MS: m/z 178.0 (M+H)$^+$.

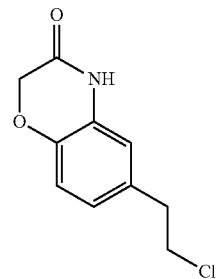 [SMILES: O=C1COc2ccc(CCCl)cc2N1]

6-(2-Chloroethyl)-2H-benzo[b][1,4]oxazin-3(4H)-one (123)

Using commercially available 6-(2-chloroacetyl)-2H-benzo[b][1,4]oxazin-3(4H)-one in the general procedure for reduction of ketones, the title compound was obtained as a white solid: $^1$H NMR (DMSO-$d_6$, 400 MHz): δ=10.69 (br. s., 1H), 6.86 (dd, J=13.0, 2.4 Hz, 2H), 6.77 (d, J=1.5 Hz, 1H), 4.53 (dd, J=3.8, 2.3 Hz, 2H), 3.77 (dd, J=3.9, 2.1 Hz, 2H), 2.93 ppm (dd, J=3.9, 2.1 Hz, 2H). ESI-MS: m/z 212.1 (M+H)$^+$.

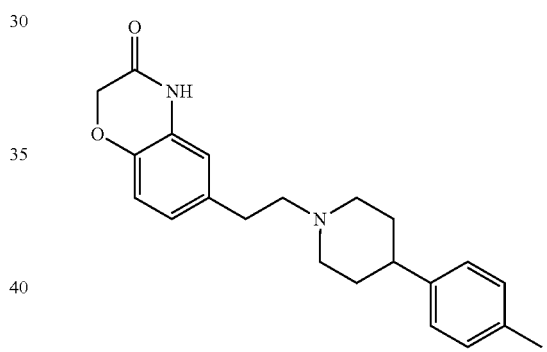

General Procedure for Alkylation of Phenethyl Chlorides

Synthesis of 6-(2-(4-p-tolylpiperidin-1-yl)ethyl)-2H-benzo[b][1,4]oxazin-3(4H)-one (124)

To a 20 mL screw cap vial was added 123 (100 mg, 0.472 mmol), 4-p-tolylpiperidine (83 mg, 0.472 mmol), K$_2$CO$_3$ (131 mg, 0.945 mmol) in DMF (2 mL). The reaction was stirred at 80° C. for 4 h. The reaction was filtered and the crude material was purified by prep HPLC-MS using a 25-95% MeCN in water gradient. The appropriate fractions were collected and concentrated in vacuo to give the title compound as a white solid: $^1$H NMR (DMSO-$d_6$, 400 MHz): δ=10.79 (br. s., 1H), 9.27 (br. s., 1H), 7.14 (br. s., 4H), 6.94 (br. s., 1H), 6.80-6.87 (m, 1H), 6.78 (br. s., 1H), 4.56 (br. s., 2H), 3.65 (br. s., 2H), 3.27 (br. s., 2H), 3.08 (br. s., 2H), 2.94 (br. s., 2H), 2.78 (br. s., 1H), 2.28 (br. s., 3H), 2.00 (br. s., 2H), 1.82 ppm (br. s., 2H). ESI-MS: m/z 351.2 (M+H)$^+$.

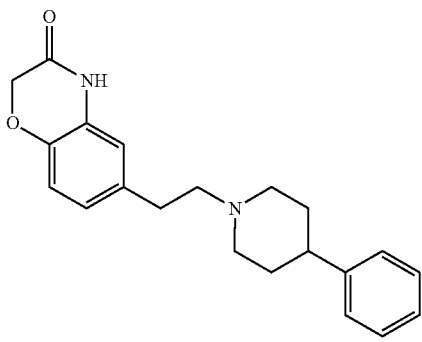 [SMILES: O=C1COc2ccc(CCN3CCC(c4ccccc4)CC3)cc2N1]

6-(2-(4-Phenylpiperidin-1-yl)ethyl)-2H-benzo[b][1,4]oxazin-3(4H)-one (125)

Using 4-phenylpiperidine in the general procedure for alkylation of phenethylchlorides, the title compound was obtained as a white solid: ¹H NMR (DMSO-d$_6$, 400 MHz): δ=10.79 (s, 1H), 9.30 (br. s., 1H), 7.31-7.40 (m, 2H), 7.26 (d, J=7.1 Hz, 3H), 6.87-6.99 (m, 1H), 6.80-6.87 (m, 1H), 6.78 (s, 1H), 4.55 (s, 2H), 3.65 (br. s., 2H), 3.20-3.34 (m, 2H), 3.00-3.17 (m, 2H), 2.88-3.00 (m, 2H), 2.83 (br. s., 1H), 2.03 (br. s., 2H), 1.88 ppm (br. s., 2H). ESI-MS: m/z 337.2 (M+H)⁺.

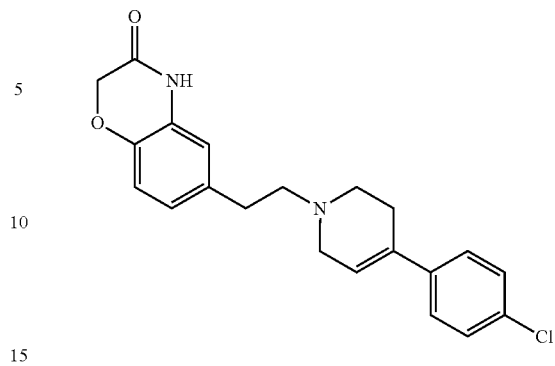

6-(2-(4-(4-Chlorophenyl)-5,6-dihydropyridin-1(2H)-yl)ethyl)-2H-benzo[b][1,4]oxazin-3(4H)-one (127)

Using 4-(4-chlorophenyl)-1,2,3,6-tetrahydropyridine in the general procedure for alkylation of phenethylchlorides, the title compound was obtained as an off-white solid: ¹H NMR (DMSO-d$_6$, 400 MHz): δ=10.79 (br. s., 1H), 9.78 (br. s., 1H), 7.55 (br. s., 2H), 7.46 (br. s., 2H), 6.93 (br. s., 1H), 6.81-6.88 (m, 1H), 6.78 (br. s., 1H), 6.27 (br. s., 1H), 4.55 (d, J=2.5 Hz, 2H), 4.07 (br. s., 1H), 3.88 (br. s., 1H), 3.75 (br. s., 1H), 3.35 (br. s., 3H), 2.96 (br. s., 2H), 2.79 ppm (br. s., 2H). ESI-MS: m/z 369.2 (M+H)⁺.

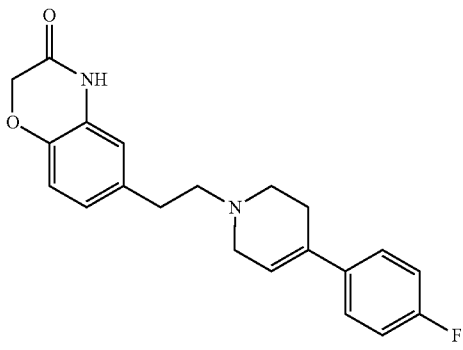 [SMILES: O=C1COc2ccc(CCN3CC=C(c4ccc(F)cc4)CC3)cc2N1]

6-(2-(4-(4-Fluorophenyl)-5,6-dihydropyridin-1(2H)-yl)ethyl)-2H-benzo[b][1,4]oxazin-3(4H)-one (126)

Using 4-(4-fluorophenyl)-1,2,3,6-tetrahydropyridine in the general procedure for alkylation of phenethylchlorides, the title compound was obtained as a yellow solid: ¹H NMR (DMSO-d$_6$, 400 MHz): δ=10.79 (br. s., 1H), 9.79 (br. s., 1H), 7.56 (d, J=5.3 Hz, 2H), 7.24 (t, J=8.2 Hz, 2H), 6.94 (d, J=7.8 Hz, 1H), 6.86 (d, J=8.1 Hz, 1H), 6.79 (br. s., 1H), 6.20 (br. s., 1H), 4.55 (s, 2H), 4.06 (br. s., 1H), 3.88 (br. s., 1H), 3.74 (br. s., 1H), 3.36 (br. s., 3H), 2.97 (br. s., 2H), 2.79 ppm (br. s., 2H). ESI-MS: m/z 353.2 (M+H)⁺.

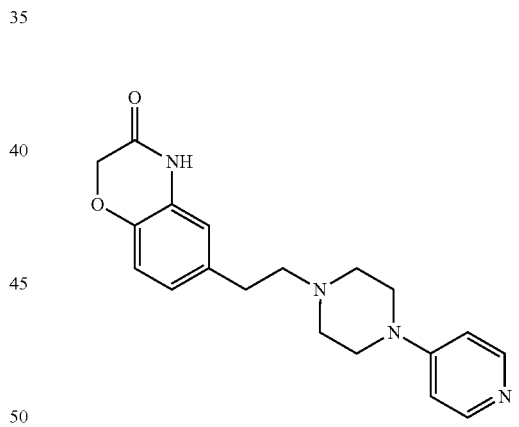

6-(2-(4-(Pyridin-4-yl)piperazin-1-yl)ethyl)-2H-benzo[b][1,4]oxazin-3(4H)-one (128)

Using 1-(pyridin-4-yl)piperazine in the general procedure for alkylation of phenethylchlorides, the title compound was obtained as a yellow solid: ¹H NMR (DMSO-d$_6$, 400 MHz): δ=10.67-10.87 (m, 1H), 9.08 (br. s., 1H), 8.29-8.46 (m, 2H), 7.20-7.38 (m, 2H), 6.71-6.98 (m, 3H), 4.49-4.62 (m, 2H), 4.38 (t, J=7.1 Hz, 2H), 3.77-3.94 (m, 2H), 3.26 (br. s., 3H), 3.03 (t, J=7.2 Hz, 1H), 2.93 (br. s., 2H), 2.52-2.59 ppm (m, 2H). ESI-MS: m/z 339.2 (M+H)⁺.

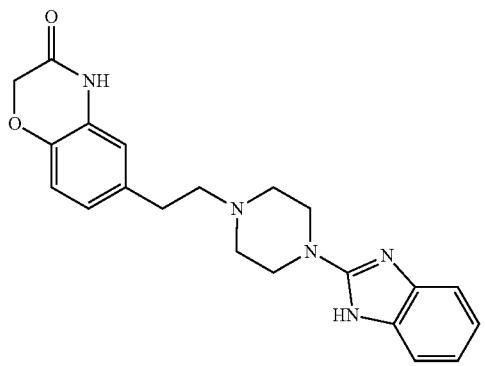 [SMILES: O=C1COc2ccc(CCN3CCN(c4nc5ccccc5[nH]4)CC3)cc2N1]

6-(2-(4-(1H-Benzo[d]imidazol-2-yl)piperazin-1-yl)ethyl)-2H-benzo[b][1,4]oxazin-3(4H)-one (129)

Using 2-(piperazin-1-yl)-1H-benzo[d]imidazole in the general procedure for alkylation of phenethylchlorides, the title compound was obtained as a white solid: $^1$H NMR (DMSO-$d_6$, 400 MHz): δ=10.80 (s, 1H), 7.45 (dd, J=5.8, 3.0 Hz, 2H), 7.26 (dd, J=5.8, 3.3 Hz, 2H), 6.89-6.98 (m, 1H), 6.80-6.87 (m, 1H), 6.77 (d, J=2.0 Hz, 1H), 4.55 (s, 2H), 2.86-2.99 (m, 4H), 2.50 (d, J=3.5 Hz, 4H), 2.45-2.53 ppm (m, 4H). ESI-MS: m/z 377.2 (M+H)$^+$.

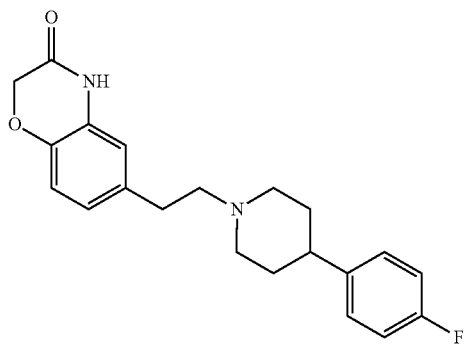 [SMILES: O=C1COc2ccc(CCN3CCC(c4ccc(F)cc4)CC3)cc2N1]

6-(2-(4-(4-Fluorophenyl)piperidin-1-yl)ethyl)-2H-benzo[b][1,4]oxazin-3(4H)-one (130)

Using 4-(4-fluorophenyl)piperidine in the general procedure for alkylation of phenethylchlorides, the title compound was obtained as an off-white solid: $^1$H NMR (DMSO-$d_6$, 400 MHz): δ=10.80 (s, 1H), 9.40 (br. s., 1H), 7.29 (dd, J=8.8, 5.6 Hz, 2H), 7.11-7.24 (m, 2H), 6.91-6.99 (m, 1H), 6.82-6.89 (m, 1H), 6.78 (d, J=2.0 Hz, 1H), 4.55 (s, 2H), 3.61-3.73 (m, 2H), 3.21-3.34 (m, 2H), 3.08 (d, J=12.9 Hz, 2H), 2.95 (d, J=8.8 Hz, 2H), 2.79-2.91 (m, 1H), 1.96-2.13 (m, 2H), 1.74-1.94 ppm (m, 2H). ESI-MS: m/z 355.2 (M+H)$^+$.

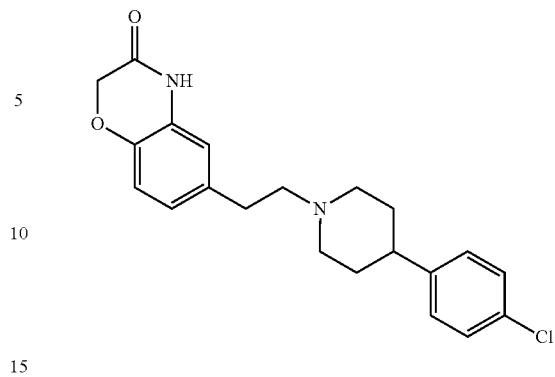

6-(2-(4-(4-Chlorophenyl)piperidin-1-yl)ethyl)-2H-benzo[b][1,4]oxazin-3(4H)-one (131)

Using 4-(4-chlorophenyl)piperidine in the general procedure for alkylation of phenethylchlorides, the title compound was obtained as a white solid: $^1$H NMR (DMSO-$d_6$, 400 MHz): δ=10.80 (s, 1H), 9.45 (br. s., 1H), 7.36-7.46 (m, 2H), 7.28 (d, J=8.6 Hz, 2H), 6.90-6.99 (m, 1H), 6.82-6.89 (m, 1H), 6.78 (d, J=2.0 Hz, 1H), 4.55 (s, 2H), 3.67 (d, J=11.6 Hz, 2H), 3.22-3.33 (m, 2H), 3.08 (d, J=12.4 Hz, 2H), 2.94 (dd, J=11.6, 5.3 Hz, 2H), 2.85 (t, J=3.5 Hz, 1H), 1.98-2.11 (m, 2H), 1.73-1.93 ppm (m, 2H). ESI-MS: m/z 371.2 (M+H)$^+$.

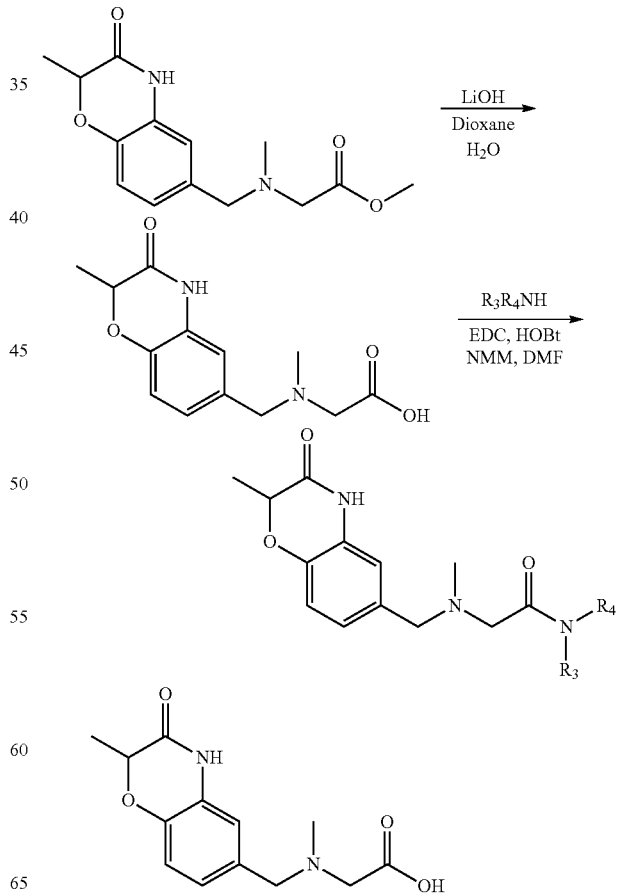

2-(Methyl((2-methyl-3-oxo-3,4-dihydro-2H-benzo[b][1,4]oxazin-6-yl)methyl)amino)acetic acid (132)

Using 88 in the general procedure for hydrolysis of carboxylic esters, the title compound was obtained as a white solid: ESI-MS: m/z 265.1 (M+H)$^+$.

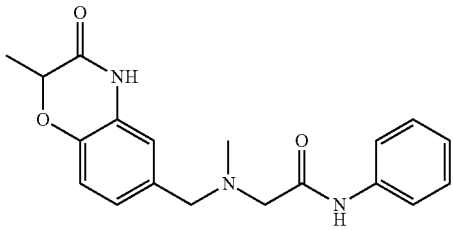 [SMILES: CC1Oc2ccc(CN(C)CC(=O)Nc3ccccc3)cc2NC1=O]

2-(Methyl((2-methyl-3-oxo-3,4-dihydro-2H-benzo[b][1,4]oxazin-6-yl)methyl)amino)-N-phenylacetamide (133)

Using 132 and aniline in the general procedure for coupling an amine to a carboxylic acid, the title compound was obtained as a white solid: $^1$H NMR (DMSO-d$_6$, 400 MHz): δ=10.90 (s, 1H), 10.53 (s, 1H), 7.55 (dd, J=8.7, 1.1 Hz, 1 H), 7.28-7.43 (m, 1H), 6.98-7.18 (m, 6H), 4.61 (d, J=6.8 Hz, 1H), 4.27 (br. s., 2H), 4.04 (br. s., 2H), 2.82 (s, 3H), 1.40 ppm (d, J=6.8 Hz, 3H). ESI-MS: m/z 340.3 (M+H)$^+$.

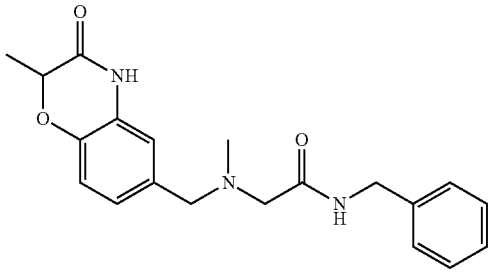 [SMILES: CC1Oc2ccc(CN(C)CC(=O)NCc3ccccc3)cc2NC1=O]

N-Benzyl-2-(methyl((2-methyl-3-oxo-3,4-dihydro-2H-benzo[b][1,4]oxazin-6-yl)methyl)amino)acetamide (134)

Using 132 and benzylamine in the general procedure for coupling an amine to a carboxylic acid, the title compound was obtained as a white solid: $^1$H NMR (DMSO-d$_6$, 400 MHz): δ=8.25 (t, J=6.1 Hz, 1H), 7.27-7.33 (m, 2H), 7.19-7.26 (m, 3H), 6.89-6.93 (m, 1H), 6.86-6.89 (m, 1H), 6.84 (d, J=1.5 Hz, 1H), 4.58-4.65 (m, 1H), 4.30 (d, J=6.3 Hz, 2H), 3.47 (s, 2H), 3.00 (s, 2H), 2.17 (s, 3H), 1.40 ppm (d, J=6.8 Hz, 3H). ESI-MS: m/z 354.3 (M+H)$^+$.

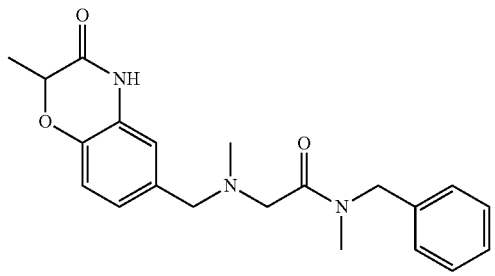 [SMILES: CC1Oc2ccc(CN(C)CC(=O)N(C)Cc3ccccc3)cc2NC1=O]

N-Benzyl-N-methyl-2-(methyl((2-methyl-3-oxo-3,4-dihydro-2H-benzo[b][1,4]oxazin-6-yl)methyl)amino)acetamide (135)

Using 132 and N-methyl-1-phenylmethanamine in the general procedure for coupling an amine to a carboxylic acid, the title compound was obtained as a white solid: $^1$H NMR (DMSO-d$_6$, 400 MHz): δ=10.62 (br. s., 1H), 7.29-7.36 (m, 2H), 7.24-7.28 (m, 1H), 7.18-7.24 (m, 1H), 7.10 (d, J=7.1 Hz, 1 H), 6.85-6.90 (m, 1H), 6.81 (d, J=8.1 Hz, 1H), 6.73-6.78 (m, 1H), 4.55-4.66 (m, 1H), 4.49 (s, 2H), 3.42-3.49 (m, 2H), 3.27 (s, 1H), 3.17 (s, 1H), 2.95 (s, 2H), 2.76 (s, 1H), 2.14-2.21 (m, 3H), 1.35-1.43 ppm (m, 3H). ESI-MS: m/z 368.3 (M+H)$^+$.

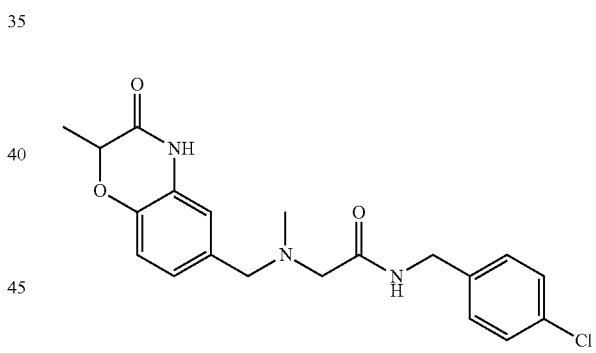

N-(4-Chlorobenzyl)-2-(methyl((2-methyl-3-oxo-3,4-dihydro-2H-benzo[b][1,4]oxazin-6-yl)methyl)amino)acetamide (136)

Using 132 and (4-chlorophenyl)methanamine in the general procedure for coupling an amine to a carboxylic acid, the title compound was obtained as a white solid: $^1$H NMR (DMSO-d$_6$, 400 MHz): δ=10.55 (br. s., 1H), 8.25 (t, J=6.2 Hz, 1H), 7.26-7.32 (m, 2H), 7.20 (d, J=8.6 Hz, 2H), 6.83-6.87 (m, 1H), 6.80-6.84 (m, 1H), 6.77 (d, J=1.8 Hz, 1H), 4.56 (q, J=6.7 Hz, 1H), 4.21 (d, J=6.3 Hz, 2H), 3.40 (s, 2H), 2.92 (s, 2H), 2.10 (s, 3H), 1.34 ppm (d, J=6.8 Hz, 3H). ESI-MS: m/z 388.3 (M+H)$^+$.

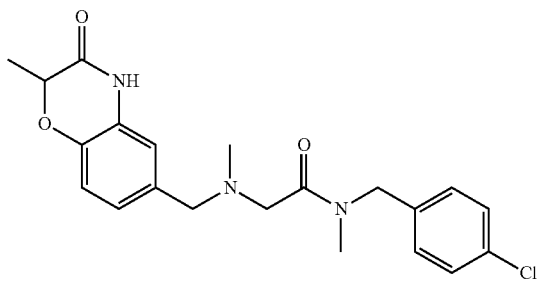 [SMILES: CC1Oc2ccc(CN(C)CC(=O)N(C)Cc3ccc(Cl)cc3)cc2NC1=O]

N-(4-Chlorobenzyl)-N-methyl-2-(methyl((2-methyl-3-oxo-3,4-dihydro-2H-benzo[b][1,4]oxazin-6-yl)methyl)amino)acetamide (137)

Using 132 and 1-(4-chlorophenyl)-N-methylmethanamine in the general procedure for coupling an amine to a carboxylic acid, the title compound was obtained as a white solid: $^1$H NMR (DMSO-$d_6$, 400 MHz): δ=10.63 (br. s., 1H), 7.34-7.41 (m, 2H), 7.24 (d, J=8.6 Hz, 2H), 7.12 (d, J=8.6 Hz, 1H), 6.85-6.90 (m, 1H), 6.78-6.83 (m, 1H), 4.57-4.66 (m, 1H), 4.47 (s, 2H), 3.41-3.48 (m, 2H), 3.26 (s, 2H), 2.94 (s, 2H), 2.74 (s, 1H), 2.13-2.20 (m, 3H), 1.35-1.44 ppm (m, 3H). ESI-MS: m/z 402.3 (M+H)$^+$.

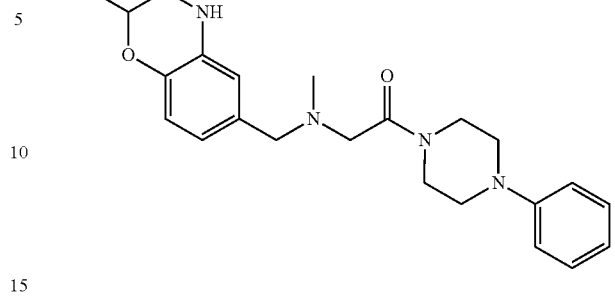

2-Methyl-6-((methyl(2-oxo-2-(4-phenylpiperazin-1-yl)ethyl)amino)methyl)-2H-benzo[b][1,4]oxazin-3(4H)-one (139)

Using 132 and 4-phenylpiperazine in the general procedure for coupling an amine to a carboxylic acid, the title compound was obtained as a white solid: $^1$H NMR (DMSO-$d_6$, 400 MHz): δ=10.69 (br. s., 1H), 7.19-7.27 (m, 2H), 6.96 (d, J=7.8 Hz, 2H), 6.87-6.91 (m, 1H), 6.83-6.87 (m, 2H), 6.78-6.83 (m, 1H), 4.57-4.67 (m, 1H), 3.63-3.71 (m, 2H), 3.58 (br. s., 2H), 3.43 (s, 2H), 3.22 (s, 2H), 3.16 (br. s., 2H), 3.11 (br. s., 2H), 2.12 (s, 3H), 1.40 ppm (d, J=6.8 Hz, 3H). ESI-MS: m/z 409.2 (M+H)$^+$.

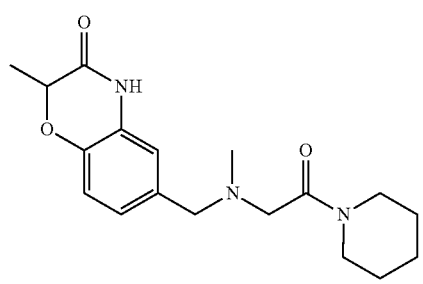 [SMILES: CC1Oc2ccc(CN(C)CC(=O)N3CCCCC3)cc2NC1=O]

2-Methyl-6-((methyl(2-oxo-2-(piperidin-1-yl)ethyl)amino)methyl)-2H-benzo[b][1,4]oxazin-3(4H)-one (138)

Using 132 and piperidine in the general procedure for coupling an amine to a carboxylic acid, the title compound was obtained as a white solid: $^1$H NMR (DMSO-$d_6$, 400 MHz): δ=10.67 (br. s., 1H), 6.87-6.91 (m, 1H), 6.80-6.86 (m, 2H), 4.60-4.66 (m, 1H), 3.41 (s, 4H), 3.34 (s, 2H), 3.14 (s, 2H), 2.11 (s, 3H), 1.58 (br. s., 2H), 1.46-1.53 (m, 2H), 1.41 ppm (d, J=6.8 Hz, 5H). ESI-MS: m/z 332.3 (M+H)$^+$.

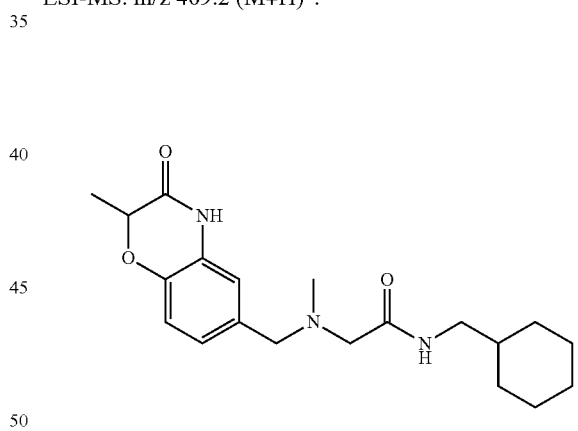

N-(Cyclohexylmethyl)-2-(methyl((2-methyl-3-oxo-3,4-dihydro-2H-benzo[b][1,4]oxazin-6-yl)methyl)amino)acetamide (140)

Using 132 and cyclohexylmethanamine in the general procedure for coupling an amine to a carboxylic acid, the title compound was obtained as a white solid: $^1$H NMR (DMSO-$d_6$, 400 MHz): δ=6.90 (s, 3H), 4.63 (d, J=6.8 Hz, 1H), 3.46 (s, 2H), 2.94 (s, 2H), 2.93 (s, 3H), 2.66-2.70 (m, 1H), 2.32-2.35 (m, 1H), 2.17 (s, 3H), 1.64 (s, 9H), 1.41 ppm (d, J=6.8 Hz, 3H). ESI-MS: m/z 360.3 (M+H)$^+$.

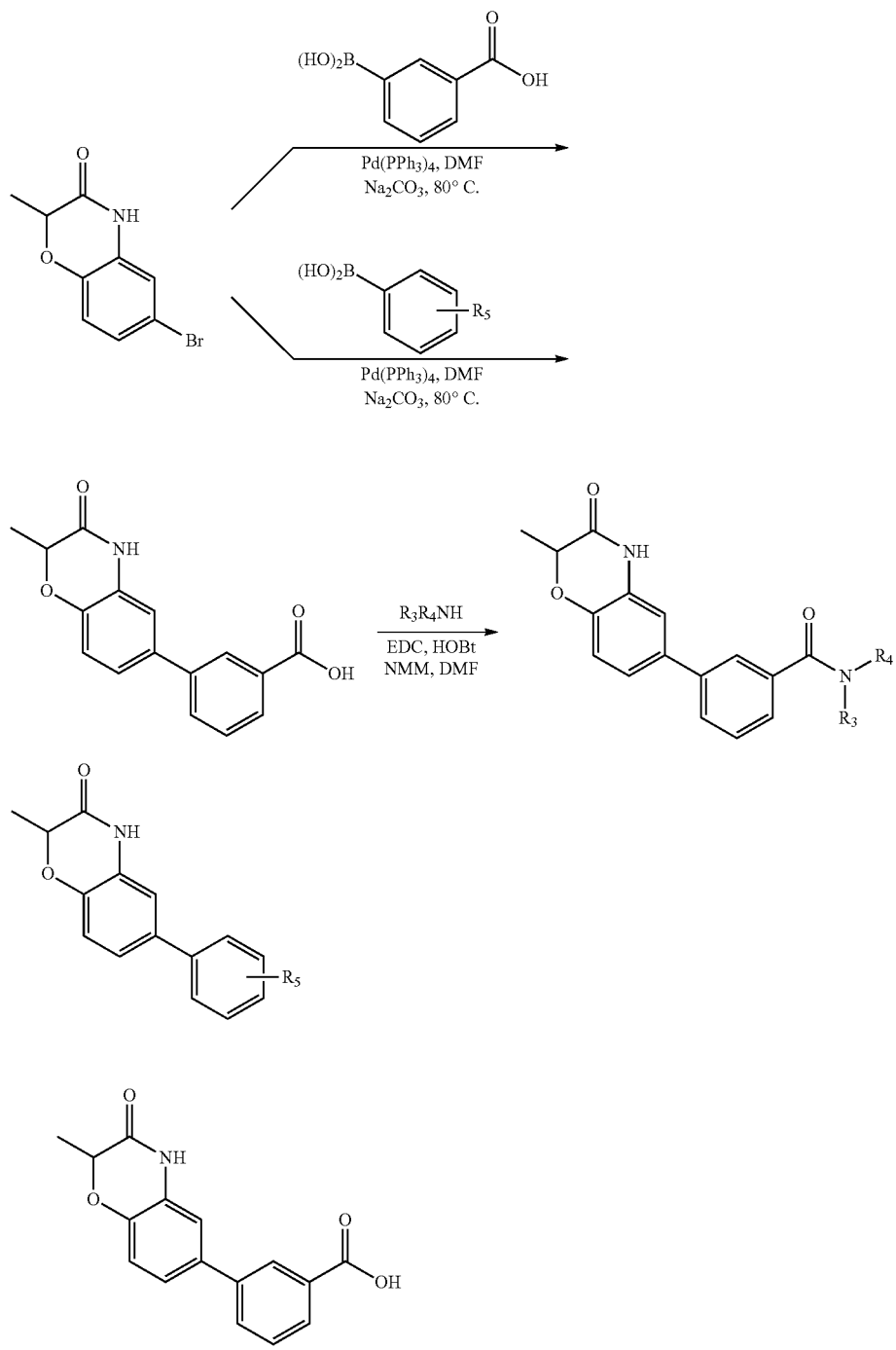

General Procedure for Pd-Catalyzed Suzuki Reactions

Synthesis of 3-(2-methyl-3-oxo-3,4-dihydro-2H-benzo[b][1,4]oxazin-6-yl)benzoic acid (141)

To a 20 mL screw cap vial was added 6-bromo-2-methyl-2H-benzo[b][1,4]oxazin-3(4H)-one 19 (100 mg, 0.5 mmol), 3-carboxy phenylboronic acid (91 mg, 0.55 mmol), Pd(PPh$_3$)$_4$ (17 mg, 0.015 mmol), and aqueous Na$_2$CO$_3$ (2M, 0.62 mL, 1.25 mmol) in DMF (4 mL). The reaction was heated at 80° C. overnight then cooled and filtered. The filtrate was purified by preparative HPLC-MS (15-60% MeCN in water). The appropriate fractions were combined and concentrated in vacuo to give a white solid: $^1$H NMR (DMSO-d$_6$, 400 MHz): δ=13.11 (br. s., 1H), 10.72 (s, 1H), 8.09 (t, J=1.6 Hz, 1H), 7.91 (dt, J=7.6, 1.4 Hz, 1H), 7.80-7.85 (m, 1H), 7.54-7.62 (m, 1H), 7.27 (dd, J=8.3, 2.3 Hz, 1H), 7.20 (d, J=2.0 Hz, 1H), 7.07 (d, J=8.3 Hz, 1H), 4.69-4.77 (m, 1H), 1.45 ppm (d, J=6.8 Hz, 3H). ESI-MS: m/z 284.2 (M+H)$^+$.

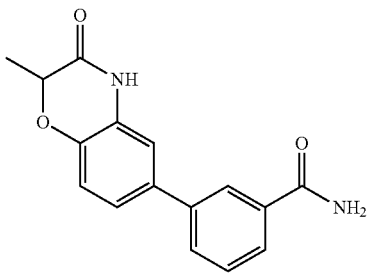 [SMILES: CC1Oc2ccc(-c3cccc(C(N)=O)c3)cc2NC1=O]

3-(2-Methyl-3-oxo-3,4-dihydro-2H-benzo[b][1,4]oxazin-6-yl)benzamide (142)

Using 141 and ammonium chloride in the general procedure for coupling an amine to a carboxylic acid, the title compound was obtained as a white solid: $^1$H NMR (DMSO-$d_6$, 400 MHz): δ=10.75 (s, 1H), 8.09 (s, 1H), 8.06 (t, J=1.6 Hz, 1H), 7.77-7.93 (m, 1H), 7.67-7.72 (m, 1H), 7.49-7.56 (m, 1H), 7.43 (s, 1H), 7.29 (dd, J=8.3, 2.3 Hz, 1H), 7.19 (d, J=2.3 Hz, 1H), 7.07 (d, J=8.3 Hz, 1H), 4.67-4.76 (m, 1H), 1.45 ppm (d, J=6.8 Hz, 3H). ESI-MS: m/z 283.2 (M+H)$^+$.

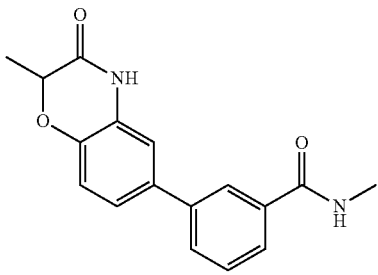

N-Methyl-3-(2-methyl-3-oxo-3,4-dihydro-2H-benzo[b][1,4]oxazin-6-yl)benzamide (143)

Using 141 and methylamine hydrochloride in the general procedure for coupling an amine to a carboxylic acid, the title compound was obtained as a white solid: $^1$H NMR (DMSO-$d_6$, 400 MHz): δ=10.75 (s, 1H), 8.55 (br. s., 1H), 8.02 (t, J=1.6 Hz, 1H), 7.76-7.81 (m, 1H), 7.67-7.71 (m, 1H), 7.50-7.56 (m, 1H), 7.28 (dd, J=8.3, 2.3 Hz, 1H), 7.18 (d, J=2.0 Hz, 1H), 7.07 (d, J=8.3 Hz, 1H), 4.72 (q, J=6.7 Hz, 1H), 2.80 (d, J=4.5 Hz, 3H), 1.45 ppm (d, J=6.8 Hz, 3H). ESI-MS: m/z 297.2 (M+H)$^+$.

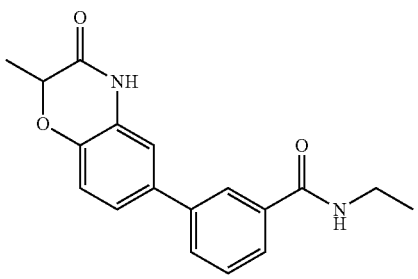 [SMILES: CCNC(=O)c1cccc(-c2ccc3c(c2)NC(=O)C(C)O3)c1]

N-Ethyl-3-(2-methyl-3-oxo-3,4-dihydro-2H-benzo[b][1,4]oxazin-6-yl)benzamide (144)

Using 141 and ethylamine in the general procedure for coupling an amine to a carboxylic acid, the title compound was obtained as a white solid: $^1$H NMR (DMSO-$d_6$, 400 MHz): δ=10.75 (s, 1H), 8.58 (t, J=5.1 Hz, 1H), 8.02 (t, J=1.6 Hz, 1H), 7.77-7.83 (m, 1H), 7.69 (ddd, J=8.1, 1.5, 1.3 Hz, 1H), 7.49-7.56 (m, 1H), 7.29 (dd, J=8.3, 2.0 Hz, 1H), 7.19 (d, J=2.0 Hz, 1H), 7.08 (d, J=8.1 Hz, 1H), 4.72 (q, 1H), 3.26-3.31 (m, 2H), 1.45 (d, J=6.8 Hz, 3H), 1.14 ppm (t, J=7.3 Hz, 3H). ESI-MS: m/z 311.3 (M+H)$^+$.

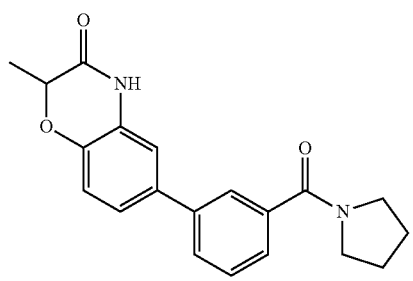 [SMILES: CC1Oc2ccc(-c3cccc(C(=O)N4CCCC4)c3)cc2NC1=O]

2-Methyl-6-(3-(pyrrolidine-1-carbonyl)phenyl)-2H-benzo[b][1,4]oxazin-3(4H)-one (145)

Using 141 and pyrrolidine in the general procedure for coupling an amine to a carboxylic acid, the title compound was obtained as a white solid: $^1$H NMR (DMSO-$d_6$, 400 MHz): δ=10.72 (s, 1H), 7.61-7.66 (m, 2H), 7.48-7.54 (m, 1H), 7.44-7.48 (m, 1H), 7.25 (dd, J=8.3, 2.0 Hz, 1H), 7.17 (d, J=2.0 Hz, 1H), 7.05 (d, J=8.3 Hz, 1H), 4.68-4.76 (m, 1H), 3.48 (t, J=6.7 Hz, 2H), 3.42 (t, J=6.4 Hz, 2H), 1.77-1.93 (m, 4H), 1.45 ppm (d, J=6.8 Hz, 3H). ESI-MS: m/z 337.3 (M+H)$^+$.

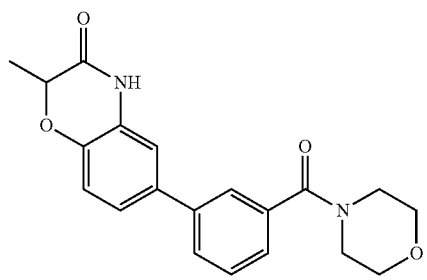 [SMILES: CC1Oc2ccc(-c3cccc(C(=O)N4CCOCC4)c3)cc2NC1=O]

2-Methyl-6-(3-(morpholine-4-carbonyl)phenyl)-2H-benzo[b][1,4]oxazin-3(4H)-one (146)

Using 141 and morpholine in the general procedure for coupling an amine to a carboxylic acid, the title compound was obtained as a white solid: $^1$H NMR (DMSO-$d_6$, 400 MHz): δ=10.74 (s, 1H), 7.62-7.66 (m, 1H), 7.54 (s, 1H), 7.50-7.53 (m, 1H), 7.34-7.39 (m, 1H), 7.25 (dd, J=8.3, 2.0 Hz, 1H), 7.16 (d, J=2.3 Hz, 1H), 7.05 (d, J=8.3 Hz, 1H), 4.72 (q, J=6.8 Hz, 1H), 3.63 (br. s., 6H), 3.37 (br. s., 2H), 1.45 ppm (d, J=6.8 Hz, 3H). ESI-MS: m/z 353.3 (M+H)$^+$.

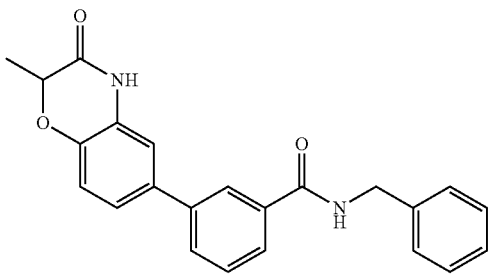 [SMILES: CC1Oc2ccc(-c3cccc(C(=O)NCc4ccccc4)c3)cc2NC1=O]

N-Benzyl-3-(2-methyl-3-oxo-3,4-dihydro-2H-benzo[b][1,4]oxazin-6-yl)benzamide (147)

Using 141 and benzylamine in the general procedure for coupling an amine to a carboxylic acid, the title compound was obtained as a white solid: $^1$H NMR (DMSO-$d_6$, 400 MHz): δ=10.75 (s, 1H), 9.17 (t, J=5.9 Hz, 1H), 8.09 (s, 1H), 7.86 (d, J=7.6 Hz, 1H), 7.69-7.74 (m, 1H), 7.52-7.58 (m, 1H), 7.34 (d, J=4.3 Hz, 4H), 7.27-7.32 (m, 1H), 7.22-7.27 (m, 1H), 7.19 (d, J=2.3 Hz, 1H), 7.07 (d, J=8.3 Hz, 1H), 4.68-4.75 (m, 1H), 4.51 (d, J=5.8 Hz, 2H), 1.45 ppm (d, J=6.8 Hz, 3H). ESI-MS: m/z 373.3 (M+H)$^+$.

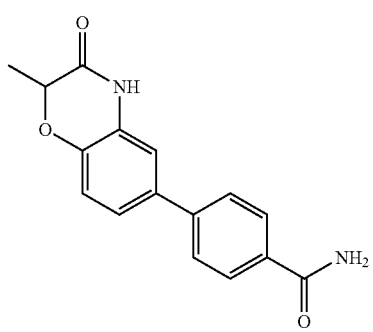

N-(3-(2-Methyl-3-oxo-3,4-dihydro-2H-benzo[b][1,4]oxazin-6-yl)phenyl)acetamide (148)

Using 3-acetamidophenylboronic acid in the general procedure for Pd-catalyzed Suzuki reactions, the title compound was obtained as a white solid: $^1$H NMR (DMSO-$d_6$, 400 MHz): δ=10.77 (s, 1H), 10.03 (s, 1H), 7.84 (t, J=1.8 Hz, 1H), 7.47-7.52 (m, 1H), 7.35 (t, J=8.0 Hz, 1H), 7.20 (d, J=8.3 Hz, 1H), 7.12-7.17 (m, 1H), 7.10 (d, J=2.0 Hz, 1H), 7.04 (d, J=8.3 Hz, 1H), 4.67-4.75 (m, 1H), 2.06 (s, 3H), 1.44 ppm (d, J=6.8 Hz, 3H). ESI-MS: m/z 297.2 (M+H)$^+$.

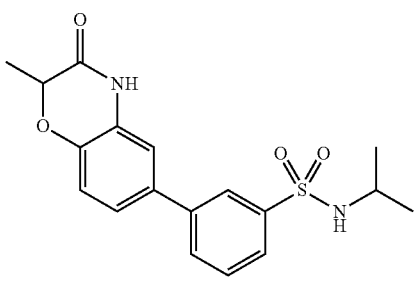 [SMILES: CC(C)NS(=O)(=O)c1cccc(-c2ccc3c(c2)NC(=O)C(C)O3)c1]

N-Isopropyl-3-(2-methyl-3-oxo-3,4-dihydro-2H-benzo[b][1,4]oxazin-6-yl)benzenesulfonamide (149)

Using 3-(N-isopropylsulfamoyl)phenylboronic acid in the general procedure for Pd-catalyzed Suzuki reactions, the title compound was obtained as a white solid: $^1$H NMR (DMSO-$d_6$, 400 MHz): δ=10.77 (s, 1H), 7.96 (t, J=1.6 Hz, 1H), 7.79-7.84 (m, 1H), 7.74-7.79 (m, 1H), 7.66 (t, J=7.3 Hz, 2H), 7.27 (dd, J=8.3, 2.3 Hz, 1H), 7.19 (d, J=2.3 Hz, 1H), 7.10 (d, J=8.3 Hz, 1H), 4.70-4.78 (m, 1H), 3.22-3.32 (m, J=13.5, 6.7, 6.6, 6.6 Hz, 1H), 1.45 (d, J=6.8 Hz, 3H), 0.95 ppm (d, J=6.6 Hz, 6H). ESI-MS: m/z 361.3 (M+H)$^+$.

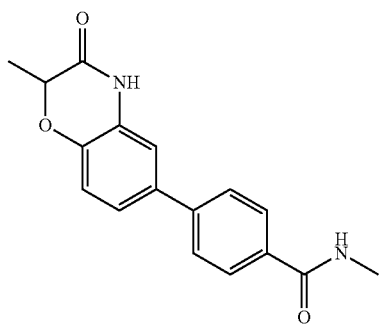

4-(2-Methyl-3-oxo-3,4-dihydro-2H-benzo[b][1,4]oxazin-6-yl)benzamide (150)

Using 4-carbamoylphenylboronic acid in the general procedure for Pd-catalyzed Suzuki reactions, the title compound was obtained as a white solid: $^1$H NMR (DMSO-$d_6$, 400 MHz): δ=10.75 (s, 1H), 7.98-8.02 (m, 1H), 7.94 (d, J=8.6 Hz, 2H), 7.59-7.65 (m, 2H), 7.35-7.40 (m, 1H), 7.28 (dd, J=8.3, 2.3 Hz, 1H), 7.19 (d, J=2.3 Hz, 1H), 7.06 (d, J=8.3 Hz, 1H), 4.68-4.77 (m, 1H), 1.45 ppm (d, J=6.8 Hz, 3H). ESI-MS: m/z 283.2 (M+H)$^+$.

N-Methyl-4-(2-methyl-3-oxo-3,4-dihydro-2H-benzo[b][1,4]oxazin-6-yl)benzamide (151)

Using 4-(methylcarbamoyl)phenylboronic acid in the general procedure for Pd-catalyzed Suzuki reactions, the title compound was obtained as a white solid: $^1$H NMR (DMSO-$d_6$, 400 MHz): δ=10.75 (s, 1H), 8.47 (d, J=4.8 Hz, 1H), 7.90 (d, J=8.6 Hz, 2H), 7.63 (d, J=8.6 Hz, 2H), 7.28 (dd, J=8.3, 2.3 Hz, 1H), 7.19 (d, J=2.3 Hz, 1H), 7.06 (d, J=8.3 Hz, 1H), 4.72 (q, J=6.8 Hz, 1H), 2.80 (d, J=4.5 Hz, 3H), 1.45 ppm (d, J=6.8 Hz, 3H). ESI-MS: m/z 297.3 (M+H)$^+$.

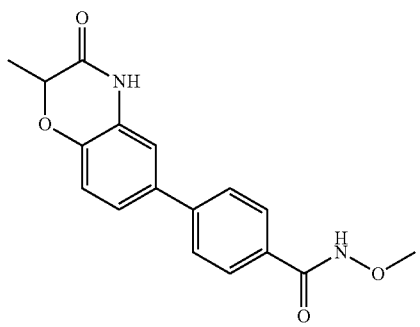

N-Methoxy-4-(2-methyl-3-oxo-3,4-dihydro-2H-benzo[b][1,4]oxazin-6-yl)benzamide (152)

Using 4-(methoxycarbamoyl)phenylboronic acid in the general procedure for Pd-catalyzed Suzuki reactions, the title compound was obtained as a white solid: $^1$H NMR (DMSO-$d_6$, 400 MHz): δ=11.78 (s, 1H), 10.76 (s, 1H), 7.82 (d, J=8.6 Hz, 2H), 7.65 (d, J=8.6 Hz, 2H), 7.28 (dd, J=8.3, 2.3 Hz, 1H), 7.19 (d, J=2.3 Hz, 1H), 7.07 (d, J=8.3 Hz, 1H), 4.68-4.76 (m, 1H), 3.72 (s, 3H), 1.45 ppm (d, J=6.8 Hz, 3H). ESI-MS: m/z 313.3 (M+H)$^+$.

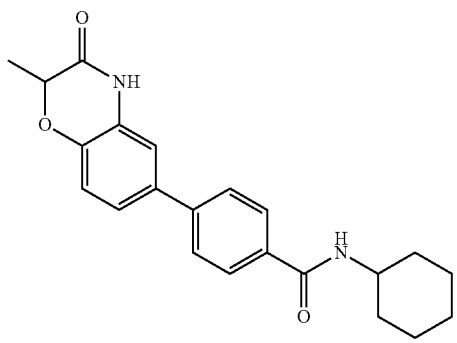 [SMILES: CC1Oc2ccc(-c3ccc(C(=O)NC4CCCCC4)cc3)cc2NC1=O]

N-Cyclohexyl-4-(2-methyl-3-oxo-3,4-dihydro-2H-benzo[b][1,4]oxazin-6-yl)benzamide (153)

Using 4-(cyclohexylcarbamoyl)phenylboronic acid in the general procedure for Pd-catalyzed Suzuki reactions, the title compound was obtained as a white solid: $^1$H NMR (DMSO-$d_6$, 400 MHz): δ=10.74 (s, 1H), 8.24 (s, 1H), 7.91 (d, J=8.6 Hz, 2H), 7.62 (d, J=8.3 Hz, 2H), 7.28 (dd, J=8.2, 2.1 Hz, 1H), 7.19 (d, J=2.3 Hz, 1H), 7.06 (d, J=8.3 Hz, 1H), 4.68-4.75 (m, 1H), 3.07-3.12 (m, 1H), 1.80-1.85 (m, 2H), 1.75 (br. s., 2H), 1.45 (d, J=6.8 Hz, 3H), 1.31 (s, 4H), 1.17 ppm (t, J=7.3 Hz, 2H). ESI-MS: m/z 365.3 (M+H)$^+$.

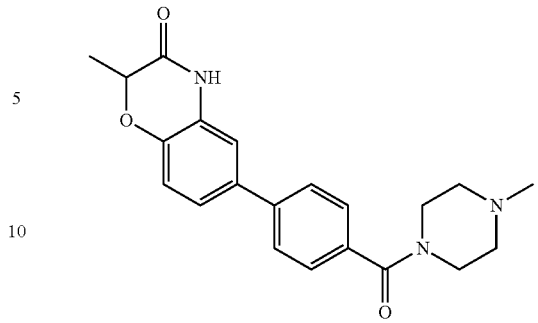

2-Methyl-6-(4-(4-methylpiperazine-1-carbonyl)phenyl)-2H-benzo[b][1,4]oxazin-3(4H)-one (154)

Using 4-(4-methylpiperazine-1-carbonyl)phenylboronic acid in the general procedure for Pd-catalyzed Suzuki reactions, the title compound was obtained as a white solid: $^1$H NMR (DMSO-$d_6$, 400 MHz): δ=10.80 (s, 1H), 9.99 (br. s., 1H), 7.62-7.68 (m, 2H), 7.54 (d, J=8.6 Hz, 2H), 7.27 (dd, J=8.3, 2.3 Hz, 1H), 7.17 (d, J=2.3 Hz, 1H), 7.07 (d, J=8.3 Hz, 1 H), 4.69-4.77 (m, 1H), 3.45 (br. s., 4H), 3.10 (br. s., 4H), 2.83 (s, 3H), 1.45 ppm (d, J=6.6 Hz, 3H). ESI-MS: m/z 366.3 (M+H)$^+$.

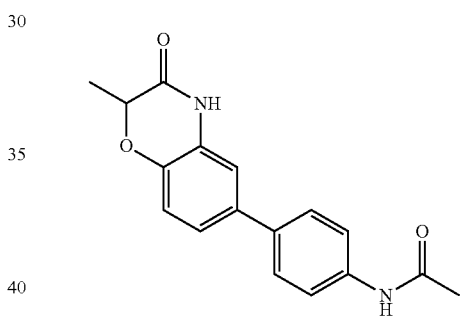

N-(4-(2-Methyl-3-oxo-3,4-dihydro-2H-benzo[b][1,4]oxazin-6-yl)phenyl)acetamide (155)

Using 4-acetamidophenylboronic acid in the general procedure for Pd-catalyzed Suzuki reactions, the title compound was obtained as a white solid: $^1$H NMR (DMSO-$d_6$, 400 MHz): δ=10.71 (s, 1H), 10.01 (s, 1H), 7.64 (d, J=8.8 Hz, 2H), 7.44-7.51 (m, 2H), 7.17 (dd, J=8.3, 2.0 Hz, 1H), 7.10 (d, J=2.3 Hz, 1H), 7.01 (d, J=8.3 Hz, 1H), 4.65-4.72 (m, 1H), 2.05 (s, 3 H), 1.44 ppm (d, J=6.8 Hz, 3H). ESI-MS: m/z 297.3 (M+H)$^+$.

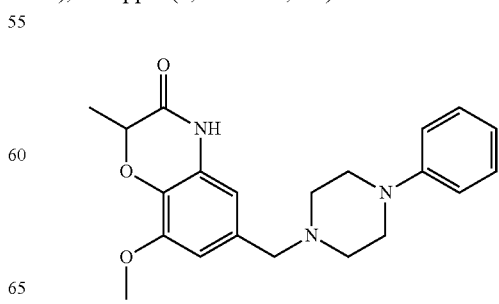

8-Methoxy-2-methyl-6-((4-phenylpiperazin-1-yl)methyl)-2H-benzo[b][1,4]oxazin-3(4H)-one (156)

Using 17 and 4-phenylpiperazine in the general procedure for reductive aminations, the title compound was obtained as a tan solid: $^1$H NMR (DMSO-d$_6$, 400 MHz): δ=10.57 (s, 1H), 7.20 (t, J=8.0 Hz, 2H), 6.92 (d, J=8.1 Hz, 2H), 6.76 (t, J=7.2 Hz, 1H), 6.63 (s, 1H), 6.52 (s, 1H), 4.58 (q, J=7.0 Hz, 1H), 3.76 (s, 3H), 3.41 (s, 2H), 3.33 (s, 4H), 3.12 (br. s., 4H), 1.40 ppm (d, J=6.8 Hz, 3H). ESI-MS: m/z 368.4 (M+H)$^+$.

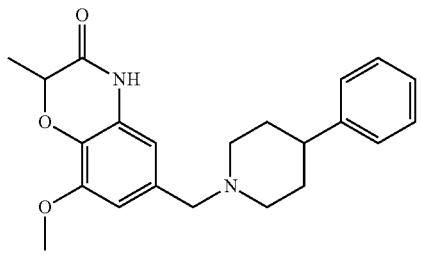 [SMILES: COc1cc(CN2CCC(c3ccccc3)CC2)cc2c1OC(C)C(=O)N2]

8-Methoxy-2-methyl-6-((4-phenylpiperidin-1-yl)methyl)-2H-benzo[b][1,4]oxazin-3(4H)-one (157)

Using 17 and 4-phenylpiperidine in the general procedure for reductive aminations, the title compound was obtained as a tan solid: $^1$H NMR (DMSO-d$_6$, 400 MHz): δ=10.55 (s, 1H), 7.21-7.32 (m, 4H), 7.14-7.21 (m, 1H), 6.62 (d, J=1.5 Hz, 1H), 6.51 (d, J=1.3 Hz, 1H), 4.58 (q, J=6.8 Hz, 1H), 3.90 (s, 2H), 3.77 (s, 3H), 3.35-3.40 (m, 3H), 2.90 (br. s., 2H), 2.01 (br. s., 1H), 1.72 (br. s., 2H), 1.61-1.67 (m, 1H), 1.40 ppm (d, J=6.8 Hz, 3 H). ESI-MS: m/z 367.4 (M+H)$^+$.

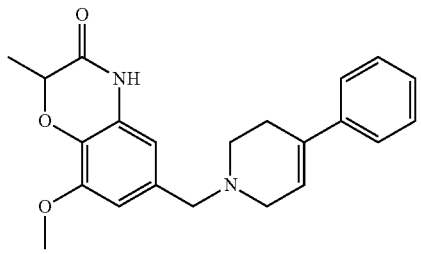 [SMILES: COc1cc(CN2CC=C(c3ccccc3)CC2)cc2c1OC(C)C(=O)N2]

8-Methoxy-2-methyl-6-((4-phenyl-5,6-dihydropyridin-1(2H)-yl)methyl)-2H-benzo[b][1,4]oxazin-3(4H)-one (158)

Using 17 and 4-phenyl-1,2,3,6-tetrahydropyridine in the general procedure for reductive aminations, the title compound was obtained as a tan solid: $^1$H NMR (DMSO-d$_6$, 400 MHz): δ=10.57 (s, 1H), 7.37-7.46 (m, 2H), 7.33 (t, J=7.6 Hz, 2 H), 7.21-7.27 (m, 1H), 6.64 (d, J=1.3 Hz, 1H), 6.54 (s, 1H), 6.15 (br. s., 1H), 4.58 (q, J=6.8 Hz, 1H), 3.90 (s, 2H), 3.77 (s, 3H), 3.47 (s, 2H), 3.06 (d, J=2.5 Hz, 2H), 2.60-2.66 (m, 2 H), 1.41 ppm (d, J=6.6 Hz, 3H). ESI-MS: m/z 365.3 (M+H)$^+$.

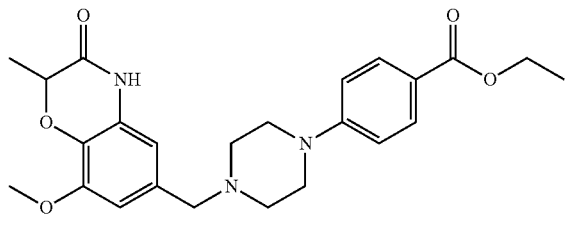 [SMILES: CCOC(=O)c1ccc(N2CCN(Cc3cc4c(c(OC)c3)OC(C)C(=O)N4)CC2)cc1]

Ethyl 4-(4-((8-methoxy-2-methyl-3-oxo-3,4-dihydro-2H-benzo[b][1,4]oxazin-6-yl)methyl)piperazin-1-yl)benzoate (159)

Using 17 and ethyl 4-(piperazin-1-yl)benzoate in the general procedure for reductive aminations, the title compound was obtained as a white solid: $^1$H NMR (DMSO-d$_6$, 400 MHz): δ=10.57 (s, 1H), 7.77 (d, J=8.6 Hz, 2H), 6.97 (d, J=8.3 Hz, 2H), 6.63 (s, 1H), 6.52 (s, 1H), 4.57 (s, 1H), 4.17-4.28 (m, 2H), 3.76 (s, 3H), 3.41 (s, 2H), 3.33 (s, 8H), 1.40 (d, J=6.6 Hz, 3H), 1.28 ppm (t, J=6.9 Hz, 3H). ESI-MS: m/z 440.4 (M+H)$^+$.

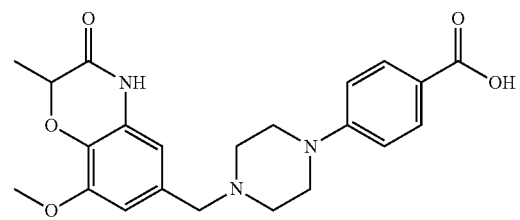 [SMILES: COc1cc(CN2CCN(c3ccc(C(=O)O)cc3)CC2)cc2c1OC(C)C(=O)N2]

4-(4-((8-Methoxy-2-methyl-3-oxo-3,4-dihydro-2H-benzo[b][1,4]oxazin-6-yl)methyl)piperazin-1-yl)benzoic acid (160)

Using 159 in the general procedure for hydrolysis of carboxylic esters, the title compound was obtained as a tan solid: $^1$H NMR (DMSO-d$_6$, 400 MHz): δ=10.85 (br. s., 1H), 7.81 (br. s., 2H), 7.09-7.19 (m, 1H), 7.02 (br. s., 2H), 6.64 (br. s., 1H), 4.65 (br. s., 1H), 4.27 (br. s., 2H), 4.02 (br. s., 2H), 3.82 (br. s., 3 H), 3.57 (d, J=2.5 Hz, 0H), 3.22-3.31 (m, 4H), 3.11 (br. s., 2H), 1.42 ppm (br. s., 3H). ESI-MS: m/z 412.4 (M+H)$^+$.

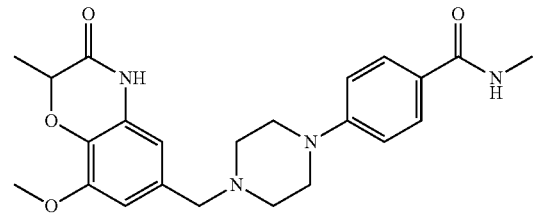

4-(4-((8-Methoxy-2-methyl-3-oxo-3,4-dihydro-2H-benzo[b][1,4]oxazin-6-yl)methyl)piperazin-1-yl)-N-methylbenzamide (161)

Using 160 and methylamine hydrochloride in the general procedure for coupling an amine to a carboxylic acid, the title compound was obtained as a tan solid, mp 256.2° C.: $^1$H NMR (DMSO-d$_6$, 400 MHz): δ=10.58 (br. s., 1H), 8.15 (br. s., 1H), 7.70 (br. s., 2H), 6.93 (br. s., 2H), 6.64 (br. s., 1H), 6.53 (br. s., 1H), 4.58 (br. s., 1H), 3.77 (br. s., 3H), 3.33 (br. s., 10H), 2.74 (br. s., 3H), 1.40 ppm (br. s., 3H). ESI-MS: m/z 425.4 (M+H)$^+$.

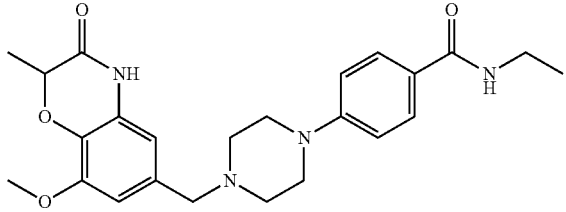 [SMILES: CCNC(=O)c1ccc(N2CCN(Cc3cc4c(c(OC)c3)OC(C)C(=O)N4)CC2)cc1]

N-Ethyl-4-(4-((8-methoxy-2-methyl-3-oxo-3,4-dihydro-2H-benzo[b][1,4]oxazin-6-yl)methyl)piperazin-1-yl)benzamide (162)

Using 160 and ethylamine hydrochloride in the general procedure for coupling an amine to a carboxylic acid, the title compound was obtained as a brown solid: $^1$H NMR (DMSO-d$_6$, 400 MHz): δ=8.17 (br. s., 1H), 7.71 (br. s., 2H), 6.93 (br. s., 2H), 6.58-6.71 (m, 0H), 6.53 (br. s., 0H), 4.59 (br. s., 0H), 3.77 (br. s., 3H), 3.39-3.47 (m, 4H), 3.01-3.29 (m, 8H), 1.41 (br. s., 3H), 1.09 ppm (br. s., 3H). ESI-MS: m/z 439.4 (M+H)$^+$.

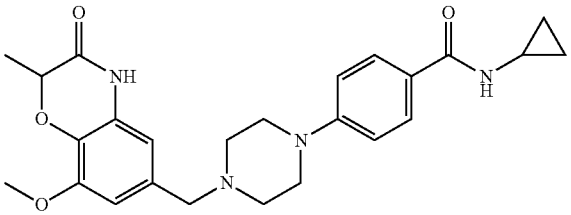 [SMILES: COc1cc(CN2CCN(c3ccc(C(=O)NC4CC4)cc3)CC2)cc2c1OC(C)C(=O)N2]

N-Cyclopropyl-4-(4-((8-methoxy-2-methyl-3-oxo-3,4-dihydro-2H-benzo[b][1,4]oxazin-6-yl)methyl)piperazin-1-yl)benzamide (163)

Using 160 and cyclopropylamine in the general procedure for coupling an amine to a carboxylic acid, the title compound was obtained as a tan solid: $^1$H NMR (DMSO-d$_6$, 400 MHz): δ=10.58 (br. s., 1H), 8.14 (br. s., 1H), 7.70 (br. s., 2H), 6.92 (br. s., 2H), 6.64 (br. s., 1H), 6.52 (br. s., 1H), 4.58 (br. s., 1H), 3.77 (d, J=4.3 Hz, 3H), 3.24 (br. s., 10H), 2.79 (br. s., 1H), 1.40 (br. s., 3H), 0.65 (br. s., 2H), 0.53 ppm (br. s., 2H). ESI-MS: m/z 451.4 (M+H)$^+$.

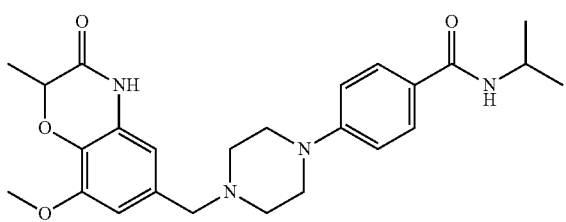 [SMILES: COc1cc(CN2CCN(c3ccc(C(=O)NC(C)C)cc3)CC2)cc2c1OC(C)C(=O)N2]

N-Isopropyl-4-(4-((8-methoxy-2-methyl-3-oxo-3,4-dihydro-2H-benzo[b][1,4]oxazin-6-yl)methyl)piperazin-1-yl)benzamide (164)

Using 160 and isopropylamine in the general procedure for coupling an amine to a carboxylic acid, the title compound was obtained as a tan solid: $^1$H NMR (DMSO-d$_6$, 400 MHz): δ=10.58 (br. s., 1H), 7.90 (br. s., 1H), 7.72 (br. s., 2H), 6.93 (br. s., 2H), 6.64 (br. s., 1H), 6.52 (br. s., 1H), 4.58 (br. s., 1H), 4.06 (br. s., 1H), 3.77 (br. s., 3H), 3.37-3.47 (m, 2H), 3.10-3.31 (m, 8H), 1.41 (br. s., 3H), 1.13 ppm (br. s., 6H). ESI-MS: m/z 453.5 (M+H)$^+$.

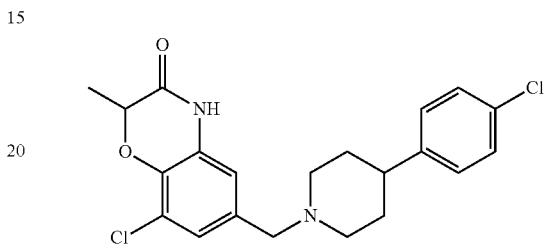

8-Chloro-6-((4-(4-chlorophenyl)piperidin-1-yl)methyl)-2-methyl-2H-benzo[b][1,4]oxazin-3(4H)-one (165)

Using 15 and 4-(4-chlorophenyl)piperidine in the general procedure for reductive aminations, the title compound was obtained as a white solid: $^1$H NMR (DMSO-d$_6$, 400 MHz): δ=11.14 (s, 1H), 7.44 (d, J=1.8 Hz, 1H), 7.40 (d, J=8.6 Hz, 2H), 7.28 (d, J=1.8 Hz, 1H), 7.25 (d, J=8.3 Hz, 2H), 6.96 (d, J=2.0 Hz, 1H), 4.83-4.90 (m, 1H), 4.27 (d, J=4.8 Hz, 2H), 3.44 (br. s., 2H), 3.04 (d, J=11.9 Hz, 2H), 2.76-2.86 (m, 1H), 1.98 (br. s., 2H), 1.79 (d, J=13.1 Hz, 2H), 1.47 ppm (d, J=6.8 Hz, 3H). ESI-MS: m/z 405.3 (M+H)$^+$.

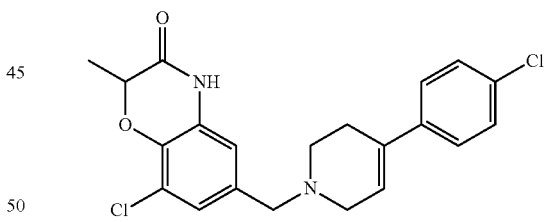

8-Chloro-6-((4-(4-chlorophenyl)-5,6-dihydropyridin-1(2H)-yl)methyl)-2-methyl-2H-benzo[b][1,4]oxazin-3(4H)-one (166)

Using 15 and 4-(4-chlorophenyl)-1,2,3,6-tetrahydropyridine in the general procedure for reductive aminations, the title compound was obtained as a yellow solid: $^1$H NMR (DMSO-d$_6$, 400 MHz): δ=11.14 (s, 1H), 7.48-7.53 (m, 2H), 7.43-7.48 (m, 2H), 7.30 (d, J=2.0 Hz, 1H), 7.00 (d, J=1.8 Hz, 1H), 6.21 (br. s., 1H), 4.83-4.91 (m, 1H), 4.35 (d, J=5.3 Hz, 2H), 3.80 (br. s., 2H), 3.62 (br. s., 1H), 3.17-3.29 (m, 1H), 2.77 (br. s., 2H), 1.47 ppm (d, J=6.8 Hz, 3H). ESI-MS: m/z 403.3 (M+H)$^+$.

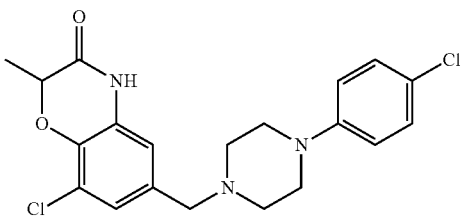 [SMILES: CC1Oc2c(Cl)cc(CN3CCN(c4ccc(Cl)cc4)CC3)cc2NC1=O]

8-Chloro-6-((4-(4-chlorophenyl)piperazin-1-yl)methyl)-2-methyl-2H-benzo[b][1,4]oxazin-3(4H)-one (167)

Using 15 and 1-(4-chlorophenyl)piperazine in the general procedure for reductive aminations, the title compound was obtained as a white solid: $^1$H NMR (DMSO-$d_6$, 400 MHz): δ=11.15 (br. s., 1H), 7.29 (d, J=8.8 Hz, 3H), 7.00 (d, J=9.1 Hz, 2H), 6.96 (br. s., 1H), 4.86 (q, J=6.7 Hz, 1H), 4.32 (br. s., 2H), 3.83 (br. s., 2H), 3.40 (br. s., 2H), 3.16 (s, 2H), 2.96 (br. s., 2H), 1.47 ppm (d, J=6.8 Hz, 3H). ESI-MS: m/z 406.3 (M+H)$^+$.

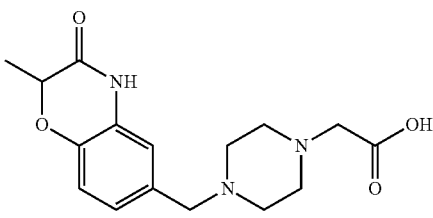 [SMILES: CC1Oc2ccc(CN3CCN(CC(=O)O)CC3)cc2NC1=O]

2-(4-((2-Methyl-3-oxo-3,4-dihydro-2H-benzo[b][1,4]oxazin-6-yl)methyl)piperazin-1-yl)acetic acid (168)

Using 102 in the general procedure for hydrolysis of a carboxylic ester, the title compound was obtained as a white solid: $^1$H NMR (400 MHz, DMSO-$d_6$) δ ppm 10.89 (s, 1H), 6.99-7.05 (m, 2H), 6.97 (s, 1H), 4.66-4.73 (m, 1H), 4.12 (br. s., 3H), 3.51 (br. s., 3H), 2.89-3.19 (m, 6H), 1.43 (d, J=6.8 Hz, 3H). ESI-MS: m/z 320.4 (M+H)$^+$.

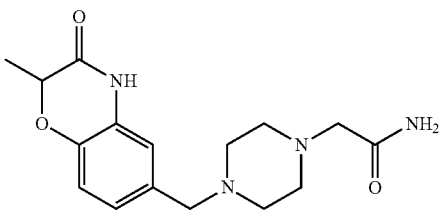 [SMILES: CC1Oc2ccc(CN3CCN(CC(N)=O)CC3)cc2NC1=O]

2-(4-((2-Methyl-3-oxo-3,4-dihydro-2H-benzo[b][1,4]oxazin-6-yl)methyl)piperazin-1-yl)acetamide (169)

Using 168 and ammonium chloride in the general procedure for coupling an amine to a carboxylic acid, the title compound was obtained as a light yellow solid: $^1$H NMR (400 MHz, DMSO-$d_6$) δ ppm 10.87 (s, 1H), 7.72 (br. s., 1H), 7.52 (br. s., 1H), 6.98-7.04 (m, 2H), 6.94-6.97 (m, 2H), 4.65-4.72 (m, 1H), 4.07 (br. s., 2H), 3.60 (br. s., 2H), 3.04-3.22 (m, 4H), 2.08 (s, 4H), 1.43 (d, J=6.6 Hz, 3H). ESI-MS: m/z 319.3 (M+H)$^+$.

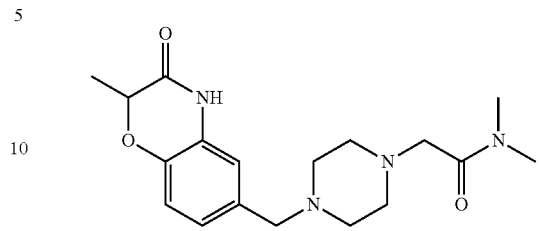

N,N-Dimethyl-2-(4-((2-methyl-3-oxo-3,4-dihydro-2H-benzo[b][1,4]oxazin-6-yl)methyl)piperazin-1-yl)acetamide (170)

Using 168 and dimethylamine in the general procedure for coupling an amine to a carboxylic acid, the title compound was obtained as a tan solid: $^1$H NMR (400 MHz, DMSO-$d_6$) δ ppm 10.59 (s, 1H), 6.78-6.92 (m, 3H), 4.59-4.66 (m, 1H), 3.34 (s, 6H), 3.10 (s, 2H), 3.00 (s, 3H), 2.79 (s, 3H), 2.23-2.49 (m, 5H), 1.40 (d, J=6.8 Hz, 3H). ESI-MS: m/z 347.3 (M+H)$^+$.

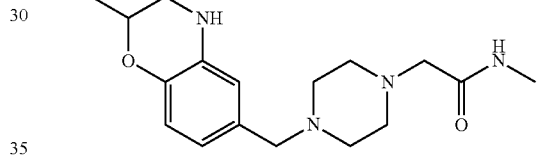

N-Methyl-2-(4-((2-methyl-3-oxo-3,4-dihydro-2H-benzo[b][1,4]oxazin-6-yl)methyl)piperazin-1-yl)acetamide (171)

Using 168 and methylamine hydrochloride in the general procedure for coupling an amine to a carboxylic acid, the title compound was obtained as a white solid: $^1$H NMR (400 MHz, DMSO-$d_6$) δ ppm 10.89 (s, 1H), 8.18 (d, J=4.5 Hz, 1H), 7.02 (s, 2H), 6.97 (s, 1H), 4.69 (q, J=6.7 Hz, 1H), 4.12 (br. s., 2H), 3.50 (br. s., 2H), 2.97-3.27 (m, 7H), 2.64 (d, J=4.5 Hz, 3H), 1.43 (d, J=6.6 Hz, 3H). ESI-MS: m/z 333.3 (M+H)$^+$.

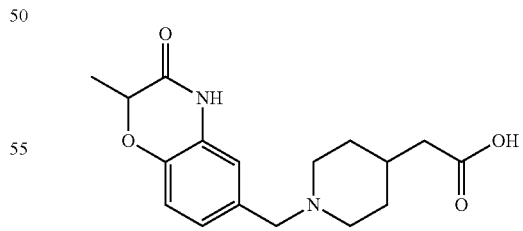

2-(1-((2-Methyl-3-oxo-3,4-dihydro-2H-benzo[b][1,4]oxazin-6-yl)methyl)piperidin-4-yl)acetic acid (172)

Using 103 in the general procedure for hydrolysis of a carboxylic ester, the title compound was obtained as a white solid: $^1$H NMR (400 MHz, DMSO-$d_6$) δ ppm 1.28-1.41 (m, 1H) 1.43 (d, J=6.82 Hz, 3H) 1.65-1.93 (m, 3H) 2.19 (d, J=6.32 Hz, 1H) 2.85-3.03 (m, 2H) 3.21-3.38 (m, 2H) 4.18 (d, J=5.31 Hz, 2H) 4.68-4.74 (m, 1H) 6.95-7.06 (m, 3H) 9.21-9.36 (m, 1H) 10.92 (s, 1H). ESI-MS: m/z 319.3 (M+H)⁺.

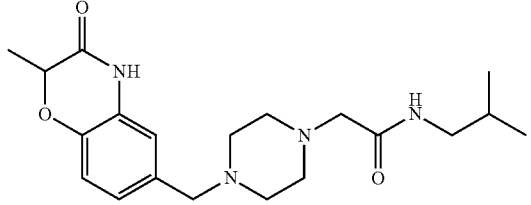 [SMILES: CC(C)CNC(=O)CN1CCN(Cc2ccc3c(c2)NC(=O)C(C)O3)CC1]

N-Isobutyl-2-(4-((2-methyl-3-oxo-3,4-dihydro-2H-benzo[b][1,4]oxazin-6-yl)methyl)piperazin-1-yl) acetamide (173)

Using 168 and 2-methylpropan-1-amine in the general procedure for coupling an amine to a carboxylic acid, the title compound was obtained as a white solid, mp 149.8° C.: ¹H NMR (400 MHz, DMSO-d₆) δ ppm 10.60 (s, 1H), 7.64 (t, J=6.1 Hz, 1H), 6.86-6.90 (m, 1H), 6.85 (d, J=1.8 Hz, 1H), 6.79-6.83 (m, 1H), 4.59-4.66 (m, 1H), 3.36 (s, 2H), 2.86-2.95 (m, 4H), 2.21-2.50 (m, 8H), 1.63-1.76 (m, J=13.5, 6.7, 6.7, 6.7, 6.7 Hz, 1H), 1.40 (d, J=6.8 Hz, 3H), 0.82 (d, J=6.8 Hz, 6H. ESI-MS: m/z 375.4 (M+H)⁺.

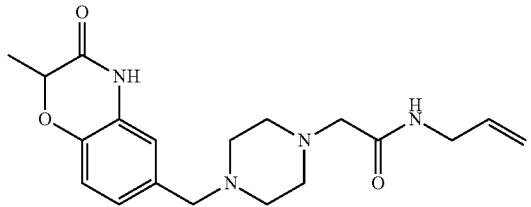 [SMILES: C=CCNC(=O)CN1CCN(Cc2ccc3c(c2)NC(=O)C(C)O3)CC1]

N-Allyl-2-(4-((2-methyl-3-oxo-3,4-dihydro-2H-benzo[b][1,4]oxazin-6-yl)methyl)piperazin-1-yl) acetamide (174)

Using 168 and prop-2-en-1-amine in the general procedure for coupling an amine to a carboxylic acid, the title compound was obtained as a light yellow solid, mp 150.8-157.6° C.: ¹H NMR (400 MHz, DMSO-d₆) δ ppm 10.60 (s, 1H), 7.82 (t, J=5.9 Hz, 1H), 6.86-6.90 (m, 1H), 6.85 (d, J=1.5 Hz, 1H), 6.79-6.83 (m, 1H), 5.74-5.85 (m, J=17.2, 10.4, 5.2, 5.2 Hz, 1H), 5.01-5.12 (m, 2H), 4.59-4.65 (m, 1H), 3.68-3.74 (m, 2H), 3.36 (s, 2H), 2.92 (s, 2H), 2.21-2.50 (m, 8H), 1.40 (d, J=6.8 Hz, 3H). ESI-MS: m/z 359.3 (M+H)⁺.

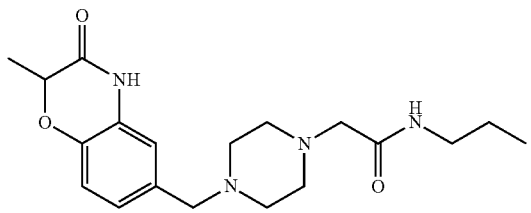 [SMILES: CCCNC(=O)CN1CCN(Cc2ccc3c(c2)NC(=O)C(C)O3)CC1]

2-(4-((2-Methyl-3-oxo-3,4-dihydro-2H-benzo[b][1,4]oxazin-6-yl)methyl)piperazin-1-yl)-N-propylacetamide (175)

Using 168 and propan-1-amine in the general procedure for coupling an amine to a carboxylic acid, the title compound was obtained as a white solid: ¹H NMR (400 MHz, DMSO-d₆) δ ppm 10.59 (s, 1H), 7.64 (t, J=5.9 Hz, 1H), 6.86-6.90 (m, 1H), 6.85 (d, J=1.8 Hz, 1H), 6.79-6.83 (m, 1H), 4.58-4.66 (m, 1H), 3.36 (s, 2H), 3.03 (q, J=6.6 Hz, 2H), 2.87 (s, 2H), 2.19-2.49 (m, 7H), 1.34-1.46 (m, 5H), 0.82 (t, J=7.5 Hz, 3H). ESI-MS: m/z 361.4 (M+H)⁺.

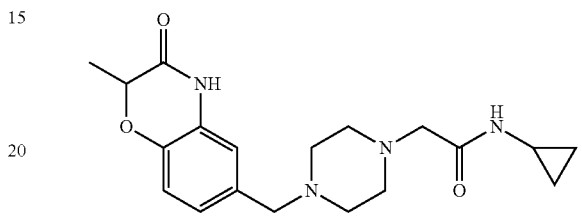

N-Cyclopropyl-2-(4-((2-methyl-3-oxo-3,4-dihydro-2H-benzo[b][1,4]oxazin-6-yl)methyl)piperazin-1-yl) acetamide (176)

Using 168 and cyclopropylamine in the general procedure for coupling an amine to a carboxylic acid, the title compound was obtained as a white solid, mp 180.5-181.1° C.: ¹H NMR (400 MHz, DMSO-d₆) δ ppm 10.59 (s, 1H), 7.65 (d, J=4.0 Hz, 1H), 6.85-6.90 (m, 1H), 6.84 (d, J=1.8 Hz, 1H), 6.78-6.83 (m, 1H), 4.58-4.66 (m, 1H), 3.34 (s, 2H), 2.84 (s, 2H), 2.57-2.66 (m, 1H), 2.19-2.49 (m, 8H), 0.56-0.63 (m, 2H), 0.39-0.46 (m, 2H). ESI-MS: m/z 359.4 (M+H)⁺.

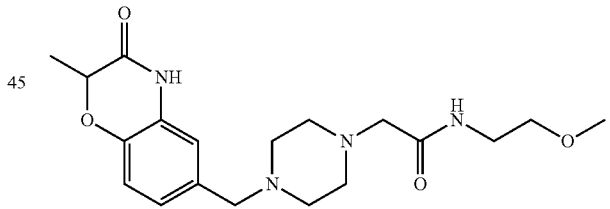

N-(2-Methoxyethyl)-2-(4-((2-methyl-3-oxo-3,4-dihydro-2H-benzo[b][1,4]oxazin-6-yl)methyl)piperazin-1-yl)acetamide (177)

Using 168 and 2-methoxyethanamine in the general procedure for coupling an amine to a carboxylic acid, the title compound was obtained as an off-white solid, mp 111.0-142.0° C.: ¹H NMR (400 MHz, DMSO-d₆) δ ppm 10.60 (s, 1H), 7.64 (t, J=5.7 Hz, 1H), 6.86-6.90 (m, 1H), 6.85 (d, J=1.8 Hz, 1H), 6.79-6.83 (m, 1H), 4.59-4.66 (m, 1H), 3.31-3.37 (m, 4H), 3.21-3.28 (m, 5H), 2.89 (s, 2H), 2.21-2.50 (m, 7H), 1.40 (d, J=6.8 Hz, 3H). ESI-MS: m/z 377.4 (M+H)⁺.

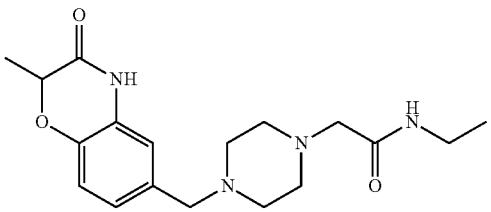 [SMILES: CCNC(=O)CN1CCN(Cc2ccc3c(c2)NC(=O)C(C)O3)CC1]

N-Ethyl-2-(4-((2-methyl-3-oxo-3,4-dihydro-2H-benzo[b][1,4]oxazin-6-yl)methyl)piperazin-1-yl)acetamide (178)

Using 168 and ethanamine in the general procedure for coupling an amine to a carboxylic acid, the title compound was obtained as an off-white solid: $^1$H NMR (400 MHz, DMSO-$d_6$) δ ppm 10.59 (s, 1H), 7.64 (t, J=5.8 Hz, 1H), 6.86-6.90 (m, 1H), 6.85 (d, J=1.8 Hz, 1H), 6.79-6.83 (m, 1H), 4.59-4.66 (m, 1H), 3.36 (s, 2H), 3.04-3.14 (m, 2H), 2.86 (s, 2H), 2.22-2.49 (m, 7H), 1.40 (d, J=6.8 Hz, 3H), 1.00 (t, J=7.2 Hz, 3H). ESI-MS: m/z 347.3 (M+H)$^+$.

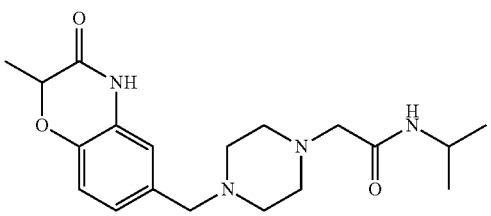 [SMILES: CC(C)NC(=O)CN1CCN(Cc2ccc3c(c2)NC(=O)C(C)O3)CC1]

N-Isopropyl-2-(4-((2-methyl-3-oxo-3,4-dihydro-2H-benzo[b][1,4]oxazin-6-yl)methyl)piperazin-1-yl)acetamide (179)

Using 168 and isopropylamine in the general procedure for coupling an amine to a carboxylic acid, the title compound was obtained as an off-white solid: $^1$H NMR (400 MHz, DMSO-$d_6$) δ ppm 10.59 (s, 1H), 7.38 (d, J=8.6 Hz, 1H), 6.86-6.89 (m, 1H), 6.84 (d, J=1.8 Hz, 1H), 6.79-6.83 (m, 1H), 4.59-4.66 (m, 1H), 3.81-3.91 (m, 1H), 3.35 (s, 2H), 2.85 (s, 2H), 2.26-2.49 (m, 8H), 1.40 (d, J=6.8 Hz, 3H), 1.05 (d, J=6.6 Hz, 6H). ESI-MS: m/z 361.4 (M+H)$^+$.

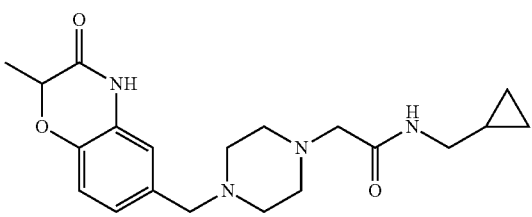 [SMILES: CC1Oc2ccc(CN3CCN(CC(=O)NCC4CC4)CC3)cc2NC1=O]

N-(Cyclopropylmethyl)-2-(4-((2-methyl-3-oxo-3,4-dihydro-2H-benzo[b][1,4]oxazin-6-yl)methyl)piperazin-1-yl)acetamide (180)

Using 168 and cyclopropylmethanamine in the general procedure for coupling an amine to a carboxylic acid, the title compound was obtained as an off-white solid: $^1$H NMR (400 MHz, DMSO-$d_6$) δ ppm 10.59 (br. s., 1H), 7.68 (t, J=5.8 Hz, 1H), 6.86-6.90 (m, 1H), 6.85 (d, J=1.8 Hz, 1H), 6.79-6.83 (m, 1H), 4.59-4.66 (m, 1H), 3.36 (s, 2H), 2.96 (t, J=6.4 Hz, 2H), 2.89 (s, 2H), 2.20-2.49 (m, 7H), 1.40 (d, J=6.8 Hz, 3H), 0.84-0.97 (m, 1H), 0.33-0.40 (m, 2H), 0.11-0.17 (m, 2H). ESI-MS: m/z 373.4 (M+H)$^+$.

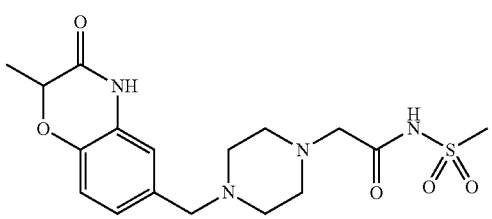

2-(4-((2-Methyl-3-oxo-3,4-dihydro-2H-benzo[b][1,4]oxazin-6-yl)methyl)piperazin-1-yl)-N-(methylsulfonyl)acetamide (181)

Using 168 and methanesulfonamide in the general procedure for coupling an amine to a carboxylic acid, the title compound was obtained as a white solid: $^1$H NMR (400 MHz, DMSO-$d_6$) δ ppm 1.43 (d, J=6.82 Hz, 3H) 2.54-2.82 (m, 2H) 2.91-3.20 (m, 4H) 3.25 (s, 3H) 3.28-3.35 (m, 2H) 4.11-4.33 (m, 2H) 4.67-4.74 (m, 1H) 6.95-7.00 (m, 1H) 7.01-7.07 (m, 2H) 9.56 (br. s., 1H) 10.92 (s, 1H). ESI-MS: m/z 397.4 (M+H)$^+$.

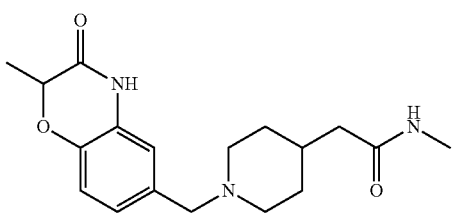

N-Methyl-2-(1-((2-methyl-3-oxo-3,4-dihydro-2H-benzo[b][1,4]oxazin-6-yl)methyl)piperidin-4-yl)acetamide (182)

Using 172 and methanamine hydrochloride in the general procedure for coupling an amine to a carboxylic acid, the title compound was obtained as a clear oil: $^1$H NMR (400 MHz, DMSO-$d_6$) δ ppm 1.23-1.39 (m, 2H) 1.43 (d, J=6.82 Hz, 2H) 1.64-1.94 (m, 3H) 2.01 (d, J=6.82 Hz, 1H) 2.53-2.58 (m, 2H) 2.83-3.11 (m, 2H) 3.11-3.36 (m, 2H) 4.17 (d, J=5.31 Hz, 2H) 4.28 (d, J=5.56 Hz, 1H) 4.68-4.74 (m, 1H) 6.95-7.06 (m, 2H) 7.80 (q, J=4.38 Hz, 1H) 9.10-9.21 (m, 1H) 10.92 (s, 1H). ESI-MS: m/z 332.4 (M+H)$^+$.

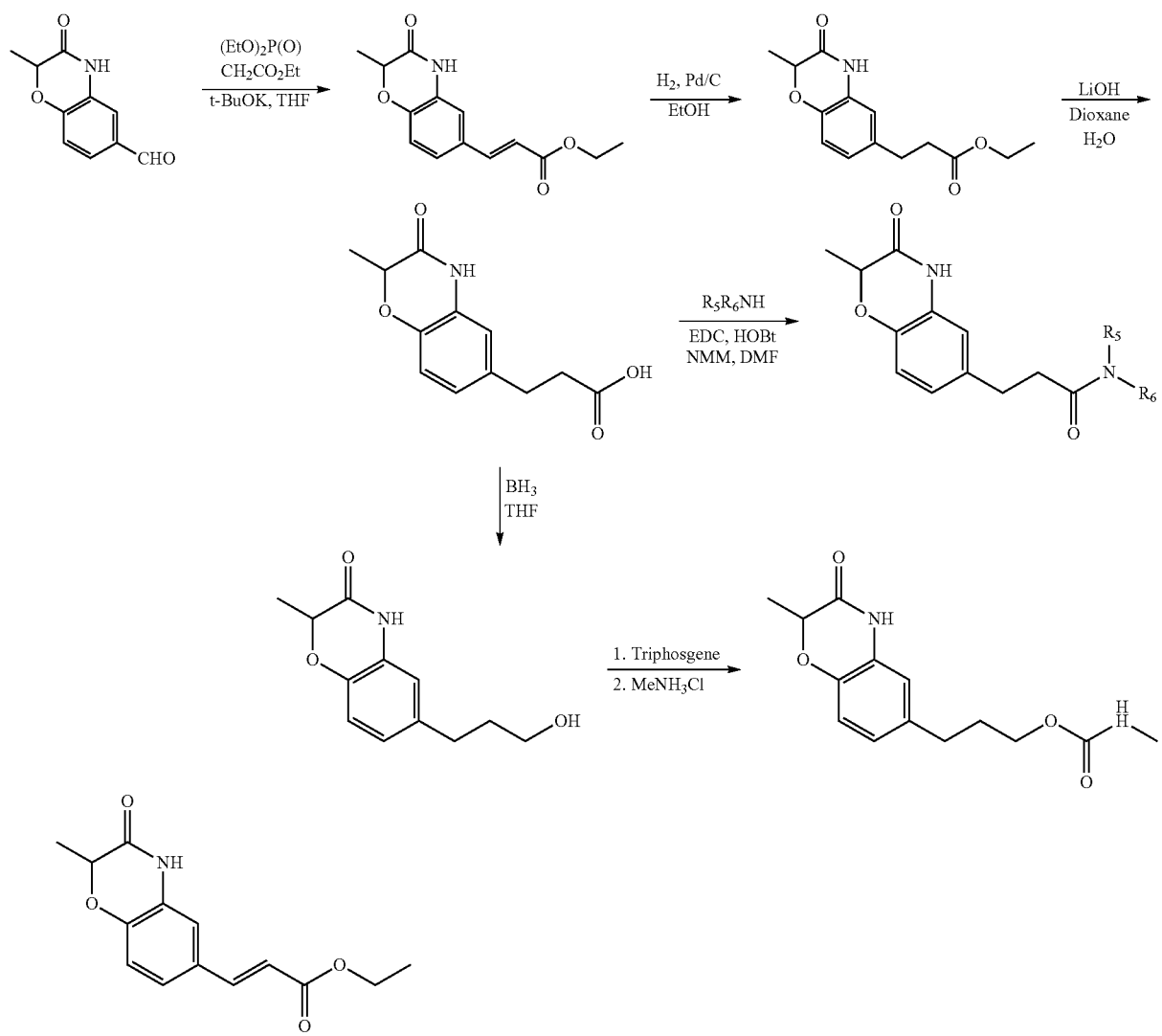

(E)-Ethyl 3-(2-methyl-3-oxo-3,4-dihydro-2H-benzo[b][1,4]oxazin-6-yl)acrylate (183)

In a 100 mL round bottom flask equipped with a magnetic stir bar was added t-BuOK (352 mg, 3.14 mmol) and THF (5 mL). The solution was cooled to 0° C. Triethylphosphonoacetate (0.576 mL, 2.88 mmol) was added slowly by syringe pump over 30 min. Using 13 (500 mg, 2.62 mmol) in THF (5 mL), the aldehyde was added via syringe pump over 30 min at 0° C. When the addition was complete, the reaction was warmed to room temperature and stirred for 2 h. The reaction was quenched with sat aqueous NH$_4$Cl (10 mL) and extracted with EtOAc. The organic layer was washed with brine, dried (MgSO$_4$) and concentrated in vacuo. The residue was purified by flash column chromatography using a gradient of 25-50% EtOAc in hexanes. The appropriate fractions were combined and concentrated in vacuo to give the title compound as a white solid (631 mg, 92% yield): $^1$H NMR (400 MHz, DMSO-d$_6$) δ ppm 1.25 (t, J=7.20 Hz, 3H) 1.43 (d, J=6.82 Hz, 3H) 4.18 (q, J=7.16 Hz, 2H) 4.70-4.77 (m, 1H) 6.38 (d, J=15.92 Hz, 1H) 7.13 (d, J=2.02 Hz, 1H) 7.33 (dd, J=8.72, 2.15 Hz, 1H) 7.56 (d, J=15.92 Hz, 1H) 10.78 (s, 1H). ESI-MS: m/z 262.2 (M+H)$^+$.

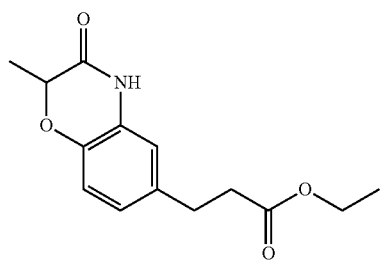 [SMILES: CCOC(=O)CCc1ccc2c(c1)NC(=O)C(C)O2]

Ethyl 3-(2-methyl-3-oxo-3,4-dihydro-2H-benzo[b][1,4]oxazin-6-yl)propanoate (184)

In a 100 mL round bottom flask equipped with a magnetic stir bar was added 183 (67 mg, 0.256 mmol), Pd/C (10% by weight, 5 mg) and EtOH (2 mL). The mixture was stirred under a hydrogen atmosphere (balloon) for 18 h. The reaction was filtered and concentrated in vacuo to give the title compound as a white solid (62 mg, 92% yield): $^1$H NMR (400 MHz, DMSO-d$_6$) δ ppm 1.15 (t, J=7.07 Hz, 3H) 1.39 (d, J=6.82 Hz, 3H) 2.54 (t, J=7.33 Hz, 2H) 2.75 (t, J=7.45 Hz, 2H) 4.04 (q, J=7.24 Hz, 2H) 4.56-4.63 (m, 1H) 6.71 (d, J=1.77 Hz, 1H) 6.76 (dd, J=8.08, 2.02 Hz, 1H) 6.85 (d, J=8.34 Hz, 1H) 10.61 (s, 1H). ESI-MS: m/z 264.2 (M+H)$^+$.

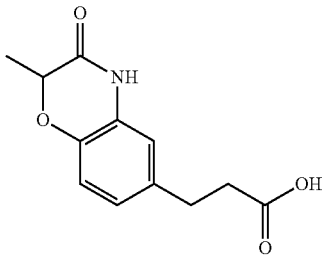 [SMILES: CC1Oc2ccc(CCC(=O)O)cc2NC1=O]

3-(2-Methyl-3-oxo-3,4-dihydro-2H-benzo[b][1,4]oxazin-6-yl)propanoic acid (185)

Using 184 in the general procedure for hydrolysis of a carboxylic ester, the title compound was obtained as a white solid: $^1$H NMR (400 MHz, DMSO-d$_6$) δ ppm 1.39 (d, J=6.82 Hz, 3H) 2.44-2.48 (m, 2H) 2.69-2.75 (m, 2H) 4.60 (q, J=6.74 Hz, 1H) 6.72 (d, J=1.77 Hz, 1H) 6.77 (dd, J=8.08, 2.02 Hz, 1H) 6.85 (d, J=8.08 Hz, 1H) 10.60 (s, 1H) 12.13 (br. s., 1H). ESI-MS: m/z 236.2 (M+H)$^+$.

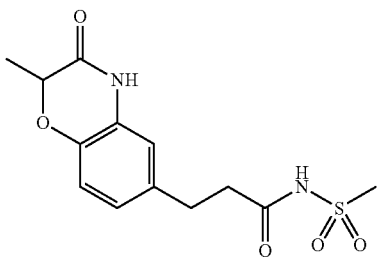

3-(2-Methyl-3-oxo-3,4-dihydro-2H-benzo[b][1,4]oxazin-6-yl)-N-(methylsulfonyl)propanamide (186)

Using 185 and methanesulfonamide in the general procedure for coupling an amine to a carboxylic acid, the title compound was obtained as a white solid: $^1$H NMR (400 MHz, DMSO-d$_6$) δ ppm 1.39 (d, J=6.57 Hz, 3H) 2.13-2.21 (m, 2H) 2.62-2.68 (m, 2H) 2.71 (s, 3H) 4.55-4.62 (m, 1H) 6.71 (d, J=1.77 Hz, 1H) 6.75 (d, J=2.02 Hz, 1H) 6.80-6.84 (m, 1H). ESI-MS: m/z 313.3 (M+H)$^+$.

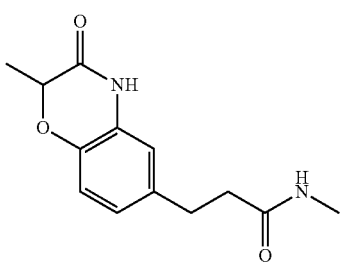

N-Methyl-3-(2-methyl-3-oxo-3,4-dihydro-2H-benzo[b][1,4]oxazin-6-yl)propanamide (187)

Using 185 and methanamine hydrochloride in the general procedure for coupling an amine to a carboxylic acid, the title compound was obtained as a white solid: $^1$H NMR (400 MHz, DMSO-d$_6$) δ ppm 1.39 (d, J=6.82 Hz, 3H) 2.29 (t, J=7.71 Hz, 2H) 2.55 (d, J=4.55 Hz, 3H) 2.67-2.74 (m, 2H) 4.55-4.63 (m, 1H) 6.70 (d, J=1.77 Hz, 1H) 6.71-6.76 (m, 1H) 6.84 (d, J=8.08 Hz, 1H) 7.70-7.80 (m, 1H). ESI-MS: m/z 249.3 (M+H)$^+$.

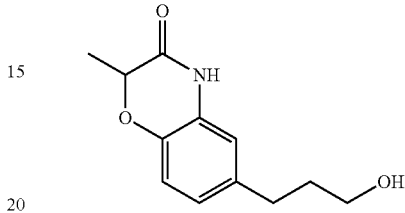

6-(3-Hydroxypropyl)-2-methyl-2H-benzo[b][1,4]oxazin-3(4H)-one (188)

To a 50 mL round bottom flask under nitrogen was added 185 (161 mg, 0.68 mmol) and THF (1 mL). The mixture was stirred magnetically at 0° C. and then BH$_3$ in THF (1 M, 2.25 mL, 2.25 mmol) was added slowly dropwise. After 1 h, the reaction was quenched with HCl in MeOH (2 M, 1.4 mL). The reaction was concentrated in vacuo and the residue was purified by preparative HPLC-MS using a 15-40% MeCN in water gradient. The appropriate fractions were collected and concentrated in vacuo to give the title compound as a white solid (39 mg, 26% yield): $^1$H NMR (400 MHz, DMSO-d$_6$) δ ppm 1.39 (d, J=6.82 Hz, 3H) 1.61-1.69 (m, 2H) 3.37-3.42 (m, 2H) 4.47 (br. s., 1H) 4.56-4.63 (m, 1H) 6.70 (d, J=2.02 Hz, 1H) 6.71-6.76 (m, 1H) 6.84 (d, J=8.08 Hz, 1H) 10.58 (s, 1H). ESI-MS: m/z 222.2 (M+H)$^+$.

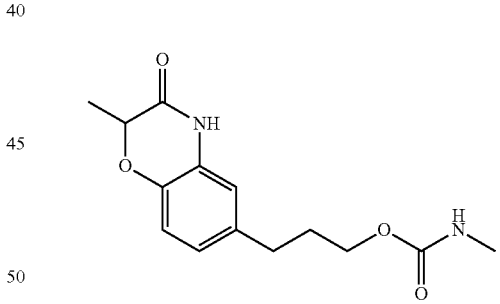

3-(2-Methyl-3-oxo-3,4-dihydro-2H-benzo[b][1,4]oxazin-6-yl)propyl methylcarbamate (189)

To a 20 mL screw cap vial equipped with a magnetic stir bar was added triphosgene (20 mg, 0.068 mmol) in toluene (0.85 mL). The mixture was cooled to 0° C. and pyridine (0.017 mL, 0.21 mmol) was added followed by 188 (38 mg, 0.17 mmol) in toluene (0.5 mL). The reaction was stirred at 0° C. for 1 h then room temperature overnight. The reaction was concentrated in vacuo then taken up in DCM (1.0 mL) and cooled to 0° C. Methylamine HCl (57 mg, 0.85 mmol) was added followed by triethylamine (0.237 mL, 1.7 mmol). The reaction was allowed to warm to room temperature and was stirred for 18 h. The reaction was concentrated in vacuo and the residue was purified by preparative HPLC-MS using 20-45% MeCN in water as the gradient. The appropriate fractions were collected and concentrated in vacuo to give the title compound as a white solid (14 mg, 29% yield): ¹H NMR (400 MHz, DMSO-d$_6$) δ ppm 1.40 (d, J=6.82 Hz, 3H) 1.72-1.83 (m, 2H) 2.51-2.55 (m, 2 H) 2.56 (d, J=4.80 Hz, 3H) 3.92 (t, J=6.57 Hz, 2H) 4.57-4.64 (m, 1H) 6.69 (d, J=1.77 Hz, 1 H) 6.74 (dd, J=8.08, 2.02 Hz, 1H) 6.86 (d, J=8.08 Hz, 1H) 6.94-7.03 (m, 1H) 10.60 (s, 1H). ESI-MS: m/z 279.2 (M+H)⁺.

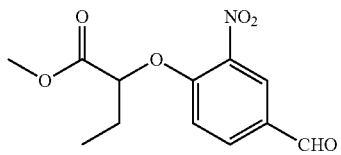 [SMILES: CCC(Oc1ccc(C=O)cc1[N+](=O)[O-])C(=O)OC]

Methyl 2-(4-formyl-2-nitrophenoxy)butanoate (190)

Using 4-hydroxy-3-nitrobenzaldehyde as the phenol and methyl-2-bromobutanoate as the alkylating agent in the general procedure of alkylation of substituted 2-nitrophenols gives a clear yellow oil: ¹H NMR (DMSO-d$_6$, 400 MHz): δ=9.94 (s, 1H), 8.44 (d, J=2.3 Hz, 1H), 8.13 (dd, J=8.8, 2.0 Hz, 1H), 7.42 (d, J=8.8 Hz, 1H), 5.36 (dd, J=6.6, 4.5 Hz, 1H), 3.70 (s, 3H), 1.88-2.05 (m, 2H), 0.98 ppm (t, J=7.5 Hz, 3H). ESI-MS: m/z 268.2 (M+H)⁺.

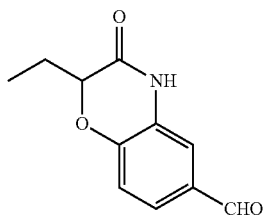

2-Ethyl-3-oxo-3,4-dihydro-2H-benzo[b][1,4]oxazine-6-carbaldehyde (191)

Using 190 in the general procedure for reduction of a nitro group and subsequent ring closure gives a brown solid: ¹H NMR (400 MHz, DMSO-d$_6$) δ ppm 0.90-1.05 (m, 3H) 1.70-1.94 (m, 2H) 4.66-4.76 (m, 1H) 7.13-7.20 (m, 1H) 7.37 (d, J=1.77 Hz, 1H) 7.49-7.59 (m, 1H) 9.81-9.88 (m, 1H) 10.96 (br. s., 1H). ESI-MS: m/z 206.2 (M+H)⁺.

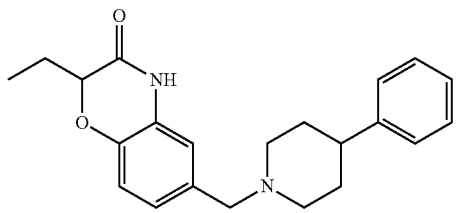 [SMILES: CCC1Oc2ccc(CN3CCC(c4ccccc4)CC3)cc2NC1=O]

2-Ethyl-6-((4-phenylpiperidin-1-yl)methyl)-2H-benzo[b][1,4]oxazin-3(4H)-one (192)

Using 191 and 4-phenylpiperidine in the general procedure for reductive aminations, the title compound was obtained as a white solid: ¹H NMR (400 MHz, DMSO-d$_6$) δ ppm 0.99 (t, J=7.45 Hz, 3H) 1.68-1.93 (m, 4H) 1.93-2.08 (m, 2H) 3.05 (d, J=12.38 Hz, 2H) 3.39-3.51 (m, 2H) 4.22-4.31 (m, 2H) 4.52-4.63 (m, 1H) 6.99 (s, 1H) 7.03-7.14 (m, 2H) 7.17-7.30 (m, 3H) 7.30-7.45 (m, 2H) 9.31 (br. s., 1H) 10.89-11.01 (m, 1H). ESI-MS: m/z 351.4 (M+H)⁺.

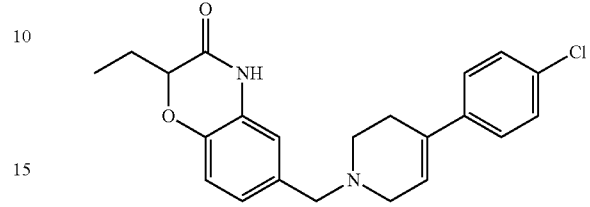

6-((4-(4-Chlorophenyl)-5,6-dihydropyridin-1(2H)-yl)methyl)-2-ethyl-2H-benzo[b][1,4]oxazin-3(4H)-one (193)

Using 191 and 4-(4-chlorophenyl)-1,2,3,6-tetrahydropyridine in the general procedure for reductive aminations, the title compound was obtained as a white solid: ¹H NMR (400 MHz, DMSO-d$_6$) δ ppm 0.98 (t, J=7.45 Hz, 3H) 1.66-1.88 (m, 2H) 2.41-2.45 (m, 1H) 2.58-2.70 (m, 2H) 2.98-3.06 (m, 2H) 3.48 (s, 2H) 4.48 (dd, J=7.83, 4.55 Hz, 1H) 6.13-6.23 (m, 1H) 6.82-6.94 (m, 3H) 7.35-7.41 (m, 2H) 7.41-7.49 (m, 2H) 10.61 (s, 1H). ESI-MS: m/z 382.8 (M+H)⁺.

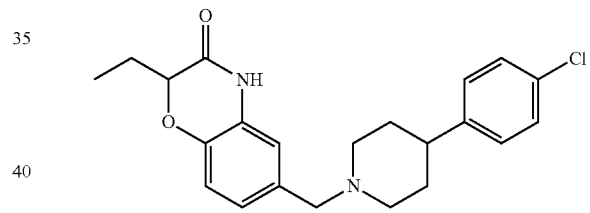

6-((4-(4-Chlorophenyl)piperidin-1-yl)methyl)-2-ethyl-2H-benzo[b][1,4]oxazin-3(4H)-one (194)

Using 191 and 4-(4-chlorophenyl)piperidine in the general procedure for reductive aminations, the title compound was obtained as a white solid: ¹H NMR (400 MHz, DMSO-d$_6$) δ ppm 0.92-1.07 (m, 3H) 1.69-1.91 (m, 4H) 1.92-2.07 (m, 2H) 2.95-3.14 (m, 2H) 3.38-3.53 (m, 2H) 4.20-4.33 (m, 2H) 4.52-4.62 (m, 1H) 6.99 (s, 1H) 7.02-7.12 (m, 2H) 7.19-7.29 (m, 2H) 7.35-7.48 (m, 2H) 9.32 (br. s., 1H) 10.90-10.98 (m, 1H). m/z 385.9 (M+H)⁺.

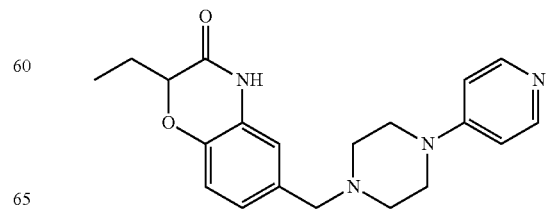

2-Ethyl-6-((4-(pyridin-4-yl)piperazin-1-yl)methyl)-2H-benzo[b][1,4]oxazin-3(4H)-one (195)

Using 191 and 1-(pyridin-4-yl)piperazine in the general procedure for reductive aminations, the title compound was obtained as a white solid, mp 113.0-128.5° C.: $^1$H NMR (400 MHz, DMSO-$d_6$) δ ppm 0.99 (t, J=7.33 Hz, 3H) 1.69-1.92 (m, 2H) 2.99-3.23 (m, 2H) 3.45 (br. s., 3H) 4.11-4.51 (m, 4H) 4.57 (dd, J=7.58, 4.55 Hz, 1H) 6.96 (s, 1H) 6.99-7.11 (m, 2H) 7.25 (d, J=7.58 Hz, 2H) 8.37 (d, J=7.33 Hz, 2H) 10.95 (br. s., 1H). ESI-MS: m/z 353.4 (M+H)$^+$.

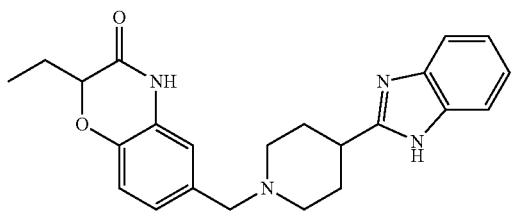 [SMILES: CCC1Oc2ccc(CN3CCC(c4nc5ccccc5[nH]4)CC3)cc2NC1=O]

6-((4-(1H-Benzo[d]imidazol-2-yl)piperidin-1-yl)methyl)-2-ethyl-2H-benzo[b][1,4]oxazin-3(4H)-one (196)

Using 191 and 2-(piperidin-4-yl)-1H-benzo[d]imidazole in the general procedure for reductive aminations, the title compound was obtained as a tan solid: $^1$H NMR (400 MHz, DMSO-$d_6$) δ ppm 0.99 (t, J=7.33 Hz, 3H) 1.69-1.92 (m, 2H) 2.99-3.23 (m, 2H) 3.45 (br. s., 3H) 4.11-4.51 (m, 4H) 4.57 (dd, J=7.58, 4.55 Hz, 1H) 6.96 (s, 1H) 6.99-7.11 (m, 2H) 7.25 (d, J=7.58 Hz, 2H) 8.37 (d, J=7.33 Hz, 2H) 10.95 (br. s., 1H). ESI-MS: m/z 391.4 (M+H)$^+$.

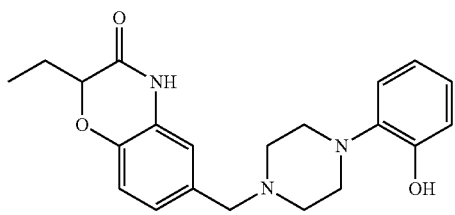 [SMILES: CCC1Oc2ccc(CN3CCN(c4ccccc4O)CC3)cc2NC1=O]

2-Ethyl-6-((4-(2-hydroxyphenyl)piperazin-1-yl)methyl)-2H-benzo[b][1,4]oxazin-3(4H)-one (197)

Using 191 and 2-(piperazin-1-yl)phenol in the general procedure for reductive aminations, the title compound was obtained as a white solid: $^1$H NMR (400 MHz, DMSO-$d_6$) δ ppm 0.99 (t, J=7.33 Hz, 3H) 1.66-1.95 (m, 2H) 2.86 (t, J=12.25 Hz, 2H) 3.21 (d, J=11.12 Hz, 2H) 3.31-3.59 (m, 4H) 4.32 (d, J=3.54 Hz, 2H) 4.58 (dd, J=7.58, 4.55 Hz, 1 H) 6.68-6.93 (m, 4H) 7.02 (d, J=1.26 Hz, 1H) 7.04-7.16 (m, 2H) 9.72 (br. s., 1H) 10.95 (s, 1H). ESI-MS: m/z 368.2 (M+H)$^+$.

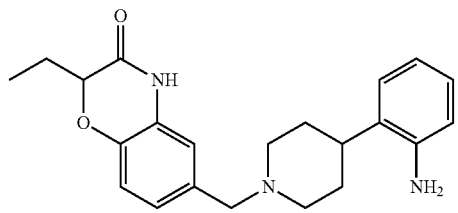 [SMILES: CCC1Oc2ccc(CN3CCC(c4ccccc4N)CC3)cc2NC1=O]

6-((4-(2-Aminophenyl)piperidin-1-yl)methyl)-2-ethyl-2H-benzo[b][1,4]oxazin-3(4H)-one (198)

Using 191 and 2-(piperazin-1-yl)aniline in the general procedure for reductive aminations, the title compound was obtained as a white solid: $^1$H NMR (400 MHz, DMSO-$d_6$) δ ppm 0.89-1.04 (m, 3H) 1.59-1.88 (m, 4H) 1.88-2.04 (m, 2H) 2.91-3.12 (m, 3H) 3.34-3.48 (m, 2H) 4.20-4.33 (m, 2H) 4.38-4.52 (m, 2H) 6.39 (d, J=7.58 Hz, 1H) 6.58 (t, J=7.07 Hz, 1H) 6.80-7.05 (m, 4H) 8.30-8.50 (m, 1H) 8.54-8.70 (m, 1H) 10.65 (s, 1H). ESI-MS: m/z 366.2 (M+H)$^+$.

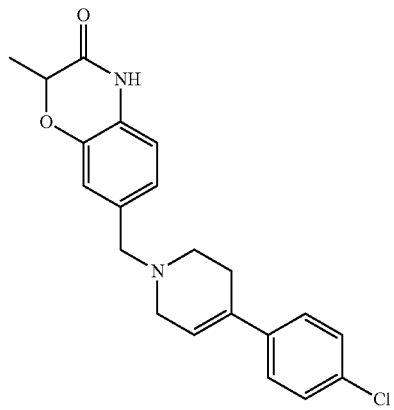 [SMILES: CC1Oc2cc(CN3CC=C(c4ccc(Cl)cc4)CC3)ccc2NC1=O]

7-((4-(4-Chlorophenyl)-5,6-dihydropyridin-1(2H)-yl)methyl)-2-methyl-2H-benzo[b][1,4]oxazin-3(4H)-one (199)

Using 20 and 4-(4-chlorophenyl)-1,2,3,6-tetrahydropyridine in the general procedure for reductive aminations, the title compound was obtained as a white solid: $^1$H NMR (400 MHz, DMSO-$d_6$) δ ppm 1.41 (d, J=6.82 Hz, 3H) 2.37-2.43 (m, 1H) 2.58-2.65 (m, 2H) 2.99-3.08 (m, 2H) 3.17 (d, J=5.31 Hz, 1H) 3.49 (s, 2H) 4.64 (q, J=6.82 Hz, 1H) 6.14-6.22 (m, 1H) 6.79-6.87 (m, 1H) 6.87-6.96 (m, 2H) 7.31-7.41 (m, 2H) 7.41-7.48 (m, 2H) 10.63 (s, 1H). ESI-MS: m/z 369.2 (M+H)$^+$.

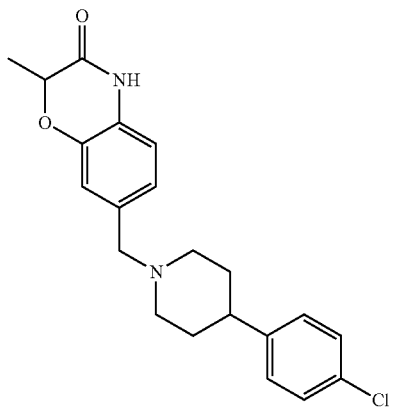 [SMILES: CC1Oc2cc(CN3CCC(c4ccc(Cl)cc4)CC3)ccc2NC1=O]

7-((4-(4-Chlorophenyl)piperidin-1-yl)methyl)-2-methyl-2H-benzo[b][1,4]oxazin-3(4H)-one (200)

Using 20 and 4-(4-chlorophenyl)piperidine in the general procedure for reductive aminations, the title compound was obtained as a white solid: $^1$H NMR (400 MHz, DMSO-$d_6$) δ ppm 1.36-1.50 (m, 3H) 1.71-1.90 (m, 2H) 1.92-2.06 (m, 1H) 2.74-2.88 (m, 1H) 2.94-3.11 (m, 2H) 3.35-3.52 (m, 3H) 4.18-4.30 (m, 2H) 4.67-4.78 (m, 1H) 6.91-7.02 (m, 1H) 7.04-7.13 (m, 1H) 7.13-7.19 (m, 1H) 7.19-7.30 (m, 2H) 7.35-7.46 (m, 2 H) 10.86 (s, 1H). ESI-MS: m/z 371.1 (M+H)$^+$.

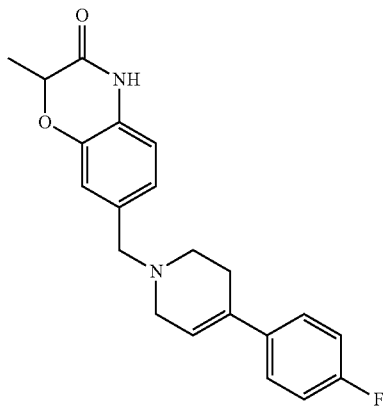 [SMILES: CC1Oc2cc(CN3CC=C(c4ccc(F)cc4)CC3)ccc2NC1=O]

7-((4-(4-Fluorophenyl)-5,6-dihydropyridin-1(2H)-yl)methyl)-2-methyl-2H-benzo[b][1,4]oxazin-3(4H)-one (201)

Using 20 and 4-(4-fluorophenyl)-1,2,3,6-tetrahydropyridine in the general procedure for reductive aminations, the title compound was obtained as a white solid: $^1$H NMR (400 MHz, DMSO-$d_6$) δ ppm 1.44 (dd, J=6.82, 1.52 Hz, 3 H) 2.69-2.85 (m, 2H) 3.56-3.68 (m, 1H) 3.78 (br. s., 2H) 4.23-4.43 (m, 2H) 4.72 (qd, J=6.74, 2.53 Hz, 1H) 6.14 (br. s., 1H) 6.96 (d, J=8.08 Hz, 1H) 7.06-7.29 (m, 4H) 7.45-7.59 (m, 2H) 9.87 (br. s., 1H) 10.86 (s, 1H). ESI-MS: m/z 353.1 (M+H)$^+$.

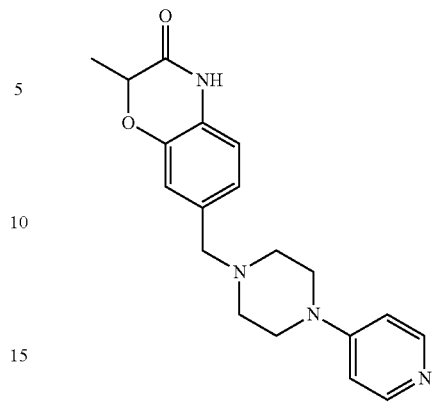

2-Methyl-7-((4-(pyridin-4-yl)piperazin-1-yl)methyl)-2H-benzo[b][1,4]oxazin-3(4H)-one (202)

Using 20 and 1-(pyridin-4-yl)piperazine in the general procedure for reductive aminations, the title compound was obtained as a white solid, mp 129.9-134.4° C.: $^1$H NMR (400 MHz, DMSO-$d_6$) δ ppm 1.43 (d, J=6.82 Hz, 3H) 1.99-2.12 (m, 1H) 2.99-3.74 (m, 6H) 4.21-4.38 (m, 3H) 4.64-4.77 (m, 1H) 6.96 (d, J=8.08 Hz, 1H) 7.01-7.17 (m, 2H) 7.26 (d, J=7.83 Hz, 2H) 8.38 (d, J=7.58 Hz, 2H) 10.87 (s, 1H). ESI-MS: m/z 339.1 (M+H)$^+$.

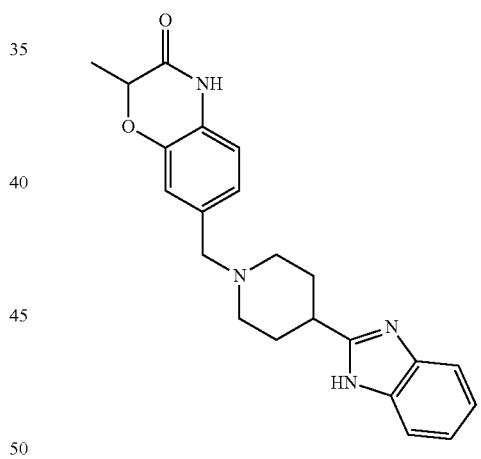

7-((4-(1H-Benzo[d]imidazol-2-yl)piperidin-1-yl)methyl)-2-methyl-2H-benzo[b][1,4]oxazin-3(4H)-one (203)

Using 20 and 2-(piperidin-4-yl)-1H-benzo[d]imidazole in the general procedure for reductive aminations, the title compound was obtained as a white solid: $^1$H NMR (400 MHz, DMSO-$d_6$) δ ppm 1.33-1.50 (m, 3H) 1.94-2.13 (m, 2H) 2.13-2.29 (m, 1H) 2.29-2.43 (m, 2H) 3.04-3.26 (m, 2H) 3.28-3.48 (m, 1H) 3.48-3.67 (m, 2 H) 4.18-4.35 (m, 2H) 4.72 (q, J=6.82 Hz, 1H) 6.87-7.02 (m, 1H) 7.02-7.19 (m, 2H) 7.32-7.52 (m, 2H) 7.64-7.78 (m, 2H) 10.82-10.92 (m, 1H). ESI-MS: m/z 377.1 (M+H)$^+$.

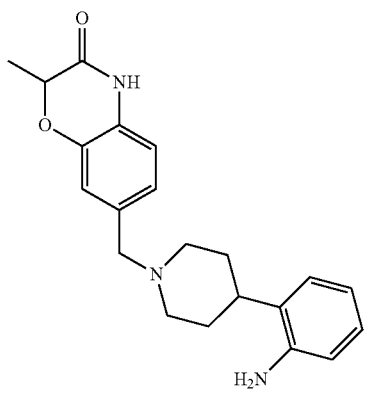 [SMILES: CC1Oc2cc(CN3CCC(c4ccccc4N)CC3)ccc2NC1=O]

7-((4-(2-aminophenyl)piperidin-1-yl)methyl)-2-methyl-2H-benzo[b][1,4]oxazin-3(4H)-one (204)

Using 20 and 2-(piperazin-1-yl)aniline in the general procedure for reductive aminations, the title compound was obtained as a white solid: $^1$H NMR (400 MHz, DMSO-$d_6$) δ ppm 1.31-1.44 (m, 3H) 1.61-1.82 (m, 2H) 1.95 (d, J=13.39 Hz, 2H) 2.90-3.13 (m, 3H) 3.35-3.48 (m, 2H) 4.25 (s, 2H) 4.53-4.69 (m, 1H) 6.40 (d, J=7.58 Hz, 1H) 6.57 (t, J=7.07 Hz, 1H) 6.77-6.86 (m, 1H) 6.86-7.02 (m, 4H) 8.31-8.50 (m, 1H) 8.53-8.70 (m, 1H) 10.61 (s, 1H). ESI-MS: m/z 352.2 (M+H)$^+$.

2-Methyl-7-((4-(4-(trifluoromethyl)phenyl)piperidin-1-yl)methyl)-2H-benzo[b][1,4]oxazin-3(4H)-one (206)

Using 20 and 4-(4-(trifluoromethyl)phenyl)piperidine in the general procedure for reductive aminations, the title compound was obtained as a white solid: $^1$H NMR (400 MHz, DMSO-$d_6$) δ ppm 1.35-1.50 (m, 3H) 1.77-1.95 (m, 2H) 1.95-2.10 (m, 2H) 2.85-3.13 (m, 3H) 3.47 (d, J=11.62 Hz, 2H) 4.19-4.32 (m, 2H) 4.65-4.79 (m, 1H) 6.90-7.02 (m, 1H) 7.10 (dd, J=8.08, 1.77 Hz, 1H) 7.14-7.20 (m, 1H) 7.46 (d, J=8.08 Hz, 2H) 7.62-7.78 (m, 2H) 10.86 (s, 1H). ESI-MS: m/z 405.4 (M+H)$^+$.

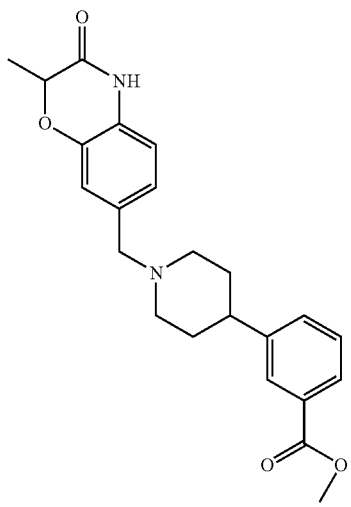 [SMILES: COC(=O)c1cccc(C2CCN(Cc3ccc4c(c3)OC(C)C(=O)N4)CC2)c1]

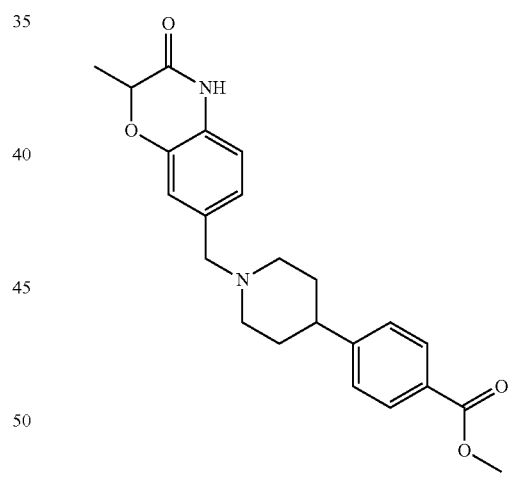

Methyl 3-(1-((2-methyl-3-oxo-3,4-dihydro-2H-benzo[b][1,4]oxazin-7-yl)methyl)piperidin-4-yl)benzoate (205)

Using 20 and methyl 3-(piperidin-4-yl)benzoate in the general procedure for reductive aminations, the title compound was obtained as a white solid: $^1$H NMR (400 MHz, DMSO-$d_6$) δ ppm 1.39-1.49 (m, 3H) 1.79-1.95 (m, 2H) 1.95-2.06 (m, 2H) 2.85-2.97 (m, 1H) 2.97-3.13 (m, 2H) 3.40-3.52 (m, 2H) 3.81-3.90 (m, 3H) 4.21-4.31 (m, 2H) 4.67-4.78 (m, 1H) 6.88-7.03 (m, 1H) 7.10 (dd, J=8.08, 1.77 Hz, 1H) 7.16 (d, J=1.52 Hz, 1H) 7.44-7.56 (m, 2H) 7.79-7.89 (m, 2H) 10.81-10.90 (m, 1H). ESI-MS: m/z 395.4 (M+H)$^+$.

Methyl 4-(1-((2-methyl-3-oxo-3,4-dihydro-2H-benzo[b][1,4]oxazin-7-yl)methyl)piperidin-4-yl)benzoate (207)

Using 20 and methyl 4-(piperidin-4-yl)benzoate in the general procedure for reductive aminations, the title compound was obtained as a white solid: $^1$H NMR (400 MHz, DMSO-$d_6$) δ ppm 1.37-1.50 (m, 3H) 1.76-1.93 (m, 2H) 2.00 (br. s., 2H) 2.83-2.95 (m, 1H) 2.95-3.11 (m, 2H) 3.40-3.51 (m, 2H) 3.77-3.88 (m, 3H) 4.21-4.30 (m, 2H) 4.67-4.76 (m, 1H) 6.89-7.00 (m, 1H) 7.09 (dd, J=7.96, 1.89 Hz, 1H) 7.13-7.19 (m, 1H) 7.37 (d, J=8.34 Hz, 2H) 7.88-7.99 (m, 2H) 10.85 (s, 1H). ESI-MS: m/z 395.4 (M+H)$^+$.

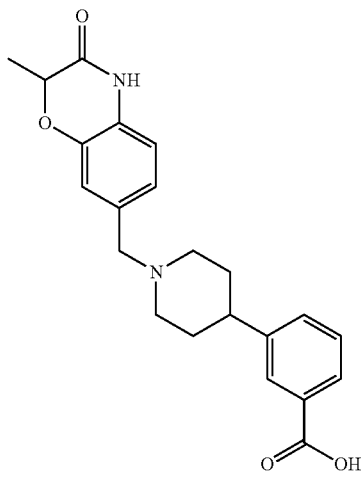 [SMILES: CC1Oc2cc(CN3CCC(c4cccc(C(=O)O)c4)CC3)ccc2NC1=O]

3-(1-((2-Methyl-3-oxo-3,4-dihydro-2H-benzo[b][1,4]oxazin-7-yl)methyl)piperidin-4-yl)benzoic acid (208)

Using 205 in the general procedure for hydrolysis of carboxylic esters, the title compound was obtained as a white solid: $^1$H NMR (400 MHz, DMSO-d$_6$) δ ppm 1.35-1.52 (m, 3H) 1.86-2.02 (m, 2H) 2.06-2.27 (m, 2H) 2.78-3.08 (m, 2H) 3.39 (br. s., 2H) 4.13-4.26 (m, 2H) 4.62-4.77 (m, 1H) 6.91-7.04 (m, 1H) 7.23 (dd, J=8.08, 1.77 Hz, 1H) 7.30-7.40 (m, 1H) 7.40-7.56 (m, 2H) 7.75-7.87 (m, 2H) 10.88 (s, 1H) 11.37 (br. s., 1H) 13.00 (br. s., 1H). ESI-MS: m/z 381.4 (M+H)$^+$.

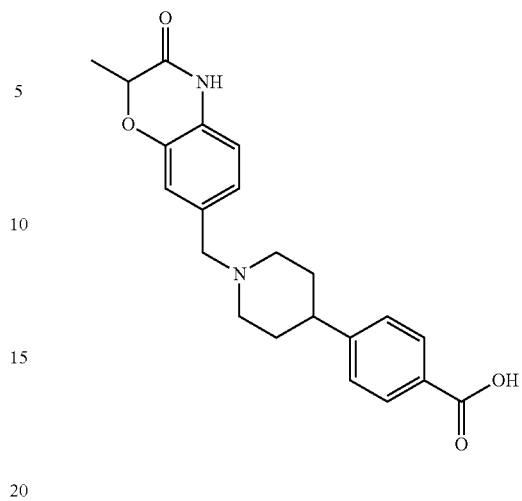

4-(1-((2-Methyl-3-oxo-3,4-dihydro-2H-benzo[b][1,4]oxazin-7-yl)methyl)piperidin-4-yl)benzoic acid (210)

Using 207 in the general procedure for hydrolysis of carboxylic esters, the title compound was obtained as a white solid: $^1$H NMR (400 MHz, DMSO-d$_6$) δ ppm 1.44 (d, J=6.82 Hz, 3H) 1.89-2.07 (m, 4H) 2.81-3.10 (m, 2H) 3.38-3.49 (m, 2H) 4.23 (d, J=4.80 Hz, 2H) 4.72 (q, J=6.74 Hz, 1H) 6.96 (d, J=8.08 Hz, 1H) 7.15 (dd, J=8.08, 1.52 Hz, 1H) 7.24 (s, 1H) 7.35 (d, J=8.59 Hz, 2H) 7.85-7.99 (m, 2H) 10.16 (br. s., 1H) 10.85 (s, 1H) 12.89 (br. s., 1H). ESI-MS: m/z 381.4 (M+H)$^+$.

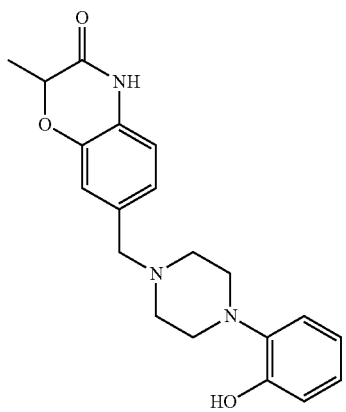 [SMILES: CC1Oc2cc(CN3CCN(c4ccccc4O)CC3)ccc2NC1=O]

7-((4-(2-Hydroxyphenyl)piperazin-1-yl)methyl)-2-methyl-2H-benzo[b][1,4]oxazin-3(4H)-one (209)

Using 20 and methyl 2-(piperazin-1-yl)phenol in the general procedure for reductive aminations, the title compound was obtained as a white solid: $^1$H NMR (400 MHz, DMSO-d$_6$) δ ppm 1.44 (d, J=6.82 Hz, 3H) 2.87 (t, J=11.87 Hz, 2H) 3.11-3.27 (m, 2H) 3.32-3.55 (m, 4H) 4.25-4.38 (m, 2H) 4.66-4.77 (m, 1H) 6.70-6.84 (m, 2H) 6.84-6.92 (m, 2 H) 6.97 (d, J=8.08 Hz, 1H) 7.12 (dd, J=8.08, 1.77 Hz, 1H) 7.17 (d, J=1.52 Hz, 1H) 9.77 (br. s., 1H) 10.87 (s, 1H). ESI-MS: m/z 354.4 (M+H)$^+$.

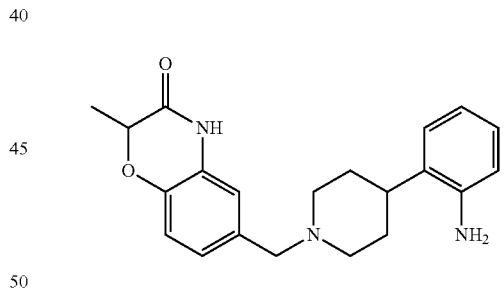

6-((4-(2-Aminophenyl)piperidin-1-yl)methyl)-2-methyl-2H-benzo[b][1,4]oxazin-3(4H)-one (211)

Using 13 and 2-(piperazin-1-yl)aniline in the general procedure for reductive aminations, the title compound was obtained as a light grey solid: $^1$H NMR (400 MHz, DMSO-d$_6$) δ ppm 1.39 (d, J=6.82 Hz, 3H) 1.72 (q, J=11.87 Hz, 2H) 1.89-2.02 (m, 2H) 2.90-3.12 (m, 3H) 3.42 (d, J=12.38 Hz, 2H) 4.27 (s, 2H) 4.60 (q, J=6.74 Hz, 1H) 6.38 (d, J=7.58 Hz, 1 H) 6.57 (t, J=7.07 Hz, 1H) 6.80-7.03 (m, 5H) 8.31-8.48 (m, 1H) 8.52-8.68 (m, 1H) 10.64 (s, 1H). ESI-MS: m/z 352.4 (M+H)$^+$.

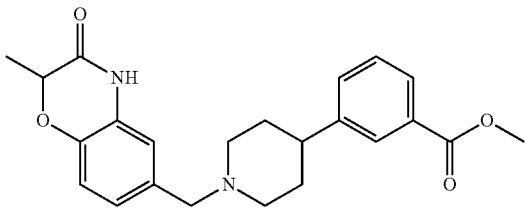

Methyl 3-(1-((2-methyl-3-oxo-3,4-dihydro-2H-benzo[b][1,4]oxazin-6-yl)methyl)piperidin-4-yl)benzoate (212)

Using 13 and methyl 3-(piperidin-4-yl)benzoate in the general procedure for reductive aminations, the title compound was obtained as a white solid: $^1$H NMR (400 MHz, DMSO-d$_6$) δ ppm 1.37-1.48 (m, 3H) 1.78-1.95 (m, 2H) 1.95-2.06 (m, 2H) 2.83-2.98 (m, 1H) 2.98-3.14 (m, 2H) 3.38-3.54 (m, 2H) 3.80-3.90 (m, 3H) 4.28 (d, J=5.05 Hz, 2H) 4.66-4.78 (m, 1H) 6.95-7.16 (m, 3H) 7.43-7.58 (m, 2H) 7.79-7.90 (m, 2H) 9.42 (br. s., 1H) 10.93 (s, 1H). ESI-MS: m/z 395.4 (M+H)$^+$.

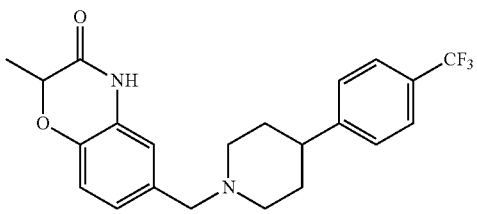 [SMILES: CC1Oc2ccc(CN3CCC(c4ccc(C(F)(F)F)cc4)CC3)cc2NC1=O]

2-Methyl-6-((4-(4-(trifluoromethyl)phenyl)piperidin-1-yl)methyl)-2H-benzo[b][1,4]oxazin-3(4H)-one (213)

Using 13 and 4-(4-(trifluoromethyl)phenyl)piperidine in the general procedure for reductive aminations, the title compound was obtained as an off-white solid, mp 216.7-218.0° C.: $^1$H NMR (400 MHz, DMSO-d$_6$) δ ppm 1.37-1.50 (m, 3H) 1.76-1.95 (m, 2H) 1.95-2.11 (m, 2H) 2.84-2.99 (m, 1H) 2.99-3.14 (m, 2H) 3.39-3.55 (m, 2H) 4.28 (d, J=4.80 Hz, 2H) 4.64-4.78 (m, 1H) 6.97-7.17 (m, 3H) 7.46 (d, J=8.08 Hz, 2H) 7.61-7.78 (m, 2H) 10.89-11.00 (m, 1H). ESI-MS: m/z 405.4 (M+H)$^+$.

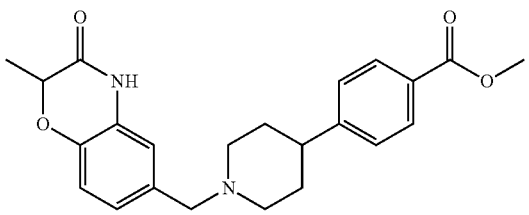

Methyl 4-(1-((2-methyl-3-oxo-3,4-dihydro-2H-benzo[b][1,4]oxazin-6-yl)methyl)piperidin-4-yl)benzoate (214)

Using 13 and methyl 4-(piperidin-4-yl)benzoate in the general procedure for reductive aminations, the title compound was obtained as an off-white solid: $^1$H NMR (400 MHz, DMSO-d$_6$) δ ppm 1.37-1.48 (m, 3H) 1.82-2.05 (m, 4H) 2.82-2.96 (m, 1H) 2.96-3.12 (m, 2H) 3.38-3.51 (m, 2H) 3.85 (s, 3H) 4.25 (d, J=5.05 Hz, 2H) 4.66-4.78 (m, 1H) 6.97-7.20 (m, 3H) 7.38 (d, J=8.34 Hz, 2H) 7.95 (d, 2H) 10.87-11.00 (m, 1H). ESI-MS: m/z 395.5 (M+H)$^+$.

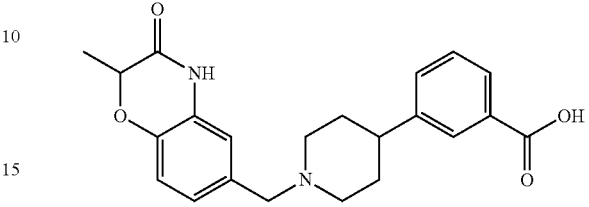

3-(1-((2-Methyl-3-oxo-3,4-dihydro-2H-benzo[b][1,4]oxazin-6-yl)methyl)piperidin-4-yl)benzoic acid (215)

Using 212 in the general procedure for hydrolysis of carboxylic esters, the title compound was obtained as a white solid: $^1$H NMR (400 MHz, DMSO-d$_6$) δ ppm 1.39-1.49 (m, 3H) 1.76-1.94 (m, 2H) 1.94-2.09 (m, 2H) 2.82-3.14 (m, 3H) 3.40-3.53 (m, 2H) 4.28 (d, J=4.80 Hz, 2H) 4.67-4.79 (m, 1H) 7.01 (s, 1H) 7.04-7.11 (m, 2H) 7.43-7.54 (m, 2H) 7.77-7.87 (m, 2H) 9.25-9.42 (m, 1H) 10.94 (s, 1H). ESI-MS: m/z 381.4 (M+H)$^+$.

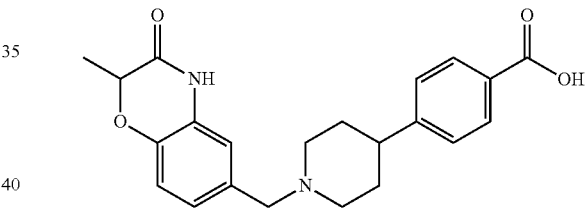

4-(1-((2-Methyl-3-oxo-3,4-dihydro-2H-benzo[b][1,4]oxazin-6-yl)methyl)piperidin-4-yl)benzoic acid (216)

Using 214 in the general procedure for hydrolysis of carboxylic esters, the title compound was obtained as a white solid: $^1$H NMR (400 MHz, DMSO-d$_6$) δ ppm 1.38-1.49 (m, 3H) 1.74-1.95 (m, 2H) 1.95-2.12 (m, 2H) 2.81-2.97 (m, 1H) 2.99-3.14 (m, 2H) 3.39-3.54 (m, 2H) 4.22-4.32 (m, 2H) 4.66-4.77 (m, 1H) 6.96-7.11 (m, 3H) 7.35 (d, J=8.34 Hz, 2H) 7.86-7.98 (m, 2H) 9.45 (br. s., 1H) 10.89-10.99 (m, 1H). ESI-MS: m/z 381.4 (M+H)$^+$.

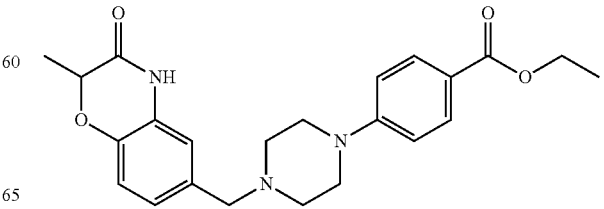

Ethyl 4-(4-((2-methyl-3-oxo-3,4-dihydro-2H-benzo[b][1,4]oxazin-6-yl)methyl)piperazin-1-yl)benzoate (217)

Using 13 and ethyl 4-(piperazin-1-yl)benzoate in the general procedure for reductive aminations, the title compound was obtained as a white solid: $^1$H NMR (400 MHz, DMSO-$d_6$) δ ppm 1.22-1.33 (m, 3H) 1.36-1.46 (m, 3H) 2.41-2.49 (m, 3H) 3.23-3.36 (m, 5H) 3.38-3.48 (m, 2H) 4.23 (q, J=7.07 Hz, 2H) 4.64 (q, J=6.74 Hz, 1H) 6.80-7.02 (m, 5H) 7.77 (d, J=9.09 Hz, 2H) 10.62 (s, 1H). ESI-MS: m/z 410.4 (M+H)$^+$.

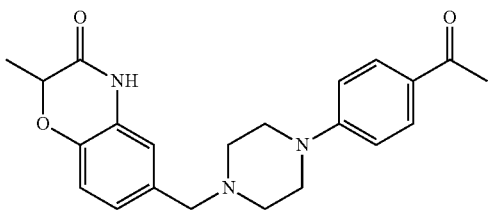 [SMILES: CC(=O)c1ccc(N2CCN(Cc3ccc4c(c3)NC(=O)C(C)O4)CC2)cc1]

6-((4-(4-Acetylphenyl)piperazin-1-yl)methyl)-2-methyl-2H-benzo[b][1,4]oxazin-3(4H)-one (218)

Using 13 and 1-(4-(piperazin-1-yl)phenyl)ethanone in the general procedure for reductive aminations, the title compound was obtained as a white solid: $^1$H NMR (400 MHz, DMSO-$d_6$) δ ppm 1.41 (d, J=6.82 Hz, 3H) 2.40-2.49 (m, 7H) 3.27-3.37 (m, 4H) 3.38-3.48 (m, 2H) 4.58-4.70 (m, 1H) 6.80-7.02 (m, 5H) 7.79 (d, J=9.09 Hz, 2H) 10.62 (s, 1H). ESI-MS: m/z 380.4 (M+H)$^+$.

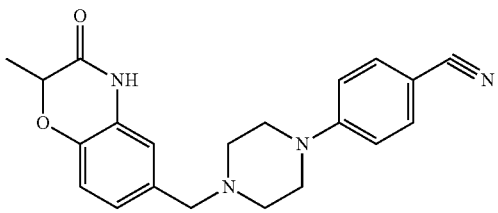 [SMILES: CC1Oc2ccc(CN3CCN(c4ccc(C#N)cc4)CC3)cc2NC1=O]

4-(4-((2-methyl-3-oxo-3,4-dihydro-2H-benzo[b][1,4]oxazin-6-yl)methyl)piperazin-1-yl)benzonitrile (219)

Using 13 and 4-(piperazin-1-yl)benzonitrile in the general procedure for reductive aminations, the title compound was obtained as a white solid, mp 266.4-268.0° C.: $^1$H NMR (400 MHz, DMSO-$d_6$) δ ppm 1.38-1.49 (m, 3H) 3.02-3.16 (m, 2H) 3.16-3.29 (m, 2H) 3.30-3.36 (m, 1H) 4.07 (d, J=13.39 Hz, 2H) 4.23-4.34 (m, 2H) 4.65-4.77 (m, 1 H) 6.99-7.20 (m, 5H) 7.66 (d, J=8.84 Hz, 2H) 10.54 (br. s., 1H) 10.94 (s, 1H). ESI-MS: m/z 363.4 (M+H)$^+$.

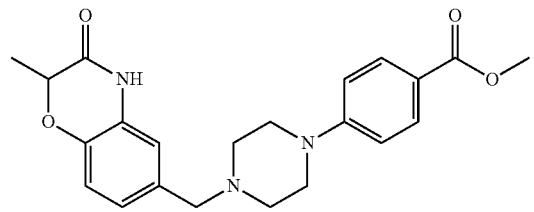

Methyl 4-(4-((2-methyl-3-oxo-3,4-dihydro-2H-benzo[b][1,4]oxazin-6-yl)methyl)piperazin-1-yl)benzoate (220)

Using 13 and methyl 4-(piperazin-1-yl)benzoate in the general procedure for reductive aminations, the title compound was obtained as a white solid: $^1$H NMR (400 MHz, DMSO-$d_6$) δ ppm 1.42 (d, 3H) 3.00-3.22 (m, 3H) 3.40 (br. s., 2 H) 3.79 (s, 3H) 4.07 (br. s., 2H) 4.32 (br. s., 2H) 4.66-4.78 (m, 1H) 6.96-7.11 (m, 5H) 7.84 (d, J=8.84 Hz, 2H) 9.94 (br. s., 1H) 10.95 (s, 1H). ESI-MS: m/z 396.4 (M+H)$^+$.

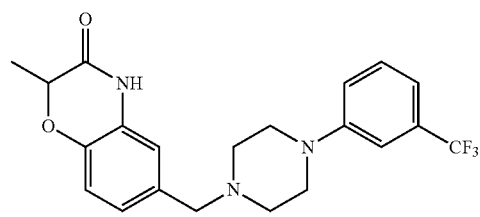 [SMILES: CC1Oc2ccc(CN3CCN(c4cccc(C(F)(F)F)c4)CC3)cc2NC1=O]

2-Methyl-6-((4-(3-(trifluoromethyl)phenyl)piperazin-1-yl)methyl)-2H-benzo[b][1,4]oxazin-3(4H)-one (221)

Using 13 and 1-(3-(trifluoromethyl)phenyl)piperazine in the general procedure for reductive aminations, the title compound was obtained as a white solid: $^1$H NMR (400 MHz, DMSO-$d_6$) δ ppm 1.44 (d, J=6.82 Hz, 3H) 3.07-3.20 (m, 2H) 3.40 (br. s., 3H) 3.91-4.05 (m, 2H) 4.31 (d, J=5.05 Hz, 2H) 4.72 (q, J=6.74 Hz, 1H) 7.00-7.11 (m, 2H) 7.16 (d, J=8.08 Hz, 2H) 7.21-7.32 (m, 2H) 7.42-7.54 (m, 1H) 10.43 (br. s., 1 H) 10.95 (s, 1H). ESI-MS: m/z 406.4 (M+H)$^+$.

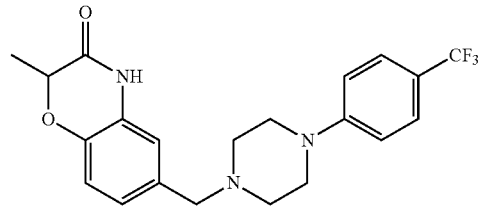 [SMILES: CC1Oc2ccc(CN3CCN(c4ccc(C(F)(F)F)cc4)CC3)cc2NC1=O]

2-Methyl-6-((4-(4-(trifluoromethyl)phenyl)piperazin-1-yl)methyl)-2H-benzo[b][1,4]oxazin-3(4H)-one (222)

Using 13 and 1-(4-(trifluoromethyl)phenyl)piperazine in the general procedure for reductive aminations, the title compound was obtained as a white solid: $^1$H NMR (400 MHz, DMSO-$d_6$) δ ppm 1.41 (d, J=6.82 Hz, 3H) 2.43-2.49 (m, 4H)

3.22-3.30 (m, 4H) 3.38-3.49 (m, 2H) 4.64 (q, J=6.74 Hz, 1H) 6.79-6.95 (m, 3H) 7.04 (d, J=8.84 Hz, 2H) 7.43-7.55 (m, 2H) 10.62 (s, 1H). ESI-MS: m/z 406.4 (M+H)+.

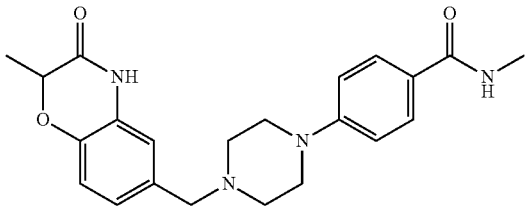

N-Methyl-4-(4-((2-methyl-3-oxo-3,4-dihydro-2H-benzo[b][1,4]oxazin-6-yl)methyl)piperazin-1-yl)benzamide (223)

Using 50 and methylamine in the general procedure for coupling an amine to a carboxylic acid, the title compound was obtained as a white solid: $^1$H NMR (400 MHz, DMSO-$d_6$) δ ppm 1.39 (d, 3H) 2.47 (d, J=4.80 Hz, 4H) 2.73 (d, J=4.29 Hz, 3H) 3.18-3.28 (m, 4H) 3.38-3.47 (m, 2H) 4.64 (q, J=6.82 Hz, 1H) 6.79-7.01 (m, 5H) 7.69 (d, J=9.09 Hz, 2H) 8.14 (q, J=4.29 Hz, 1H) 10.63 (s, 1H). ESI-MS: m/z 395.4 (M+H)+.

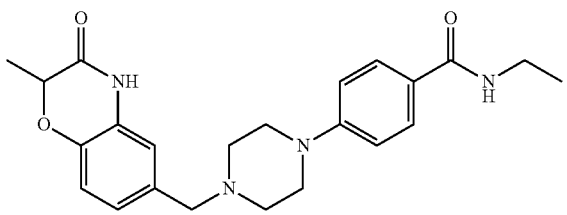

N-Ethyl-4-(4-((2-methyl-3-oxo-3,4-dihydro-2H-benzo[b][1,4]oxazin-6-yl)methyl)piperazin-1-yl)benzamide (224)

Using 50 and ethylamine in the general procedure for coupling an amine to a carboxylic acid, the title compound was obtained as a white solid, mp 250.2-255.7° C.: $^1$H NMR (400 MHz, DMSO-$d_6$) δ ppm 1.09 (t, J=7.07 Hz, 3 H) 1.41 (d, J=6.82 Hz, 3H) 2.44-2.48 (m, 4H) 3.16-3.29 (m, 6H) 3.38-3.46 (m, 2H) 4.57-4.71 (m, 1H) 6.81-6.98 (m, 5H) 7.71 (d, J=8.84 Hz, 2H) 8.18 (t, J=5.56 Hz, 1H) 10.64 (s, 1H). ESI-MS: m/z 409.4 (M+H)+.

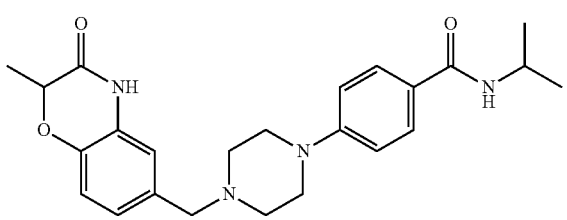

N-Isopropyl-4-(4-((2-methyl-3-oxo-3,4-dihydro-2H-benzo[b][1,4]oxazin-6-yl)methyl)piperazin-1-yl)benzamide (225)

Using 50 and isopropylamine in the general procedure for coupling an amine to a carboxylic acid, the title compound was obtained as a white solid: $^1$H NMR (400 MHz, DMSO-$d_6$) δ ppm 1.08-1.17 (m, 6H) 1.41 (d, J=6.82 Hz, 3 H) 2.44-2.48 (m, 4H) 3.18-3.28 (m, 4H) 3.42 (s, 2H) 3.97-4.15 (m, 1H) 4.58-4.70 (m, 1 H) 6.80-6.97 (m, 5H) 7.66-7.77 (m, 2H) 7.91 (d, J=7.83 Hz, 1H) 10.57-10.68 (m, 1H). ESI-MS: m/z 423.5 (M+H)+.

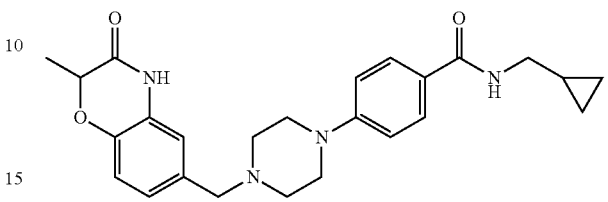

N-(Cyclopropylmethyl)-4-(4-((2-methyl-3-oxo-3,4-dihydro-2H-benzo[b][1,4]oxazin-6-yl)methyl)piperazin-1-yl)benzamide (226)

Using 50 and cyclopropylmethanamine in the general procedure for coupling an amine to a carboxylic acid, the title compound was obtained as a white solid: $^1$H NMR (400 MHz, DMSO-$d_6$) δ ppm 0.16-0.23 (m, 2H) 0.36-0.44 (m, 2H) 0.92-1.05 (m, 1H) 1.41 (d, J=6.57 Hz, 3H) 2.44-2.48 (m, 4H) 3.10 (t, J=6.32 Hz, 2H) 3.18-3.29 (m, 4H) 3.42 (s, 2H) 4.58-4.71 (m, 1H) 6.79-6.99 (m, 5H) 7.73 (d, J=8.84 Hz, 2H) 8.27 (t, J=5.68 Hz, 1H) 10.63 (s, 1H). ESI-MS: m/z 435.5 (M+H)+.

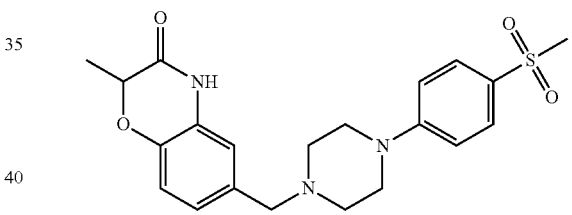

2-Methyl-6-((4-(4-(methylsulfonyl)phenyl)piperazin-1-yl)methyl)-2H-benzo[b][1,4]oxazin-3(4H)-one (227)

Using 13 and 1-(4-(methylsulfonyl)phenyl)piperazine in the general procedure for reductive aminations, the title compound was obtained as a white solid: $^1$H NMR (400 MHz, DMSO-$d_6$) δ ppm 1.36-1.48 (m, 3H) 2.42-2.49 (m, 4H) 3.08 (s, 3H) 3.31 (br. s., 2H) 3.37-3.47 (m, 2H) 4.57-4.69 (m, 1H) 6.80-6.96 (m, 3H) 7.00-7.12 (m, 2H) 7.60-7.73 (m, 2H) 10.62 (s, 1H). ESI-MS: m/z 416.5 (M+H)+.

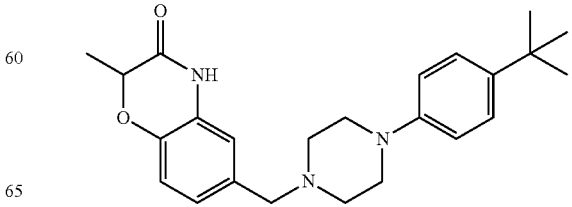

6-((4-(4-tert-Butylphenyl)piperazin-1-yl)methyl)-2-methyl-2H-benzo[b][1,4]oxazin-3(4H)-one (228)

Using 13 and 1-(4-tert-butylphenyl)piperazine in the general procedure for reductive aminations, the title compound was obtained as an off-white solid: $^1$H NMR (400 MHz, DMSO-d$_6$) δ ppm 1.16-1.25 (m, 9H) 1.36-1.43 (m, 3H) 2.45-2.49 (m, 3H) 3.00-3.15 (m, 4H) 3.37-3.46 (m, 2H) 4.54-4.69 (m, 1H) 6.77-6.95 (m, 5H) 7.15-7.26 (m, 2 H) 10.61 (s, 1H). ESI-MS: m/z 394.5 (M+H)$^+$.

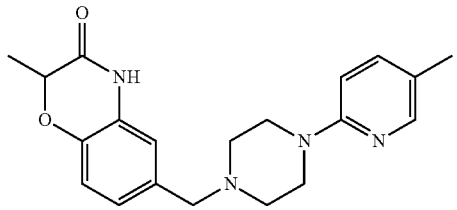

2-Methyl-6-((4-(5-methylpyridin-2-yl)piperazin-1-yl)methyl)-2H-benzo[b][1,4]oxazin-3(4H)-one (229)

Using 13 and 1-(5-methylpyridin-2-yl)piperazine in the general procedure for reductive aminations, the title compound was obtained as a pale beige solid: $^1$H NMR (400 MHz, DMSO-d$_6$) δ ppm 1.36-1.44 (m, 3H) 2.13 (s, 3H) 2.42 (t, J=4.80 Hz, 4H) 3.35-3.47 (m, 6H) 4.50-4.74 (m, 1H) 6.73 (d, J=8.59 Hz, 1H) 6.79-6.94 (m, 3 H) 7.36 (dd, J=8.59, 2.02 Hz, 1H) 7.89-7.97 (m, 1H) 10.61 (s, 1H). ESI-MS: m/z 353.4 (M+H)$^+$.

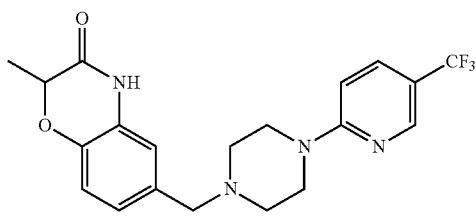

2-Methyl-6-((4-(5-(trifluoromethyl)pyridin-2-yl)piperazin-1-yl)methyl)-2H-benzo[b][1,4]oxazin-3(4H)-one (230)

Using 13 and 1-(5-(trifluoromethyl)pyridin-2-yl)piperazine in the general procedure for reductive aminations, the title compound was obtained as a pale beige solid: $^1$H NMR (400 MHz, DMSO-d$_6$) δ ppm 1.37-1.44 (m, 3H) 2.42 (t, J=4.93 Hz, 4H) 3.37-3.50 (m, 2H) 3.55-3.69 (m, 4H) 4.56-4.71 (m, 1H) 6.81-6.99 (m, 4H) 7.78 (dd, J=9.09, 2.53 Hz, 1H) 8.30-8.46 (m, 1H) 10.62 (s, 1H). ESI-MS: m/z 406.4 (M+H)$^+$.

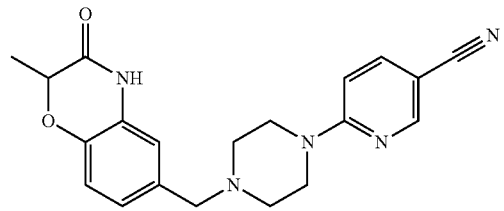 [SMILES: CC1Oc2ccc(CN3CCN(c4ccc(C#N)cn4)CC3)cc2NC1=O]

6-(4-((2-Methyl-3-oxo-3,4-dihydro-2H-benzo[b][1,4]oxazin-6-yl)methyl)piperazin-1-yl)nicotinonitrile (231)

Using 13 and 6-(piperazin-1-yl)nicotinonitrile in the general procedure for reductive aminations, the title compound was obtained as an off-white solid: $^1$H NMR (400 MHz, DMSO-d$_6$) δ ppm 1.42 (d, 3H) 2.35-2.46 (m, 4H) 3.36-3.45 (m, 2H) 3.59-3.69 (m, 4H) 4.64 (q, J=6.74 Hz, 1H) 6.80-6.95 (m, 4H) 7.84 (dd, J=9.09, 2.53 Hz, 1 H) 8.47 (d, J=1.77 Hz, 1H) 10.62 (s, 1H). ESI-MS: m/z 364.4 (M+H)$^+$.

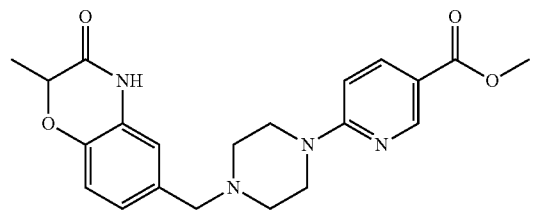

Methyl 6-(4-((2-methyl-3-oxo-3,4-dihydro-2H-benzo[b][1,4]oxazin-6-yl)methyl)piperazin-1-yl)nicotinate (232)

Using 13 and methyl 6-(piperazin-1-yl)nicotinate in the general procedure for reductive aminations, the title compound was obtained as a white solid: $^1$H NMR (400 MHz, DMSO-d$_6$) δ ppm 1.37-1.49 (m, 3H) 2.98-3.16 (m, 2H) 3.16-3.30 (m, 2H) 3.33-3.49 (m, 2H) 3.73-3.85 (m, 3H) 4.23-4.34 (m, 2H) 4.50-4.64 (m, 2 H) 4.71 (q, J=6.82 Hz, 1H) 6.92-7.11 (m, 4H) 7.98-8.09 (m, 1H) 8.68 (d, J=2.27 Hz, 1H) 10.94 (s, 1H). ESI-MS: m/z 397.4 (M+H)$^+$.

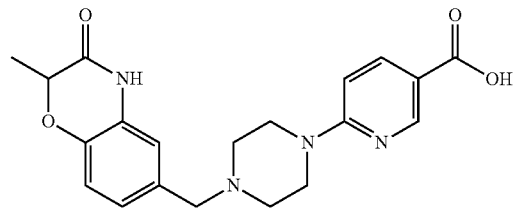 [SMILES: CC1Oc2ccc(CN3CCN(c4ccc(C(=O)O)cn4)CC3)cc2NC1=O]

6-(4-((2-Methyl-3-oxo-3,4-dihydro-2H-benzo[b][1,4]oxazin-6-yl)methyl)piperazin-1-yl)nicotinic acid (233)

Using 232 in the general procedure for hydrolysis of carboxylic esters, the title compound was obtained as a pale yellow solid, mp 242.6-248.4° C.: $^1$H NMR (400 MHz, DMSO-d$_6$) δ ppm 1.37-1.46 (m, 3H) 2.35-2.47 (m, 4H) 3.38-

3.50 (m, 2H) 3.52-3.75 (m, 4H) 4.64 (q, J=6.65 Hz, 1H) 6.74-7.01 (m, 4H) 7.92 (dd, J=9.09, 2.27 Hz, 1 H) 8.61 (d, J=2.02 Hz, 1H) 10.62 (s, 1H) 12.36-12.66 (m, 1H). ESI-MS: m/z 383.4 (M+H)⁺.

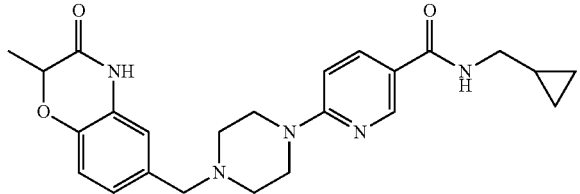 [SMILES: CC1Oc2ccc(CN3CCN(c4ccc(C(=O)NCC5CC5)cn4)CC3)cc2NC1=O]

N-(Cyclopropylmethyl)-6-(4-((2-methyl-3-oxo-3,4-dihydro-2H-benzo[b][1,4]oxazin-6-yl)methyl)piperazin-1-yl)nicotinamide (234)

Using 233 and cyclopropylmethanamine in the general procedure for coupling an amine to a carboxylic acid, the title compound was obtained as an off-white solid: $^1$H NMR (400 MHz, DMSO-d$_6$) δ ppm 0.13-0.25 (m, 2H) 0.36-0.46 (m, 2H) 0.92-1.05 (m, 1H) 1.41 (d, J=6.82 Hz, 3H) 2.36-2.46 (m, 4H) 3.10 (t, J=6.19 Hz, 2H) 3.38-3.46 (m, 2H) 3.52-3.63 (m, 4H) 4.56-4.72 (m, 1H) 6.77-6.97 (m, 4H) 7.95 (dd, J=9.09, 2.53 Hz, 1H) 8.34 (t, J=5.68 Hz, 1H) 8.59 (d, J=2.27 Hz, 1H) 10.63 (s, 1H). ESI-MS: m/z 436.5 (M+H)⁺.

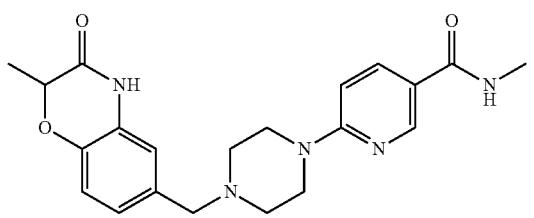

N-Methyl-6-(4-((2-methyl-3-oxo-3,4-dihydro-2H-benzo[b][1,4]oxazin-6-yl)methyl)piperazin-1-yl)nicotinamide (235)

Using 232 and methylamine in the general procedure for coupling an amine to a carboxylic acid, the title compound was obtained as a white solid: $^1$H NMR (400 MHz, DMSO-d$_6$) δ ppm 1.41 (d, J=6.57 Hz, 3H) 2.36-2.46 (m, 4 H) 2.74 (d, J=4.55 Hz, 3H) 3.37-3.45 (m, 2H) 3.51-3.63 (m, 4H) 4.64 (q, J=6.82 Hz, 1H) 6.76-6.94 (m, 4H) 7.91 (dd, J=8.97, 2.40 Hz, 1H) 8.16-8.25 (m, 1H) 8.56 (d, J=2.27 Hz, 1 H) 10.62 (s, 1H). ESI-MS: m/z 396.4 (M+H)⁺.

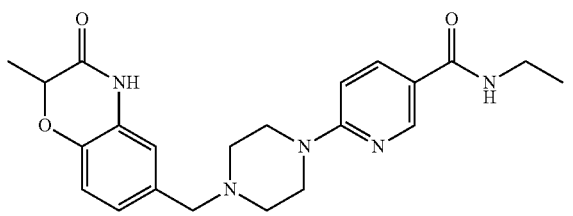 [SMILES: CCNC(=O)c1ccc(N2CCN(Cc3ccc4c(c3)NC(=O)C(C)O4)CC2)nc1]

N-Ethyl-6-(4-((2-methyl-3-oxo-3,4-dihydro-2H-benzo[b][1,4]oxazin-6-yl)methyl)piperazin-1-yl)nicotinamide (236)

Using 232 and ethylamine in the general procedure for coupling an amine to a carboxylic acid, the title compound was obtained as a white solid: $^1$H NMR (400 MHz, DMSO-d$_6$) δ ppm 1.03-1.15 (m, 3H) 1.41 (d, J=6.82 Hz, 3 H) 2.35-2.46 (m, 4H) 3.18-3.29 (m, 2H) 3.41 (s, 2H) 3.49-3.65 (m, 4H) 4.64 (q, 1H) 6.76-6.95 (m, 4H) 7.93 (dd, J=8.97, 2.40 Hz, 1H) 8.23 (t, J=5.43 Hz, 1H) 8.57 (d, J=2.27 Hz, 1H) 10.62 (s, 1H). ESI-MS: m/z 410.4 (M+H)⁺.

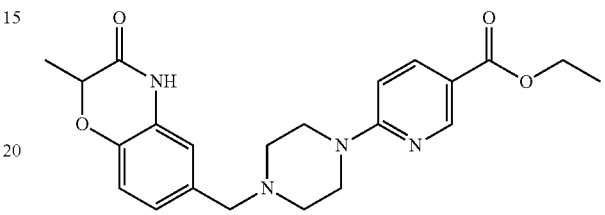

Ethyl 6-(4-((2-methyl-3-oxo-3,4-dihydro-2H-benzo[b][1,4]oxazin-6-yl)methyl)piperazin-1-yl)nicotinate (237)

Using 13 and ethyl 6-(piperazin-1-yl)nicotinate in the general procedure for reductive aminations, the title compound was obtained as a light yellow solid: $^1$H NMR (400 MHz, DMSO-d$_6$) δ ppm 1.23-1.33 (m, 3H) 1.36-1.45 (m, 3H) 2.42 (t, J=4.80 Hz, 4H) 3.37-3.47 (m, 2H) 3.58-3.71 (m, 4H) 4.24 (q, J=7.07 Hz, 2H) 4.64 (q, 1H) 6.80-6.98 (m, 4H) 7.93 (dd, J=9.09, 2.27 Hz, 1H) 8.57-8.68 (m, 1H) 10.63 (s, 1 H). ESI-MS: m/z 411.4 (M+H)⁺.

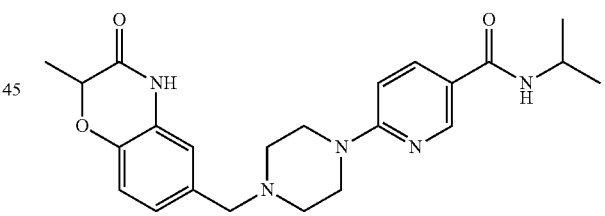

N-Isopropyl-6-(4-((2-methyl-3-oxo-3,4-dihydro-2H-benzo[b][1,4]oxazin-6-yl)methyl)piperazin-1-yl)nicotinamide (238)

Using 232 and isopropylamine in the general procedure for coupling an amine to a carboxylic acid, the title compound was obtained as an off-white solid: $^1$H NMR (400 MHz, DMSO-d$_6$) δ ppm 1.14 (d, J=6.57 Hz, 6H) 1.41 (d, J=6.82 Hz, 3H) 2.37-2.46 (m, 4H) 3.37-3.46 (m, 2H) 3.51-3.63 (m, 4H) 3.99-4.14 (m, 1 H) 4.58-4.69 (m, 1H) 6.76-6.95 (m, 4H) 7.88-8.01 (m, 2H) 8.57 (d, J=2.27 Hz, 1H) 10.62 (s, 1H). ESI-MS: m/z 424.5 (M+H)⁺.

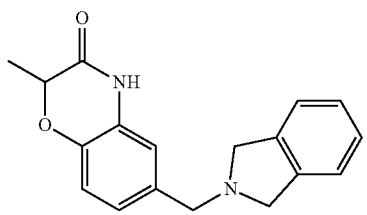 [SMILES: CC1Oc2ccc(CN3Cc4ccccc4C3)cc2NC1=O]

6-(Isoindolin-2-ylmethyl)-2-methyl-2H-benzo[b][1,4]oxazin-3(4H)-one (239)

Using 13 and isoindoline in the general procedure for reductive aminations, the title compound was obtained as a tan solid: $^1$H NMR (400 MHz, DMSO-d$_6$) δ ppm 1.31-1.48 (m, 3H) 3.71-3.87 (m, 6H) 4.64 (q, J=6.82 Hz, 1H) 6.83-6.99 (m, 3H) 7.10-7.29 (m, 4H) 10.62 (s, 1H). ESI-MS: m/z 295.3 (M+H)$^+$.

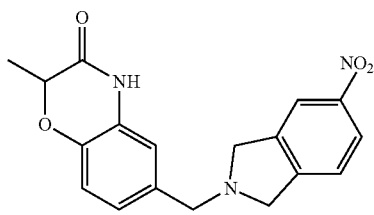 [SMILES: CC1Oc2ccc(CN3Cc4ccc([N+](=O)[O-])cc4C3)cc2NC1=O]

2-Methyl-6-((5-nitroisoindolin-2-yl)methyl)-2H-benzo[b][1,4]oxazin-3(4H)-one (240)

Using 13 and 5-nitroisoindoline in the general procedure for reductive aminations, the title compound was obtained as a light yellow solid: $^1$H NMR (400 MHz, DMSO-d$_6$) δ ppm 1.35-1.47 (m, 3H) 3.73-3.83 (m, 2H) 3.86-3.99 (m, 4H) 4.58-4.69 (m, 1H) 6.88-6.97 (m, 3H) 7.51 (d, J=8.08 Hz, 1H) 8.04-8.18 (m, 2H) 10.63 (s, 1H). ESI-MS: m/z 340.3 (M+H)$^+$.

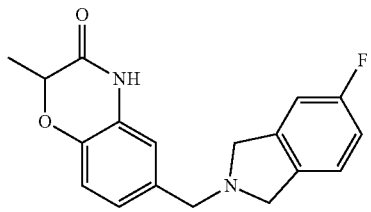 [SMILES: CC1Oc2ccc(CN3Cc4ccc(F)cc4C3)cc2NC1=O]

6-((5-Fluoroisoindolin-2-yl)methyl)-2-methyl-2H-benzo[b][1,4]oxazin-3(4H)-one (241)

Using 13 and 5-fluoroisoindoline in the general procedure for reductive aminations, the title compound was obtained as a white solid: $^1$H NMR (400 MHz, DMSO-d$_6$) δ ppm 1.37-1.50 (m, 3H) 4.43-4.65 (m, 5H) 4.72 (q, J=6.74 Hz, 1H) 7.02-7.17 (m, 3H) 7.17-7.36 (m, 2H) 7.44 (dd, J=8.21, 5.18 Hz, 1H) 10.94 (s, 2H). ESI-MS: m/z 313.3 (M+H)$^+$.

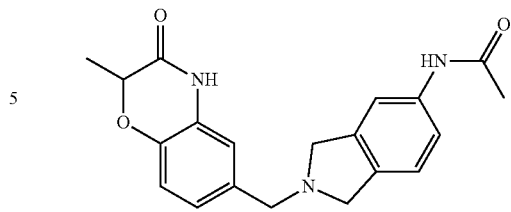

N-(2-((2-Methyl-3-oxo-3,4-dihydro-2H-benzo[b][1,4]oxazin-6-yl)methyl)isoindolin-5-yl)acetamide (242)

Using 13 and N-(isoindolin-5-yl)acetamide in the general procedure for reductive aminations, the title compound was obtained as an off-white solid: $^1$H NMR (400 MHz, DMSO-d$_6$) δ ppm 1.41 (d, J=6.82 Hz, 3H) 2.01 (s, 3H) 3.68-3.84 (m, 6H) 4.64 (q, J=6.82 Hz, 1H) 6.84-6.99 (m, 3H) 7.12 (d, J=8.08 Hz, 1H) 7.27-7.38 (m, 1H) 7.49 (s, 1 H) 9.88 (s, 1H) 10.63 (s, 1H). ESI-MS: m/z 352.4 (M+H)$^+$.

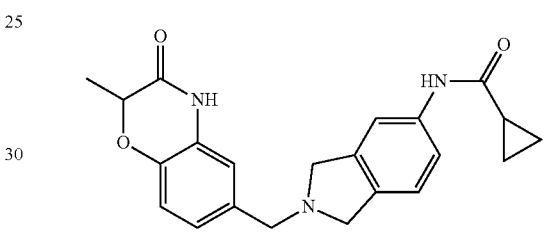

N-(2-((2-Methyl-3-oxo-3,4-dihydro-2H-benzo[b][1,4]oxazin-6-yl)methyl)isoindolin-5-yl)cyclopropan-ecarboxamide (243)

Using 13 and N-(isoindolin-5-yl)cyclopropanecarboxamide in the general procedure for reductive aminations, the title compound was obtained as a white solid: $^1$H NMR (400 MHz, DMSO-d$_6$) δ ppm 0.72-0.87 (m, 4H) 1.44 (d, J=6.82 Hz, 3H) 1.71-1.84 (m, 1H) 4.40-4.66 (m, 6H) 4.66-4.80 (m, 1 H) 7.01-7.17 (m, 3H) 7.31 (d, J=8.34 Hz, 1H) 7.47 (dd, J=8.46, 1.64 Hz, 1H) 7.73 (s, 1H) 10.35 (s, 1H) 10.93 (s, 1H). ESI-MS: m/z 378.4 (M+H)$^+$.

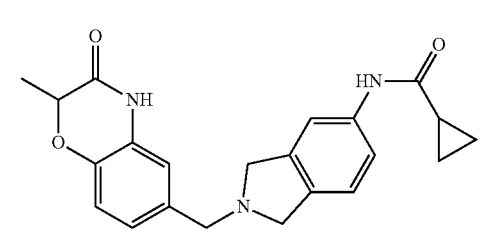 [SMILES: CC1Oc2ccc(CN3Cc4ccc(NC(=O)C5CC5)cc4C3)cc2NC1=O]

N-(2-((2-Methyl-3-oxo-3,4-dihydro-2H-benzo[b][1,4]oxazin-6-yl)methyl)isoindolin-5-yl)benzamide (244)

Using 13 and N-(isoindolin-5-yl)benzamide in the general procedure for reductive aminations, the title compound was obtained as a white solid: $^1$H NMR (400 MHz, DMSO-d$_6$) δ ppm 1.45 (d, J=6.82 Hz, 3H) 4.54 (d, J=5.05 Hz, 6H) 4.72 (q, J=6.74 Hz, 1H) 7.01-7.11 (m, 2H) 7.11-7.19 (m, 1H) 7.38 (d, J=8.34 Hz, 1H) 7.48-7.72 (m, 4H) 7.86-8.00 (m, 3H) 10.41 (s, 1H) 10.94 (s, 1H). ESI-MS: m/z 414.4 (M+H)⁺.

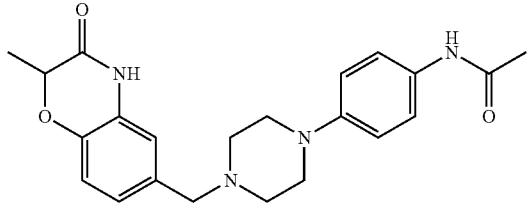 [SMILES: CC(=O)Nc1ccc(N2CCN(Cc3ccc4c(c3)NC(=O)C(C)O4)CC2)cc1]

N-(4-(4-((2-Methyl-3-oxo-3,4-dihydro-2H-benzo[b][1,4]oxazin-6-yl)methyl)piperazin-1-yl)phenyl)acetamide (245)

Using 13 and N-(4-(piperazin-1-yl)phenyl)acetamide in the general procedure for reductive aminations, the title compound was obtained as an off-white solid: $^1$H NMR (400 MHz, DMSO-d$_6$) δ ppm 1.38-1.50 (m, 3H) 1.99 (s, 3H) 2.87-3.04 (m, 2H) 3.04-3.25 (m, 2H) 3.35-3.47 (m, 1H) 3.67-3.78 (m, 2H) 4.30 (br. s., 2H) 4.71 (q, J=6.65 Hz, 1H) 6.91 (d, J=8.84 Hz, 2H) 7.06 (d, J=10.61 Hz, 2H) 7.10-7.19 (m, 1H) 7.45 (d, J=8.84 Hz, 2H) 9.78 (s, 1H) 10.15 (br. s., 1H) 10.94 (s, 1H). ESI-MS: m/z 395.4 (M+H)⁺.

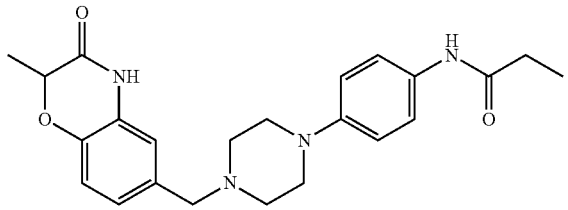 [SMILES: CCC(=O)Nc1ccc(N2CCN(Cc3ccc4c(c3)NC(=O)C(C)O4)CC2)cc1]

N-(4-(4-((2-Methyl-3-oxo-3,4-dihydro-2H-benzo[b][1,4]oxazin-6-yl)methyl)piperazin-1-yl)phenyl)propionamide (246)

Using 13 and N-(4-(piperazin-1-yl)phenyl)propionamide in the general procedure for reductive aminations, the title compound was obtained as an off-white solid: $^1$H NMR (400 MHz, DMSO-d$_6$) δ ppm 1.00-1.10 (m, 3H) 1.41 (d, J=6.82 Hz, 3H) 2.25 (q, J=7.58 Hz, 2H) 2.44-2.49 (m, 3H) 2.98-3.11 (m, 4H) 3.37-3.46 (m, 2H) 4.64 (q, J=6.74 Hz, 1H) 6.80-6.94 (m, 5H) 7.41 (d, J=9.09 Hz, 2H) 9.61 (s, 1H) 10.61 (s, 1H). ESI-MS: m/z 409.4 (M+H)⁺.

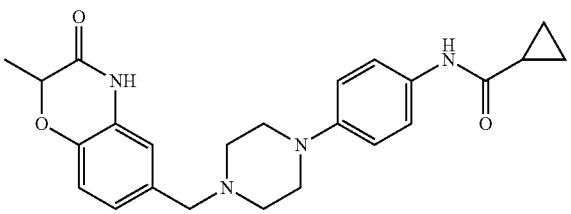 [SMILES: CC1Oc2ccc(CN3CCN(c4ccc(NC(=O)C5CC5)cc4)CC3)cc2NC1=O]

N-(4-(4-((2-methyl-3-oxo-3,4-dihydro-2H-benzo[b][1,4]oxazin-6-yl)methyl)piperazin-1-yl)phenyl)cyclopropanecarboxamide (247)

Using 13 and N-(4-(piperazin-1-yl)phenyl)cyclopropanecarboxamide in the general procedure for reductive aminations, the title compound was obtained as an off-white solid: $^1$H NMR (400 MHz, DMSO-d$_6$) δ ppm 0.67-0.80 (m, 4H) 1.41 (d, J=6.82 Hz, 3H) 1.65-1.79 (m, 1H) 2.44-2.49 (m, 3H) 3.05 (br. s., 4H) 3.37-3.45 (m, 2H) 4.64 (q, J=6.82 Hz, 1H) 6.80-6.94 (m, 5H) 7.41 (d, J=9.09 Hz, 2H) 9.93 (s, 1H) 10.61 (s, 1H). ESI-MS: m/z 421.5 (M+H)⁺.

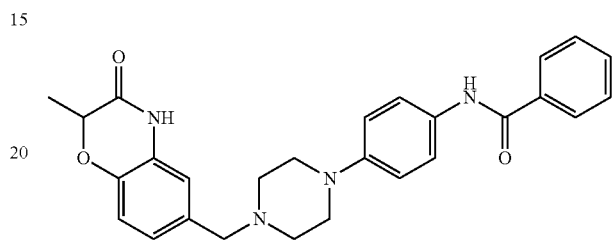

N-(4-(4-((2-Methyl-3-oxo-3,4-dihydro-2H-benzo[b][1,4]oxazin-6-yl)methyl)piperazin-1-yl)phenyl)benzamide (248)

Using 13 and N-(4-(piperazin-1-yl)phenyl)benzamide in the general procedure for reductive aminations, the title compound was obtained as an off-white solid: $^1$H NMR (400 MHz, DMSO-d$_6$) δ ppm 1.36-1.47 (m, 3H) 3.09 (d, J=4.55 Hz, 4H) 3.38-3.47 (m, 2H) 4.58-4.70 (m, 1H) 6.80-6.99 (m, 5H) 7.45-7.65 (m, 5H) 7.86-7.99 (m, 2H) 10.05 (s, 1H) 10.62 (s, 1H). ESI-MS: m/z 457.5 (M+H)⁺.

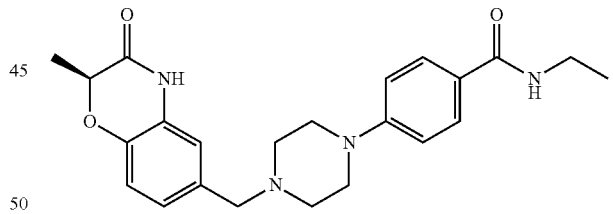

(S)-N-Ethyl-4-(4-((2-methyl-3-oxo-3,4-dihydro-2H-benzo[b][1,4]oxazin-6-yl)methyl)piperazin-1-yl)benzamide (249)

Chiral HPLC separation of 224 provided the title compound as a pale beige solid: $^1$H NMR (400 MHz, DMSO-d$_6$) δ ppm 1.09 (t, J=7.20 Hz, 3 H) 1.41 (d, J=6.82 Hz, 3H) 2.45-2.49 (m, 4H) 3.17-3.29 (m, 6H) 3.42 (s, 2H) 4.58-4.71 (m, 1H) 6.82-6.98 (m, 5H) 7.71 (d, J=8.84 Hz, 2H) 8.17 (t, J=5.56 Hz, 1H) 10.56-10.66 (m, 1H). ESI-MS: m/z 409.4 (M+H)⁺.

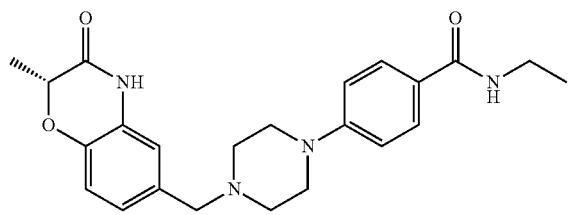 [SMILES: CCNC(=O)c1ccc(N2CCN(Cc3ccc4c(c3)NC(=O)[C@@H](C)O4)CC2)cc1]

(R)-N-Ethyl-4-(4-((2-methyl-3-oxo-3,4-dihydro-2H-benzo[b][1,4]oxazin-6-yl)methyl)piperazin-1-yl)benzamide (250)

Chiral HPLC separation of 224 provided the title compound as a pale beige solid: $^1$H NMR (400 MHz, DMSO-d$_6$) δ ppm 1.09 (t, J=7.20 Hz, 3 H) 1.41 (d, J=6.82 Hz, 3H) 2.45-2.49 (m, 4H) 3.17-3.29 (m, 6H) 3.42 (s, 2H) 4.58-4.71 (m, 1H) 6.82-6.98 (m, 5H) 7.71 (d, J=8.84 Hz, 2H) 8.17 (t, J=5.56 Hz, 1H) 10.56-10.66 (m, 1H). ESI-MS: m/z 409.4 (M+H)$^+$.

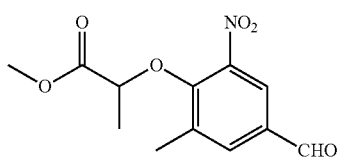 [SMILES: COC(=O)C(C)Oc1c(C)cc(C=O)cc1[N+](=O)[O-]]

Methyl 2-(4-formyl-2-methyl-6-nitrophenoxy)propanoate (251)

Using 4-hydroxy-3-methyl-5-nitrobenzaldehyde as the phenol and methyl-2-bromopropanoate as the alkylating agent in the general procedure of alkylation of substituted 2-nitrophenols gives a light tan solid: $^1$H NMR (400 MHz, DMSO-d$_6$) δ ppm 1.49-1.56 (m, 3H) 2.42 (s, 3H) 3.62 (s, 3H) 4.82 (q, J=6.82 Hz, 1H) 8.10 (d, J=1.52 Hz, 1H) 8.29 (d, J=1.52 Hz, 1H) 9.98 (s, 1H). ESI-MS: m/z 268.2 (M+H)$^+$.

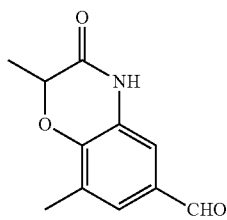

2,8-Dimethyl-3-oxo-3,4-dihydro-2H-benzo[b][1,4]oxazine-6-carbaldehyde (252)

Using methyl 2-(4-formyl-2-methyl-6-nitrophenoxy)propanoate in the general procedure for reduction of a nitro group and subsequent ring closure gives a tan solid: $^1$H NMR (400 MHz, DMSO-d$_6$) δ ppm 1.46 (d, J=6.82 Hz, 3H) 2.24 (s, 3H) 4.83 (q, J=6.82 Hz, 1H) 7.24 (d, J=1.52 Hz, 1H) 7.44 (d, J=1.26 Hz, 1H) 9.79-9.83 (m, 1H) 10.90 (s, 1H). ESI-MS: m/z 206.2 (M+H)$^+$.

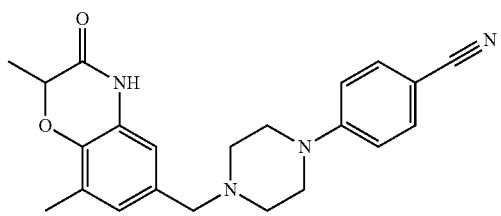 [SMILES: Cc1cc(CN2CCN(c3ccc(C#N)cc3)CC2)cc2c1OC(C)C(=O)N2]

4-(4-((2,8-Dimethyl-3-oxo-3,4-dihydro-2H-benzo[b][1,4]oxazin-6-yl)methyl)piperazin-1-yl)benzonitrile (253)

Using 252 and 4-(piperazin-1-yl)benzonitrile in the general procedure for reductive aminations, the title compound was obtained as an off-white solid: $^1$H NMR (400 MHz, DMSO-d$_6$) δ ppm 1.37-1.43 (m, 3H) 2.15 (s, 3H) 2.40-2.48 (m, 4H) 3.28-3.33 (m, 4H) 3.37 (s, 2H) 4.58-4.66 (m, 1H) 6.66-6.81 (m, 2H) 7.00 (d, J=9.09 Hz, 2H) 7.58 (d, J=9.09 Hz, 2H) 10.56 (s, 1H). ESI-MS: m/z 377.4 (M+H)$^+$.

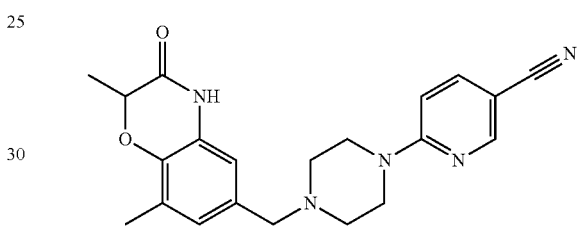

6-(4-((2,8-Dimethyl-3-oxo-3,4-dihydro-2H-benzo[b][1,4]oxazin-6-yl)methyl)piperazin-1-yl)nicotinonitrile (254)

Using 252 and 6-(piperazin-1-yl)nicotinonitrile in the general procedure for reductive aminations, the title compound was obtained as a white solid: $^1$H NMR (400 MHz, DMSO-d$_6$) δ ppm 1.35-1.45 (m, 3H) 2.15 (s, 3H) 2.41 (t, J=4.93 Hz, 4H) 3.36 (s, 2H) 3.59-3.69 (m, 4H) 4.63 (q, J=6.82 Hz, 1H) 6.65-6.79 (m, 2H) 6.91 (d, J=9.35 Hz, 1H) 7.84 (dd, J=9.09, 2.27 Hz, 1H) 8.47 (d, J=1.77 Hz, 1 H) 10.56 (s, 1H). ESI-MS: m/z 378.4 (M+H)$^+$.

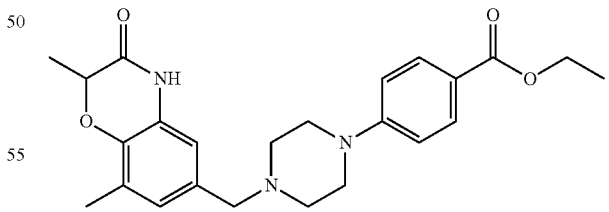

Ethyl 4-(4-((2,8-dimethyl-3-oxo-3,4-dihydro-2H-benzo[b][1,4]oxazin-6-yl)methyl)piperazin-1-yl)benzoate (255)

Using 252 and ethyl 4-(piperazin-1-yl)benzoate in the general procedure for reductive aminations, the title compound was obtained as a white solid: $^1$H NMR (400 MHz, DMSO-d$_6$) δ ppm 1.28 (t, J=7.20 Hz, 3H) 1.37-1.45 (m, 3H) 2.16 (s, 3H) 2.46 (br. s., 3H) 3.30 (br. s., 4H) 3.37 (br. s., 2H) 4.23 (q, J=7.07 Hz, 2H) 4.57-4.69 (m, 1H) 6.74 (d, J=10.36 Hz, 2H) 6.90-7.03 (m, 2H) 7.73-7.83 (m, 2H) 10.57 (s, 1 H). ESI-MS: m/z 424.5 (M+H)$^+$.

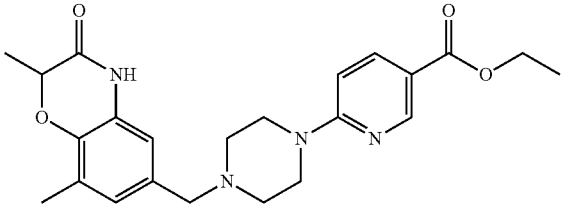 [SMILES: CCOC(=O)c1ccc(N2CCN(Cc3cc(C)c4c(c3)NC(=O)C(C)O4)CC2)nc1]

Ethyl 6-(4-((2,8-dimethyl-3-oxo-3,4-dihydro-2H-benzo[b][1,4]oxazin-6-yl)methyl)piperazin-1-yl)nicotinate (256)

Using 252 and ethyl 6-(piperazin-1-yl)nicotinate in the general procedure for reductive aminations, the title compound was obtained as an off-white solid, mp 206.0-206.5° C.: $^1$H NMR (400 MHz, DMSO-d$_6$) δ ppm 1.28 (t, J=7.07 Hz, 3 H) 1.37-1.44 (m, 3H) 2.16 (s, 3H) 2.42 (t, J=4.80 Hz, 4H) 3.37 (s, 2H) 3.59-3.69 (m, 4H) 4.24 (q, J=7.07 Hz, 2H) 4.58-4.68 (m, 1H) 6.69-6.78 (m, 2H) 6.86 (d, J=8.84 Hz, 1H) 7.93 (dd, J=9.09, 2.53 Hz, 1H) 8.60-8.66 (m, 1H) 10.57 (s, 1H). ESI-MS: m/z 425.4 (M+H)$^+$.

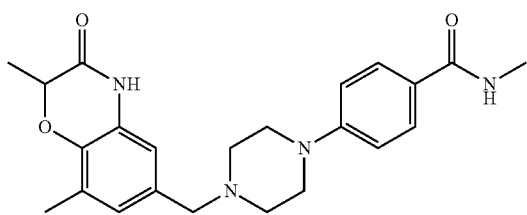

4-(4-((2,8-Dimethyl-3-oxo-3,4-dihydro-2H-benzo[b][1,4]oxazin-6-yl)methyl)piperazin-1-yl)-N-methylbenzamide (257)

Using 255 in the general procedure for hydrolysis of carboxylic esters followed by reaction of the resulting acid with methylamine in the general procedure for coupling an amine to a carboxylic acid, the title compound was obtained as a white solid: $^1$H NMR (400 MHz, DMSO-d$_6$) δ ppm 1.41 (d, J=6.82 Hz, 3H) 2.16 (s, 3H) 2.41-2.49 (m, 4H) 2.73 (d, J=4.29 Hz, 3H) 3.19-3.27 (m, 4H) 3.37 (s, 2H) 4.63 (q, J=6.82 Hz, 1H) 6.74 (d, J=9.35 Hz, 2H) 6.92 (d, J=9.09 Hz, 2H) 7.70 (d, J=9.09 Hz, 2H) 8.06-8.20 (m, 1H) 10.55 (s, 1H). ESI-MS: m/z 409.4 (M+H)$^+$.

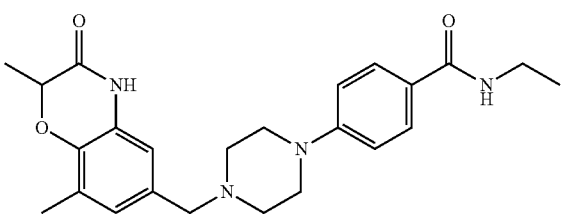 [SMILES: CCNC(=O)c1ccc(N2CCN(Cc3cc(C)c4c(c3)NC(=O)C(C)O4)CC2)cc1]

4-(4-((2,8-Dimethyl-3-oxo-3,4-dihydro-2H-benzo[b][1,4]oxazin-6-yl)methyl)piperazin-1-yl)-N-ethylbenzamide (258)

Using 255 in the general procedure for hydrolysis of carboxylic esters followed by reaction of the resulting acid with ethylamine in the general procedure for coupling an amine to a carboxylic acid, the title compound was obtained as a white solid: $^1$H NMR (400 MHz, DMSO-d$_6$) δ ppm 1.09 (t, J=7.20 Hz, 3H) 1.41 (d, J=6.82 Hz, 3H) 2.16 (s, 3H) 2.42-2.48 (m, 4H) 3.19-3.29 (m, 6H) 3.37 (s, 2H) 4.63 (q, J=6.82 Hz, 1H) 6.74 (d, J=9.35 Hz, 2H) 6.92 (d, J=9.09 Hz, 2H) 7.71 (d, J=8.84 Hz, 2H) 8.17 (t, J=5.56 Hz, 1H) 10.55 (s, 1H). ESI-MS: m/z 423.5 (M+H)$^+$.

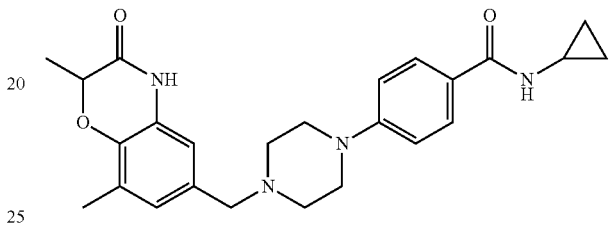

N-Cyclopropyl-4-(4-((2,8-dimethyl-3-oxo-3,4-dihydro-2H-benzo[b][1,4]oxazin-6-yl)methyl)piperazin-1-yl)benzamide (259)

Using 255 in the general procedure for hydrolysis of carboxylic esters followed by reaction of the resulting acid with cyclopropylamine in the general procedure for coupling an amine to a carboxylic acid, the title compound was obtained as a white solid, mp 256.7-262.8° C.: $^1$H NMR (400 MHz, DMSO-d$_6$) δ ppm 0.48-0.56 (m, 2H) 0.61-0.69 (m, 2H) 1.41 (d, J=6.57 Hz, 3H) 2.16 (s, 3H) 2.41-2.48 (m, 4H) 2.79 (tq, J=7.39, 3.83 Hz, 1H) 3.18-3.27 (m, 4H) 3.37 (s, 2H) 4.56-4.68 (m, 1H) 6.68-6.81 (m, 2H) 6.91 (d, J=9.09 Hz, 2H) 7.69 (d, J=8.84 Hz, 2H) 8.13 (d, J=4.04 Hz, 1H) 10.55 (s, 1H). ESI-MS: m/z 435.5 (M+H)$^+$.

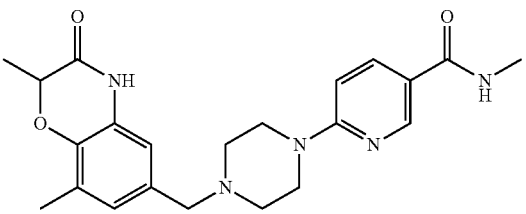

6-(4-((2,8-Dimethyl-3-oxo-3,4-dihydro-2H-benzo[b][1,4]oxazin-6-yl)methyl)piperazin-1-yl)-N-methylnicotinamide (260)

Using 255 in the general procedure for hydrolysis of carboxylic esters followed by reaction of the resulting acid with methylamine in the general procedure for coupling an amine to a carboxylic acid, the title compound was obtained as a pale beige solid: $^1$H NMR (400 MHz, DMSO-d$_6$) δ ppm 1.41 (d, J=6.82 Hz, 3H) 2.16 (s, 3H) 2.42 (t, J=4.80 Hz, 4H) 2.74 (d, J=4.55 Hz, 3H) 3.38 (s, 2H) 3.48-3.66 (m, 4 H) 4.63 (q, J=6.74 Hz, 1H) 6.64-6.89 (m, 3H) 7.91 (dd, J=9.09, 2.53 Hz, 1H) 8.20 (q, J=4.29 Hz, 1H) 8.56 (d, J=2.27 Hz, 1H) 10.55 (s, 1H). ESI-MS: m/z 410.4 (M+H)+.

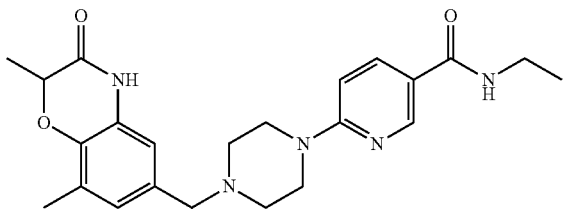 [SMILES: CCNC(=O)c1ccc(N2CCN(Cc3cc(C)c4c(c3)NC(=O)C(C)O4)CC2)nc1]

6-(4-((2,8-Dimethyl-3-oxo-3,4-dihydro-2H-benzo[b][1,4]oxazin-6-yl)methyl)piperazin-1-yl)-N-ethylnicotinamide (261)

Using 255 in the general procedure for hydrolysis of carboxylic esters followed by reaction of the resulting acid with ethylamine in the general procedure for coupling an amine to a carboxylic acid, the title compound was obtained as a pale beige solid: $^1$H NMR (400 MHz, DMSO-d$_6$) δ ppm 1.10 (t, J=7.20 Hz, 3H) 1.41 (d, J=6.82 Hz, 3H) 2.16 (s, 3H) 2.42 (t, J=4.80 Hz, 4H) 3.19-3.29 (m, 2H) 3.37 (s, 2 H) 3.49-3.65 (m, 4H) 4.58-4.69 (m, 1H) 6.68-6.88 (m, 3H) 7.93 (dd, J=8.97, 2.40 Hz, 1 H) 8.23 (t, J=5.56 Hz, 1H) 8.57 (d, J=2.27 Hz, 1H) 10.55 (s, 1H). ESI-MS: m/z 424.5 (M+H)+.

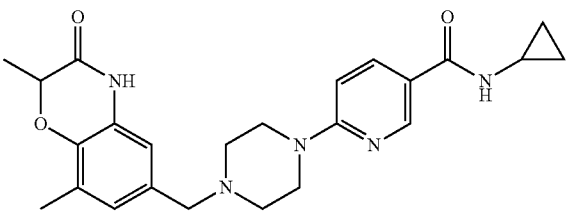 [SMILES: Cc1cc(CN2CCN(c3ccc(C(=O)NC4CC4)cn3)CC2)cc2c1OC(C)C(=O)N2]

N-Cyclopropyl-6-(4-((2,8-dimethyl-3-oxo-3,4-dihydro-2H-benzo[b][1,4]oxazin-6-yl)methyl)piperazin-1-yl)nicotinamide (262)

Using 255 in the general procedure for hydrolysis of carboxylic esters followed by reaction of the resulting acid with cyclopropylamine in the general procedure for coupling an amine to a carboxylic acid, the title compound was obtained as a pale beige solid: $^1$H NMR (400 MHz, DMSO-d$_6$) δ ppm 0.49-0.56 (m, 2H) 0.62-0.70 (m, 2H) 1.41 (d, J=6.57 Hz, 3H) 2.16 (s, 3H) 2.35-2.45 (m, 4H) 2.78 (tq, J=7.28, 3.82 Hz, 1H) 3.36 (s, 2H) 3.45-3.65 (m, 4H) 4.63 (q, J=6.82 Hz, 1H) 6.64-6.87 (m, 3H) 7.90 (dd, J=8.97, 2.40 Hz, 1H) 8.20 (d, J=3.79 Hz, 1H) 8.54 (d, J=2.27 Hz, 1 H) 10.55 (s, 1H). ESI-MS: m/z 436.5 (M+H)+.

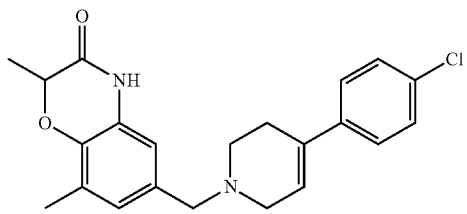 [SMILES: Cc1cc(CN2CC=C(c3ccc(Cl)cc3)CC2)cc2c1OC(C)C(=O)N2]

6-((4-(4-Chlorophenyl)-5,6-dihydropyridin-1(2H)-yl)methyl)-2,8-dimethyl-2H-benzo[b][1,4]oxazin-3(4H)-one (263)

Using 252 and 4-(4-chlorophenyl)-1,2,3,6-tetrahydropyridine in the general procedure for reductive aminations, the title compound was obtained as a white solid: $^1$H NMR (400 MHz, DMSO-d$_6$) δ ppm 1.35-1.46 (m, 3H) 2.16 (s, 3H) 2.39-2.47 (m, 2H) 2.57-2.66 (m, 2H) 3.02 (d, J=3.03 Hz, 2H) 3.44 (s, 2H) 4.63 (q, J=6.82 Hz, 1H) 6.14-6.24 (m, 1H) 6.71-6.77 (m, 2H) 7.33-7.41 (m, 2H) 7.41-7.49 (m, 2 H) 10.50-10.60 (m, 1H). ESI-MS: m/z 383.8 (M+H)+.

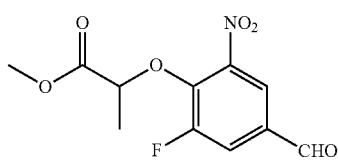

Methyl 2-(2-fluoro-4-formyl-6-nitrophenoxy)propanoate (264)

Using 3-fluoro-4-hydroxy-5-nitrobenzaldehyde as the phenol and methyl-2-bromopropanoate as the alkylating agent in the general procedure of alkylation of substituted 2-nitrophenols gives a yellow solid: $^1$H NMR (400 MHz, DMSO-d$_6$) δ ppm 1.56 (d, J=6.57 Hz, 3H) 3.66 (s, 3H) 5.27 (qd, J=6.78, 1.64 Hz, 1H) 8.10-8.18 (m, 1H) 8.31-8.38 (m, 1H) 9.95 (d, J=2.02 Hz, 1H). ESI-MS: m/z 272.1 (M+H)+.

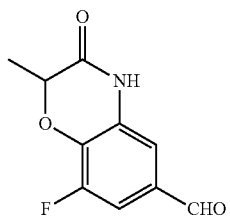

8-Fluoro-2-methyl-3-oxo-3,4-dihydro-2H-benzo[b][1,4]oxazine-6-carbaldehyde (265)

Using methyl 2-(2-fluoro-4-formyl-6-nitrophenoxy)propanoate in the general procedure for reduction of a nitro group and subsequent ring closure gives a brown solid: $^1$H NMR (400 MHz, DMSO-d$_6$) δ ppm 1.46-1.53 (m, 3H) 4.90-5.01 (m, 1H) 7.26 (s, 1H) 7.50 (dd, J=10.36, 1.26 Hz, 1H) 9.83 (s, 1H) 11.16 (s, 1H). ESI-MS: m/z 210.1 (M+H)+.

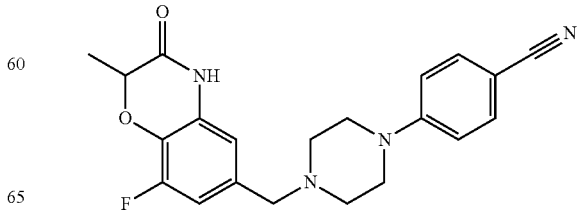

4-(4-((8-Fluoro-2-methyl-3-oxo-3,4-dihydro-2H-benzo[b][1,4]oxazin-6-yl)methyl)piperazin-1-yl)benzonitrile (266)

Using 265 and 4-(piperazin-1-yl)benzonitrile in the general procedure for reductive aminations, the title compound was obtained as a light brown solid: ¹H NMR (400 MHz, DMSO-$d_6$) δ ppm 1.44 (d, J=6.82 Hz, 3H) 2.43-2.48 (m, 4 H) 3.31 (br. s., 4H) 3.42 (s, 2H) 4.75 (q, J=6.74 Hz, 1H) 6.72 (s, 1H) 6.84 (dd, J=11.24, 1.64 Hz, 1H) 7.01 (d, J=9.09 Hz, 2H) 7.58 (d, J=8.84 Hz, 2H) 10.83 (s, 1H). ESI-MS: m/z 381.4 (M+H)⁺.

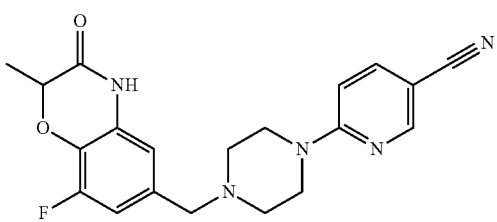 [SMILES: CC1Oc2c(F)cc(CN3CCN(c4ccc(C#N)cn4)CC3)cc2NC1=O]

6-(4-((8-fluoro-2-methyl-3-oxo-3,4-dihydro-2H-benzo[b][1,4]oxazin-6-yl)methyl)piperazin-1-yl)nicotinonitrile (267)

Using 265 and 6-(piperazin-1-yl)nicotinonitrile in the general procedure for reductive aminations, the title compound was obtained as a light brown solid: ¹H NMR (400 MHz, DMSO-$d_6$) δ ppm 1.36-1.49 (m, 3H) 2.42 (t, J=4.67 Hz, 4H) 3.42 (s, 2H) 3.65 (d, J=4.55 Hz, 4H) 4.75 (q, J=6.82 Hz, 1H) 6.72 (s, 1H) 6.79-6.99 (m, 2H) 7.84 (dd, J=9.09, 2.27 Hz, 1H) 8.47 (d, J=2.02 Hz, 1H) 10.83 (s, 1H). ESI-MS: m/z 382.4 (M+H)⁺.

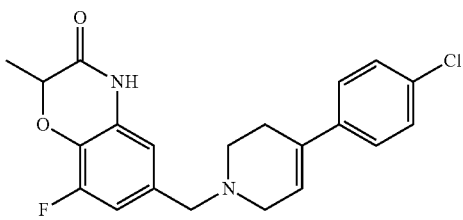 [SMILES: CC1Oc2c(F)cc(CN3CC=C(c4ccc(Cl)cc4)CC3)cc2NC1=O]

6-((4-(4-Chlorophenyl)-5,6-dihydropyridin-1(2H)-yl)methyl)-8-fluoro-2-methyl-2H-benzo[b][1,4]oxazin-3(4H)-one (268)

Using 265 and 4-(4-chlorophenyl)-1,2,3,6-tetrahydropyridine in the general procedure for reductive aminations, the title compound was obtained as a light brown solid, mp 214.1-233.3° C.: ¹H NMR (400 MHz, DMSO-$d_6$) δ ppm 1.20-1.33 (m, 1H) 1.34-1.53 (m, 3H) 2.38-2.48 (m, 2H) 2.56-2.72 (m, 2H) 3.05 (br. s., 2H) 3.49 (br. s., 2H) 4.67-4.82 (m, 1H) 6.20 (br. s., 1H) 6.65-6.96 (m, 2H) 7.26-7.55 (m, 3H) 10.82 (br. s., 1H). ESI-MS: m/z 387.8 (M+H)⁺.

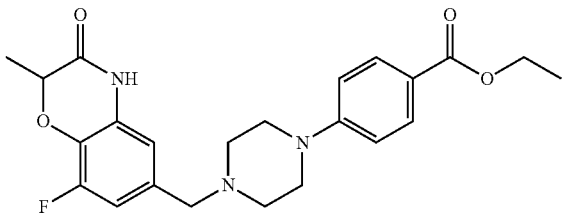

Ethyl 4-(4-((8-fluoro-2-methyl-3-oxo-3,4-dihydro-2H-benzo[b][1,4]oxazin-6-yl)methyl)piperazin-1-yl)benzoate (269)

Using 265 and ethyl 4-(piperazin-1-yl)benzoate in the general procedure for reductive aminations, the title compound was obtained as a tan solid: ¹H NMR (400 MHz, DMSO-$d_6$) δ ppm 1.19-1.34 (m, 3H) 1.40-1.54 (m, 3H) 2.44-2.49 (m, 4H) 3.27-3.32 (m, 4H) 3.39-3.48 (m, 2H) 4.23 (q, J=7.07 Hz, 2H) 4.76 (q, J=6.74 Hz, 1H) 6.73 (s, 1H) 6.85 (dd, J=11.37, 1.52 Hz, 1H) 6.97 (d, J=9.09 Hz, 2H) 7.78 (d, J=9.09 Hz, 2H) 10.83 (s, 1H). ESI-MS: m/z 428.4 (M+H)⁺.

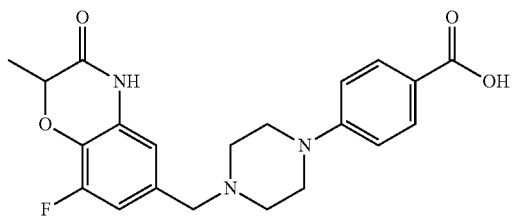

4-(4-((8-Fluoro-2-methyl-3-oxo-3,4-dihydro-2H-benzo[b][1,4]oxazin-6-yl)methyl)piperazin-1-yl)benzoic acid (270)

Using 269 in the general procedure for hydrolysis of carboxylic esters, the title compound was obtained as a brown solid: ¹H NMR (400 MHz, DMSO-$d_6$) δ ppm 1.47 (d, J=6.82 Hz, 3H) 2.81-3.28 (m, 4H) 4.02 (br. s., 2H) 4.30 (br. s., 2H) 4.82 (d, J=6.57 Hz, 1H) 6.70-7.12 (m, 3H) 7.23 (br. s., 1H) 7.81 (d, J=8.34 Hz, 2H) 10.70 (br. s., 1H) 11.14 (br. s., 1H) 12.43 (d, J=6.32 Hz, 1H). ESI-MS: m/z 400.4 (M+H)⁺.

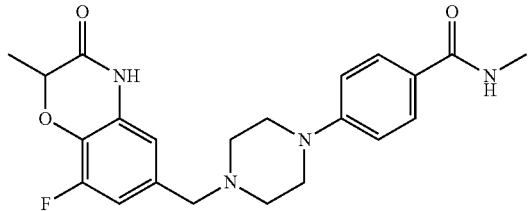

4-(4-((8-Fluoro-2-methyl-3-oxo-3,4-dihydro-2H-benzo[b][1,4]oxazin-6-yl)methyl)piperazin-1-yl)-N-methylbenzamide (271)

Using 270 and methylamine in the general procedure for coupling an amine to a carboxylic acid, the title compound was obtained as a tan solid: ¹H NMR (400 MHz, DMSO-$d_6$) δ ppm 1.45 (d, J=6.57 Hz, 3H) 2.74 (d, J=4.55 Hz, 3H)

3.16-3.28 (m, 4H) 3.42 (s, 2H) 4.76 (q, J=6.74 Hz, 1H) 6.73 (s, 1H) 6.84 (d, J=11.12 Hz, 1H) 6.93 (d, J=8.84 Hz, 2H) 7.70 (d, J=8.84 Hz, 2H) 8.07-8.20 (m, 1H) 10.83 (s, 1H). ESI-MS: m/z 413.4 (M+H)$^+$.

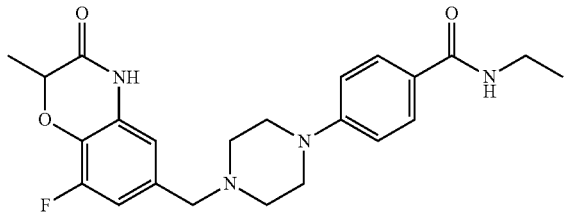 [SMILES: CCNC(=O)c1ccc(N2CCN(Cc3cc(F)c4c(c3)NC(=O)C(C)O4)CC2)cc1]

N-Ethyl-4-(4-((8-fluoro-2-methyl-3-oxo-3,4-dihydro-2H-benzo[b][1,4]oxazin-6-yl)methyl)piperazin-1-yl)benzamide (272)

Using 270 and ethylamine in the general procedure for coupling an amine to a carboxylic acid, the title compound was obtained as a tan solid: $^1$H NMR (400 MHz, DMSO-d$_6$) δ ppm 1.09 (t, J=7.20 Hz, 3H) 1.45 (d, J=6.57 Hz, 3H) 3.17-3.28 (m, 6H) 3.42 (s, 2H) 4.76 (q, J=6.82 Hz, 1H) 6.73 (s, 1H) 6.85 (d, J=11.12 Hz, 1 H) 6.93 (d, J=8.84 Hz, 2H) 7.71 (d, J=8.84 Hz, 2H) 8.17 (t, J=5.43 Hz, 1H) 10.83 (s, 1H). ESI-MS: m/z 427.4 (M+H)$^+$.

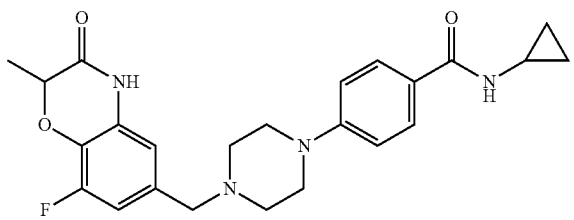 [SMILES: CC1Oc2c(F)cc(CN3CCN(c4ccc(C(=O)NC5CC5)cc4)CC3)cc2NC1=O]

N-Cyclopropyl-4-(4-((8-fluoro-2-methyl-3-oxo-3,4-dihydro-2H-benzo[b][1,4]oxazin-6-yl)methyl)piperazin-1-yl)benzamide (273)

Using 270 and cyclopropylamine in the general procedure for coupling an amine to a carboxylic acid, the title compound was obtained as a tan solid: $^1$H NMR (400 MHz, DMSO-d$_6$) δ ppm 0.47-0.56 (m, 2H) 0.60-0.69 (m, 2H) 1.44 (d, J=6.82 Hz, 3H) 2.44-2.49 (m, 4H) 2.74-2.86 (m, 1H) 3.24 (br. s., 4H) 3.42 (s, 2H) 4.75 (q, J=6.65 Hz, 1H) 6.73 (s, 1H) 6.80-6.88 (m, 1H) 6.92 (d, J=8.84 Hz, 2H) 7.69 (d, J=8.84 Hz, 2H) 8.13 (d, J=4.04 Hz, 1H) 10.83 (s, 1H). ESI-MS: m/z 439.4 (M+H)$^+$.

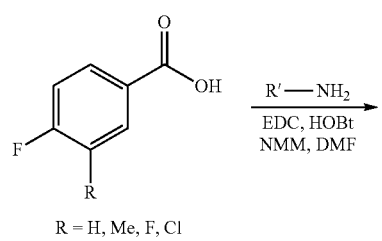

R = H, Me, F, Cl

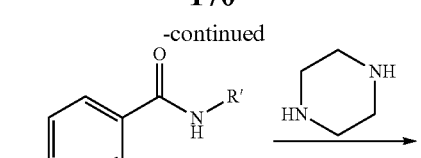

R = H, F, Cl
R' = Me, Et, iPr, cPr

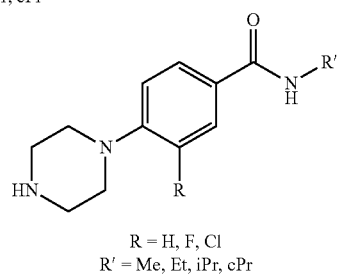

R = H, F, Cl
R' = Me, Et, iPr, cPr

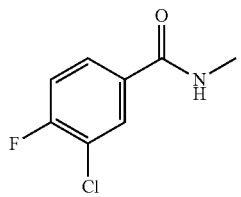

General Procedure for Coupling of Amines to Carboxylic Acids

Synthesis of 3-chloro-4-fluoro-N-methylbenzamide (274)

To a suspension of 3-chloro-4-fluorobenzoic acid (25.0 g, 143 mmol), methylamine hydrochloride (11.60 g, 172 mmol), N1-((ethylimino)methylene)-N3,N3-dimethylpropane-1,3-diamine hydrochloride (41.2 g, 215 mmol), and 1H-benzo[d][1,2,3]triazol-1-ol hydrate (32.9 g, 215 mmol) in DMF (150 mL) was added 4-methylmorpholine (79 mL, 716 mmol) at 23° C. The reaction was stirred at 23° C. for 3 hr. The reaction mixture was diluted with water (500 mL) to furnish a yellow-orange solution. The solution was stirred overnight at 23° C. affording a suspension. The suspension was filtered, washed with H$_2$O (3×100 mL), and the resulting solid was dried in vacuo at 30° C. to provide the title compound as an off-white solid (14.24 g, 76 mmol, 53.0% yield). $^1$H NMR (400 MHz, DMSO-d$_6$) δ ppm 2.78 (d, J=4.55 Hz, 3H) 7.53 (t, J=8.97 Hz, 1H) 7.86 (ddd, J=8.59, 4.80, 2.27 Hz, 1H) 8.04 (dd, J=7.20, 2.15 Hz, 1H) 8.51-8.65 (m, 1H). ESI-MS: m/z 188.0 (M+H)$^+$. Mp=108.3-110.0° C.

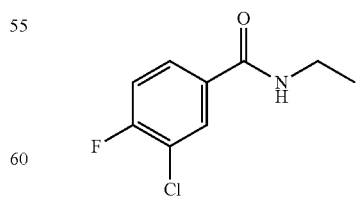

3-Chloro-4-fluoro-N-ethylbenzamide (275)

Using ethanamine hydrochloride and 3-chloro-4-fluorobenzoic acid in the general procedure for coupling of amines to carboxylic acids, the title compound was obtained as an off-white solid (77% yield). ¹H NMR (400 MHz, DMSO-d₆) δ ppm 1.12 (t, J=7.20 Hz, 3H) 3.28 (qd, J=7.16, 5.56 Hz, 2H) 7.53 (t, J=8.84 Hz, 1H) 7.87 (ddd, J=8.72, 4.80, 2.15 Hz, 1H) 8.06 (dd, J=7.33, 2.27 Hz, 1H) 8.61 (t, J=4.67 Hz, 1H). ESI-MS: m/z 202.0 (M+H)⁺. mp=101.7-101.8° C.

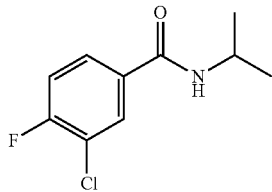

3-Chloro-4-fluoro-N-isopropylbenzamide (276)

Using isopropylamine hydrochloride and 3-chloro-4-fluorobenzoic acid in the general procedure for coupling of amines to carboxylic acids, the title compound was obtained as a white solid (81% yield). ESI-MS: m/z 216 (M+H)⁺.

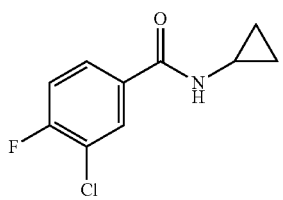 [SMILES: O=C(NC1CC1)c1ccc(F)c(Cl)c1]

3-Chloro-N-cyclopropyl-4-fluorobenzamide (277)

Using cyclopropylamine and 3-chloro-4-fluorobenzoic acid in the general procedure for coupling of amines to carboxylic acids, the title compound was obtained as a white solid (89% yield). ¹H NMR (DMSO-d₆, 400 MHz): δ=8.56 (d, J=3.5 Hz, 1H), 8.03 (dd, J=7.3, 2.3 Hz, 1H), 7.85 (ddd, J=8.6, 4.8, 2.3 Hz, 1H), 7.52 (t, J=9.0 Hz, 1H), 2.83 (tq, J=7.4, 3.9 Hz, 1H), 0.66-0.75 (m, 2H), 0.53-0.61 ppm (m, 2H). ESI-MS: m/z 214.0 (M+H)⁺.

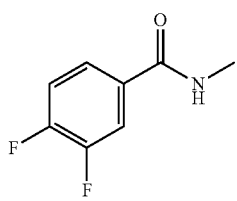

3,4-Difluoro-N-methylbenzamide (278)

Using methanamine hydrochloride and 3,4-difluorobenzoic acid in the general procedure for coupling of amines to carboxylic acids, the title compound was obtained as an off-white solid (75% yield). ¹H NMR (400 MHz, DMSO-d₆) δ ppm 2.78 (d, J=4.55 Hz, 3H) 7.55 (dt, J=10.61, 8.34 Hz, 1H) 7.72 (dddd, J=8.59, 4.55, 2.15, 1.39 Hz, 1H) 7.86 (ddd, J=11.68, 7.89, 2.15 Hz, 1H) 8.48-8.59 (m, 1H). ESI-MS: m/z 172.1 (M+H)⁺. mp=142.7-145.0° C.

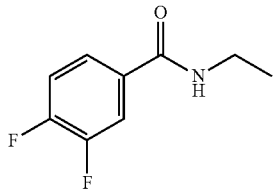

3,4-Difluoro-N-ethylbenzamide (279)

Using ethanamine hydrochloride and 3,4-difluorobenzoic acid in the general procedure for coupling of amines to carboxylic acids, the title compound was obtained as an off-white solid (56% yield). ¹H NMR (400 MHz, DMSO-d₆) δ ppm 1.12 (t, J=7.20 Hz, 3H) 3.28 (qd, J=7.24, 5.56 Hz, 2H) 7.55 (dt, J=10.48, 8.40 Hz, 1H) 7.73 (m, J=7.33, 4.74, 2.08, 1.14, 1.14 Hz, 1H) 7.88 (ddd, J=11.75, 7.83, 2.15 Hz, 1H) 8.58 (t, J=4.93 Hz, 1H). ESI-MS: m/z 186.1 (M+H)⁺. mp=94.1-96.2° C.

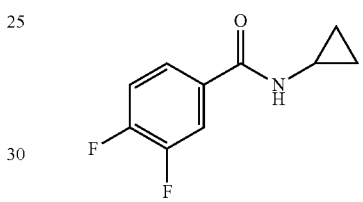

N-Cyclopropyl-3,4-difluorobenzamide (280)

Using cyclopropylamine and 3,4-difluorobenzoic acid in the general procedure for coupling of amines to carboxylic acids, the title compound was obtained as an off-white solid (89% yield). ¹H NMR (400 MHz, DMSO-d₆) δ ppm 0.52-0.63 (m, 2H) 0.63-0.74 (m, 2H) 2.83 (tq, J=7.42, 3.98 Hz, 1H) 7.52 (dt, J=10.55, 8.37 Hz, 1H) 7.66-7.75 (m, 1H) 7.85 (ddd, J=11.68, 7.89, 2.15 Hz, 1H) 8.42-8.60 (m, 1H). ESI-MS: m/z 198.1 (M+H)⁺. mp=104.1-108.4° C.

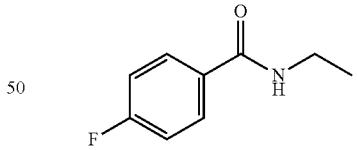

N-Ethyl-4-fluorobenzamide (281)

To a solution of ethylamine (69.4 mL, 139 mmol) and triethylamine (21.10 mL, 151 mmol) in DCM (150 mL) was added p-fluorobenzoyl chloride (15.13 mL, 126 mmol) at 0° C. The reaction was stirred at 0° C. for 1 hr and then warmed slowly to room temperature. The reaction mixture was diluted with water. The layers were separated and the organic layer was washed with brine, dried over MgSO₄, filtered, and the organic phase stripped to dryness via rotary evaporation. The organic extract was dried in vacuo to provide the title compound as a tan solid (21 g, 100% yield).

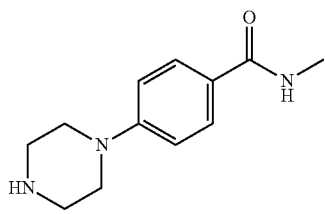 [SMILES: CNC(=O)c1ccc(N2CCNCC2)cc1]

General Procedure for Nucleophilic Aromatic Substitution Reactions with Piperazine Synthesis of N-methyl-4-(piperazin-1-yl)benzamide (282)

To a solution of 4-fluoro-N-methylbenzamide (6 g, 39.2 mmol) in DMSO (24.0 mL) was added piperazine (16.87 g, 196 mmol) at 23° C. The reaction was stirred at 120° C. for 68 hr. The reaction mixture was poured into ice (261 g) and the reaction vessel was rinsed with $H_2O$ (~50 mL). Next, Celite (30 g) was added to aid the filtration. The resulting suspension was warmed to 100° C., cooled to ~40° C., filtered, and rinsed with warm $H_2O$ (4×50 mL). The resulting solid was dried in vacuo. The filtrate was stirred at room temperature overnight affording a suspension. The suspension was filtered, rinsed with $H_2O$ (3×25 mL), and the resulting solid was dried in vacuo. The cloudy filtrate was filtered once again through a medium fritted funnel and rinsed with $H_2O$ (3×10 mL). Added NaCl (200.1 g) to the filtrate, cooled on ice, filtered, rinsed with cold $H_2O$ (3×25 mL), and dried the resulting solid in vacuo. Re-suspended the purified product in $H_2O$ (30 mL), stirred for 30 min at 23° C., filtered, rinsed with $H_2O$ (3×5 mL), and dried the resulting solid in vacuo. The purified product was re-suspended in ACN (25 mL), agitated for 10 min, and dried in vacuo. This procedure was repeated three times to provide the title compound as a white solid (5.64 g, 25.7 mmol, 65.7% yield). $^1$H NMR (400 MHz, DMSO-$d_6$) δ ppm 2.29 (br. s., 1H) 2.74 (d, J=4.55 Hz, 3H) 2.77-2.86 (m, 4H) 3.08-3.18 (m, 4H) 6.91 (m, 2H) 7.69 (m, 2H) 8.13 (q, J=4.04 Hz, 1H). ESI-MS: m/z 220.2 (M+H)$^+$. mp=153.9-156.5° C.

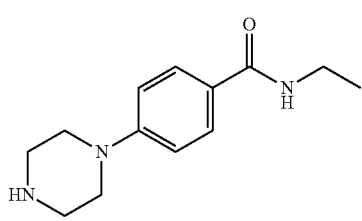 [SMILES: CCNC(=O)c1ccc(N2CCNCC2)cc1]

N-Ethyl-4-(piperazin-1-yl)benzamide (283)

Using N-ethyl-4-fluorobenzamide 281 in the general procedure for nucleophilic aromatic substitution reactions with piperazine, the title compound was obtained as a white solid (77% yield). $^1$H NMR (400 MHz, DMSO-$d_6$) δ ppm 1.10 (t, J=7.07 Hz, 3H) 2.25 (br. s., 1H) 2.76-2.86 (m, 4H) 3.09-3.18 (m, 4H) 3.21-3.28 (m, 2H) 6.90 (m, J=8.84 Hz, 2H) 7.67-7.75 (m, 2H) 8.11 (t, J=5.31 Hz, 1H). ESI-MS: m/z 234.2 (M+H)$^+$. mp=131.3-134.4° C.

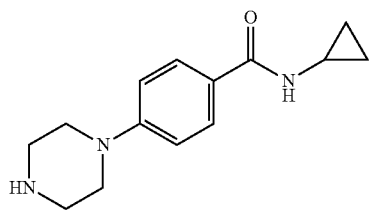 [SMILES: O=C(NC1CC1)c1ccc(N2CCNCC2)cc1]

N-Cyclopropyl-4-(piperazin-1-yl)benzamide (284)

Using N-cyclopropyl-4-fluorobenzamide in the general procedure for nucleophilic aromatic substitution reactions, the title compound was obtained as an off-white solid (15% yield). $^1$H NMR (400 MHz, DMSO-$d_6$) δ ppm 0.47-0.58 (m, 2H) 0.58-0.73 (m, 2H) 2.28 (br. s., 1H) 2.70-2.88 (m, 5H) 3.04-3.21 (m, 4H) 6.90 (m, J=9.09 Hz, 2H) 7.69 (m, J=8.84 Hz, 2H) 8.12 (d, J=3.79 Hz, 1H). ESI-MS: m/z 246.2 (M+H)$^+$. mp=175.1-177.2° C.

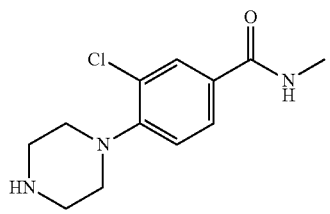 [SMILES: CNC(=O)c1ccc(N2CCNCC2)c(Cl)c1]

3-Chloro-N-methyl-4-(piperazin-1-yl)benzamide (285)

Using 3-chloro-4-fluoro-N-methylbenzamide 274 in the general procedure for nucleophilic aromatic substitution reactions, the title compound was obtained as a white solid (29% yield). $^1$H NMR (400 MHz, DMSO-$d_6$) δ ppm 2.59-2.70 (m, 2H) 2.73-2.79 (m, 3H) 2.87-2.93 (m, 2H) 2.95-3.01 (m, 2H) 3.03-3.11 (m, 2H) 3.23-4.03 (m, 1H) 7.14-7.23 (m, 1H) 7.77 (dd, J=8.46, 2.15 Hz, 1 H) 7.85-7.90 (m, 1H) 8.38-8.48 (m, 1H). ESI-MS: m/z 254.2 (M+H)$^+$. mp=176.4-189.1° C.

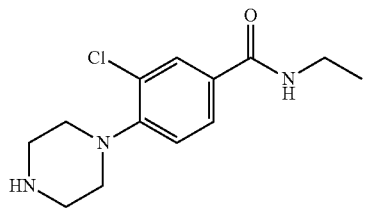 [SMILES: CCNC(=O)c1ccc(N2CCNCC2)c(Cl)c1]

3-Chloro-N-ethyl-4-(piperazin-1-yl)benzamide (286)

Using 3-chloro-4-fluoro-N-ethylbenzamide 275 in the general procedure for nucleophilic aromatic substitution reactions, the title compound was obtained as an off-white solid (74% yield). $^1$H NMR (400 MHz, DMSO-$d_6$) δ ppm 1.10 (t, J=7.20 Hz, 3H) 2.24 (br. s., 1H) 2.81-2.87 (m, 4H) 2.90-2.98 (m, 4H) 3.26 (qd, J=7.24, 5.56 Hz, 2H) 7.15 (d, J=8.59 Hz, 1H) 7.77 (dd, J=8.34, 2.02 Hz, 1 H) 7.87 (d, J=2.27 Hz, 1H) 8.43 (t, J=5.56 Hz, 1H). ESI-MS: m/z 268.2 (M+H)$^+$. mp=117.3-118.7° C.

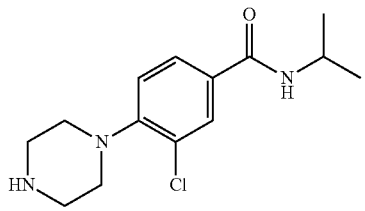 [SMILES: CC(C)NC(=O)c1ccc(N2CCNCC2)c(Cl)c1]

3-Chloro-N-isopropyl-4-(piperazin-1-yl)benzamide (287)

Using 3-chloro-4-fluoro-N-isopropylbenzamide 276 in the general procedure for nucleophilic aromatic substitution reactions, the title compound was obtained as an off-white solid (51% yield). ESI-MS: m/z 282.2 (M+H)⁺.

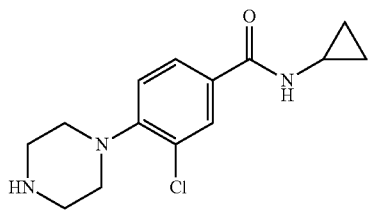 [SMILES: O=C(NC1CC1)c1ccc(N2CCNCC2)c(Cl)c1]

3-Chloro-N-cyclopropyl-4-(piperazin-1-yl)benzamide (288)

Using 3-chloro-N-cyclopropyl-4-fluorobenzamide 277 in the general procedure for nucleophilic aromatic substitution reactions, the title compound was obtained as a white solid (77% yield). ESI-MS: m/z 280.2 (M+H)⁺.

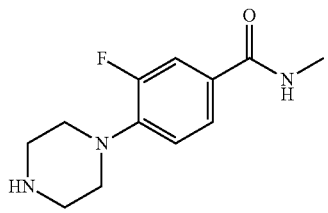 [SMILES: CNC(=O)c1ccc(N2CCNCC2)c(F)c1]

3-Fluoro-N-methyl-4-(piperazin-1-yl)benzamide (289)

Using 3,4-difluoro-N-methylbenzamide 278 in the general procedure for nucleophilic aromatic substitution reactions, the title compound was obtained as white solid (43% yield). $^1$H NMR (400 MHz, DMSO-d$_6$) δ ppm 2.34 (br. s., 1H) 2.57-2.66 (m, 1H) 2.72-2.79 (m, 3H) 2.80-2.88 (m, 3H) 2.95-3.04 (m, 3H) 3.07-3.16 (m, 1H) 6.99-7.11 (m, 1H) 7.52-7.65 (m, 2H) 8.29-8.38 (m, 1H). ESI-MS: m/z 238.2 (M+H)⁺. mp=174.1-192.9° C.

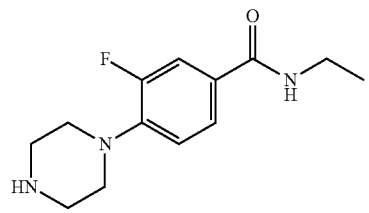 [SMILES: CCNC(=O)c1ccc(N2CCNCC2)c(F)c1]

3-Fluoro-N-ethyl-4-(piperazin-1-yl)benzamide (290)

Using 3,4-difluoro-N-ethylbenzamide 279 in the general procedure for nucleophilic aromatic substitution reactions, the title compound was obtained as white solid (80% yield). $^1$H NMR (400 MHz, DMSO-d$_6$) δ ppm 1.10 (t, J=7.20 Hz, 3H) 2.31 (br. s., 1H) 2.79-2.87 (m, 4H) 2.95-3.03 (m, 4H) 3.26 (qd, J=7.20, 5.68 Hz, 2H) 7.03 (t, J=8.59 Hz, 1H) 7.55-7.65 (m, 2H) 8.35 (t, J=5.43 Hz, 1 H). ESI-MS: m/z 252.2 (M+H)⁺. mp=142.4-144.9° C.

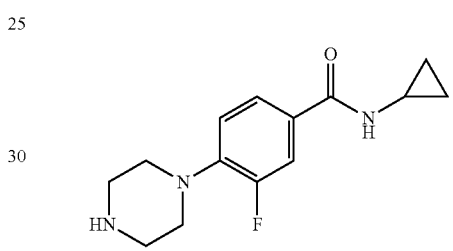

N-Cyclopropyl-3-fluoro-4-(piperazin-1-yl)benzamide (291)

Using N-cyclopropyl-3,4-difluorobenzamide 280 in the general procedure for nucleophilic aromatic substitution reactions, the title compound was obtained as white solid (33% yield). $^1$H NMR (400 MHz, DMSO-d$_6$) δ ppm 0.51-0.61 (m, 2H) 0.61-0.71 (m, 2H) 2.55-2.68 (m, 1H) 2.71-2.91 (m, 5H) 2.92-3.09 (m, 4H) 6.97-7.09 (m, 1H) 7.51-7.65 (m, 2H) 8.27 (d, J=4.04 Hz, 1H). ESI-MS: m/z 264.2 (M+H)⁺. mp=140.9-143.1° C.

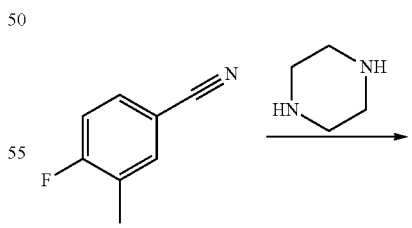

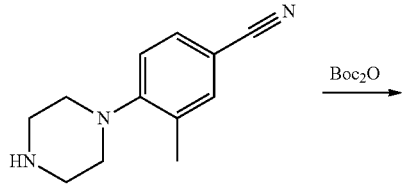

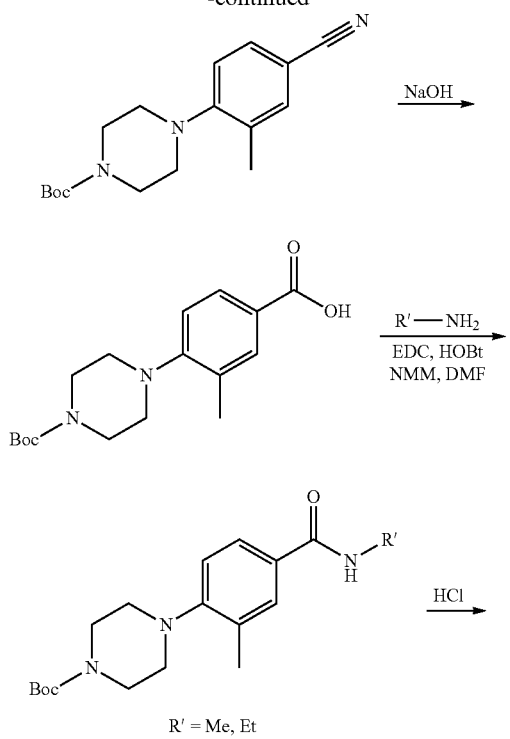

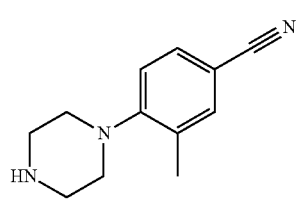

3-Methyl-4-(piperazin-1-yl)benzonitrile (292)

To a solution of 4-fluoro-3-methylbenzonitrile (2.5 g, 18.50 mmol) in DMSO (10.0 mL) was added piperazine (7.97 g, 92 mmol) at 23° C. The reaction was stirred at 140° C. for 16 hr. The reaction mixture was poured into H$_2$O (100 mL) and the reaction vessel was rinsed with H$_2$O (~50 mL). The resulting suspension was filtered, rinsed with H$_2$O (3×10 mL) and the resulting solid was dried in vacuo to provide the title compound as a white solid (2.593 g, 12.88 mmol, 69.6% yield). $^1$H NMR (400 MHz, DMSO-d$_6$) δ ppm 2.21-2.30 (m, 3H) 2.57-2.70 (m, 1H) 2.83 (s, 8H) 7.03-7.09 (m, 1H) 7.55-7.62 (m, 2H). ESI-MS: m/z 202.1 (M+H)$^+$.

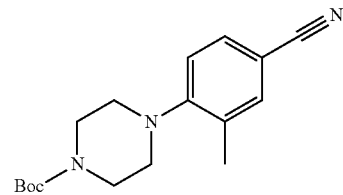 [SMILES: Cc1cc(C#N)ccc1N1CCN(C(=O)OC(C)(C)C)CC1]

tert-Butyl 4-(4-cyano-2-methylphenyl)piperazine-1-carboxylate (293)

To a solution of 3-methyl-4-(piperazin-1-yl)benzonitrile 292 (2.533 g, 12.59 mmol) in THF (25 mL) and MeOH (25 mL) was added di-tert-butyl dicarbonate (3.09 mL, 13.47 mmol) at 10° C. The reaction was stirred at 10° C. for 15 min, warmed to 23° C., and stirred at for 18 hr. The resulting suspension was filtered, rinsed with THF (3×5 mL) and the filtrate was concentrated in vacuo. $^1$H NMR (400 MHz, DMSO-d$_6$) δ ppm 1.42 (s, 9H) 2.28 (s, 3H) 2.83-2.92 (m, 4 H) 3.42-3.52 (m, 4H) 7.08-7.13 (m, 1H) 7.57-7.65 (m, 2H). ESI-MS: m/z 302.1 (M+H)$^+$.

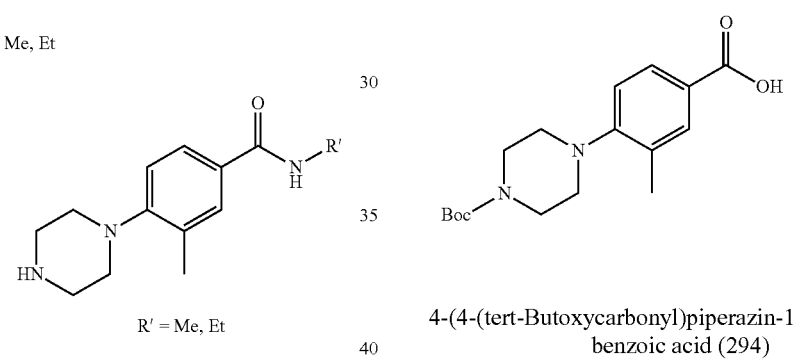

4-(4-(tert-Butoxycarbonyl)piperazin-1-yl)-3-methylbenzoic acid (294)

To a suspension of tert-butyl 4-(4-cyano-2-methylphenyl)piperazine-1-carboxylate 293 (3.685 g, 12.23 mmol) in EtOH (Ratio: 1.000, 50 mL) and water (Ratio: 1.000, 10 mL) was added sodium hydroxide solution (8.48 mL, 162 mmol) at 23° C. The NaOH solution was rinsed forward with water (ratio: 1.000, 2.5 mL) The reaction was stirred at 90° C. for 10 hr. The reaction mixture was cooled to 23° C., neutralized with 3N HCl (52 mL), filtered, rinsed with H$_2$O (3×10 mL), and the resulting solid was dried in vacuo to provide the title compound as an off-white solid (3.588 g, 11.20 mmol, 92% yield). $^1$H NMR (400 MHz, DMSO-d$_6$) δ ppm 1.42 (s, 9H) 2.29 (s, 3H) 2.81-2.90 (m, 4H) 3.42-3.53 (m, 4H) 7.05 (d, J=8.08 Hz, 1H) 7.70-7.77 (m, 2H) 12.61 (br. s., 1H). ESI-MS: m/z 321.2 (M+H)$^+$.

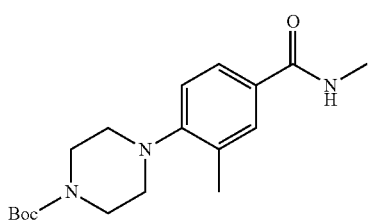 [SMILES: CNC(=O)c1ccc(N2CCN(C(=O)OC(C)(C)C)CC2)c(C)c1]

tert-Butyl 4-(2-methyl-4-(methylcarbamoyl)phenyl)-piperazine-1-carboxylate (295)

To a suspension of 4-(4-(tert-butoxycarbonyl)piperazin-1-yl)-3-methylbenzoic acid 294 (2.0 g, 6.24 mmol), methanamine hydrochloride (0.506 g, 7.49 mmol), N1-((ethylimino)methylene)-N3,N3-dimethylpropane-1,3-diamine hydrochloride (1.795 g, 9.36 mmol), and 1H-benzo[d][1,2,3]triazol-1-ol hydrate (1.434 g, 9.36 mmol) in DMF (8.5 mL) was added 4-methylmorpholine (3.43 mL, 31.2 mmol) at 23° C. The reaction was stirred at 23° C. for 2 hr. The reaction mixture was diluted with water (100 mL) and the product was extracted with EtOAc (3×100 mL). The organic extracts were combined, washed with 1N HCl (50 mL), saturated NaHCO$_3$ (50 mL), H$_2$O (50 mL), and brine (50 mL), dried over MgSO$_4$, filtered, rinsed with EtOAc, and dried in vacuo to provide the title compound as a yellow oil (1.90 g, 5.70 mmol, 91% yield). $^1$H NMR (400 MHz, DMSO-d$_6$) δ ppm 1.42 (s, 9H) 2.28 (s, 3H) 2.75 (d, J=4.55 Hz, 3H) 2.79-2.87 (m, 4H) 3.42-3.52 (m, 4H) 7.03 (d, J=8.34 Hz, 1H) 7.62 (dd, J=8.34, 2.27 Hz, 1H) 7.64-7.69 (m, 1H) 8.26 (q, J=4.46 Hz, 1H). ESI-MS: m/z 334.3 (M+H)$^+$.

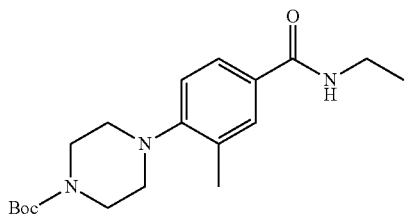 [SMILES: CCNC(=O)c1ccc(N2CCN(C(=O)OC(C)(C)C)CC2)c(C)c1]

tert-Butyl 4-(4-(ethylcarbamoyl)-2-methylphenyl)piperazine-1-carboxylate (296)

4-(4-(tert-butoxycarbonyl)piperazin-1-yl)-3-methylbenzoic acid 294 (0.866 g, 2.70 mmol), ethanamine hydrochloride (0.264 g, 3.24 mmol), N1-((ethylimino)methylene)-N3,N3-dimethylpropane-1,3-diamine hydrochloride (0.777 g, 4.05 mmol) and 1H-benzo[d][1,2,3]triazol-1-ol hydrate (0.621 g, 4.05 mmol) were suspended in DMF (3.68 mL) and 4-methylmorpholine (1.486 mL, 13.52 mmol) was added. The reaction mixture was stirred at ambient temperature for 2 h, diluted with water (50 mL), and extracted with ethyl acetate (3×75 mL). The combined organic extracts were washed with 1N HCl(aq., 25 mL), NaHCO$_3$ (sat. aq., 25 mL), water (25 mL), and brine (25 mL), dried over MgSO$_4$, concentrated in vacuo, and dried under vacuum to afford the title compound as a white solid (0.9327 g, 2.68 mmol, 99% yield). $^1$H NMR (DMSO-d$_6$, 400 MHz): δ=8.24 (t, J=5.4 Hz, 1H), 7.66 (d, J=1.8 Hz, 2H), 7.03 (d, J=8.3 Hz, 1H), 3.42-3.52 (m, 4H), 3.20-3.27 (m, 2H), 2.78-2.87 (m, 4H), 2.28 (s, 3H), 1.43 (s, 9H), 1.10 ppm (t, J=7.2 Hz, 3H). ESI-MS: m/z 348.4 (M+H)$^+$.

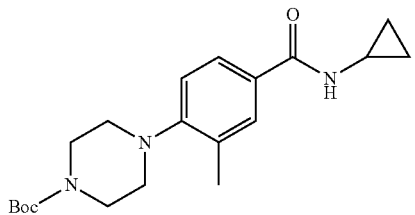 [SMILES: Cc1cc(C(=O)NC2CC2)ccc1N1CCN(C(=O)OC(C)(C)C)CC1]

tert-Butyl 4-(4-(cyclopropylcarbamoyl)-2-methylphenyl)piperazine-1-carboxylate (297)

Cyclopropylamine (0.389 mL, 5.62 mmol), N1-((ethylimino)methylene)-N3,N3-dimethylpropane-1,3-diamine hydrochloride (1.346 g, 7.02 mmol), and 1H-benzo[d][1,2,3]triazol-1-ol hydrate (1.075 g, 7.02 mmol) in DMF (6.4 mL) was added 4-methylmorpholine (2.57 mL, 23.41 mmol) at 23° C. The reaction was stirred at 23° C. for 2 hr. The reaction mixture was diluted with water (50 mL) and the product was extracted with EtOAc (3×50 mL). The organic extracts were combined, washed with 1N HCl (25 mL), saturated NaHCO$_3$ (25 mL), H$_2$O (25 mL), and brine (25 mL), dried over MgSO$_4$, filtered, rinsed with EtOAc, and dried in vacuo to provide the title compound as a light yellow solid (1.53 g, 4.26 mmol, 91% yield). $^1$H NMR (400 MHz, DMSO-d$_6$) δ ppm 0.51-0.60 (m, 2H) 0.60-0.70 (m, 2H) 1.42 (s, 9H) 2.28 (s, 3H) 2.77-2.87 (m, 5H) 3.41-3.53 (m, 4H) 7.02 (d, J=8.08 Hz, 1H) 7.61 (dd, J=8.21, 1.89 Hz, 1H) 7.64 (d, J=1.77 Hz, 1H) 8.25 (d, J=4.29 Hz, 1H). ESI-MS: m/z 360.3 (M+H)$^+$. mp=111.0-115.4° C.

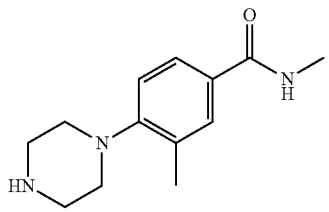 [SMILES: CNC(=O)c1ccc(N2CCNCC2)c(C)c1]

N,3-Dimethyl-4-(piperazin-1-yl)benzamide (298)

To tert-butyl 4-(2-methyl-4-(methylcarbamoyl)phenyl)piperazine-1-carboxylate (1.90 g, 5.70 mmol) was added hydrochloric acid solution (17.10 mL, 68.4 mmol) in dioxane at 23° C. The reaction was stirred at 23° C. for 30 min. The resulting suspension was diluted with Et$_2$O (20 mL), filtered, rinsed with Et$_2$O (3×10 mL), and the resulting solid was dried in vacuo to provide the title compound as an off-white, hygroscopic solid (1.70 g, 5.55 mmol, 97% yield). $^1$H NMR (400 MHz, DMSO-d$_6$) δ ppm 2.28 (s, 3H) 2.72-2.79 (m, 3H) 3.05-3.14 (m, 4H) 3.17-3.28 (m, 4H) 7.06 (d, J=8.34 Hz, 1H) 7.64-7.68 (m, 1H) 7.68-7.70 (m, 1H) 8.29-8.39 (m, 1H) 9.36 (br. s., 2H). ESI-MS: m/z 234.2 (M+H)$^+$.

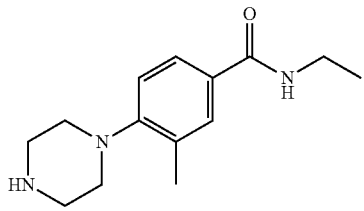 [SMILES: CCNC(=O)c1ccc(N2CCNCC2)c(C)c1]

N-Ethyl-3-methyl-4-(piperazin-1-yl)benzamide (299)

tert-butyl 4-(4-(ethylcarbamoyl)-2-methylphenyl)piperazine-1-carboxylate 296 (0.9323 g, 2.68 mmol) was diluted with 4.0M HCl in dioxane (8 mL) and stirred for 30 min. The thick white precipitate that formed was diluted with ethyl ether (10 mL) and stirred until a fine suspension resulted. The precipitate was filtered under nitrogen, washed with ether (5 mL) and dried in vacuum to afford the title compound as a white solid (0.7528 g, 2.65 mmol, 99% yield). $^1$H NMR (400 MHz, DMSO-$d_6$) δ ppm 1.10 (t, J=7.20 Hz, 3H) 2.29 (s, 3H) 3.00-3.14 (m, 4H) 3.16-3.32 (m, 6H) 7.07 (d, J=8.34 Hz, 1H) 7.62-7.71 (m, 2H) 8.34 (t, J=5.43 Hz, 1H) 9.17 (br. s., 2 H). ESI-MS: m/z 248.2 (M+H)$^+$.

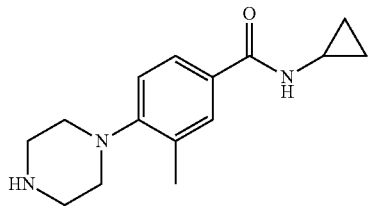 [SMILES: Cc1cc(C(=O)NC2CC2)ccc1N1CCNCC1]

N-Cyclopropyl-3-methyl-4-(piperazin-1-yl)benzamide (300)

To tert-butyl 4-(4-(cyclopropylcarbamoyl)-2-methylphenyl)piperazine-1-carboxylate 297 (1.490 g, 4.15 mmol) was added hydrochloric acid solution (8.72 mL, 34.9 mmol) in dioxane at 23° C. The reaction was stirred at 23° C. for 30 min. The resulting suspension was diluted with Et$_2$O (10 mL), filtered, rinsed with Et$_2$O (3×5 mL), and the resulting solid was dried in vacuo to provide the title compound as an off-white solid (1.37 g, 4.15 mmol, 100% yield). $^1$H NMR (400 MHz, DMSO-$d_6$) δ ppm 0.51-0.61 (m, 2H) 0.61-0.70 (m, 2H) 2.28 (s, 3H) 2.82 (tq, J=7.41, 3.99 Hz, 1H) 3.02-3.13 (m, 4H) 3.14-3.29 (m, 4H) 7.05 (d, J=8.34 Hz, 1H) 7.62-7.69 (m, 2 H) 8.32 (d, J=4.29 Hz, 1H) 9.38 (br. s., 2H). ESI-MS: m/z 260.2 (M+H)$^+$. mp=171.5-172.8° C.

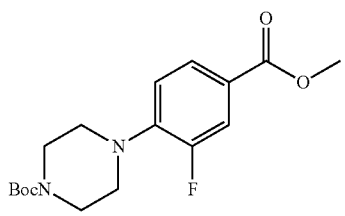 [SMILES: COC(=O)c1ccc(N2CCN(C(=O)OC(C)(C)C)CC2)c(F)c1]

tert-Butyl 4-(2-fluoro-4-(methoxycarbonyl)phenyl)piperazine-1-carboxylate (301)

Potassium carbonate (5.56 g, 40.3 mmol) and tert-butyl piperazine-1-carboxylate (6.92 g, 37.2 mmol) were combined; methyl 3,4-difluorobenzoate (5.33 g, 31.0 mmol) was added, and the reaction mixture was stirred at 90° C. for 1 d. The mixture was triturated with ethyl acetate (3×5 mL) and the combined organic extracts were filtered, concentrated down to about 5-10 mL, and subjected to flash column chromatography on silica gel (120 g SiO$_2$, hexanes:ethyl acetate 1:0 to 4:1) to afford the title compound as a white solid (4.702 g, 13.90 mmol, 44.9% yield). ESI-MS: m/z 339 (M+H)$^+$.

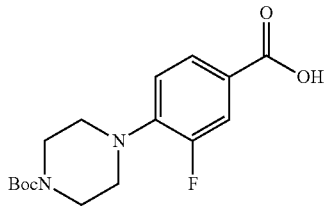 [SMILES: CC(C)(C)OC(=O)N1CCN(c2ccc(C(=O)O)cc2F)CC1]

4-(4-(tert-Butoxycarbonyl)piperazin-1-yl)-3-fluorobenzoic acid (302)

tert-butyl 4-(2-fluoro-4-(methoxycarbonyl)phenyl)piperazine-1-carboxylate 301 (4.6 g, 13.59 mmol) was suspended in 1,4-dioxane (68.0 mL) and treated with 1N LiOH (68.0 mL, 68.0 mmol). The reaction mixture was stirred at room temperature for 23 h. The reaction mixture was concentrated in vacuo until most of the dioxane was gone and acidified with HCl (4.5 N) until a thick precipitate resulted. The precipitate was filtered, washed with water, and dried in vacuum to afford the title compound as a brown solid (4.40 g, 13.57 mmol, 100% yield). ESI-MS: m/z 325 (M+H)$^+$.

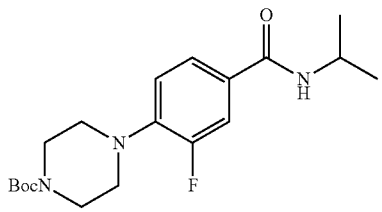 [SMILES: CC(C)NC(=O)c1ccc(N2CCN(C(=O)OC(C)(C)C)CC2)c(F)c1]

tert-Butyl 4-(2-fluoro-4-(isopropylcarbamoyl)phenyl)piperazine-1-carboxylate (303)

4-(4-(tert-butoxycarbonyl)piperazin-1-yl)-3-fluorobenzoic acid 302 (1.1 g, 3.39 mmol), propan-2-amine (0.241 g, 4.07 mmol), N1-((ethylimino)methylene)-N3,N3-dimethylpropane-1,3-diamine hydrochloride (0.975 g, 5.09 mmol) and 1H-benzo[d][1,2,3]triazol-1-ol hydrate (0.779 g, 5.09 mmol) were suspended in DMF (13.57 mL) and 4-methylmorpholine (1.864 mL, 16.96 mmol) was added. The reaction mixture was stirred at ambient temperature for 2 h, diluted with water (50 mL), and extracted with ethyl acetate (3×100 mL). The combined organic extracts were washed with brine (3×50 mL), dried over MgSO$_4$, and concentrated in vacuo to afford the title compound as an off-white solid (1.11 g, 3.04 mmol, 89% yield). ESI-MS: m/z 366 (M+H)$^+$.

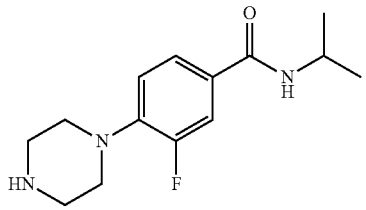 [SMILES: CC(C)NC(=O)c1ccc(N2CCNCC2)c(F)c1]

3-Fluoro-N-isopropyl-4-(piperazin-1-yl)benzamide (304)

tert-butyl 4-(2-fluoro-4-(isopropylcarbamoyl)phenyl)piperazine-1-carboxylate 303 (1.10 g, 3.01 mmol) was diluted

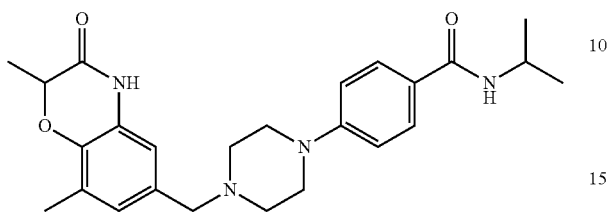

4-(4-((2,8-Dimethyl-3-oxo-3,4-dihydro-2H-benzo[b]
[1,4]oxazin-6-yl)methyl)piperazin-1-yl)-N-methyl-
benzamide (305)

Using 255 in the general procedure for hydrolysis of carboxylic esters followed by reaction of the resulting acid with isopropylamine in the general procedure for coupling an amine to a carboxylic acid, the title compound was obtained as a white solid: $^1$H NMR (DMSO-d$_6$, 400 MHz): δ=10.67 (s, 1H), 8.02 (d, J=7.8 Hz, 1H), 7.84 (d, J=8.8 Hz, 2H), 7.04 (d, J=8.8 Hz, 2H), 6.86 (d, J=9.6 Hz, 2H), 4.75 (q, J=6.8 Hz, 1H), 4.18 (dd, J=14.0, 6.7 Hz, 1H), 3.49 (s, 2H), 3.35 (br. s., 4H), 2.59 (br. s., 4 H), 2.28 (s, 3H), 1.53 (d, J=6.8 Hz, 3H), 1.25 ppm (d, J=6.6 Hz, 6H). ESI-MS: m/z 437 (M+H)$^+$.

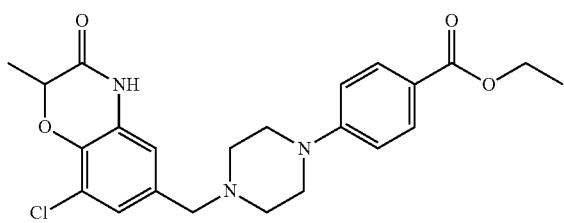 [SMILES: CCOC(=O)c1ccc(N2CCN(Cc3cc(Cl)c4c(c3)NC(=O)C(C)O4)CC2)cc1]

Ethyl 4-(4-((8-chloro-2-methyl-3-oxo-3,4-dihydro-
2H-benzo[b][1,4]oxazin-6-yl)methyl)piperazin-1-yl)
benzoate (306)

Using 15 and ethyl 4-(piperazin-1-yl)benzoate in the general procedure for reductive aminations, the title compound was obtained as a white solid: $^1$H NMR (400 MHz, DMSO-d6) δ ppm 1.28 (t, J=7.07 Hz, 3H) 1.44 (d, J=6.82 Hz, 3 H) 2.45-2.48 (m, 4H) 3.31 (d, J=4.55 Hz, 4H) 3.42 (s, 2H) 4.23 (q, J=7.24 Hz, 2H) 4.79 (q, J=6.82 Hz, 1H) 6.85 (d, J=1.52 Hz, 1H) 6.96 (d, J=8.84 Hz, 2H) 7.01 (d, J=1.52 Hz, 1H) 7.77 (d, J=9.09 Hz, 2H) 10.83 (s, 1H). ESI-MS: m/z 444.4 (M+H)$^+$.

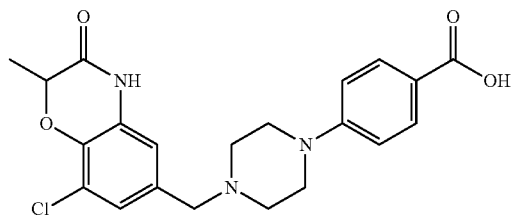 [SMILES: CC1Oc2c(Cl)cc(CN3CCN(c4ccc(C(=O)O)cc4)CC3)cc2NC1=O]

4-(4-((8-Chloro-2-methyl-3-oxo-3,4-dihydro-2H-
benzo[b][1,4]oxazin-6-yl)methyl)piperazin-1-yl)
benzoic acid (307)

Using 306 in the general procedure for hydrolysis of carboxylic esters, the title compound was obtained as a white solid: $^1$H NMR (400 MHz, DMSO-d6) δ ppm 1.47 (d, J=6.82 Hz, 3H) 3.05-3.27 (m, 4H) 3.38-3.44 (m, 2 H) 4.05 (d, J=12.63 Hz, 2H) 4.31 (d, J=4.29 Hz, 2H) 4.87 (q, J=6.82 Hz, 1H) 6.97-7.07 (m, 3H) 7.37 (s, 1H) 7.82 (d, J=8.59 Hz, 2H) 11.16 (s, 1H) 12.46 (br. s., 1H). ESI-MS: m/z 416.3 (M+H)$^+$.

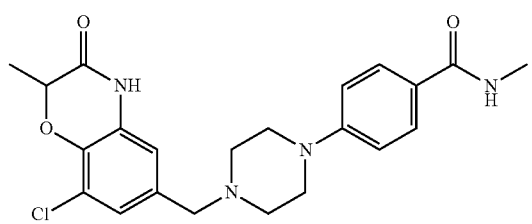

4-(4-((8-Chloro-2-methyl-3-oxo-3,4-dihydro-2H-
benzo[b][1,4]oxazin-6-yl)methyl)piperazin-1-yl)-N-
methylbenzamide (308)

Using 307 and methylamine hydrochloride in the general procedure for coupling an amine to a carboxylic acid, the title compound was obtained as a white solid: $^1$H NMR (400 MHz, DMSO-d6) δ ppm 1.44 (d, J=6.82 Hz, 3H) 2.45-2.49 (m, 4H) 2.73 (d, J=4.55 Hz, 3H) 3.24 (br. s., 4H) 3.42 (s, 2H) 4.79 (q, J=6.74 Hz, 1H) 6.86 (d, J=1.77 Hz, 1H) 6.93 (d, J=8.84 Hz, 2H) 7.01 (d, J=1.52 Hz, 1H) 7.70 (d, J=8.84 Hz, 2H) 8.13 (d, J=4.55 Hz, 1H) 10.83 (s, 1H). ESI-MS: m/z 429.4 (M+H)$^+$.

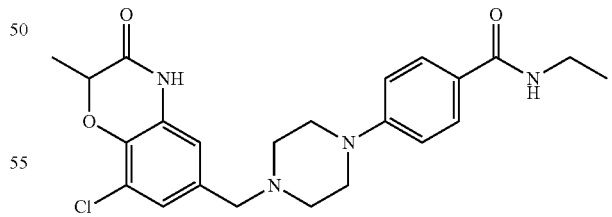

4-(4-((8-Chloro-2-methyl-3-oxo-3,4-dihydro-2H-
benzo[b][1,4]oxazin-6-yl)methyl)piperazin-1-yl)-N-
ethylbenzamide (309)

Using 307 and ethylamine hydrochloride in the general procedure for coupling an amine to a carboxylic acid, the title compound was obtained as a white solid: $^1$H NMR (400 MHz, DMSO-d6) δ ppm 1.09 (t, J=7.20 Hz, 3H) 1.44 (d, J=6.82 Hz,

--- with 4.0M HCl in dioxane (3 mL) and stirred for 30 min. The thick white precipitate that formed was diluted with ethyl ether (10 mL) and stirred until a fine suspension resulted. The precipitate was filtered under nitrogen and dried in vacuum to afford the title compound as a white solid. ESI-MS: m/z 302 (M+H)$^+$.

3H) 2.44-2.48 (m, 4H) 3.18-3.28 (m, 6H) 3.42 (s, 2 H) 4.79 (q, J=6.74 Hz, 1H) 6.86 (s, 1H) 6.93 (d, J=8.84 Hz, 2H) 7.01 (s, 1H) 7.71 (d, J=8.59 Hz, 2H) 8.17 (t, J=5.31 Hz, 1H) 10.84 (s, 1H). ESI-MS: m/z 443.4 (M+H)+.

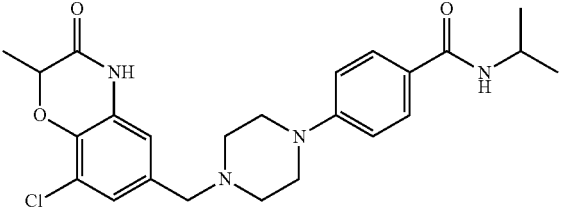 [SMILES: CC(C)NC(=O)c1ccc(N2CCN(Cc3cc(Cl)c4c(c3)NC(=O)C(C)O4)CC2)cc1]

4-(4-((8-Chloro-2-methyl-3-oxo-3,4-dihydro-2H-benzo[b][1,4]oxazin-6-yl)methyl)piperazin-1-yl)-N-isopropylbenzamide (310)

Using 307 and isopropylamine in the general procedure for coupling an amine to a carboxylic acid, the title compound was obtained as a white solid: $^1$H NMR (400 MHz, DMSO-d$_6$) δ ppm 1.13 (d, J=6.57 Hz, 6H) 1.44 (d, J=6.82 Hz, 3H) 2.44-2.49 (m, 4H) 3.24 (br. s., 4H) 3.43 (s, 2H) 3.99-4.13 (m, 1H) 4.79 (q, J=6.65 Hz, 1H) 6.86 (s, 1H) 6.92 (d, J=8.59 Hz, 2H) 7.01 (s, 1H) 7.72 (d, J=8.59 Hz, 2H) 7.90 (d, J=7.58 Hz, 1H) 10.83 (s, 1H). ESI-MS: m/z 457.4 (M+H)+.

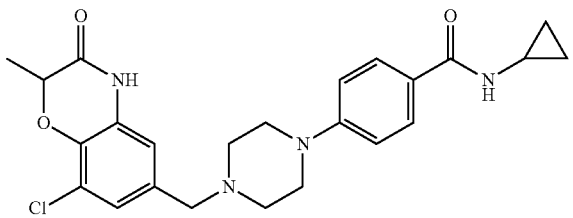 [SMILES: CC1Oc2c(Cl)cc(CN3CCN(c4ccc(C(=O)NC5CC5)cc4)CC3)cc2NC1=O]

4-(4-((8-Chloro-2-methyl-3-oxo-3,4-dihydro-2H-benzo[b][1,4]oxazin-6-yl)methyl)piperazin-1-yl)-N-cyclopropylbenzamide (311)

Using 307 and cyclopropylamine in the general procedure for coupling an amine to a carboxylic acid, the title compound was obtained as a white solid: $^1$H NMR (400 MHz, DMSO-d6) δ ppm 0.50-0.56 (m, 2H) 0.62-0.69 (m, 2H) 1.45 (d, J=6.82 Hz, 3H) 2.45-2.49 (m, 4H) 2.80 (td, J=7.26, 3.66 Hz, 1H) 3.25 (br. s., 4H) 3.43 (s, 2H) 4.80 (q, J=6.74 Hz, 1H) 6.87 (s, 1H) 6.92 (d, J=8.84 Hz, 2H) 7.01 (s, 1H) 7.70 (d, J=8.84 Hz, 2H) 8.14 (d, J=3.79 Hz, 1H) 10.84 (s, 1H). ESI-MS: m/z 455.4 (M+H)+.

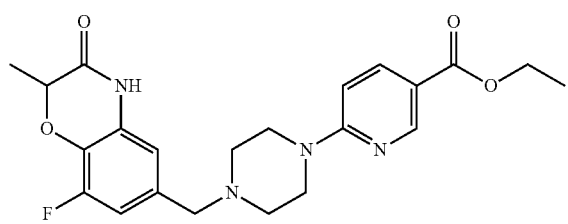 [SMILES: CCOC(=O)c1ccc(N2CCN(Cc3cc(F)c4c(c3)NC(=O)C(C)O4)CC2)nc1]

Ethyl 6-(4-((8-fluoro-2-methyl-3-oxo-3,4-dihydro-2H-benzo[b][1,4]oxazin-6-yl)methyl)piperazin-1-yl)nicotinate (312)

Using 265 and ethyl 6-(piperazin-1-yl)nicotinate in the general procedure for reductive aminations, the title compound was obtained as a white solid: $^1$H NMR (DMSO-d$_6$, 400 MHz): δ=10.84 (s, 1H), 8.58-8.67 (m, 1H), 7.94 (dd, J=9.1, 2.3 Hz, 1H), 6.79-6.92 (m, 2H), 6.73 (s, 1H), 4.76 (q, J=6.8 Hz, 1H), 4.25 (q, J=7.1 Hz, 2 H), 3.58-3.72 (m, 4H), 3.42 (s, 2H), 2.44 (t, J=4.8 Hz, 4H), 1.45 (d, J=6.8 Hz, 3H), 1.29 ppm (t, J=7.1 Hz, 3H). ESI-MS: m/z 429.4 (M+H)+.

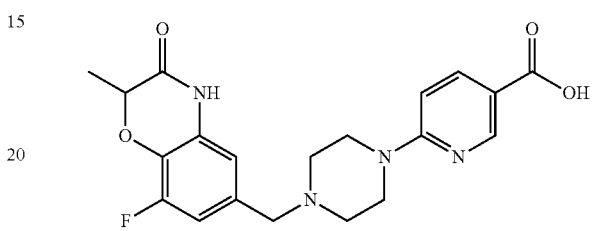

6-(4-((8-Fluoro-2-methyl-3-oxo-3,4-dihydro-2H-benzo[b][1,4]oxazin-6-yl)methyl)piperazin-1-yl)nicotinic acid (313)

Using 312 in the general procedure for hydrolysis of carboxylic esters, the title compounds was obtained as a white solid: $^1$H NMR (DMSO-d$_6$, 400 MHz): δ=12.53 (br. s., 1H), 10.84 (s, 1H), 8.62 (d, J=2.0 Hz, 1H), 7.93 (dd, J=9.0, 1.9 Hz, 1H), 6.85 (d, J=9.6 Hz, 2H), 6.73 (s, 1H), 4.76 (q, J=6.7 Hz, 1H), 3.64 (br. s., 4H), 3.42 (s, 2H), 2.44 (br. s., 4H), 1.45 ppm (d, J=6.8 Hz, 3H). ESI-MS: m/z 401.4 (M+H)+.

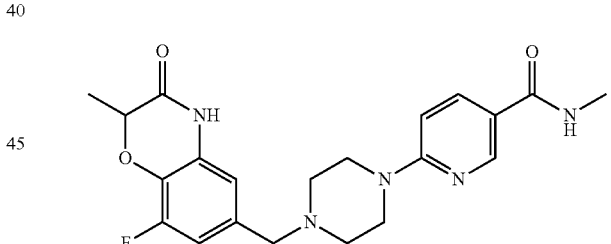

6-(4-((8-Fluoro-2-methyl-3-oxo-3,4-dihydro-2H-benzo[b][1,4]oxazin-6-yl)methyl)piperazin-1-yl)-N-methylnicotinamide (314)

Using 313 and methylamine hydrochloride in the general procedure for coupling an amine to a carboxylic acid, the title compound was obtained as a white solid: $^1$H NMR (DMSO-d$_6$, 400 MHz): δ=11.16 (s, 1H), 8.63 (d, J=2.3 Hz, 1H), 8.32 (d, J=4.5 Hz, 1H), 8.03 (dd, J=9.0, 2.4 Hz, 1H), 7.09 (dd, J=11.1, 1.8 Hz, 1H), 6.98 (d, J=9.1 Hz, 1H), 6.85 (s, 1H), 4.84 (q, J=6.7 Hz, 1H), 4.53 (d, J=10.4 Hz, 2H), 4.30 (s, 2H), 3.42 (br. s., 2H), 2.99-3.28 (m, 4H), 2.76 (d, J=4.3 Hz, 3H), 1.48 ppm (d, J=6.8 Hz, 3H). ESI-MS: m/z 414.4 (M+H)+.

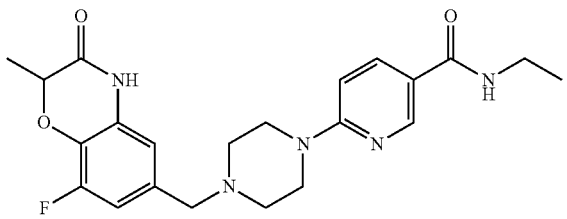 [SMILES: CCNC(=O)c1ccc(N2CCN(Cc3cc(F)c4c(c3)NC(=O)C(C)O4)CC2)nc1]

N-Ethyl-6-(4-((8-fluoro-2-methyl-3-oxo-3,4-dihydro-2H-benzo[b][1,4]oxazin-6-yl)methyl)piperazin-1-yl)nicotinamide (315)

Using 313 and ethylamine hydrochloride in the general procedure for coupling an amine to a carboxylic acid, the title compound was obtained as a white solid: $^1$H NMR (DMSO-d$_6$, 400 MHz): δ=10.82 (br. s., 1H), 8.58 (d, J=2.3 Hz, 1 H), 8.24 (t, J=5.4 Hz, 1H), 7.94 (dd, J=9.0, 2.4 Hz, 1H), 6.77-6.90 (m, 2H), 6.73 (s, 1H), 4.69-4.82 (m, 1H), 3.53-3.64 (m, 4H), 3.42 (s, 2H), 3.19-3.31 (m, 2H), 2.44 (t, J=4.8 Hz, 4H), 1.45 (d, J=6.8 Hz, 3H), 1.10 ppm (t, J=7.2 Hz, 3H). ESI-MS: m/z 428.4 (M+H)$^+$.

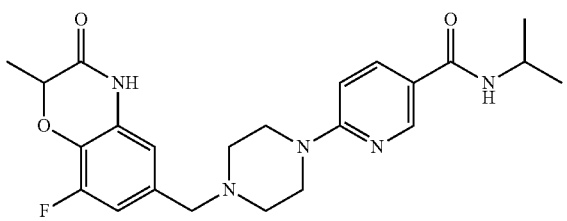 [SMILES: CC(C)NC(=O)c1ccc(N2CCN(Cc3cc(F)c4c(c3)NC(=O)C(C)O4)CC2)nc1]

6-(4-((8-Fluoro-2-methyl-3-oxo-3,4-dihydro-2H-benzo[b][1,4]oxazin-6-yl)methyl)piperazin-1-yl)-N-isopropylnicotinamide (316)

Using 313 and isopropylamine in the general procedure for coupling an amine to a carboxylic acid, the title compound was obtained as a white solid: $^1$H NMR (DMSO-d$_6$, 400 MHz): δ=10.76 (s, 1H), 8.51 (d, J=2.3 Hz, 1H), 7.81-7.95 (m, 2H), 6.71-6.83 (m, 2H), 6.66 (s, 1H), 4.69 (q, J=6.8 Hz, 1H), 3.91-4.09 (m, 1H), 3.44-3.60 (m, 4H), 3.35 (s, 2H), 2.37 (t, J=4.7 Hz, 4H), 1.38 (d, J=6.8 Hz, 3H), 1.07 ppm (d, J=6.6 Hz, 6H). ESI-MS: m/z 442.4 (M+H)$^+$.

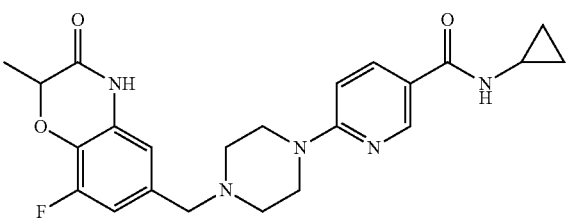

N-Cyclopropyl-6-(4-((8-fluoro-2-methyl-3-oxo-3,4-dihydro-2H-benzo[b][1,4]oxazin-6-yl)methyl)piperazin-1-yl)nicotinamide (317)

Using 313 and cyclopropylamine in the general procedure for coupling an amine to a carboxylic acid, the title compound was obtained as a white solid: $^1$H NMR (DMSO-d$_6$, 400 MHz): δ=10.76 (s, 1H), 8.48 (d, J=2.3 Hz, 1H), 8.13 (d, J=4.0 Hz, 1H), 7.84 (dd, J=9.1, 2.5 Hz, 1H), 6.70-6.83 (m, 2H), 6.64 (d, J=11.4 Hz, 1H), 4.69 (q, J=6.8 Hz, 1H), 3.44-3.57 (m, 4H), 3.35 (s, 2H), 2.72 (td, J=7.2, 3.8 Hz, 1H), 2.36 (t, J=4.8 Hz, 4H), 1.38 (d, J=6.8 Hz, 3H), 0.54-0.67 (m, 2H), 0.40-0.52 ppm (m, 2H). ESI-MS: m/z 440.4 (M+H)$^+$.

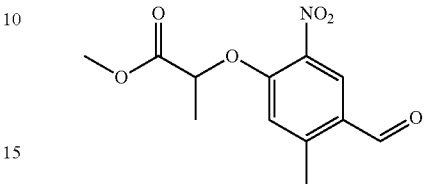

Methyl 2-(4-formyl-5-methyl-2-nitrophenoxy)propanoate (318)

Using 4-hydroxy-2-methyl-5-nitrobenzaldehyde as the phenol and methyl-2-bromopropanoate as the alkylating agent in the general procedure for alkylation of substituted-2-nitrophenols gives the title compound as a white solid: $^1$H NMR (400 MHz, DMSO-d6) δ ppm 1.58 (d, J=6.82 Hz, 3 H) 2.66 (s, 3H) 3.70 (s, 3H) 5.47 (q, J=6.82 Hz, 1H) 7.26 (s, 1H) 8.36 (s, 1H) 10.11. ESI-MS: m/z 268.2 (M+H)$^+$.

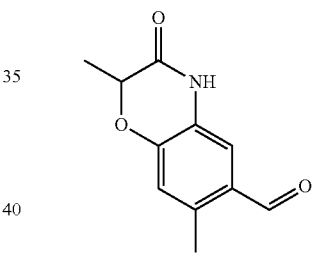

2,7-Dimethyl-3-oxo-3,4-dihydro-2H-benzo[b][1,4]oxazine-6-carbaldehyde (319)

Using 318 in the general procedure for reduction of a nitro group and subsequent ring closure gives the title compound as an off-white solid: $^1$H NMR (400 MHz, DMSO-d6) δ ppm 1.44 (d, J=6.82 Hz, 3H) 2.54 (s, 3H) 4.76-4.83 (m, 1H) 6.93 (s, 1H) 7.31 (s, 1H) 10.11 (s, 1H) 10.84 (s, 1H). ESI-MS: m/z 206.1 (M+H)$^+$.

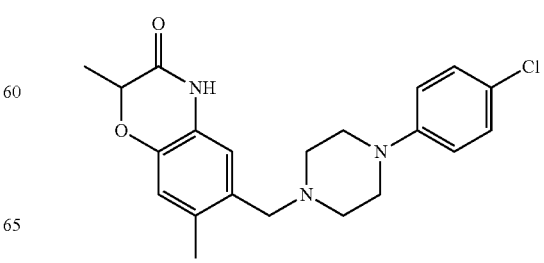

6-((4-(4-Chlorophenyl)piperazin-1-yl)methyl)-2,7-dimethyl-2H-benzo[b][1,4]oxazin-3(4H)-one (320)

Using 319 and 1-(4-chlorophenyl)piperazine in the general procedure for reductive aminations, the title compound was obtained as a white solid: ¹H NMR (400 MHz, DMSO-d6) δ ppm 1.39 (d, J=6.82 Hz, 3H) 2.23 (s, 3H) 2.46-2.50 (m, 4 H) 3.07-3.14 (m, 4H) 3.34-3.42 (m, 2H) 4.57-4.63 (m, 1H) 6.77 (s, 1H) 6.83 (s, 1H) 6.93 (m, 2H) 7.22 (m, 2H) 10.50 (s, 1H). ESI-MS: m/z 386.3 (M+H)⁺.

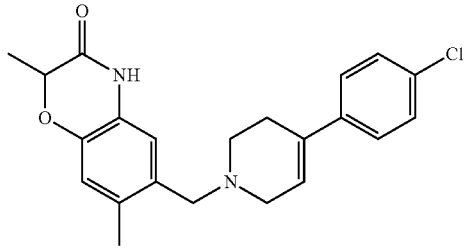 [SMILES: Cc1cc2c(cc1CN1CC=C(c3ccc(Cl)cc3)CC1)NC(=O)C(C)O2]

6-((4-(4-Chlorophenyl)-5,6-dihydropyridin-1(2H)-yl)methyl)-2,7-dimethyl-2H-benzo[b][1,4]oxazin-3(4H)-one (321)

Using 319 and 4-(4-chlorophenyl)-1,2,3,6-tetrahydropyridine in the general procedure for reductive aminations, the title compound was obtained as a white solid: ¹H NMR (400 MHz, DMSO-d6) δ ppm 1.39 (d, J=6.82 Hz, 3H) 2.22 (s, 3H) 2.41-2.48 (m, 2H) 2.60-2.65 (m, 2H) 3.04-3.10 (m, 2H) 3.39-3.48 (m, 2H) 4.57-4.63 (m, 1H) 6.19-6.23 (m, 1H) 6.77 (s, 1H) 6.86 (s, 1H) 7.38 (m, 2H) 7.45 (m, 2H) 10.49 (s, 1H). ESI-MS: m/z 383.3 (M+H)⁺.

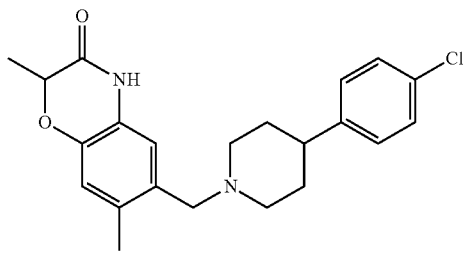 [SMILES: Cc1cc2c(cc1CN1CCC(c3ccc(Cl)cc3)CC1)NC(=O)C(C)O2]

6-((4-(4-Chlorophenyl)piperidin-1-yl)methyl)-2,7-dimethyl-2H-benzo[b][1,4]oxazin-3(4H)-one (322)

Using 319 and 4-(4-chlorophenyl)piperidine in the general procedure for reductive aminations, the title compound was obtained as a white solid: ¹H NMR (400 MHz, DMSO-d6) δ ppm 1.39 (d, J=6.57 Hz, 3H) 1.52-1.64 (m, 2H) 1.68-1.77 (m, 2H) 2.00-2.09 (m, 2H) 2.22 (s, 3H) 2.52-2.56 (m, 1H) 2.85-2.92 (m, 2H) 3.34-3.40 (m, 2H) 4.56-4.63 (m, 1H) 6.76 (s, 1H) 6.82 (s, 1H) 7.27 (m, 2H) 7.34 (m, 2H) 10.48 (s, 1H). ESI-MS: m/z 385.3 (M+H)⁺.

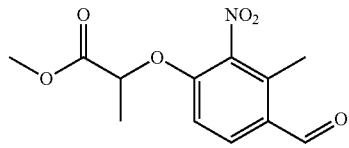 [SMILES: COC(=O)C(C)Oc1ccc(C=O)c(C)c1[N+](=O)[O-]]

Methyl 2-(4-formyl-3-methyl-2-nitrophenoxy)propanoate (323)

Using 4-hydroxy-2-methyl-3-nitrobenzaldehyde as the phenol and methyl-2-bromopropanoate as the alkylating agent in the general procedure for alkylation of substituted-2-nitrophenols gives the title compound as a white solid: ¹H NMR (400 MHz, DMSO-d6) δ ppm 1.51 (d, J=6.82 Hz, 3 H) 2.50 (s, 3H) 3.69 (s, 3H) 5.40 (q, J=6.82 Hz, 1H) 7.29 (d, J=9.09 Hz, 1H) 8.00 (d, J=8.84 Hz, 1H) 10.12 (s, 1H). ESI-MS: m/z 268.2 (M+H)⁺.

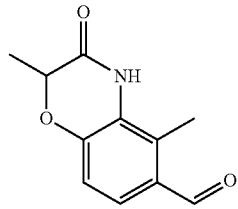

2,5-Dimethyl-3-oxo-3,4-dihydro-2H-benzo[b][1,4]oxazine-6-carbaldehyde (324)

Using 323 in the general procedure for reduction of nitro group and subsequent ring closure gives the title compound as an off white solid: ESI-MS: m/z 206.1 (M+H)⁺.

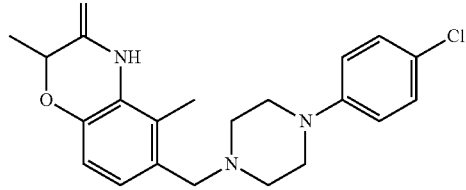

6-((4-(4-Chlorophenyl)piperazin-1-yl)methyl)-2,5-dimethyl-2H-benzo[b][1,4]oxazin-3(4H)-one (325)

Using 324 and 1-(4-chlorophenyl)piperazine in the general procedure for reductive aminations, the title compound was obtained as a white solid: ¹H NMR (400 MHz, DMSO-d6) δ ppm 1.40 (d, J=6.57 Hz, 3H) 2.24 (s, 3H) 2.43-2.49 (m, 4 H) 3.04-3.12 (m, 4H) 3.36-3.46 (m, 2H) 4.51-4.58 (m, 1H) 6.77 (d, J=8.08 Hz, 1H) 6.84 (d, J=8.34 Hz, 1H) 6.92 (m, 2H) 7.21 (m, 2H) 10.13 (s, 1H). ESI-MS: m/z 386.3 (M+H)⁺.

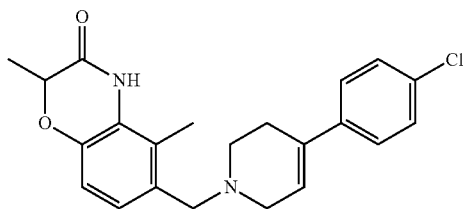 [SMILES: Cc1c(CN2CC=C(c3ccc(Cl)cc3)CC2)ccc2c1NC(=O)C(C)O2]

6-((4-(4-Chlorophenyl)-5,6-dihydropyridin-1(2H)-yl)methyl)-2,5-dimethyl-2H-benzo[b][1,4]oxazin-3(4H)-one (326)

Using 324 and 4-(4-chlorophenyl)-1,2,3,6-tetrahydropyridine in the general procedure for reductive aminations, the title compound was obtained as a white solid: $^1$H NMR (400 MHz, DMSO-d6) δ ppm 1.41 (d, J=6.82 Hz, 3H) 2.24 (s, 3H) 2.37-2.46 (m, 2H) 2.58-2.65 (m, 2H) 3.01-3.07 (m, 2H) 3.43-3.52 (m, 2H) 4.55 (q, J=6.65 Hz, 1H) 6.15-6.22 (m, 1H) 6.77 (d, J=8.08 Hz, 1H) 6.86 (d, J=8.08 Hz, 1H) 7.34-7.40 (m, 2H) 7.41-7.48 (m, 2H) 10.13 (s, 1H). ESI-MS: m/z 383.3 (M+H)$^+$.

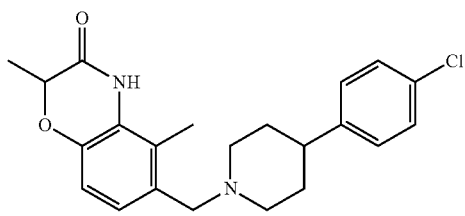 [SMILES: Cc1c(CN2CCC(c3ccc(Cl)cc3)CC2)ccc2c1NC(=O)C(C)O2]

6-((4-(4-Chlorophenyl)piperidin-1-yl)methyl)-2,5-dimethyl-2H-benzo[b][1,4]oxazin-3(4H)-one (327)

Using 324 and 4-(4-chlorophenyl)piperidine in the general procedure for reductive aminations, the title compound was obtained as a white solid: $^1$H NMR (400 MHz, DMSO-d$_6$) δ ppm 1.40 (d, J=6.57 Hz, 3H) 1.46-1.64 (m, 2H) 1.64-1.77 (m, 2H) 1.97-2.08 (m, 2H) 2.24 (s, 3H) 2.51-2.55 (m, 1H) 2.83-2.92 (m, 2H) 3.34-3.41 (m, 2H) 4.51-4.57 (m, 1H) 6.76 (d, J=8.08 Hz, 1H) 6.83 (d, J=8.08 Hz, 1H) 7.26 (m, 2 H) 7.32 (m, 2H) 10.12 (s, 1H). ESI-MS: m/z 385.3 (M+H)$^+$.

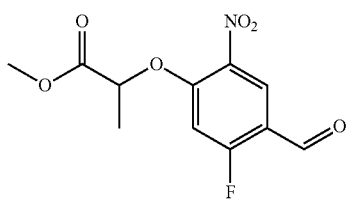 [SMILES: COC(=O)C(C)Oc1cc(F)c(C=O)cc1[N+](=O)[O-]]

Methyl 2-(5-fluoro-4-formyl-2-nitrophenoxy)propanoate (328)

Using 2-fluoro-4-hydroxy-5-nitrobenzaldehyde as the phenol and methyl-2-bromopropanoate as the alkylating agent in the general procedure for alkylation of substituted-2-nitrophenols gives the title compound as a white solid: ESI-MS: m/z 272.1 (M+H)$^+$.

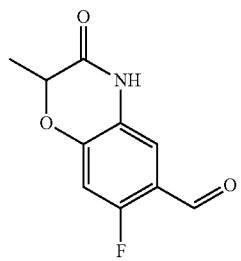

7-Fluoro-2-methyl-3-oxo-3,4-dihydro-2H-benzo[b][1,4]oxazine-6-carbaldehyde (329)

Using 328 in the general procedure for reduction of nitro group and subsequent ring closure gives the title compound as an off white solid: $^1$H NMR (400 MHz, DMSO-d6) δ ppm 1.46 (d, J=6.82 Hz, 3H) 4.89 (q, J=6.82 Hz, 1H) 7.11 (d, J=11.12 Hz, 1H) 7.29 (d, J=6.82 Hz, 1H) 10.09 (s, 1H) 10.93 (s, 1H). ESI-MS: m/z 210.1 (M+H)$^+$.

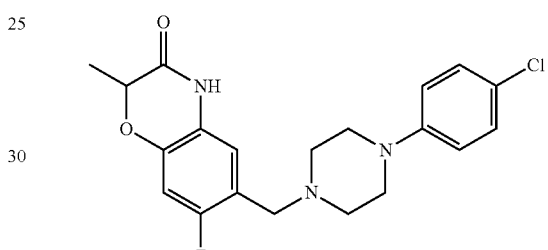

6-((4-(4-Chlorophenyl)piperazin-1-yl)methyl)-7-fluoro-2-methyl-2H-benzo[b][1,4]oxazin-3(4H)-one (330)

Using 328 and 1-(4-chlorophenyl)piperazine in the general procedure for reductive aminations, the title compound was obtained as a white solid: $^1$H NMR (400 MHz, DMSO-d6) δ ppm 1.42 (d, J=6.82 Hz, 3H) 2.50-2.54 (m, 4H) 3.07-3.16 (m, 4H) 3.42-3.51 (m, 2H) 4.69 (q, J=6.82 Hz, 1H) 6.88 (d, J=10.36 Hz, 1H) 6.90-6.96 (m, 3H) 7.18-7.25 (m, 2H) 10.64 (s, 1H). ESI-MS: m/z 390.3 (M+H)$^+$.

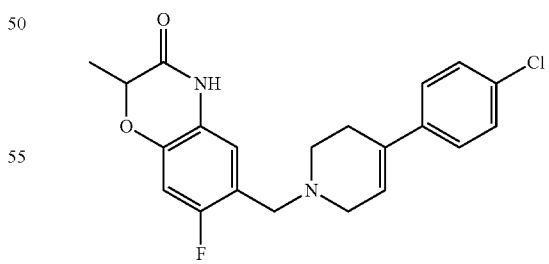

6-((4-(4-Chlorophenyl)-5,6-dihydropyridin-1(2H)-yl)methyl)-7-fluoro-2-methyl-2H-benzo[b][1,4]oxazin-3(4H)-one (331)

Using 328 and 4-(4-chlorophenyl)-1,2,3,6-tetrahydropyridine in the general procedure for reductive aminations, the title compound was obtained as an off-white solid: ¹H NMR (400 MHz, DMSO-d6) δ ppm 1.42 (d, J=6.82 Hz, 3 H) 2.41-2.48 (m, 2H) 2.60-2.69 (m, 2H) 3.04-3.11 (m, 2H) 3.54 (s, 2H) 4.69 (q, J=6.65 Hz, 1H) 6.18-6.22 (m, 1H) 6.88 (d, J=10.36 Hz, 1H) 6.96 (d, J=7.33 Hz, 1H) 7.36-7.40 (m, 2H) 7.42-7.47 (m, 2H) 10.63 (s, 1H). ESI-MS: m/z 387.3 (M+H)⁺.

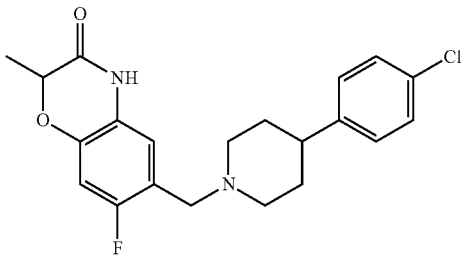 [SMILES: CC1Oc2cc(F)c(CN3CCC(c4ccc(Cl)cc4)CC3)cc2NC1=O]

6-((4-(4-Chlorophenyl)piperidin-1-yl)methyl)-7-fluoro-2-methyl-2H-benzo[b][1,4]oxazin-3(4H)-one (332)

Using 328 and 4-(4-chlorophenyl)piperidine in the general procedure for reductive aminations, the title compound was obtained as a white solid: ¹H NMR (400 MHz, DMSO-d6) δ ppm 1.41 (d, J=6.82 Hz, 3H) 1.52-1.77 (m, 4H) 2.00-2.11 (m, 2H) 2.51-2.55 (m, 1H) 2.85-2.94 (m, 2H) 3.40-3.48 (m, 2H) 4.69 (q, J=6.82 Hz, 1H) 6.86 (d, J=10.36 Hz, 1H) 6.93 (d, J=7.07 Hz, 1H) 7.26 (m, 2H) 7.34 (m, 2H) 10.63 (s, 1H). ESI-MS: m/z 389.3 (M+H)⁺.

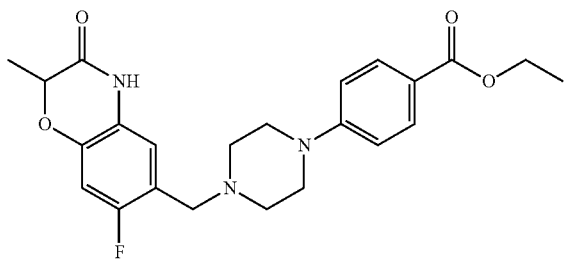 [SMILES: CCOC(=O)c1ccc(N2CCN(Cc3cc4c(cc3F)OC(C)C(=O)N4)CC2)cc1]

Ethyl 4-(4-((7-fluoro-2-methyl-3-oxo-3,4-dihydro-2H-benzo[b][1,4]oxazin-6-yl)methyl)piperazin-1-yl)benzoate (333)

Using 328 and ethyl 4-(piperazin-1-yl)benzoate in the general procedure for reductive aminations, the title compound was obtained as an off-white solid: ¹H NMR (400 MHz, DMSO-d6) δ ppm 1.28 (t, J=7.20 Hz, 3H) 1.42 (d, J=6.82 Hz, 3H) 2.50-2.55 (m, 4H) 3.26-3.33 (m, 4H) 3.43-3.52 (m, 2H) 4.23 (q, J=7.07 Hz, 2 H) 4.66-4.73 (m, 1H) 6.88 (d, J=10.36 Hz, 1H) 6.92-7.00 (m, 3H) 7.75-7.80 (m, 2H) 10.65 (s, 1H). ESI-MS: m/z 428.4 (M+H)⁺.

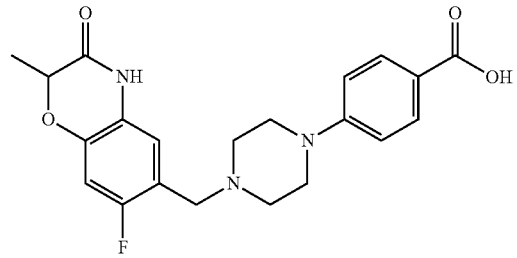 [SMILES: CC1Oc2cc(F)c(CN3CCN(c4ccc(C(=O)O)cc4)CC3)cc2NC1=O]

4-(4-((7-Fluoro-2-methyl-3-oxo-3,4-dihydro-2H-benzo[b][1,4]oxazin-6-yl)methyl)piperazin-1-yl)benzoic acid (334)

Using 333 in the general procedure for hydrolysis of carboxylic esters, the title compound was obtained as an off-white solid: ¹H NMR (400 MHz, DMSO-d6) δ ppm 1.36-1.50 (m, 3H) 3.14-3.38 (m, 5H) 3.40-3.51 (m, 3 H) 3.94-4.13 (m, 1H) 4.29-4.44 (m, 1H) 4.62-4.83 (m, 1H) 6.87-7.17 (m, 4H) 7.70-7.88 (m, 2H) 10.54-10.72 (m, 1H) 11.02 (br. s., 1H) 12.39 (br. s., 1H). ESI-MS: m/z 400.2 (M+H)⁺.

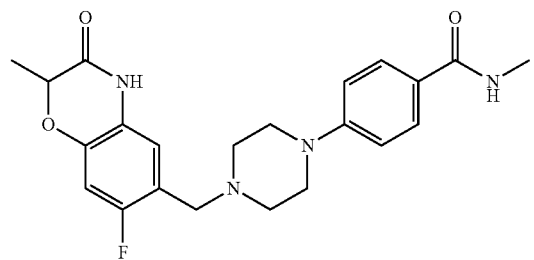

4-(4-((7-Fluoro-2-methyl-3-oxo-3,4-dihydro-2H-benzo[b][1,4]oxazin-6-yl)methyl)piperazin-1-yl)-N-methylbenzamide (335)

Using 334 and methylamine hydrochloride in the general procedure for coupling an amine to a carboxylic acid, the title compound was obtained as an off-white solid: ¹H NMR (400 MHz, DMSO-d6) δ ppm 1.42 (d, J=6.82 Hz, 3H) 2.51-2.56 (m, 4H) 2.74 (d, J=4.29 Hz, 3H) 3.19-3.27 (m, 4H) 3.47 (s, 2 H) 4.70 (q, J=6.65 Hz, 1H) 6.86-6.97 (m, 4H) 7.70 (d, J=8.84 Hz, 2H) 8.14 (q, J=4.13 Hz, 1 H) 10.65 (s, 1H). ESI-MS: m/z 413.3 (M+H)⁺.

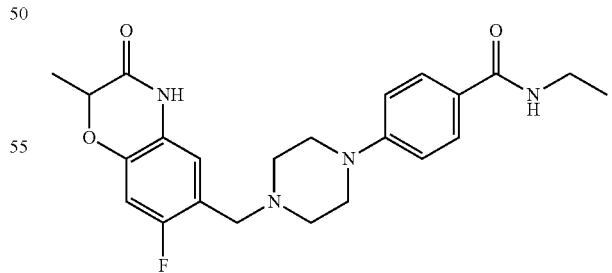

N-Ethyl-4-(4-((7-fluoro-2-methyl-3-oxo-3,4-dihydro-2H-benzo[b][1,4]oxazin-6-yl)methyl)piperazin-1-yl)benzamide (336)

Using 334 and ethylamine hydrochloride in the general procedure for coupling an amine to a carboxylic acid, the title compound was obtained as an off-white solid: ¹H NMR (400 MHz, DMSO-d6) δ ppm 1.09 (t, J=7.20 Hz, 3H) 1.42 (d, J=6.82 Hz, 3H) 2.51-2.56 (m, 4H) 3.16-3.29 (m, 6H) 3.42-3.53 (m, 2H) 4.70 (q, J=6.65 Hz, 1H) 6.85-6.98 (m, 4H) 7.71 (d, J=8.84 Hz, 2H) 8.17 (t, J=5.56 Hz, 1H) 10.65 (s, 1H). ESI-MS: m/z 427.4 (M+H)⁺.

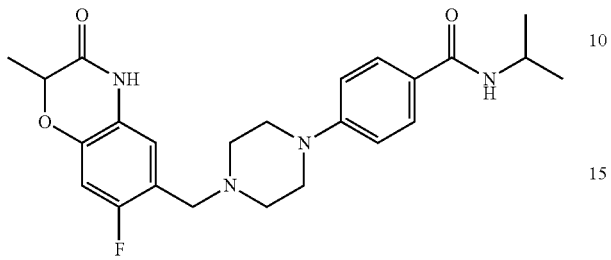

4-(4-((7-Fluoro-2-methyl-3-oxo-3,4-dihydro-2H-benzo[b][1,4]oxazin-6-yl)methyl)piperazin-1-yl)-N-isopropylbenzamide (337)

Using 334 and isopropyl amine in the general procedure for coupling an amine to a carboxylic acid, the title compound was obtained as an off-white solid: ¹H NMR (400 MHz, DMSO-d6) δ ppm 1.13 (d, J=6.57 Hz, 6 H) 1.42 (d, J=6.82 Hz, 3H) 2.51-2.57 (m, 4H) 3.17-3.28 (m, 4H) 3.43-3.53 (m, 2H) 4.06 (dq, J=13.67, 6.64 Hz, 1H) 4.70 (q, J=6.74 Hz, 1H) 6.85-6.98 (m, 4H) 7.72 (d, J=8.84 Hz, 2 H) 7.90 (d, J=7.83 Hz, 1H) 10.65 (s, 1H). ESI-MS: m/z 441.4 (M+H)⁺.

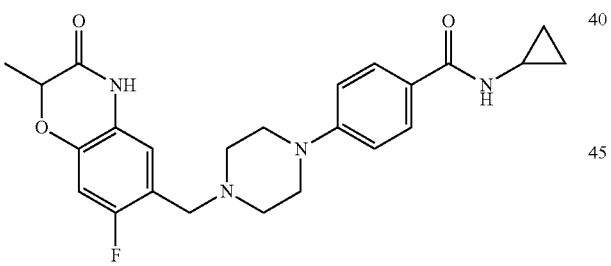

N-Cyclopropyl-4-(4-((7-fluoro-2-methyl-3-oxo-3,4-dihydro-2H-benzo[b][1,4]oxazin-6-yl)methyl)piperazin-1-yl)benzamide (338)

Using 334 and isopropyl amine in the general procedure for coupling an amine to a carboxylic acid, the title compound was obtained as an off-white solid: ¹H NMR (400 MHz, DMSO-d6) δ ppm 0.49-0.56 (m, 2 H) 0.61-0.69 (m, 2H) 1.42 (d, J=6.82 Hz, 3H) 2.51-2.58 (m, 4H) 2.74-2.83 (m, 1H) 3.17-3.28 (m, 4H) 3.42-3.52 (m, 2H) 4.69 (q, J=6.99 Hz, 1H) 6.84-6.99 (m, 4H) 7.69 (d, J=8.84 Hz, 2H) 8.13 (d, J=4.04 Hz, 1H) 10.64 (s, 1H). ESI-MS: m/z 439.4 (M+H)⁺.

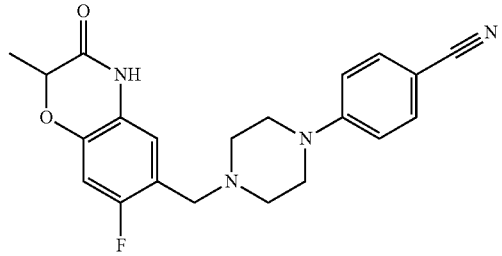 [SMILES: CC1Oc2cc(F)c(CN3CCN(c4ccc(C#N)cc4)CC3)cc2NC1=O]

4-(4-((7-Fluoro-2-methyl-3-oxo-3,4-dihydro-2H-benzo[b][1,4]oxazin-6-yl)methyl)piperazin-1-yl)benzonitrile (339)

Using 328 and 4-(piperazin-1-yl)benzonitrile in the general procedure for reductive aminations, the title compound was obtained as an off-white solid: ¹H NMR (400 MHz, DMSO-d6) δ ppm 1.42 (d, J=6.82 Hz, 3H) 2.45-2.50 (m, 4 H) 3.27-3.33 (m, 4H) 3.43-3.51 (m, 2H) 4.70 (q, J=6.65 Hz, 1H) 6.88 (d, J=10.36 Hz, 1H) 6.94 (d, J=7.33 Hz, 1H) 7.01 (m, 2H) 7.58 (m, 2H) 10.65 (s, 1H). ESI-MS: m/z 381.3 (M+H)⁺.

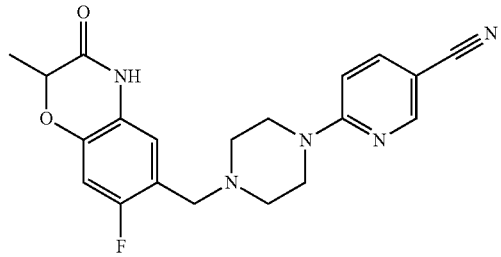 [SMILES: CC1Oc2cc(F)c(CN3CCN(c4ccc(C#N)cn4)CC3)cc2NC1=O]

6-(4-((7-Fluoro-2-methyl-3-oxo-3,4-dihydro-2H-benzo[b][1,4]oxazin-6-yl)methyl)piperazin-1-yl)nicotinonitrile (340)

Using 328 and 6-(piperazin-1-yl)nicotinonitrile in the general procedure for reductive aminations, the title compound was obtained as an off-white solid: ¹H NMR (400 MHz, DMSO-d6) δ ppm 1.42 (d, J=6.82 Hz, 3 H) 2.41-2.48 (m, 4H) 3.43-3.51 (m, 2H) 3.60-3.69 (m, 4H) 4.69 (q, J=6.82 Hz, 1H) 6.88 (d, J=10.36 Hz, 1H) 6.90-6.95 (m, 2H) 7.84 (dd, J=9.09, 2.27 Hz, 1H) 8.46-8.49 (m, 1H) 10.65 (s, 1H). ESI-MS: m/z 382.3 (M+H)⁺.

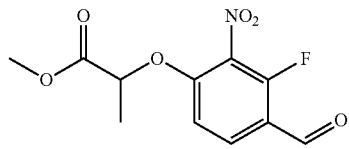 [SMILES: COC(=O)C(C)Oc1ccc(C=O)c(F)c1[N+](=O)[O-]]

Methyl 2-(3-fluoro-4-formyl-2-nitrophenoxy)propanoate (341)

Using 2-fluoro-4-hydroxy-3-nitrobenzaldehyde as the phenol and methyl-2-bromopropanoate as the alkylating agent in the general procedure for alkylation of substituted-2-nitrophenols gives the title compound as a white solid: ESI-MS: m/z 272.1 (M+H)+.

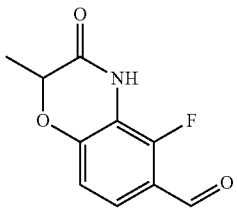

5-Fluoro-2-methyl-3-oxo-3,4-dihydro-2H-benzo[b][1,4]oxazine-6-carbaldehyde (342)

Using 341 in the general procedure for reduction of nitro group and subsequent ring closure gives the title compound as an off-white solid: $^1$H NMR (400 MHz, DMSO-d6) δ ppm 1.47 (d, J=6.82 Hz, 3H) 4.89 (q, J=6.82 Hz, 1H) 6.99 (d, J=8.59 Hz, 1H) 7.44 (dd, J=8.46, 7.45 Hz, 1H) 10.07 (s, 1H) 11.16 (s, 1H). ESI-MS: m/z 210.1 (M+H)+.

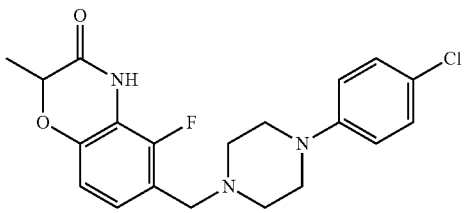 [SMILES: CC1Oc2ccc(CN3CCN(c4ccc(Cl)cc4)CC3)c(F)c2NC1=O]

6-((4-(4-Chlorophenyl)piperazin-1-yl)methyl)-5-fluoro-2-methyl-2H-benzo[b][1,4]oxazin-3(4H)-one (343)

Using 342 and 1-(4-chlorophenyl)piperazine in the general procedure for reductive aminations, the title compound was obtained as an off-white solid: $^1$H NMR (400 MHz, DMSO-d6) δ ppm 1.43 (d, J=6.57 Hz, 3H) 2.46-2.50 (m, 4H) 3.06-3.15 (m, 4H) 3.51 (s, 2H) 4.67-4.74 (m, 1H) 6.80 (d, J=8.34 Hz, 1H) 6.89-6.97 (m, 3H) 7.18-7.24 (m, 2H) 10.84 (s, 1H). ESI-MS: m/z 390.3 (M+H)+.

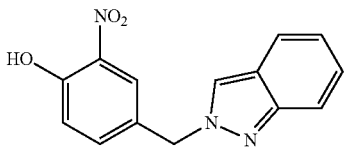 [SMILES: O=[N+]([O-])c1cc(Cn2cc3ccccc3n2)ccc1O]

4-((2H-Indazol-2-yl)methyl)-2-nitrophenol (344A)

In a 100 mL round-bottomed flask was added 4-(chloromethyl)-2-nitrophenol (1.0 g, 5.33 mmol), 1H-indazole (0.630 g, 5.33 mmol), and potassium carbonate (0.884 g, 6.40 mmol) in DMF (26.7 mL). The mixture was stirred at 23° C. for 18 h. The reaction was diluted with water (100 mL) and the resulting solid was isolated by filtration, washed with water, and dried in vacuo. The crude solid was purified via ISCO flash chromatography (0-75% EtOAc in hexanes; 40 g column) to give the title compound as a yellow solid (341 mg, 24% yield): $^1$H NMR (DMSO-d6, 400 MHz): δ=8.50 (d, J=1.0 Hz, 1H), 7.82 (d, J=2.0 Hz, 1H), 7.68-7.72 (m, 1H), 7.56-7.61 (m, 1H), 7.48 (dd, J=8.6, 2.3 Hz, 1H), 7.10 (dd, J=8.5, 7.2 Hz, 2H), 7.00-7.06 (m, 1H), 5.62 ppm (s, 2H). ESI-MS: m/z 270.2 (M+H)+.

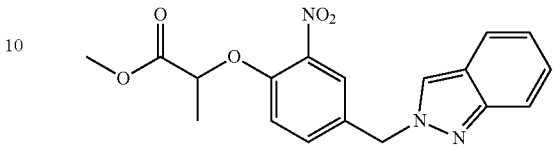

Methyl 2-(4-((2H-indazol-2-yl)methyl)-2-nitrophenoxy)propanoate (344B)

Using 4-((2H-indazol-2-yl)methyl)-2-nitrophenol as the phenol and methyl-2-bromopropanoate as the alkylating agent in the general procedure for alkylation of substituted-2-nitrophenols gives a light yellow solid: $^1$H NMR (400 MHz, DMSO-d6) δ ppm 1.51 (d, J=6.82 Hz, 3H) 3.66 (s, 3H) 5.24 (q, J=6.82 Hz, 1H) 5.66 (s, 2H) 7.00-7.08 (m, 1H) 7.19-7.29 (m, 2H) 7.54-7.63 (m, 2H) 7.71 (d, J=8.34 Hz, 1H) 7.94 (d, J=2.02 Hz, 1H) 8.52 (s, 1H). ESI-MS: m/z 356.2 (M+H)+.

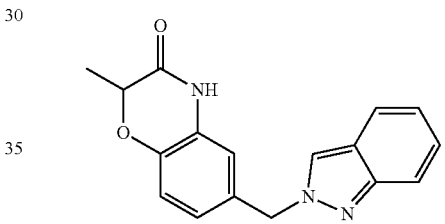

6-((2H-Indazol-2-yl)methyl)-2-methyl-2H-benzo[b][1,4]oxazin-3(4H)-one (344)

Using 344B in the general procedure for reduction of nitro group and subsequent ring closure gives an off-white solid: $^1$H NMR (400 MHz, DMSO-d6) δ ppm 1.38 (d, J=6.82 Hz, 3H) 4.62 (q, J=6.99 Hz, 1H) 5.55 (s, 2H) 6.85 (s, 1H) 6.94 (s, 2H) 7.03 (t, J=7.58 Hz, 1H) 7.22 (t, J=7.07 Hz, 1H) 7.58 (d, J=8.84 Hz, 1H) 7.70 (d, J=8.08 Hz, 1H) 8.45 (s, 1H) 10.64 (br. s., 1 H). ESI-MS: m/z 294.2 (M+H)+.

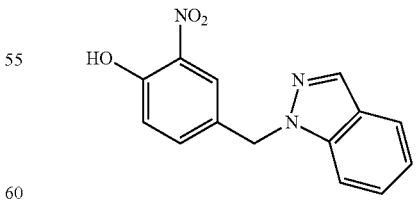

4-((1H-Indazol-1-yl)methyl)-2-nitrophenol (345A)

Isolated as a minor component from the purification of 344A: ESI-MS: m/z 270.2 (M+H)+.

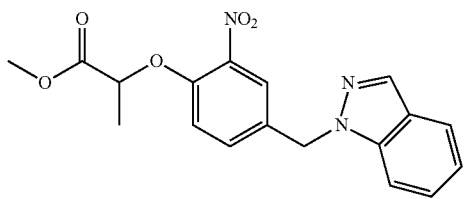 [SMILES: COC(=O)C(C)Oc1ccc(Cn2ncc3ccccc32)cc1[N+](=O)[O-]]

Methyl 2-(4-((1H-indazol-1-yl)methyl)-2-nitrophenoxy)propanoate (345B)

Using 4-((1H-indazol-1-yl)methyl)-2-nitrophenol 345A as the phenol and methyl-2-bromopropanoate as the alkylating agent in the general procedure for alkylation of substituted-2-nitrophenols gives the title compound as a light yellow solid: ESI-MS: m/z 356.2 (M+H)⁺.

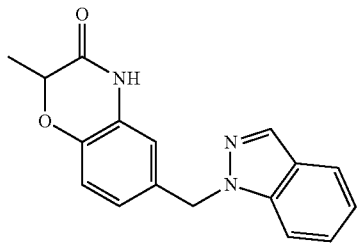 [SMILES: CC1Oc2ccc(Cn3ncc4ccccc43)cc2NC1=O]

6-((1H-Indazol-1-yl)methyl)-2-methyl-2H-benzo[b][1,4]oxazin-3(4H)-one (345)

Using 345B in the general procedure for reduction of nitro group and subsequent ring closure gives the title compound as an off-white solid: $^1$H NMR (400 MHz, DMSO-d6) δ ppm 1.36 (d, J=6.82 Hz, 3H) 4.59 (q, J=6.82 Hz, 1H) 5.57 (s, 2H) 6.76-6.78 (m, 1H) 6.82-6.90 (m, 2 H) 7.11-7.16 (m, 1H) 7.35-7.40 (m, 1H) 7.69 (dq, J=8.49, 0.96 Hz, 1H) 7.77 (dt, J=8.08, 1.01 Hz, 1H) 8.10 (d, J=1.01 Hz, 1H) 10.58 (s, 1H). ESI-MS: m/z 294.2 (M+H)⁺.

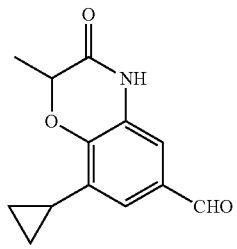 [SMILES: CC1Oc2c(cc(C=O)cc2C2CC2)NC1=O]

8-Cyclopropyl-2-methyl-3-oxo-3,4-dihydro-2H-benzo[b][1,4]oxazine-6-carbaldehyde (346A)

To a suspension of potassium phosphate, tribasic (0.141 g, 0.665 mmol), potassium cyclopropyltrifluoroborate (0.049 g, 0.332 mmol), 8-chloro-2-methyl-3-oxo-3,4-dihydro-2H-benzo[b][1,4]oxazine-6-carbaldehyde 15 (0.05 g, 0.222 mmol) in toluene (Ratio: 5.00, 5 mL) and water (Ratio: 1.000, 1.0 mL) was added PdOAc₂ (3.73 mg, 0.017 mmol) and dicyclohexyl(2',6'-diisopropoxybiphenyl-2-yl)phosphine (0.016 g, 0.033 mmol) at 23° C. The reaction was stirred at 110° C. for 14 hr. The reaction mixture was poured into water (2 mL) and extracted with Et₂O (3×5 mL). The organic layer was dried over Na₂SO₄, filtered, and the organic phase stripped to dryness via rotary evaporation. The resulting crude material was reconstituted in DCM (0.25 mL) and purified via medium pressure chromatography using a gradient eluant of 1-5% MeOH:DCM. The appropriate fractions were combined and solvent was removed via rotary evaporation. The late eluting fractions were dried in vacuo to provide the title compound as an off-white solid (0.0283 g, 0.122 mmol, 55.2% yield). $^1$H NMR (400 MHz, DMSO-d6) δ ppm 0.69-0.81 (m, 2H) 0.91-1.04 (m, 2H) 1.48 (d, J=6.57 Hz, 3H) 2.15 (tt, J=8.49, 5.15 Hz, 1H) 4.85 (q, J=6.82 Hz, 1H) 7.13 (d, J=1.77 Hz, 1H) 7.19 (d, J=1.77 Hz, 1H) 9.79 (s, 1H) 10.89 (s, 1H). ESI-MS: m/z 232.1 (M+H)⁺.

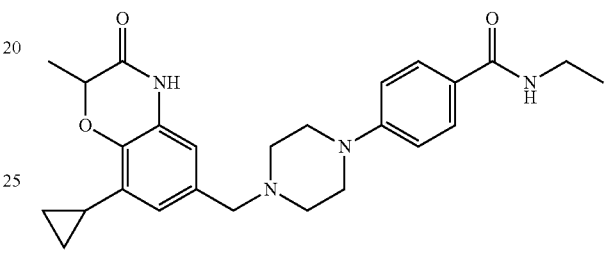

4-(4-((8-Cyclopropyl-2-methyl-3-oxo-3,4-dihydro-2H-benzo[b][1,4]oxazin-6-yl)methyl)piperazin-1-yl)-N-ethylbenzamide (346)

Using 346A and N-ethyl-4-(piperazin-1-yl)benzamide 283 in the general procedure for reductive aminations, the title compound was obtained as an off-white solid: $^1$H NMR (400 MHz, DMSO-d₆) δ ppm 0.60-0.70 (m, 2H) 0.88-0.94 (m, 2H) 1.09 (t, J=7.07 Hz, 3H) 1.43 (d, J=6.57 Hz, 3H) 2.04-2.12 (m, 1H) 2.41-2.49 (m, 4H) 3.17-3.29 (m, 6H) 3.36 (s, 2H) 4.64 (q, J=6.82 Hz, 1H) 6.41 (d, J=1.52 Hz, 1H) 6.69 (d, J=1.77 Hz, 1H) 6.92 (m, J=9.09 Hz, 2H) 7.71 (m, J=8.84 Hz, 2H) 8.17 (t, J=5.56 Hz, 1H) 10.55 (s, 1H). ESI-MS: m/z 449.4 (M+H)⁺.

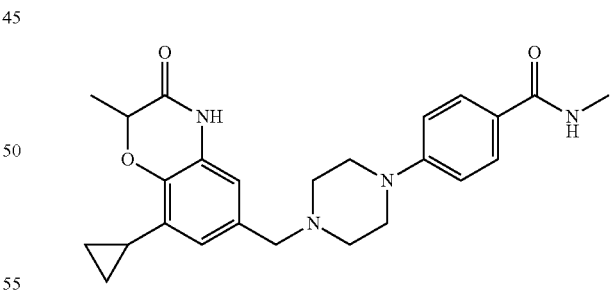

4-(4-((8-Cyclopropyl-2-methyl-3-oxo-3,4-dihydro-2H-benzo[b][1,4]oxazin-6-yl)methyl)piperazin-1-yl)-N-methylbenzamide (347)

Using 346A and N-methyl-4-(piperazin-1-yl)benzamide 282 in the general procedure for reductive aminations, the title compound was obtained as a white solid: $^1$H NMR (400 MHz, DMSO-d₆) δ ppm 0.60-0.71 (m, 2H) 0.87-0.95 (m, 2H) 1.43 (d, J=6.82 Hz, 3H) 2.04-2.12 (m, 1H) 2.40-2.48 (m, 4 H) 2.73 (d, J=4.55 Hz, 3H) 3.18-3.26 (m, 4H) 3.36 (s, 2H)

4.61-4.67 (m, 1H) 6.41 (d, J=1.77 Hz, 1H) 6.69 (d, J=1.77 Hz, 1H) 6.93 (m, 2H) 7.69 (m, 2H) 8.14 (q, J=4.21 Hz, 1H) 10.55 (s, 1H). ESI-MS: m/z 435.4 (M+H)$^+$. mp=256.1-258.6° C.

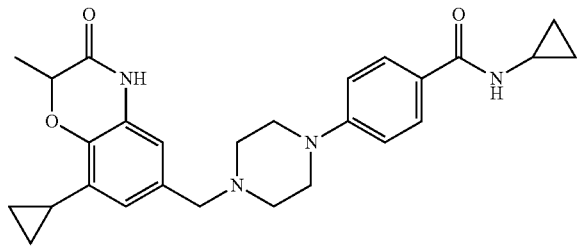 [SMILES: CC1Oc2c(cc(CN3CCN(c4ccc(C(=O)NC5CC5)cc4)CC3)cc2C2CC2)NC1=O]

N-Cyclopropyl-4-(4-((8-cyclopropyl-2-methyl-3-oxo-3,4-dihydro-2H-benzo[b][1,4]oxazin-6-yl)methyl)piperazin-1-yl)benzamide (348)

Using 346A and N-cyclopropyl-4-(piperazin-1-yl)benzamide 284 in the general procedure for reductive aminations, the title compound was obtained as an off-white solid: $^1$H NMR (400 MHz, DMSO-d$_6$) δ ppm 0.50-0.57 (m, 2H) 0.61-0.70 (m, 4H) 0.89-0.95 (m, 2H) 1.43 (d, J=6.82 Hz, 3H) 2.03-2.12 (m, 1H) 2.40-2.49 (m, 4H) 2.76-2.83 (m, 1H) 3.19-3.26 (m, 4H) 3.37 (br. s., 2H) 4.64 (q, J=6.82 Hz, 1H) 6.41 (d, J=1.52 Hz, 1H) 6.67-6.73 (m, 1H) 6.91 (m, J=8.84 Hz, 2H) 7.70 (m, J=8.59 Hz, 2H) 8.17 (d, J=3.54 Hz, 1H) 10.57 (s, 1H). ESI-MS: m/z 461.4 (M+H)$^+$. mp=202.5-207.3° C.

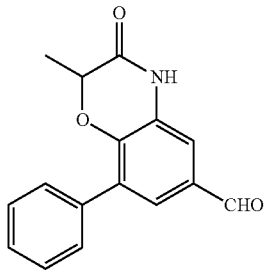 [SMILES: CC1Oc2c(cc(C=O)cc2-c2ccccc2)NC1=O]

2-Methyl-3-oxo-8-phenyl-3,4-dihydro-2H-benzo[b][1,4]oxazine-6-carbaldehyde (349A)

To a solution of potassium phosphate, tribasic (0.564 g, 2.66 mmol), potassium phenyltrifluoroborate (0.245 g, 1.330 mmol), and 8-chloro-2-methyl-3-oxo-3,4-dihydro-2H-benzo[b][1,4]oxazine-6-carbaldehyde 15 (0.2 g, 0.886 mmol) in toluene (Ratio: 4.00, 16 mL) and water (Ratio: 1.000, 4.0 mL) was added PdOAc$_2$ (0.015 g, 0.066 mmol) and dicyclohexyl (2',6'-diisopropoxybiphenyl-2-yl)phosphine (0.062 g, 0.133 mmol) at 23° C. The reaction was stirred at 115° C. for 42 hr. The reaction mixture was poured into water (2 mL) and extracted with Et$_2$O (3×5 mL). The organic layer was dried over Na$_2$SO$_4$, filtered, and the organic phase stripped to dryness via rotary evaporation. The resulting crude material was purified via medium pressure chromatography using a gradient eluant of CH$_2$Cl$_2$/MeOH. The appropriate fractions were combined and concentrated via rotary evaporation. The impure material was reconstituted in DMSO (1.0 mL) and purified via preparative mass trigger LCMS using a gradient eluant of 45-70% ACN:0.05% TFA (aq). The early fractions were combined and the solvent was removed via rotary evaporation. The purified product was dried in vacuo to provide the title compound as an off-white solid (0.0459 g, 0.172 mmol, 19.37% yield). $^1$H NMR (400 MHz, DMSO-d$_6$) δ ppm 1.44 (d, J=6.82 Hz, 3H) 4.85-4.92 (m, 1H) 7.38-7.43 (m, 2H) 7.46-7.51 (m, 2H) 7.57-7.62 (m, 2H) 7.64 (d, J=2.02 Hz, 1H) 9.91 (s, 1H) 11.04 (s, 1H). ESI-MS: m/z 268.1 (M+H)$^+$.

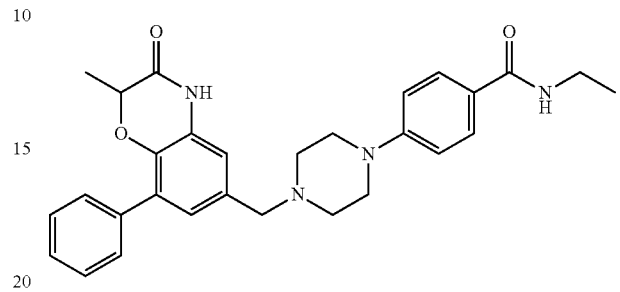

N-Ethyl-4-(4-((2-methyl-3-oxo-8-phenyl-3,4-dihydro-2H-benzo[b][1,4]oxazin-6-yl)methyl)piperazin-1-yl)benzamide (349)

Using 349A and N-ethyl-4-(piperazin-1-yl)benzamide 283 in the general procedure for reductive aminations, the title compound was obtained as a white solid: $^1$H NMR (400 MHz, DMSO-d$_6$) δ ppm 1.09 (t, J=7.20 Hz, 3H) 1.39 (d, J=6.82 Hz, 3H) 2.51-2.55 (m, 4H) 3.19-3.30 (m, 6H) 3.48 (s, 2H) 4.67 (q, J=6.57 Hz, 1H) 6.87-6.97 (m, 4H) 7.31-7.38 (m, 1H) 7.40-7.47 (m, 2H) 7.51-7.56 (m, 2H) 7.71 (d, J=8.84 Hz, 2H) 8.17 (t, J=5.68 Hz, 1H) 10.72 (br. s., 1H). ESI-MS: m/z 485.4 (M+H)$^+$.

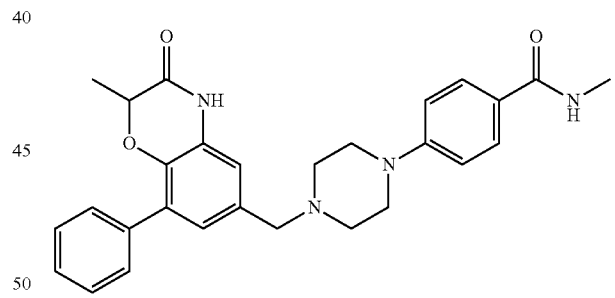

N-Methyl-4-(4-((2-methyl-3-oxo-8-phenyl-3,4-dihydro-2H-benzo[b][1,4]oxazin-6-yl)methyl)piperazin-1-yl)benzamide (350)

Using 349A and N-methyl-4-(piperazin-1-yl)benzamide 282 in the general procedure for reductive aminations, the title compound was obtained as a white solid: $^1$H NMR (400 MHz, DMSO-d$_6$) δ ppm 1.40 (d, J=6.82 Hz, 3H) 2.51-2.57 (m, 4H) 2.73 (d, J=4.55 Hz, 3H) 3.18-3.29 (m, 4H) 3.48 (s, 2H) 4.70 (q, J=6.65 Hz, 1H) 6.90-6.96 (m, 4H) 7.32-7.37 (m, 1H) 7.41-7.46 (m, 2H) 7.51-7.56 (m, 2H) 7.66-7.72 (m, 2H) 8.13 (q, J=4.38 Hz, 1H) 10.71 (s, 1H). ESI-MS: m/z 471.4 (M+H)$^+$. mp=184.9-188.9° C.

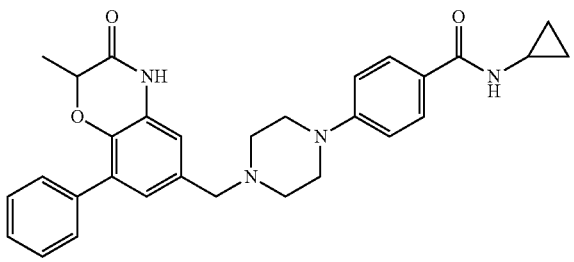 [SMILES: CC1Oc2c(cc(CN3CCN(c4ccc(C(=O)NC5CC5)cc4)CC3)cc2-c2ccccc2)NC1=O]

N-Cyclopropyl-4-(4-((2-methyl-3-oxo-8-phenyl-3,4-dihydro-2H-benzo[b][1,4]oxazin-6-yl)methyl)piperazin-1-yl)benzamide (351)

Using 349A and N-cyclopropyl-4-(piperazin-1-yl)benzamide 284 in the general procedure for reductive aminations, the title compound was obtained as an off-white solid: $^1$H NMR (400 MHz, DMSO-d$_6$) δ ppm 0.48-0.59 (m, 2H) 0.59-0.69 (m, 2H) 1.40 (d, J=6.82 Hz, 3H) 2.51-2.56 (m, 4H) 2.75-2.82 (m, 1H) 3.19-3.29 (m, 4H) 3.48 (s, 2H) 4.70 (q, J=6.74 Hz, 1H) 6.92 (m, 4H) 7.32-7.37 (m, 1H) 7.41-7.46 (m, 2H) 7.51-7.57 (m, 2H) 7.69 (d, J=9.09 Hz, 2H) 8.13 (d, J=4.04 Hz, 1H) 10.71 (s, 1H). ESI-MS: m/z 497.3 (M+H)$^+$. mp=217.0-223.5° C.

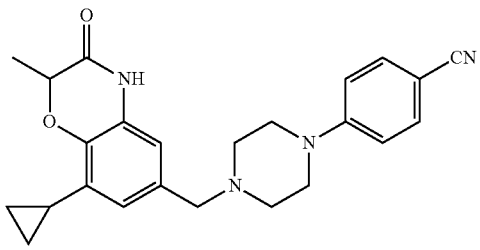 [SMILES: CC1Oc2c(cc(CN3CCN(c4ccc(C#N)cc4)CC3)cc2C2CC2)NC1=O]

4-(4-((8-Cyclopropyl-2-methyl-3-oxo-3,4-dihydro-2H-benzo[b][1,4]oxazin-6-yl)methyl)piperazin-1-yl)benzonitrile (352)

Using 346A and 4-(piperazin-1-yl)benzonitrile in the general procedure for reductive aminations, the title compound was obtained as a white solid: $^1$H NMR (400 MHz, DMSO-d$_6$) δ ppm 0.58-0.71 (m, 2H) 0.85-0.96 (m, 2H) 1.42 (d, J=6.82 Hz, 3H) 2.05-2.12 (m, 1H) 2.38-2.48 (m, 4H) 3.27-3.32 (m, 4H) 3.36 (s, 2H) 4.64 (q, J=6.74 Hz, 1H) 6.41 (d, J=1.52 Hz, 1H) 6.68 (d, J=1.77 Hz, 1H) 7.00 (m, J=9.09 Hz, 2H) 7.57 (m, 2H) 10.56 (br. s., 1H). ESI-MS: m/z 403.4 (M+H)$^+$. mp=194.3-195.5° C.

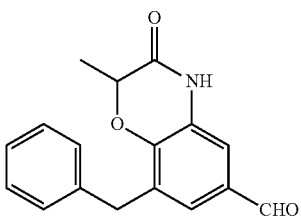 [SMILES: CC1Oc2c(Cc3ccccc3)cc(C=O)cc2NC1=O]

8-Benzyl-2-methyl-3-oxo-3,4-dihydro-2H-benzo[b][1,4]oxazine-6-carbaldehyde (353A)

To a suspension of potassium phosphate, tribasic (0.564 g, 2.66 mmol), potassium benzyltrifluoroborate (0.263 g, 1.330 mmol), 8-chloro-2-methyl-3-oxo-3,4-dihydro-2H-benzo[b][1,4]oxazine-6-carbaldehyde 15 (0.2 g, 0.886 mmol) in toluene (Ratio: 5.00, 20 mL) and water (Ratio: 1.000, 4.0 mL) was added PdOAc$_2$ (0.015 g, 0.066 mmol) and dicyclohexyl(2',6'-diisopropoxybiphenyl-2-yl)phosphine (0.062 g, 0.133 mmol) at 23° C. The reaction was stirred at 115° C. for 20 hr. The reaction mixture was poured into water (2 mL) and extracted with Et$_2$O (3×5 mL). The organic layer was dried over Na$_2$SO$_4$, filtered, and the organic phase stripped to dryness via rotary evaporation. The resulting crude material was reconstituted in DCM (1.0 mL) and purified via medium pressure chromatography using a gradient eluant of 1-5% MeOH:DCM. The appropriate fractions were combined and solvent was removed via rotary evaporation. The late eluting fractions were dried in vacuo to provide a yellow solid. The yellow solid was re-suspended in IPA (1.0 mL), heated at reflux to furnish a solution, cooled to room temperature, filtered, rinsed with IPA, and dried in vacuo to provide the title compound as an off-white solid (0.0704 g, 0.250 mmol, 28.2% yield). $^1$H NMR (400 MHz, DMSO-d$_6$) δ ppm 1.36 (d, J=6.82 Hz, 3H) 3.98 (s, 2H) 4.75-4.81 (m, 1H) 7.16-7.32 (m, 6H) 7.45 (d, J=2.02 Hz, 1H) 9.80 (s, 1H) 10.93 (s, 1H). ESI-MS: m/z 282.2 (M+H)$^+$. mp=163.2-166.1° C.

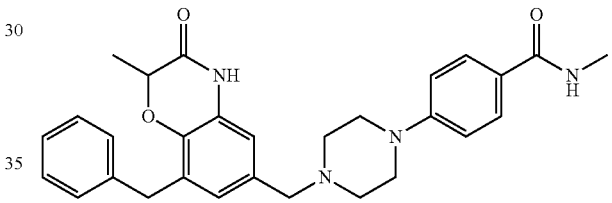

4-(4-((8-Benzyl-2-methyl-3-oxo-3,4-dihydro-2H-benzo[b][1,4]oxazin-6-yl)methyl)piperazin-1-yl)-N-methylbenzamide (353)

Using 353A and N-methyl-4-(piperazin-1-yl)benzamide 282 in the general procedure for reductive aminations, the title compound was obtained as a light grey solid: $^1$H NMR (400 MHz, DMSO-d$_6$) δ ppm 1.32 (d, J=6.82 Hz, 3H) 2.42-2.49 (m, 4H) 2.74 (d, J=4.29 Hz, 3H) 3.16-3.28 (m, 4H) 3.38 (s, 2 H) 3.89 (s, 2H) 4.54-4.60 (m, 1H) 6.73-6.82 (m, 2H) 6.92 (m, 2H) 7.14-7.19 (m, 1H) 7.19-7.23 (m, 2H) 7.24-7.30 (m, 2H) 7.70 (m, 2H) 8.14 (q, J=4.29 Hz, 1H) 10.60 (s, 1H). ESI-MS: m/z 485.4 (M+H)$^+$. mp=227.0-230.9° C.

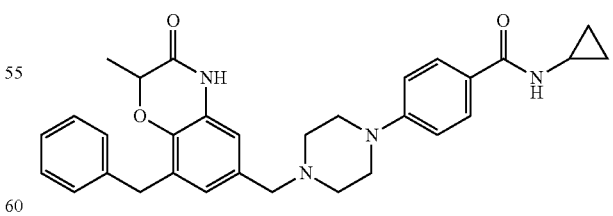

4-(4-((8-Benzyl-2-methyl-3-oxo-3,4-dihydro-2H-benzo[b][1,4]oxazin-6-yl)methyl)piperazin-1-yl)-N-cyclopropylbenzamide (354)

Using 353A and N-cyclopropyl-4-(piperazin-1-yl)benzamide 284 in the general procedure for reductive aminations, the title compound was obtained as a light grey solid: $^1$H NMR (400 MHz, DMSO-$d_6$) δ ppm 0.49-0.55 (m, 2H) 0.62-0.69 (m, 2H) 1.31 (d, J=6.82 Hz, 3H) 2.42-2.49 (m, 4H) 2.75-2.82 (m, 1H) 3.17-3.25 (m, 4H) 3.38 (s, 2H) 3.89 (s, 2H) 4.57 (q, J=6.74 Hz, 1H) 6.73-6.82 (m, 2 H) 6.91 (d, J=9.09 Hz, 2H) 7.14-7.19 (m, 1H) 7.19-7.24 (m, 2H) 7.24-7.30 (m, 2H) 7.69 (d, J=9.09 Hz, 2H) 8.14 (d, J=4.04 Hz, 1H) 10.60 (s, 1H). ESI-MS: m/z 511.4 (M+H)$^+$. mp=192.3-203.2° C.

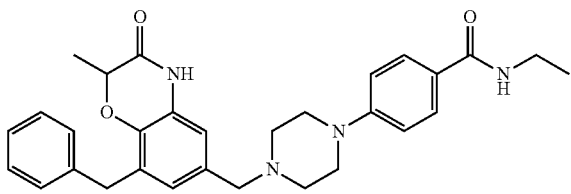 [SMILES: CCNC(=O)c1ccc(N2CCN(Cc3cc(Cc4ccccc4)c4c(c3)NC(=O)C(C)O4)CC2)cc1]

4-(4-((8-Benzyl-2-methyl-3-oxo-3,4-dihydro-2H-benzo[b][1,4]oxazin-6-yl)methyl)piperazin-1-yl)-N-ethylbenzamide (355)

Using 353A and N-ethyl-4-(piperazin-1-yl)benzamide 283 in the general procedure for reductive aminations, the title compound was obtained as a light grey solid: $^1$H NMR (400 MHz, DMSO-$d_6$) δ ppm 1.09 (t, J=7.20 Hz, 3H) 1.32 (d, J=6.82 Hz, 3H) 2.41-2.49 (m, 4H) 3.16-3.29 (m, 6H) 3.38 (s, 2H) 3.89 (s, 2H) 4.53-4.60 (m, 1H) 6.75-6.82 (m, 2H) 6.93 (m, 2H) 7.14-7.19 (m, 1H) 7.19-7.23 (m, 2 H) 7.24-7.29 (m, 2H) 7.71 (m, 2H) 8.17 (t, J=5.68 Hz, 1H) 10.59 (s, 1H). ESI-MS: m/z 499.4 (M+H)$^+$. mp=198.1-205.7° C.

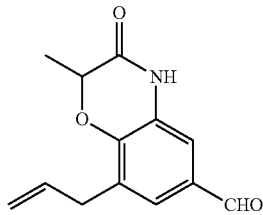 [SMILES: C=CCc1cc(C=O)cc2c1OC(C)C(=O)N2]

8-Allyl-2-methyl-3-oxo-3,4-dihydro-2H-benzo[b][1,4]oxazine-6-carbaldehyde (356A)

To a solution of potassium phosphate, tribasic (0.564 g, 2.66 mmol), potassium allyltrifluoroborate (0.197 g, 1.330 mmol), and 8-chloro-2-methyl-3-oxo-3,4-dihydro-2H-benzo[b][1,4]oxazine-6-carbaldehyde 15 (0.2 g, 0.886 mmol) in toluene (Ratio: 5.00, 20 mL) and water (Ratio: 1.000, 4.0 mL) was added PdOAc$_2$ (0.015 g, 0.066 mmol) and dicyclohexyl (2',6'-diisopropoxybiphenyl-2-yl)phosphine (0.062 g, 0.133 mmol) at 23° C. The reaction was stirred at 115° C. for 48 hr. The reaction mixture was poured into water (2 mL) and extracted with Et$_2$O (3×5 mL). The organic layer was dried over Na$_2$SO$_4$, filtered, and the organic phase stripped to dryness via rotary evaporation. The resulting crude material was reconstituted in DCM (0.25 mL) and purified via medium pressure chromatography using a gradient eluant of 1-5% MeOH:DCM. The appropriate fractions were combined and solvent was removed via rotary evaporation. The impure material was reconstituted in DMSO (1.0 mL) and purified via preparative mass trigger LCMS using a gradient eluant of 45-70% ACN:0.05% TFA (aq). The collected fractions were combined and the solvent was removed via rotary evaporation to provide the title compound as an off-white solid (0.007 g, 0.030 mmol, 3.41% yield). $^1$H NMR (400 MHz, DMSO-$d_6$) δ ppm 1.44 (d, J=6.82 Hz, 3H) 3.38-3.42 (m, 2H) 4.82 (q, J=6.82 Hz, 1H) 5.06-5.12 (m, 2H) 5.91-6.01 (m, 1H) 7.28 (d, J=2.02 Hz, 1H) 7.42 (d, J=2.02 Hz, 1H) 9.82 (s, 1H) 10.93 (s, 1H). ESI-MS: m/z 232.2 (M+H)$^+$.

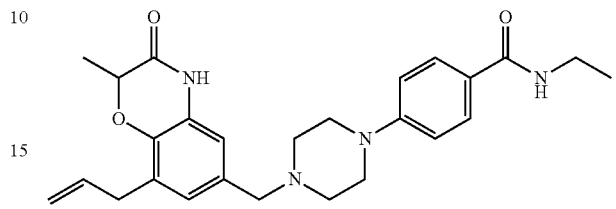

4-(4-((8-Allyl-2-methyl-3-oxo-3,4-dihydro-2H-benzo[b][1,4]oxazin-6-yl)methyl)piperazin-1-yl)-N-ethylbenzamide (356)

Using 356A and N-ethyl-4-(piperazin-1-yl)benzamide 283 in the general procedure for reductive aminations, the title compound was obtained as an off-white solid: $^1$H NMR (400 MHz, DMSO-$d_6$) δ ppm 1.09 (t, J=7.20 Hz, 3H) 1.39 (d, J=6.82 Hz, 3H) 2.43-2.49 (m, 4H) 3.18-3.29 (m, 6H) 3.30-3.32 (m, 2H) 3.39 (s, 2H) 4.61 (q, J=6.82 Hz, 1H) 5.01-5.07 (m, 2H) 5.93 (m, J=16.86, 10.17, 6.57, 6.57 Hz, 1H) 6.77 (d, J=2.02 Hz, 1H) 6.73 (d, J=2.02 Hz, 1H) 6.92 (m, 2H) 7.71 (m, 2H) 8.18 (t, J=5.56 Hz, 1H) 10.60 (br. s., 1H). ESI-MS: m/z 449.4 (M+H)$^+$.

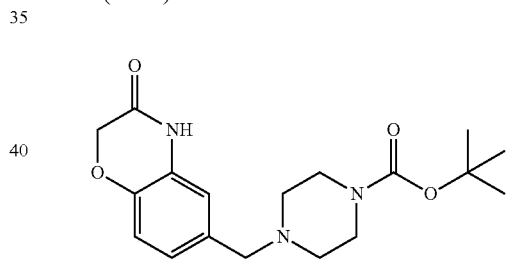

tert-Butyl 4-((3-oxo-3,4-dihydro-2H-benzo[b][1,4]oxazin-6-yl)methyl)piperazine-1-carboxylate (357)

In a 20 mL scintillation vial was added potassium 44-(tert-butoxycarbonyl)piperazin-1-yl)methyl)trifluoroborate (280 mg, 1.050 mmol), 2-dicyclohexylphosphino-2',4',6'-tri-isopropyl-1,1'-biphenyl (28.6 mg, 0.060 mmol), cesium carbonate (977 mg, 3.00 mmol) and palladium(II) acetate (6.73 mg, 0.030 mmol), followed by a solution of 6-bromo-2H-benzo[b][1,4]oxazin-3(4H)-one (228 mg, 1.000 mmol) in THF (4.0 mL) and water (0.4 mL). The mixture was heated at 80° C. for 18 h. The reaction was heated for an additional 24 h. The reaction was cooled, filtered, and purified by prep HPLC 15-40% acetonitrile in water. The appropriate fractions were collected and concentrated in vacuo to give the title compound as an off-white solid (114 mg, 0.328 mmol, 32.8% yield). $^1$H NMR (400 MHz, DMSO-$d_6$) δ ppm 1.42 (s, 9H) 2.94-3.08 (m, 4H) 3.30 (d, J=9.85 Hz, 2H) 4.03 (d, J=11.12 Hz, 2H) 4.26 (br. s., 2H) 4.62 (s, 2H) 6.98 (s, 1H) 7.04 (s, 2H) 11.00 (s, 1H). ESI-MS: m/z 348.2 (M+H)$^+$.

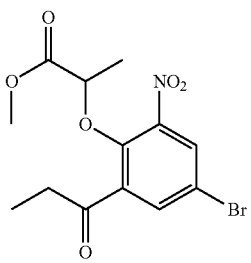 [SMILES: CCC(=O)c1cc(Br)cc([N+](=O)[O-])c1OC(C)C(=O)OC]

Methyl
2-(4-bromo-2-nitro-6-propionylphenoxy)propanoate (358A)

Using 1-(5-bromo-2-hydroxy-3-nitrophenyl)propan-1-one as the phenol and methyl-2-bromopropanoate as the alkylating agent in the general procedure for alkylation of substituted 2-nitrophenols gives the title compound as a gold oil: $^1$H NMR (400 MHz, DMSO-$d_6$) δ ppm 1.03-1.10 (m, 3H) 1.44 (d, J=6.82 Hz, 3H) 3.00-3.12 (m, 2H) 3.59 (s, 3H) 4.56 (q, J=6.82 Hz, 1H) 8.07 (d, J=2.53 Hz, 1H) 8.34 (d, J=2.53 Hz, 1H). ESI-MS: m/z 361.1 (M+H)$^+$.

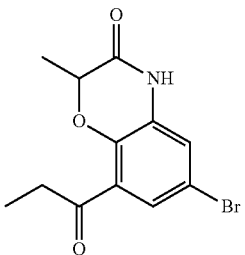 [SMILES: CCC(=O)c1cc(Br)cc2c1OC(C)C(=O)N2]

6-Bromo-2-methyl-8-propionyl-2H-benzo[b][1,4]oxazin-3(4H)-one (358B)

Using 358A in the general procedure for reduction of a nitro group and subsequent ring closure gives the title compound as a black solid: ESI-MS: m/z 300.1 (M+H)$^+$.

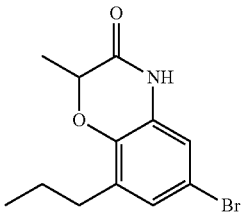 [SMILES: CCCc1cc(Br)cc2c1OC(C)C(=O)N2]

6-Bromo-2-methyl-8-propyl-2H-benzo[b][1,4]oxazin-3(4H)-one (358C)

In a 20 mL scintillation vial was added 6-bromo-2-methyl-8-propionyl-2H-benzo[b][1,4]oxazin-3(4I)-one 358B (517 mg, 1.734 mmol) and triethylsilane (0.554 mL, 3.47 mmol) in TFA (7.0 mL) and stirred at 40° C. for 4 h. The reaction was concentrated in vacuo and the residue was taken up in EtOAc (25 mL), washed with sat aq NaHCO$_3$ and brine, dried over MgSO$_4$, and concentrated in vacuo. The residue was purified via ISCO flash chromatography (0-100% EtOAc in hexanes; 40 g column). Collected fractions gave the title compound as a yellow solid (249 mg, 0.876 mmol, 50.5% yield). $^1$H NMR (400 MHz, DMSO-$d_6$): δ=10.69 (s, 1H), 6.98 (d, J=2.5 Hz, 1H), 6.87 (d, J=2.3 Hz, 1H), 4.65 (q, J=6.8 Hz, 1H), 1.48-1.58 (m, 2H), 1.38 (d, J=6.8 Hz, 5H), 0.87 ppm (t, J=7.3 Hz, 3H). ESI-MS: m/z 284.1 (M+H)$^+$.

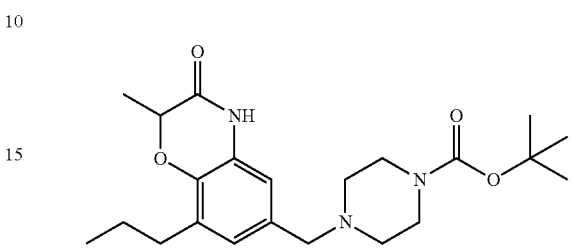

tert-Butyl 4-((2-methyl-3-oxo-8-propyl-3,4-dihydro-2H-benzo[b][1,4]oxazin-6-yl)methyl)piperazine-1-carboxylate (358D)

In a 20 mL scintillation vial was added potassium 44-(tert-butoxycarbonyl)piperazin-1-yl)methyl)trifluoroborate (141 mg, 0.528 mmol), 2-Dicyclohexylphosphino-2',4',6'-tri-isopropyl-1,1'-biphenyl (XPhos) (14.39 mg, 0.030 mmol), cesium carbonate (492 mg, 1.510 mmol) and palladium(II) acetate (3.39 mg, 0.015 mmol), followed by a solution of 6-bromo-2-methyl-8-propyl-2H-benzo[b][1,4]oxazin-3(4H)-one 358C (143 mg, 0.503 mmol) in THF (2.0 mL) and water (0.2 mL). The mixture was heated at 80° C. for 18 h. The mixture was purified via ISCO flash chromatography (0-75% EtOAc in hexanes; 40 g column). Collected fractions gave the title compound as a gold oil (94 mg, 0.233 mmol, 46.3% yield). $^1$H NMR (DMSO-$d_6$, 400 MHz): δ=10.54 (s, 1H), 6.71 (d, J=1.5 Hz, 2H), 4.56-4.64 (m, 1H), 3.34 (s, 4H), 3.25-3.32 (m, 4H), 2.28 (t, J=4.9 Hz, 4 H), 1.47-1.60 (m, 2H), 1.39 (d, J=6.8 Hz, 12H), 1.18 ppm (t, J=7.1 Hz, 3H). ESI-MS: m/z 404.4 (M+H)$^+$.

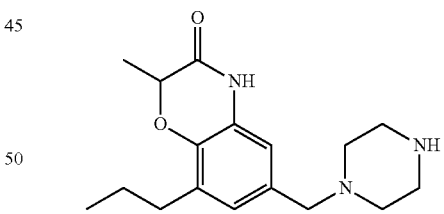

2-Methyl-6-(piperazin-1-ylmethyl)-8-propyl-2H-benzo[b][1,4]oxazin-3(4H)-one (358E)

In a 20 mL scintillation vial was added tert-butyl 4-((2-methyl-3-oxo-8-propyl-3,4-dihydro-2H-benzo[b][1,4]oxazin-6-yl)methyl)piperazine-1-carboxylate 358D (90 mg, 0.223 mmol) and TFA (2.0 mL, 26.0 mmol) in DCM (2.0 mL) and stirred at 23° C. for 1 h. The reaction was concentrated in vacuo, taken up in MeOH, and filtered through a PL-HCO$_3$ MP resin column to give the free base. The MeOH filtrate was concentrated in vacuo to give the title compound as a yellow solid (68 mg, 0.224 mmol, 100% yield). $^1$H NMR (400 MHz, DMSO-$d_6$) δ ppm 0.88 (t, J=7.33 Hz, 3H) 1.38 (d, J=6.82 Hz, 3H) 1.53 (dt, 2H) 2.43-2.49 (m, 4H) 2.52 (br. s., 2H) 3.00 (d, J=4.29 Hz, 4H) 3.33 (br. s., 1H) 3.39 (s, 2H) 4.60 (q, J=6.74 Hz, 1H) 6.63-6.76 (m, 2H) 10.58 (s, 1H). ESI-MS: m/z 304.3 (M+H)⁺.

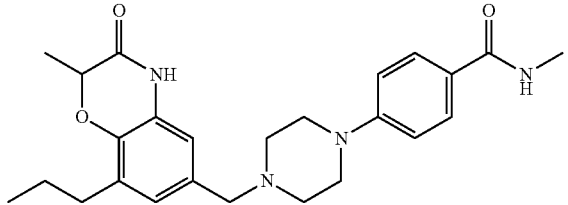 [SMILES: CCCc1cc(CN2CCN(c3ccc(C(=O)NC)cc3)CC2)cc2c1OC(C)C(=O)N2]

N-Methyl-4-(4-((2-methyl-3-oxo-8-propyl-3,4-dihydro-2H-benzo[b][1,4]oxazin-6-yl)methyl)piperazin-1-yl)benzamide (358)

In a 20 mL scintillation vial was added 2-methyl-6-(piperazin-1-ylmethyl)-8-propyl-2H-benzo[b][1,4]oxazin-3(4H)-one 358E (67 mg, 0.221 mmol) and 4-fluoro-N-methylbenzamide (50.7 mg, 0.331 mmol) in DMSO (1.104 mL) and stirred at 120° C. for 4 h. DBU (0.133 mL, 0.883 mmol) was added and the reaction mixture was stirred at 120° C. for 18 h. The reaction was concentrated in vacuo to remove DBU, and then K₂CO₃ (61.0 mg, 0.442 mmol) was added. The mixture was heated overnight at 120° C. The reaction was subsequently filtered and the crude material was purified by prep HPLC 20-45% acetonitrile in water. The appropriate fractions were collected and concentrated in vacuo to give the title compound as a yellow solid (18 mg, 0.041 mmol, 18.67% yield). ¹H NMR (DMSO-d₆, 400 MHz): δ=10.89 (s, 1H), 10.73 (br. s., 1H), 8.04 (br. s., 1H), 7.75 (d, J=8.8 Hz, 1H), 7.24 (s, 1H), 7.11 (s, 1H), 6.95-7.04 (m, 2H), 6.87 (d, J=2.0 Hz, 1H), 4.66-4.72 (m, 1H), 4.64 (d, J=6.6 Hz, 2H), 3.26 (t, J=7.1 Hz, 2H), 3.03 (q, J=6.7 Hz, 2H), 2.30-2.45 (m, 3H), 1.61-1.67 (m, 2H), 1.55 (d, J=6.8 Hz, 5H), 1.40 (d, J=6.8 Hz, 3H), 0.86-0.93 ppm (m, 3H). ESI-MS: m/z 437.4 (M+H)⁺.

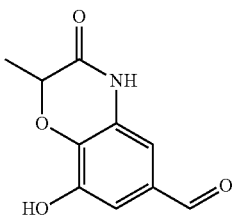

8-Hydroxy-2-methyl-3-oxo-3,4-dihydro-2H-benzo[b][1,4]oxazine-6-carbaldehyde (359A)

In a 20 mL scintillation vial was added 8-methoxy-2-methyl-3-oxo-3,4-dihydro-2H-benzo[b][1,4]oxazine-6-carbaldehyde 17 (111 mg, 0.502 mmol) and boron tribromide (2.0 mL, 2.000 mmol) in DCM (2.5 mL) and stirred at −10° C. for 1 h then slowly warmed to 23° C. and stirred overnight. The reaction was quenched with MeOH, taken up in EtOAc, washed with water and brine, dried over MgSO₄, and concentrated in vacuo to give the title compound as a tan solid (100 mg, 0.483 mmol, 96% yield). ¹H NMR (400 MHz, DMSO-d6) δ ppm 1.45 (d, J=6.82 Hz, 3H) 4.75 (q, J=6.82 Hz, 1H) 6.92 (d, J=2.02 Hz, 1H) 7.03 (d, J=1.77 Hz, 1H) 9.74 (s, 1H) 9.98 (br. s., 1H) 10.85 (s, 1H). ESI-MS: m/z 208.0 (M+H)⁺.

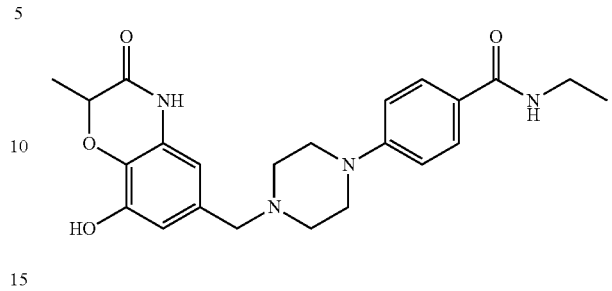

N-Ethyl-4-(4-((8-hydroxy-2-methyl-3-oxo-3,4-dihydro-2H-benzo[b][1,4]oxazin-6-yl)methyl)piperazin-1-yl)benzamide (359)

Using 359A and N-ethyl-4-(piperazin-1-yl)benzamide 283 in the general procedure for reductive aminations, the title compound was obtained as an off-white solid: ¹H NMR (400 MHz, DMSO-d₆) δ ppm 1.03 (t, J=7.07 Hz, 3H) 1.37 (d, J=6.82 Hz, 3H) 2.90-3.13 (m, 4H) 3.13-3.24 (m, 2H) 3.33 (br. s., 2H) 3.92 (d, J=12.63 Hz, 2H) 4.16 (br. s., 2H) 4.57 (q, J=6.65 Hz, 1H) 6.43 (d, J=1.77 Hz, 1H) 6.57 (d, J=1.52 Hz, 1H) 6.94 (d, J=8.84 Hz, 2H) 7.70 (d, J=8.84 Hz, 2H) 8.18 (t, J=5.43 Hz, 1H) 9.66 (d, J=9.35 Hz, 1H) 10.75 (s, 1H). ESI-MS: m/z 425.4 (M+H)⁺.

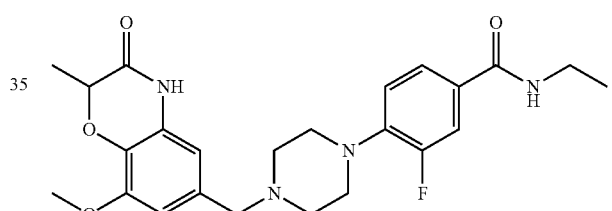

N-Ethyl-3-fluoro-4-(4-((8-methoxy-2-methyl-3-oxo-3,4-dihydro-2H-benzo[b][1,4]oxazin-6-yl)methyl)piperazin-1-yl)benzamide (360)

Using 17 and N-ethyl-3-fluoro-4-(piperazin-1-yl)benzamide in the general procedure for reductive aminations, the title compound was obtained as a tan solid: ¹H NMR (400 MHz, DMSO-d₆) δ ppm 1.10 (t, J=7.20 Hz, 3H) 1.41 (d, J=6.57 Hz, 3H) 2.54 (br. s., 4H) 3.11 (br. s., 4H) 3.21-3.31 (m, 2H) 3.43 (s, 2H) 3.78 (s, 3H) 4.59 (q, J=6.82 Hz, 1H) 6.52 (d, J=1.26 Hz, 1H) 6.64 (d, J=1.26 Hz, 1 H) 7.01-7.11 (m, 1H) 7.55-7.66 (m, 2H) 8.36 (t, J=5.43 Hz, 1H) 10.58 (s, 1H). ESI-MS: m/z 457.4 (M+H)⁺. mp=228-229° C.

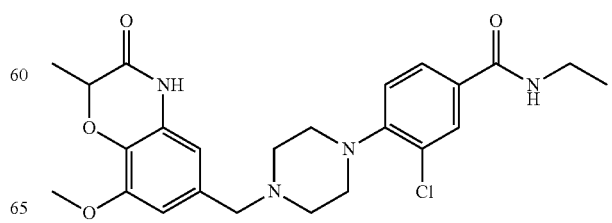

3-Chloro-N-ethyl-4-(4-((8-methoxy-2-methyl-3-oxo-3,4-dihydro-2H-benzo[b][1,4]oxazin-6-yl)methyl)piperazin-1-yl)benzamide (361)

Using 17 and 3-chloro-N-ethyl-4-(piperazin-1-yl)benzamide 286 in the general procedure for reductive aminations, the title compound was obtained as a white solid: $^1$H NMR (DMSO-$d_6$, 400 MHz): δ=10.58 (s, 1 H), 8.44 (t, J=5.6 Hz, 1H), 7.88 (d, J=2.3 Hz, 1H), 7.78 (dd, J=8.3, 2.0 Hz, 1H), 7.19 (d, J=8.6 Hz, 1H), 6.65 (d, J=1.5 Hz, 1H), 6.53 (d, J=1.8 Hz, 1H), 4.54-4.63 (m, 1H), 3.78 (s, 3H), 3.44 (s, 2H), 3.21-3.31 (m, 2H), 3.06 (br. s., 4H), 2.55 (br. s., 4H), 1.41 (d, J=6.8 Hz, 3H), 1.11 ppm (t, J=7.2 Hz, 3H). ESI-MS: m/z 473.3 (M+H)$^+$; mp=119-121° C.

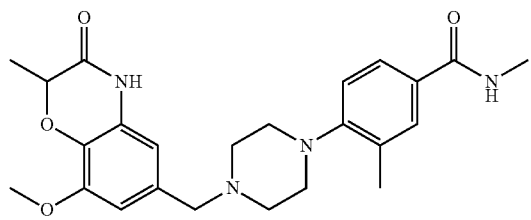

4-(4-((8-Methoxy-2-methyl-3-oxo-3,4-dihydro-2H-benzo[b][1,4]oxazin-6-yl)methyl)piperazin-1-yl)-N,3-dimethylbenzamide (362)

Using 17 and N,3-dimethyl-4-(piperazin-1-yl)benzamide 298 in the general procedure for reductive aminations, the title compound was obtained as a white solid: $^1$H NMR (DMSO-$d_6$, 400 MHz): δ=10.57 (s, 1H), 8.23 (d, J=4.8 Hz, 1H), 7.54-7.66 (m, 2H), 7.02 (d, J=8.1 Hz, 1H), 6.64 (d, J=1.8 Hz, 1H), 6.52 (d, J=1.8 Hz, 1H), 4.52-4.65 (m, 1H), 3.77 (s, 3H), 3.43 (s, 2H), 2.89 (br. s., 4H), 2.74 (d, J=4.5 Hz, 3H), 2.53-2.57 (m, 4H), 2.26 (s, 3H), 1.40 ppm (d, J=6.8 Hz, 3H). ESI-MS: m/z 439.4 (M+H)$^+$.

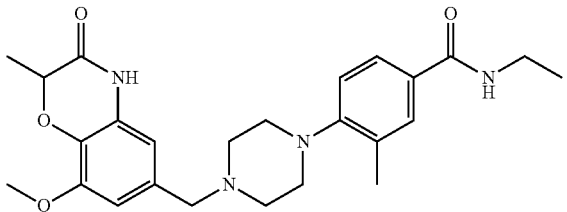 [SMILES: CCNC(=O)c1ccc(N2CCN(Cc3cc4c(c(OC)c3)OC(C)C(=O)N4)CC2)c(C)c1]

N-ethyl-4-(4-((8-methoxy-2-methyl-3-oxo-3,4-dihydro-2H-benzo[b][1,4]oxazin-6-yl)methyl)piperazin-1-yl)-3-methylbenzamide (363)

Using 17 and N-ethyl-3-methyl-4-(piperazin-1-yl)benzamide 299 in the general procedure for reductive aminations, the title compound was obtained as a white solid: $^1$H NMR (DMSO-$d_6$, 400 MHz): δ=9.81 (s, 1H), 8.26 (t, J=5.6 Hz, 1H), 7.55-7.69 (m, 2H), 7.02 (d, J=8.3 Hz, 1H), 6.64 (d, J=1.8 Hz, 1H), 6.52 (d, J=1.8 Hz, 1H), 4.51-4.65 (m, 1H), 3.77 (s, 3H), 3.43 (s, 2H), 3.19-3.29 (m, 2H), 2.89 (br. s., 4H), 2.51-2.57 (m, 4H), 2.26 (s, 3H), 1.40 (d, J=6.8 Hz, 3H), 1.09 ppm (t, J=7.2 Hz, 3H). ESI-MS: m/z 453.4 (M+H)$^+$.

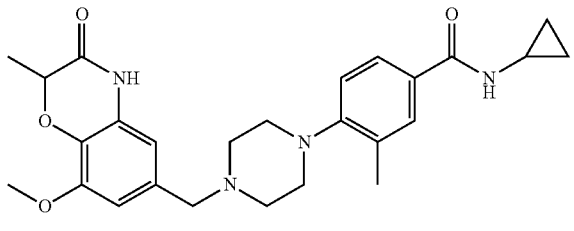

N-Cyclopropyl-4-{4-[(8-methoxy-2-methyl-3-oxo-3,4-dihydro-2H-1,4-benzoxazin-6-yl)methyl]piperazin-1-yl}-3-methylbenzamide (364)

Using 17 and N-cyclopropyl-3-methyl-4-(piperazin-1-yl)benzamide 300 in the general procedure for reductive aminations, the title compound was obtained as a white solid: ESI-MS: m/z 465.4 (M+H)$^+$.

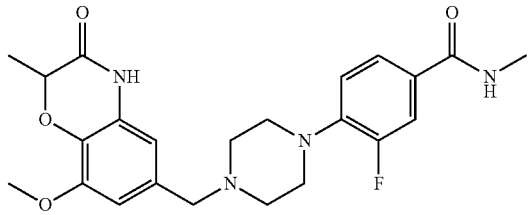

3-Fluoro-4-(4-((8-methoxy-2-methyl-3-oxo-3,4-dihydro-2H-benzo[b][1,4]oxazin-6-yl)methyl)piperazin-1-yl)-N-methylbenzamide (365)

Using 17 and 3-fluoro-N-methyl-4-(piperazin-1-yl)benzamide 289 in the general procedure for reductive aminations, the title compound was obtained as a tan solid: $^1$H NMR (400 MHz, DMSO-$d_6$) δ ppm 1.41 (d, J=6.82 Hz, 3H) 2.51-2.58 (m, 4H) 2.75 (d, J=4.55 Hz, 3H) 3.03-3.18 (m, 4H) 3.42 (s, 2H) 3.77 (s, 3H) 4.58 (q, J=6.82 Hz, 1H) 6.52 (d, J=1.52 Hz, 1H) 6.61-6.66 (m, 1H) 7.05 (t, J=8.72 Hz, 1H) 7.54-7.64 (m, 2H) 8.33 (q, J=4.38 Hz, 1H) 10.57 (s, 1H). ESI-MS: m/z 443.4 (M+H)$^+$. mp=240.9-244.1° C.

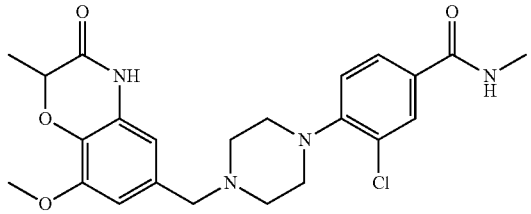

3-Chloro-4-(4-((8-methoxy-2-methyl-3-oxo-3,4-dihydro-2H-benzo[b][1,4]oxazin-6-yl)methyl)piperazin-1-yl)-N-methylbenzamide (366)

Using 17 and 3-chloro-N-methyl-4-(piperazin-1-yl)benzamide 285 in the general procedure for reductive aminations, the title compound was obtained as a white solid: $^1$H NMR (400 MHz, DMSO-$d_6$) δ ppm 1.41 (d, J=6.82 Hz, 3H) 2.51-2.61 (m, 4H) 2.76 (d, J=4.55 Hz, 3H) 2.97-3.14 (m, 4 H) 3.43 (s, 2H) 3.77 (s, 3H) 4.55-4.62 (m, 1H) 6.52 (d, J=1.77 Hz, 1H)

6.64 (d, J=1.52 Hz, 1H) 7.19 (d, J=8.34 Hz, 1H) 7.76 (dd, J=8.46, 2.15 Hz, 1H) 7.86 (d, J=2.27 Hz, 1H) 8.42 (q, J=4.38 Hz, 1H) 10.58 (br. s., 1H). ESI-MS: m/z 459.3 (M+H)$^+$. mp=199.7-202.7° C.

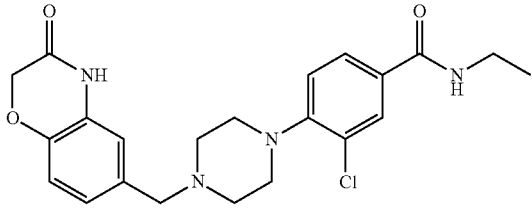 [SMILES: CCNC(=O)c1ccc(N2CCN(Cc3ccc4c(c3)NC(=O)CO4)CC2)c(Cl)c1]

3-Chloro-N-ethyl-4-(4-((3-oxo-3,4-dihydro-2H-benzo[b][1,4]oxazin-6-yl)methyl)piperazin-1-yl)benzamide (367)

Using 12 and 3-chloro-N-ethyl-4-(piperazin-1-yl)benzamide 286 in the general procedure for reductive aminations, the title compound was obtained as a white solid: $^1$H NMR (400 MHz, DMSO-d$_6$) δ ppm 1.11 (t, J=7.20 Hz, 3H) 2.95-3.10 (m, 2H) 3.16-3.34 (m, 4H) 3.38-3.62 (m, 4H) 4.37 (br. s., 2H) 4.64 (s, 2H) 7.00-7.12 (m, 3H) 7.27 (d, J=8.34 Hz, 1H) 7.82 (dd, J=8.34, 2.02 Hz, 1H) 7.94 (d, J=2.02 Hz, 1 H) 8.50 (t, J=5.43 Hz, 1H) 11.01 (s, 1H). ESI-MS: m/z 429.4 (M+H)$^+$.

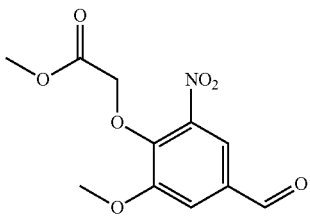 [SMILES: COC(=O)COc1c(OC)cc(C=O)cc1[N+](=O)[O-]]

Methyl 2-(4-formyl-2-methoxy-6-nitrophenoxy)acetate (368)

Using 4-hydroxy-3-methoxy-5-nitrobenzaldehyde as the phenol and methyl 2-bromoacetate as the alkylating agent in the general procedure for alkylation of substituted 2-nitrophenols gives the title compound as a dark orange oil: $^1$H NMR (400 MHz, DMSO-d$_6$) δ ppm 3.66 (s, 3H) 3.97 (s, 3 H) 4.98 (s, 2H) 7.83 (d, J=1.77 Hz, 1H) 8.05 (d, J=1.77 Hz, 1H) 9.97 (s, 1H). ESI-MS: m/z 270.1 (M+H)$^+$.

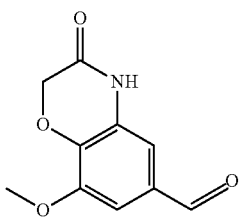

8-Methoxy-3-oxo-3,4-dihydro-2H-benzo[b][1,4]oxazine-6-carbaldehyde (369)

Using 368 in the general procedure for reduction of a nitro group and subsequent ring closure gives the title compound as a brown solid: $^1$H NMR (400 MHz, DMSO-d$_6$) δ ppm 3.85 (s, 3H) 4.68 (s, 2H) 7.07 (d, J=1.52 Hz, 1H) 7.24 (d, J=1.26 Hz, 1H) 9.81 (s, 1H) 10.96 (s, 1H). ESI-MS: m/z 208.1 (M+H)$^+$.

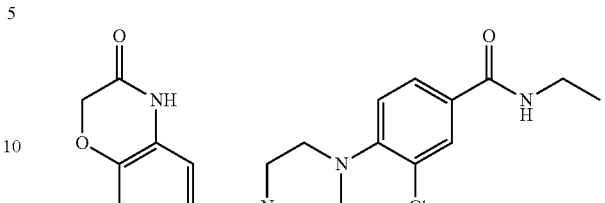

3-Chloro-N-ethyl-4-(4-((8-methoxy-3-oxo-3,4-dihydro-2H-benzo[b][1,4]oxazin-6-yl)methyl)piperazin-1-yl)benzamide (370)

Using 369 and 3-chloro-N-ethyl-4-(piperazin-1-yl)benzamide 286 in the general procedure for reductive aminations, the title compound was obtained as a white solid: $^1$H NMR (400 MHz, DMSO-d$_6$) δ ppm 1.11 (t, J=7.20 Hz, 3H) 2.97-3.12 (m, 2H) 3.17-3.34 (m, 4H) 3.38-3.62 (m, 4H) 3.78-3.88 (m, 3H) 4.35 (d, J=4.55 Hz, 2H) 4.59 (s, 2H) 6.68 (s, 1H) 6.89 (s, 1H) 7.28 (d, J=8.59 Hz, 1H) 7.82 (dd, J=8.34, 1.77 Hz, 1H) 7.94 (d, J=2.02 Hz, 1H) 8.50 (t, J=5.31 Hz, 1H) 10.95 (s, 1H). ESI-MS: m/z 459.4 (M+H)$^+$.

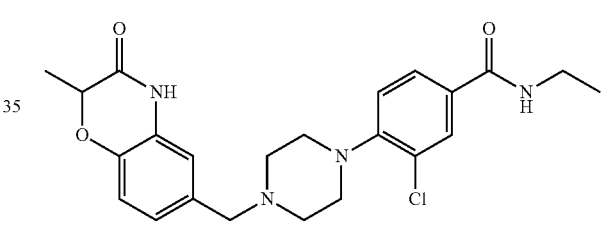

3-Chloro-N-ethyl-4-(4-((2-methyl-3-oxo-3,4-dihydro-2H-benzo[b][1,4]oxazin-6-yl)methyl)piperazin-1-yl)benzamide (371)

Using 13 and 3-chloro-N-ethyl-4-(piperazin-1-yl)benzamide 286 in the general procedure for reductive aminations, the title compound was obtained as a white solid: $^1$H NMR (400 MHz, DMSO-d$_6$) δ ppm 1.10 (t, J=7.20 Hz, 3H) 1.41 (d, J=6.82 Hz, 3H) 2.51-2.62 (m, 4H) 2.92-3.18 (m, 4H) 3.20-3.31 (m, 2H) 3.44 (s, 2H) 4.64 (q, J=6.74 Hz, 1H) 6.84-6.94 (m, 3H) 7.18 (d, J=8.59 Hz, 1H) 7.77 (dd, J=8.46, 2.15 Hz, 1H) 7.88 (d, J=2.02 Hz, 1H) 8.43 (t, J=5.56 Hz, 1H) 10.63 (s, 1H). ESI-MS: m/z 443.3 (M+H)$^+$. mp=238.8-242.9° C.

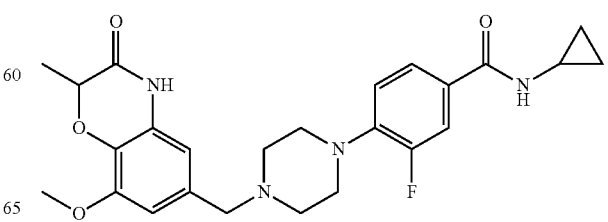

N-Cyclopropyl-3-fluoro-4-{4-[(8-methoxy-2-methyl-3-oxo-3,4-dihydro-2H-1,4-benzoxazin-6-yl)methyl]piperazin-1-yl}benzamide (372)

Using 17 and N-cyclopropyl-3-fluoro-4-(piperazin-1-yl)benzamide 291 in the general procedure for reductive aminations, the title compound was obtained as a tan solid: $^1$H NMR (DMSO-d$_6$, 400 MHz): δ=10.58 (s, 1H), 8.32 (d, J=4.3 Hz, 1H), 7.54-7.63 (m, 2H), 7.04 (t, J=8.8 Hz, 1H), 6.64 (d, J=1.5 Hz, 1H), 6.52 (d, J=1.8 Hz, 1H), 4.55-4.62 (m, 1H), 3.77 (s, 3H), 3.42 (s, 2H), 3.11 (br. s., 4H), 2.81 (ttd, J=7.4, 3.9, 3.7 Hz, 1H), 2.52 (br. s., 4H), 1.41 (d, J=6.8 Hz, 3H), 0.64-0.71 (m, 2H), 0.51-0.57 ppm (m, 2H). ESI-MS: m/z 469.4 (M+H)$^+$; mp=233° C.

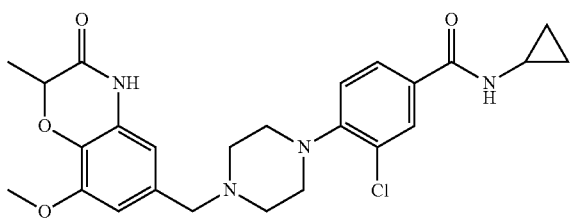 [SMILES: COc1cc(CN2CCN(c3ccc(C(=O)NC4CC4)cc3Cl)CC2)cc2c1OC(C)C(=O)N2]

3-Chloro-N-cyclopropyl-4-(4-((8-methoxy-2-methyl-3-oxo-3,4-dihydro-2H-benzo[b][1,4]oxazin-6-yl)methyl)piperazin-1-yl)benzamide (373)

Using 17 and 3-chloro-N-cyclopropyl-4-(piperazin-1-yl)benzamide 288 in the general procedure for reductive aminations, the title compound was obtained as a white solid: $^1$H NMR (DMSO-d$_6$, 400 MHz): δ=10.51 (s, 1H), 8.32 (d, J=4.0 Hz, 1H), 7.79 (d, J=2.0 Hz, 1H), 7.68 (dd, J=8.6, 2.0 Hz, 1 H), 7.11 (d, J=8.6 Hz, 1H), 6.57 (d, J=1.8 Hz, 1H), 6.45 (d, J=1.8 Hz, 1H), 4.51 (q, J=6.7 Hz, 1H), 3.66-3.73 (m, 3H), 3.36 (s, 2H), 2.98 (br. s., 4H), 2.75 (tq, J=7.4, 3.8 Hz, 1H), 2.47 (br. s., 4H), 1.34 (d, J=6.8 Hz, 3H), 0.56-0.65 (m, 2H), 0.43-0.51 ppm (m, 2H). ESI-MS: m/z 485.4 (M+H)$^+$. mp=226° C.

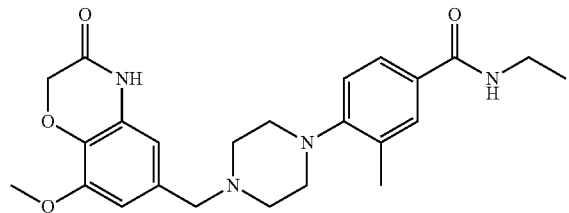 [SMILES: CCNC(=O)c1ccc(N2CCN(Cc3cc4c(c(OC)c3)OCC(=O)N4)CC2)c(C)c1]

N-Ethyl-4-(4-((8-methoxy-3-oxo-3,4-dihydro-2H-benzo[b][1,4]oxazin-6-yl)methyl)piperazin-1-yl)-3-methylbenzamide (374)

Using 369 and N-ethyl-3-methyl-4-(piperazin-1-yl)benzamide 299 in the general procedure for reductive aminations, the title compound was obtained as a tan solid: $^1$H NMR (400 MHz, DMSO-d$_6$) δ ppm 1.10 (t, J=7.20 Hz, 3H) 2.27 (s, 3H) 2.52 (br. s., 4H) 2.89 (br. s., 4H) 3.20-3.30 (m, 2H) 3.43 (s, 2H) 3.72-3.82 (m, 3H) 4.47-4.55 (m, 2H) 6.46-6.57 (m, 1H) 6.60-6.69 (m, 1H) 7.03 (d, J=8.08 Hz, 1H) 7.58-7.70 (m, 2H) 8.27 (t, J=5.43 Hz, 1H) 10.64 (s, 1H). ESI-MS: m/z 439.4 (M+H)$^+$. mp=208.1-224.9° C.

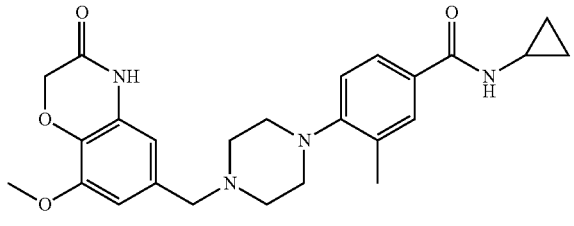 [SMILES: COc1cc(CN2CCN(c3ccc(C(=O)NC4CC4)cc3C)CC2)cc2c1OCC(=O)N2]

N-cyclopropyl-4-(4-((8-methoxy-3-oxo-3,4-dihydro-2H-benzo[b][1,4]oxazin-6-yl)methyl)piperazin-1-yl)-3-methylbenzamide (375)

Using 369 and N-cyclopropyl-3-methyl-4-(piperazin-1-yl)benzamide 300 in the general procedure for reductive aminations, the title compound was obtained as a tan solid: $^1$H NMR (400 MHz, DMSO-d$_6$) δ ppm 0.49-0.57 (m, 2H) 0.63-0.71 (m, 2H) 2.26 (s, 3H) 2.52-2.58 (m, 4H) 2.76-2.84 (m, 1H) 2.84-2.94 (m, 4H) 3.43 (s, 2H) 3.77 (s, 3H) 4.51 (s, 2H) 6.48-6.56 (m, 1H) 6.61-6.67 (m, 1H) 7.02 (d, J=8.08 Hz, 1H) 7.55-7.65 (m, 2H) 8.23 (d, J=4.29 Hz, 1H) 10.64 (s, 1H). ESI-MS: m/z 451.4 (M+H)$^+$. mp=219.6-228.3° C.

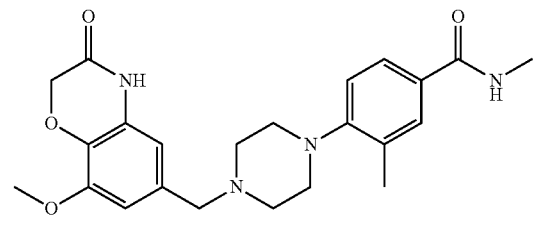

4-(4-((8-Methoxy-3-oxo-3,4-dihydro-2H-benzo[b][1,4]oxazin-6-yl)methyl)piperazin-1-yl)-N,3-dimethylbenzamide (376)

Using 369 and N,3-dimethyl-4-(piperazin-1-yl)benzamide 298 in the general procedure for reductive aminations, the title compound was obtained as a tan solid: $^1$H NMR (400 MHz, DMSO-d$_6$) δ ppm 2.26 (s, 3H) 2.51-2.59 (m, 4H) 2.74 (d, J=4.55 Hz, 3H) 2.89 (br. s., 4H) 3.43 (s, 2H) 3.77 (s, 3H) 4.51 (s, 2H) 6.53 (d, J=1.52 Hz, 1H) 6.64 (d, J=1.52 Hz, 1H) 7.02 (d, J=8.34 Hz, 1H) 7.58-7.67 (m, 2H) 8.19-8.28 (m, 1H) 10.63 (s, 1H). ESI-MS: m/z 425.4 (M+H)$^+$. mp=233.8-235.4° C.

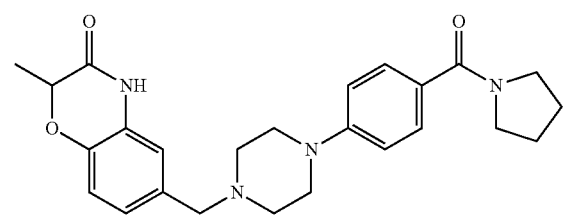 [SMILES: CC1Oc2ccc(CN3CCN(c4ccc(C(=O)N5CCCC5)cc4)CC3)cc2NC1=O]

2-Methyl-6-((4-(4-(pyrrolidine-1-carbonyl)phenyl)piperazin-1-yl)methyl)-2H-benzo[b][1,4]oxazin-3(4H)-one (377)

Using 50 and pyrrolidine in the general procedure for coupling an amine to a carboxylic acid, the title compound was obtained as a pale beige solid: ¹H NMR (400 MHz, DMSO-d₆) δ ppm 1.41 (d, J=6.57 Hz, 3H) 1.81 (br. s., 4H) 2.45-2.49 (m, 4H) 3.21 (br. s., 4H) 3.37-3.50 (m, 6H) 4.64 (q, J=6.74 Hz, 1H) 6.82-6.96 (m, 5H) 7.42 (d, J=8.84 Hz, 2H) 10.62 (s, 1H). ESI-MS: m/z 435.4 (M+H)⁺.

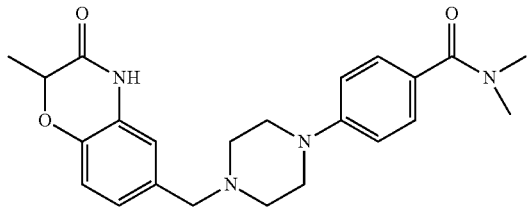

N,N-Dimethyl-4-(4-((2-methyl-3-oxo-3,4-dihydro-2H-benzo[b][1,4]oxazin-6-yl)methyl)piperazin-1-yl)benzamide (378)

Using 50 and dimethylamine HCl in the general procedure for coupling an amine to a carboxylic acid, the title compound was obtained as a pale beige solid: ¹H NMR (400 MHz, DMSO-d₆) δ ppm 1.41 (d, J=6.82 Hz, 3H) 2.44-2.49 (m, 4H) 2.94 (s, 6H) 3.14-3.25 (m, 4H) 3.38-3.46 (m, 2H) 4.64 (q, J=6.82 Hz, 1H) 6.81-6.98 (m, 5H) 7.29 (d, J=8.84 Hz, 2H) 10.62 (s, 1H). ESI-MS: m/z 409.4 (M+H)⁺.

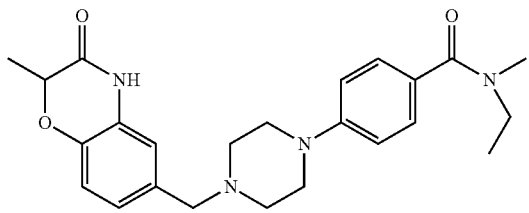

N-Ethyl-N-methyl-4-(4-((2-methyl-3-oxo-3,4-dihydro-2H-benzo[b][1,4]oxazin-6-yl)methyl)piperazin-1-yl)benzamide (379)

Using 50 and N-ethyl-N-methylamine HCl in the general procedure for coupling an amine to a carboxylic acid, the title compound was obtained as a pale beige solid: ¹H NMR (400 MHz, DMSO-d₆) δ ppm 1.09 (t, J=7.07 Hz, 3H) 1.41 (d, J=6.82 Hz, 3H) 2.40-2.49 (m, 4H) 2.90 (s, 3H) 3.20 (br. s., 4H) 3.42 (br. s., 2H) 4.64 (q, J=6.57 Hz, 1H) 6.81-7.00 (m, 5H) 7.25 (d, J=8.59 Hz, 2H) 10.62 (br. s., 1H). ESI-MS: m/z 423.4 (M+H)⁺.

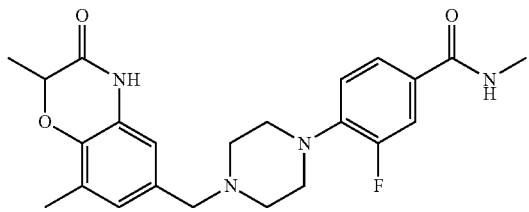

4-(4-((2,8-Dimethyl-3-oxo-3,4-dihydro-2H-benzo[b][1,4]oxazin-6-yl)methyl)piperazin-1-yl)-3-fluoro-N-methylbenzamide (380)

Using 16 and 3-fluoro-N-methyl-4-(piperazin-1-yl)benzamide 289 in the general procedure for reductive aminations, the title compound was obtained as an off-white solid: ¹H NMR (400 MHz, DMSO-d₆) δ ppm 1.38-1.45 (m, 3H) 2.14-2.20 (m, 3H) 2.52-2.54 (m, 4H) 2.76 (d, J=4.55 Hz, 3H) 3.10 (br. s., 4 H) 3.39 (s, 2H) 4.57-4.69 (m, 1H) 6.69-6.80 (m, 2H) 7.05 (t, J=8.72 Hz, 1H) 7.52-7.66 (m, 2H) 8.34 (d, J=4.55 Hz, 1H) 10.56 (s, 1H). ESI-MS: m/z 427.3 (M+H)⁺.

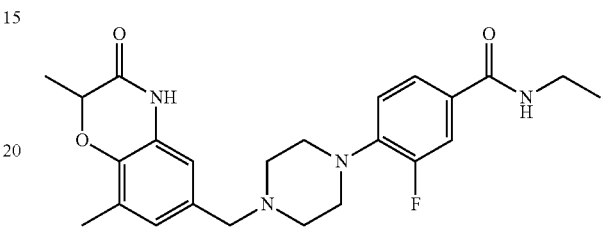

4-(4-((2,8-Dimethyl-3-oxo-3,4-dihydro-2H-benzo[b][1,4]oxazin-6-yl)methyl)piperazin-1-yl)-N-ethyl-3-fluorobenzamide (381)

Using 16 and 3-fluoro-N-ethyl-4-(piperazin-1-yl)benzamide 290 in the general procedure for reductive aminations, the title compound was obtained as an off-white solid: ¹H NMR (400 MHz, DMSO-d₆) δ ppm 1.03 (t, J=7.20 Hz, 3H) 1.30-1.37 (m, 3H) 2.05-2.13 (m, 3H) 2.44-2.48 (m, 4H) 3.02 (br. s., 4H) 3.13-3.23 (m, 2H) 3.23-3.29 (m, 3H) 4.51-4.60 (m, 1H) 6.61-6.72 (m, 2H) 6.98 (t, J=8.84 Hz, 1H) 7.47-7.59 (m, 2H) 8.29 (t, J=5.56 Hz, 1H) 10.48 (s, 1H). ESI-MS: m/z 441.3 (M+H)⁺. mp=241.7-245.2° C.

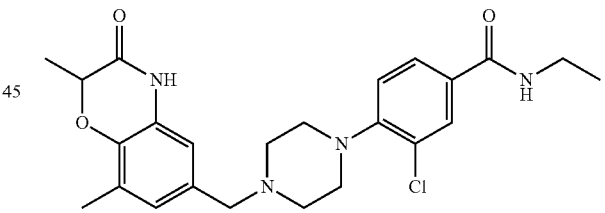

3-Chloro-4-(4-((2,8-dimethyl-3-oxo-3,4-dihydro-2H-benzo[b][1,4]oxazin-6-yl)methyl)piperazin-1-yl)-N-ethylbenzamide (382)

Using 16 and 3-chloro-N-ethyl-4-(piperazin-1-yl)benzamide 286 in the general procedure for reductive aminations, the title compound was obtained as an off-white solid: ¹H NMR (400 MHz, DMSO-d₆) δ ppm 1.11 (t, J=7.20 Hz, 3H) 1.39-1.44 (m, 3H) 2.14-2.18 (m, 3H) 2.52-2.57 (m, 4H) 3.04 (br. s., 4H) 3.21-3.31 (m, 2H) 3.37-3.44 (m, 2H) 4.58-4.68 (m, 1H) 6.69-6.80 (m, 2H) 7.18 (d, J=8.59 Hz, 1H) 7.77 (dd, J=8.34, 2.02 Hz, 1H) 7.88 (d, J=2.02 Hz, 1H) 8.44 (t, J=5.56 Hz, 1 H) 10.56 (s, 1H). ESI-MS: m/z 457.3 (M+H)⁺. mp=227.4-228.4° C.

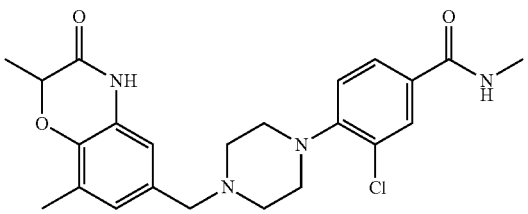

3-Chloro-4-(4-((2,8-dimethyl-3-oxo-3,4-dihydro-2H-benzo[b][1,4]oxazin-6-yl)methyl)piperazin-1-yl)-N-methylbenzamide (383)

Using 16 and 3-chloro-N-methyl-4-(piperazin-1-yl)benzamide 285 in the general procedure for reductive aminations, the title compound was obtained as an off-white solid: $^1$H NMR (400 MHz, DMSO-d$_6$) δ ppm 1.41 (d, J=6.57 Hz, 3H) 2.17 (s, 3H) 2.52-2.61 (m, 4H) 2.76 (d, J=4.55 Hz, 3H) 3.04 (br. s., 4H) 3.37-3.46 (m, 2H) 4.63 (q, J=6.82 Hz, 1H) 6.75 (d, J=13.64 Hz, 2H) 7.19 (d, J=8.59 Hz, 1H) 7.76 (dd, J=8.34, 2.02 Hz, 1H) 7.86 (d, J=2.02 Hz, 1H) 8.42 (q, J=4.38 Hz, 1H) 10.56 (s, 1H). ESI-MS: m/z 443.3 (M+H)$^+$. mp=231.8-231.9° C.

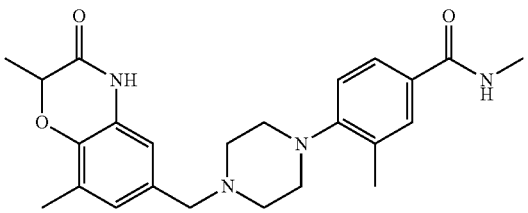

4-(4-((2,8-Dimethyl-3-oxo-3,4-dihydro-2H-benzo[b][1,4]oxazin-6-yl)methyl)piperazin-1-yl)-N,3-dimethylbenzamide (384)

Using 16 and N,3-dimethyl-4-(piperazin-1-yl)benzamide 298 in the general procedure for reductive aminations, the title compound was obtained as a white solid: $^1$H NMR (400 MHz, DMSO-d$_6$) δ ppm 1.41 (d, J=6.82 Hz, 3H) 2.17 (s, 3H) 2.26 (s, 3H) 2.52-2.62 (m, 4H) 2.75 (d, J=4.55 Hz, 3H) 2.81-2.97 (m, 4H) 3.37-3.46 (m, 2H) 4.58-4.68 (m, 1H) 6.68-6.80 (m, 2H) 7.02 (d, J=8.34 Hz, 1H) 7.57-7.68 (m, 2H) 8.24 (q, J=4.38 Hz, 1H) 10.56 (s, 1H). ESI-MS: m/z 423.3 (M+H)$^+$. mp=113.2-120.0° C.

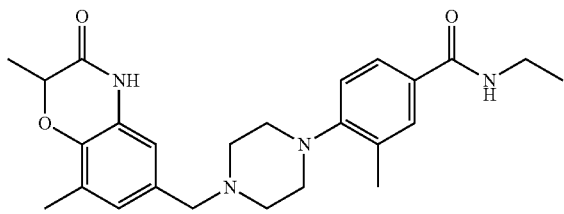 [SMILES: CCNC(=O)c1ccc(N2CCN(Cc3cc(C)c4c(c3)NC(=O)C(C)O4)CC2)c(C)c1]

4-(4-((2,8-Dimethyl-3-oxo-3,4-dihydro-2H-benzo[b][1,4]oxazin-6-yl)methyl)piperazin-1-yl)-N-ethyl-3-methylbenzamide (385)

Using 16 and N-ethyl-3-methyl-4-(piperazin-1-yl)benzamide 299 in the general procedure for reductive aminations, the title compound was obtained as an pale beige solid: $^1$H NMR (400 MHz, DMSO-d$_6$) δ ppm 1.09 (t, J=7.07 Hz, 3H) 1.34-1.45 (m, 3H) 2.15 (s, 3H) 2.25 (s, 3H) 2.50-2.54 (m, 4H) 2.78-2.96 (m, 4H) 3.18-3.29 (m, 2H) 3.39 (s, 2H) 4.56-4.68 (m, 1H) 6.67-6.79 (m, 2H) 7.01 (d, J=8.34 Hz, 1H) 7.56-7.68 (m, 2H) 8.25 (t, J=5.56 Hz, 1H) 10.55 (s, 1H). ESI-MS: m/z 437.4 (M+H)$^+$. mp=223.4-230.1° C.

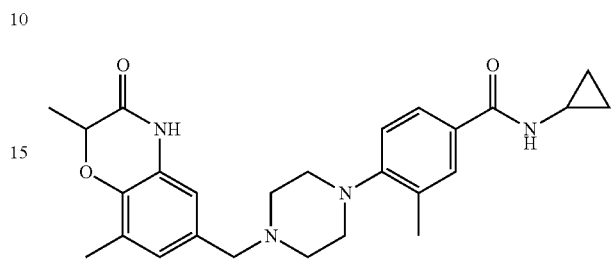

N-Cyclopropyl-4-(4-((2,8-dimethyl-3-oxo-3,4-dihydro-2H-benzo[b][1,4]oxazin-6-yl)methyl)piperazin-1-yl)-3-methylbenzamide (386)

Using 16 and N-cyclopropyl-3-methyl-4-(piperazin-1-yl)benzamide 300 in the general procedure for reductive aminations, the title compound was obtained as an pale beige solid: $^1$H NMR (400 MHz, DMSO-d$_6$) δ ppm 0.51-0.57 (m, 2H) 0.64-0.70 (m, 2H) 1.38-1.43 (m, 3H) 2.16 (s, 3H) 2.25 (s, 3H) 2.52-2.55 (m, 4H) 2.76-2.94 (m, 5H) 3.40 (s, 2H) 4.57-4.68 (m, 1H) 6.69-6.79 (m, 2H) 6.97-7.06 (m, 1H) 7.55-7.66 (m, 2H) 8.23 (d, J=4.29 Hz, 1H) 10.56 (br. s., 1H). ESI-MS: m/z 449.4 (M+H)$^+$. mp=240.9-242.5° C.

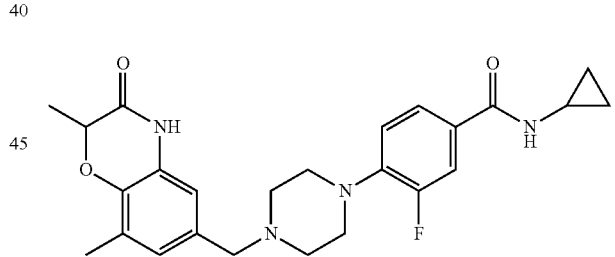

N-Cyclopropyl-4-(4-((2,8-dimethyl-3-oxo-3,4-dihydro-2H-benzo[b][1,4]oxazin-6-yl)methyl)piperazin-1-yl)-3-fluorobenzamide (387)

Using 16 and N-cyclopropyl-3-fluoro-4-(piperazin-1-yl)benzamide 291 in the general procedure for reductive aminations, the title compound was obtained as a white solid: $^1$H NMR (400 MHz, DMSO-d$_6$) δ ppm 0.50-0.57 (m, 2H) 0.63-0.72 (m, 2H) 1.40 (d, J=6.82 Hz, 3H) 2.15 (s, 3H) 2.51 (br. s., 4H) 2.74-2.87 (m, 1H) 3.02-3.14 (m, 4H) 3.38 (s, 2H) 4.56-4.68 (m, 1H) 6.67-6.79 (m, 2H) 7.03 (t, J=8.84 Hz, 1H) 7.50-7.65 (m, 2H) 8.31 (d, J=4.04 Hz, 1H) 10.55 (s, 1H). ESI-MS: m/z 453.4 (M+H)$^+$. mp=252.9-253.0° C.

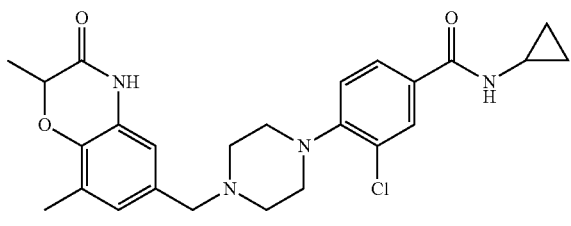 [SMILES: Cc1cc(CN2CCN(c3ccc(C(=O)NC4CC4)cc3Cl)CC2)cc2c1OC(C)C(=O)N2]
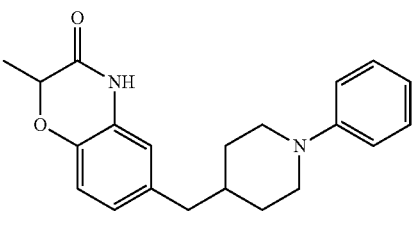

3-Chloro-N-cyclopropyl-4-(4-((2,8-dimethyl-3-oxo-3,4-dihydro-2H-benzo[b][1,4]oxazin-6-yl)methyl)piperazin-1-yl)benzamide (388)

Using 16 and 3-chloro-N-cyclopropyl-4-(piperazin-1-yl)benzamide 288 in the general procedure for reductive aminations, the title compound was obtained as a white solid: $^1$H NMR (400 MHz, DMSO-d$_6$) δ ppm 0.49-0.59 (m, 2H) 0.63-0.73 (m, 2H) 1.40 (d, J=6.82 Hz, 3H) 2.16 (s, 3H) 2.51-2.59 (m, 4H) 2.81 (tq, J=7.36, 3.94 Hz, 1H) 3.03 (br. s., 4H) 3.36-3.45 (m, 2H) 4.56-4.68 (m, 1H) 6.68-6.79 (m, 2H) 7.10-7.19 (m, 1H) 7.74 (dd, J=8.59, 2.02 Hz, 1H) 7.85 (d, J=2.02 Hz, 1H) 8.39 (d, J=4.29 Hz, 1H) 10.55 (s, 1H). ESI-MS: m/z 469.4 (M+H)$^+$. mp=251.7-255.4° C.

2-Methyl-6-((1-phenylpiperidin-4-yl)methyl)-2H-benzo[b][1,4]oxazin-3(4H)-one (389)

To a 20 mL screw cap vial, under N$_2$, 4-methylene-1-phenylpiperidine (0.0906 g, 0.523 mmol) was diluted with 0.5M THF solution of 9-BBN (1.046 mL, 0.523 mmol) and stirred at 75° C. for 1 hr. The reaction mixture was then added to a suspension of 6-bromo-2-methyl-2H-benzo[b][1,4]oxazin-3(4H)-one 19 (0.127 g, 0.523 mmol), PdCl$_2$(dppf)-CH$_2$Cl$_2$ adduct (0.0128 g, 0.016 mmol) and K$_2$CO$_3$ (0.145 g, 1.046 mmol) in DMF (1.0 mL) and water (0.1 mL) and stirred at 60° C. for 4 hr. The mixture was cooled to RT, diluted with water (20 mL) and extracted with ethyl acetate (2×20 mL). The combined organic layers was washed with brine, dried with MgSO$_4$, filtered and concentrated in vacuo. Purification by flash column chromatography (10%-50% EA/Hex) provided the desired product as a pale yellow solid. $^1$H NMR (400 MHz, DMSO-d$_6$) δ ppm 1.21-1.32 (m, 2H) 1.40 (d, J=6.82 Hz, 3H) 1.47 (br. s., 1 H) 1.64 (d, J=13.14 Hz, 2H) 2.45 (d, J=6.82 Hz, 2H) 2.52-2.62 (m, 2H) 3.59-3.70 (m, 2H) 4.55-4.67 (m, 1H) 6.65-6.78 (m, 3H) 6.81-6.94 (m, 3H) 7.11-7.22 (m, 2H) 10.58 (s, 1 H). ESI-MS: m/z 337.3 (M+H)$^+$.

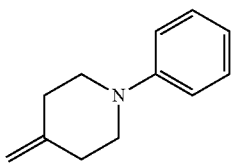

4-Methylene-1-phenylpiperidine (389A)

In a 50 mL round bottom flask, methyltriphenylphosphonium iodide (1.384 g, 3.42 mmol) was suspended in THF (10.0 mL) and cooled to 0° C. N-Butyllithium (1.370 mL, 3.42 mmol) was added drop-wise and the resulting yellow suspension was stirred at 0° C. for 30 min. A solution of 1-phenylpiperidin-4-one (0.500 g, 2.85 mmol) in THF (5.0 mL) was added drop-wise and the orange, yellow suspension was then allowed to slowly warm to 23° C. over 2 hr. The reaction mixture was quenched with sat. NH$_4$Cl (30 mL), the aq. layer was extracted with EtOAc (2×50 mL) and the combined organic extracts were washed with brine (30 mL), dried over MgSO$_4$, filtered, and concentrated in vacuo. The crude yellow oil was purified by flash chromatography (EtOAc: Hex, 1:9 isocratic) affording the title compound as a clear, light yellow oil (0.0906 g, 18.33% yield). $^1$H NMR (400 MHz, DMSO-d$_6$) δ ppm 2.14-2.39 (m, 4H) 3.12-3.29 (m, 4 H) 4.74 (s, 2H) 6.64-6.85 (m, 1H) 6.87-7.07 (m, 2H) 7.08-7.29 (m, 2H). ESI-MS: m/z 174.1 (M+H)$^+$.

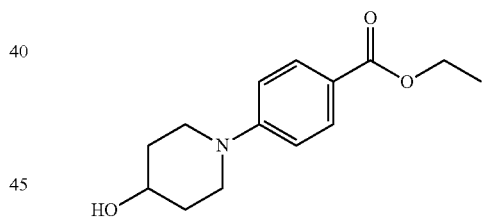

Ethyl 4-(4-hydroxypiperidin-1-yl)benzoate (390A)

In a 200 mL round bottom flask, piperidin-4-ol (2.165 g, 21.41 mmol) and K$_2$CO$_3$ (2.96 g, 21.41 mmol) were suspended in MeCN (51.0 mL). Ethyl 4-fluorobenzoate (2.62 mL, 17.84 mmol) was added and the reaction mixture was stirred under reflux (95° C.) for 96 hr. The reaction was cooled to RT, diluted with EtOAc (100 mL) and washed with water (50 mL). Dried organic layer with MgSO$_4$, filtered, and concentrated in vacuo. The product was purified by re-crystallization using EtOAc/hexanes, affording the title compound as a white solid (0.878 g, 19.74% yield). $^1$H NMR (400 MHz, DMSO-d$_6$) δ ppm 1.28 (t, J=7.07 Hz, 3H) 1.34-1.47 (m, 2H) 1.73-1.85 (m, 2H) 3.03 (ddd, J=13.14, 9.98, 3.16 Hz, 2H) 3.63-3.77 (m, 3H) 4.23 (q, J=7.07 Hz, 2H) 4.72 (d, J=4.04 Hz, 1H) 6.86-7.05 (m, 2H) 7.66-7.85 (m, 2H). ESI-MS: m/z 250.2 (M+H)$^+$.

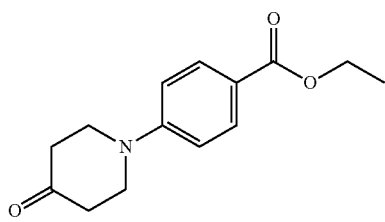 [SMILES: CCOC(=O)c1ccc(N2CCC(=O)CC2)cc1]

Ethyl 4-(4-oxopiperidin-1-yl)benzoate (390B)

In a 200 mL round-bottomed flask, ethyl 4-(4-hydroxypiperidin-1-yl)benzoate 390A (0.878 g, 3.52 mmol), DCC (2.202 g, 10.67 mmol), and DMSO (5.0 mL, 70.5 mmol) were taken up in benzene (9.52 mL) to give a colorless solution. The mixture was then cooled in an ice/brine bath. Pyridine (0.26 mL, 3.21 mmol) and TFA (0.12 mL, 1.558 mmol) were added sequentially and in a drop-wise manner, while maintaining the reaction mixture at <5° C. Once the additions were complete, the reaction was allowed to stir at the cooler temperature and then slowly warmed to 23° C. over a 24 hr period. The reaction was diluted with EtOAc (50 mL) and stirred at 23° C. overnight. The undissolved white solid (dicyclohexylurea) was removed by filtration and rinsed with additional EtOAc. The organic layer was washed with brine, dried with MgSO$_4$, filtered, and concentrated to clear oil. The oil was triturated with hexanes and gently stirred overnight. A white solid was collected by filtration and dried in vacuo. Re-crystallization in CCl$_4$ gave a fine solid (dicyclohexylurea impurity) that was removed by vacuum filtration. The CCl$_4$ filtrate was concentrated to yellow oil and dried in vacuo to afford the title compound as a yellow solid (0.575 g, 66.0% yield). $^1$H NMR (400 MHz, DMSO-d$_6$) δ ppm 1.29 (t, J=7.07 Hz, 3H) 2.45 (t, J=6.06 Hz, 4H) 3.74 (t, J=6.06 Hz, 4H) 4.24 (q, J=7.07 Hz, 2H) 6.97-7.09 (m, 2H) 7.75-7.86 (m, 2H). ESI-MS: m/z 248.2 (M+H)$^+$.

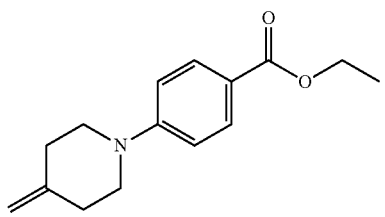 [SMILES: C=C1CCN(c2ccc(C(=O)OCC)cc2)CC1]

Ethyl 4-(4-methylenepiperidin-1-yl)benzoate (390C)

Using ethyl 4-(4-oxopiperidin-1-yl)benzoate 390B (0.575 g, 2.325 mmol), Wittig olefination was carried out as described for 389A. The title compound was obtained as an off-white crystalline solid (0.338 g, 59.3% yield). $^1$H NMR (400 MHz, DMSO-d$_6$) δ ppm 1.21-1.38 (m, 3H) 2.18-2.30 (m, 4H) 3.37-3.50 (m, 4H) 4.23 (q, J=7.16 Hz, 2H) 4.78 (s, 2H) 6.95-7.04 (m, 2H) 7.72-7.82 (m, 2H). ESI-MS: m/z 246.2 (M+H)$^+$.

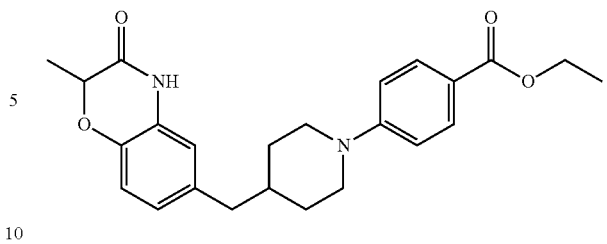

Ethyl 4-(4-((2-methyl-3-oxo-3,4-dihydro-2H-benzo[b][1,4]oxazin-6-yl)methyl)piperidin-1-yl)benzoate (390D)

Ethyl 4-(4-methylenepiperidin-1-yl)benzoate 390C (145.8 mg, 0.594 mmol) was taken up with 0.5M THF solution of 9-BBN (1.189 mL, 0.594 mmol) under nitrogen and stirred at 75° C. for 1 h. The reaction mixture was then added to a suspension of 6-bromo-2-methyl-2H-benzo[b][1,4]oxazin-3(4H)-one 19 (144 mg, 0.594 mmol), PdCl$_2$(dppf)-CH$_2$Cl$_2$ adduct (14.56 mg, 0.018 mmol) and potassium carbonate (164 mg, 1.189 mmol) in DMF (2.0 mL) and water (0.2 mL) and stirred at 60° C. The reaction was pulled, cooled to RT, and diluted with water (10 mL) and EtOAc (10 mL). The aqueous layer was extracted with ethyl acetate (2×20 mL); the organic layer was separated and washed with brine, dried over MgSO$_4$, filtered, and concentrated in vacuo. Flash column chromatography (10%-20%-30% EA/Hex) provided the desired product as an off-white solid (62 mg, 25% yield). $^1$H NMR (400 MHz, DMSO-d6) δ ppm 1.09-1.32 (m, 6H) 1.35-1.46 (m, 2H) 1.56-1.76 (m, 3H) 2.43 (d, J=6.82 Hz, 2H) 2.77 (t, J=11.75 Hz, 2H) 3.82-3.96 (m, 2H) 4.22 (q, J=7.07 Hz, 2H) 4.56-4.66 (m, 1H) 6.63-6.77 (m, 2H) 6.86 (d, J=8.08 Hz, 1H) 6.94 (d, J=9.09 Hz, 2H) 7.69-7.82 (m, 2H) 10.59 (s, 1H). ESI-MS: m/z 409.4 (M+H)$^+$.

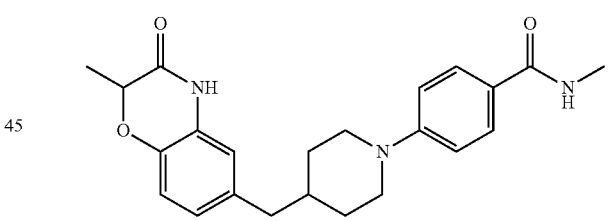

N-Methyl-4-(4-((2-methyl-3-oxo-3,4-dihydro-2H-benzo[b][1,4]oxazin-6-yl)methyl)piperidin-1-yl)benzamide (390)

Saponification of 390D was performed using the general procedure for hydrolysis of carboxylic esters. The resulting carboxylic acid and methylamine hydrochloride were used in the general procedure for coupling an amine to a carboxylic acid to give the title compound as a pinkish, tan solid. $^1$H NMR (400 MHz, DMSO-d$_6$) δ ppm 1.13-1.28 (m, 2H) 1.40 (d, J=6.57 Hz, 3H) 1.55-1.71 (m, 3H) 2.44 (d, J=6.57 Hz, 2H) 2.62-2.78 (m, 5H) 3.82 (d, J=12.63 Hz, 2H) 4.61 (q, J=6.65 Hz, 1H) 6.65-6.77 (m, 2H) 6.82-6.95 (m, 3H) 7.67 (d, J=9.09 Hz, 2H) 8.05-8.15 (m, 1H) 10.59 (s, 1H). ESI-MS: m/z 394.3 (M+H)$^+$.

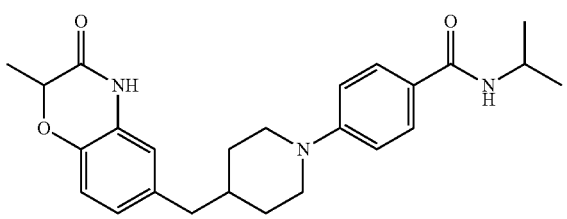

N-Isopropyl-4-(4-((2-methyl-3-oxo-3,4-dihydro-2I-benzo[b][1,4]oxazin-6-yl)methyl)piperidin-1-yl)benzamide (391)

Saponification of 390D was performed using the general procedure for hydrolysis of carboxylic esters. The resulting carboxylic acid and isopropylamine were used in the general procedure for coupling an amine to a carboxylic acid to give the title compound as an off-white solid. $^1$H NMR (400 MHz, DMSO-d$_6$) δ ppm 1.13 (d, J=6.57 Hz, 6H) 1.17-1.29 (m, 2H) 1.40 (d, J=6.82 Hz, 3H) 1.58-1.69 (m, 3H) 2.41-2.47 (m, 2H) 2.63-2.75 (m, 2H) 3.82 (d, J=12.38 Hz, 2H) 4.00-4.12 (m, 1H) 4.61 (q, J=6.74 Hz, 1H) 6.65-6.77 (m, 2H) 6.88 (dd, J=12.88, 8.59 Hz, 3H) 7.70 (d, J=9.09 Hz, 2H) 7.86 (d, J=7.58 Hz, 1H) 10.59 (s, 1H). ESI-MS: m/z 422.4 (M+H)$^+$.

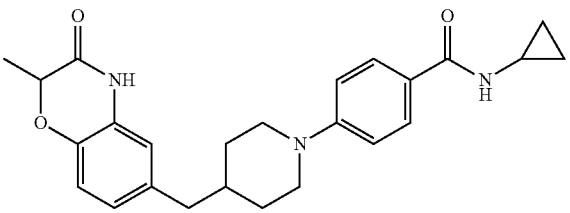 [SMILES: CC1Oc2ccc(CC3CCN(c4ccc(C(=O)NC5CC5)cc4)CC3)cc2NC1=O]

N-Cyclopropyl-4-(4-((2-methyl-3-oxo-3,4-dihydro-2I-benzo[b][1,4]oxazin-6-yl)methyl)piperidin-1-yl)benzamide (392)

Saponification of 390D was performed using the general procedure for hydrolysis of carboxylic esters. The resulting carboxylic acid and isopropylamine were used in the general procedure for coupling an amine to a carboxylic acid to give the title compound as a white solid. $^1$H NMR (400 MHz, DMSO-d$_6$) δ ppm 0.46-0.57 (m, 2H) 0.60-0.70 (m, 2H) 1.12-1.29 (m, 2H) 1.40 (d, J=6.82 Hz, 3H) 1.56-1.71 (m, 3 H) 2.44 (d, J=6.57 Hz, 2H) 2.63-2.84 (m, 3H) 3.82 (d, J=12.63 Hz, 2H) 4.61 (q, J=6.74 Hz, 1H) 6.65-6.76 (m, 2H) 6.82-6.93 (m, 3H) 7.66 (d, J=8.84 Hz, 2H) 8.10 (d, J=4.04 Hz, 1 H) 10.59 (s, 1H). ESI-MS: m/z 422.4 (M+H)$^+$. ESI-MS: m/z 420.3 (M+H)$^+$.

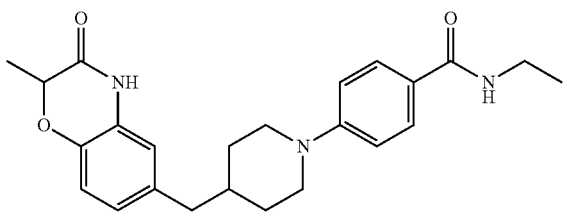 [SMILES: CCNC(=O)c1ccc(N2CCC(Cc3ccc4c(c3)NC(=O)C(C)O4)CC2)cc1]

N-Ethyl-4-(4-((2-methyl-3-oxo-3,4-dihydro-2H-benzo[b][1,4]oxazin-6-yl)methyl)piperidin-1-yl)benzamide (393)

Saponification of 390D was performed using the general procedure for hydrolysis of carboxylic esters. The resulting carboxylic acid and ethylamine hydrochloride were used in the general procedure for coupling an amine to a carboxylic acid to give the title compound as a pinkish, tan solid. $^1$H NMR (400 MHz, DMSO-d$_6$) δ ppm 1.09 (t, J=7.20 Hz, 3H) 1.13-1.31 (m, 2H) 1.40 (d, J=6.82 Hz, 3H) 1.56-1.72 (m, 3H) 2.44 (d, J=6.82 Hz, 2H) 2.62-2.78 (m, 2H) 3.17-3.29 (m, 2H) 3.76-3.89 (m, 2 H) 4.61 (q, J=6.82 Hz, 1H) 6.63-6.78 (m, 2H) 6.88 (dd, J=15.41, 8.59 Hz, 3H) 7.68 (d, J=9.09 Hz, 2H) 8.13 (t, J=5.43 Hz, 1H) 10.59 (s, 1H). ESI-MS: m/z 408.4 (M+H)$^+$.

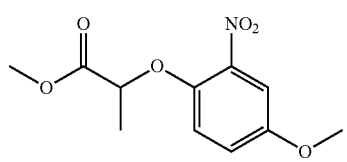

Methyl 2-(4-methoxy-2-nitrophenoxy)propanoate (394A)

Using 4-methoxy-2-nitrophenol as the phenol and methyl-2-bromopropanoate as the alkylating agent in the general procedure for alkylation of substituted-2-nitrophenols gives the title compound as a light yellow solid (5.35 g, 70.9% yield). $^1$H NMR (400 MHz, DMSO-d$_6$) δ ppm 1.50 (d, J=6.82 Hz, 3H) 3.67 (s, 3H) 3.78 (s, 3H) 5.12 (q, J=6.65 Hz, 1H) 7.15-7.27 (m, 2H) 7.39-7.49 (m, 1H). ESI-MS: m/z 256.1 (M+H)$^+$.

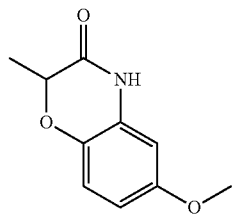

6-Methoxy-2-methyl-2H-benzo[b][1,4]oxazin-3(4H)-one (394B)

Using methyl 2-(4-methoxy-2-nitrophenoxy)propanoate (394A) (5.35 g, 20.92 mmol) in the general procedure for reduction of nitro group and subsequent ring closure gives the title compound as a tan solid (4.08 g, 100% yield). $^1$H NMR (400 MHz, DMSO-d$_6$) δ ppm 1.39 (d, J=5.05 Hz, 3H) 3.69 (br. s., 3H) 4.57 (br. s., 1H) 6.47 (br. s., 2H) 6.88 (d, J=8.34 Hz, 1H) 10.58 (br. s., 1H). ESI-MS: m/z 194.0 (M+H)$^+$.

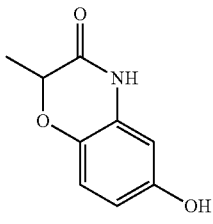

6-Hydroxy-2-methyl-2H-benzo[b][1,4]oxazin-3(4H)-one (394C)

Under $N_2$, a 50 mL round-bottomed flask was charged with a 1M solution of $BBr_3$ (3.11 mL, 3.11 mmol), then cooled in an ice/brine bath. To the cooled solution, was added dropwise, 6-methoxy-2-methyl-2H-benzo[b][1,4]oxazin-3(4H)-one 394B (0.2 g, 1.035 mmol) in anhydrous DCM (4 mL). The reaction was stirred under $N_2$ and then allowed to slowly warm to 23° C. After 2 hr, ice cold water (25 mL) was slowly added to the reaction mixture. The product was collected by vacuum filtration, washed with water, and dried in vacuo to give a light tan solid (0.116 g, 62.5% yield). $^1H$ NMR (400 MHz, DMSO-$d_6$) δ ppm 1.37 (d, J=6.57 Hz, 3H) 4.44-4.57 (m, 1H) 6.24-6.32 (m, 1H) 6.36 (d, J=2.78 Hz, 1H) 6.74 (d, J=8.59 Hz, 1H) 9.15 (s, 1H) 10.50 (s, 1 H). ESI-MS: m/z 180.1 $(M+H)^+$.

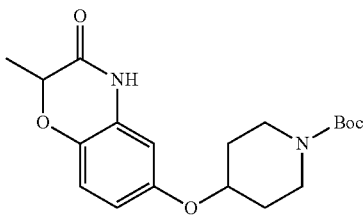 [SMILES: CC1Oc2ccc(OC3CCN(C(=O)OC(C)(C)C)CC3)cc2NC1=O]

tert-Butyl 4-(2-methyl-3-oxo-3,4-dihydro-2H-benzo[b][1,4]oxazin-6-yloxy)piperidine-1-carboxylate (394D)

In a 40 mL vial, 6-hydroxy-2-methyl-2H-benzo[b][1,4]oxazin-3(4H)-one 394C (0.200 g, 1.116 mmol), tert-butyl 4-hydroxypiperidine-1-carboxylate (0.225 g, 1.116 mmol), and $PPh_3$ (0.439 g, 1.674 mmol) were suspended in THF (5.58 mL) to give a brown solution. The mixture was cooled to 0° C. To the cooled mixture was added DEAD drop-wise. The reaction was slowly warmed to 23° C. and stirred for 18 hr. The crude material was purified by prep HPLC-MS (45-85% MeCN in water). The fractions were collected and concentrated in vacuo to give the title compound (0.223 g, 55.1% yield). $^1H$ NMR (400 MHz, DMSO-$d_6$) δ ppm 1.33-1.44 (m, 9H) 1.44-1.59 (m, 2H) 1.86 (ddd, J=9.47, 6.32, 3.16 Hz, 2H) 3.06-3.24 (m, 2H) 3.33-3.71 (m, 5H) 4.32-4.44 (m, 1H) 4.57 (q, J=6.65 Hz, 1H) 6.48 (d, J=2.78 Hz, 1H) 6.55 (dd, J=8.84, 2.78 Hz, 1H) 6.86 (d, J=8.59 Hz, 1H) 10.56 (s, 1H). ESI-MS: m/z 307.2 and 263.2 $(M+H)^+$.

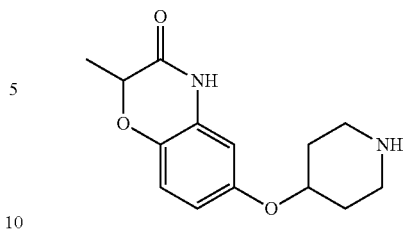

2-Methyl-6-(piperidin-4-yloxy)-2H-benzo[b][1,4]oxazin-3(4H)-one (394E)

To a 40 mL vial containing tert-butyl 4-(2-methyl-3-oxo-3,4-dihydro-2H-benzo[b][1,4]oxazin-6-yloxy)piperidine-1-carboxylate 394D (0.223 g, 0.615 mmol) was added 50% solution of TFA in DCM (2.0 mL, 12.98 mmol) to give a clear brown solution. The reaction was monitored by HPLC. At 0.5 hr, the reaction was pulled and concentrated in vacuo, affording the product as a clear, brown oil (0.161 g, 100% yield). ESI-MS: m/z 263.2 $(M+H)^+$.

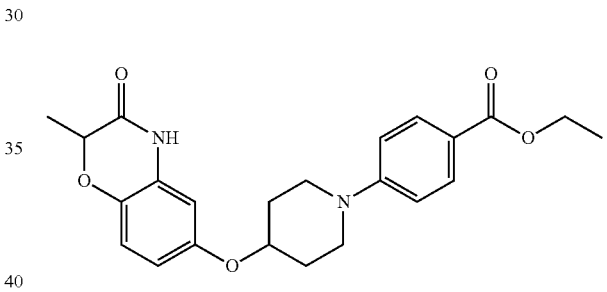

Ethyl 4-(4-(2-methyl-3-oxo-3,4-dihydro-2H-benzo[b][1,4]oxazin-6-yloxy)piperidin-1-yl)benzoate (394)

In a 20 mL screw cap vial, 6-hydroxy-2-methyl-2H-benzo[b][1,4]oxazin-3(4H)-one (0.116 g, 0.647 mmol), ethyl 4-(4-hydroxypiperidin-1-yl)benzoate 394E (0.194 g, 0.777 mmol), and $PPh_3$ (0.204 g, 0.777 mmol) were suspended in THF (3.24 mL) to give a brown solution. The mixture was cooled to 0° C.; then DEAD was added in a drop-wise manner. The reaction was slowly warmed to 23° C. and stirred for 18 hr. The crude material was purified by prep HPLC-MS (45-85% MeCN in water). The fractions were collected and concentrated in vacuo affording the product as a light pink solid (0.0219 g, 8.24% yield). $^1H$ NMR (400 MHz, DMSO-$d_6$) δ ppm 1.21-1.34 (m, 3H) 1.34-1.45 (m, 3H) 1.58-1.72 (m, 2H) 1.92-2.05 (m, 2H) 3.16-3.31 (m, 2H) 3.62-3.77 (m, 3H) 4.24 (q, J=7.07 Hz, 2H) 4.46 (tt, J=7.77, 3.73 Hz, 1H) 4.58 (q, J=6.65 Hz, 1H) 6.51 (d, J=2.78 Hz, 1H) 6.57 (dd, J=8.84, 2.78 Hz, 1H) 6.88 (d, J=8.84 Hz, 1H) 6.95-7.06 (m, 2H) 7.78 (d, J=8.84 Hz, 1H) 10.57 (s, 1H). ESI-MS: m/z 411.3 $(M+H)^+$.

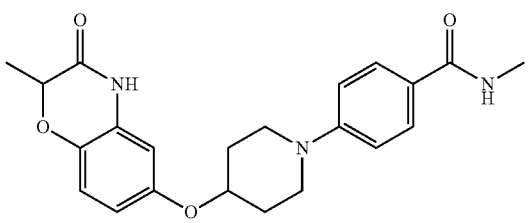

N-Methyl-4-(4-(2-methyl-3-oxo-3,4-dihydro-2H-benzo[b][1,4]oxazin-6-yloxy)piperidin-1-yl)benzamide (395)

In a 4 mL screw cap vial, 2-methyl-6-(piperidin-4-yloxy)-2H-benzo[b][1,4]oxazin-3(4H)-one 394E (0.054 g, 0.206 mmol), $K_2CO_3$ (0.142 g, 1.029 mmol), and 4-fluoro-N-methylbenzamide (0.038 g, 0.247 mmol) were suspended in DMSO (0.412 mL) to give a brown suspension. The reaction was stirred at 120° C. for 72 hr. The crude material was purified by prep HPLC-MS (40-75% MeCN in water). The fractions were collected and concentrated in vacuo affording the product as a tan solid (0.0186 g, 22.85% yield). $^1$H NMR (400 MHz, DMSO-$d_6$) δ ppm 1.34-1.47 (m, 3H) 1.59-1.74 (m, 2H) 1.93-2.07 (m, 2H) 2.71-2.82 (m, 3H) 3.09-3.23 (m, 2H) 3.61 (br. s., 2H) 4.38-4.50 (m, 1H) 4.58 (q, J=6.65 Hz, 1H) 4.68 (d, J=6.57 Hz, 1H) 6.50 (d, J=2.78 Hz, 1H) 6.53-6.62 (m, 1H) 6.67 (dd, J=8.72, 2.91 Hz, 1H) 6.88 (d, J=8.84 Hz, 1H) 6.94-7.06 (m, 2H) 7.71 (d, J=8.84 Hz, 2H) 7.81-7.88 (m, 1H) 8.10-8.20 (m, 1H) 10.57 (s, 1H). ESI-MS: m/z 396.3 (M+H)$^+$.

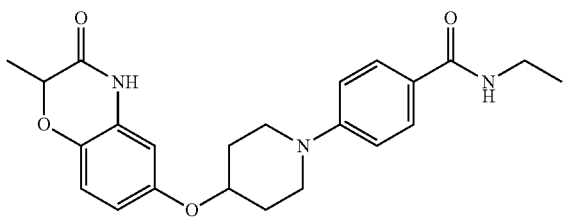 [SMILES: CCNC(=O)c1ccc(N2CCC(Oc3ccc4c(c3)NC(=O)C(C)O4)CC2)cc1]

N-Ethyl-4-(4-(2-methyl-3-oxo-3,4-dihydro-2H-benzo[b][1,4]oxazin-6-yloxy)piperidin-1-yl)benzamide (396)

Using N-ethyl-4-fluorobenzamide 281 as the alkylating agent, the reaction with 394E was carried out as described for 395 providing the title compound as a tan solid (0.0051 g, 6.0% yield). $^1$H NMR (400 MHz, DMSO-$d_6$) δ ppm 1.10 (t, J=7.20 Hz, 3H) 1.40 (d, J=6.57 Hz, 3H) 1.59-1.74 (m, 2H) 1.92-2.07 (m, 1H) 3.08-3.34 (m, 3H) 3.54-3.69 (m, 2H) 4.36-4.50 (m, 1H) 4.58 (q, J=6.65 Hz, 1H) 6.50 (d, J=2.78 Hz, 1H) 6.52-6.63 (m, 1H) 6.88 (d, J=8.59 Hz, 1H) 6.92-7.04 (m, 2H) 7.72 (d, J=8.84 Hz, 2H) 8.18 (s, 1 H) 10.56 (s, 1H). ESI-MS: m/z 410.3 (M+H)$^+$.

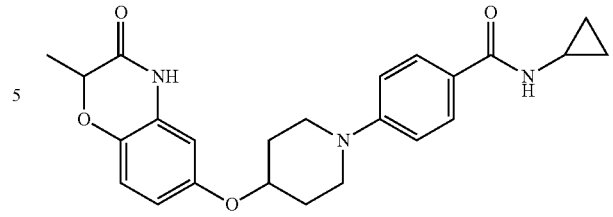

N-Cyclopropyl-4-(4-(2-methyl-3-oxo-3,4-dihydro-2H-benzo[b][1,4]oxazin-6-yloxy)piperidin-1-yl)benzamide (397)

Using N-cyclopropyl-4-fluorobenzamide as the alkylating agent, the reaction with 394E was carried out as described for 395 providing the title compound as a tan solid (0.0308 g, 35.5% yield). $^1$H NMR (400 MHz, DMSO-$d_6$) δ ppm 0.50-0.57 (m, 2H) 0.62-0.70 (m, 2H) 1.35-1.43 (m, 3H) 1.59-1.73 (m, 2H) 1.92-2.05 (m, 2 H) 2.80 (tq, J=7.34, 3.95 Hz, 1H) 3.11-3.22 (m, 2H) 3.56-3.69 (m, 2H) 4.38-4.49 (m, 1 H) 4.54-4.62 (m, 1H) 6.50 (d, J=2.78 Hz, 1H) 6.57 (dd, J=8.84, 2.78 Hz, 1H) 6.88 (d, J=8.84 Hz, 1H) 6.96 (d, J=9.09 Hz, 2H) 7.70 (d, J=8.84 Hz, 2H) 8.14 (d, J=4.29 Hz, 1H) 10.57 (s, 1H). ESI-MS: m/z 422.3 (M+H)$^+$.

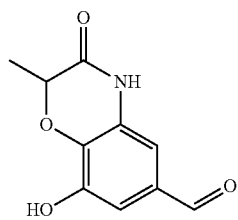

8-Hydroxy-2-methyl-3-oxo-3,4-dihydro-2H-benzo[b][1,4]oxazine-6-carbaldehyde (398A)

To a 200 mL round-bottomed flask cooled in an ice/brine bath was added $BBr_3$ (3.4 g, 13.56 mmol) in DCM (30 mL) under $N_2$. A solution of 17 in DCM (10 mL) was added drop-wise to the cooled $BBr_3$ solution. The reaction was stirred under $N_2$ for 1 hr, then allowed to warm to 23° C. After 2 hr, the reaction was poured over ice and the resulting solid was isolated by vacuum filtration, washed with water, and dried in vacuo to give a tan solid (0.722 g, 77% yield): $^1$H NMR (400 MHz, DMSO-$d_6$) δ ppm 1.40-1.50 (m, 3H) 4.76 (q, J=6.74 Hz, 1H) 6.93 (d, J=2.02 Hz, 1H) 7.04 (d, J=2.02 Hz, 1H) 9.72-9.77 (m, 1H) 9.95-10.01 (m, 1H) 10.85 (s, 1H). ESI-MS: m/z 208.0 (M+H)$^+$.

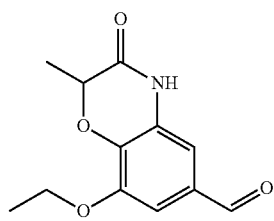 [SMILES: CCOc1cc(C=O)cc2c1OC(C)C(=O)N2]

8-Ethoxy-2-methyl-3-oxo-3,4-dihydro-2H-benzo[b][1,4]oxazine-6-carbaldehyde (398B)

To a 20 mL screw cap vial was added 8-hydroxy-2-methyl-3-oxo-3,4-dihydro-2H-benzo[b][1,4]oxazine-6-carbaldehyde 398A (0.619 g, 2.99 mmol) and cesium carbonate (0.973 g, 2.99 mmol). The mixture was suspended in DMF (5.98 mL) and then cooled in an ice bath. Iodoethane (0.241 mL, 2.99 mmol) was added in 2 portions over 5 minutes. The reaction mixture was stirred for 2 hr, slowly warmed to 23° C., and the stirred for 18 hr. The crude material was purified by prep HPLC-MS (30-50% MeCN in water, basic mode) and the fractions were collected and concentrated in vacuo. The resulting solid was isolated by filtration, washed with water and dried in vacuo to give a tan solid (0.404 g, 57% yield): $^1$H NMR (400 MHz, DMSO-$d_6$) δ ppm 1.36 (t, J=6.95 Hz, 3H) 1.46 (d, J=6.82 Hz, 3H) 4.14 (qd, J=6.99, 1.77 Hz, 2H) 4.72-4.88 (m, 1H) 7.07 (d, J=1.77 Hz, 1H) 7.24 (d, J=1.77 Hz, 1H) 9.82 (s, 1H) 10.92 (s, 1H). ESI-MS: m/z 236.1 (M+H)$^+$.

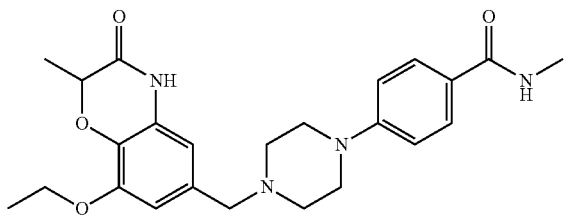 [SMILES: CCOc1cc(CN2CCN(c3ccc(C(=O)NC)cc3)CC2)cc2c1OC(C)C(=O)N2]

4-(4-((8-Ethoxy-2-methyl-3-oxo-3,4-dihydro-2H-benzo[b][1,4]oxazin-6-yl)methyl)piperazin-1-yl)-N-methylbenzamide (398)

Using 398B and N-methyl-4-(piperazin-1-yl)benzamide 282 in the general procedure for reductive aminations, the title compound was obtained as a white solid: $^1$H NMR (400 MHz, DMSO-$d_6$) δ ppm 1.32 (t, J=7.07 Hz, 3H) 1.37-1.44 (m, 3H) 2.41-2.49 (m, 4H) 2.74 (d, J=4.55 Hz, 3H) 3.24 (d, J=5.05 Hz, 4H) 3.40 (s, 2H) 3.98-4.12 (m, 2H) 4.55-4.65 (m, 1H) 6.51 (d, J=1.77 Hz, 1 H) 6.63 (d, J=1.77 Hz, 1H) 6.94 (d, J=8.84 Hz, 2H) 7.70 (d, J=8.84 Hz, 2H) 8.14 (q, J=4.72 Hz, 1H) 10.57 (s, 1H). ESI-MS: m/z 439.4 (M+H)$^+$. mp 228.2-233.0° C.

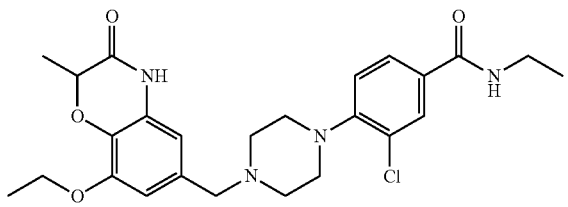 [SMILES: CCNC(=O)c1ccc(N2CCN(Cc3cc4c(c(OCC)c3)OC(C)C(=O)N4)CC2)c(Cl)c1]

3-Chloro-4-(4-((8-ethoxy-2-methyl-3-oxo-3,4-dihydro-2H-benzo[b][1,4]oxazin-6-yl)methyl)piperazin-1-yl)-N-ethylbenzamide (399)

Using 398B and 3-chloro-N-ethyl-4-(piperazin-1-yl)benzamide 286 in the general procedure for reductive aminations, the title compound was obtained as a white solid: $^1$H NMR (400 MHz, DMSO-$d_6$) δ ppm 1.11 (t, J=7.20 Hz, 3H) 1.29-1.38 (m, 3H) 1.38-1.47 (m, 3H) 2.52-2.59 (m, 4H) 3.05 (br. s., 4H) 3.20-3.31 (m, 2H) 3.43 (s, 2H) 3.99-4.09 (m, 2H) 4.55-4.65 (m, 1H) 6.51 (d, J=1.77 Hz, 1H) 6.60-6.67 (m, 1H) 7.19 (d, J=8.59 Hz, 1H) 7.77 (dd, J=8.59, 2.02 Hz, 1H) 7.88 (d, J=2.02 Hz, 1H) 8.44 (t, J=5.56 Hz, 1H) 10.58 (s, 1H). ESI-MS: m/z 487.4 (M+H)$^+$. mp 186.6-198.7° C.

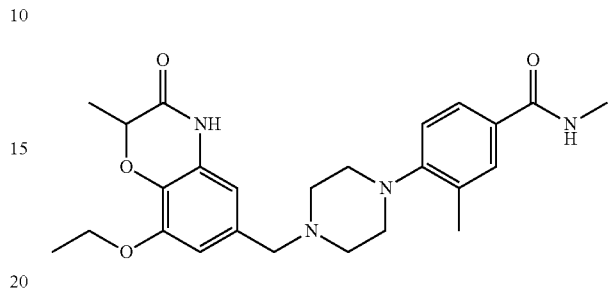

4-(4-((8-Ethoxy-2-methyl-3-oxo-3,4-dihydro-2H-benzo[b][1,4]oxazin-6-yl)methyl)piperazin-1-yl)-N,3-dimethylbenzamide (400)

Using 398B and N,3-dimethyl-4-(piperazin-1-yl)benzamide-2HCl in the general procedure for reductive aminations, the title compound was obtained as a white solid: $^1$H NMR (400 MHz, DMSO-$d_6$) δ ppm 1.33 (t, J=6.95 Hz, 3H) 1.41 (d, J=6.82 Hz, 3H) 2.26 (s, 3H) 2.52-2.57 (m, 4H) 2.75 (d, J=4.29 Hz, 3H) 2.89 (br. s., 4H) 3.42 (s, 2H) 4.04 (d, J=7.07 Hz, 2H) 4.55-4.65 (m, 1H) 6.52 (s, 1H) 6.63 (s, 1H) 7.03 (d, J=8.34 Hz, 1H) 7.58-7.67 (m, 2H) 8.24 (d, J=4.04 Hz, 1H) 10.57 (s, 1 H). ESI-MS: m/z 453.4 (M+H)$^+$. mp 173.4-180.5° C.

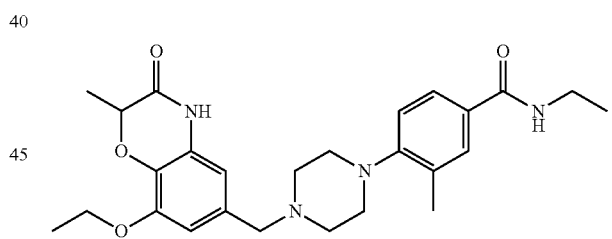

4-(4-((8-Ethoxy-2-methyl-3-oxo-3,4-dihydro-2H-benzo[b][1,4]oxazin-6-yl)methyl)piperazin-1-yl)-N-ethyl-3-methylbenzamide (401)

Using 398B and N-ethyl-3-methyl-4-(piperazin-1-yl)benzamide-2HCl in the general procedure for reductive aminations, the title compound was obtained as a white solid: $^1$H NMR (400 MHz, DMSO-$d_6$) δ ppm 1.09 (t, J=7.07 Hz, 3H) 1.32 (t, J=6.95 Hz, 3H) 1.40 (d, J=6.57 Hz, 3H) 2.26 (s, 3H) 2.51-2.59 (m, 4H) 2.88 (br. s., 4H) 3.19-3.29 (m, 2H) 3.42 (s, 2H) 3.98-4.09 (m, 2H) 4.55-4.64 (m, 1H) 6.51 (d, J=1.52 Hz, 1H) 6.63 (d, J=1.52 Hz, 1H) 7.02 (d, J=8.34 Hz, 1H) 7.55-7.69 (m, 2H) 8.26 (t, J=5.56 Hz, 1H) 10.57 (s, 1H). ESI-MS: m/z 467.4 (M+H)$^+$. mp 199.8-199.9° C.

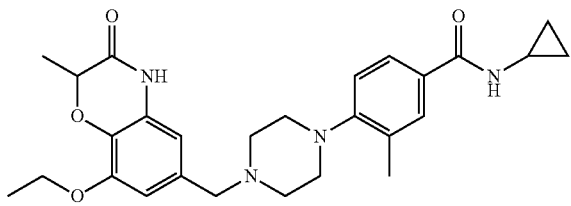 [SMILES: CCOc1cc(CN2CCN(c3ccc(C(=O)NC4CC4)cc3C)CC2)cc2c1OC(C)C(=O)N2]

N-Cyclopropyl-4-(4-((8-ethoxy-2-methyl-3-oxo-3,4-dihydro-2H-benzo[b][1,4]oxazin-6-yl)methyl)piperazin-1-yl)-3-methylbenzamide (402)

Using 398B and N-cyclopropyl-3-methyl-4-(piperazin-1-yl)benzamide-2HCl in the general procedure for reductive aminations, the title compound was obtained as a white solid: $^1$H NMR (400 MHz, DMSO-$d_6$) δ ppm 0.51-0.57 (m, 2H) 0.63-0.70 (m, 2H) 1.33 (t, J=7.07 Hz, 3H) 1.41 (d, J=6.82 Hz, 3H) 2.25 (s, 3H) 2.52-2.60 (m, 4H) 2.81 (td, J=7.26, 3.92 Hz, 1H) 2.89 (br. s., 4H) 3.42 (s, 2H) 3.98-4.10 (m, 2H) 4.54-4.66 (m, 1H) 6.51 (d, J=1.52 Hz, 1H) 6.63 (d, J=1.77 Hz, 1H) 7.01 (d, J=8.08 Hz, 1H) 7.55-7.66 (m, 2H) 8.23 (d, J=4.04 Hz, 1H) 10.57 (s, 1H). ESI-MS: m/z 479.5 (M+H)$^+$. mp 223.4-223.5° C.

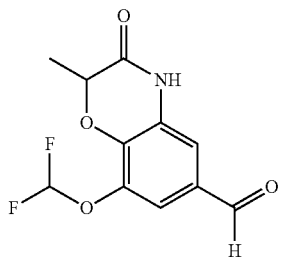 [SMILES: CC1Oc2c(cc(C=O)cc2OC(F)F)NC1=O]

8-(Difluoromethoxy)-2-methyl-3-oxo-3,4-dihydro-2H-benzo[b][1,4]oxazine-6-carbaldehyde (403A)

A 40 mL vial cooled in a dry ice/acetone bath was charged with chlorodifluoromethane (0.209 g, 2.413 mmol) followed by the addition of 8-hydroxy-2-methyl-3-oxo-3,4-dihydro-2H-benzo[b][1,4]oxazine-6-carbaldehyde 398A (0.5 g, 2.413 mmol), Cs$_2$CO$_3$ (0.786 g, 2.413 mmol) and DMF (4.83 mL). The dry ice/acetone bath was removed; and with continued stirring, the reaction was slowly warmed to 23° C. After 2.5 hr, the reaction was transferred to a sand bath and stirred at 70° C. for 72 hr. The crude material was purified by prep HPLC-MS (30-55% MeCN in water, basic mode). The fractions were collected and concentrated in vacuo to give the title compound as a white solid (0.404 g, 57% yield): $^1$H NMR (400 MHz, DMSO-$d_6$) δ ppm 1.44-1.51 (m, 3H) 4.93 (q, J=6.82 Hz, 1H) 7.08-7.28 (m, 1H) 7.32 (d, J=1.77 Hz, 1H) 7.46 (d, J=1.01 Hz, 1H) 9.83-9.88 (m, 1H) 11.14 (s, 1H). ESI-MS: m/z 258.1 (M+H)$^+$.

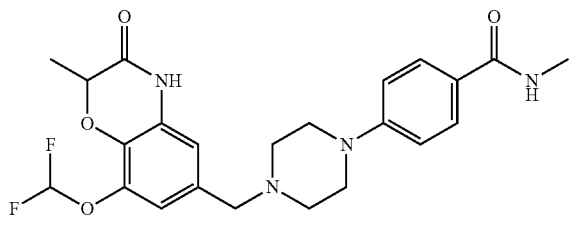

4-(4-((8-(Difluoromethoxy)-2-methyl-3-oxo-3,4-dihydro-2H-benzo[b][1,4]oxazin-6-yl)methyl)piperazin-1-yl)-N-methylbenzamide (403)

Using 403A and N-methyl-4-(piperazin-1-yl)benzamide 282 in the general procedure for reductive aminations, the title compound was obtained as a white solid: $^1$H NMR (400 MHz, DMSO-$d_6$) δ ppm 1.43 (d, J=6.82 Hz, 3H) 2.45-2.49 (m, 4H) 2.73 (d, J=4.55 Hz, 3H) 3.24 (d, J=4.80 Hz, 4H) 3.43 (s, 2H) 4.74 (q, J=6.74 Hz, 1H) 6.80 (s, 2H) 6.93 (d, J=9.09 Hz, 2H) 6.95-7.35 (m, 1H) 7.70 (d, J=8.84 Hz, 2H) 8.10-8.17 (m, 1H) 10.80 (s, 1H). ESI-MS: m/z 461.4 (M+H)$^+$. mp 210.4-213.0° C.

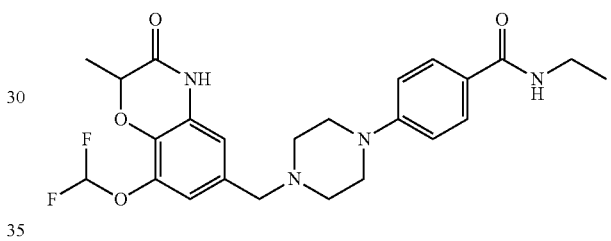

4-(4-((8-(Difluoromethoxy)-2-methyl-3-oxo-3,4-dihydro-2H-benzo[b][1,4]oxazin-6-yl)methyl)piperazin-1-yl)-N-ethylbenzamide (404)

Using 403A and N-ethyl-4-(piperazin-1-yl)benzamide 283 in the general procedure for reductive aminations, the title compound was obtained as a white solid: $^1$H NMR (400 MHz, DMSO-$d_6$) δ ppm 1.09 (t, J=7.20 Hz, 3H) 1.43 (d, J=6.82 Hz, 3H) 2.46-2.49 (m, 4H) 3.19-3.29 (m, 6H) 3.43 (s, 2H) 4.70-4.77 (m, 1H) 6.80 (s, 2H) 6.93 (d, J=8.84 Hz, 2H) 6.95-7.34 (m, 1H) 7.71 (d, J=9.09 Hz, 2H) 8.17 (t, J=5.56 Hz, 1H) 10.80 (s, 1H). ESI-MS: m/z 475.4 (M+H)$^+$. mp 219.3-223.8° C.

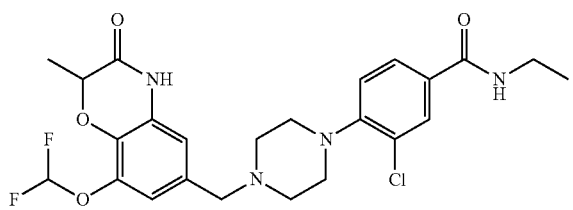 [SMILES: CCNC(=O)c1ccc(N2CCN(Cc3cc4c(c(OC(F)F)c3)OC(C)C(=O)N4)CC2)c(Cl)c1]

3-Chloro-4-(4-((8-(difluoromethoxy)-2-methyl-3-oxo-3,4-dihydro-2H-benzo[b][1,4]oxazin-6-yl)methyl)piperazin-1-yl)-N-ethylbenzamide (405)

Using 403A and 3-chloro-N-ethyl-4-(piperazin-1-yl)benzamide 286 in the general procedure for reductive aminations, the title compound was obtained as a white solid: $^1$H NMR (400 MHz, DMSO-d$_6$) δ ppm 1.10 (t, J=7.20 Hz, 3H) 1.39-1.46 (m, 3H) 2.52-2.61 (m, 4H) 3.05 (br. s., 4H) 3.21-3.30 (m, 2H) 3.45 (s, 2H) 4.70-4.78 (m, 1H) 6.78-6.83 (m, 2H) 7.13-7.21 (m, 2H) 7.77 (dd, J=8.59, 2.02 Hz, 1H) 7.87 (d, J=2.02 Hz, 1H) 8.43 (t, J=5.56 Hz, 1H) 10.81 (s, 1H). ESI-MS: m/z 509.3 (M+H)$^+$. mp 101.7-104.0° C.

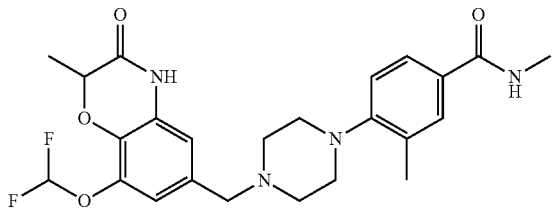 [SMILES: CNC(=O)c1ccc(N2CCN(Cc3cc4c(c(OC(F)F)c3)OC(C)C(=O)N4)CC2)c(C)c1]

4-(4-((8-(Difluoromethoxy)-2-methyl-3-oxo-3,4-dihydro-2H-benzo[b][1,4]oxazin-6-yl)methyl)piperazin-1-yl)-N,3-dimethylbenzamide (406)

Using 403A and N,3-dimethyl-4-(piperazin-1-yl)benzamide 298 in the general procedure for reductive aminations, the title compound was obtained as a white solid: $^1$H NMR (400 MHz, DMSO-d$_6$) δ ppm 1.36-1.49 (m, 3H) 2.26 (s, 3H) 2.52-2.62 (m, 4H) 2.74 (d, J=4.55 Hz, 3H) 2.89 (br. s., 4H) 3.41-3.50 (m, 2H) 4.74 (q, J=6.65 Hz, 1H) 6.81 (s, 2H) 6.92-7.37 (m, 2H) 7.56-7.66 (m, 2H) 8.23 (d, J=4.55 Hz, 1H) 10.81 (s, 1H). ESI-MS: m/z 475.4 (M+H)$^+$.

Biological Testing

The activity of compounds as PARP inhibitors may be assayed in vitro, in vivo or in a cell line. Provided below are descriptions of an in vitro enzymatic PARP activity assay for activity against PARP and a PARP cellular chemopotentiation assay.

Enzymatic PARP Assay

Dissociation Constant ($K_D$) from Surface Plasmon Resonance

Enzyme Preparation

The catalytic domain of Human PARP was cloned and prepared as described in Kinoshita, et al. FEBS Letters (2006), 556:43-46. Purified enzyme was stored at −80° C. in 25 mM Tris(hydroxymethyl)aminomethane ('Tris') pH 7.4, 150 mM NaCl, 2 mM dithiothreitol (DTT) at a concentration of 6 mg/mL.

Biacore Assays

Biacore affinity assays for test compounds were conducted on a Biacore T100 (GE Healthcare) as follows. A Series S Sensor Chip CM5 (part number BR-1006-68, GE Healthcare) was activated for amide coupling with an Amine Coupling Kit (part number BR-1000-50, GE Healthcare) as described by the manufacturer. The mobile phase buffer consisted of Biacore buffer HBS-P (part number BR-1003-68, GE Healthcare) supplemented with 1% v/v dimethylsulfoxide (DMSO), 0.5 mM Tris(2-carboxyethyl)phosphine hydrochloride (TCEP), and 5 mM MgCl$_2$. Enzyme samples (2 μL/6 mg/mL) stored at −80° C. were diluted to 0.080 mg/mL with 10 mM 4-morpholineethanesulfonic acid (MES) pH 6.5 and then mounted on the activated Biacore CM5 chip at a flow rate of 10 μL/min for 240 seconds. When successfully mounted, a signal of approximately 8,000 reflective units was observed. Test compounds were diluted 9 times 2-fold serially in mobile phase buffer (listed above) at 1% v/v DMSO final to generate a concentration gradient bracketing their anticipated $K_D$s. Biacore mounted PARP was given a 1 minute exposure (association phase) to various concentrations of test compounds to observe a steady state equilibrium or an on-rate. The exposure was followed with a dissociation phase of 5 minutes. The association and dissociation phases were at a flow rate of 50 μL/min and a temperature of 25° C.

Biacore Binding Analysis

Rapid Equilibrium Model:

If the test compound binding displayed rapid equilibrium, a plot of steady state response versus concentration was generated and the equation Rmax*[compound]/([compound]+$K_D$) was fit to the profile. Parameters R$_{max}$ (response at saturation) and $K_D$ (binding constant) were calculated through a nonlinear least squares fitting of the equation to the data by use of the Biacore T100 analysis software.

Slow Binding Model:

If the binding of the test compound did not achieve equilibrium within the 1 minute exposure, the association rate constant and the dissociation rate constant for the test compound were calculated through the simultaneous analysis of the family of progress curves obtained from the concentration gradient experiment. Parameter optimization was through a nonlinear least squares analysis of the association phase Response=R$_{max}$*(1−exp(−(k$_{on}$[cmpd]+k$_{off}$)*t)) and dissociation phase Response=R$_{max}$*exp(−(k$_{on}$[cmpd]+k$_{off}$)*t) by use of the Biacore T100 analysis software. The binding constant $K_D$ was calculated from the definition $K_D$=k$_{off}$/k$_{on}$ Inhibition Constant (IC$_{50}$) from PARP ELISA Inhibition of PARP catalytic activity was determined by use of an ELISA-based colorimetric PARP/Apoptosis Assay kit (part number 4684-096-K HT, Trevigen). To each histone coated well in the 96-well plate supplied by the manufacturer (part number 4677-096-P) is added 39 μL, of PARP buffer (part number 4671-096-02) and 1 μL, of test compound dissolved in DMSO (diluted serially 3-fold 11 times). After mixing, 5 μL of 0.1 nM PARP (part number 4684-096-01) is added and the solution allowed to stand at ambient temperature for 10 minutes. PARP catalysis is initiated with the addition of 5 μL of 100 μM β-nicotinamide adenine dinucleotide (NAD+) (part number 4684-096-02) with activated DNA (part number 4671-096-06). After 10 minutes of catalysis the reaction is quenched by solvent aspiration followed by irrigation of the assay wells 4 times with phosphate buffered saline (PBS) containing 0.1% t-Octylphenoxypolyethoxyethanol (Triton® X-100). Mouse Anti-poly ADP ribose (PAR) monoclonal antibody, goat antimouse immunoglobulin G (IgG)-horse radish peroxidase (HRP) conjugate and HRP substrate are added according to the manufacture's specifications to generate a colorimetric signal proportional to PARP catalytic activity. An IC$_{50}$ for the test compound is calculated from the equation Absorbance=(A$_{max}$−background)/(1+([cmpd]/IC$_{50}$)^n)+background fit to the 12 point test compound concentration gradient via nonlinear least squares.

Potentiation Factor (PF$_{50}$) Determination from PARP Cellular Chemopotentiation Assay Jurkat cell line was maintained according to the supplier (American Type Culture Collection (Rockville, Md.)). Cells were seeded in 96-well tissue culture microplates at 10,000 cells per well and cultured for 24 hours prior to addition of compounds, TMZ (Temozolomide) or DMSO (dimethylsulfoxide) vehicle. After 96 hours of treatment, the conversion of MTS ([3-(4,5-dimethylthiazol-2-yl)-5-(3-carboxymethoxyphenyl)-2-(4-sulfophenyl)-2H-tetrazolium, inner salt], Promega, Madison, Wis.) by metabolically active cells was determined through measuring the $OD_{490\,nm}$ with a Spectramax microplate reader (Molecular Devices, San Diego, Calif.). To generate concentration-response curves, cells were treated in duplicate with a range of serial compound dilutions (final DMSO concentration was 0.5%) in the absence or presence of 100 μM TMZ chemoreagent. The percentage of viable cells per well was calculated by correction for background and normalizing against DMSO-treated cells. $EC_{50}$ values for inhibition of cell viability were calculated using XLfit4 MicroSoft Excel curve-fitting software. Chemopotentiation factor $PF_{50}$ was calculated as the ratio of $EC_{50}$ values of cells co-treated without and with TMZ, respectively.

It should be noted that a variety of other expression systems and hosts are also suitable for the expression of PARP, as would be readily appreciated by one of skill in the art.

Table 1 lists $IC_{50}$, $K_D$, and $PF_{50}$ values for select compounds of the present invention. In Table 1, $IC_{50}$ values are expressed in terms of $pIC_{50}$, where $pIC_{50}=-\log_{10}IC_{50}$ and $IC_{50}$ has units of mol/L. Similarly, Table 1 lists $K_D$ values in terms of $pK_D$, where $pK_D=-\log_{10}K_D$ and $K_D$ has units of mol/L

TABLE 1

$pIC_{50}$, $pK_D$, and $PF_{50}$ Values of Exemplified Compounds Against PARP

| Compound | $pIC_{50}$ | pKD | $PF_{50}$ |
|---|---|---|---|
| 23 | — | 4.1-4.9 | — |
| 24 | — | 4.1-4.9 | — |
| 25 | — | 6.0-6.9 | — |
| 26 | — | 5.0-5.9 | — |
| 27 | — | 4.1-4.9 | — |
| 28 | — | 4.1-4.9 | — |
| 29 | — | 5.0-5.9 | — |
| 30 | — | 5.0-5.9 | — |
| 31 | — | 7.0-7.9 | — |
| 32 | — | 5.0-5.9 | — |
| 33 | — | 6.0-6.9 | — |
| 34 | — | 7.0-7.9 | — |
| 35 | — | ≥8 | — |
| 36 | — | 6.0-6.9 | — |
| 37 | — | 7.0-7.9 | — |
| 38 | — | ≥8 | — |
| 39 | — | <5 | — |
| 40 | — | 6.0-6.9 | — |
| 41 | — | <6 | — |
| 42 | — | 5.0-5.9 | — |
| 43 | — | 5.0-5.9 | — |
| 45 | — | 7.0-7.9 | — |
| 46 | — | 7.0-7.9 | 1.0-1.9 |
| 47 | — | ≥8 | — |
| 48 | — | 6.0-6.9 | 1.0-1.9 |
| 49 | — | ≥8 | ≤0.9 |
| 50 | — | 7.0-7.9 | — |
| 51 | — | 6.0-6.9 | — |
| 52 | — | 7.0-7.9 | ≤0.9 |
| 53 | — | 7.0-7.9 | ≤0.9 |
| 54 | — | 7.0-7.9 | ≤0.9 |
| 55 | — | 5.0-5.9 | — |
| 56 | — | 7.0-7.9 | — |
| 57 | — | 7.0-7.9 | 1.0-1.9 |
| 58 | — | 7.0-7.9 | ≤0.9 |
| 59 | — | 7.0-7.9 | 2.0-9.9 |
| 60 | — | 6.0-6.9 | 1.0-1.9 |
| 61 | 7.0-7.4 | ≥8 | ≤0.9 |
| 62 | — | ≥8 | ≤0.9 |
| 63 | — | ≥8 | — |
| 64 | — | 4.1-4.9 | — |
| 65 | — | 4.1-4.9 | — |
| 66 | — | ≤4.0 | — |
| 67 | — | 4.1-4.9 | — |

TABLE 1-continued $pIC_{50}$, $pK_D$, and $PF_{50}$ Values of Exemplified Compounds Against PARP

| Compound | $pIC_{50}$ | pKD | $PF_{50}$ |
|---|---|---|---|
| 70 | — | — | 1.0-1.9 |
| 72 | — | 6.0-6.9 | ≤0.9 |
| 73 | — | 5.0-5.9 | — |
| 74 | — | 6.0-6.9 | 1.0-1.9 |
| 76 | — | 6.0-6.9 | — |
| 77 | — | 6.0-6.9 | 1.0-1.9 |
| 78 | — | 5.0-5.9 | — |
| 79 | — | <5 | — |
| 80 | — | 6.0-6.9 | ≤0.9 |
| 81 | — | 7.0-7.9 | ≤0.9 |
| 82 | — | <5 | — |
| 83 | — | <5 | — |
| 84 | — | <5 | — |
| 85 | — | 5.0-5.9 | — |
| 86 | — | 4.1-4.9 | — |
| 87 | — | 5.0-5.9 | — |
| 88 | — | 4.1-4.9 | — |
| 89 | — | 5.0-5.9 | 1.0-1.9 |
| 90 | — | 5.0-5.9 | — |
| 91 | — | 5.0-5.9 | — |
| 92 | — | 4.1-4.9 | — |
| 93 | — | 5.0-5.9 | — |
| 94 | — | 5.0-5.9 | — |
| 95 | — | 5.0-5.9 | — |
| 96 | — | 6.0-6.9 | — |
| 97 | — | ≥8 | ≤0.9 |
| 99 | — | 6.0-6.9 | — |
| 100 | — | 7.0-7.9 | — |
| 101 | — | ≥8 | 1.0-1.9 |
| 102 | — | 5.0-5.9 | — |
| 104 | — | ≤4.0 | — |
| 105 | — | ≤4.0 | — |
| 106 | — | ≤4.0 | — |
| 107 | — | ≤4.0 | — |
| 108 | — | ≤4.0 | — |
| 109 | — | 5.0-5.9 | — |
| 110 | — | ≤4.0 | — |
| 111 | — | ≤4.0 | — |
| 112 | — | ≤4.0 | — |
| 113 | — | ≤4.0 | — |
| 114 | — | 4.1-4.9 | — |
| 115 | — | ≤4.0 | — |
| 116 | — | 4.1-4.9 | — |
| 117 | — | 5.0-5.9 | — |
| 118 | — | 5.0-5.9 | — |
| 119 | — | 4.1-4.9 | — |
| 120 | — | ≤4.0 | — |
| 121 | — | <6 | — |
| 122 | — | ≤4.0 | — |
| 124 | — | 6.0-6.9 | 1.0-1.9 |
| 125 | — | 4.1-4.9 | — |
| 126 | — | 5.0-5.9 | — |
| 127 | — | 5.0-5.9 | — |
| 128 | — | 4.1-4.9 | — |
| 129 | — | 4.1-4.9 | — |
| 130 | — | 5.0-5.9 | — |
| 131 | — | 5.0-5.9 | — |
| 132 | — | 5.0-5.9 | — |
| 134 | — | 5.0-5.9 | — |
| 135 | — | 4.1-4.9 | — |
| 136 | — | 5.0-5.9 | — |
| 137 | — | ≤4.0 | — |
| 138 | — | 4.1-4.9 | — |
| 139 | — | 5.0-5.9 | 1.0-1.9 |
| 140 | — | 5.0-5.9 | — |
| 141 | — | 5.0-5.9 | — |
| 142 | — | 5.0-5.9 | — |
| 143 | — | <5 | — |
| 144 | — | 4.1-4.9 | — |
| 145 | — | <5 | — |
| 146 | — | <5 | — |
| 147 | — | <5 | — |
| 148 | — | <5 | — |
| 149 | — | <5 | — |
| 150 | — | <5 | — |

TABLE 1-continued pIC$_{50}$, pK$_D$, and PF$_{50}$ Values of Exemplified Compounds Against PARP

| Compound | pIC$_{50}$ | pKD | PF$_{50}$ |
| --- | --- | --- | --- |
| 151 | — | <5 | — |
| 152 | — | <5 | — |
| 153 | — | <5 | — |
| 154 | — | <5 | — |
| 155 | — | <5 | — |
| 156 | ≤6.9 | ≥8 | 1.0-1.9 |
| 157 | — | 7.0-7.9 | 1.0-1.9 |
| 158 | — | 7.0-7.9 | 1.0-1.9 |
| 159 | ≤6.9 | >7.5 | — |
| 160 | ≤6.9 | 6.0-6.9 | — |
| 161 | ≥7.5 | >7.5 | ≥10.0 |
| 162 | ≥7.5 | >7.5 | 2.0-9.9 |
| 163 | ≥7.5 | >7.5 | ≥10.0 |
| 164 | ≥7.5 | >7.5 | ≥10.0 |
| 165 | ≤6.9 | — | — |
| 166 | ≤6.9 | — | 1.0-1.9 |
| 167 | 7.0-7.4 | — | ≤0.9 |
| 168 | — | ≤4.0 | — |
| 171 | — | 6.0-6.9 | ≤0.9 |
| 172 | — | <5 | — |
| 173 | — | 5.0-5.9 | — |
| 174 | — | 5.0-5.9 | — |
| 175 | — | <5 | — |
| 176 | — | <5 | — |
| 177 | — | <5 | — |
| 178 | — | <5 | — |
| 179 | — | <5 | — |
| 180 | — | <5 | — |
| 181 | — | <5 | — |
| 182 | — | 4.1-4.9 | — |
| 188 | — | <5 | — |
| 189 | — | <5 | — |
| 192 | — | ≥8 | 1.0-1.9 |
| 193 | — | ≤4.0 | — |
| 194 | — | ≤4.0 | — |
| 195 | — | ≤4.0 | — |
| 196 | — | ≤4.0 | — |
| 197 | ≤6.9 | ≥8 | 1.0-1.9 |
| 198 | — | 4.1-4.9 | — |
| 199 | — | ≤4.0 | — |
| 200 | — | 4.1-4.9 | — |
| 201 | — | ≤4.0 | — |
| 202 | — | ≤4.0 | — |
| 203 | — | ≤4.0 | — |
| 204 | — | 4.1-4.9 | — |
| 209 | — | 4.1-4.9 | — |
| 210 | — | 4.1-4.9 | — |
| 211 | — | ≤4.0 | — |
| 212 | — | ≤4.0 | — |
| 213 | — | 6.0-6.9 | 1.0-1.9 |
| 214 | 7.0-7.4 | ≥8 | ≤0.9 |
| 215 | — | ≤4.0 | — |
| 216 | — | 5.0-5.9 | — |
| 217 | ≤6.9 | ≥8 | ≤0.9 |
| 218 | ≤6.9 | — | ≤0.9 |
| 219 | ≥7.5 | ≥8 | ≤0.9 |
| 220 | 7.0-7.4 | ≥8 | 1.0-1.9 |
| 221 | — | 5.0-5.9 | — |
| 222 | ≤6.9 | 7.0-7.9 | 1.0-1.9 |
| 223 | ≥7.5 | ≥8 | ≤0.9 |
| 224 | ≥7.5 | ≥8 | 2.0-9.9 |
| 225 | ≥7.5 | ≥8 | ≤0.9 |
| 226 | 7.0-7.4 | — | ≤0.9 |
| 227 | — | — | 1.0-1.9 |
| 229 | — | ≥8 | 1.0-1.9 |
| 230 | — | 7.0-7.9 | 1.0-1.9 |
| 231 | ≥7.5 | ≥8 | 1.0-1.9 |
| 232 | 7.0-7.4 | ≥8 | 1.0-1.9 |
| 233 | ≤6.9 | 5.0-5.9 | — |
| 234 | 7.0-7.4 | ≥8 | 1.0-1.9 |
| 235 | ≥7.5 | ≥8 | 2.0-9.9 |
| 236 | ≥7.5 | ≥8 | ≤0.9 |
| 237 | ≤6.9 | ≥8 | ≤0.9 |
| 238 | 7.0-7.4 | 7.0-7.9 | 1.0-1.9 |
| 239 | ≤6.9 | 6.0-6.9 | — |
| 240 | ≤6.9 | 6.0-6.9 | — |
| 241 | — | ≥8 | — |
| 242 | — | 5.0-5.9 | — |
| 243 | — | 5.0-5.9 | ≤0.9 |
| 244 | — | 5.0-5.9 | ≤0.9 |
| 245 | ≤6.9 | — | — |
| 246 | ≤6.9 | — | — |
| 247 | ≤6.9 | — | — |
| 248 | ≤6.9 | — | — |
| 249 | ≥7.5 | — | 1.0-1.9 |
| 250 | ≥7.5 | — | 2.0-9.9 |
| 253 | ≥7.5 | ≥8 | 2.0-9.9 |
| 254 | ≥7.5 | 7.0-7.9 | 2.0-9.9 |
| 255 | 7.0-7.4 | 7.0-7.9 | ≤0.9 |
| 256 | — | 6.0-6.9 | 1.0-1.9 |
| 257 | ≥7.5 | ≥8 | 2.0-9.9 |
| 258 | ≥7.5 | — | ≥10.0 |
| 259 | ≥7.5 | ≥8 | ≥10.0 |
| 260 | — | ≥8 | 2.0-9.9 |
| 261 | 7.0-7.4 | ≥8 | 2.0-9.9 |
| 262 | — | ≥8 | 2.0-9.9 |
| 263 | ≤6.9 | <5 | — |
| 266 | — | ≥8 | ≤0.9 |
| 267 | ≥7.5 | ≥8 | 1.0-1.9 |
| 268 | ≤6.9 | <5 | — |
| 269 | ≤6.9 | 6.0-6.9 | — |
| 270 | ≤6.9 | 5.0-5.9 | — |
| 271 | 7.0-7.4 | ≥8 | ≤0.9 |
| 272 | 7.0-7.4 | >7.5 | 1.0-1.9 |
| 273 | ≥7.5 | >7.5 | ≤0.9 |
| 305 | 7.5 | — | 1.9 |
| 306 | 7.1 | — | 1.3 |
| 307 | <6.7 | — | — |
| 308 | 7.7 | — | 6.3 |
| 309 | 8.3 | — | 5.2 |
| 310 | 7.5 | — | — |
| 311 | 7.4 | — | — |
| 312 | <6.7 | — | — |
| 313 | <6.7 | — | — |
| 314 | 7.5 | — | 1.8 |
| 315 | 7.3 | — | — |
| 316 | 7.0 | — | — |
| 317 | 7.3 | — | — |
| 320 | 6.7 | — | — |
| 321 | 8.7 | — | 1.4 |
| 322 | <6.7 | — | — |
| 325 | <6.7 | — | — |
| 326 | <6.7 | — | — |
| 327 | <6.7 | — | — |
| 330 | <6.7 | — | — |
| 331 | <6.7 | — | 1.3 |
| 332 | <6.7 | — | — |
| 333 | <6.7 | — | — |
| 334 | <6.7 | — | — |
| 335 | 7.2 | — | 0.3 |
| 336 | 7.0 | — | 2.1 |
| 337 | 6.7 | — | — |
| 338 | 7.1 | — | 0.4 |
| 339 | 7.1 | — | 1.0 |
| 340 | 7.2 | — | 0.9 |
| 343 | 6.7 | — | — |
| 344 | <6.7 | — | 1.3 |
| 345 | 7.1 | — | 1.2 |
| 346 | 7.0 | — | 8.6 |
| 347 | 7.0 | — | 10.1 |
| 348 | 6.6 | — | >5 |
| 349 | <6.7 | — | — |
| 350 | <6.7 | — | 2.1 |
| 351 | <6.7 | — | 1.0 |
| 352 | 7.1 | — | 6.3 |
| 353 | <6.7 | — | 1.3 |
| 354 | <6.7 | — | 1.0 |
| 355 | <6.7 | — | 1.3 |
| 356 | 7.1 | — | — |
| 357 | <6.7 | — | — |

TABLE 1-continued pIC$_{50}$, pK$_D$, and PF$_{50}$ Values of Exemplified Compounds Against PARP

| Compound | pIC$_{50}$ | pKD | PF$_{50}$ |
|---|---|---|---|
| 358 | <6.7 | — | >3.0 |
| 359 | 7.8 | — | >6.0 |
| 360 | 7.4 | — | 3.1 |
| 361 | 7.6 | — | >3500 |
| 362 | 7.5 | — | >1700 |
| 363 | 7.5 | — | 6522 |
| 364 | 6.9 | — | 4365 |
| 365 | 7.5 | — | 1.3 |
| 366 | 7.6 | — | 4.6 |
| 367 | <6.7 | — | 2.5 |
| 370 | 7.1 | — | 5.0 |
| 371 | 7.8 | — | >20 |
| 372 | 7.7 | — | 1.0 |
| 373 | 7.7 | — | 3.2 |
| 374 | 7.5 | — | <2.0 |
| 375 | 7.8 | — | >2.0 |
| 376 | 7.8 | — | >6.0 |
| 377 | <6.7 | — | 1.0 |
| 378 | <6.7 | — | — |
| 379 | <6.7 | — | — |
| 380 | 7.3 | — | 4.0 |
| 381 | 7.4 | — | >2 |
| 382 | 7.1 | — | 3.4 |
| 383 | 7.3 | — | 3.2 |
| 384 | 7.4 | — | 8.4 |
| 385 | 7.3 | — | 5.9 |
| 386 | 7.3 | — | >5.0 |
| 387 | 7.3 | — | >5.0 |
| 388 | 7.1 | — | 6558 |
| 389 | <6.7 | — | 1.1 |
| 390 | <6.7 | — | 1.0 |
| 391 | <6.7 | — | — |
| 392 | <6.7 | — | — |
| 393 | <6.7 | — | — |
| 394 | <6.7 | — | — |
| 395 | <6.7 | — | — |
| 396 | <6.7 | — | — |
| 397 | <6.7 | — | — |
| 398 | 7.1 | — | >2.0 |
| 399 | 7.2 | — | >4.0 |
| 400 | 7.5 | — | 1211 |
| 401 | 7.3 | — | >5000 |
| 402 | 7.4 | — | >10000 |
| 403 | 7.2 | — | >2.0 |
| 404 | 7.5 | — | >2.0 |
| 405 | 6.9 | — | 5.3 |
| 406 | 7.2 | — | 13 |

It will be apparent to those skilled in the art that various modifications and variations can be made in the compounds, compositions, kits, and methods of the present invention without departing from the spirit or scope of the invention. Thus, it is intended that the present invention cover the modifications and variations of this invention provided they come within the scope of the appended claims and their equivalents.

What is claimed is:

1. A compound of the formula:

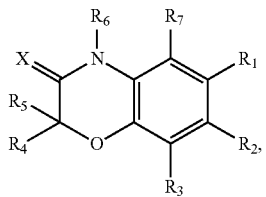

a tautomer thereof, or a pharmaceutically acceptable salt of the compound or tautomer, wherein:

X is O;

$R_1$ is -$L_1$-$R_9$;

$R_2$ is selected from the group consisting of hydrogen, halo, and ($C_{1-3}$)alkyl;

$R_3$ is selected from the group consisting of hydrogen, halo, hydroxy, ($C_{1-3}$)alkyl, ($C_{1-3}$)alkoxy, and aryl($C_{1-10}$) alkyl;

$R_4$ is selected from the group consisting of hydrogen, halo, and ($C_{1-3}$)alkyl;

$R_5$ is methyl;

$R_6$ is hydrogen;

$R_7$ is selected from the group consisting of hydrogen, halo, and ($C_{1-3}$)alkyl;

$L_1$ is selected from the group consisting of —CH$_2$— and;

$R_9$ is selected from the group consisting of

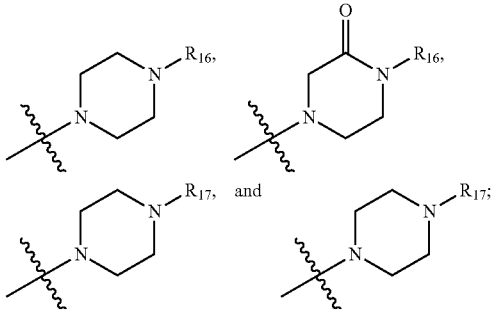

$R_{16}$ and $R_{17}$ are each independently selected from the group consisting of ($C_{3-12}$)cycloalkyl, hetero($C_{3-12}$)cycloalkyl, ($C_{9-12}$)bicycloalkyl, hetero($C_{3-12}$)bicycloalkyl, ($C_{6-12}$)aryl, ($C_{1-10}$)heteroaryl, ($C_{9-12}$)bicycloaryl and hetero($C_{4-12}$)bicycloaryl, each unsubstituted or substituted through available valencies with one or more substituents independently selected from the group consisting of halo, nitro, cyano, oxo, hydroxy, ($C_{1-10}$)alkoxy, carbonyl, amido, amino, ($C_{1-10}$)alkyl, halo($C_{1-10}$)alkyl, sulfonyl($C_{1-10}$)alkyl, and ($C_{6-12}$)aryl, wherein carbonyl, amido, and amino are each independently substituted with hydrogen, hydroxy, ($C_{1-10}$) alkoxy, ($C_{1-10}$)alkyl, ($C_{3-12}$)cycloalkyl, hetero($C_{3-12}$)cycloalkyl or ($C_{6-12}$)aryl.

2. The compound, tautomer, or pharmaceutically acceptable salt according to claim 1, wherein $R_2$ is hydrogen.

3. The compound, tautomer, or pharmaceutically acceptable salt according to claim 1, wherein $R_3$ is hydrogen.

4. The compound, tautomer, or pharmaceutically acceptable salt according to claim 1, wherein $R_4$ is hydrogen.

5. The compound, tautomer, or pharmaceutically acceptable salt according to claim 1, wherein $R_7$ is hydrogen.

6. The compound, tautomer, or pharmaceutically acceptable salt according to claim 1, wherein $R_{16}$ and $R_{17}$ are each independently selected from phenyl and pyridinyl, each unsubstituted or substituted through available valencies with one or more substituents independently selected from the group consisting of halo, nitro, cyano, oxo, hydroxy, ($C_{1-10}$) alkoxy, carbonyl, amido, amino, ($C_{1-10}$)alkyl, halo($C_{1-10}$) alkyl, sulfonyl($C_{1-10}$)alkyl, and ($C_{6-12}$)aryl, wherein carbonyl, amido, and amino are each independently substituted with hydrogen, hydroxy, ($C_{1-10}$)alkoxy, ($C_{1-10}$)alkyl, ($C_{3-12}$) cycloalkyl, hetero($C_{3-12}$)cycloalkyl or ($C_{6-12}$)aryl.

7. The compound, tautomer, or pharmaceutically acceptable salt according to claim 6, wherein $R_{16}$ or $R_{17}$ has the formula:

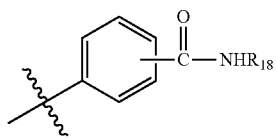

wherein:
$R_{18}$ is selected from the group consisting of hydrogen, hydroxy, $(C_{1-10})$alkoxy, $(C_{6-12})$aryloxy, hetero$(C_{1-10})$aryloxy, amino, $(C_{1-10})$alkylamino, $(C_{1-10})$alkyl, halo$(C_{1-10})$alkyl, hydroxy$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{4-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{6-12})$aryl, hetero$(C_{1-10})$aryl, $(C_{9-12})$bicycloaryl and hetero$(C_{4-12})$bicycloaryl, each substituted or unsubstituted.

8. The compound, tautomer, or pharmaceutically acceptable salt according to claim 7, wherein $R_{16}$ or $R_{17}$ has the formula:

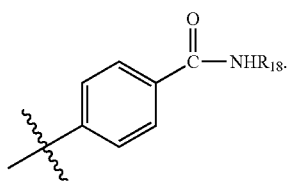

9. The compound, tautomer, or pharmaceutically acceptable salt according to claim 7, wherein $R_{18}$ is selected from the group consisting of hydrogen and $(C_{1-3})$alkyl.

10. The compound according to claim 1, which is selected from the following compounds:

2-Methyl-6-((4-phenylpiperidin-1-yl)methyl)-2H-benzo[b][1,4]oxazin-3(4H)-one;
2-Methyl-6-((4-phenylpiperazin-1-yl)methyl)-2H-benzo[b][1,4]oxazin-3(4H)-one;
6-((4-(4-Fluorophenyl)-5,6-dihydropyridin-1(2H)-yl)methyl)-2-methyl-2H-benzo[b][1,4]oxazin-3(4H)-one;
6-((4-(4-Chlorophenyl)-5,6-dihydropyridin-1(2H)-yl)methyl)-2-methyl-2H-benzo[b][1,4]oxazin-3(4H)-one;
2-Methyl-6-((4-p-tolylpiperidin-1-yl)methyl)-2H-benzo[b][1,4]oxazin-3(4H)-one ;
6-((4-(4-Fluorophenyl)piperidin-1-yl)methyl)-2-methyl-2H-benzo[b][1,4]oxazin-3(4H)-one;
6-((4-(4-Chlorophenyl)piperidin-1-yl)methyl)-2-methyl-2H-benzo[b][1,4]oxazin-3(4H)-one;
2-Methyl-6-((4-(3-phenyl-1,2,4-thiadiazol-5-yl)piperazin-1-yl)methyl)-2H-benzo[b][1,4]oxazin-3(4H)-one;
6-((4-Cyclopentylpiperazin-1-yl)methyl)-2-methyl-2H-benzo[b][1,4]oxazin-3(4H)-one;
6-((4-(1H-Benzo[d]imidazol-2-yl)piperazin-1-yl)methyl)-2-methyl-2H-benzo[b][1,4]oxazin-3(4H)-one;
(S)-2-Methyl-6-((4-phenylpiperidin-1-yl)methyl)-2H-benzo[b][1,4]oxazin-3(4H)-one;
(R)-2-Methyl-6-((4-phenylpiperidin-1-yl)methyl)-2H-benzo[b][1,4]oxazin-3(4H)-one;
6-((4-(1H-Benzo[d]imidazol-2-yl)piperidin-1-yl)methyl)-2-methyl-2H-benzo[b][1,4]oxazin-3(4H)-one;
2-Methyl-6-((4-(4-nitrophenyl)piperazin-1-yl)methyl)-2H-benzo[b][1,4]oxazin-3(4H)-one;
4-(4-((2-Methyl-3-oxo-3,4-dihydro-2H-benzo[b][1,4]oxazin-6-yl)methyl)piperazin-1-yl)benzoic acid;
6-((4-Cycloheptylpiperazin-1-yl)methyl)-2-methyl-2H-benzo[b][1,4]oxazin-3(4H)-one;
1,3,7-Trimethyl-8-(4-((2-methyl-3-oxo-3,4-dihydro-2H-benzo[b][1,4]oxazin-6-yl)methyl)piperazin-1-yl)-1H-purine-2,6(3H,7H)-dione;
6-((4-(4-Aminophenyl)piperazin-1-yl)methyl)-2-methyl-2H-benzo[b][1,4]oxazin-3(4H)-one;
6-((4-(6-Fluorobenzo[d]isoxazol-3-yl)piperidin-1-yl)methyl)-2-methyl-2H-benzo[b][1,4]oxazin-3(4H)-one;
6-((4-(2-Hydroxyphenyl)piperazin-1-yl)methyl)-2-methyl-2H-benzo[b][1,4]oxazin-3(4H)-one;
2-Methyl-6-((4-phenyl-5,6-dihydropyridin-1(2H)-yl)methyl)-2H-benzo[b][1,4]oxazin-3(4H)-one;
2-Methyl-6-((4-phenyl-5,6-dihydropyridin-1(2H)-yl)methyl)-2H-benzo[b][1,4]oxazin-3(4H)-one;
6-((4-(2-Methoxyphenyl)piperazin-1-yl)methyl)-2-methyl-2H-benzo[b][1,4]oxazin-3(4H)-one;
6-((4-(5-Chloropyridin-2-yl)piperazin-1-yl)methyl)-2-methyl-2H-benzo[b][1,4]oxazin-3(4H)-one;
(S)-6-((4-(4-Chlorophenyl)-5,6-dihydropyridin-1(2H)-yl)methyl)-2-methyl-2H-benzo[b][1,4]oxazin-3(4H)-one;
(R)-6-((4-(4-Chlorophenyl)-5,6-dihydropyridin-1(2H)-yl)methyl)-2-methyl-2H-benzo[b][1,4]oxazin-3(4H)-one;
2-Methyl-6-((3-oxo-4-phenylpiperazin-1-yl)methyl)-2H-benzo[b][1,4]oxazin-3(4H)-one;
7-Chloro-2-methyl-6-((4-phenylpiperazin-1-yl)methyl)-2H-benzo[b][1,4]oxazin-3(4H)-one;
2-Methyl-6-(4-phenylpiperidin-1-ylsulfonyl)-2H-benzo[b][1,4]oxazin-3(4H)-one;
8-Methoxy-2-methyl-6-((4-phenylpiperazin-1-yl)methyl)-2H-benzo[b][1,4]oxazin-3(4H)-one;
8-Methoxy-2-methyl-6-((4-phenylpiperidin-1-yl)methyl)-2H-benzo[b][1,4]oxazin-3(4H)-one;
8-Methoxy-2-methyl-6-((4-phenyl-5,6-dihydropyridin-1(2H)-yl)methyl)-2H-benzo[b][1,4]oxazin-3(4H)-one;
Ethyl 4-(4-((8-methoxy-2-methyl-3-oxo-3,4-dihydro-2H-benzo[b][1,4]oxazin-6-yl)methyl)piperazin-1-yl)benzoate;
4-(4-((8-Methoxy-2-methyl-3-oxo-3,4-dihydro-2H-benzo[b][1,4]oxazin-6-yl)methyl)piperazin-1-yl)benzoic acid;
4-(4-((8-Methoxy-2-methyl-3-oxo-3,4-dihydro-2H-benzo[b][1,4]oxazin-6-yl)methyl)piperazin-1-yl)-N-methylbenzamide;
N-Ethyl-4-(4-((8-methoxy-2-methyl-3-oxo-3,4-dihydro-2H-benzo[b][1,4]oxazin-6-yl)methyl)piperazin-1-yl)benzamide;
N-Cyclopropyl-4-(4-((8-methoxy-2-methyl-3-oxo-3,4-dihydro-2H-benzo[b][1,4]oxazin-6-yl)methyl)piperazin-1-yl)benzamide;
N-Isopropyl-4-(4-((8-methoxy-2-methyl-3-oxo-3,4-dihydro-2H-benzo[b][1,4]oxazin-6-yl)methyl)piperazin-1-yl)benzamide;
8-Chloro-6-((4-(4-chlorophenyl)piperidin-1-yl)methyl)-2-methyl-2H-benzo[b][1,4]oxazin-3(4H)-one;
8-Chloro-6-((4-(4-chlorophenyl)-5,6-dihydropyridin-1(2H)-yl)methyl)-2-methyl-2H-benzo[b][1,4]oxazin-3(4H)-one;
8-Chloro-6-((4-(4-chlorophenyl)piperazin-1-yl)methyl)-2-methyl-2H-benzo[b][1,4]oxazin-3(4H)-one;
Methyl 3-(1-((2-methyl-3-oxo-3,4-dihydro-2H-benzo[b][1,4]oxazin-6-yl)methyl)piperidin-4-yl)benzoate;
2-Methyl-6-((4-(4-(trifluoromethyl)phenyl)piperidin-1-yl)methyl)-2H-benzo[b][1,4]oxazin-3(4H)-one;

Methyl 4-(1-((2-methyl-3-oxo-3,4-dihydro-2H-benzo[b][1,4]oxazin-6-yl)methyl)piperidin-4-yl)benzoate;
3-(1-((2-Methyl-3-oxo-3,4-dihydro-2H-benzo[b][1,4]oxazin-6-yl)methyl)piperidin-4-yl)benzoic acid;
4-(1-((2-Methyl-3-oxo-3,4-dihydro-2H-benzo[b][1,4]oxazin-6-yl)methyl)piperidin-4-yl)benzoic acid;
Ethyl 4-(4-((2-methyl-3-oxo-3,4-dihydro-2H-benzo[b][1,4]oxazin-6-yl)methyl)piperazin-1-yl)benzoate;
6-((4-(4-Acetylphenyl)piperazin-1-yl)methyl)-2-methyl-2H-benzo[b][1,4]oxazin-3(4H)-one;
4-(4-((2-methyl-3-oxo-3,4-dihydro-2H-benzo[b][1,4]oxazin-6-yl)methyl)piperazin-1-yl)benzonitrile;
Methyl 4-(4-((2-methyl-3-oxo-3,4-dihydro-2H-benzo[b][1,4]oxazin-6-yl)methyl)piperazin-1-yl)benzoate;
2-Methyl-6-((4-(3-(trifluoromethyl)phenyl)piperazin-1-yl)methyl)-2H-benzo[b][1,4]oxazin-3(4H)-one;
2-Methyl-6-((4-(4-(trifluoromethyl)phenyl)piperazin-1-yl)methyl)-2H-benzo[b][1,4]oxazin-3(4H)-one;
N-Methyl-4-(4-((2-methyl-3-oxo-3,4-dihydro-2H-benzo[b][1,4]oxazin-6-yl)methyl)piperazin-1-yl)benzamide;
N-Ethyl-4-(4-((2-methyl-3-oxo-3,4-dihydro-2H-benzo[b][1,4]oxazin-6-yl)methyl)piperazin-1-yl)benzamide;
N-Isopropyl-4-(4-((2-methyl-3-oxo-3,4-dihydro-2H-benzo[b][1,4]oxazin-6-yl)methyl)piperazin-1-yl)benzamide;
N-(Cyclopropylmethyl)-4-(4-((2-methyl-3-oxo-3,4-dihydro-2H-benzo[b][1,4]oxazin-6-yl)methyl)piperazin-1-yl)benzamide;
2-Methyl-6-((4-(4-(methylsulfonyl)phenyl)piperazin-1-yl)methyl)-2H-benzo[b][1,4]oxazin-3(4H)-one;
6-((4-(4-tert-Butylphenyl)piperazin-1-yl)methyl)-2-methyl-2H-benzo[b][1,4]oxazin-3(4H)-one;
2-Methyl-6-((4-(5-methylpyridin-2-yl)piperazin-1-yl)methyl)-2H-benzo[b][1,4]oxazin-3(4H)-one;
2-Methyl-6-((4-(5-(trifluoromethyl)pyridin-2-yl)piperazin-1-yl)methyl)-2H-benzo[b][1,4]oxazin-3(4H)-one;
6-(4-((2-Methyl-3-oxo-3,4-dihydro-2H-benzo[b][1,4]oxazin-6-yl)methyl)piperazin-1-yl)nicotinonitrile;
Methyl 6-(4-((2-methyl-3-oxo-3,4-dihydro-2H-benzo[b][1,4]oxazin-6-yl)methyl)piperazin-1-yl)nicotinate;
6-(4-((2-Methyl-3-oxo-3,4-dihydro-2H-benzo[b][1,4]oxazin-6-yl)methyl)piperazin-1-yl)nicotinic acid;
N-(Cyclopropylmethyl)-6-(4-((2-methyl-3-oxo-3,4-dihydro-2H-benzo[b][1,4]oxazin-6-yl)methyl)piperazin-1-yl)nicotinamide;
N-Methyl-6-(4-((2-methyl-3-oxo-3,4-dihydro-2H-benzo[b][1,4]oxazin-6-yl)methyl)piperazin-1-yl)nicotinamide;
N-Ethyl-6-(4-((2-methyl-3-oxo-3,4-dihydro-2H-benzo[b][1,4]oxazin-6-yl)methyl)piperazin-1-yl)nicotinamide;
Ethyl 6-(4-((2-methyl-3-oxo-3,4-dihydro-2H-benzo[b][1,4]oxazin-6-yl)methyl)piperazin-1-yl)nicotinate;
N-Isopropyl-6-(4-((2-methyl-3-oxo-3,4-dihydro-2H-benzo[b][1,4]oxazin-6-yl)methyl)piperazin-1-yl)nicotinamide;
N-(4-(4-((2-Methyl-3-oxo-3,4-dihydro-2H-benzo[b][1,4]oxazin-6-yl)methyl)piperazin-1-yl)phenyl)acetamide;
N-(4-(4-((2-Methyl-3-oxo-3,4-dihydro-2H-benzo[b][1,4]oxazin-6-yl)methyl)piperazin-1-yl)phenyl)propionamide;
N-(4-(4-((2-methyl-3-oxo-3,4-dihydro-2H-benzo[b][1,4]oxazin-6-yl)methyl)piperazin-1-yl)phenyl)cyclopropanecarboxamide;
N-(4-(4-((2-Methyl-3-oxo-3,4-dihydro-2H-benzo[b][1,4]oxazin-6-yl)methyl)piperazin-1-yl)phenyl)benzamide;
(S)—N-Ethyl-4-(4-((2-methyl-3-oxo-3,4-dihydro-2H-benzo[b][1,4]oxazin-6-yl)methyl)piperazin-1-yl)benzamide;
(R)—N-Ethyl-4-(4-((2-methyl-3-oxo-3,4-dihydro-2H-benzo[b][1,4]oxazin-6-yl)methyl)piperazin-1-yl)benzamide;
4-(4-((2,8-Dimethyl-3-oxo-3,4-dihydro-2H-benzo[b][1,4]oxazin-6-yl)methyl)piperazin-1-yl)benzonitrile;
6-(4-((2,8-Dimethyl-3-oxo-3,4-dihydro-2H-benzo[b][1,4]oxazin-6-yl)methyl)piperazin-1-yl)nicotinonitrile;
Ethyl 4-(4-((2,8-dimethyl-3-oxo-3,4-dihydro-2H-benzo[b][1,4]oxazin-6-yl)methyl)piperazin-1-yl)benzoate;
Ethyl 6-(4-((2,8-dimethyl-3-oxo-3,4-dihydro-2H-benzo[b][1,4]oxazin-6-yl)methyl)piperazin-1-yl)nicotinate;
4-(4-((2,8-Dimethyl-3-oxo-3,4-dihydro-2H-benzo[b][1,4]oxazin-6-yl)methyl)piperazin-1-yl)-N-methylbenzamide;
4-(4-((2,8-Dimethyl-3-oxo-3,4-dihydro-2H-benzo[b][1,4]oxazin-6-yl)methyl)piperazin-1-yl)-N-ethylbenzamide;
N-Cyclopropyl-4-(4-((2,8-dimethyl-3-oxo-3,4-dihydro-2H-benzo[b][1,4]oxazin-6-yl)methyl)piperazin-1-yl)benzamide;
6-(4-((2,8-Dimethyl-3-oxo-3,4-dihydro-2H-benzo[b][1,4]oxazin-6-yl)methyl)piperazin-1-yl)-N-methylnicotinamide;
6-(4-((2,8-Dimethyl-3-oxo-3,4-dihydro-2H-benzo[b][1,4]oxazin-6-yl)methyl)piperazin-1-yl)-N-ethylnicotinamide;
N-Cyclopropyl-6-(4-((2,8-dimethyl-3-oxo-3,4-dihydro-2H-benzo[b][1,4]oxazin-6-yl)methyl)piperazin-1-yl)nicotinamide;
6-((4-(4-Chlorophenyl)-5,6-dihydropyridin-1(2H)-yl)methyl)-2,8-dimethyl-2H-benzo[b][1,4]oxazin-3(4H)-one;
4-(4-((8-Fluoro-2-methyl-3-oxo-3,4-dihydro-2H-benzo[b][1,4]oxazin-6-yl)methyl)piperazin-1-yl)benzonitrile;
6-(4-((8-fluoro-2-methyl-3-oxo-3,4-dihydro-2H-benzo[b][1,4]oxazin-6-yl)methyl)piperazin-1-yl)nicotinonitrile;
6-((4-(4-Chlorophenyl)-5,6-dihydropyridin-1(2H)-yl)methyl)-8-fluoro-2-methyl-2H-benzo[b][1,4]oxazin-3(4H)-one;
Ethyl 4-(4-((8-fluoro-2-methyl-3-oxo-3,4-dihydro-2H-benzo[b][1,4]oxazin-6-yl)methyl)piperazin-1-yl)benzoate;
4-(4-((8-Fluoro-2-methyl-3-oxo-3,4-dihydro-2H-benzo[b][1,4]oxazin-6-yl)methyl)piperazin-1-yl)benzoic acid;
4-(4-((8-Fluoro-2-methyl-3-oxo-3,4-dihydro-2H-benzo[b][1,4]oxazin-6-yl)methyl)piperazin-1-yl)-N-methylbenzamide;
N-Ethyl-4-(4-((8-fluoro-2-methyl-3-oxo-3,4-dihydro-2H-benzo[b][1,4]oxazin-6-yl)methyl)piperazin-1-yl)benzamide;
N-Cyclopropyl-4-(4-((8-fluoro-2-methyl-3-oxo-3,4-dihydro-2H-benzo[b][1,4]oxazin-6-yl)methyl)piperazin-1-yl)benzamide;
4-(4-((2,8-Dimethyl-3-oxo-3,4-dihydro-2H-benzo[b][1,4]oxazin-6-yl)methyl)piperazin-1-yl)-N-methylbenzamide;
Ethyl 4-(4-((8-chloro-2-methyl-3-oxo-3,4-dihydro-2H-benzo[b][1,4]oxazin-6-yl)methyl)piperazin-1-yl)benzoate;

4-(4-((8-Chloro-2-methyl-3-oxo-3,4-dihydro-2H-benzo[b][1,4]oxazin-6-yl)methyl)piperazin-1-yl)benzoic acid;
4-(4-((8-Chloro-2-methyl-3-oxo-3,4-dihydro-2H-benzo[b][1,4]oxazin-6-yl)methyl)piperazin-1-yl)-N-methylbenzamide;
4-(4-((8-Chloro-2-methyl-3-oxo-3,4-dihydro-2H-benzo[b][1,4]oxazin-6-yl)methyl)piperazin-1-yl)-N-ethylbenzamide;
4-(4-((8-Chloro-2-methyl-3-oxo-3,4-dihydro-2H-benzo[b][1,4]oxazin-6-yl)methyl)piperazin-1-yl)-N-isopropylbenzamide;
4-(4-((8-Chloro-2-methyl-3-oxo-3,4-dihydro-2H-benzo[b][1,4]oxazin-6-yl)methyl)piperazin-1-yl)-N-cyclopropylbenzamide;
Ethyl 6-(4-((8-fluoro-2-methyl-3-oxo-3,4-dihydro-2H-benzo[b][1,4]oxazin-6-yl)methyl)piperazin-1-yl)nicotinate;
6-(4-((8-Fluoro-2-methyl-3-oxo-3,4-dihydro-2H-benzo[b][1,4]oxazin-6-yl)methyl)piperazin-1-yl)nicotinic acid;
6-(4-((8-Fluoro-2-methyl-3-oxo-3,4-dihydro-2H-benzo[b][1,4]oxazin-6-yl)methyl)piperazin-1-yl)-N-methylnicotinamide;
N-Ethyl-6-(4-((8-fluoro-2-methyl-3-oxo-3,4-dihydro-2H-benzo[b][1,4]oxazin-6-yl)methyl)piperazin-1-yl)nicotinamide;
6-(4-((8-Fluoro-2-methyl-3-oxo-3,4-dihydro-2H-benzo[b][1,4]oxazin-6-yl)methyl)piperazin-1-yl)-N-isopropylnicotinamide;
N-Cyclopropyl-6-(4-((8-fluoro-2-methyl-3-oxo-3,4-dihydro-2H-benzo[b][1,4]oxazin-6-yl)methyl)piperazin-1-yl)nicotinamide;
6-((4-(4-Chlorophenyl)piperazin-1-yl)methyl)-2,7-dimethyl-2H-benzo[b][1,4]oxazin-3(4H)-one;
6-((4-(4-Chlorophenyl)-5,6-dihydropyridin-1(2H)-yl)methyl)-2,7-dimethyl-2H-benzo[b][1,4]oxazin-3(4H)-one;
6-((4-(4-Chlorophenyl)piperidin-1-yl)methyl)-2,7-dimethyl-2H-benzo[b][1,4]oxazin-3(4H)-one;
6-((4-(4-Chlorophenyl)piperazin-1-yl)methyl)-2,5-dimethyl-2H-benzo[b][1,4]oxazin-3(4H)-one;
6-((4-(4-Chlorophenyl)-5,6-dihydropyridin-1(2H)-yl)methyl)-2,5-dimethyl-2H-benzo[b][1,4]oxazin-3(4H)-one;
6-((4-(4-Chlorophenyl)piperidin-1-yl)methyl)-2,5-dimethyl-2H-benzo[b][1,4]oxazin-3(4H)-one;
6-((4-(4-Chlorophenyl)piperazin-1-yl)methyl)-7-fluoro-2-methyl-2H-benzo[b][1,4]oxazin-3(4H)-one;
6-((4-(4-Chlorophenyl)-5,6-dihydropyridin-1(2H)-yl)methyl)-7-fluoro-2-methyl-2H-benzo[b][1,4]oxazin-3(4H)-one;
6-((4-(4-Chlorophenyl)piperidin-1-yl)methyl)-7-fluoro-2-methyl-2H-benzo[b][1,4]oxazin-3(4H)-one;
Ethyl 4-(4-((7-fluoro-2-methyl-3-oxo-3,4-dihydro-2H-benzo[b][1,4]oxazin-6-yl)methyl)piperazin-1-yl)benzoate;
4-(4-((7-Fluoro-2-methyl-3-oxo-3,4-dihydro-2H-benzo[b][1,4]oxazin-6-yl)methyl)piperazin-1-yl)benzoic acid;
4-(4-((7-Fluoro-2-methyl-3-oxo-3,4-dihydro-2H-benzo[b][1,4]oxazin-6-yl)methyl)piperazin-1-yl)-N-methylbenzamide;
N-Ethyl-4-(4-((7-fluoro-2-methyl-3-oxo-3,4-dihydro-2H-benzo[b][1,4]oxazin-6-yl)methyl)piperazin-1-yl)benzamide;
4-(4-((7-Fluoro-2-methyl-3-oxo-3,4-dihydro-2H-benzo[b][1,4]oxazin-6-yl)methyl)piperazin-1-yl)-N-isopropylbenzamide;
N-Cyclopropyl-4-(4-((7-fluoro-2-methyl-3-oxo-3,4-dihydro-2H-benzo[b][1,4]oxazin-6-yl)methyl)piperazin-1-yl)benzamide;
4-(4-((7-Fluoro-2-methyl-3-oxo-3,4-dihydro-2H-benzo[b][1,4]oxazin-6-yl)methyl)piperazin-1-yl)benzonitrile;
6-(4-((7-Fluoro-2-methyl-3-oxo-3,4-dihydro-2H-benzo[b][1,4]oxazin-6-yl)methyl)piperazin-1-yl)nicotinonitrile;
6-((4-(4-Chlorophenyl)piperazin-1-yl)methyl)-5-fluoro-2-methyl-2H-benzo[b][1,4]oxazin-3(4H)-one;
4-(4-((8-Benzyl-2-methyl-3-oxo-3,4-dihydro-2H-benzo[b][1,4]oxazin-6-yl)methyl)piperazin-1-yl)-N-methylbenzamide;
4-(4-((8-Benzyl-2-methyl-3-oxo-3,4-dihydro-2H-benzo[b][1,4]oxazin-6-yl)methyl)piperazin-1-yl)-N-cyclopropylbenzamide;
4-(4-((8-Benzyl-2-methyl-3-oxo-3,4-dihydro-2H-benzo[b][1,4]oxazin-6-yl)methyl)piperazin-1-yl)-N-ethylbenzamide;
4-(4-((8-Allyl-2-methyl-3-oxo-3,4-dihydro-2H-benzo[b][1,4]oxazin-6-yl)methyl)piperazin-1-yl)-N-ethylbenzamide;
N-Methyl-4-(4-((2-methyl-3-oxo-8-propyl-3,4-dihydro-2H-benzo[b][1,4]oxazin-6-yl)methyl)piperazin-1-yl)benzamide;
N-Ethyl-4-(4-((8-hydroxy-2-methyl-3-oxo-3,4-dihydro-2H-benzo[b][1,4]oxazin-6-yl)methyl)piperazin-1-yl)benzamide;
N-Ethyl-3-fluoro-4-(4-((8-methoxy-2-methyl-3-oxo-3,4-dihydro-2H-benzo[b][1,4]oxazin-6-yl)methyl)piperazin-1-yl)benzamide;
3-Chloro-N-ethyl-4-(4-((8-methoxy-2-methyl-3-oxo-3,4-dihydro-2H-benzo[b][1,4]oxazin-6-yl)methyl)piperazin-1-yl)benzamide;
4-(4-((8-Methoxy-2-methyl-3-oxo-3,4-dihydro-2H-benzo[b][1,4]oxazin-6-yl)methyl)piperazin-1-yl)-N,3-dimethylbenzamide;
N-ethyl-4-(4-((8-methoxy-2-methyl-3-oxo-3,4-dihydro-2H-benzo[b][1,4]oxazin-6-yl)methyl)piperazin-1-yl)-3-methylbenzamide;
N-Cyclopropyl-4-{4-[(8-methoxy-2-methyl-3-oxo-3,4-dihydro-2H-1,4-benzoxazin-6-yl)methyl]piperazin-1-yl}-3-methylbenzamide;
3-Fluoro-4-(4-((8-methoxy-2-methyl-3-oxo-3,4-dihydro-2H-benzo[b][1,4]oxazin-6-yl)methyl)piperazin-1-yl)-N-methylbenzamide;
3-Chloro-4-(4-((8-methoxy-2-methyl-3-oxo-3,4-dihydro-2H-benzo[b][1,4]oxazin-6-yl)methyl)piperazin-1-yl)-N-methylbenzamide;
3-Chloro-N-ethyl-4-(4-((2-methyl-3-oxo-3,4-dihydro-2H-benzo[b][1,4]oxazin-6-yl)methyl)piperazin-1-yl)benzamide;
N-Cyclopropyl-3-fluoro-4-{4-[(8-methoxy-2-methyl-3-oxo-3,4-dihydro-2H-1,4-benzoxazin-6-yl)methyl]piperazin-1-yl}benzamide;
3-Chloro-N-cyclopropyl-4-(4-((8-methoxy-2-methyl-3-oxo-3,4-dihydro-2H-benzo[b][1,4]oxazin-6-yl)methyl)piperazin-1-yl)benzamide;
N-Ethyl-4-(4-((8-methoxy-3-oxo-3,4-dihydro-2H-benzo[b][1,4]oxazin-6-yl)methyl)piperazin-1-yl)-3-methylbenzamide;

N-cyclopropyl-4-(4-((8-methoxy-3-oxo-3,4-dihydro-2H-benzo[b][1,4]oxazin-6-yl)methyl)piperazin-1-yl)-3-methylbenzamide;

4-(4-((8-Methoxy-3-oxo-3,4-dihydro-2H-benzo[b][1,4]oxazin-6-yl)methyl)piperazin-1-yl)-N,3-dimethylbenzamide;

2-Methyl-6-((4-(4-(pyrrolidine-1-carbonyl)phenyl)piperazin-1-yl)methyl)-2H-benzo[b][1,4]oxazin-3(4H)-one;

N,N-Dimethyl-4-(4-((2-methyl-3-oxo-3,4-dihydro-2H-benzo[b][1,4]oxazin-6-yl)methyl)piperazin-1-yl)benzamide;

N-Ethyl-N-methyl-4-(4-((2-methyl-3-oxo-3,4-dihydro-2H-benzo[b][1,4]oxazin-6-yl)methyl)piperazin-1-yl)benzamide;

4-(4-((2,8-Dimethyl-3-oxo-3,4-dihydro-2H-benzo[b][1,4]oxazin-6-yl)methyl)piperazin-1-yl)-3-fluoro-N-methylbenzamide;

4-(4-((2,8-Dimethyl-3-oxo-3,4-dihydro-2H-benzo[b][1,4]oxazin-6-yl)methyl)piperazin-1-yl)-N-ethyl-3-fluorobenzamide;

3-Chloro-4-(4-((2,8-dimethyl-3-oxo-3,4-dihydro-2H-benzo[b][1,4]oxazin-6-yl)methyl)piperazin-1-yl)-N-ethylbenzamide;

3-Chloro-4-(4-((2,8-dimethyl-3-oxo-3,4-dihydro-2H-benzo[b][1,4]oxazin-6-yl)methyl)piperazin-1-yl)-N-methylbenzamide;

4-(4-((2,8-Dimethyl-3-oxo-3,4-dihydro-2H-benzo[b][1,4]oxazin-6-yl)methyl)piperazin-1-yl)-N,3-dimethylbenzamide;

4-(4-((2,8-Dimethyl-3-oxo-3,4-dihydro-2H-benzo[b][1,4]oxazin-6-yl)methyl)piperazin-1-yl)-N-ethyl-3-methylbenzamide;

N-Cyclopropyl-4-(4-((2,8-dimethyl-3-oxo-3,4-dihydro-2H-benzo[b][1,4]oxazin-6-yl)methyl)piperazin-1-yl)-3-methylbenzamide;

N-Cyclopropyl-4-(4-((2,8-dimethyl-3-oxo-3,4-dihydro-2H-benzo[b][1,4]oxazin-6-yl)methyl)piperazin-1-yl)-3-fluorobenzamide;

3-Chloro-N-cyclopropyl-4-(4-((2,8-dimethyl-3-oxo-3,4-dihydro-2H-benzo[b][1,4]oxazin-6-yl)methyl)piperazin-1-yl)benzamide;

4-(4-((8-Ethoxy-2-methyl-3-oxo-3,4-dihydro-2H-benzo[b][1,4]oxazin-6-yl)methyl)piperazin-1-yl)-N-methylbenzamide;

3-Chloro-4-(4-((8-ethoxy-2-methyl-3-oxo-3,4-dihydro-2H-benzo[b][1,4]oxazin-6-yl)methyl)piperazin-1-yl)-N-ethylbenzamide;

4-(4-((8-Ethoxy-2-methyl-3-oxo-3,4-dihydro-2H-benzo[b][1,4]oxazin-6-yl)methyl)piperazin-1-yl)-N,3-dimethylbenzamide;

4-(4-((8-Ethoxy-2-methyl-3-oxo-3,4-dihydro-2H-benzo[b][1,4]oxazin-6-yl)methyl)piperazin-1-yl)-N-ethyl-3-methylbenzamide;

N-Cyclopropyl-4-(4-((8-ethoxy-2-methyl-3-oxo-3,4-dihydro-2H-benzo[b][1,4]oxazin-6-yl)methyl)piperazin-1-yl)-3-methylbenzamide;

4-(4-((8-(Difluoromethoxy)-2-methyl-3-oxo-3,4-dihydro-2H-benzo[b][1,4]oxazin-6-yl)methyl)piperazin-1-yl)-N-methylbenzamide;

4-(4-((8-(Difluoromethoxy)-2-methyl-3-oxo-3,4-dihydro-2H-benzo[b][1,4]oxazin-6-yl)methyl)piperazin-1-yl)-N-ethylbenzamide;

3-Chloro-4-(4-((8-(difluoromethoxy)-2-methyl-3-oxo-3,4-dihydro-2H-benzo[b][1,4]oxazin-6-yl)methyl)piperazin-1-yl)-N-ethylbenzamide;

4-(4-((8-(Difluoromethoxy)-2-methyl-3-oxo-3,4-dihydro-2H-benzo[b][1,4]oxazin-6-yl)methyl)piperazin-1-yl)-N,3-dimethylbenzamide;

a tautomer of any one of the aforementioned compounds;

a stereoisomer of any one of the aforementioned compounds or tautomer; and a pharmaceutically acceptable salt of any one of the aforementioned compounds, tautomer or stereoisomer.

11. A pharmaceutical composition comprising a compound, tautomer, or pharmaceutically acceptable salt as defined in any one of claims 1, 2, 3, 4, 5, 6, 7, 8, 9, and 10 and a pharmaceutically acceptable excipient.

12. A method for treating a disease state in a subject, the method comprising administering to the subject a therapeutically effective amount of a compound, tautomer, or pharmaceutically acceptable salt as defined in any one of claims 1, 2, 3, 4, 5, 6, 7, 8, 9, and 10, wherein the disease state is selected from the group consisting of metabolic disease, reperfusion injury, and ischemic condition.

* * * * *

UNITED STATES PATENT AND TRADEMARK OFFICE
CERTIFICATE OF CORRECTION

PATENT NO. : 8,669,249 B2
APPLICATION NO. : 13/260680
DATED : March 11, 2014
INVENTOR(S) : Jason W. Brown et al.

It is certified that error appears in the above-identified patent and that said Letters Patent is hereby corrected as shown below:

In the Claims

Column 242, claim 1, line 14:
"$L_1$ is selected from the group consisting of -$CH_2$- and;" should read --$L_1$ is selected from the group consisting of -$CH_2$- and -$SO_2$-;--.

Signed and Sealed this
Thirtieth Day of September, 2014

Michelle K. Lee
*Deputy Director of the United States Patent and Trademark Office*